US009056090B2

(12) United States Patent
Colloca et al.

(10) Patent No.: US 9,056,090 B2
(45) Date of Patent: Jun. 16, 2015

(54) HEPATITIS C VIRUS NUCLEIC ACID VACCINE

(75) Inventors: Stefano Colloca, Rome (IT); Antonella Folgori, Rome (IT); Armin Lahm, Rome (IT); Alfredo Nicosia, Rome (IT)

(73) Assignee: MSD Italia SRL, Rome (IT)

( * ) Notice: Subject to any disclaimer, the term of this patent is extended or adjusted under 35 U.S.C. 154(b) by 1568 days.

(21) Appl. No.: 11/922,309

(22) PCT Filed: Jun. 13, 2006

(86) PCT No.: PCT/EP2006/005697
§ 371 (c)(1),
(2), (4) Date: Dec. 14, 2007

(87) PCT Pub. No.: WO2006/133911
PCT Pub. Date: Dec. 21, 2006

(65) Prior Publication Data
US 2009/0035277 A1  Feb. 5, 2009

Related U.S. Application Data

(60) Provisional application No. 60/691,523, filed on Jun. 17, 2005, provisional application No. 60/699,514, filed on Jul. 15, 2005.

(51) Int. Cl.
C12N 15/861 (2006.01)
C12N 7/00 (2006.01)
C12N 7/01 (2006.01)
A61K 39/29 (2006.01)
C07K 14/005 (2006.01)
A61K 39/00 (2006.01)

(52) U.S. Cl.
CPC ......... *A61K 39/29* (2013.01); *A61K 2039/5258* (2013.01); *A61K 2039/53* (2013.01); *C07K 14/005* (2013.01); *C07K 2319/00* (2013.01); *C12N 2710/10343* (2013.01); *C12N 2770/24222* (2013.01); *C12N 2770/24234* (2013.01)

(58) Field of Classification Search
None
See application file for complete search history.

(56) References Cited

U.S. PATENT DOCUMENTS

| 5,122,458 | A | 6/1992 | Post et al. |
| 5,994,083 | A | 11/1999 | Felici et al. |
| 6,033,908 | A | 3/2000 | Bout et al. |
| 6,428,792 | B1 | 8/2002 | Valenzuela et al. |
| 8,216,834 | B2 * | 7/2012 | Colloca et al. ............. 435/320.1 |

FOREIGN PATENT DOCUMENTS

| WO | WO95/32733 | 12/1995 |
| WO | WO97/47358 | 12/1997 |
| WO | WO98/43703 | 10/1998 |
| WO | WO99/52463 | 10/1999 |
| WO | WO99/30132 | 11/1999 |
| WO | WO01/30812 | 5/2001 |
| WO | WO01/38360 | 5/2001 |
| WO | WO03000851 | 1/2003 |
| WO | WO03/031588 | 4/2003 |
| WO | WO2004/018627 | 3/2004 |
| WO | WO2005/071093 | 8/2005 |
| WO | WO2006/133911 | 12/2006 |

OTHER PUBLICATIONS

Kinloch, R. et al., "Sequence comparison of Subgroup C serotypes 2 and 5", JBC, 1984, vol. 259: pp. 6431-6436.*
Bett et al., 'Packaging Capacity and Stability of Human Adenovirus Type 5 Vectors', Journal of Virology, vol. 67, No. 10, pp. 5911-5921 (1993).
Blight et al., 'Efficient Initiation of HCV RNA Replication in Cell Culture', Science, vol. 290, pp. 1972-1974 (2000).
Catalucci et al., 'An Adenovirus Type 5 (Ad5) Amplicon-Based Packaging Cell Line for Production of High-Capacity Helper-Independent ΔE1-E2-E3-E4 Ad5 Vectors', Journal of Virology, vol. 79, pp. 6400-6409 (2005).
Chamberlain, et al., 'Complete nucleoside sequence of a type 4 hepatitis C virus variant, the predominant genotype in the Middle East', Journal of General Virology, vol. 78, pp. 1341-1347 (1997).
Chapman et al., 'Effect of intron A from human cytomegalovirus (Towne) immediate-early gene on heterologous expression in mammalian cells', Nucleic Acids research, vol. 19, No. 14, pp. 3979-3986 (1991).
Choo et al., 'Isolation of a cDNA Clone Derived from a Blood-Borne Non-A, Non-B Viral Hepatitis Genome', Science, vol. 244, pp. 362-364 (1989).
Choo et al., 'An Assay for Circulating antibodies to a Major Etiologic Virus of Human Non-A, Non-B Hepatitis', Science, vol. 244, 359-362 (1989).
Cho et al., 'Enhanced cellular immunity to hepatitis C virus nonstructural proteins by code livery of granulocyte macrophage-colony stimulating factor gene in intramuscular DAN immunizaton', Vaccine, vol. 17, pp. 1136-1144 (1999).
Chroboczek, et al., 'The Sequence of the Genome of Adenovirus Type 5 and its Comparison with the Genome of Adenovirus Type 2', Virology, vol. 186, pp. 280-285 (1992).
Danthinne et al., 'Production of first generation adenovirus vectors: a review', Gene Therapy, vol. 7, pp. 1707-1714 (2000).
De Francesco et al., 'Approaching a new era for hepatitis C virus therapy: inhibitors of the NS3-4A serine protease and the NS5B RNA-dependent RNA polymerase', Antiviral Research, vol. 58, pp. 1-16 (2005).

(Continued)

*Primary Examiner* — Michael Burkhart
(74) *Attorney, Agent, or Firm* — Wolf, Greenfield & Sacks, P.C.

(57) ABSTRACT

The present invention features nucleic acid constructs that can be used as a HCV nucleic acid vaccine, vaccine component, or in the production of a HCV vaccine. Described constructs include those: (1) encoding for a chimeric HCV polypeptide containing a NS3-4A region based on a first HCV strain and an NS3-NS4A-NS4B-NS5A or an NS3-NS4A-NS4B-NS5A-NS5B region based on a second strain; and (2) a chimpanzee based adenovector encoding an HCV polypeptide.

18 Claims, 45 Drawing Sheets

(56) References Cited

OTHER PUBLICATIONS

Donnelly, et al. 'DNA Vaccines', Annu. Rev. Immunol., vol. 15, pp. 617-648 (1997).
Fallaux et al., 'New Helper Cells and Matched Early Region 1-Deleted Adenovirus Vectors Prevent Generation of Replication Competent adenoviruses', Human Gene Therapy, vol. 9, pp. 1909-1917 (1998).
Gilbert et al., 'Enhanced CD8 T cell immunogenicity and protective efficacy in a mouse malaria model using a recombinant adenoviral vaccine in heterologous prime-boost immunization regimes', Vaccine, vol. 20, pp. 1039-1045 (2002).
Hitt et al. 'Human Adenovirus Vectors for Gene Transfer into Mammalian Cells', Gene Therapy—Advances in Pharmacology, vol. 40, pp. 137-206 (1997).
Hitt et al., Methods in Molecular Genetics, vol. 9, pp. 13-30 (1995).
Kolykhalon et al., 'Hepatitis C virus-Encoded Enzymatic Activities and Conserved RNA Elements in the 3" Nontranslated Region are Essential for Virus Replication In Vivo', Journal of Virology, vol. 74, No. 4, pp. 2046-2051 (2000).
Kozak, Marilyn 'Point Mutations Define a Sequence Flanking the AUG Initiator Codon That Modulates Translation by Eukaryotic Ribosomes', Cell, vol. 44, pp. 283-292 (1986).
Hagstrom et al. 'Improved muscle-derived expression of human coagulation factor IX from a skeletal actin/CMV hybrid enhancer/promoter', Blood, vol. 95, pp. 2536-2542 (2000).
Li et al., 'Synthetic muscle promoters: activities exceeding naturally occurring regulatory sequences', Nature Biotechnology, vol. 17, pp. 241-245 (1999).
Lohmann et al., 'Biochemical Properties of Hepatitis C Virus NS5B RNA-Dependent RNA Polymerase and Identification of Amino Acid Sequence Motifs Essential for Enzymatic Activity', Journal of Virology, vol. 71, pp. 8415-8425 (1997).
Newman et al. 'Use of Nonionic Block Copolymers in Vaccines and Therapeutics', Reviews in Therapeutic Drug Carrier Systems, vol. 15, pp. 89-142 (1998).
Pawlotsky et al., 'Hepatitis C virus genetic variability: pathogenic and clinical implications', Clinics in Liver Disease, vol. 7, pp. 45-66 (2003.
Russell et al. 'Update on adenovirus and vectors', Journal of General Virology, vol. 81, pp. 2573-2604 (2000).
Schneider et al., 'Efficient Transformation of Primary Human Amniocytes by E1 Functions of Ad5: Generation of New Cell Lines for Adenoviral Vector Production', Human Gene Therapy, vol. 11, pp. 2105-2116 (2000).
Simmonds, Peter, 'The origin and evolution of hepatitis viruses in humans', Journal of General Virology, vol. 82, pp. 693-712 (1977).
Simmonds, Peter, 'Genetic diversity and evolution of hepatitis C virus—15 years on', J. General Virol., vol. 85, pp. 3173-3188 (2004).
Takamizawa, et al. 'Structure and Organization of the Hepatitis C Virus Genome Isolated from Human Carriers', J. Virol., vol. 65, pp. 1105-1111 (1991).
Walker et al. 'Hepatitis C virus therapies: current treatments, targets and future perspectives', Antiviral Chemistry & chemotherapy, vol. 14, pp. 21 (2003).
Xu et al. 'Optimization of transcriptional regulatory elements for constructing plasmid vectors', Gene, vol. 272, pp. 149-156 (2001).
Zein, Nizar N., 'Experimental and emerging therapies for chronic hepatitis C virus infection', Expert Opinion Investig. Drugs, vol. 10, pp. 1457-1469 (2001).
Tatsis, et al., "Adenoviruses as Vaccine Vectors", Molecular Therapy, vol. 10(4), pp. 616-629.
Barnes et al., Novel adenovirus-based vaccines induce broad and sustained T cell responses to HCV in man. Sci Transl Med. Jan. 4, 2012;4(115):115ra1. doi: 10.1126/scitranslmed.3003155.
Berkner et al., Development of adenovirus vectors for the expression of heterologous genes. Biotechniques. Jul.-Aug. 1988;6(7):616-29.
Capone et al., A novel adenovirus type 6 (Ad6)-based hepatitis C virus vector that overcomes preexisting anti-ad5 immunity and induces potent and broad cellular immune responses in rhesus macaques. J Virol. Feb. 2006;80(4):1688-99.
Figueredo et al., Priming and boosting efficiency of chimp and human adenoviral vectors in the setting of pre-existing immunity in non-human primates. Mol Ther. 2005;11:s56.
Folgori et al., A T-cell HCV vaccine eliciting effective immunity against heterologous virus challenge in chimpanzees. Nat Med. Feb. 2006;12(2):190-7. Epub Feb. 5, 2006.
Roy et al., Characterization of a family of chimpanzee adenoviruses and development of molecular clones for gene transfer vectors. Hum Gene Ther. May 2004;15(5):519-30.
Database Geneseq [Online] Mar. 25, 2003, EBI accession No. GSP:ABP56662, Database accession No. ABP56662.
Database UniProt [Online] Dec. 7, 2004, EBI accession No. UNIPROT:Q5VHB3, database accession No. Q5VHB3.
Database Geneseq [Online] Jan. 11, 1999, EBI accession No. GSP:AAW79538, database accession No. AAW79538.

* cited by examiner

```
   1 MAPITAYAQQ TRGLLGTIVT SLTGRDKNVV AGEVQVLSTA TQTFLGTTVG
  51 GVMWTVYHGA GSRTLAGVKH PALQMYTNVD QDLVGWPAPP GAKSLEPCTC
 101 GSADLYLVTR DADVIPARRR GDSTASLLSP RPLARLKGSS GGPVMCPSGH
 151 VAGIFRAAVC TRGVAKALQF IPVETLSTQA RSPSFSDNST PPAVPQSYQV
 201 GYLHAPTGSG KSTKVPAAYV AQGYNVLVLN PSVAATLGFG SFMSRAYGID
 251 PNIRTGNRTV TTGAKLTYST YGKFLAGGGC SGGAYDVIIC DDCHAQDATS
 301 ILGIGTVLDQ AETAGVRLTV LATATPPGSI TVPHSNIEEV ALGSEGEIPF
 351 YGKAIPIACI KGGRHLIFCH SKKKCDKMAS KLRGMGLNAV AYYRGLDVSV
 401 IPTTGDVVVC ATDALMTGFT GDFDSVIDCN VAVEQYVDFS LDPTFSIETC
 451 TAPQDAVSRS QRRGRTGRGR LGTYRYVTPG ERPSGMFDSV VLCECYDAGC
 501 SWYDLQPAET TVRLRAYLST PGLPVCQDHL DLWESVFTGL THIDAHFLSQ
 551 TKQAGLNFSY LTAYQATVCA RAQAPPPSWD ETWKCLVRLK PTLHGPTPLL
 601 YRLGPVQNEI CLTHPITKYV MACMSADLEV TTSTWVLLGG VLAAVAAYCL
 651 SVGCVVIVGH IELGGKPALV PDKEVLYQQY DEMEECSQAR MAPITAYSQQ
 701 TRGLLGCIIT SLTGRDKNQV EGEVQVVSTA TQSFLATCVN GVCWTVYHGA
 751 GSKTLAGPKG PITQMYTNVD QDLVGWQAPP GARSLTPCTC GSSDLYLVTR
 801 HADVIPVRRR GDSRGSLLSP RPVSYLKGSS GGPLLCPSGH AVGIFRAAVC
 851 TRGVAKAVDF VPVESMETTM RSPVFTDNSS PPAVPQSFQV AHLHAPTGSG
 901 KSTKVPAAYA AQGYKVLVLN PSVAATLGFG AYMSKAHGID PNIRTGVRTI
 951 TTGAPVTYST YGKFLADGGC SGGAYDIIIC DECHSTDSTT ILGIGTVLDQ
1001 AETAGARLVV LATATPPGSV TVPHPNIEEV ALSNTGEIPF YGKAIPIEAI
1051 RGGRHLIFCH SKKKCDELAA KLSGLGINAV AYYRGLDVSV IPTIGDVVVV
1101 ATDALMTGYT GDFDSVIDCN TCVTQTVDFS LDPTFTIETT TVPQDAVSRS
1151 QRRGRTGRGR RGIYRFVTPG ERPSGMFDSS VLCECYDAGC AWYELTPAET
1201 SVRLRAYLNT PGLPVCQDHL EFWESVFTGL THIDAHFLSQ TKQAGDNFPY
1251 LVAYQATVCA RAQAPPPSWD QMWKCLIRLK PTLHGPTPLL YRLGAVQNEV
1301 TLTHPITKYI MACMSADLEV VTSTWVLVGG VLAALAAYCL TTGSVVIVGR
1351 IILSGRPAIV PDREFLYQEF DEMEECASHL PYIEQGMQLA EQFKQKALGL
1401 LQTATKQAEA AAPVVESKWR ALETFWAKHM WNFISGIQYL AGLSTLPGNP
1451 AIASLMAFTA SITSPLTTQS TLLFNILGGW VAAQLAPPSA ASAFVGAGIA
1501 GAAVGSIGLG KVLVDILAGY GAGVAGALVA FKVMSGEMPS TEDLVNLLPA
1551 ILSPGALVVG VVCAAILRRH VGPGEGAVQW MNRLIAFASR GNHVSPTHYV
1601 PESDAAARVT QILSSLTITQ LLKRLHQWIN EDCSTPCSGS WLRDVWDWIC
1651 TVLTDFKTWL QSKLLPQLPG VPFFSCQRGY KGVWRGDGIM QTTCPCGAQI
1701 TGHVKNGSMR IVGPKTCSNT WHGTFPINAY TTGPCTPSPA PNYSRALWRV
1751 AAEEYVEVTR VGDFHYVTGM TTDNVKCPCQ VPAPEFFTEV DGVRLHRYAP
1801 ACRPLLREEV TFQVGLNQYL VGSQLPCEPE PDVAVLTSML TDPSHITAET
1851 AKRRLARGSP PSLASSSASQ LSAPSLKATC TTHHVSPDAD LIEANLLWRQ
1901 EMGGNITRVE SENKVVVLDS FDPLRAEEDE REVSVPAEIL RKSKKFPAAM
1951 PIWARPDYNP PLLESWKDPD YVPPVVHGCP LPPIKAPPIP PPRRKRTVVL
2001 TESSVSSALA ELATKTFGSS ESSAVDSGTA TALPDQASDD GDKGSDVESY
2051 SSMPPLEGEP GDPDLSDGSW STVSEEASED VVCCSMSYTW TGALITPCAA
2101 EESKLPINAL SNSLLRHHNM VYATTSRSAG LRQKKVTFDR LQVLDDHYRD
2151 VLKEMKAKAS TVKAKLLSVE EACKLTPPHS AKSKFGYGAK DVRNLSSKAV
2201 NHIHSVWKDL LEDTVTPIDT TIMAKNEVFC VQPEKGGRKP ARLIVFPDLG
2251 VRVCEKMALY DVVSTLPQVV MGSSYGFQYS PGQRVEFLVN TWKSKKNPMG
2301 FSYDTRCFDS TVTENDIRVE ESIYQCCDLA PEARQAIKSL TERLYIGGPL
2351 TNSKGQNCGY RRCRASGVLT TSCGNTLTCY LKASAACRAA KLQDCTMLVN
2401 AAGLVVICES AGTQEDAASL RVFTEAMTRY SAPPGDPPQP EYDLELITSC
2451 SSNVSVAHDA SGKRVYYLTR DPTTPLARAA WETARHTPVN SWLGNIIMYA
2501 PTLWARMILM THFFSILLAQ EQLEKALDCQ IYGACYSIEP LDLPQIIERL
2551 HGLSAFSLHS YSPGEINRVA SCLRKLGVPP LRVWRHRARS VRARLLSQGG
2601 RAATCGKYLF NWAVKTKLKL TPIPAASQLD LSGWFVAGYS GGDIYHSLSR
2651 ARPRWFMLCL LLLSVGVGIY LLPNR
```

Fig. 1

```
TCGCGCGTTTCGGTGATGACGGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGATGCGTAAGGAGAAAATACCGCATCA
GATTGGCTATTGGCCATTGCATACGTTGTATCCATATCATAATATGTACATTTATATTGGCTCATGTCCAACATTACC
GCCATGTTGACATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACGCCCAACGACCCCCGCCCATTGACGTCAATAAT
GACGTATGTTCCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGGTAAATGGCCCGCCTGGCA
TTTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGA
CGTCAATGGGAGTTTGTTTTGGCACCAAAATCAACGGGACTTTCCAAAATGTCGTAACAACTCCGCCCCATTGACGCA
AATGGGCGGTAGGCGTGTACGGTGGGAGGTCTATATAAGCAGAGCTCGTTTAGTGAACCGTCAGATCGCCTGGAGACG
CCATCCACGCTGTTTTGACCTCCATAGAAGACACCGGGACCGATCCAGCCTCCGCGGCCGGGAACGGTGCATTGGAAC
GCGGATTCCCCGTGCCAAGAGTGACGTAAGTACCGCCTATAGACTCTATAGGCACACCCCTTTGGCTCTTATGCATGC
TATACTGTTTTTGGCTTGGGGCCTATACACCCCCGCTTCCTTATGCTATAGGTGATGGTATAGCTTAGCCTATAGGTG
TGGGTTATTGACCATTATTGACCACTCCCCTATTGGTGACGATACTTTCCATTACTAATCCATAACATGGCTCTTTGC
CACAACTATCTCTATTGGCTATATGCCAATACTCTGTCCTTCAGAGACTGACACGGACTCTGTATTTTTACAGGATGG
GGTCCCATTTATTATTTACAAATTCACATATACAACAACGCCGTCCCCCGTGCCCGCAGTTTTTATTAAACATAGCGT
GGGATCTCCACGCGAATCTCGGGTACGTGTTCCGGACATGGGCTCTTCTCCGGTAGCGGCGGAGCTTCCACATCCGAG
CCCTGGTCCCATGCCTCCAGCGGCTCATGGTCGCTCGGCAGCTCCTTGCTCCTAACAGTGGAGGCCAGACTTAGGCAC
AGCACAATGCCCACCACCACCAGTGTGCCGCACAAGGCCGTGGCGGTAGGGTATGTGTCTGAAAATGAGCGTGGAGAT
TGGGCTCGCACGGCTGACGCAGATGAAGACTTAAGGCAGCGGCAGAAGAAGATGCAGGCAGCTGAGTTGTTGTATTC
TGATAAGAGTCAGAGGTAACTCCCGTTGCGGTGCTGTTAACGGTGGAGGGCAGTGTAGTCTGAGCAGTACTCGTTGCT
GCCGCGCGCCACCAGACATAATAGCTGACAGACTAACAGACTGTTCCTTTCCATGGGTCTTTTCTGCAGTCACCGT
CCTTAGAATTCCGCCACCATGGCCCCTATCACCGCCTATGCCCAGCAGACAAGAGGCCTGCTGGGCACCATCGTGACA
AGCCTGACCGGCAGAGACAAGAATGTGGTGGCCGGCGAAGTGCCCCCGTGCCCGCAGTTTTTATTAAACATAGCGT
ACCACAGTGGGCGGCGTGATGTGGACAGTGTACCACGGAGCCGGCTCTAGAACACTGGCCGGCGTGAAGCACCCTGCC
CTGCAGATGTATACCAACGTGGATCAGGATCTTGTGGGGTGCCTGCCCCTCCTGGCGCCAAGTCTCTGGAGCCTTGT
ACCTGCGGCAGCGCCGATCTGTACCTGGTGACCAGGGACGCCGATGTGATCCCCGCCAGAAGAAGAGGCGATAGCACC
GCCAGCCTGCTGTCTCCGCGGCCGCTGGCCAGACTGAAGGGAAGCAGCGGCGGACCTGTGATGTGTCCTAGCGGCCAC
GTGGCCGGCATCTTTAGAGCCGCCGTGTGTACAAGAGGCGTGGCCAAGGCCCTGCAGTTTATCCCTGTGGAGACCCTG
AGCACCCAGGCCAGAAGCCCTAGCTTCAGCGACAACAGCACCCCTCCTGCCGTGCCTCAGAGCTACCAAGTGGGCTAC
CTGCACGCCCCTACAGGCTCTGGCAAGTCCACCAAAGTGCCTGCCGCCTATGTGGCCCAGGGCTACAATGTGCTGGTG
CTGAACCCTTCTGTGGCCGCCACACTGGGCTTTGGCAGCTTCATGAGCAGGGCCTACGGCATCGACCCCAATATCCGG
ACCGGCAACAGAACCGTGACAACCGGCGCCAAGCTGACCTACAGCACCTACGGCAAGTTCCTGGCCGGAGGAGGATGT
AGCGGCGGAGCCTACGACGTGATCATCGCGACGATTGCCACGCCCAGGATGCCACAAGCATCCTGGGCATCGGGACC
GTGCTGGATCAGGCCGAAACAGCCGGAGTGAGACTGACAGTGCTGGCCACAGCCACACCTCCTGGCAGCATCACAGTG
CCCCACAGCAATATCGAAGAAGTGGCCCTGGGCAGCGAGCAGGGCAGATCCCTTTTTACGGGAAGGCCATCCCTATCGCC
TGTATCAAGGGCGGCAGGCACCTGATCTTCTGCCACAGCAAGAAAAAGTGTGACAAGATGGCCAGCAAGCTGAGAGGC
ATGGGCCTGAATGCCGTGGCCTACTACAGAGGCCTGGACGTGTCTGTGATCCCTACCACCGGCGATGTGGTGGTGTGT
GCCACCGATGCCCTGATGACCGGCTTCACCGGCGATTTCGACAGCGTGATCGATTGCAACGTGGCCGTGGAGCAGTAC
GTGGACTTCGACCTGGACCCTACATTCAGCATCGAGACCTTCACCAGGATGCCGTGTCCGGTCTCAGAGA
AGAGGCAGAACCGGCAGAGGCAGACTGGGCACCTACAGATACGTGACCCCTGGCGAGAGACCTAGCGGCATGTTTGAC
AGCGTGGTGCTGTGCGAGTGTTACGATGCCGGCTGCTCCTGGTACGATCTGCAGCCTGCCGAGACCACTGTGAGGCTG
AGAGCCTACCTGTCTACCCCTGGCCTGCCTGTGTGTCAGGATCACCTGGACCTGTGGGAGAGCGTGTTTACCGGCCTG
ACACACATCGACGCCCACTTTCTGAGCCAGACAAAACAGGCCGGCTGAACTTCAGCTACCTGACCGCCTACCAGGCC
ACAGTGTGTGCTAGAGCCCAGGCCCCTCCTCCTAGCTGGGATGAGACCTGGAAGTGCCTTGTGAGACTGAAGCCAACC
CTGCACGGACCTACCCCACTGCTGTATAGACTGGGCCCCGTGCAGAACGAGATCTGCCTGACCCACCCTATCACCAAG
TACGTGATGGCCTGCATGAGCGCTGATCTGGAAGTGACCACCTCCACTTGGGTGCTGCTGGGGGGCGTGCTAGCCGCC
GTGGCCGCCTATTGTCTGTCTCGTGGGCTGCGTGGTGATTGTGGGCCACATCGAGCTGGGAGGAAGGCCTGCCCTGGTG
CCCGATAAGGAAGTGCTCTACCAGCAGTACGACGAGATGGAGGAGTGTAGCCAGGCTAGAATGGCCCCCATCACCGCC
TACAGCCAGCAGACCCGCGGCCTGCTGGGCTGCATCATCACCAGCCTGACCGGCCGCGACAAGAACCAGGTGGAGGGC
GAGGTGCAGGTGGTGAGCACCGCCACCCAGAGCTTCCTGGCCACCTGCGTGAACGGCGTGTGCTGGACCGTGTACCAC
GGCGCCGGCAGCAAGACCCTGGCCGGCCCCAAGGGCCCCATCACCCAGATGTACACCAACGTGGACCAGGACCTGGTG
GGCTGGCAGGCCCCCCCGGCGCCCGCAGCCTGACCCCTGCACCTGCGGCAGCAGCGACCTGTACCTGGTGACCCGC
CACGCCGACGTGATCCCCGTGCGCCGCCGCGGCGACAGCCGCGGCAGCCTGCTGAGCCCCGCCCCGTGAGCTACCTG
AAGGGCAGCAGCGGCGGCCCCCTGCTGTGCCCCAGCGGCCACGCCGTGGGCATCTTCCGCGCCGCCGTGTGCACCCGC
GGCGTGGCCAAGGCCGTGGACTTCGTGCCCGTGGAGAGCATGGAGACCACCATGCGCAGCCCCGTGTTCACCGACAAC
AGCAGCCCCCCCGCCGTGCCCCAGAGCTTCCAGGTGGCCCACCTGCACGCCCCCACCGGCAGCGGCAAGAGCACCAAG
GTGCCCGCCGCCTACGCCGCCCAGGGCTACAAGGTGCTGGTGCTGAACCCCAGCGTGGCCGCCACCCTGGGCTTCGGC
```

Fig. 2A

```
GCCTACATGAGCAAGGCCCACGGCATCGACCCCAACATCCGCACCGGCGTGCGCACCATCACCACCGGCGCCCCCGTG
ACCTACAGCACCTACGGCAAGTTCCTGGCCGACGGCGGCTGCAGCGGCGGCGCCTACGACATCATCATCTGCGACGAG
TGCCACAGCACCGACAGCACCACCATCCTGGGCATCGGCACCGTGCTGGACCAGGCCGAGACCGCCGGCGCCCGCCTG
GTGGTGCTGGCCACCGCCACCCCCCCCGGCAGCGTGACCGTGCCCCACCCCAACATCGAGGAGGTGGCCCTGAGCAAC
ACCGGCGAGATCCCCTTCTACGGCAAGGCCATCCCCATCGAGGCCATCCGCGGCGGCCGCCACCTGATCTTCTGCCAC
AGCAAGAAGAAGTGCGACGAGCTGGCCGCCAAGCTGAGCGGCCTGGGCATCAACGCCGTGGCCTACTACCGCGGCCTG
GACGTGAGCGTGATCCCCACCATCGGCGACGTGGTGGTGGTGGCCACCGACGCCCTGATGACCGGCTACACCGGCGAC
TTCGACAGCGTGATCGACTGCAACACCTGCGTGACCCAGACCGTGGACTTCAGCCTGGACCCCACCTTCACCATCGAG
ACCACCACCGTGCCCCAGGACGCCGTGAGCCGCAGCCAGCCGCCGGGCCGCACCGGCCGCGGCCGCCGCGGCATCTAC
CGCTTCGTGACCCCCGGCGAGCGCCCCAGCGGCATGTTCGACAGCAGCGTGCTGTGCGAGTGCTACGACGCCGGCTGC
GCCTGGTACGAGCTGACCCCCGCCGAGACCAGCGTGCGCCTGCGCGCCTACCTGAACACCCCCGGCCTGCCCGTGTGC
CAGGACCACCTGGAGTTCTGGGAGAGCGTGTTCACCGGCCTGACCCACATCGACGCCCACTTCCTGAGCCAGACCAAG
CAGGCCGGCGACAACTTCCCCTACCTGGTGGCCTACCAGGCCACCGTGTGCGCCCGCGCCCAGGCCCCCCCCCCCAGC
TGGGACCAGATGTGGAAGTGCCTGATCCGCCTGAAGCCCACCCTGCACGGCCCCACCCCCCTGCTGTACCGCCTGGGC
GCCGTGCAGAACGAGGTGACCCTGACCCACCCCATCACCAAGTACATCATGGCCTGCATGAGCGCCGACCTGGAGGTG
GTGACCAGCACCTGGGTGCTGGTGGGCGGCGTGCTGGCCGCCCTGGCCGCCTACTGCCTGACCACCGGCAGCGTGGTG
ATCGTGGGCCGCATCATCCTGAGCGGCCGCCCCGCCATCGTGCCCGACCGCGAGTTCCTGTACCAGGAGTTCGACGAG
ATGGAGGAGTGCGCCAGCCACCTGCCCTACATCGAGCAGGGCATGCAGCTGGCCGAGCAGTTCAAGCAGAAGGCCCTG
GGCCTGCTGCAGAACGCCACCAAGCAGGCCGAGGCCGCCGCCCCGTGGTGGAGAGCAAGTGGCGCGCCCTGGAGACC
TTCTGGGCCAAGCACATGTGGAACTTCATCAGCGGCATCCAGTACCTGGCCGGCCTGAGCACCCTGCCCGGCAACCCC
GCCATCGCCAGCCTGATGGCCTTCACCGCCAGCATCACCAGCCCCCTGACCACCCAGAGCACCCTGCTGTTCAACATC
CTGGGCGGCTGGGTGGCCGCCCAGCTGGCCCCCCCCAGCGCCGCCAGCGCCTTCGTGGGCGCCGGCATCGCCGGCGCC
GCCGTGGGCAGCATCGGCCTGGGCAAGGTGCTGGTGGACATCCTGGCCGGCTACGGCGCCGGCGTGGCCGGCGCCCTG
GTGGCCTTCAAGGTGATGAGCGGCGAGATGCCCAGCACCGAGGACCTGGTGAACCTGCTGCCCGCCATCCTGAGCCCC
GGCGCCCTGGTGGTGGGCGTGGTGTGCGCCGCCATCCTGCGCCGCCACGTGGGCCCCGGCGAGGGCGCCGTGCAGTGG
ATGAACCGCCTGATCGCCTTCGCCAGCCGCGGCAACCACGTGAGCCCCACCCACTACGTGCCCGAGAGCGACGCCGCC
GCCCGCGTGACCCAGATCCTGAGCAGCCTGACCATCACCCAGCTGCTGAAGCGCCTGCACCAGTGGATCAACGAGGAC
TGCAGCACCCCCTGCAGCGGCAGCTGGCTGCGCGACGTGTGGGACTGATCTGCACCGTGCTGACCGACTTCAAGACC
TGGCTGCAGAGCAAGCTGCTGCCCCAGCTGCCCGGCGTGCCCTTCTTCAGCTGCCAGCGCGGCTACAAGGGCGTGTGG
CGCGGCGACGGCATCATGCAGACCACCTGCCCCTGCGGCGCCCAGATCACCGGCCACGTGAAGAACGGCAGCATGCGC
ATCGTGGGCCCCAAGACCTGCAGCAACACCTGGCACGGCACCTTCCCCATCAACGCCTACACCACCGGCCCCTGCACC
CCCAGCCCCGCCCCCAACTACAGCCGCGCCCTGTGGCGCGTGGCCGCCGAGGAGTACGTGGAGGTGACCCGCGTGGGC
GACTTCCACTACGTGACCGGCATGACCACCGACAACGTGAAGTGCCCCTGCCAGGTGCCCGCCCCCGAGTTCTTCACC
GAGGTGGACGGCGTGCGCCTGCACCGCTACGCCCCCGCCTGCCGCCCCCTGCTGCGCGAGGAGGTGACCTTCCAGGTG
GGCCTGAACCAGTACCTGGTGGGCAGCCAGCTGCCCTGCGAGCCCGAGCCCGACGTGGCCGTGCTGACCAGCATGCTG
ACCGACCCCAGCCACATCACCGCCGAGACCGCCAAGCGCCGCCTGGCCCGCGGCAGCCCCCCCAGCCTGGCCAGCAGC
AGCGCCAGCCAGCTGAGCGCCCCCAGCCTGAAGGCCACCTGCACCACCCACCACGTGAGCCCCGACGCCGACCTGATC
GAGGCCAACCTGCTGTGGCGCCAGGAGATGGGCGGCAACATCACCCGCGTGGAGAGCGAGAACAAGGTGGTGGTGCTG
GACAGCTTCGACCCCCTGCGCGCCGAGGAGGACGAGCGCGAGGTGAGCGTGCCCGCCGAGATCCTGCGCAAGAGCAAG
AAGTTCCCCGCCGCCATGCCCATCTGGGCCCGCCCCGACTACAACCCCCCCCTGCTGGAGAGCTGGAAGGACCCCGAC
TACGTGCCCCCCGTGGTGCACGGCTGCCCCCTGCCCCCCCATCAAGGCCCCCCCATCCCCCCCCCCGCCGCAAGCGC
ACCGTGGTGCTGACCGAGAGCAGCGTGAGCGAGCTGCCCGTCCTGGCCGAGCTGGCCACCAAGACCTTCCGCAGCAGCGAGAGC
AGCGCCGTGGACAGCGGCACCGCCACCGCCCTGCCCGACCAGGCCAGCGACGACGGCGACAAGGGCAGCGACGTGGAG
AGCTACAGCAGCATGCCCCCCCTGGAGGGCGAGCCCGGCGACCCCGACCTGAGCGACGGCAGCTGGAGCACCGTGAGC
GAGGAGGCCAGCGAGGACGTGGTGTGCTGCAGCATGAGCTACACCTGGACCGGCGCCCTGATCACCCCCTGCGCCGCC
GAGGAGAGCAAGCTGCCCATCAACGCCCTGAGCAACAGCCTGCTGCGCCACCACAACATGGTGTACGCCACCACCAGC
CGCAGCGCCGGCCTGCGCCAGAAGAAGGTGACCTTCGACCGCCTGCAGGTGCTGGACGACCACTACCGCGACGTGCTG
AAGGAGATGAAGGCCAAGGCCAGCACCGTGAAGGCCAAGCTGCTGAGCGTGGAGGAGGCCTGCAAGCTGACCCCCCCC
CACAGCGCCAAGAGCAAGTTCGGCTACGGCGCCAAGGACGTGCGCAACCTGAGCAGCAAGGCCGTGAACCACATCCAC
AGCGTGTGGAAGGACCTGCTGGAGGACACCGTGACCCCCATCGACACCACCATCATGGCCAAGAACGAGGTGTTCTGC
GTGCAGCCCGAGAAGGGCGGCCGCAAGCCCGCCCGCCTGATCGTGTTCCCCGACCTGGGCGTGCGCGTGTGCGAGAAG
ATGGCCCTGTACGACGTGGTGAGCACCCTGCCCCAGGTGGTGATGGGCAGCAGCTACGGCTTCCAGTACAGCCCCGGC
CAGCGCGTGGAGTTCCTGGTGAACACCTGGAAGAGCAAGAAGAACCCCATGGGCTTCAGCTACGACACCCGCTGCTTC
GACAGCACCGTGACCGAGAACGACATCCGCGTGGAGGAGAGCATCTACCAGTGCTGCGACCTGGCCCCCGAGGCCCGC
CAGGCCATCAAGAGCCTGACCGAGCGCCTGTACATCGGCGGCCCCCTGACCAACAGCAAGGGCCAGAACTGCGGCTAC
CGCCGCTGCCGCGCCAGCGGCGTGCTGACCACCAGCTGCGGCAACACCCTGACCTGCTACCTGAAGGCCAGCGCCGCC
TGCCGCGCCGCCAAGCTGCAGGACTGCACCATGCTGGTGAACGGCGACGACCTGGTGGTGATCTGCGAGAGCGCCGGC
ACCCAGGAGGACGCCGCCAGCCTGCGCGTGTTCACCGAGGCCATGACCCGCTACAGCGCCCCCCCGGCGACCCCCCC
CAGCCCGAGTACGACCTGGAGCTGATCACCAGCTGCAGCAGCAACGTGAGCGTGGCCCACGACGCCAGCGGCAAGCGC
GTGTACTACCTGACCCGCGACCCCACCACCCCCCTGGCCCGCGCCGCCTGGGAGACCGCCCGCCACACCCCCGTGAAC
```

Fig. 2B

```
AGCTGGCTGGGCAACATCATCATGTACGCCCCCACCCTGTGGGCCCGCATGATCCTGATGACCCACTTCTTCAGCATC
CTGCTGGCCCAGGAGCAGCTGGAGAAGGCCCTGGACTGCCAGATCTACGGCGCCTGCTACAGCATCGAGCCCCTGGAC
CTGCCCCAGATCATCGAGCGCCTGCACGGCCTGAGCGCCTTCAGCCTGCACAGCTACAGCCCCGGCGAGATCAACCGC
GTGGCCAGCTGCCTGCGCAAGCTGGGCGTGCCCCCCCTGCGCGTGTGGCGCCACCGCGCCCGCAGCGTGCGCGCCCGC
CTGCTGAGCCAGGGCGGCCGCGCCGCCACCTGCGGCAAGTACCTGTTCAACTGGGCCGTGAAGACCAAGCTGAAGCTG
ACCCCCATCCCCGCCGCCAGCCAGCTGGACCTGAGCGGCTGGTTCGTGGCCGGCTACAGCGGCGGCGACATCTACCAC
AGCCTGAGCCGCGCCCGCCCCCGCTGGTTCATGCTGTGCCTGCTGCTGCTGAGCGTGGGCGTGGGCATCTACCTGCTG
CCCAACCGCTAAATTTAAATGTTTAAACGTCGACAGCGGCCGCGATCTGCTGTGCCTTCTAGTTGCCAGCCATCTGTT
GTTTGCCCCTCCCCCGTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGCCGCAGCGGCCAGGTGCTGAAGAATTGACCCGGTTCCT
CCTGGGCCAGAAAGAAGCAGGCACATCCCCTTCTCTGTGACACACCCTGTCCACGCCCCTGGTTCTTAGTTCCAGCCC
CACTCATAGGACACTCATAGCTCAGGAGGGCTCCGCCTTCAATCCCACCCGCTAAAGTACTTGGAGCGGTCTCTCCCT
CCCTCATCAGCCCACCAAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATAGAATTTCTTCCGCTTCCTCGCTCACTGAC
TCGCTGCGCTCGGTCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCTGCGCTCTG
CTGAAGCCAGTTACCTTCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCGGGGGGGGGGGCGCTGAGGTCTG
CCTCGTGAAGAAGGTGTTGCTGACTCATACCAGGCCTGAATCGCCCCATCATCCAGCCAGAAAGTGAGGGAGCCACGG
TTGATGAGAGCTTTGTTGTAGGTGGACCAGTTGGTGATTTTGAACTTTTGCTTTGCCACGGAACGGTCTGCGTTGTCG
GGAAGATGCGTGATCTGATCCTTCAACTCAGCAAAAGTTCGATTTATTCAACAAAGCCGCCGTCCCGTCAAGTCAGCG
TAATGCTCTGCCAGTGTTACAACCAATTAACCAATTCTGATTAGAAAAACTCATCGAGCATCAAATGAAACTGCAATT
TATTCATATCAGGATTATCAATACCATATTTTTGAAAAAGCCGTTTCTGTAATGAAGGAGAAAACTCACCGAGGCAGT
TCCATAGGATGGCAAGATCCTGGTATCGGTCTGCGATTCCGACTCGTCCAACATCAATCAAACCTATTAATTTCCCCT
CGTCAAAAATAAGGTTATCAAGTGAGAAATCACCATGAGTGACGACTGAATCCGGTGAGAATGGCAAAAGCTTATGCA
TTTCTTTCCAGACTTGTTCAACAGGCCAGCCATTACGCTCGTCATCAAAATCACTCGCATCAACCAAACCGTTATTCA
TTCGTGATTGCGCCTGAGCGAGACGAAATACGCGATCGCTGTTAAAAGGACAATTACAAACAGGAATCGAATGCAACC
GGCGCAGGAACACTGCCAGCGCATCAACAATATTTTCACCTGAATCAGGATATTCTTCTAATACCTGGAATGCTGTTT
TCCCGGGGATCGCAGTGGTGAGTAACCATGCATCATCAGGAGTACGGATAAAATGCTTGATGGTCGGAAGAGGCATAA
ATTCCGTCAGCCAGTTTAGTCTGACCATCTCATCTGTAACATCATTGGCAACGCTACCTTTGCCATGTTTCAGAAACA
ACTCTGGCGCATCGGGCTTCCCATACAATCGATAGATTGTCGCACCTGATTGCCCGACATTATCGCGAGCCCATTTAT
ACCCATATAAATCAGCATCCATGTTGGAATTTAATCGCGGCCTCGAGCAAGACGTTTCCCGTTGAATATGGCTCATAA
CACCCCTTGTATTACTGTTTATGTAAGCAGACAGTTTTATTGTTCATGATGATATATTTTTATCTTGTGCAATGTAAC
ATCAGAGATTTTGAGACACAACGTGGCTTTCCCCCCCCCCCCATTATTGAAGCATTTATCAGGGTTATTGTCTCATGA
GCGGATACATATTTGAATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCTTTCGTC
```

Fig. 2C

```
MAPITAYSQQTRGLLGCIITSLTGRDKNQVEGEVQVVSTATQSFLATCVNGVCWTVYHGAGSKTLAGPKGPITQMYTN
VDQDLVGWQAPPGARSLTPCTCGSSDLYLVTRHADVIPVRRRGDSRGSLLSPRPVSYLKGSSGGPLLCPSGHAVGIFR
AAVCTRGVAKAVDFVPVESMETTMRSPVFTDNSSPPAVPQSFQVAHLHAPTGSGKSTKVPAAYAAQGYKVLVLNPSVA
ATLGFGAYMSKAHGIDPNIRTGVRTITTGAPVTYSTYGKFLADGGCSGGAYDIIICDECHSTDSTTILGIGTVLDQAE
TAGARLVVLATATPPGSVTVPHPNIEEVALSNTGEIPFYGKAIPIEAIRGGRHLIFCHSKKKCDELAAKLSGLGINAV
AYYRGLDVSVIPTIGDVVVVATDALMTGYTGDFDSVIDCNTCVTQTVDFSLDPTFTIETTTVPQDAVSRSQRRGRTGR
GRRGIYRFVTPGERPSGMFDSSVLCECYDAGCAWYELTPAETSVRLRAYLNTPGLPVCQDHLEFWESVFTGLTHIDAH
FLSQTKQAGDNFPYLVAYQATVCARAQAPPPSWDQMWKCLIRLKPTLHGPTPLLYRLGAVQNEVTLTHPITKYIMACM
SADLEVVTSTWVLVGGVLAALAAYCLTTGSVVIVGRIILSGRPAIVPDREFLYQEFDEMEECASHLPYIEQGMQLAEQ
FKQKALGLLQTATKQAEAAAPVVESKWRALETFWAKHMWNFISGIQYLAGLSTLPGNPAIASLMAFTASITSPLTTQS
TLLFNILGGWVAAQLAPPSAASAFVGAGIAGAAVGSIGLGKVLVDILAGYGAGVAGALVAFKVMSGEMPSTEDLVNLL
PAILSPGALVVGVVCAAILRRHVGPGEGAVQWMNRLIAFASRGNHVSPTHYVPESDAAARVTQILSSLTITQLLKRLH
QWINEDCSTPCSGSWLRDVWDWICTVLTDFKTWLQSKLLPQLPGVPFFSCQRGYKGVWRGDGIMQTTCPCGAQITGHV
KNGSMRIVGPKTCSNTWHGTFPINAYTTGPCTPSPAPNYSRALWRVAAEEYVEVTRVGDFHYVTGMTTDNVKCPCQVP
APEFFTEVDGVRLHRYAPACRPLLREEVTFQVGLNQYLVGSQLPCEPEPDVAVLTSMLTDPSHITAETAKRRLARGSP
PSLASSSASQLSAPSLKATCTTHHVSPDADLIEANLLWRQEMGGNITRVESENKVVVLDSFDPLRAEEDEREVSVPAE
ILRKSKKFPAAMPIWARPDYNPPLLESWKDPDYVPPVVHGCPLPPIKAPPIPPPRRKRTVVLTESSVSSALAELATKT
FGSSESSAVDSGTATALPDQASDDGDKGSDVESYSSMPPLEGEPGDPDLSDGSWSTVSEEASEDVVCCSMSYTWTGAL
ITPCAAEESKLPINALSNSLLRHHNMVYATTSRSAGLRQKKVTFDRLQVLDDHYRDVLKEMKAKASTVKAKLLSVEEA
CKLTPPHSAKSKFGYGAKDVRNLSSKAVNHIHSVWKDLLEDTVTPIDTTIMAKNEVFCVQPEKGGRKPARLIVFPDLG
VRVCEKMALYDVVSTLPQVVMGSSYGFQYSPGQRVEFLVNTWKSKKNPMGFSYDTRCFDSTVTENDIRVEESIYQCCD
LAPEARQAIKSLTERLYIGGPLTNSKGQNCGYRRCRASGVLTTSCGNTLTCYLKASAACRAAKLQDCTMLVNAAGLVV
ICESAGTQEDAASLRVFTEAMTRYSAPPGDPPQPEYDLELITSCSSNVSVAHDASGKRVYYLTRDPTTPLARAAWETA
RHTPVNSWLGNIIMYAPTLWARMILMTHFFSILLAQEQLEKALDCQIYGACYSIEPLDLPQIIERLHGLSAFSLHSYS
PGEINRVASCLRKLGVPPLRVWRHRARSVRARLLSQGGRAATCGKYLFNWAVKTKLKLTPIPAASQLDLSGWFVAGYS
GGDIYHSLSRARPRWFMLCLLLLSVGVGIYLLPNR
```

Fig. 3

```
MKRTKTSDESFNPVYPYDTESGPPSVPFLTPPFVSPDGFQESPPGVLSLNLAEPLVTSHGMLALKMGSGLSLDDAGNL
TSQDITTASPPLKKTKTNLSLETSSPLTVSTSGALTVAAAAPLAVAGTSLTMQSEAPLTVQDAKLTLATKGPLTVSEG
KLALQTSAPLTAADSSTLTVSATPPINVSSGSLGLDMEDPMYTHDGKLGIRIGGPLRVVDSLHTLTVVTGNGLTVDNN
ALQTRVTGALGYDTSGNLQLRAAGGMRIDANGQLILNVAYPFDAQNNLSLRLGQGPLYINTDHNLDLNCNRGLTTTTT
NNTKKLETKISSGLDYDTNGAVIIKLGTGLSFDNTGALTVGNTGDDKLTLWTTPDPSPNCRIHSDKDCKFTLVLTKCG
SQILASVAALAVSGNLASITGTVASVTIFLRFDQNGVLMENSSLDRQYWNFRNGNSTNAAPYTNAVGFMPNLAAYPKT
QSQTAKNNIVSQVYLNGDKSKPMTLTITLNGTNESSETSQVSHYSMSFTWAWESGQYATETFATNSFTFSYIAEQ
```

Fig. 4A

```
MATPSMMPQWSYMHISGQDASEYLSPGLVQFARATESYFSLSNKFRNPTVAPTHDVTTDRSQRLTLRFIPVDREDTAY
SYKARFTLAVGDNRVLDMASTYFDIRGVLDRGPTFKPYSGTAYNSLAPKGAPNSCEWEQEETQAVEEAAEEEEDADG
QAEEEQAATKKTHVYAQAPLSGEKISKDGLQIGTDATATEQKPIYADPTFQPEPQIGESQWNEADATVAGGRVLKKST
PMKPCYGSYARPTNANGGQGVLTANAQGQLESQVEMQFFSTSENARNEANNIQPKLVLYSEDVHMETPDTHLSYKPAK
SDDNSKIMLGQQSMPNRPNYIGFRDNFIGLMYYNSTGNMGVLAGQASQLNAVVDLQDRNTELSYQLLLDSMGDRTRYF
SMWNQAVDSYDPDVRIIENHGTEDELPNYCFPLGGIGVTDTYQAVKTNNGNNGGQVTWTKDETFADRNEIGVGNNFAM
EINLSANLWRNFLYSNVALYLPDKLKYNPSNVDISDNPNTYDYMNKRVVAPGLVDCYINLGARWSLDYMDNVNPFNHH
RNAGLRYRSMLLGNGRYVPFHIQVPQKFFAIKNLLLLPGSYTYEWNFRKDVNMVLQSSLGNDLRVDGASIKFESICLY
ATFFPMAHNTASTLEAMLRNDTNDQSFNDYLSAANMLYPIPANATNVPISIPSRNWAAFRGWAFTRLKTKETPSLGSG
FDPYYTYSGSIPYLDGTFYLNHTFKKVSVTFDSSVSWPGNDRLLTPNEFEIKRSVDGEGYNVAQCNMTKDWFLVQMLA
NYNIGYQGFYIPESYKDRMYSFFRNFQPMSRQVVDQTKYKDYQEVGIIHQHNNSGFVGYLAPTMREGQAYPANFPYPL
IGKTAVDSITQKKFLCDRTLWRIPFSSNFMSMGALSDLGQNLLYANSAHALDMTFEVDPMDEPTLLYVLFEVFDVVRV
HQPHRGVIETVYLRTPFSAGNATT
```
Fig. 4B

MRRAAMYQEGPPPSYESVVGAAAAAPSSPFASQLLEPPYVPPRYLRPTGGRNSIRYSELAPLFDTTRVYLVDNKSADV
ASLNYQNDHSNFLTTVIQNNDYSPSEASTQTINLDDRSHWGGDLKTILHTNMPNVNEFMFTNKFKARVMVSRSHTKED
RVELKYEWVEFELPEGNYSETMTIDLMNNAIVEHYLKVGRQNGVLESDIGVKFDTRNFRLGLDPVTGLVMPGVYTNEA
FHPDIILLPGCGVDFTYSRLSNLLGIRKRQPFQEGFRITYEDLEGGNIPALLDVEAYQDSLKENEAGQEDTTPAASAA
AEQGEDAADTAAADGAEADPAMVVEAPEQEEDMNDSAVRGDTFVTRGEEKQAEAEAAAEEKQLAAAAAAAALAAAEAE
SEGTKPAKEPVIKPLTEDSKKRSYNLLKDSTNTAYRSWYLAYNYGDPSTGVRSWTLLCTPDVTCGSEQVYWSLPDMMQ
DPVTFRSTRQVSNFPVVGAELLPVHSKSFYNDQAVYSQLIRQFTSLTHVFNRFPENQILARPPAPTITTVSENVPALT
DHGTLPLRNSIGGVQRVTVTDARRRTCPYVYKALGIVSPRVLSSRTF

Fig. 4C

MSKKRVRVDDDFDPVYPYDADNAPTVPFINPPFVSSDGFQEKPLGVLSLRLADPVTTKNGEITLKLGEGVDLDSSGKL
ISNTATKAAAPLSFSNNTISLNMDHPFYTKDGKLSLQVSPPLNILRTSILNTLALGFGSGLGLRGSALAVQLVSPLTF
DTDGNIKLTLDRGLHVTTGDAIESNISWAKGLKFEDGAIATNIGNGLEFGSSSTETGVDDAYPIQVKLGSGLSFDSTG
AIMAGNKEDDKLTLWTTPDPSPNCQILAENDAKLTLCLTKCGSQILATVSVLVVGSGNLNPITGTVSSAQVFLRFDAN
GVLLTEHSTLKKYWGYRQGDSIDGTPYTNAVGFMPNLKAYPKSQSSTTKNNIVGQVYMNGDVSKPMLLTITLNGTDDS
NSTYSMSFSYTWTNGSYVGATFGANSYTFSYIAQE

Fig. 4D

MATPSMLPQWAYMHIAGQDASEYLSPGLVQFARATDTYFSLGNKFRNPTVAPTHDVTTDRSQRLTLRFVPVDREDNTY
SYKVRYTLAVGDNRVLDMASTYFDIRGVLDRGPSFKPYSGTAYNSLAPKGAPNTSQWKDSDSKMHTFGVAAMPGVVGK
KIEADGLPIGIDSSSGTDTIIYADKTFQPEPQVGSDSWVDTNGAEEKYGGRALKDTTNMKPCYGSFARPTNKEGGQAN
IKDSETASTTPNYDIDLAFFDSKNIAANYDPDIVMYTENVELQTPDTHIVFKPGTSDESSEANLGQQAMPNRPNYIGF
RDNFIGLMYYNSTGNMGVLAGQASQLNAVVDLQDRNTELSYQLLLDSLGDRTRYFSMWNQAVDSYDPDVRIIENHGVE
DELPNYCFPLNGVGFTDTYQGVKVKTDTAATGTNGTQWDKDDTTVSTANEIHSGNPFAMEINIQANLWRNFLYANVAL
YLPDSYKYTPANITLPTNTNTYDYMNGRVVAPSLVDAYINIGARWSLDPMDNVNPFNHHRNAGLRYRSMLLGNGRYVP
FHIQVPQKFFAIKSLLLLPGSYTYEWNFRKDVNMILQSSLGNDLRTDGASIAFTSINLYATFFPMAHNTASTLEAMLR
NDTNDQSFNDYLSAANMLYPIPANATNVPISIPSRNWAAFRGWSFTRLKTRETPSLGSGFDPYFVYSGSIPYLDGTFY
LNHTFKKVSITFDSSVSWPGNDRLLTPNEFEIKRTVDGEGYNVAQCNMTKDWFLVQMLAHYNIGYQGFYVPEGYKDRM
YSFFRNFQPMSRQVVDEVNYKDYQAVTLAYQHNNSGFVGYLAPTMRQGQPYPANYPYPLIGKSAVASVTQKKFLCDRV
MWRIPFSSNFMSMGALTDLGQNMLYANSAHALDMNFEVDPMDESTLLYVVFEVFDVVRVHQPHRGVIEAVYLRTPFSA
GNATT

Fig. 4E

```
ATGTCAGATTCTTGCTCCTGTCCCTCCGCACCCACTATCTTCATGTTGTTGCAGATGAAGCGCACCAAAACGTCTGAC
GAGAGCTTCAACCCCGTGTACCCCTATGACACGGAAAGCGGCCTCTCCCTCCGTCCCTTTCCTCACCCCTCCCTTCGTG
TCTCCCGATGGATTCCAAGAAAGCCCCCCGGGGTCCTGTCTCTGAACCTGGCCGAGCCCCTGGTCACTTCCCACGGC
ATGCTCGCCCTGAAAATGGGAAGTGGCCTCTCCCTGGACGACGCTGGCAACCTCACCTCTCAAGATATCACCACCGCT
AGCCCTCCCCTCAAAAAAACCAAGACCAACCTCAGCCTAGAAACCTCATCCCCCCTAACTGTAAGCACCTCAGGCGCC
CTCACCGTAGCAGCCGCCGCTCCCCTGGCCATGGCCGGCCACCTCCCTCACCATGCAATCAGAGGCCCCCCCTGACAGTA
CAGGATGCAAAACTCACCCTGGCCACCAAAGGCCCCCTGACCGTGTCTGAAGGCAAACTGGCCTTGCAAACATCGGCC
CCGCTGACGGCCGCTGACAGCAGCACCCTCACCGTTAGCGCCACACCACCAATTAATGTAAGCAGTGGAAGTTTAGGC
TTAGACATGGAAGACCCTATGTATACTCACGATGGAAAACTGGGAATAAGAATTGGGGGTCCACTAAGAGTAGTAGAC
AGCTTGCACACACTCACTGTAGTTACCGGAAATGACTAACTGTAGATAACAATGCCCTCCAAACTAGAGTTACGGGC
GCCCTAGGTTATGACACATCAGGAAATCTACAATTGAGAGCTGCAGGAGGTATGCGAATTGATGCAAATGGCCAACTT
ATCCTTAATGTGGCATACCCATTTGATGCTCAGAACAATCTCAGCCTTAGACTTGGTCAGGGACCCCTGTATATAAAC
ACAGACCACAACCTGGATTTGAATTGCAACAGAGGTCTAACCACAACTACCACCAACAACACAAAAAAACTTGAGACT
AAAATTAGCTCAGGCTTAGACTATGACACACCAATGGTGCTGTCATTATTAAACTTGGCACTGGTCTAAGCTTCGACAAC
ACAGGCGCCCTAACTGTGGGAAACACTGGTGATGATAAACTGACTCTGTGACGACCCCAGACCCATCTCCAAATTGC
AGAATTCACTCAGACAAAGACTGCAAGTTTACTCTAGTCCTAACTAAGTGTGGAAGCCAAATCCTGGCCTCTGTCGCC
GCCCTAGCGGTATCAGGAAATCTGGCTTCGATAACAGGCACCGTTGCCAGCGTTACCATCTTTCTCAGATTTGATCAG
AATGGAGTGCTTATGGAAAACTCCTCGCTAGACAGGCAGTACTGGAACTTCAGAAATGGCAACTCAACTAACGCTGCC
CCCTACACCAATGCAGTTGGGTTCATGCCAAACCTCGCAGCATACCCCAAAACGCAAAGCCAGACTGCTAAAAACAAC
ATTGTAAGTCAGGTTTACTTGAATGGAGACAAATCCAAACCCATGACCCTTACCATCACCCTCAATGGAACTAATGAA
TCCAGTGAAACTAGCCAGGTGAGTCACTACTCCATGCATTTACATGGGCTTGGGAAAGTGGGCAATATGCCACTGAA
ACCTTTGCCACCAACTCCTTCACCTTTTCTTACATTGCTGAACAA
```

Fig. 4F

```
ATGGCGACCCCATCGATGATGCCGCAGTGGTCGTACATGCACATCTCGGGCCAGGACGCCTCGGAGTACCTGAGCCCC
GGGCTGGTGCAGTTCGCCCGCGCCACCGAGAGCTACTTCAGCCTGAGTAACAAGTTTAGGAACCCCACGGTGGCGCCC
ACGCACGATGTGACCACCGACCGGTCTCAGCGCCTGACGCTGCGGTTCATTCCCGTGGACCGCGAGGACACCGCGTAC
TCGTACAAGGCGCGGTTCACCCTGGCCGTGGGCGACAACCGCGTGCTGGACATGGCCTCCACCTACTTTGACATCCGC
GGGGTGCTGGACCGGGGTCCCACTTTCAAGCCCTACTCTGGCACCGCCTACAACTCCCTGGCCCCCAAGGGCGCTCCC
AACTCCTGCGAGTGGGAGCAAGAGGAAACTCAGGCAGTTGAAGAAGCAGCAGAAGAGGAAGAAGAAGATGCTGACGGT
CAAGCTGAGGAAGAGCAAGCAGCTACCAAAAAGACTCATGTATATGCTCAGGCTCCCCTTTCTGGCGAAAAAATTAGT
AAAGATGGTCTGCAAATAGGAACGGACGCTACAGCTACAGAACAAAAACCTATTTATGCAGACCCTACATTCCAGCCC
GAACCCCAAATCGGGGAGTCCCAGTGGAATGAGGCAGATGCTACAGTCGCCGGCGGTAGAGTGCTAAAGAAATCTACT
CCCATGAAACCATGCTATGGTTCCTATGCAAGACCCACAAATGCTAATGGAGGTCAGGGTGTACTAACGGCAAATGCC
CAGGGACAGCTAGAATCTCAGGTTGAAATGCAATTCTTTTCAACTTCTGAAAACGCCCGTAACGAGGCTAACAACATT
CAGCCCAAATTGGTGCTGTATAGTGAGGATGTGCACATGGAGACCCCGGATACGCACCTTTCTTACAAGCCCGCAAAA
AGCGATGACAATTCAAAAATCATGCTGGGTCAGCAGTCCATGCCCAACAGACCTAATTACATCGGCTTCAGAGACAAC
TTTATCGGCCTCATGTATTACAATAGCACTGGCAACATGGGAGTGCTTGCAGGTCAGGCCTCTCAGTTGAATGCAGTG
GTGGACTTGCAAGACAGAAACACAGAACTGTCCTACCAGCTCTTGCTTGATTCCATGGGTGACAGAACCAGATACTTT
TCCATGTGGAATCAGGCAGTGGACAGTTATGACCCAGATGTTAGAATTATTGAAAATCATGGAACTGAAGACGAGCTC
CCCAACTATTGTTTCCCTCTGGGTGCATAGGGGTAACTGACACTTACCAGGCTGTTAAAACCAACAATGGCAATAAC
GGGGGCCAGGTGACTTGGACAAAAGATGAAACTTTTGCAGATCGCAATGAAATAGGGGTGGGAAACAATTTCGCTATG
GAGATCAACCTCAGTGCCAACCTGTGGAGAAACTTCCTGTACTCCAACGTGGCGCTGTACCTACCAGACAAGCTTAAG
TACAACCCCTCCAATGTGGACATCTCTGACAACCCCAACACCTACGATTACATGAACAAGCGAGTGGTGGCCCCGGGG
CTGGTGGACTGCTACATCAACCTGGGCGCGCGCTGGTCGCTGGACTACATGGACAACGTCAACCCCTTCAACCACCAC
CGCAATGCGGGCCTGCGCTACCGCTCCATGCTCCTGGGCAACGGGCGCTACGTGCCCTTCCACATCCAGGTGCCCCAG
AAGTTCTTTGCCATCAAGAACCTCCTCCTCCTGCCGGGCTCCTACACCTACGAGTGGAACTTCAGGAAGGATGTCAAC
ATGGTCCTCCAGAGCTCTCTGGGTAACGATCTCAGGGTGGACGGGGCCAGCATCAAGTTCGAGAGCATCTGCCTCTAC
GCCACCTTCTTCCCCATGGCCCACAACACGGCCTCCACGCTCGAGGCCATGCTCAGGAACGACACCAACGACCAGTCC
TTCAATGACTACCTTTCCGCCGCCAACATGCTCTACCCCATACCCGCCAACGCCACCAACGTCCCCATCTCCATCCCC
TCGCGCAACTGGGCGGCCTTCCGCGGCTGGGCCTTCACCCGCCTCAAGACCAAGGAGACCCCCTCCCTGGGCTCGGGA
TTCGACCCCTACTACACCTACTCGGGCTCTATTCCCTACCTGGCAGGCACCTTCTACCTCAACCACACTTTCAAGAAG
GTCTCGGTCACCTTCGACTCCTCGGTCAGCTGGCCGGGCAACGACCGTCTGCTCACCCCCAACGAGTTCGAGATCAAG
CGCTCGGTCGACGGGGAAGGCTACAACGTGGCCAGTGCAACATGACCAAGGACTGGTTCCTGGTCCAGATGCTGGCC
AACTACAACATCGGCTACCAGGGCTTCTACATCCCAGAGAGCTACAAGGACAGGATGTACTCCTTCTTCAGGAACTTC
CAGCCCATGAGCCGGCAGGTGGTGGACCAGACCAAGTACCAGGAGGTGGGCATCATCCACCAGCACAAC
AACTCGGGCTTCGTGGGCTACCTCGCCCCCACCATGCGCGAGGGACAGGCCTACCCCGCCAACTTCCCCTACCCGCTC
ATAGGCAAGACCGCGGTCGACAGCATCACCCAGAAAAAGTTCCTCTGCGACCGCACCCTCTGGCGCATCCCCTTCTCC
AGCAACTTCATGTCCATGGGTGCGCTCTCGGACCTGGGCCAGAACTTGCTCTACGCCAACTCCGCCCACGCCCTCGAC
ATGACCTTCGAGGTCGACCCCATGGACGAGCCCACCCTTCTCTATGTTCTGTTCGAAGTCTTTGACGTGGTCCGGGTC
CACCAGCCGCACCGCGGCGTCATCGAGACCGTGTACGCCCTTCTCGGCCGGCAACGCCACCACC
```
Fig. 4G

```
ATGCGGCGCGCGGCGATGTACCAGGAGGGGACCTCCTCCCTCTTACGAGAGCGTGGTGGGCGCGGCGGCGGCGGCGCCC
TCTTCTCCCTTTGCGTCGCAGCTGCTGGAGCCGCCGTACGTGCCTCCGCGCTACCTGCGGCCTACGGGGGGGAGAAAC
AGCATCCGTTACTCGGAGCTGGCGCCCCTGTTCGACACCACCCGGGTGTACCTGGTGGACAACAAGTCGGCGGACGTG
GCCTCCCTGAACTACCAGAACGACCACAGCAATTTTTTGACCACGGTCATCCAGAACAATGACTACAGCCCGAGCGAG
GCCAGCACCCAGACCATCAATCTGGATGACCGGTCGCACTGGGGCGGCGACCTGAAAACCATCCTGCACACCAACATG
CCCAACGTGAACGAGTTCATGTTCACCAATAAGTTCAAGGCGCGGGTGATGGTGTCGCGCTCGCACCAAGGAAGAC
CGGGTGGAGCTGAAGTACGAGTGGGTGGAGTTCGAGCTGCCAGAGGGCAACTACTCCGAGACCATGACCATTGACCTG
ATGAACAACGCGATCGTGGAGCACTATCTGAAAGTGGGCAGGCAAAACGGGGTCCTGGAGAGCGACATCGGGGTCAAG
TTCGACACCAGGAACTTCCGCCTGGGGCTGGACCCCGTGACCGGGCTGGTTATGCCCGGGGTGTACACCAACGAGGCC
TTCCATCCCGACATCATCCTGCTGCCCCGGCTGCGGGGTGGACTTCACTTACAGCCGCCTGAGCAACCTCCTGGGCATC
CGCAAGCGGCAGCCCTTCCAGGAGGGCTTCAGGATCACCTACGAGGACCTGGAGGGGGCAACATCCCCGCGCTCCTC
GATGTGGAGGCCTACCAGGATAGCTTGAAGGAAATGAGGCGGGACAGGAGGATACCACCCCCGCCGCCTCCGCCGCC
GCCGAGCAGGGCGAGGATGCTGCTGACACCGCGGCCGCGGACGGGGCAGAGGCCGACCCCGCTATGGTGGTGGAGGCT
CCCGAGCAGGAGGAGGATATGAATGACAGTGCGGTGCGGCGGAGACACCTTCGTCACCCGGGGGAGGAAAAGCAAGCG
GAGGCCGAGGCGCGCGGCCGAGGAAAAGCAACTGGCGGCAGCAGCGGCGGCGGCGTTGGCCGCGGCGGAGGCTGAG
TCTGAGGGGACCAAGCCCGCCAAGGAGCCCGTGATTAAGCCCCTGACCGAAGATAGCAAGAAGCGCAGTTACAACCTG
CTCAAGGACAGCACCAACACCGCGTACCGCAGCTGGTACCTGGCCTACAACTACGGCGACCCGTCGACGGGGGTGCGC
TCCTGACCCTGCTGTGCACGCCGGACGTGACCTGCGGCTCGGACGTGACCAGGTGTACTGGTCGCTGCCCGACATGATGCAA
GACCCCGTGACCTTCCGCTCCACGCGGCAGGTCAGCAACTTCCCGGTGGTGGGCGCCGAGCTGCTGCCCGTGCACTCC
AAGAGCTTCTACAACGACCAGGCCGTCTACTCCCAGCTCATCCGCCAGTTCACCTCTCTGACCCACGTGTTCAATCGC
TTTCCTGAGAACCAGATTCTGGCGCGCCCGCCCGCCCCCACCATCACCACCGTCAGTGAAAACGTTCCTGCTCTCACA
GATCACGGGACGCTACCGCTGCGCAACAGCATCGGAGGAGTCCAGCGAGTGACCGTTACTGACGCCAGACGCCGCACC
TGCCCCTACGTTTACAAGGCCTTGGGCATAGTCTCGCCGCGCGTCCTTTCCAGCCGCACTTTT
```
Fig. 4H

```
ATGTCCAAAAAGCGCGTCCGGGTGGATGATGACTTCGACCCCGTCTACCCCTACGATGCAGACAACGCACCGACCGTG
CCCTTCATCAACCCCCCCTTCGTCTCTTCAGATGGATTCCAAGAGAAGCCCCTGGGGGTGCTGTCCCTGCGACTGGCC
GACCCCGTCACCACCAAGAACGGGGAAATCACCCTCAAGCTGGGAGAGGGGTGGACCTCGACTCCTCGGGAAAACTC
ATCTCCAACACGGCCACCAAGGCCGCCGCCCCTCTCAGTTTTTCCAACAACACCATTTCCCTTAACATGGATCACCCC
TTTTACACTAAAGATGGAAAATTATCCTTACAAGTTTCTCCACCATTAAATATACTGAGAACAAGCATTCTAAACACA
CTAGCTTTAGGTTTTGGATCAGGTTTAGGACTCCGTGGCTCTGCCTTGGCAGTACAGTTAGTCTCTCCACTTACATTT
GATACTGATGGAAACATAAAGCTTACCTTAGACAGAGGTTTGCATGTTACAACAGGAGATGCAATTGAAAGCAACATA
AGCTGGGCTAAAGGTTTAAAATTTGAAGATGGAGCCATAGCAACCAACATTGGAAATGGGTTAGAGTTTGGAAGCAGT
AGTACAGAAACAGGTGTTGATGATGCTTACCCAATCCAAGTTAAACTTGGATCTGGCCTTAGCTTTGACAGTACAGGA
GCCATAATGGCTGGTAACAAAGAAGACGATAAACTCACTTTGTGGACAACACCTGATCCATCGCCAAACTGTCAAATA
CTCGCAGAAAATGATGCAAAACTAACACTTTGCTTGACTAAATGTGGTAGTCAAATACTGGCCACTGTGTCAGTCTTA
GTTGTAGGAAGTGGAAACCTAAACCCCATTACTGGCACCGTAAGCAGTGCTCAGGTGTTTCTACGTTTTGATGCAAAC
GGTGTTCTTTTAACAGAACATTCTACACTAAAAAAATACTGGGGGTATAGGCAGGGAGATAGCATAGATGGCACTCCA
TATACCAATGCTGTAGGATTCATGCCCAATTTAAAAGCTTATCCAAAGTCACAAAGTTCTACTACTAAAAATAATATA
GTAGGGCAAGTATACATGAATGGAGATGTTTCAAAACCTATGCTTCTCACTATAACCCTCAATGGTACTGATGACAGC
AACAGTACATATTCAATGTCATTTTCATACACCTGGACTAATGGAAGCTATGTTGGAGCAACATTTGGGCTAACTCT
TATACCTTCTCATACATCGCCCAAGAATGA
```

Fig. 4I

```
ATGTATGTCCGCCGACCAGAAGGAGGAAGAGGCGCGTCGCCGAGTTGCAAGATGGCCACCCCATCGATGCTGCCCCAG
TGGGCGTACATGCACATCGCCGGACAGGACGCTTCGGAGTACCTGAGTCCGGGTCTGGTGCAGTTCGCCCGCGCCACA
GACACCTACTTCAGTCTGGGGAACAAGTTTAGGAACCCCACGGTGGCGCCCACGCACGATGTGACCACCGACCGCAGC
CAGCGGCTGACGCTGCGCTTCGTGCCCGTGGACCGCGAGGACAACACCTACTCGTACAAAGTGCGCTACACGCTGGCC
GTGGGCGACAACCGCGTGCTGGACATGGCCAGCACCTACTTTGACATCCGCGGCGTGCTGGATCGGGGCCCCAGCTTC
AAACCCTACTCCGGCACCGCCTACAACAGCCTAGCTCCCAAGGGAGCGCCCAACACCTCACAGTGGAAGGATTCCGAC
AGCAAAATGCATACTTTTGGAGTTGCTGCCATGCCCGGTGTTGTTGGTAAAAAAATAGAAGCCGATGGTCTGCCTATT
GGAATAGATTCATCCTCTGGAACTGACACCATAATTTATGCTGATAAAACTTTCCAACCAGAGCCACAGGTTGGAAGT
GACAGTTGGGTCGACACCAATGGTGCAGAGGAAAAATATGGAGGTAGAGCTCTTAAGGACACTACAAACATGAAGCCC
TGCTACGGTTCTTTTGCCAGGCCTACCAACAAAGAAGGTGGACAGGCTAACATAAAAGATTCTGAAACTGCCAGCACT
ACTCCTAACTATGATATAGATTTGGCATTCTTTGACAGCAAAAATATTGCAGCTAACTACGATCCAGATATTGTAATG
TACACAGAAAATGTTGAGTTGCAAACTCCAGATACTCATATTGTGTTTAAGCCAGGAACTTCAGATGAAAGTTCAGAA
GCCAATTTGGGCCAGCAGGCCATGCCCAACAGACCCAACTACATCGGGTTCAGAGACAACTTTATCGGGCTCATGTAC
TACAACAGCACTGGCAATATGGGTGTACTGGCTGGTCAGGCCTCCCAGCTAAATGCTGTGGTGGACTTGCAGGACAGA
AACACCGAACTGTCCTACCAGCTCTTGCTTGACTCTCTGGGTGACAGAACCAGGTATTTCAGTATGTGGAATCAGGCG
GTGGACAGCTATGACCCCGATGTGCGCATTATTGAAAATCACGGTGTGGAGGATGAACTCCCCAATTATTGCTTCCCT
TTGAATGGTGTAGGCTTTACAGATACTTACCAGGGTGTTAAAGTTAAGACAGATACAGCCGCTACTGGTACCAATGGA
ACGCAGTGGGACAAAGATGATACCACAGTCAGCACTGCCAATGAGATCCACTCAGGCAATCCTTTCGCCATGGAGATC
AACATCCAGGCCAACCTGTGGCGGAACTTCCTCTACGCGAACGTGGCGCTGTACCTGCCCGACTCCTACAAGTACACG
CCGGCCAACATCACGCTGCCGACCAACACCAACACCTACGATTACATGAACGGCCGCGTGGTGGCGCCCTCGCTGGTG
GACGCCTACATCAACATCGGGGCGCGTGGTCGCTGGACCCCATGGACAACGTCAACCCCTTCAACCACCACCGCAAC
GCGGGCCTGCGCTGCCTCCATGCTCCTGGGCAACGGGCGCTACGTGCCCTTCCACATCCAGGTGCCCCAAAAGTTT
TTCGCCATCAAGAGCCTCCTGCTCCTGCCCGGGTCCTACACCTACGAGTGGAACTTCCGCAAGGACGTCAACATGATC
CTGCAGAGCTCCCTCGGCAACGACCTGCCACGGACGGGGCCTCCATCGCCTTCACCAGCATCAACCTCTACGCCACC
TTCTTCCCCATGGCGCACAACACCGCCTCCACGCTCGAGGCCATGCTGCGCAACGACACCAACGACCAGTCCTTCAAC
GACTACCTCTCGGCGGCCAACATGCTCTACCCCATCCCGGCCAACGCCACCAACGTGCCCATCTCCATCCCCTCGCGC
AACTGGGCCGCCTTCCGCGGATGGTCCTTCACGCGCCTCAAGACCCGCGAGACGCCCTCGCTCGGCTCCGGGTTCGAC
CCCTACTTCGTCTACTCGGGCTCCATCCCCTACCTCGACGGCACCTTCTACCTCAACCACACCTTCAAGAAGGTCTCC
ATCACCTTCGACTCCTCCGTCAGCTGGCCCGGCAACGACCGCCTCCTGACGCCCAACGAGTTCGAAATCAAGCGCACC
GTCGACGGAGAGGGATACAACGTGGCCCAGTGCAACATGACCAAGGACTGGTTCCTGGTCCAGATGCTGGCCCACTAC
AACATCGGCTACCAGGGCTTCTACGTGCCCGAGGGCTACAAGGACCGCATGTACTCCTTCTTCCGCAACTTCCAGCCC
ATGAGCCGCCAGGTCGTGGACGAGGTCAACTACAAGGACTACCAGGCCGTCACCCTGGCCTACCAGCACAACAACTCG
GGCTTCGTCGGCTACCTCGCGCCCACCATGCGCCAGGGCCAGCCCTACCCCGCCAACTACCCCTACCCCGCTCATCGGC
AAGAGCGCCGTCGCCAGCGTCACCCAGAAAAAGTTCCTCTGCGACCGGTCATGTGGCGCATCCCCTTCTCCAGCAAC
TTCATGTCCATGGGCGCGCTCACCGACCTCGGCCAGAACATGCTCTACGCCAACTCCGCCCACGCGCTAGACATGAAT
TTCGAAGTCGACCCCATGGATGAGTCCACCCTTCTCTATGTTGTCTTCGAAGTCTTCGACGTCGTCCGAGTGCACCAG
CCCCACCGCGGCGTCATCGAGGCCGTCTACCTGCGCACGCCCTTCTCGGCCGGCAACGCCACCACCTAA
```

Fig. 4J

```
CATCATCAATAATATACCTTATTTTGGATTGAAGCCAATATGATAATGAGATGGGCGGCGCGAGGCGGGGCGCGGGGC
GGGAGGCGGGTTTGGGGGCGGGCCGGCGGGCGGGGCGGTGTGGCGGAAGTGGACTTTGTAAGTGTGGCGGATGTGACT
TGCTAGTGCCGGGCGCGGTAAAAGTGACGTTTTCCGTGCGCGACAACGCCCCCGGGAAGTGACATTTTTCCCGCGGTT
TTTACCGGATGTTGTAGTGAATTTGGGCGTAACCAAGTAAGATTTGGCCATTTTCGCGGGAAAACTGAAACGGGGAAG
TGAAATCTGATTAATTTTGCGTTAGTCATACCGCGTAATATTTGTCTAGGGCCGAGGGACTTTGGCCGATTACGTGGA
GGACTCGCCCAGGTGTTTTTTGAGGTGAATTTCCGCGTTCCGGGTCAAAGTCTCCGTTTTATTATTATAGGATATCCC
ATTGCATACGTTGTATCCATATCATAATATGTACATTTATATTGGCTCATGTCCAACATTACCGCCATGTTGACATTG
ATTATTGACTAGTTATTAATAGTAATCAATTACGGGGTCATTAGTTCATAGCCCATATATGGAGTTCCGCGTTACATA
ACTTACGGTAAATGGCCCGCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGCCCACTTGGCAGTACATCA
AGTGTATCATATGCCAAGTACGCCCCCTATTGACGTCAATGACGGTAAATGGCCCGCCTGGCATTATGCCCAGTACAT
GACCTTATGGGACTTTCCTACTTGGCAGTACATCTACGTATTAGTCATCGCTATTACCATGGTGATGCGGTTTTGGCA
GTACATCAATGGGCGTGGATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCATTGACGCAAATGGGCGGTAGGCG
TGTACGGTGGGAGGTCTATATAAGCAGAGCTCGTTTAGTGAACCGTCAGATCGCCTGGAGACGCCATCCACGCTGTTT
TGACCTCCATAGAAGACACCGGGACCGATCCAGCCTCCGCGGCCGGGAACGGTGCATTGGAACGCGGATTCCCCGTGC
CAAGAGTGAGATCTGCCACCATGGCGCCCATCACGGCCTACTCCCAACAGACGCGGGGCCTACTTGGTTGCATCATCA
CTAGCCTTACAGGCCGGGACAAGAACCAGGTCGAGGGAGAGGTTCAGGTGGTTTCCACCGCAACACAATCCTTCCTGG
CGACCTGCGTCAACGGCGTGTGTTGGACCGTTTACCATGGTGCTGGCTCAAAGACCTTAGCCGGCCCAAAGGGGCCAA
TCACCCAGATGTACACTAATGTGGACCAGGACCTCGTCGGCTGGCAGGCGCCCCCCGGGGCGCGTTCCTTGACACCAT
GCACCTGTGGCAGCTCAGACCTTTACTTGGTCACGAGACATGCTGACGTCATTCCGGTGCGCCGGCGGGCGACAGTA
GGGGGAGCCTGCTCTCCCCCAGGCCTGTCTCTCCTACTTGAAGGGCTCTTCGGGTGGTCCACTGCTCTGCCCTTCGGGGC
ACGCTGTGGGCATCTTCCGGGCTGCCGTATGCACCCGGGGGGTTGCGAAGGCGGTGGACTTTGTGCCCGTAGAGTCCA
TGGAAACTACTATGCGGTCTCCGGTCTTCACGGACAACTCATCCCCCCGGCCGTACCGCAGTCATTTCAAGTGGCCC
ACCTACACGCTCCCACTGGCAGCGGCAAGAGTACTAAAGTGCCGGCTGCATATGCAGCCCAAGGGTACAAGGTGCTCG
TCCTCAATCCGTCCGTTGCCGCTACCTTAGGGTTTGGGGCGTATATGTCTAAGGCACACGGTATTGACCCCAACATCA
GAACTGGGGTAAGGACCATTACCACAGGCGCCCCCGTCACATACTCTACCTATGCAAGTTTCTTGCCGATGGTGGTT
GCTCTGGGGGCGCTTATGACATCATAATATGTGATGAGTGCCATTCAACTGACTCGACTACAATCTTGGGCATCGGCA
CAGTCCTGGACCAAGCGGAGACGGCTGGAGCGCGGCTTGTCGTGCTCGCCACCGCTACGCCTCCGGGATCGGTCACCG
TGCCACACCCAAACATCGAGGAGGTGGCCTTGTCTAATACTGGAGAGATCCCCTTCTATGGCAAAGCCATCCCCATTG
AAGCCATCAGGGGGGAAGGCATCTCATTTTCTGTCATTCCAAGAAGAAGTGCGACGAGCTCGCCGCAAAGCTGTCAG
GCCTCGGAATCAACGCTGTGGCGTATTACCGGGGGCTCGATGTGTCCGTCATACCAACTATCGGAGACGTCGTTGTCG
TGGCAACAGACGCTCTGATGACGGGCTATACGGGCGACTTTGACTCAGTGATCGACTGTAACACATGTGTCACCCAGA
CAGTCGACTTCAGCTTGGATCCCACCTTCACCATTGAGACGACGACCGTGCCTCAAGACGCAGTGTCGCGCTCGCAGC
GGCGGGGTAGGACTGGCAGGGGTAGGAGAGGCATCTACAGGTTTGTGACTCCGGGAGAACGGCCCTCGGGCATGTTCG
ATTCCTCGGTCCTGTGTGAGTGCTATGACGCGGGCTGTGCTTGGTACGAGCTCACCCCCGCCGAGACCTCGGTTAGGT
TGCGGGCCTACCTGAACACACCGAAGGGTTGCCCGTTTGCCAGGACCACCTGGAGTTCTGGGAGAGTGTCTTCACAGGCC
TCACCCACATAGATGCACACTTCTTGTCCCAGACCAAGCAGGCAGGAGACAACTTCCCCTACCTGGTAGCATACCAAG
CCACGGTGTGCGCCAGGGCTCAGGCCCCACCTCCATCATGGGATCAAATGTGGAAGTGTCTCATACGGCTGAAACCTA
CGCTGCACGGGCCAACACCCTTGCTGTACAGGCTGGGAGCCGTCCAAAATGAGGTCACCCTCACCCACCCCATAACCA
AATACATCATGGCATGCATGTCGGCTGACCTGGAGGTCGTCACTAGCACCTGGGTGCTGGTGGGCGGAGTCCTTGCAG
CTCTGGCCGCGTATTGCCTGACAACAGGCAGTGTGGTCATTGTGGGTAGGATTATCTTGTCCGGGAGGCCGGCTATTG
TTCCCGACAGGGAGTTTCTCTACCAGGAGTTCGATGAAATGGAAGAGTGCGCCTCGCACCTCCCTTACATCGAGCAGG
GAATGCAGCTCGCCGAGCAATTCAAGCAGAAAGCGCTCGGGTTACTGCAAACAGCCACCAAACAAGCGGAGGCTGCTG
CTCCCGTGGTGGAGTCCAAGTGGCGAGCCCTTGAGGACATTCTGGGCGAAGCACATGTGGAATTTCATCAGCGGGATAC
AGTACTTAGCAGGCTTATCCACTCTGCCTGGGAACCCCGCAATAGCATCATTGATGGCATTCACAGCCTCTATCACCA
GCCCGCTCACCACCCAAAGTACCCTCCTGTTTAACATCTTGGGGGGGTGGGTGGCTGCCCAACTCGCCCCCCCCAGCG
CCGCTTCGGCTTTCGTGGGCGCCGGCATCGCCGGTGCGGCTGTTGGCAGCATAGGCCTTGGGAAGGTGCTTGTGGACA
TTCTGGCGGGTTATGGAGCAGGAGTGGCCGGCGCGCTCGTGGCCTTCAAGGTCATGAGCGGCGAGATGCCCTCCACCG
AGGACCTGGTCAATACTTCCTGCCATCCTCTCTCCTGGCGCCCTGGTCGTCGGGGTCGTGTGTGCAGCAATACTGC
GTCGACACGTGGGTCCGGGAGAGGGGGCTGTGCAGTGGATGAACCGGCTGATAGCGTTCGCCTCGCGGGGTAATCATG
TTTCCCCCACGCACTGTCTGAGAGCGACCGCGAGCGCGCGTGTTACTCAGATCCTCTCCAGCCTTACCATCACTC
AGCTGCTGAAAAGGCTCCACCAGTGGATTAATGAAGACTGCTCCACACCGTGTTCCGGCTCGTGGCTAAGGGATGTTT
GGGACTGGATATGCACGGTGTTGACTGACTTCAAGACCTGCTCCAGTCCAAGCTCCTGCCGCAGCTACCGGGAGTCC
CTTTTTTCTCGTGCCAACGCGGGTACAAGGGAGTCTGGCGGGGAGACGGCATCATGCAAACCACCTGCCCATGTGGAG
CACAGATCACCGGACATGTCAAAAACGGTTCCATGAGGATCGTCGGGCCTAAGACCTGCAGCAACACGTGGCATGGAA
CATTCCCCATCAACGCATACACCACGGGCCCCTGCACACCCTCTCCAGCGCCAAACTATTCTAGGGCGCTGTGGCGGG
TGGCCGCTGAGGAGTACGTGGAGGTCACGCGGGTGGGGGATTTCCACTACGTGACGGGCATGACCACTGACAACGTAA
AGTGCCCATGCCAGGTTCCGGCTCCTGAATTCTTCACGGAGGTGGACGGAGTGCGGTTGCACAGGTACGCTCCGGCGT
GCAGGCCTCTCCTACGGGAGGAGGTTACATTCCAGGTCGGCTCAACCAATACCTGGTTGGGTCACAGCTACCATGCG
AGCCCGAACCGGATGTAGCAGTGCTCACTTCCATGCTCACCGACCCCTCCCACATCACAGCAGAAACGGCTAAGCGTA
```

Fig. 5A

```
GGTTGGCCAGGGGGTCTCCCCCCTCCTTGGCCAGCTCTTCAGCTAGCCAGTTGTCTGCGCCTTCCTTGAAGGCGACAT
GCACTACCCACCATGTCTCTCCGGACGCTGACCTCATCGAGGCCAACCTCCTGTGGCGGCAGGAGATGGGCGGGAACA
TCACCCGCGTGGAGTCGGAGAACAAGGTGGTAGTCCTGGACTCTTTCGACCCGCTTCGAGCGGAGGAGGATGAGAGGG
AAGTATCCGTTCCGGCGGAGATCCTGCGGAAATCCAAGAAGTTCCCCGCAGCGATGCCCATCTGGGCGCGCCCGGATT
ACAACCCTCCACTGTTAGAGTCCTGGAAGGACCCGGACTACGTCCCTCCGGTGGTGCACGGGTGCCCGTTGCCACCTA
TCAAGGCCCCTCCAATACCACCTCCACGGAGAAAGAGGACGGTTGTCCTAACAGAGTCCTCCGTGTCTTCTGCCTTAG
CGGAGCTCGCTACTAAGACCTTCGGCAGCTCCGAATCATCGGCCGTCGACAGCGGCACGGCGACCGCCCTTCCTGACC
AGGCCTCCGACGACGGTGACAAAGGATCCGACGTTGAGTCGTACTCCTCCATGCCCCCCCTTGAGGGGGAACCGGGGG
ACCCCGATCTCAGTGACGGGTCTTGGTCTACCGTGAGCGAGGAAGCTAGTGAGGATGTCGTCTGCTGCTCAATGTCCT
ACACATGGACAGGCGCCTTGATCACGCCATGCGCTGCGGAGGAAAGCAAGCTGCCCATCAACGCGTTGAGCAACTCTT
TGCTGCGCCACCATAACATGGTTTATGCCACAACATCTCGCAGCGCAGGCCTGCGGCAGAAGAAGGTCACCTTTGACA
GACTGCAAGTCCTGGACGACCACTACCGGGACGTGCTCAAGGAGATGAAGGCGAAGGCGTCCACAGTTAAGGCTAAAC
TCCTATCCGTAGAGGAAGCCTGCAAGCTGACGCCCCCACATTCGGCCAAATCCAAGTTTGGCTATGGGGCAAAGGACG
TCCGGAACCTATCCAGCAAGGCCGTTAACCACATCCACTCCGTGTGGAAGGACTTGCTGGAAGACACTGTGACACCAA
TTGACACCACCATCATGGCAAAAAATGAGGTTTTCTGTGTCCAACCAGAGAAAGGAGGCCGTAAGCCAGCCCGCCTTA
TCGTATTCCCAGATCTGGGAGTCCGTGTATGCGAGAAGATGGCCCTCTATGATGTGGTCTCCACCCTTCCTCAGGTCG
TGATGGGCTCCTCATACGGATTCCAGTACTCTCCTGGGCAGCGAGTCGAGTTCCTGGTGAATACCTGGAAATCAAAGA
AAAACCCCATGGGCTTTTCATATGCACTCGCTGTTTCGACTCAACGGTCACCGAGAACGACATCCGTGTTGAGGAGT
CAATTTACCAATGTTGTGACTTGGCCCCCGAAGCCAGACAGGCCATAAAATCGCTCACAGAGCGGCTTTATATCGGGG
GTCCTCTGACTAATTCAAAAGGGCAGAACTGCGGTTATCGCCGGTGCCGCGCGAGCGGCGTGCTGACGACTAGCTGCG
GTAACACCCTCACATGTTACTTGAAGGCCTCTGCAGCCTGTCGAGCTGCGAAGCTCCAGGACTGCACGATGCTCGTGA
ACGCCGCCGGCCTTGTCGTTATCTGTGAAAGCGCGGGAACCCAAGAGGACGCGGCGAGCCTACGAGTCTTCACGGAGG
CTATGACTAGGTACTCTGCCCCCCCCGGGACCCGCCCAACCAGAATACGACTTGGAGCTGATAACATCATGTTCCT
CCAATGTGTCGGTCGCCCACGATGCATCAGGCAAAAGGGTGTACTACCTCACCCGTGATCCCACCACCCCCCTCGCAC
GGGCTGCGTGGGAAACAGCTAGACACACTCCAGTTAACTCCTGGCTAGGCAACATTATCATGTATGCGCCCACTTTGT
GGGCAAGGATGATTCTGATGACTCACTTCTTCTCCATCCTTCTAGCACAGGAGCAACTTGAAAAAGCCCTGGACTGCC
AGATCTACGGGGCCTGTTACTCCATTGAGCCACTTGACCTACCTCAGATCATTGAACGACTCCATGGCCTTAGCGCAT
TTTCACTCCATAGTTACTCTCCAGGTGAGATCAATAGGGTGGCTTCATGCCTCAGGAAACTTGGGGTACCACCCTTGC
GAGTCTGGAGACATCGGGCCAGGAGCGTCCGCGCTAGGCTACTGTCCCAGGGGGGGAGGGCCGCCACTTGTGGCAAGT
ACCTCTTCAACTGGGCAGTGAAGACCAAACTCAAACTCACTCCAATCCCGGCTGCGTCCCAGCTGGACTTGTCCGGCT
GGTTCGTTGCTGGTTACAGCGGGGGAGACATATATCACAGCGTGTCTCGTGCCCGACCCGTGTCGTTCATGCTGTGCC
TACTCCTACTTTCTGTAGGGGTAGGCATCTACCTGCTCCCCAACCGATAAATCTAGAGCTGTGCCTTCTAGTTGCCAG
CCATCTGTTGTTTGCCCCTCCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGGGGCAGCACAGCAAGGGGGAG
GATTGGGAAGACAATAGCAGGCATGCTGGGGATGCGGTGGGCGATATCAGCGATCGCTGAGGTGGGTGAGTGGGCGTG
GCCTGGGGTGGTCATGAAAATATATAAGTTGGGGGTCTTAGGGTCTCTTTATTTGTGTTGCAGAGACCGCCGGAGCCA
TGAGCGGGAGCAGCAGCAGCAGCAGTAGCAGCAGCGCCTTGGATGGCAGCATCGTGAGCCCTTATTTGACGACGCGGA
TGCCCCACTGGGCCGGGGTGCGTCAGAATGTGATGGGCTCCAGCATCGACGGCCGACCCGTCCTGCCCGCAAATTCCG
CCACGCTGACCTATGCGACCGTCGCGGGGACGCCGTTGGACGCCACCGCCGCCGCCGCCGCCACCGCAGCCGCCTCGG
CCGTGCGCAGCCTGGCCACGGACTTTGCATTCCTGGGACCACTGGCGACAGGGGCTACTTCTCGGGCGCTGCTGCCG
CCGTTCGCGATGACAAGCTGACCGCCCTGCTGGCGCAGTTGGATGCGCTTACTCGGGAACTGGGTGACCTTTCTCAGC
AGGTCATGGCCCTGCGCCAGCAGGTCTCCTCCCTGCAAGCTGGCGGGAATGCTTCTCCCACAAATGCCGTTTAAGATA
AATAAAACCAGACTCTGTTTGGATTAAAGAAAAGTAGCAAGTGCATTGCTCTCTTTATTTCATAATTTTCCGCGCGCG
ATAGGCCCTAGACCAGCGTTCTCGGTCGTTGAGGGTGCGGTGTATCTTCTCCAGGACGTGGTAGAGGTGGCTCTGGAC
GTTGAGATACATGGGCATGAGCCCGTCCCGGGGGTGGAGGTAGCACCACTGCAGAGCTTCATGCTCCGGGGTGGTGTT
GTAGATGATCCAGTCGTAGCAGGAGCGCTGGGCATGGTGCCTAAAAATGTCCTTCAGCAGCAGGCCGATGGCCAGGGG
GAGGCCCTTGGTGTAAGTGTTTACAAAACGGTTAAGTTGGGAAGGGTGCATTCGGGGAGAGATGATGTGCATCTTGGA
CTGTATTTTTAGATTGGCGATGTTTCCGCCCAGATCCCTTCTGGGATTCATGTTGTGCAGGACCACCAGTACAGTGTA
TCCGGTGCACTTGGGGAATTTGTCATGCAGCTTAGAGGGAAAAGCGTGGAAGAACTTGGAGACGCCCTTGTGGCCTCC
CAGATTTTCCATGCATTCGTCCATGATGATGGCAATGCCTCGCGGGAGGCAGCTTGGGCAAAGATATTTCTGGGGTC
GCTGACGTCGTAGTTGTGTTCCAGGGTGAGGTCGTCATAGGCCATTTTTACAAAGCGCGGGCGGAGGGTGCCCGACTG
GGGGATGATGGTCCCCTCTGGCCCTGGGGCGTAGTTGCCCTCGCAGATCTGCATTTCCCAGGCCTTAATCTCGGAGGG
GGGAATCATATCCACCTGCGGGGCGATGAAGAAAACGGTTTCCGGAGCCGGGGAGATTAACTGGGTTGCAGCTGGTAGTTTAGAGA
TCTAAGCAGCTGTGATTTTCCACAACCGGTGGGCCCATAAATAACACCTATAACCGGTTGCAGCTGGTAGTTTAGAGA
GCTGCAGCTGCCGTCGTCCCGGAGGAGGGGGCCACCTCGTTGAGCATGTCCCTGACGCGCATGTTCTCCCCGACCAG
ATCCGCCAGAAGGCGCTCGCCGCCCAGGGACAGCAGCTCTTGCAAGGAAGCAAAGTTTTTCAGCGGCTTGAGGCCGTC
CGCCGTGGCATGTTTTTCAGGGTCTGGCTCAGCAGCTCCAGGCGGTCCCAGAGCTCGGTGACGTGCTCTACGGCATC
TCTATCCAGCATATCTCCTCGTTTCGCGGGTTGGGGCGACTTTCGCTGTAGGGCACCAAGCGGTGGTCGTCCAGCGGG
GCCAAAGTCATGTCCTTCCATGGGCGCAGGGTCCTCGTCAGGGTGGTCTGGGTCACGGTGAAGGGTGCGCTCCGGGC
TGAGCGCTTGCCAAGGTGCGCTTGAGGCTGGTTCTGCTGGTGCTGAAGCGCTGCCGGTCTTCGCCCTGCGCGTCGGCC
```

Fig. 5B

```
AGGTAGCATTTGACCATGGTGTCATAGTCCAGCCCCTCCGCGGCGTGTCCCTTGGCGCGCAGCTTGCCCTTGGAGGTG
GCGCCGCACGAGGGGCAGAGCAGGCTCTTGAGCGCGTAGAGCTTGGGGGCGAGGAAGACCGATTCGGGGGAGTAGGCG
TCCGCGCCGCAGACCCCGCACACGGTCTCGCACTCCACCAGCCAGGTGAGCTCGGGGCGCGCCGGGTCAAAAACCAGG
TTTCCCCCATGCTTTTTGATGCGTTTCTTACCTCGGGTCTCCATGAGGTGGTGTCCCCGCTCGGTGACGAAGAGGCTG
TCCGTGTCTCCGTAGACCGACTTGAGGGGTCTTTTCTCCAGGGGGGTCCCTCGGTCTTCCTCGTAGAGGAACTCGGAC
CACTCTGAGACGAAGGCCCGCGTCCAGGCCAGGACGAAGGAGGCTATGTGGGAGGGGTAGCGGTCGTTGTCCACTAGG
GGGTCCACCTTCTCCAAGGTGTGAAGACACATGTCGCCTTCCTCCGGCGTCCAGGAAGGTGATTGGCTTGTAGGTGTAG
GCCACGTGACCGGGGGTTCCTGACGGGGGGGTATAAAAGGGGGTGGGGGCGCGCTCGTCGTCACTCTCTTCCGCATCG
CTGTCTGCGAGGGCCAGCTGCTGGGGTGAGTATTCCCTCTCGAAGGCGGGCATGACCTCCGCGCTGAGGTTGTCAGTT
TCCAAAAACGAGGAGGATTTGATGTTCACCTGTCCCGAGGTGATACCTTTGAGGGTACCCGCGTCCATCTGGTCAGAA
AACACGATCTTTTTATTGTCCAGCTTGGTGGCGAACGACCCGTAGAGGGCGTTGGAGAGCAGCTTGGCGATGGAGCGC
AGGGTCTGGTTCTTGTCCCTGTCGGCGCGCTCCTTGGCCGCGATGTTGAGCTGCACGTACTCGCGCGCGACGCAGCGC
CACTCGGGGAAGACGGTGGTGCGCTCGTCGGGCACCAGGCGCACGCGCCAGCCGCGGTTGTGCAGGGTGACCAGGTCC
ACGCTGGTGGCGACCTCGCCGCGCAGGCGCTCGTTGGTCCAGCAGAGACGGCCGCCCTTGCGCGAGCAGAAGGGGGGC
AGGGGGTCGAGCTGGGTCTCGTCCGGGGGGTCCGCGTCCACGGTGAAAACCCCGGGGCGCAGGCGCGCGTCGAAGTAG
TCTATCTTGCAACCTTGCATGTCCAGCGCCTGCTGCCAGTCGCGGGCGGCGAGCGCGCGCTCGTAGGGGTTGAGCGGC
GGGCCCCAGGGCATGGGGTGGGTGAGTGCGGAGGCGTACATGCCGCAGATGTCATAGACGTAGAGGGGCTCCCGCAGG
ACCCCGATGTAGGTGGGGTAGCAGCGGCCGCCGCGGATGCTGGCGCGCACGTAGTCATACAGCTCGTGCGAGGGGGCG
AGGAGGTCGGGGCCCAGGTTGGTGCGGGCGGGGCGCTCCGCGCGGAAGACGATCTGCCTGAAGATGGCATGCGAGTTG
GAAGAGATGGTGGGGCGCTGGAAGACGTTGAAGCTGGCGTCCTGCAGGCCGACGGCGTCGCGCACGAAGGAGGCGTAG
GAGTCGCGCAGCTTGTGTACCAGCTCGGCGGTGACCTGCACGTCGAGCGCGCAGTAGTCGAGGGTCTCGCGGATGATG
TCATATTTAGCCTGCCCCTTCTTTTTCCACAGCTCGCGGTTGAGGACAAACTCTTCGCGGTCTTTCCAGTACTCTTGG
ATCGGGAAACCGTCCGGTTCCGAACGGTAAGAGCCTAGCATGTAGAACTGGTTGACGGCCTGGTAGGCGCAGCAGCCC
TTCTCCACGGGGAGGGCGTAGGCCTGCGCGGCCTTGCGGAGCGAGGTGTGGGTCAGGGCGAAGGTGTCCCTGACCATG
ACTTTGAGGTACTGGTGCTTGAAGTCGGAGTCGTCGCAGCCGCCCCGCTCCCAGAGCGAGAAGTCGGTGCGCTTCTTG
GAGCGGGGGTTGGGCAGAGCGAAGGTGACATCGTTGAAGAGGATTTTGCCCGCGCGGGGCATGAAGTTGCGGGTGATG
CGGAAGGGCCCCGGCACTTCAGAGCGGTTGTTGATGACCTGGGCGGCGAGCACGATCTCGTCGAAGCCGTTGATGTTG
TGGCCCACGATGTAGAGTTCCAGGAAGCGGGGCCGGCCCTTTACGGTGGGCAGCTTCTTTAGCTCTTCGTAGGTGAGC
TCCTCGGGCGAGGCGAGGCCGTGCTCGGCCAGGGCCCAGTCCGCGAGGTGCGGGTTGTCTCTGAGGAAGGACTCCCAG
AGGTCGCGGGCCAGGAGGGTCTGCAGGCGGTCCCTGAAGGTCCTGAACTGGCGGCCCACGGCCATTTTTTCGGGGGTG
ATGCAGTAGAAGGTGAGGGGGTCTTGCTGCCAGCGGTCCCAGTCGAGCTGCAGGGCGAGGTCGCGCGCGGCGGTGACC
AGGCGCTCGTCGCCCCCGAATTTCATGACCAGCATGAAGGGCACGAGCTGCTTTCCGAAGGCCCCCATCCAAGTGTAG
GTCTCTACATCGTAGGTGACAAAGAGGCGCTCCGTGCGAGGATGCGAGCCGATCGGGAAGAACTGGATCTCCCGCCAC
CAGTTGGAGGAGTGGCTGTTGATGTGGTGGAAGTAGAAGTCCCGTCGCCGGGCCGAACACTCGTGCTGGCTTTTGTAA
AAGCGAGCGCAGTACTGGCAGCGCTGCACGGGCTGTACCTCCTGCACGAGATGCACCTTTCGCCCGCGCACGAGGAAG
CCGAGGGGAAATCTGAGCCCCCCGCCTGGCTCGCGGCATAGCCTGGTCGTTCTTCTACTTTGGATGCGTGTCCGTCTCCG
TCTGGCTCCTCGAGGGGTGTTACGGTGGAGCGGACCACCACGCGCGCGAGCCGCAGGTCCAGATATCGGCGCGCGGC
GGTCGGAGTTTGATGACGACATCGCGCAGCTGGGAGCTGTCCATGGTCTGGAGCTCCCGCGGCGGCGGCAGGTCAGCC
GGGAGTTCTTGCAGGTTCACCTCGCAGAGTCGGGCCAGGGCGCGGGGCAGGTCTAGGTGGTACCTGATCTCTAGGGGC
GTGTTGGTGGCGGCGTCGATGGCTTGCAGGAGCCCGCATCCCCGGGGGGCGACGACGGTGCCCCGCGGGGTGGTGGTG
GTGGTGGTGGTGGTGGTGGCGGTGCAGCTCAGAAGCGGTGCCGCGGGCGGGCCCCCGGAGGTAGGGGGGCTCCG
GTCCCGCCGGCAGGGCGGCAGCGGCACGTCGGCGTGGAGCGCGGGCAGGAGTTGGTGCTGTGCCCGGAGGTTGCTGG
CGAAGGCGACGACGCGGCGGTTGATCTCCTGGATCTGGCGCCTCTGCGTGAAGACGACGGGCCCGGTGAGCTTGAACC
TGAAAGAGAGTTCGACAGAATCAATCTCGGTGTCATTGACCGCGGCCTGGCGCAGGATCTCCTGCACGTCTCCCGAGT
TGTCTTGGTAGGCGATCTCGGCCATGAACTGCTCGATCTCTTCCTCCTGGAGGTCTCCGCGTCCGGCGCGTTCCACGG
TGGCCGCCAGGTCGTTGGAGATGCGCCCCATGAGCTGCGAGAAGGCGTTGAGTCCGCCCTCGTTCCAGACTCGGCTGT
AGACCACGCCCCCTGGTCATCGCGGGCGCGCATGACCACCTGCGCGAGGTTGAGCTCCACGTGCCGCGCGAAGACGG
CGTAGTTGCGCAGACGCTGGAAGAGGTAGTTGAGGGTGGTGGCGGTGTGCTCGGCCACGAAGAAGTTCATGACCCAGC
GGCGCAACGTGGATTCGTTGATGTCCCCCAAGGCCTCCAGCCGTTCCATGGCCTCGTAGAAGTCCACGGCGAAGTTGA
AAAACTGGGAGTTGCGCGCCGACACGGTCAACTCCTCCTCCAGAAGACGGATGAGCTCGGCGACGGTGTCGCGCACCT
CGCGCTCGAAGGCTATGGGGATCTCTTCCTCCGCTAGCATCACCACCTCCTCCTCTTCCTCCTCTTCTGGCACTTCCA
TGATGGCTTCCTCCTCTTCGGGGGGCGGCGGCGGCGGCGGTGGGGGAGGGGGCGCTCTGCGCCGGCGGCGGCGCACCG
GGAGGCGGTCCACGAAGCGCGCGATCATCTCCCCGCGGCGGCGGCGCATGGTCTCGGTGACGGCGCGGCCGTTCTCCC
GGGGGCGCAGTTGGAAGACGCCGCCGGACATCTGGTGCTGGGGCGGGTGGCCGTGAGGCAGCGAAACGGCGCTGACGA
TGCATCTCAACAATTGCTGCGTAGGTACGCCGCCGAGGGACCTGAGGGAGTCCATATCCACCGGATCCGAAAACCTTT
CGAGGAAGGCGTCTAACCAGTCGCAGTCGCAAGGTAGGCTGAGCACCGTGGCGGGCGGCGGGGGTGGGGGAGTGTC
TGGCGGAGGTGCTGCTGATGATGTAATTGAAGTAGGCGGACTTGACACGGCGGATGGTCGACAGGAGCACCATGTCCT
TGGGTCCGGCCTGCTGGATGCGGAGGCGGTCGGCTATGCCCCAGGCTTCGTTCTGGCATCGGCGCAGGTCCTTGTAGT
AGTCTTGCATGAGCCTTTCCACCGGCACCTCTTCTCCTTCCTCTTCTGCTTCTTCCATGTCTGCTTCGGCCCTGGGGC
GGCGCCGCGCCCCCCTGCCCCCCATGCGCGTGACCCCGAACCCCCTGAGCGGTTGGAGCAGGGCCAGGTCGGCGACGA
```

Fig. 5C

```
CGCGCTCGGCCAGGATGGCCTGCTGCACCTGCGTGAGGGTGGTTTGGAAGTCATCCAAGTCCACGAAGCGGTGGTAGG
CGCCCGTGTTGATGGTGTAGGTGCAGTTGGCCATGACGGACCAGTTGACGGTCTGGTGGCCCGGTTGCGACATCTCGG
TGTACCTGAGTCGCGAGTAGGCGCGGGAGTCGAAGACGTAGTCGTTGCAAGTCCGCACCAGGTACTGGTAGCCCACCA
GGAAGTGCGGCGGCGGCTGGCGGTAGAGGGGCCAGCGCAGGGTGGCGGGGGCTCCGGGGGCCAGGTCTTCCAGCATGA
GGCGGTGGTAGGCGTAGATGTACCTGGACATCCAGGTGATACCCGCGGCGGTGGTGGAGGCGCGCGGGAAGTCGCGCA
CCCGGTTCCAGATGTTGCGCAGGGGCAGAAAGTGCTCCATGGTAGGCGTGCTCTGTCCAGTCAGACGCGCGCAGTCGT
TGATACTCTAGACCAGGGAAAACGAAAGCCGGTCAGCGGGCACTCTTCCGTGGTCTGGTGAATAGATCGCAAGGGTAT
CATGGCGGAGGGCCTCGGTTCGAGCCCCGGGTCCGGGCCGGACGGTCCGCCATGATCCACGCGGTTACCGCCCGCGTG
TCGAACCCAGGTGTGCGACGTCAGACAACGGTGGAGTGTTCCTTTTGGCGTTTTTCTGGCCGGGCGCCGGCGTCGCGT
AAGAGACTAAGCCGCGAAAGCGAAAGCAGTAAGTGGCTCGCTCCCCGTAGCCGGAGGGATCCTTGCTAAGGGTTGCGT
TGCCGGCGAACCCCGGTTCGAATCCCGTACTCGGGCCGGCCGGACCCGCGGCTAAGGTGTTGGATTGGCCTCCCCTCG
TATAAAGACCCCGCTTGCGGATTGACTCCGGACACGGGGACGAGCCCCTTTTATTTTTGCTTTCCCCAGATGCATCCG
GTGCTGCGGCAGATGCGCCCCCCGCCCCAGCAGCAGCAACAACACCAGCAAGAGCGGCAGCAACAGCAGCGGGAGTCA
TGCAGGGCCCCCTCACCCACCCTCGGCGGGCCGGCCACCTCGGCGTCCGCGGCCGTGTCTGGCGCCTGCGGCGGCGGC
GGGGGGCCGGCTGACGACCCCGAGGAGCCCCCGCGGCGCAGGGCCAGACACTACCTGGACCTGGAGGAGGGCGAGGGC
CTGGCGCGGCTGGGGGCGCCGTCTCCCGAGCGCCACCCGCGGGTGCAGCTGAAGCGCGACTCGCGCGAGGCGTACGTG
CCTCGGCAGAACCTGTTCAGGGACCGCGCGGGCGAGGAGCCCGAGGAGATGCGGGACAGGAGGTTCAGCGCAGGGCGG
GAGCTGCGGCAGGGGCTGAACCGCGAGCGGCTGCTGCGCGAGGAGGACTTTGAGCCCGACGCGCGGACGGGGATCAGC
CCCGCGCGCGCGCACGTGGCGCGCCGACCTGGTGACGGCGTACGAGCAGACGGTGAACCAGGAGATCAACTTCCAA
AAGAGTTTCAACAACCACGTGCGCACGCTGGTGGCGCGCGAGGAGGTGACCATCGGGCTGATGCACCTGTGGGACTTT
GTAAGCGCGCTGGTGCAGAACCCCAACAGCAAGCCTCTGACGGCGCAGCTGTTCCTGATAGTGCAGCACAGCAGGGAC
AACGAGGCGTTTAGGGACGCGCTGCTGAACATCACCGAGCCCGAGGGTCGGTGGCTGCTGGACCTGATTAACATCCTG
CAGAGCATAGTGGTGCAGGAGCGCAGCCTGAGCCTGGCCGACAAGGTGGCGGCCATCAACTACTCGATGCTGAGCCTG
GGCAAGTTTTACGCGCGCAAGATCTACCAGACGCCGTACGTGCCCATAGACAAGGAGGTGAAGATCGACGGTTTTTAC
ATGCGCATGGCGCTGAAGGTGCTCACCCTGAGCGACGACCTGGGCGTGTACCGCAACGAGCGCATCCACAAGGCCGTG
AGCGTGAGCCGGCGGCGCGAGCTGAGCGACCGCGAGCTGATGCACAGCCTGCAGCGGGCGCTGGCGGGCGCCGGCAGC
GGCGACAGGGAGGCGGAGTCCTACTTCGATGCGGGGGCGGACCTGCGCTGGGCGCCCAGCCGGCGGGGCCCTGGAGGCC
GCGGGGGTCCGCGAGGACTATGACGAGGACGGCGAGGAGGATGAGGAGTACGAGCTAGAGGAGGGCGAGTACCTGGAC
TAAACCGCGGGTGGTGTTTCCGGTAGATGCAAGACCCGAACGTGGTGGACCCGGCGCTGCGGGCGGCTCTGCAGAGCC
AGCCGTCCGGCCTTAACTCCTCAGACGACTGGCGACAGGTCATGGACCGGCATCATGTCGCTGACGGCGCGTAACCCGG
ACGCGTTCCGGCAGCAGCCGCAGGCCAACAGGCTCTCCGCCATCCTGGAGGCGGTGGTGCCCTGCGCGCTCGAACCCCA
CGCACGAGAAGGTGCTGGCCATAGTGAACGCGCTGGCCGAGAACAGGGCCATCCGCCCGGACGAGGCCGGGCTGGTGT
ACGACGCGCTGCTGCAGCGCGTGGCCCGCTACAACAGCGGCAACGTGCAGACCAACCTGGACCGGCTGGTGGGGGACG
TGCGCGAGGCGGTGGCGCAGCGCGAGCGCGCGGATCGGCAGGGCAACCTGGGCTCCATGGTGGCGCTGAATGCCTTCC
TGAGCACGCAGCCGGCCAACGTGCCGCGGGGGCAGGAAGACTACACCAACTTTGTGAGCGCGCTGCGGCTGATGGTGA
CCGAGACCCCCCAGAGCGAGGTGTACCAGTCGGGCCCGGACTACTTCTTCCAGACCAGCAGACAGGGCCTGCAGACGG
TGAACCTGAGCCAGGCTTTCAAGAACCTGCGGGGGCTGTGGGGCGTGAAGGCGCCCACCGGCGACCGGGCGACGGTGT
CCAGCCTGCTGACGCCCAACTCGCGCCTGCTGCTGCTGATCGCGCCGTTCACGGACAGCGGCAGCGTGTCCCGGG
ACACCTACCTGGGCACCTGCTGACCCTGTACCGCGAGGCCATCGGGCAGGCGCAGGTGGACGAGCACACCTTCCAGG
AGATCACCAGCGTGAGCCGCGCGCTGGGGCAGGAGGACACGAGCAGCCTGGAGGCGACTCTGAACTACCTGCTGACCA
ACCGGCGGCAGAAGATTCCCTCGCTGCACAGCCTGACCTCCGAGGAGGAGCGCATCTTGCGCTACGTGCAGCAGAGCG
TGAGCCTGAACCTGATGCGCGACGGGGTGACGCCCAGCGTGGCGCTGGACATGACCGCGCAACATGGAACCGGGCA
TGTACGCCGCGCACCGGCCTTACATCAACCGCTGATGGACTACCTGCATCGCGCGGCGGCCGTGAACCCCGAGTACT
TTACCAACGCCATCCTGAACCCGCACTGGCTCCGCCGCCCGGGTTCTACAGCGGGGCTTCGAGGTCCCGGAGGCCA
ACGATGGCTTCCTGTGGGACGACATGGACGACAGCGTGTTCTCCCCGCGGCCGCAGGCGCTGGCGGAAGCGTCCCTGC
TGCGTCCCAAGAGGAGGAGGAGGCGAGTCGCCGCCGCGGCAGCAGCGGCGTGGCTTCTCTGTCCGAGCTGGGGG
CGGCAGCCGCCGCGCGCCCCGGGTCCCTGGGCGGCAGCCCCTTTCCGAGCCTGGTGGGGTCTCTGCACAGCGAGCGCA
CCACCCGCCCTCGGCTGCTGGGCGAGGACGAGTACCTGAATAACTCCCTGCTGCAGCCGGTGCGGGAGAAAAACCTGC
CCCCGCCTTCCCCAACAACGGGATAGAGAGCCTGGTGGACAAGATGAGCAGATGGAAGACCTATGCGCAGGAGCACA
GGGACGCGCCCGCGCTCCGGCCGCCCACGCGGCGCCAGCGCCACGACCGGCAGCGGGGGCTGGTGTGGGATGACGAGG
ACTCCGCGGACGATAGCAGCGTGCTGGACCTGGGAGGGAGCGGCAACCCGTTCGCGCACCTGCGCCCCCGCCTGGGA
GGATGTTTTAAAAAAAAAAAAAGCAAGAAGCATGATGCAAAATTAAATAAAACTCACCAAGGCCATGGCGACCGAGCG
TTGGTTTCTTGTGTTCCCTTCAGTATGCGGCGCGCGGCGATGTACCAGGAGGGACCTCCTCCCTCTTACGAGAGCGTG
GTGGGCGGCGGCGGCGGCGCCCTCTTCTCCCTTTGCGTCGCAGCTGCTGGAGCCCGTGGCTTCTCCGCGCTAC
CTGCGGCCTACGGGGGGAGAAACAGCATCCGTTACTCGGAGCTGGCGCCCCTGTTCGACACCACCCGGGTGTACCTG
GTGGACAACAAGTCGGCGGACGTGGCCTCCCTGAACTACCAGAACGACCACAGCAATTTTTTGACCACGGTCATCCAG
AACAATGACTACAGCCCCGAGCGAGGCCAGCACCCAGACCATCAATCTGGATGACCGGTCGCACTGGGGCGGCGACCTG
AAAACCATCCTGCACACCAACATGCCCAACGTGAACGAGTTCATGTTCACCAATAAGTTCAAGGCGCGGGTGATGGTG
TCGCGCTCGCACACCAAGGAAGACCGGGTGGAGCTGAAGTACGAGTGGGTGGAGTTCGAGCTGCCAGAGGGCAACTAC
TCCGAGACCATGACCATTGACCTGATGAACAACGCGATCGTGGAGCACTATCTGAAAGTGGGCAGGCAAAACGGGGTC
```

Fig. 5D

```
CTGGAGAGCGACATCGGGGTCAAGTTCGACACCAGGAACTTCCGCCTGGGGCTGGACCCCGTGACCGGGCTGGTTATG
CCCGGGGTGTACACCAACGAGGCCTTCCATCCCGACATCATCCTGCTGCCCGGCTGCGGGGTGGACTTCACTTACAGC
CGCCTGAGCAACCTCCTGGGCATCCGCAAGCGGCAGCCCTTCCAGGAGGGCTTCAGGATCACCTACGAGGACCTGGAG
GGGGGCAACATCCCCGCGCTCCTCGATGTGGAGGCCTACCAGGATAGCTTGAAGGAAAATGAGGCGGGACAGGAGGAT
ACCACCCCCGCCGCCTCCGCCGCCGCCGAGCAGGGCGAGGATGCTGCTGACACCGCGGCCGCGGACGGGGCAGAGGCC
GACCCCGCTATGGTGGTGGAGGCTCCCGAGCAGGAGGAGGATATGAATGACAGTGCGGTGCGCGGACACCTTCGTC
ACCCGGGGGGAGGAAAAGCAAGCGGAGGCCGAGGCCGCGGCCGAGGAAAAGCAACTGGCGGCAGCAGCGGCGGCGGCG
GCGTTGGCCGCGGCGGAGGCTGAGTCTGAGGGGACCAAGCCCGCCAAGGAGCCCGTGATTAAGCCCCTGACCGAAGAT
AGCAAGAAGCGCAGTTACAACCTGCTCAAGGACAGCACCAACACCGCGTACCGCAGCTGGTACCTGGCCTACAACTAC
GGCGACCCGTCGACGGGGGTGCGCTCCTGGACCCTGCTGTGCACGCCGGACGTGACCTGCGGCTCGGAGCAGGTGTAC
TGGTCGCTGCCCGACATGATGCAAGACCCCGTGACCTTCCGCTCCACGCGGCAGGTCAGCAACTTCCCGGTGGTGGGC
GCCGAGCTGCTGCCCGTGCACTCCAAGAGCTTCTACAACGACCAGGCCGTCTACTCCCAGCTCATCCGCCAGTTCACC
TCTCTGACCCACGTGTTCAATCGCTTTCCTGAGAACCAGATTCTGGCGCGCCCGCCCGCCCCCACCATCACCACCGTC
AGTGAAAACGTTCCTGCTCTCACAGATCACGGGACGCTACCGCTGCGCAACAGCATCGGAGGAGTCCAGCGAGTGACC
GTTACTGACGCCAGACGCCGCACCTGCCCCTACGTTTACAAGGCCTTGGGCATAGTCTCGCCGCGCGTCCTTTCCAGC
CGCACTTTTTGAGCAACACCACCATCATGTCCATCCTGATCTCACCCAGCAATAACTCCGGCTGGGGACTGCTGCGCG
CGCCCAGCAAGATGTTCGGAGGGGCGAGGAAGCGTTCCGAGCAGCACCCGTGCGCGTGCGCGGGCACTTCCGCGCCC
CCTGGGGAGCGCACAAACGCGGCCGCGCGGGGCGCACCACCGTGGACGACGCCATCGACTCGGTGGTGGAGCAGGCGC
GCAACTACAGGCCCGCGGTCTCTACCGTGGACGCGGCCATCCAGACCGTGGTGCGGGGCGCGCGGCGGTACGCCAAGC
TGAAGAGCCGCCGGAAGCGCGTGGCCCGCCGCCACCGCCGCCGACCCGGGGCCGCCGCCAAACGCGCCGCCGCGGCCC
TGCTTCGCCGGGCCAAGCGCACGGGCCGCCGCGCCGCCATGAGGGCCGCGCGCCGCCGCCGCTTGGCCGCCGGCATCACCGCCG
CCACCATGGCCCCCCGTACCCGAAGACGCGCGGCCGCCGCCGCCGCCGCCATCAGTGACATGGCCAGCAGGCGCC
GGGGCAACGTGTACTGGGTGCGCGACTCGGTGACCGGCACGCGCGTGCCCGTGCGCTTCCGCCCCCCGCGGACTTGAG
ATGATGTGAAAAAACAACACTGAGTCTCCTGCTGTTGTGTGTATCCCAGCGGCGGCGGCGCGCGCAGCGTCATGTCCA
AGCGCAAAATCAAGAAGAGATGCTCCAGGTCGTCGCGCCGGAGATCTATGGGCCCCCCGAAGAAGGAAGAGCAGGATT
CGAAGCCCCGCAAGATAAAGCGGGTCAAAAAGAAAAAGAAAGATGATGACGATGCCGATGGGGAGGTGGAGTTCCTGC
GCGCCACGGCGCCCAGGCGCCCGGTGCAGTGGAAGGGCCGGCGCGTAAAGCGCGTCCTGCGCCCCGGCACCGCGGTGG
TCTTCACGCCCGGCGAGCGCTCCACCCGGACTTTCAAGCGCGTCTATGACGAGGTGTACGGCGACGAAGACCTGCTGG
AGCAGGCCAACGAGCGCTTCGGAGAGTTTGCTTACGGGAAGCGTCAGCGGGCGCTGGGGAAGGAGGACCTGCTGGCGC
TGCCGCTGGACCAGGGCAACCCCACCCCCAGTCTGAAGCCCGTGACCCTGCAGCAGGTGCTGCCGAGCAGCGCACCCT
CCGAGGCGAAGCGGGGTCTGAAGCGCGAGGGCGGCGACCTGGCGCCCACCGTGCAGCTCATGGTGCCCAAGCGGCAGA
GGCTGGAGGATGTGCTGGAGAAAATGAAAGTAGACCCCGGTCTGCAGCCGGACATCAGGGTCCGTCCCATCAAGCAGG
TGGCGCCGGGCCTCGGCGTGCAGACCGTGGACGTGGTCATCATCCCACCGGCAACTCCCCCGCCGCCACCACCACTACCG
CTGCCTCCACGGACATGGAGACACAGACCGATCCCGCCGCAGCCGCAGCCGCCGCCGCAGCCGCGACCTCCTCGGCGG
AGGTGCAGACGGACCCCTGGCTGCCGCCGGCGATGTCAGCTCCCGCGCGCGCCGCGGACGCAGAAAGTACGGCGCCG
CCAACGCGCTCCTGCCCGAGTACGCCCTTGCATCCTTCCATCGCGCCCACCCCCGGCTACCGAGGCTATACCTACCGCC
CGCGAAGAGCCAAGGGTTCCACCCGCCGTCCCCGCCGACGCGCCGCCGCCACCACCCGCCGCCGCCGCCGCAGACGCC
AGCCCGCACTGGCTCCAGTCTCCGTGAGGAGAGTGGCGCGCGACGGACACACCCTGGTGCTGCCCAGGGCGCGCTACC
ACCCCAGCATCGTTTAAAAGCCTGTTGTGGTTCTTGCAGATATGGCCCTCACTTGCCGCCTCCGTTTCCGGTGCCGG
GATACCGAGGAGGAAGATCGCGCCGCAGGAGGGGTCTGGCCGGCCGCGGCCTGAGCGGAGGCAGCCGCCGCGCGCACC
GGCGGCGACGCGCCACCAGCCGACGCATGCGCGGCGGGGTGCTGCCCCTGTTAATCCCCCTGATCGCCGCGGCGATCG
GCGCCGTGCCCGGGATCGCCTCCGTGGCCTTGCAAGCGTCCCAGAGGCATTGACAGACTTGCAAACTTGCAAATATGG
AAAAAAAAAAAAAACCCCAATAAAAAGTCTAGACTCTCACGCTCGCTTGGTCCTGTGACTATTTTGTAGAATGGAAGA
CATCAACTTTGCGTCGCTGGCCCCGCGTCACGGCTCGACGCCGTTCCTGGGACACTGGAACGATATCGGCACCAGCAA
CATGAGCGGTGGCGCCTTCAGTTGGGGCTCTCTGTGGAGCGGCATTAAAAGTATCGGGTCTGCCGTTAAAAATTACGG
CTCCCGGGCCTGGAACAGCAGCACGGGCCAGATGTTGAGAGACAAGTTGAAAGAGCAGAACTTCCAGCAGAAGGTGGT
GGAGGGCCTGGCCTCCGGCATCAACGGGGTGGTGGACCTGGCCAACCAGGCCGTGCAGAATAAAATCAACAGCAGACT
GGACCCCCGGCCGCCGGTGGAGGAGGTGCCGCCGGCGTCTGGAGACGGTGTCCCCCGATGGGCGTGCGAGAAGCGCCC
GCGGCCCGATAGGGAAGAGACCACTCTGGTCACGCAGACCGATGAGCCGCCCCCGTATGAGGAGGCCCTAAAGCAAGG
TCTGCCCACCACGCGCCCATCGCGCCCATGGCCACCGGGTGGTGGGCCGCCACACCCCGCCACGCTGGACTTGCC
TCCGCCCGCCGATGTGCCGCAGCAGCAGAAGGCGGCACAGCCGGGCCCGCCCGCGACCGCCTCCCGTTCCTCCGCCGG
TCCTCTGCGCCGCGGCCAGCGGCCCCCGCGGGGGGTCGCGAGGCACGGCAACTGGCAGAGCACGCTGAACAGCAT
CGTGGGTCTGGGGGTGCGGTCCGTGAAGCGCCGCCGATGCTACTGAATAGCTTAGCTAACGTGTTGTATGTGTGTATG
CGCCCTATGTCGCCGCCAGAGGAGCTGCTGAGTCGCCGCCGTTCGCGCGCCCACCACCACCGCCACTCCGCCCCTCAA
GATGGCGACCCCATCGATGATGCCGCAGTGGTCGTACATGCACATCTCGGGCCAGGACGCCTCGGAGTACCTGAGCCC
CGGGCTGGTGCAGTTCGCCCCGCCCACCGAGAGCTACTTCAGCCTGAGTAACAAGTTTAGGAACCCCACGGTGGCGCC
CACGCACGATGTGACCACCGACCGGTCTCAGCGCCTGACGCTGCGGTTCATTCCCGTGGACCGCGAGGACACCGCGTA
CTCGTACAAGGCGCGGTTCACCCTGGCCGTGGGCGACAACCGCGTGCTGGACATGGCCTCCACCTACTTTGACATCCG
CGGGGTGCTGGACCGGGGTCCCACTTTCAAGCCCTACTCTGGCACCGCCTACAACTCCCTGGCCCCAAGGGCGCTCC
CAACTCCTGCGAGTGGGAGCAAGAGGAAACTCAGGCAGTTGAAGAAGCAGCAGAAGAGGAAGAAGAAGATGCTGACGG
TCAAGCTGAGGAAGAGCAAGCAGCTACCAAAAAGACTCATGTATATGCTCAGGCTCCCCTTTCTGGCGAAAAAATTAG
```

Fig. 5E

```
TAAAGATGGTCTGCAAATAGGAACGGACGCTACAGCTACAGAACAAAAACCTATTTATGCAGACCCTACATTCCAGCC
CGAACCCCAAATCGGGGAGTCCCAGTGGAATGAGGCAGATGCTACAGTCGCCGGCGGTAGAGTGCTAAAGAAATCTAC
TCCCATGAAACCATGCTATGGTTCCTATGCAAGACCCACAAATGCTAATGGAGGTCAGGGTGTACTAACGGCAAATGC
CCAGGGACAGCTAGAATCTCAGGTTGAAATGCAATTCTTTTCAACTTCTGAAAACGCCCGTAACGAGGCTAACAACAT
TCAGCCCAAATTGGTGCTGTATAGTGAGGATGTGCACATGGAGACCCCGGATACGCACCTTTCTTACAAGCCCGCAAA
AAGCGATGACAATTCAAAAATCATGCTGGGTCAGCAGTCCATGCCCAACAGACCTAATTACATCGGCTTCAGAGACAA
CTTTATCGGCCTCATGTATTACAATAGCACTGGCAACATGGGAGTGCTTGCAGGTCAGGCCTCTCAGTTGAATGCAGT
GGTGGACTTGCAAGACAGAAACACAGAACTGTCCTACCAGCTCTTGCTTGATTCCATGGGTGACAGAACCAGATACTT
TTCCATGTGGAATCAGGCAGTGGACAGTTATGACCCAGATGTTAGAATTATTGAAAATCATGGAACTGAAGACGAGCT
CCCCAACTATTGTTTCCCTCTGGGTGGCATAGGGGTAACTGACACTTACCAGGCTGTTAAAACCAACAATGGCAATAA
CGGGGGCCAGGTGACTTGGACAAAAGATGAAACTTTTGCAGATCGCAATGAAATAGGGGTGGGAAACAATTTCGCTAT
GGAGATCAACCTCAGTGCCAACCTGTGGAGAAACTTCCTGTACTCCAACGTGGCGCTGTACCTACCAGACAAGCTTAA
GTACAACCCCTCCAATGTGGACATCTCTGACAACCCCAACACCTACGATTACATGAACAAGCGAGTGGTGGCCCCGGG
GCTGGTGGACTGCTACATCAACCTGGGCGCGCGCTGGTCGCTGGACTACATGGACAACGTCAACCCCTTCAACCACCA
CCGCAATGCGGGCCTGCGCTACCGCTCCATGCTCCTGGGCAACGGGCGCTACGTGCCCTTCCACATCCAGGTGCCCCA
GAAGTTCTTTGCCATCAAGAACCTCCTCCTCCTGCCGGGCTCCTACACCTACGAGTGGAACTTCAGGAAGGATGTCAA
CATGGTCCTCCAGAGCTCTCTGGGTAACGATCTCAGGGTGGACGGGGCCAGCATCAAGTTCGAGAGCATCTGCCTCTA
CGCCACCTTCTTCCCCATGGCCCACAACACGCCTCCACGCTCGAGGCCATGCTCAGGAACGACACCAACGACCAGTC
CTTCAATGACTACCTTTCCGCCGCCAACATGCTCTACCCCATACCCGCCAACGCCACCAACGTCCCCATCTCCATCCC
CTCGCGCAACTGGGCGGCCTTCCGCGGCTGGGCCTTCACCCGCCTCAAGACCAAGGAGACCCCCTCCCTGGGCTCGGG
ATTCGACCCCTACTACACCTACTCGGGCTCTATTCCCTACCTGGACGGCACCTTCTACCTCAACCACACTTTCAAGAA
GGTCTCGGTCACCTTCGACTCCTCGGTCAGCTGGCCGGGCAACGACCGTCTGCTCACCCCCAACGAGTTCGAGATCAA
GCGCTCGGTCGACGGGGAAGGCTACAACGTGGCCCAGTGCAACATGACCAAGGACTGGTTCCTGGTCAGATGCTGGC
CAACTACAACATCGGCTACCAGGGCTTCTACATCCCAGAGAGCTACAAGGACAGGATGTACTCCTTCTTCAGGAACTT
CCAGCCCATGAGCCGGCAGGTGGTGACCAGACCAAGTACAAGGACTACCAGGAGGTGGGCATCATCCACCAGCACAA
CAACTCGGGCTTCGTGGGCTACCTCGCCCCCACCATGCGCGAGGGACAGGCCTACCCCGCCAACTTCCCCTACCCGCT
CATAGGCAAGACCGCGGTCGACAGCATCACCCAGAAAAAGTTCCTCTGCGACCGCACCCTCTGGCGCATCCCCTTCTC
CAGCAACTTCATGTCCATGGGTGCGCTCTCGGACCTGGGCCAGAACTTGCTCTACGCCAACTCCGCCCACGCCCTCGA
CATGACCTTCGAGGTCGACCCCATGGACGAGCCCACCCTTCTCTATGTTCTGTTCGAAGTCTTTGACGTGGTCCGGGT
CCACCAGCCGCACCGCGGCGTCATCGAGACCGTGTACCTGCGTACGCCCTTCTCGGCCGGCAACGCCACCACCTAAAG
AAGCAAGCCGCAGTCATCGCCGCCTGCATGCCGTCGGGTTCCACCGAGCAAGAGCTCAGGGCATCGTCAGAGACCTG
GGATGCGGGCCCTATTTTTTGGGCACCTTCGACAAGCGCTTCCCTGGCTTTGTCTCCCCACACAAGCTGGCCTGCGCC
ATCGTCAACACGGCCGGCCGCGAGACCGGGGGCGTGCTGGCCTTTGCCTGGAACCCGCGCTCCAAAACATGC
TTCCTCTTTGACCCCTTCGGCTTTTCGGACCAGCGGCTCAAGCAAATCTACGAGTTCGAGTACGAGGGCTTGCTGCGT
CGCAGCGCCATCGCCTCCTCGCCCGACCGCTGCGTCACCCTCGAAAAGTCCACCCAGACCGTGCAGGGGCCCGACTCG
GCCGCCTGCGGTCTCTTCTGCTGCATGTTTCTGCACGCCTTTGTGCACTGGCCTCAGAGTCCCATGGACCGCAACCCC
ACCATGAACTTGCTGACGGGGGTGCCCAACTCCATGCTCCAAAGCCCCCAGGTCGAGCCCACCCTGCGCCGCAACCAG
GAGCAGCTCTACAGCTTCCTGGAGCGCCACTCGCCCTACTTCCGCCGCCACAGCGCACAGATCAGGAGGGCCACCTCC
TTCTGCCACTTGCAAGAGATGCAAGAAGGGTAATAACGATGTACACACTTTTTTCTCAATAAATGGCATTTTTTTTTT
ATTTATACAAGCTCTCTGGGGTATTCATTTCCCACCACCACCACCCGCCGTTGTCGCCATCTGGCTCTATTTAGAAAT
CGAAAGGGTTCTGCCGGGAGTCGCCGTGCGCCACGGGCAGGGACACGTTGCGATACTGGTAGCGGGTGCCCCACTTGA
ACTCGGGCACCACCAGGCGAGGCAGCTCGGGGAAGTTTTCGCTCCACAGGCTGCGGGTCAGCACCAGCGCGTTCATCA
GGTCGGGCGCCGAGATCTTGAAGTCGCAGTTGGGGCCGCCGCCCTGCGCGCGCGAGTTGCGGTACACCGGGTTGCAGC
ACTGGAACACCAACAGCGCCGGGTGCTTCACGCTGGCCAGCACGCTGCGGTGCGGAGATCAGCTCGGCCGTCCAGGTCCT
CCGGCGTTGCTCAGCGCGAACGGGGTCATCTTGGGCACTTGCCGCCCAGGAAGGGCGCGTGCCCCGGTTTCGAGTTGC
AGTCGCAGCGCAGCGGGATCAGCAGGTGCCCGTGCCCGGACTCGGCGTTGGGGTACAGCGCGCGCATGAAGGCCTGCA
TCTGGCGGAAGGCCATCTGGGCCTTGGCGCCCTCCGAGAAGAACATGCCGCAGGACTTGCCCGAGAACTGGTTTGCGG
GGCAGCTGGCGTCGTGCAGGCAGCAGCGCGCGTCGGTGTTGGCGATCTGCACCACGTTGCGCCCCCACCGGTTCTTCA
CGATCTTGGCCTTGGACGATTGCTCCTTCAGCGCGCGCTGCCCGTTCTCGCTGGTCACATCCATCTCGATCACATGTT
CCTTGTTCACCATGCTGCTGCCGTGCAGACACTTCAGCTCGCCCTCCGTCTCGGTGCAGCGGTGCTGCCACAGCGCGC
AGCCCGTGGGCTCGAAAGACTTGTAGGTCACCTCCGCGAAGGACTGCAGGTACCCCTGCAAAAAGCGGCCCATCATGG
TCACGAAGGTCTTGTTGCTGCTGAAGGTCAGCTGCAGCCCGCGGTGCTCCTCGTTCAGCCAGGTCTTGCACACGGCCG
CCAGCGCCTCCACCTGGTCGGGCAGCATCTTGAAGTTCACCTTCAGCTCATTCTCCACGTGGTACTTGTCCATCAGCG
TGCGCGCCGCCTCCATGCCCTCTCCCAGGCCGACACCAGCGGCAGGCTCACGGGGTTCTTCACCATCACCGTGGCCG
CCGCCTCCGCCGCGCTTTCGCTTTCCGCCCCGCTGTTCTCTTCCTCTTCCTCCTCTTCCTCGCCGCCGCCCACTCGCA
GCCCCCGCACCACGGGGTCGTCTTCCTGCAGGCGCTGCACCTTGCCGTTGCGCCCCTGCTTGATGCGCACGG
GCGGGTTGCTGAAGCCCACCATCACCAGCGCGGCCTCTTCTTGCTCGTCCTCGCTGTCCAGAATGACCTCCGGGGAGG
GGGGGTTGGTCATCCTCAGTACCGAGGCACGCTTCTTTTTCTTCCTGGGGCGTTCGCCAGCTCCGCGGCTGCGGCCG
CTGCCGAGGTCGAAGGCCGAGGGCTGGGCGTGCGCGGCACCAGCGCGTCTTGCGAGCCGTCCTCGTCCTCCTCGGACT
CGAGACGGAGGCGGGCCCGCTTCTTCGGGGGCGCGCGGGGCGGCGGAGGCGGCGGCGGCGACGGAGACGGGGACGAGA
```

Fig. 5F

```
CATCGTCCAGGGTGGGTGGACGGCGGGCCGCGCCGCGTCCGCGCTCGGGGGTGGTTTCGCGCTGGTCCTCTTCCCGAC
TGGCCATCTCCCACTGCTCCTTCTCCTATAGGCAGAAAGAGATCATGGAGTCTCTCATGCGAGTCGAGAAGGAGGAGG
ACAGCCTAACCGCCCCCTCTGAGCCCTCCACCACCGCCGCCACCACCGCCAATGCCGCCGCGGACGACGCGCCCACCG
AGACCACCGCCAGTACCACCCTCCCCAGCGACGCACCCCCGCTCGAGAATGAAGTGCTGATCGAGCAGGACCCGGGTT
TTGTGAGCGGAGAGGAGGATGAGGTGGATGAGAAGGAGAAGGAGGAGGTCGCCGCCTCAGTGCCAAAAGAGGATAAAA
AGCAAGACCAGGACGACGCAGATAAGGATGAGACAGCAGTCGGGCGGGGGAACGGAAGCCATGATGCTGATGACGGCT
ACCTAGACGTGGGAGACGACGTGCTGCTTAAGCACCTGCACCGCCAGTGCGTCATCGTCTGCGACGCGCTGCAGGAGC
GCTGCGAAGTGCCCCTGGACGTGGCGGAGGTCAGCCGCGCCTACGAGCGGCACCTCTTCGCGCCGCACGTGCCCCCCA
AGCGCCGGGAGAACGGCACCTGCGAGCCCAACCCGCGTCTCAACTTCTACCCGGTCTTCGCGGTACCCGAGGTGCTGG
CCACCTACCACATCTTCTTCCAAAACTGCAAGATCCCCCTCTCCTGCCGCGCTAACCGCACCCGCGCCGACAAAACCC
TGACCCTGCGGCAGGGCGCCCACATACCTGATATTGCCTCTCTGGAGGAAGTGCCCAAGATCTTCGAGGGTCTCGGTC
GCGACGAGAAACGGGCGGCGAACGCTCTGCACGGAGACAGCGAAAACGAGAGTCACTCGGGGGTGCTGGTGGAGCTCG
AGGGCGACAACGCGCGCCTGGCCGTACTCAAGCGCAGCATAGAGGTCACCCACTTTGCCTACCCGGCGCTCAACCTGC
CCCCCAAGGTCATGAGTGTGGTCATGGGCGAGCTCATCATGCGCCGCGCTCAGCCCCTGGCCGCGGATGCAAACTTGC
AAGAGTCCTCCGAGGAAGGCCTGCCCGCGGTCAGCGACGAGCAGCTAGCGCGCTGGCTGGAGACCGCGACCCCGCGC
AGCTGGAGGAGCGGCGCAAGCTCATGATGGCCGCGGTGCTGGTCACCGTGGAGCTCGAGTGTCTGCAGCGCTTCTTCG
CGGACCCCGAGATGCAGCGCAAGCTCGAGGAGACCCTGCACTACACCTTCCGCCAGGGCTACGTGCGCAGGCCTGCA
AGATCTCCAACGTGGAGCTCTGCAACCTGGTCTCCTACCTGGGCATCCTGCACGAGAACCGCCTCGGGCAGAACGTCC
TGCACTCCACCCTCAAAGGGGAGGCGCGCCGCGACTACATCCGCGACTGCGCCTACCTCTTCCTCTGCTACACCTGGC
AGACGCCATGGGGGTCTGGCAGCAGTGCCTGGAGGAGCGCAACCTCAAGGAGCTGGAAAAGCTACTCAAGCGCACCC
TCAGGGACCTCTGGACGGGCTTCAACGAGCGCTCGGTGGCCGCCGCGCTGGCGGACATCATCTTCCCCGAGCGCCTGC
TCAAGACCCTGCAGCAGGGCCTGCCCGACTTCACCAGCCAGAGCATGCTGCAGAACTTTAGGACTTTCATCCTGGAGC
GCTCGGGCATCCTGCCTGCCACTTGCTGCGCGCTGCCCAGCGACTTCGTGCCCATCAAGTACAGGGAGTGCCCGCCGC
CGCTCTGGGGCCACTGCTACCTCTTCCAGCTGGCCAACTACCTCGCCTACCACTCGGACCTCATGGAAGACGTGAGCG
GCGAGGGCCTGCTCGAGTGCCACTGCCGCTGCAACCTCTGCACGCCCCACCGCTCTCTAGTCTGCAACCCGCAGCTGC
TCAGCGAGAGTCAGATTATCGGTACCTTCGAGCTGCAGGGTCCCTCGCCTGACGAGAAGTCCGCGGCTCCGGGCTGA
AACTCACTCCGGGGCTGTGGACTTCCGCCTACCTACGCAAATTTGTACCTGAGGACTACCACGCCCACGAGATCAGGT
TCTACGAAGACCAATCCCGCCCGCCCAAGGCGGAGCTCACCGCCTGCGTCATCACCCCAGGGGCACATCCTGGGCCAAT
TGCAAGCCATCAACAAAGCCCGCCGAGAGTTCTTGCTGAAAAAGGGTCGGGGGGTGTACCTGGACCCCCAGTCCGGCG
AGGAGCTAAACCCGCTACCCCCGCCGCCGCCCCAGCAGCGGGACCTTGCTTCCCAGGATGGCACCCAGAAAGAAGCAG
CAGCCGCCGCCGCCGCAGCCATACATGCTTCTGGAGGAAGAGGAGGAGGACTGGGACAGTCAGGCAGAGGAGGTTTCG
GACGAGGAGCAGGAGGAGATGATGGAAGACTGAGGAGGACAGCAGCCTAGACGAGGAAGCTTCAGAGGCCGAAGAG
GTGGCAGACGCAACACCATCACCCTCGGTCGCAGCCCCCTCGCCGGGGCCCCTGAAATCCTCCGAACCCAGCACCAGC
GCTATAACCTCCGCTCCTCCGGCGCCGGCGCCACCCGCCCGCAGACCCAACCGTAGATGGGACACCACAGGAACCGGG
GTCGGTAAGTCCAAGTGCCCGCCGCCACCGCAGCAGCAGCAGCAGCGCCAGGGCTACCGCTCGTGGCGCGGGCAC
AAGAACGCCATAGTCGCCTGCTTGCAAGACTGCGGGGGCAACATCTCTTTCGCCCGGCGCTTCCTGCTATTCCACCAC
GGGGTCGCCTTTCCCCGCAATGTCCTGCATTACTACCGTCATCTCTACAGCCCCTACTGCAGCGGCGACCCAGAGGCG
GCAGCGGCAGCCACAGCGGCGACCACCACCTAGGAAGATATCCTCCGCGGGCAAGACAGCGGCAGCAGCGGCCAGGAG
ACCCGCGGCAGCAGCGGCGGGAACGGTGGGCGCACTGCGCCTCTCGCCCAACGAACCCCTCTCGACCCGGGAGCTCAG
ACACAGGATCTTCCCCACTTTGTATGCCATCTTCCAACAGACAGAGGCCAGGAGCAGGAGCTGAAAATAAAAAACAG
ATCTCTGCGCTCCCTCACCCGCAGCTGTCTGTATCACAAAAGCGAAGATCAGCTTCGGCGCACGCTGGAGGACGCGGA
GGCACTCTTCAGCAAATACTGCGCGCTCACTCTTAAAGACTAGCTCCGCGCCCTTCTCGAATTTAGGCGGGAGAAAAC
TACGTCATCGCCGCGCCGCCCAGCCCGCCCAGCCGAGATGAGCAAAGAGATTCCCACGCCATACATGTGGAGCTAC
CAGCCGCAGATGGGACTCGCCGCGGGAGCGGCCCAGGACTACTCCACCCGCATGAACTACATGAGCGCGGGACCCCAC
ATGATCTCACAGGTCAACGGGATCCGCGCCCAGCGAAACCAAATACTGCTGGAACAGGCGGCCATCACCGCCACGCCC
CGCCATAATCTCAACCCCCGAAATTGGCCCGCCGCCCTCGTGTACCAGGAAACCCCCTCCGCCACCACCGTACTACTT
CCGCGTGACGCCCAGGCCGAAGTCCAGATGACTAACTGCAGGGGCGCAGCTCGCGGGCGGCTTTCGTCACGGGCGCGG
CCGCTCCGACCAGGTATAAGACACCTGATGATCAGAGGCCGAGGTATCCAGCTCAACGACGAGTCGGTGAGCTCTTCG
CTCGGTCTCCGTCCGGACGGAACTTTCCAGCTCGCCGGATCCGGCCGCTCTTCGTTCACGCCCGCCAGGCGTACCTG
ACTCTGCAGACCTCGTCCTCGGAGCCCCGCTCCGGAGGCATCGGAACCCTCCAGTTCGTGGAGGAGTTCGTGCCCTCG
GTCTACTTCAACCCCTTCTCGGGACCTCCCGGACGCTACCCCGACCAGTTCATTCCGAACTTTGACGCGGTGAAGGAC
TCGGCGGACGGCTACGACTGAATGTCAGGTGCCGAGGCAGAGCAGCTTCGCCTGAGACACCTCGAGCACTGCCGCCGC
CACAAGTGCTTCGCCCGCGGTTCCGGTGAGTTCTGCTACTTTCAGCTACCCGAGGAGCATACCGAGGGGCCGGCGCAC
GGCGTCCGCCTGACCACCCACCAGGGCGAGGTTACCTGTTCCCTCATCCGGGAGTTCACCCTCCGTCCCCTGCTAGTGGAG
CGGGAGCGGGGTCCCTGTGTCCTAACTATCGCCTGCAACTGCCCTAACCCTGGATTACATCAAGATCTTTGCTGTCAT
CTCTGTGCTGAGTTTAATAAACGCTGAGATCAGAATCTACTGGGAATTCGATTTAGTCCCCTTTAACTAATCAAACAC
TGGAATCAATAAAAAGAATCACTTACTTAAAATCAGACAGCAGGTCTCTGTCCAGTTTATTCAGCAGCACCTCCTTCC
CCTCCTCCCAACTCTGGTACTCCAAACGCCTTCGGCGGCAAACTTCCTCCACACCCTGAAGGGAATGTCAGATTCTT
GCTCCTGTCCCTCCGCACCCACTATCTTCATGTTGTTGCAGATGAAGCGCACCAAAACGTCTGACGAGAGCTTCAACC
```

Fig. 5G

```
CCGTGTACCCCTATGACACGGAAAGCGGCCCTCCCTCCGTCCCTTTCCTCACCCCTCCCTTCGTGTCTCCCGATGGAT
TCCAAGAAAGCCCCCCGGGGTCCTGTCTCTGAACCTGGCCGAGCCCCTGGTCACTTCCCACGGCATGCTCGCCCTGA
AAATGGGAAGTGGCCTCTCCCTGGACGACGCTGGCAACCTCACCTCTCAAGATATCACCACCGCTAGCCCTCCCCTCA
AAAAAACCAAGACCAACCTCAGCCTAGAAACCTCATCCCCCCTAACTGTAAGCACCTCAGGCGCCCTCACCGTAGCAG
CCGCCGCTCCCCTGGCAGTGGCCGGCACCTCCCTCACCATGCAATCAGAGGCCCCCCTGACAGTACAGGATGCAAAAC
TCACCCTGGCCACCAAAGGCCCCCTGACCGTGTCTGAAGGCAAACTGGCCTTGCAAACATCGGCCCCGCTGACGGCCG
CTGACAGCAGCACCCTCACCGTTAGCGCCACACCACCAATTAATGTAAGCAGTGGAAGTTTAGGCTTAGACATGGAAG
ACCCTATGTATACTCACGATGGAAAACTGGGAATAAGAATTGGGGGTCCACTAAGAGTAGTAGACAGCTTGCACACAC
TCACTGTAGTTACCGGAAATGGACTAACTGTAGATAACAATGCCCTCCAAACTAGAGTTACGGGCGCCCTAGGTTATG
ACACATCAGGAAATCTACAATTGAGAGCTGCAGGAGGTATGCGAATTGATGCAAATGGCCAACTTATCCTTAATGTGG
CATACCCATTTGATGCTCAGAACAATCTCAGCCTTAGACTTGGTCAGGGACCCCTGTATATAAACACAGACCACAACC
TGGATTTGAATTGCAACAGAGGTCTAACCACAACTACCACCAACAACACAAAAAAACTTGAGACTAAAATTAGCTCAG
GCTTAGACTATGACACCATGGTGCTGTCATTATTAAACTTGGCACTGGTCTAAGCTTCGACAACACAGGCGCCCTAA
CTGTGGGAAACACTGGTGATGATAAACTGACTCTGTGGACGACCCCAGACCCATCTCCAAATTGCAGAATTCACTCAG
ACAAAGACTGCAAGTTTACTCTAGTCCTAACTAAGTGTGGAAGCCAAATCCTGGCCTCTGTCGCCGCCCTAGCGGTAT
CAGGAAATCTGGCTTCGATAACAGGCACCGTTGCCAGCGTTACCATCTTTCTCAGATTTGATCAGAATGGAGTGCTTA
TGGAAAACTCCTCGCTAGACAGGCAGTACTGGAACTTCAGAAATGCCAACTCAACTAACGCTGCCCCCTACACCAATG
CAGTTGGGTTCATGCCAAACCTCGCAGCATACCCCAAAACGCAAAGCCAGACTGCTAAAAACAACATTGTAAGTCAGG
TTTACTTGAATGGAGACAAATCCAAACCCATGACCCTTACCATCACCCTCAATGGAACTAATGAATCCAGTGAAACTA
GCCAGGTGAGTCACTACTCCATGTCATTTACATGGGCTTGGGAAAGTGGGCAATATGCCACTGAAACCTTTGCCACCA
ACTCCTTCACCTTTTCTTACATTGCTGAACAATAAAAAGCATGACACTGATGTTCATTTCTGATTCTTATTTTATTAT
TTTCAAACACAACAAAATCATTCAAGTCATTCTTCCATCTTAGCTTAATAGACACAGTAGCTTAATAGACCCAGTAGT
GCAAAGCCCCATTCTAGCTTATAACTAGTGGAGAAGTACTCGCCTACATGGGGGTAGAGTCATAATCGTGCATCAGGA
TAGGGCGGTGGTGCTGCAGCAGCGCGCGAATAAACTGCTGCCGCCGCCGCTCCGTCCTGCAGGAATACAACATGGCAG
TGGTCTCCTCAGCGATGATTCGCACCGCCCGCAGCATAAGGCGCCTTGTCCTCCGGGCACAGCAGCGCACCCTGATCT
CACTTAAATCAGCACAGTAACTGCAGCACAGCACCACAATATTGTTCAAAATCCCACAGTGCAAGGCGCTGTATCCAA
AGCTCATGGCGGGGACCACAGAACCCACGTGGCCATCATACCACAAGCGCAGGTAGATTAAGTGGCGACCCCTCATAA
ACACGCTGGACATAAACATTACCTCTTTTGGCATGTTGTAATTCACCACCTCCCGGTACCATATAAACCTCTGATTAA
ACATGGCGCCATCCACCACCATCCTAAACCAGCTGGCCAAAACCTGCCCGCCGGCTATACACTGCAGGGAACCGGGAC
TGGAACAATGACAGTGGAGAGCCCAGGACTCGTAACCATGGATCATCATGCTCGTCATGATATCAATGTTGGCACAAC
ACAGGCACACGTGCATACACTTCCTCAGGATTACAAGCTCCTCCCGCGTTAGAACCATATCCCAGGGAACAACCCATT
CCTGAATCAGCGTAAATCCCACACTGCAGGGAAGACCTCGCACGTAACTCACGTTGTGCATTGTCAAAGTGTTACATT
CGGGCAGCAGCGGATGATCCTCCAGTATGGTAGCGCGGGTTTCTGTCTCAAAAGGAGGTAGACGATCCCTACTGTACG
GAGTGCGCCGAGACAACCGAGATCGTGTTGGTCGTAGTGTCATGCCAAATGGAACGCCGGACGTAGTCATATTTCCTG
AAGTCTTAGATCTCTCAACGCAGCACCAGCACCAACACTTCGCAGTGTAAAAGGCCAAGTGCCGAGAGAGTATATATA
GGAATAAAAAGTGACGTAAACGGGCAAAGTCCAAAAAACGCCCAGAAAACCGCACGCGAACCTACGCCCCGAAACGA
AAGCCAAAAAACACTAGACACTCCCTTCCGGCGTCAACTTCCGCTTTCCCACGCTACGTCACTTGCCCCAGTCAAACA
AACTACATATCCCGAACTTCCAAGTCGCCACGCCCAAAACACCGCCTACACCTCCCCGCCCGCCGGCCCGCCCCCAAA
CCCGCCTCCCGCCCCGCGCCCCGCCCCGCGCCGCCCATCTCATTATCATATTGGCTTCAATCCAAAATAAGGTATATT
ATTGATGATG
```

Fig. 5H

```
CATCATCAATAATATACCTTATTTTGGATTGAAGCCAATATGATAATGAGATGGGCGGCGCGAGGCGGGGCGCGGGGC
GGGAGGCGGGTTTGGGGGCGGGCCGGCGGGCGGGGCGGTGTGGCGGAAGTGGACTTTGTAAGTGTGGCGGATGTGACT
TGCTAGTGCCGGGCGCGGTAAAAGTGACGTTTTCCGTGCGCGACAACGCCCCCGGGAAGTGACATTTTTCCCGCGGTT
TTTACCGGATGTTGTAGTGAATTTGGGCGTAACCAAGTAAGATTTGGCCATTTTCGCGGGAAAACTGAAACGGGGAAG
TGAAATCTGATTAATTTTGCGTTAGTCATACCGCGTAATATTTGTCTAGGGCCGAGGGACTTTGGCCGATTACGTGGA
GGACTCGCCCAGGTGTTTTTTGAGGTGAATTTCCGCGTTCCGGGTCAAAGTCTCCGTTTTATTATTATAGTCAGCTGA
CGCGGAGTGTATTTATACCCTCTGATCTCGTCAAGAGGCCACTCTTGAGTGCCAGCGAGTAGAGTTTTCTCCTCTGCC
GCTCTCCGCTCCGCTCCGCTCGGCTCTGACACCGGGGAAAAAATGAGACATTTCACCTACGATGGCGGTGTGCTCACC
GGCCAGCTGGCTGCTGAGGTCCTGGACACCCTGATCGAGGAGGTATTGGCCGATAATTATCCTCCCTCGACTCCTTTT
GAGCCACCTACACTTCACGAACTATACGATCTGGATGTGGTGGGGCCCAGCGATCCGAACGAGCAGGCGGTTTCCAGT
TTTTTTCCAGAGTCCATGTTGTTGGCCAGCCAGGAGGGGGTCGAACTTGAGACCCCTCCTCCGATCGTGGATTCCCCC
GATCCGCCGCAGCTGACTAGGCAGCCCGAGCGCTGTGCGGGACCTGAGACTATGCCCCAGCTGCTACCTGAGGTGATC
GATCTCACCTGTAATGAGTCTGGTTTTCCACCCAGCGAGGATGAGGACGAAGAGGGTGAGCAGTTTGTGTTAGATTCT
GTGGAACAACCCGGGCGAGGATGCAGGTCTTGTCAATATCACCGGAAAAACACAGGAGACTCCCAGATTATGTGTTCT
CTGTGTTATATGAAGATGACCTGTATGTTTATTTACAGTAAGTTTATCATCGGTGGGCAGGTGGCGTATAGTGTGGGT
GGTGGTCTTTGGGGGGTTTTTTAATATATGTCAGGGGTTATGCTGAAGACTTTTTTATTGTGATTTTTAAAGGTCCAG
TGTCTGAGCCCGAGCAAGAACCTGAACCGGAGCCTGAGCCTTCTCGCCCCAGGAGAAAGCCTGTAATCTTAACTAGAC
CCAGCGCACCGGTAGCGAGAGGCCTCAGCAGCGCGGAGACCACCGACTCCGGTGCTTCCTCATCACCCCCGGAGATTC
ACCCCCTGGTGCCCCTATGTCCCGTTAAGCCCGTTGCCGTGAGAGTCAGTGGGCGGCGGTCTGCTGTGGAGTGCATTG
AGGACTTGCTTTTTGATTCACAGGAACCTTTGGACTTGAGCTTGAAACGCCCCAGGCATTAAACCTGGTCACCTGGAC
TGAATGAGTTGACGCCTATGTTTGCTTTTGAATGACTTAATGTGTATAGATAATAAAGAGTGAGATAATGTTTTAATT
GCATGGTGTGTTTAACTTGGGCGGAGTCTGCTGGGTATATAAGCTTCCCTGGGCTAAACTTGGTTACACTTGACCTCA
TGGAGGCCTGGGAGTGTTTGGAGAACTTTGCCGGAGTTCGTGCCTTGCTGGACGAGAGCTCTAACAATACCTCTTGGT
GGTGGAGGTATTTGTGGGGCTCTCCCCAGGGCAAGTTAGTTTGTAGAATCAAGGAGGATTACAAGTGGGAATTTGAAG
AGCTTTTGAAATCCTGTGGTGAGCTATTGGATTCTTTGAATCTAGGCCACCAGGCTCTCTTCCAGGAGAAGGTCATCA
GGACTTTGGATTTTTCCACACCGGGGCGCATTGCAGCCGCGGTTGCTTTTCTAGCTTTTTTGAAGGATAGATGGAGCG
AAGAGACCCACTTGAGTTCGGGCTACGTCCTGGATTTTCTGGCCATGCAACTGTGGAGAGCATGGATCAGACACAAGA
ACAGGCTGCAACTGTTGTCTTCCGTCCGCCCGTTGCTGATTCCGGCGGAGGAGCAACAGGCCGGGTCAGAGGACCGGG
CCCGTCGGGATCCGGAGGAGAGGGCACCGAGGCCGGGCGAGAGGAGCGCGCTGAACCTGGGAACCGGGCTGAGCGGCC
ATCCACATCGGGAGTGAATGTCGGGCAGGTGGTGGATTCTTTTTCCAGAACTGCGGCGGATTTTGACTATTAGGGAGGA
TGGGCAATTTGTTAAGGGTCTTAAGAGGGAGAGGGGGGCTTCTGAGCATAACGAGGAGGCCAGTAATTTAGCTTTTAG
CTTGATGACCAGACACCGTCCAGAGTGCATCACTTTTCAGCAGATTAAGGACAATTGTGCCAATGAGTTGGATCTGTT
GGGTCAGAAGTATAGCATAGAGCAGCTGACCACTTACTGGCTGCAGCCGGGTGATGATCTGGAGGAAGCTATTAGGGT
GTATGCTAAGGTGGCCCTGCGGCCCGATTGCAAGTACAAGCTCAAGGGGCTGGTGAATATCAGGAATTGTTGCTACAT
TTCTGGCAACGGGGCGGAGGTGGAGATAGAGACCGAAGACAGGGTGGCTTTCAGATGCAGCATGATGAATATGTGGCC
GGGGGGTGCTGGGCATGGACGGGGTGGTGATTATGAATGTGAGGTTCACGGGGCCCAACTTTAACGGCACGGTGTTTTT
GGGGAACACCAACCTGGTCCTGCACGGGGTGAGCTTCTATGGGTTTAACAACACCTGTGTGGAGGCCTGGACCGATGT
GAAGGTCCGCGGTTGCGCCTTTTATGGATGTTGGAAGGCCATAGTGAGCCGCCCTAAGAGCAGGAGTTCCATTAAGAA
ATGCTTGTTTGAGAGGTGCACCTTGGGGATCCTGGCCGAGGGCAACTGCAGGGTGCGCCACAATGTGGCCTCCGAGTG
CGGTTGCTTCATGCTAGTCAAGAGCGTGGCGGTAATCAAGCATAATATGGTGTGCGGCAACAGCGAGGACAAGGCCTC
ACAGATGCTGACCTGCCGTGATGCTGGAACTGCCACTTGCTGAAGACCATCCATGTAACCAGCCACAGCCGGAAGGCCTG
GCCCGTGTTCGAGCACAACTTGCTGACCCGCTGCTCCTTGCATCTGGGCAACAGGCGGGGGGTGTTCCTGCCCTATCA
ATGCAACTTTAGTCACACCAAGATCTTGCTAGAGCCCGAGAGCATGTCCAAGGTGAACTTGAACGGGGTGTTTGACAT
GACCATGAAGATCTGGAAGGTGCTGAGGTACGACGAGACCAGGTCCCGGTGCAGACCCTGCGAGTGCGGGGGCAAGCA
TATGAGGAACCAGCCCGTGATGCTGGATGTGACCGAGGAGCTGGAGGACAGACCACTTGGTTCTGGCCTGCACCAGGGC
CGAGTTTGGTTCTAGCGATGAAGACACAGATTGAGGTGGGTGAGTGGGCGTGGCCTGGGGTGGTCATGAAAATATATA
AGTTGGGGGTCTTAGGGTCTCTTTATTTGTGTTGCAGAGACCGCCGGAGCCATGAGCGGGAGCAGCAGCAGCAGCAGT
AGCAGCAGCGCCTTGGATGGCAGCATCGTGAGCCCTTATTTGACGACGCGGATGCCCCACTGGGCCGGGGTGCGTCAG
AATGTGATGGCATCGACGGCCGACCCGTCCTGCCCGCAAATTCCGCCACGCTGACCCATGCTGACCTATGCGACCGTCGCG
GGGACGCCGTTGGACGCCACCGCCGCCGCCGCCACCGGCAGCCGCCTCGGCCGTGCGCAGCCTGGCCACGGACTTT
GCATTCCTGGGACCACTGGCGACAGGGGCTACTTCTCGGGCCGCTGCTGCCGCCGTTCGCGATGACAAGCTGACCGCC
CTGCTGGCGCAGTTGGATGCGCTTACTCGGGAACTGGGTGACCTTTCTCAGCAGGTCATGGCCCTGCGCCAGCAGGTC
TCCTCCCTGCAAGCTGGCGGGAATGCTTCTCCCACAAATGCCGTTTAAGATAAATAAAACCAGACTCTGTTTGGATTA
AGAAAAGTAGCAAGTGCATTGCTCTCTTTATTTCATAATTTTCCGCGCGCGATAGGCCCTAGACCAGCGTTCTCGGT
CGTTGAGGGTGCGGTGTATCTTCCAGGACGTGGTAGAGGTGCTCTGGACGTTGAGATACATGGGCATGAGCCCGT
CCCGGGGGTGGAGGTAGCACCACTGCAGAGCTTCATGCTCCGGGGTGGTGTTGTAGATGATCCAGTCGTAGCAGGAGC
GCTGGGCATGGTGCCTAAAAATGTCCTTCAGCAGCAGGCCGATGCCAGGGGAGGCCCTTGGTGTAAGTGTTTACAA
AACGGTTAAGTTGGGAAGGGTGCATTCGGGGAGAGATGATGTGCATCTTGGACTGTATTTTTAGATTGGCGATGTTTC
CGCCCAGATCCCTTCTGGGATTCATGTTGTGCAGGACCACCAGTACAGTGTATCCGGTGCACTTGGGGAATTTGTCAT
GCAGCTTAGAGGGAAAAGCGTGGAAGAACTTGGAGACGCCCTTGTGGCCTCCCAGATTTTCCATGCATTCGTCCATGA
```

Fig. 6A

```
TGATGGCAATGGGCCCGCGGGAGGCAGCTTGGGCAAAGATATTTCTGGGGTCGCTGACGTCGTAGTTGTGTTCCAGGG
TGAGGTCGTCATAGGCCATTTTTACAAAGCGCGGGCGGAGGGTGCCCGACTGGGGGATGATGGTCCCCTCTGGCCCTG
GGGCGTAGTTGCCCTCGCAGATCTGCATTTCCCAGGCCTTAATCTCGGAGGGGGGAATCATATCCACCTGCGGGGCGA
TGAAGAAAACGGTTTCCGGAGCCGGGGAGATTAACTGGGATGAGAGCAGGTTTCTAAGCAGCTGTGATTTTCCACAAC
CGGTGGGCCCATAAATAACACCTATAACCGGTTGCAGCTGGTAGTTTAGAGAGCTGCAGCTGCCGTCGTCCCGGAGGA
GGGGGGCCACCTCGTTGAGCATGTCCCTGACGCGCATGTTCTCCCCGACCAGATCCGCCAGAAGGCGCTCGCCGCCCA
GGGACAGCAGCTCTTGCAAGGAAGCAAAGTTTTTCAGCGGCTTGAGGCCGTCCGCCGTGGGCATGTTTTTCAGGGTCT
GGCTCAGCAGCTCCAGGCGGTCCCAGAGCTCGGTGACGTGCTCTACGGCATCTCTATCCAGCATATCTCCTCGTTTCG
CGGGTTGGGGCGACTTTCGCTGTAGGGCACCAAGCGGTGGTCGTCCAGCGGGGCCAAAGTCATGTCCTTCCATGGGCG
CAGGGTCCTCGTCAGGGTGGTCTGGGTCACGGTGAAGGGGTGCGCTCCGGGCTGAGCGCTTGCCAAGGTGCGCTTGAG
GCTGGTTCTGCTGGTGCTGAAGCGCTGCCGGTCTTCGCCCTGCGCGTCGGCCAGGTAGCATTTGACCATGGTGTCATA
GTCCAGCCCCTCCGCGGCGTGTCCCTTGGCGCGCAGCTTGCCCTTGGAGGTGGCGCCGCACGAGGGGCAGAGCAGGCT
CTTGAGCGCGTAGAGCTTGGGGGCGAGGAAGACCGATTCGGGGGAGTAGGCGTCCGCGCCGCAGACCCCGCACACGGT
CTCGCACTCCACCAGCCAGGTGAGCTCGGGGCGCGCCGGGTCAAAAACCAGGTTTCCCCCATGCTTTTTGATGCGTTT
CTTACCTCGGGTCTCCATGAGGTGGTGTCCCCGCTCGGTGACGAAGAGGCTGTCCGTGTCTCCGTAGACCGACTTGAG
GGGTCTTTTCTCCAGGGGGGTCCCTCGGTCTTCCTCGTAGAGGAACTCGGACCACTCTGAGACGAAGGCCCGCGTCCA
GGCCAGGACGAAGGAGGCTATGTGGGAGGGGTAGCGGTCGTTGTCCACTAGGGGGTCCACCTTCTCCAAGGTGTGAAG
ACACATGTCGCCTTCCTCGGCGTCCAGGAAGGTGATTGGCTTGTAGGTGTAGGCCACGTGACCGGGGGTTCCTGACGG
GGGGGTATAAAAGGGGGTGGGGGCGCGCTCGTCGTCACTCTCTTCCGCATCGCTGTCTGCGAGGGCCAGCTGCTGGGG
TGAGTATTCCCTCTCGAAGGCGGGCATGACCTCCGCGCTGAGGTTGTCAGTTTCCAAAAACGAGGAGGATTTGATGTT
CACCTGTCCCGAGGTGATACCTTTGAGGGTACCCGCGTCCATCTGGTCAGAAAACACGATCTTTTTATTGTCCAGCTT
GGTGGCGAACGACCCGTAGAGGGCGTTGGAGAGCAGCTTGGCGATGGAGCGCAGGGTCTGGTTCTTGTCCCTGTCGGC
GCGCTCCTTGGCCGCGATGTTGAGCTGCACGTACTCGCGCGCGACGCAGCGCCACTCGGGGAAGACGGTGGTGCGCTC
GTCGGGCACCAGGCGCACGCGCCAGCCGCGGTTGTGCAGGGTGACCAGGTCCACGCTGGTGGCGACCTCGCCGCGCAG
GCGCTCGTTGGTCCAGCAGAGACGGCCGCCCTTGCGCGAGCAGAAGGGGGCAGGGGTCGAGCTGGGTCTCGTCCGG
GGGGTCCGCGTCCACGGTGAAAACCCCGGGGCGCAGGCGCGCGTCGAAGTAGTCTATCTTGCAACCTTGCATGTCCAG
CGCCTGCTGCCAGTCGCGGGCGGCGAGCGCCGCGCTGTAGGGGTTGAGCGGCGGGCCCCAGGGCATGGGGTGGGTGAG
TGCGGAGGCGTACATGCCGCAGATGTCATAGACGTAGAGGGGCTCCCGCAGGACCCCGATGTAGGTGGGGTAGCAGCG
GCCGCCGCGGATGCTGGCGCGCACGTAGTCATACAGCTCGTGCGAGGGGGCGAGGAGGTCGGGGCCCAGGTTGGTGCG
GGCGGGGCGCTCCGCGCGGAAGACGATCTGCCTGAAGATGGCATGCGAGTTGGAAGAGATGGTGGGGCGCTGGAAGAC
GTTGAAGCTGGCGTCCTGCAGGCCGACGGCGTCGCGCACGAAGGAGGCGTAGGAGTCGCGCAGCTTGTGTACCAGCTC
GGCGGTGACCTGCACGTCGAGCGCGCAGTAGTCGAGGGTCTCGCGGATGATGTCATATTTAGCCTGCCCCTTCTTTTT
CCACAGCTCGCGGTTGAGGACAAACTCTTCGCGGTCTTTCCAGTACTCTTGGATCGGGAAACCGTCCGGTTCCGAACG
GTAAGAGCCTAGCATGTAGAACTGGTTGACGGCCTGGTAGGCGCAGCAGCCCTTCTCCACGGGGAGGGCGTAGGCCTG
CGCGGCCTTGCGGAGCGAGGTGTGGGTCAGGGCGAAGGTGTCCCTGACCATGACTTTGAGGTACTGGTGCTTGAAGTC
GGAGTCGTCGCAGCCGCCCCGCTCCCAGAGCGAGAAGTCGGTGCGCTTCTTGGAGCGGGGGTTGGGCAGAGCGAAGGT
GACATCGTTGAAGAGGATTTTGCCCGCGCGGGGCATGAAGTTGCGGGTGATGCGGAAGGGCCCCGGCACTTCAGAGCG
GTTGTTGATGACCTGGGCGGCGAGCACGATCTCGTCGAAGACGTTGATGTTGTGGCCCACGATGTAGAGTTCCAGGAA
GCGGGGCCGGCCCTTTACGGTGGGCAGCTTCTTTAGCTCTTCGTAGGTGAGCTCCTCGGGCGAGGCGAGGCCGTGCTC
GGCCAGGGCCCAGTCCGCGAGGTGCGGGTTGTCTCTGAGGAAGGACTCCCAGAGGTCGCGGGCCAGGAGGGTCTGCAG
GCGGTCCCTGAAGGTCCTGAACTGGCGGCCCACGGCCATTTTTCGGGGGTGATGCAGTAGAAGGTGAGGGGGTCTTG
CTGCCAGCGGTCCCAGTCGAGCTGCAGGGCGAGGTCGCGCGGCGGTGACCAGGCGCTCGTCGCCCCCGAATTTCAT
GACCAGCATGAAGGGCACGAGCTGCTTTCCGAAGGCCCCCATCCAAGTGTAGGTCTCTACATCGTAGGTGACAAAGAG
GCGCTCCGTGCGAGGATGCGAGCCGATCGGGAAGAACTGGATCTCCCGCCACCAGTTGGAGGAGTGGCTGTTGATGTG
GTGGAAGTAGAAGTCCCGTCGCCGGGCCGAACACTCGTGCTGGCTTTTGTAAAAGCGAGCGCAGTACTGGCAGCGCTG
CACGGGCTGTACCTCCTGCACGAGATGCACCTTTCGCCCGCGCACGAGGAAGCCGAGGGGAAATCTGAGCCCCCCGCC
TGGCTCGCGGCATGGCTGGTGCTCTTCTACTTTGGATGCGTGTCCGTCTCCGTCTGGCTCCTCGAGGGGTGTTACGGT
GGAGCGGACCACCACGCCGCGCGAGCCGCAGGTCCAGATATCGGCGCGCGGCGGTCGGAGTTTGATGACGACATCGCG
CAGCTGGGAGCTGTCCATGGTCTGGAGCTCCCGCGGCGGCGGCAGGTCAGCCGGGAGTTCTTGCAGGTTCACCTCGCA
GAGTCGGGCCAGGGCGCGGGGCAGGTCTAGGTGGTACCTGATCTCTAGGGGCGTGTTGGTGGCGGCGTCGATGGCTTG
CAGGAGCCCGCATCCCCGGGGGGCGACGACGGTGCCCCGCGGGGTGGTGGTGGTGGTGGTGGTGGTGGCGGT
GCAGCTCAGAAGCGGTGCCGCGGGCGGGCCCCCGGAGGTAGGGGGGGCTCCGGTCCCGCCGGCAGGGCGGCAGCGGC
ACGTCGGCGTGGAGCGCGGGCAGGAGTTGGTGCTGTGCCCGGAGGTTGCTGGCGAAGGCGACGACGCGGCGGTTGATC
TCCTGGATCTGGCGCCTCTGCGTGAAGACGACGGGCCCGGTGAGCTTGAACCTGAAAGAGAGTTCGACAGAATCAATC
TCGGTGTCATTGACCGCGGCCTGGCGCAGGATCTCCTGCACGTCTCCCGAGTTGTCTTGGTAGGCGATCTCGGCCATG
AACTGCTCGATCTCTTCCTCCTGGAGGTCTCCGCGTCCGGCGCGTTCCACGGTGGCCGCCAGGTCGTTGGAGATGCGC
CCCATGAGCTGCGAGAAGGCGTTGAGTCCGCCCTCGTTCCAGACTCGGCTGTAGACCACGCCCCCTCTGTCATCGCGG
GCGCGCATGACCACCTGCGCGAGGTTGAGCTCCACGTGCCGCGCGAAGACGGCTAGTTGCGCAGACGCTGGAAGAGG
TAGTTGAGGGTGGTGGCGGTGTGCTCGGCCACGAAGAAGTTCATGACCCAGCGCGCAACGTGGATTCGTTGATGTCC
CCCAAGGCCTCCAGCCGTTCCATGGCCTCGTAGAAGTCCACGGCGAAGTTGAAAAACTGGGAGTTGCGCGCCGACACG
```

Fig. 6B

```
GTCAACTCCTCCTCCAGAAGACGGATGAGCTCGGCGACGGTGTCGCGCACCTCGCGCTCGAAGGCTATGGGGATCTCT
TCCTCCGCTAGCATCACCACCTCCTCCTCTTCCTCCTCTTCTGGCACTTCCATGATGGCTTCCTCCTCTTCGGGGGGC
GGCGGCGGCGGCGGTGGGGGAGGGGCGCTCTGCGCCGGCGGCGGCGCACCGGGAGGCGGTCCACGAAGCGCGCGATC
ATCTCCCGCGGCGGCGGCGCATGGTCTCGGTGACGGCGCGGCCGTTCTCCCGGGGGCGCAGTTGGAAGACGCCGCCG
GACATCTGGTGCTGGGGCGGGTGGCCGTGAGGCAGCGAAACGGCGCTGACGATGCATCTCAACAATTGCTGCGTAGGT
ACGCCGCCGAGGGACCTGAGGGAGTCCATATCCACCGGATCCGAAAACCTTTCGAGGAAGGCGTCTAACCAGTCGCAG
TCGCAAGGTAGGCTGAGCACCGTGGCGGGCGGCGGGGGGTGGGGGGAGTGTCTGGCGGAGGTGCTGCTGATGATGTAA
TTGAAGTAGGCGGACTTGACACGGCGGATGGTCGACAGGAGCACCATGTCCTTGGGTCCGGCCTGCTGGATGCGGAGG
CGGTCGGCTATGCCCCAGGCTTCGTTCTGGCATCGGCGCAGGTCCTTGTAGTAGTCTTGCATGAGCCTTTCCACCGGC
ACCTCTTCTCCTTCCTCTTCTGCTTCTTCCATGTCTGCTTCGGCCCTGGGGCGGCGCCGCGCCCCCTGCCCCCCATG
CGCGTGACCCCGAACCCCCTGAGCGGTTGGAGCAGGGCCAGGTCGGCGACGACGCGCTCGGCCAGGATGGCCTGCTGC
ACCTGCGTGAGGGTGGTTTGGAAGTCATCCAAGTCCACGAAGCGGTGGTAGGCGCCCGTGTTGATGGTGTAGGTGCAG
TTGGCCATGACGGACCAGTTGACGGTCTGGTGGCCCGGTTGCGACATCTCGGTGTACCTGAGTCGCGAGTAGGCGCGG
GAGTCGAAGACGTAGTCGTTGCAAGTCCGCACCAGGTACTGGTAGCCCACCAGGAAGTGCGGCGGCGGCTGGCGGTAG
AGGGGCCAGCGCAGGGTGGCGGGGGCTCCGGGGGCCAGGTCTTCCAGCATGAGGCGGTGGTAGGCGTAGATGTACCTG
GACATCCAGGTGATACCCGCGGCGGTGGTGGAGGCGCGCGGGAAGTCGCGCACCCGGTTCCAGATGTTGCGCAGGGGC
AGAAAGTGCTCCATGGTAGGCGTGCTCTGTCCAGTCAGACGCGCGCAGTCGTTGATACTCTAGACCAGGGAAAACGAA
AGCCGGTCAGCGGGCACTCTTCCGTGGTCTGGTGAATAGATCGCAAGGGTATCATGGCGGAGGGCCTCGGTTCGAGCC
CCGGGTCCGGGCCGGACGGTCCGCCATGATCCACGCGGTTACCGCCCGCGTGTCGAACCCAGGTGTGCGACGTCAGAC
AACGGTGGAGTGTTCCTTTTGGCGTTTTTCTGGCCGGGCGCCGGCGTCGCGTAAGAGACTAAGCCGCGAAAGCGAAAG
CAGTAAGTGGCTCGCTCCCCGTAGCCGGAGGGATCCTTGCTAAGGGTTGCGTTGCGGCGAACCCCGGTTCGAATCCCG
TACTCGGGCCGGCCGGACCCGCGGCTAAGGTGTTGGATTGGCCTCCCCCTCGTATAAAGACCCCGCTTGCGGATTGAC
TCCGGACACGGGGACGAGCCCCTTTTATTTTTGCTTTCCCCAGATGCATCCGGTGCTGCGGCAGATGCGCCCCCGCC
CCAGCAGCAGCAACAACACCAGCAAGAGCGGCAGCAACAGCAGCGGGAGTCATGCAGGGCCCCTCACCCACCCTCGG
CGGGCCGGCCACCTCGGCGTCCGCGGCCGTGTCTGGCGCCTGCGGCGGCGGCGGGGGGCCGGCTGACGACCCCGAGGA
GCCCCCGCGGCCGCAGGGCCAGACACTACCTGGACCTGGAGGAGGGCGAGGGCCTGGCGCGGCTGGGGGCGCCGTCTCC
CGAGCGCCACCCGCGGGTGCAGCTGAAGCGCGACTCGCGCGAGGCGTACGTGCCTCGGCAGAACCTGTTCAGGGACCG
CGCGGGCGAGGAGCCCGAGGAGATGCGGGACAGGAGGTTCAGCGCAGGGCGGGAGCTGCGGCAGGGGCTGAACCGCGA
GCGGCTGCTGCGCGAGGAGGACTTTGAGCCCGACGCGCGGACGGGGATCAGCCCCGCGCGCGCACGTGGCGGCCGC
CGACCTGGTGACGGCGTACGAGCAGACGGTGAACCAGGAGATCAACTTCCAAAAGAGTTTCAACAACCACGTGCGCAC
GCTGGTGGCGCGCGAGGAGGTGACCATCGGGCTGATGCACCTGTGGGACTTTGTAAGCGCGCTGGTGCAGAACCCCAA
CAGCAAGCCTCTGACGGCGCAGCTGTTCCTGATAGTGCAGCACAGCAGGGACAACGAGGCGTTTAGGGACGCGCTGCT
GAACATCACCGAGCCCGAGGGTCGGTGGCTGCTGGACCTGATTAACATCCTGCAGAGCATAGTGGTGCAGGAGCGCAG
CCTGAGCCTGGCCGACAAGGTGGCGGCCATCAACTACTCGATGCTGAGCCTGGGCAAGTTTTACGCGCAAGATCTA
CCAGACGCCGTACGTGCCCATAGACAAGGAGGTGAAGATCGACGGTTTTTACATGCGCATGGCGCTGAAGGTGCTCAC
CCTGAGCGACGACCTGGGCGTGTACCGCAACGAGCGCATCCACAAGGCCGTGAGCGTGAGCCGGCGGCGCGAGCTGAG
CGACCCGCGAGCTGATGCACGACCTGCAGCGGGCCTGGCGGGCGCCGGCGACAGGGAGGCGGAGTCCTACTT
CGATGCGGGGCGGACCTGCGCTGGGCGCCCAGCCGGCGGGCCCTGGAGGCCGCGGGGGTCCGCGAGGACTATGACGA
GGACGGCGAGGAGGATGAGGAGTACGAGCTAGAGGAGGGCGAGTACCTGGACTAAACCGCGGGTGGTGTTTCCGGTAG
ATGCAAGACCCGAACGTGGTGGACCCGGCGCTGCGGGCGGCTCTGCAGAGCCAGCCGTCCGGCCTTAACTCCTCAGAC
GACTGGCGACAGGTCATGGACCGCATCATGTCGCTGACGGCGCGTAACCCGGACGCGTTCCGGCAGCAGCCGCAGGCC
AACAGGCTCTCCGCCATCCTGGAGGCGGTGGTGCCTGCGCGCTCGAACCCCACGCACGAGAAGGTGCTGGCCATAGTG
AACGCGCTGGCCGAGAACAGGGCCATCCGCCCGGACGAGGCCGGGCTGGTGTACGACGCGCTGCTGCAGCGCGTGGCC
CGCTACAACAGCGGCAACGTGCAGACCAACCTGGACCGGCTGGTGGGGACGTGCGCGAGGCGGTGGCGCAGCGCGAG
CGCGCGGATCGGCAGGGCAACCTGGGCTCCATGGTGGCCGTGAATGCCTTCCTGAGCACGCAGCCGGCCAACGTGCCG
CGGGGCAGGAAGACTACACCAACTTTGTGAGCGCGCTGCGGCTGATGGTGACCGAGACCCCCCAGAGCGAGGTGTAC
CAGTCGGGCCCGGACTACTTCTTCCAGACCAGCAGACAGGGCCTGCAGACGGTGAACCTGAGCCAGGCTTTCAAGAAC
CTGCGGGGCTGTGGGGCGTGAAGGCGCCCACCGGCGACCGGGCGACGGTGTCCAGCCTGCTGACGCCCAACTCGCGC
CTGCTGCTGCTGCTGATCGCGCCGTTCACGGACAGCGGCAGCGTGTCCCGGGACACCTACCTGGGGCACCTGCTGACC
CTGTACCGCGAGGCCATCGGGCAGGCGCAGGTGGACGAGCACACCTTCCAGGAGATCACCAGCGTGAGCCGCGCGCTG
GGGCAGGAGGACACGAGCAGCCTGGAGGCGACTCTGAACTACCTGCTGACCAACCGGCGGCAGAAGATTCCCTCGCTG
CACAGCCTGACCTCCGAGGAGGAGCGCATCTTGCGCTACGTGCAGCAGAGCGTGAAGCGTGAACCTGATGCGCGACGGG
GTGACGCCCAGCGTGGCGCTGGACATGACCGCGCGCAACATGGAACCGGGCATGTACGCCGCGCACCGGCCTTACATC
AACCGCCTGATGGACTACCTGCATCGCGCGGCGGCCGTGAACCCCGAGTACTTTACCAACGCCATCCTGAACCCGCAC
TGGCTCCCGCCGCCCGGGTTCTACAGCGGGGGCTTCGAGGTCCCGGAGGCCAACGATGGCTTCCTGTGGGACGACATG
GACGACAGCGTGTTCTCCCCGCGGCCGCAGGCGCTGGCGGAAGCGTCCCTGCTGCGTCCCAAGAAGGAGGAGGAGGAG
GCGAGTCGCCGCCGCGCAGCAGCGGCGTGGCTTCTCTGTCCGAGCTGGGGGCGGCAGCCGCCGCGCGCCCCGGGTCC
CTGGGCGGCAGCCCCTTTCCGAGCCTGGTGGGGTCTCTGCACAGCGAGCGCACCACCCGCCCTCGGCTGCTGGGCAG
GACGAGTACCTGAATAACTCCCTGCTGCAGCCGGTGCGGGAGAAAAACCTGCCCCCCGCCTTCCCCAACAACGGGATA
GAGAGCCTGGTGGACAAGATGAGCAGATGGAAGACCTATGCGCAGGAGCACAGGGACGCGCCCGCGCTCCGGCCGCCC
ACGCGGCGCCAGCGCCACGACCGGCAGCGGGGCGTGGTGTGGGATGACGAGGACTCCGCGGACGATAGCAGCGTGCTG
```

Fig. 6C

```
GACCTGGGAGGGAGCGGCAACCCGTTCGCGCACCTGCGCCCCGCCTGGGGAGGATGTTTTAAAAAAAAAAAAAGCAA
GAAGCATGATGCAAAATTAAATAAAACTCACCAAGGCCATGGCGACCGAGCGTTGGTTTCTTGTGTTCCCTTCAGTAT
GCGGCGCGCGGCGATGTACCAGGAGGGACCTCCTCCCTCTTACGAGAGCGTGGTGGGCGCGGCGGCGGCGGCGCCCTC
TTCTCCCTTTGCGTCGCAGCTGCTGGAGCCGCCGTACGTGCCTCCGCGCTACCTGCGGCCTACGGGGGGGAGAAACAG
CATCCGTTACTCGGAGCTGGCGCCCCTGTTCGACACCACCCGGGTGTACCTGGTGGACAACAAGTCGGCGGACGTGGC
CTCCCTGAACTACCAGAACGACCACAGCAATTTTTTGACCACGGTCATCCAGAACAATGACTACAGCCCGAGCGAGGC
CAGCACCCAGACCATCAATCTGGATGACCGGTCGCACTGGGGCGGCGACCTGAAAACCATCCTGCACCACCAACATGCC
CAACGTGAACGAGTTCATGTTCACCAATAAGTTCAAGGCGCGGGTGATGGTGTCGCGCTCGCACACCAAGGAAGACCG
GGTGGAGCTGAAGTACGAGTGGGTGGAGTTCGAGCTGCCAGAGGGCAACTACTCCGAGACCATGACCATTGACCTGAT
GAACAACGCGATCGTGGAGCACTATCTGAAAGTGGGCAGGCAAAACGGGGTCCTGGAGAGCGACATCGGGGTCAAGTT
CGACACCAGGAACTTCCGCCTGGGGCTGGACCCCGTGACCGGGCTGGTTATGCCCGGGGTGTACACCAACGAGGCCTT
CCATCCCGACATCATCCTGCTGCCCGGCTGCGGGGTGGACTTCACTTACAGCCGCCTGAGCAACCTCCTGGGCATCCG
CAAGCGGCAGCCCTTCCAGGAGGGCTTCAGGATCACCTACGAGGACCTGGAGGGGGGCAACATCCCCGCGCTCCTCGA
TGTGGAGGCCTACCAGGATAGCTTGAAGGAAAATGAGGCGGGACAGGAGGATACCACCCCCGCCGCCTCCGCCGCCGC
CGAGCAGGGCGAGGATGCTGCTGACACCGCGGCCGCGGACGGGGCAGAGGCCGACCCCGCTATGGTGGTGGAGGCTCC
CGAGCAGGAGGAGGATATGAATGACAGTGCGGTGCGCGGAGACACCTTCGTCACCCGGGGGGAGGAAAAGCAAGCGGA
GGCCGAGGCCGCGGCCGAGGAAAAGCAACTGGCCGGCAGCAGCGGCGGCGGCGGCGTTGGCGCGGCGGAGGCTGAGTC
TGAGGGGACCAAGCCCGCCAAGGAGCCCGTGATTAAGCCCCTGACCGAAGATAGCAAGAAGCGCAGTTACAACCTGCT
CAAGGACAGCACCAACACCGCGTACCGCAGCTGGTACCTGGCCTACAACTACGGCGACCCGTCGACGGGGGTGCGCTC
CTGGACCCTGCTGTGCACGCCGGACGTGACCTGCGGCTCGGAGCAGGTGTACTGGTCGCTGCCCGACATGATGCAAGA
CCCCGTGACCTTCCGCTCCACGCGGCAGGTCAGCAACTTCCCGGTGGTGGGCGCCGAGCTGCTGCCCGTGCACTCCAA
GAGCTTCTACAACGACCAGGCCGTCTACTCCCAGCTCATCCGCCAGTTCACCTCTCTGACCCACGTGTTCAATCGCTT
TCCTGAGAACCACAGATTCTGGCGCGCCCGCCCGCCCCCACCATCACCACCGTCAGTGAAAACGTTCCTGCTCTCACAGA
TCACGGGACGCTACCGCTGCGCAACAGCATCGGAGGAGTCCAGCGAGTGACCGTTACTGACGCCAGACGCCGCACCTG
CCCCTACGTTTACAAGGCCTTGGGCATAGTCTCGCCGCGCGTCCTTTCCAGCCGCACTTTTTGAGCAACACCACCATC
ATGTCCATCCTGATCTCACCCAGCAATAACTCCGGCTGGGGACTGCTGCGCGCGCCCAGCAAGATGTTCGGAGGGGCG
AGGAAGCGTTCCGAGCAGCACCCCGTGCGCGTGCGCGGGCACTTCCGCGCCCCTCGGGGAGCGCACAAACGCGGCCGC
GCGGGGCGCACCACCGTGGACGACGCCATCGACTCGGTGGTGGAGCAGGCGCGCAACTACAGGCCCGCGGTCTCTACC
GTGGACGCGGCCATCCAGACCGTGGTGCGGGGCGCGCGGCGGTACGCCAAGCTGAAGAGCCGCCGGAAGCGCGTGGCC
CGCCGCCACCGCCGCGACCCGGGGCGCGCCAAACGCGCCGCCGCGGCCCTGCTTCGCGGGCCAAGCGCACGGGC
CGCCGCGCCGCCATGAGGGCCGCGCGCCGCTTGGCCGCCGGCATCACCGCCGCCACCATGGCCCCCGTACCCGAAGA
CGCGCGGCCGCCGCCGCCGCCGCCATCAGTGACATGGCCAGCAGGCGCGGGGCAACGTGTACTGGGTGCGCGAC
TCGGTGACCGGCACGCGCGTGCCCGTGCGCTTCCGCCCCCGCGGACTTGAGATGATGTGAAAAAACAACACTGAGTC
TCCTGCTGTTGTGTGTATCCCAGCGGCGGCGGCGCGCAGCGTCATGTCCAAGCGCAAAATCAAAGAAGAGATGCTC
CAGGTCGTCGCGCCGGAGATCTATGGGCCCCCGAAGAAGGAAGAGCAGGATTCGAAGCCCCGCAAGATAAAGCGGGTC
AAAAAGAAAAAGAAAGATGATGACGATGCCGATGGGGAGGTGGAGTTCCTGCGCGCCACGGCGCCCAGGCGCCCGGTG
CAGTGGAAGGGCCGGCGCGTAAAGCGCGTCCTGCGCCCCGGCACCGCGGTGGTCTTCACGCCCGGCGAGCGCTCCACC
CGGACTTTCAAGCGCGTCTATGACGAGGTGTACGGCGACGAAGACCTGCTGGAGCAGGCCAACGAGCGCTTCGGAGAG
TTTGCTTACGGAAGCGTCAGCGGGCGCTGGGGAAGGAGGACCTGCTGGCGCTGCCGCTGGACCAGGGCAACCCCACC
CCCAGTCTGAAGCCCGTGACCCTGCAGCAGGTGCTGCCGAGCAGCGCACCCTCCGAGGCGAAGCGGGGTCTGAAGCGC
GAGGGCGGCGACCTGGCGCCCACCGTGCAGCTCATGGTGCCCAAGCGGCAGAGGCGTGGAGGATGTGCTGGAGAAAATG
AAAGTAGACCCCGGTCTGCAGCCGGACATCAGGGTCCGTCCCATCAAGCAGGTGGCGCCGGGCCTCGGCGTGCAGACC
GTGGACGTGGTCATCCCCACCGGCAACTCCCCCGCCGCCACCACCACTACCGCTGCCTCCACGGACATGGAGACACAG
ACCGATCCCGCCGCAGCCGCAGCCGCCGCCGCAGCCGCGACCTCCTCGGCGGAGGTGCAGACGGACCCCTGGCTGCCG
CCGGCGATGTCAGCTCAGCCGCGCGCCGCGGACGCAGAAAGTACGGCGCCGCCAACGCGCTCCTGCCCGAGTACGCC
TTGCATCCTTCCATCGCGCCCACCCCCGGCTACCGAGGCTATACCTACCGCCCGCGAAGAGCCAAGGGTTCCACCCGC
CGTCCCCGCCGACGCGCCGCCGCCACCACCCGCCGCCGCCGCCGCAGACGCCAGCCCGCACTGGCTCCAGTCTCCGTG
AGGAGAGTGGCGCGCGACGGACACACCCTGGTGCTGCCCAGGGCGCGCTACCACCCCAGCATCGTTTAAAAGCCTGTT
GTGGTTCTTGCAGATATGGCCCTCACTTGCCGCCTCCGTTTCCCGGTGCCGGGATACCGAGGAGGAAGATCGCGCCGG
AGGAGGGGTCTGGCCGGCCGGCCGGGCCTGAGCGGAGGCAGCCGCCGCGCACCGGCGGCGACGCGCCACCAGCCGACGC
ATGCGCGGCGGGGTGCTGCCCCTGTTAATCCCCTGATCGCCGCGGCGATCGGCGCCGTGCCCGGGATCGCCTCCGTG
GCCTTGCAAGCGTCCCAGAGGCATTGACAGACTTGCAAACTTGCAAATATGGAAAAAAAAAAAAAACCCCAATAAAAA
GTCTAGACTCTCAGCGCTCGCTTGGTCCTGTGACTATTTTGTAGAATGGAAGACATCAACTTTGCGTCGCTGGCCCCGC
GTCACGGCTCGCGCCCGTTCCTGGGACACTGGAACGATATCGGCACCAGCAACATGAGCGGTGGCGCCTTCAGTTGGG
GCTCTCTGTGGAGCGGCATTAAAAGTATCGGGTCTGCCGTTAAAAATTACGGCTCCCGGGCCTGGAACAGCAGCACGG
GCCAGATGTTGAGAGACAAGTTGAAAGAGCAGAACTTCCAGCAGAAGGTGGTGGAGGGCCTGGCCTCCGGCATCAACG
GGGTGGTGGACCTGGCCAACCAGGCCGTGCAGAATAAAATCAACAGCAGACTGGACCCCCGGCCCGCGGTGGAGGAGG
TGCCGCCGGCGCTGGAGACGGTGTCCCCCGATGGGCGTGCGAGAAGCGCCCGCGGCCCGATAGGGAAGAGACCACTC
TGGTCACGCAGACCGATGAGCCGCCCCCGTATGAGGAGGCCCTAAAGCAAGGTCTGCCCACCACGCGGCCCATCGCGC
CCATGGCCACCGGGTGGTGGGCCGCCACACCCCCGCCACGCTGGACTTGCCTCCGCCCGCCGATGTGCCGCAGCAGC
AGAAGGCGGCACAGCCGGGCCCGCCCGCGACCGCCTCCCGTTCCTCCGCCGGTCCTCTGCGCCGCGCGGCCAGCGGCC
```

Fig. 6D

```
CCCGCGGGGGGGTCGCGAGGCACGGCAACTGGCAGAGCACGCTGAACAGCATCGTGGGTCTGGGGGTGCGGTCCGTGA
AGCGCCGCCGATGCTACTGAATAGCTTAGCTAACGTGTTGTATGTGTGTATGCGCCCTATGTCGCCGCCAGAGGAGCT
GCTGAGTCGCCGCCGTTCGCGCGCCCACCACCACCGCCACTCCGCCCCTCAAGATGGCGACCCCATCGATGATGCCGC
AGTGGTCGTACATGCACATCTCGGGCCAGGACGCCTCGGAGTACCTGAGCCCCGGGCTGGTGCAGTTCGCCCGCGCCA
CCGAGAGCTACTTCAGCCTGAGTAACAAGTTTAGGAACCCCACGGTGGCGCCCACGCACGATGTGACCACCGACCGGT
CTCAGCGCCTGACGCTGCGGTTCATTCCCGTGGACCGCGGAGGACACCGCGTACTCGTACAAGGCGCGGTTCACCCTGG
CCGTGGGCGACAACCGCGTGCTGGACATGGCCTCCACCTACTTTGACATCCGCGGGGTGCTGGACCGGGGTCCCACTT
TCAAGCCCTACTCTGGCACCGCCTACAACTCCCTGGCCCCCAAGGGCGCTCCCAACTCCTGCGAGTGGGAGCAAGAGG
AAACTCAGGCAGTTGAAGAAGCAGCAGAAGAGGAAGAAGAAGATGCTGACGGTCAAGCTGAGGAAGAGCAAGCAGCTA
CCAAAAAGACTCATGTATATGCTCAGGCTCCCCTTTCTGGCGAAAAAATTAGTAAAGATGGTCTGCAAATAGGAACGG
ACGCTACAGCTACAGAACAAAAACCTATTTATGCAGACCCTACATTCCAGCCCGAACCCCAAATCGGGGAGTCCCAGT
GGAATGAGGCAGATGCTACAGTCGCCGGCGGTAGAGTGCTAAAGAAATCTACTCCCATGAAACCATGCTATGGTTCCT
ATGCAAGACCCACAAATGCTAATGGAGGTCAGGGTGTACTAACGGCAAATGCCCAGGGACAGCTAGAATCTCAGGTTG
AAATGCAATTCTTTTCAACTTCTGAAAACGCCCGTAACGAGGCTAACAACATTCAGCCCAAATTGGTGCTGTATAGTG
AGGATGTGCACATGGAGACCCCGGATACGCACCTTTCTTACAAGCCCGCAAAAAGCGATGACAATTCAAAAATCATGC
TGGGTCAGCAGTCCATGCCCAACAGACCTAATTACATCGGCTTCAGAGACAACTTTATCGGCCTCATGTATTACAATA
GCACTGGCAACATGGGAGTGCTTGCAGGTCAGGCCTCTCAGTTGAATGCAGTGGTGGACTTGCAAGACAGAAACACAG
AACTGTCCTACCAGCTCTTGCTTGATTCCATGGGTGACAGAACCAGATACTTTTCCATGTGGAATCAGGCAGTGGACA
GTTATGACCCAGATGTTAGAATTATTGAAAATCATGGAACTGAAGACGAGCTCCCCAACTATTGTTTCCCTCTGGGTG
GCATAGGGGTAACTGACACTTACCAGGCTGTTAAAACCAACAATGGCAATAACGGGGGCCAGGTGACTTGGACAAAAG
ATGAAACTTTTGCAGATCGCAATGAAATAGGGGTGGGAAACAATTTCGCTATGGAGATCAACCTCAGTGCCAACCTGT
GGAGAAACTTCCTGTACTCCAACGTGGCGCTGTACCTACCAGACAAGCTTAAGTACAACCCCTCCAATGTGGACATCT
CTGACAACCCCAACACCTACGATTACATGAACAAGCGAGTGGTGGCCCCGGGGCTGGTGGACTGCTACATCAACCTGG
GCGCGCGCTGGTCGCTGGACTACATGGACAACGTCAACCCCTTCAACCACCACCGCAATGCGGGCCTGCGCTACCGCT
CCATGCTCCTGGGCAACGGGCGCTACGTGCCCTTCCACATCCAGGTGCCCCAGAAGTTCTTTGCCATCAAGAACCTCC
TCCTCCTGCCGGGCTCCTACACCTACGAGTGGAACTTCAGGAAGGATGTCAACATGGTCCTCCAGAGCTCTCTGGGTA
ACGATCTCAGGGTGGACGGGGCCAGCATCAAGTTCGAGAGCATCTGCCTCTACGCCACCTTCTTCCCCATGGCCCACA
ACACGGCCTCCACGCTCGAGGCCATGCTCAGGAACGACACCAACGACCAGTCCTTCAATGACTACCTTTCCGCCGCCA
ACATGCTCTACCCCATACCCGCCAACGCCACCAACGTCCCCATCTCCATCCCCTCGCGCAACTGGGCGGCCTTCCGCG
GCTGGGCCTTCACCCGCCTCAAGACCAAGGAGACCCCCTCCCTGGGCTCGGGATTCGACCCCTACTACACCTACTCGG
GCTCTATTCCCTACCTGGACGGCACCTTCTACCTCAACCACACTTTCAAGAAGGTCTCGGTCACCTTCGACTCCTCGG
TCAGCTGGCCGGGCAACGACCGTCTGCTCACCCCCAACGAGTTCGAGATCAAGCGCTCGGTCGACGGGGAAGGCTACA
ACGTGGCCAGTGCAACATGACCAAGGACTGGTTCCTGGTCCAGATGCTGGCCAACTACAACATCGGCTACCAGGGCT
TCTACATCCCAGAGAGCTACAAGGACAGGATGTACTCCTTCTTCAGGAACTTCCAGCCCCATGAGCCGGCAGGTGGTGG
ACCAGACCAAGTACAAGGACTACCAGGAGGTGGGCATCATCCACCAGCACAACAACTCGGGCTTCGTGGGCTACCTCG
CCCCCACCATGCGCGAGGGACAGGCCTACCCCGCCAACTTCCCCTACCCGCTCATAGGCAAGACCGCGGTCGACAGCA
TCACCCAGAAAAAGTTCCTCTGCGACCGCACCCTCTGGCGCATCCCCTTCTCCAGCAACTTCATGTCCATGGGTGCGC
TCTCGGACCTGGGCCAGAACTTGCTCTACGCCAACTCCGCCCACGCCCTCGACATGACCTTCGAGGTCGACCCCATGG
ACGAGCCCACCCTTCTCTATGTTCTGTTCGAAGTCTTTGACGTGGTCCGGGTCCACCAGCCGCACCGCGGCGTCATCG
AGACCGTGTACCTGCGTACGCCCTTCTCGGCCGGCAACGCCACCACCTAAAGAAGCAAGCCGCAGTCATCGCCGCCTG
CATGCCGTCGGGTTCCACCGAGCAAGAGCTCAGGGCCATCGTCAGAACTGGGATGCGGGCCCTATTTTTTGGGCAC
CTTCGACAAGCGCTTCCCTGGCTTTGTCTCCCACACAAGCTGGCCTGCGCCATCGTCAACACGGCCGGCCGCGAGAC
CGGGGGCGTGCACTGGCTGGCCTTTGCCTGGAACCCGCGCTCCAAAACATGCTTCCTCTTTGACCCCTTCGGCTTTTC
GGACCAGCGGCTCAAGCAAATCTACGAGTTCGAGTACGAGGGCTTGCTGCGTCGCAGCGCCATCGCCTCCTCGCCCGA
CCGCTGCGTCACCCTCGAAAAGTCCACCCAGACCGTGCAGGGGCCCGACTCGGCCGCCTGCGGTCTCTTCTGCTGCAT
GTTTCTGCACGCCTTTGTGCACTGGCCTCAGAGTCCCATGGACCGCCAACCCCACCATGAACTTGCTGACGGGGGTGCC
CAACTCCATGCTCCAAAGCCCCCAGGTCGAGCCCACCCTGCGCCGCAACCAGGAGCAGCTCTACAGCTTCCTGGAGCG
CCACTCGCCCTACTTCCGCCGCCACAGCGCACAGATCAGGAGGGCCACCTCCTTCTGCCACTTGCAAGAGATGCAAGA
AGGGTAATAACGATGTACACACTTTTTTTCAATAAATGGCATTTTTTTTATTTATACAAGCTCTCTGGGGTATTC
ATTTCCCACCACCACCACCGCCGTTGTCGCCATCTGGCTCTATTTAGAAATCGAAAGGGTTCTGCCGGGAGTCGCCG
TGCGCCACGGGCAGGGACACGTTGCGATACTGGTAGCGGGTGCCCCACTTGAACTCGGGCACCACCAGGCGAGGCAGC
TCGGGGAAGTTTTCGCTCCACAGGCTGCGGGTCAGCACCAGCGCGTTCATCAGGTCGGGCGCCGAGATCTTGAAGTCG
CAGTTGGGGCCGCCGCCTGCGCGCGCGAGTTGCGCGGTACACCGGGTTGCAGCACTGGAACACCAACAGCGCGGGTGC
TTCACGCTGGCCAGCACGCTGCGGTCGGAGATCAGCTCGGCGTCCAGGTCCTCCGCGTTGCTCAGCGCGAACGGGGTC
ATCTTGGGCACTTGCCGCCCAGGAAGGGCGCGTGCCCCGGTTTCGAGTTGCAGTCGCAGCGCAGCGGGATCAGCAGG
TGCCCGTGCCCGGACTCGGCGTTGGGGTACAGCGCGCGCATGAAGGCCTGCATCTGGCGGAAGGCCATCGGGCCTTG
GCGCCCTCCGAGAAGAACATGCCGCAGGACTTGCCCGAGAACTGGTTTGCGGGGCAGCTGGCGTCGTGCAGGCAGCAG
CGCGCGTCGGTGTTGGCGATCTGCACCACGTTGCGCCCCACCGGTTCTTCACGATCTTGGCCTTGGACGATTGCTCC
TTCAGCGCGCGCTGCCCGTTCTCGCTGGTCACATCCATCTCGATCACATGTTCCTTGTTCACCATGCTGCTGCCGTGC
AGACACTTCAGCTCGCCCTCCGTCTCGGTGCAGCGGTGCTGCCACAGCGCGCAGCCCGTGGGCTCGAAAGACTTGTAG
GTCACCTCCGCGAAGGACTGCAGGTACCCCTGCAAAAAGCGGCCCATCATGGTCACGAAGGTCTTGTTGCTGCTGAAG
```

Fig. 6E

```
GTCAGCTGCAGCCCGCGGTGCTCCTCGTTCAGCCAGGTCTTGCACACGGCCGCCAGCGCCTCCACCTGGTCGGGCAGC
ATCTTGAAGTTCACCTTCAGCTCATTCTCCACGTGGTACTTGTCCATCAGCGTGCGCGCCGCCTCCATGCCCTTCTCC
CAGGCCGACACCAGCGGCAGGCTCACGGGGTTCTTCACCATCACCGTGGCCGCCGCCTCCGCCGCGCTTTCGCTTTCC
GCCCCGCTGTTCTCTTCCTCTTCCTCCTCTTCCTCGCCGCCGCCCACTCGCAGCCCCGCACCACGGGGTCGTCTTCC
TGCAGGCGCTGCACCTTGCGCTTGCCGTTGCGCCCCTGCTTGATGCGCACGGGCGGGTTGCTGAAGCCCACCATCACC
AGCGCGGCCTCTTCTTGCTCGTCCTCGCTGTCCAGAATGACCTCCGGGGAGGGGGGGTTGGTCATCCTCAGTACCGAG
GCACGCTTCTTTTTCTTCCTGGGGGCGTTCGCCAGCTCCGCGGCTGCCGCCGAGGTCGAAGGCCGAGGGCTG
GGCGTGCGCGGCACCAGCGCGTCTTGCGAGCCGTCCTCGTCCTCCTCGGACTCGAGACGGAGGCGGGCCCGCTTCTTC
GGGGGCGCGCGGGGCGGCGGAGGCGGCGGCGGCGACGGAGACGGGGACGAGACATCGTCCAGGGTGGGTGGACGGCGG
GCCGCGCCGCGTCCGCGCTCGGGGGTGGTTTCGCGCTGGTCCTCTTCCCGACTGGCCATCTCCCACTGCTCCTTCTCC
TATAGGCAGAAAGAGATCATGGAGTCTCTCATGCGAGTCGAGAAGGAGGAGGACAGCCTAACCGCCCCCTCTGAGCCC
TCCACCACCGCCGCCACCACCGCCAATGCCGCCGCGGACGACGCGCCCACCGAGACCACCGCCAGTACCACCCTCCCC
AGCGACGCACCCCCGCTCGAGAATGAAGTGCTGATCGAGCAGGACCCGGGTTTTGTGAGCGGAGAGGAGGATGAGGTG
GATGAGAAGGAGAAGGAGGAGGTCGCCGCCTCAGTGCCAAAAGAGGATAAAAAGCAAGACCAGGACGACGCAGATAAG
GATGAGACAGCAGTCGGGCGGGGGAACGGAAGCCATGATGCTGATGACGGCTACCTAGACGTGGGAGACGACGTGCTG
CTTAAGCACCTGCACCGCCAGTGCGTCATCGTCTGCGACGCGCTGCAGGAGCGCTGCGAAGTGCCCCTGGACGTGGCG
GAGGTCAGCCGCGCCTACGAGCGGCACCTCTTCGCGCCGCACGTGCCCCCAAGCGCGGGAGAACGGCACCTGCGAG
CCCAACCCGCGTCTCAACTTCTACCCGGTCTTCGCGGTACCCGAGGTGCTGGCCACCTACCACATCTTCTTCCAAAAC
TGCAAGATCCCCCTCTCCTGCCGCGCTAACCGCACCCGCCGCGACAAAACCCTGACCCTGCGGCAGGGCGCCCACATA
CCTGATATTGCCTCTCTGGAGGAAGTGCCCAAGATCTTCGAGGGTCTCGGTCGCGACGAGAAACGGGCGGCGAACGCT
CTGCACGGAGACAGCGAAAACGAGAGTCACTCGGGGGTGCTGGTGGAGCTCGAGGGCGACAACGCGCGCCTGCCGTA
CTCAAGCGCAGCATAGAGGTCACCCACTTTGCCTACCCGGCGCTCAACCTGCCCCCCAAGGTCATGAGTGTGGTCATG
GGCGAGCTCATCATGCGCCGCGCTCAGCCCCTGGCCGCGGATGCAAACTTGCAAGAGTCCTCCGAGGAAGGCCTGCCC
GCGGTCAGCGACGAGCAGCTAGCGCGCTGGCTGGAGACCCGCGACCCCGCGCAGCTGGAGGAGCGGCGCAAGCTCATG
ATGGCCGCGGTGCTGGTCACCGTGGAGCTCGAGTGTCTGCAGCGCTTCTTCGCGGACCCCGAGATGCAGCGCAAGCTC
GAGGAGACCCTGCACTACACCTTCCGCCAGGGCTACGTGCGCCAGGCCTGCAAGATCTCCAACGTGGAGCTCTGCAAC
CTGGTCTCCTACCTGGGCATCCTGCACGAGAACCGCCTCGGGCAGGAACGTCCTGCACTCCACCCTCAAAGGGGAGGCG
CGCCGCGACTACATCCGCGACTGCGCCTACCTCTTCCTCTGCTACACCTGGCAGACGGCCATGGGGGTCTGGCAGCAG
TGCCTGGAGGAGCGCAACCTCAAGGAGCTGGAAAAGCTACTCAAGCGCACCCTCAGGGACCTCTGGACGGGCTTCAAC
GAGCGCTCGGTGGCCGCCGCGCTGGCGGACATCATCTTCCCCGAGCGCCTGCTCAAGACCCTGCAGCAGGGCCTGCCC
GACTTCATCAGCCAGAGCATGCTGCAGAACTTTAGGACTTTCATCCTGGAGCGCTCGGGCATCCTGCCTGCCACTTGC
TGCGCGCTGCCCAGCGACTTCGTGCCCATCAAGTACAGGGAGTGCCCGCCGCCGCTCTGGGGCCACTGCTACCTCTTC
CAGCTGGCCAACTACCTCGCCTACCACTCGGACCTCATGGAAGACGTGAGCGGCGAGGGCCTGCTCGAGTGCCACTGC
CGCTGCAACCTCTGCACGCCCCACCGCTCTCTAGTCTGCAACCCGCAGCTGCTCAGCGAGAGTCAGATTATCGGTACC
TTCGAGCTGCAGGGTCCCTCGCCTGACGAGAAGTCCGCCTCCGGGCTGAAACTCACTCCGGGGCTGTGGACTTCC
GCCTACCTACGCAAATTTGTACCTGAGGACTACCACGCCCACGAGATCAGGTTCTACGAAGACCAATCCCGCCCGCCC
AAGGCGGAGCTCACCGCCTGCGTCATCACCCAGGGGCACATCCTGGGCAATTGCAAGCCATCAACAAAGCCCGCCGA
GAGTTCTTGCTGAAAAAGGGTCGGGGGGTGTACCTGGACCCCCAGTCCGGCGAGGAGCTAAACCCGCTACCCCCGCCG
CCGCCCCAAGCAGCGGGACCTTGCTTCCCCAGGATGGCACCCAGAAAGAAGCAGCAGCCGCCGCCGCCGCAGCCATACAT
GCTTCTGGAGGAAGAGGAGGAGGACTGGGACAGTCAGGCAGAGGAGGTTTCGGACGAGGAGCAGGAGGAGATGATGGA
AGACTGGGAGGAGGACAGCAGCCTAGACGAGGAAGCTTCAGAGGCCGAAGAGGTGGCAGACGCAACACCATCACCCTC
GGTCGCAGCCCCCTCGCCGGGGCCCCTGAAATCCTCCGAACCCAGCACCAGCGCTATAACCTCCGCTCCTCCGGCGCC
GGCGCCACCCGCCCGCAGACCCAACCGTAGATGGACACCACCAAGGAACCGGGGTCGGTAAGTCCAAGTGCCGCCGCC
GCCACCGCAGCAGCAGCAGCAGCGCCAGGGCTACCGCTCGTGGCGCGGGCACAAGAACGCCATAGTCGCCTGCTTGCA
AGACTGCGGGGCAACATCTCTTTCGCCCGGCGCTTCCTGCTATTCCACCACGGGGTCGCCTTTCCCCGCAATGTCCT
GCATTACTACCGTCATCTCTACAGCCCCTACTGCAGCGGCGACCCAGAGGCGGCAGCGGCAGCCACAGCGGCGACCAC
CACCTAGGAAGATATCCTCCGCGGGCAAGACAGCGGCGACAGCGGCCAGCAGCAGCAGCAGCGGCGGGAGCGG
TGGGCGCACTGCGCCTCTCGCCCAACGAACCCCTCTCGACCCGGGAGCTCAGACACAGGATCTTCCCCACTTTGTATG
CCATCTTCCAACAGAGCAGAGGCCAGGAGCAGGAGCTGAAAATAAAAACAGATCTCTGCGCTCCCTCACCCGCAGCT
GTCTGTATCACAAAAGCGAAGATCAGCTTCGGCGCACGCTGGAGGACGCGGAGGCACTCTTCAGCAAATACTGCGCGC
TCACTCTTAAAGACTAGCTCCGCGCCCTTCTCGAATTTAGGCGGGAGAAAACTACGTCATCGCCGGCCGCCGCCAGC
CCGCCCAGCCGAGATGAGCAAAGAGATTCCCACGCCATACATGTGGAGCTACCAGCCGCAGATGGGACTCGCGGCGGG
AGCGGCCCAGGACTACTCCACCCGCATGAACTACATGAGCGCGGGACCCCACATGATCTCACAGGTCAACGGGATCCG
CGCCCAGCGAAACCAAATACTGCTGGAACAGGCGGCCATCACCGCCACGCCCCGCCATAATCTCAACCCCCGAAATTG
GCCCGCCGCCCTCGTGTACCAGGAAACCCCCTCCGCCACCGTACTACTTCCGCGTGACGCCCAGGCCGAAGTCCA
GATGACTAACTCAGGGGCGCAGCTCGCGGGCGGCTTTCGTCACGGGCGCGGCCGCTCCGACCAGGTATAAGACACCT
GATGATCAGAGGCCGAGGTATCCAGCTCAACGACGAGTCGGTGAGCTCTTCGCTCGGTCTCCGTCCGGACGAACTTT
CCAGCTCGCCGGATCCGGCCGCTCTTCGTTCACGCCCCGCCAGGCGTACCTGACTCTGCAGACCTCGTCCTCGGAGCC
CCGCTCCGGAGGCATCGGAACCCTCCAGTTCGTGGAGGAGTTCGTGCCCTCGGTCTACTTCAACCCCTTCTCGGGACC
TCCCGGACGTACCCCGACCAGTTCATTCCGAACTTTGACGCGGTGAAGGACTCGGCGGACGGCTACGACTGAATGTC
AGGTGCCGAGGCAGAGCAGCTTCGCCTGAGACACCTCGAGCACTGCCGCCGCCACAAGTGCTTCGCCCGCGGTTCCGG
```

Fig. 6F

```
TGAGTTCTGCTACTTTCAGCTACCCGAGGAGCATACCGAGGGGCCGGCGCACGGCGTCCGCCTGACCACCCAGGGCGA
GGTTACCTGTTCCCTCATCCGGGAGTTCACCCTCCGTCCCCTGCTAGTGGAGCGGGAGCGGGGTCCCTGTGTCCTAAC
TATCGCCTGCAACTGCCCTAACCCTGGATTACATCAAGATCTTTGCTGTCATCTCTGTGCTGAGTTTAATAAACGCTG
AGATCAGAATCTACTGGGGCTCCTGTCGCCATCCTGTGAACGCCACCGTCTTCACCCACCCCGACCAGGCCCAGGCGA
ACCTCACCTGCGGTCTGCATCGGAGGGCCAAGAAGTACCTCACCTGGTACTTCAACGGCACCCCCTTTGTGGTTTACA
ACAGCTTCGACGGGGACGGAGTCTCCCTGAAAGACCAGCTCTCCGGTCTCAGCTACTCCATCCACAAGAACACCACCC
TCCAACTCTTCCCTCCCTACCTGCCGGGAACCTACGAGTGCGTCACCGGCCGCTGCACCCACCTCACCCGCCTGATCG
TAAACCAGAGCTTTCCGGGAACAGATAACTCCCTCTTCCCCAGAACAGGAGGTGAGCTCAGGAAACTCCCCGGGGACC
AGGGCGGAGACGTACCTTCGACCCTTGTGGGGTTAGGATTTTTTATTACCGGGTTGCTGGCTCTTTTAATCAAAGCTT
CCTTGAGATTTGTTCTTTCCTTCTACGTGTATGAACACCTCAGCCTCCAATAACTCTACCCTTTCTTCGGAATCAGGT
GACTTCTCTGAAATCGGGCTTGGTGTGCTGCTTACTCTGTTGATTTTTTTCCTTATCATACTCAGCCTTCTGTGCCTC
AGGCTCGCCGCCTGCTGCGCACACATCTATATCTACTGCTGGTTGCTCAAGTGCAGGGGTCGCCACCCAAGATGAACA
GGTACATGGTCCTATCGATCCTAGGCCTGCTGGCCCTGGCGGCCTGCAGCGCCGCCAAAAAAGAGATTACCTTTGAGG
AGCCCGCTTGCAATGTAACTTTCAAGCCCGAGGGTGACCAATGCACCACCCTCGTCAAATGCGTTACCAATCATGAGA
GGCTGCGCATCGACTACAAAAACAAAACTGGCCAGTTTGCGGTCTATAGTGTGTTTACGCCCGGAGACCCCTCTAACT
ACTCTGTCACCGTCTTCCAGGGCGGACAGTCTAAGATATTCAATTACACTTTCCCTTTTTATGAGTTATGCGATGCGG
TCATGTACATGTCAAAACAGTACAACCTGTGGCCTCCCTCTCCCAGGCGTGTGTGGAAAATACTGGGTCTTACTGCT
GTATGGCTTTGGCAATCACTACGCTCGCTCTAATCTGCACGGTGCTATACATAAAATTCAGGCAGAGGCGAATCTTTA
TCGATGAAAAGAAAATGCCTTGATCGCTAACACCGGCTTTCTATCTGCAGAATGAATGCAATCACCTCCCTACTAATC
ACCACCACCCTCCTTGCGATTGCCCATGGGTTGACACGAATCGAAGTGCCAGTGGGGTCCAATGTCACCATGGTGGGC
CCCGCCGGCAATTCCACCCTCATGTGGGAAAAATTTGTCCGCAATCAATGGGTTCATTTCTGCTCTAACCGAATCAGT
ATCAAGCCCAGAGCCATCTGCGATGGGCAAAATCTAACTCTGATCAATGTGCAAATGATGGATGCTGGGTACTATTAC
GGGCAGCGGGGAGAAATCATTAATTACTGGCGACCCCACAAGGACTACATGCTGCATGTAGTCGAGGCACTTCCCACT
ACCACCCCCACTACCACCTCTCCCACCACCACTACCACCACTACTACTACTACTACTACCACTACCGCTGCCCGCCAT
ACCCGCAAAAGCACCATGATTAGCACAAAGCCCCCTCGTGCTCACTCCCACGCCGGCGGGCCCATCGGTGCGACCTCA
GAAACCACCGAGCTTTGCTTCTGCCAATGCACTAACGCCAGCGCTCATGAACTGTTCGACCTGGAGAATGAGGATGCC
CAGCAGAGCTCCGCTTGCCTGACCCAGGAGGCTGTGGAGCCCGTTGCCCTGAAGCAGATCGGTGATTCAATAATTGAC
TCTTCTTCTTTTGCCACTCCCGAATACCCTCCCGATTCTACTTTCCACATCACGGGTACCAAAGACCCCTAACCTCTCT
TTCTACCTGATGCTGCTGCTCTGTATCTCTGTGGTCTCTTCCGCGCTGATGTTACTGGGGATGTTCTGCTGCCTGATC
TGCCGCAGAAAGAGAAAAGCTCGCTCTCAGGGCCAACCACTGATGCCCTTCCCCTACCCCCCGGATTTTGCAGATAAC
AAGATATGAGCTCGCTGCTGACACTAACCGCTTTACTAGCCTGCGCTCTAACCCTTGTCGCTTGCGACTCGAGATTCC
ACAATGTCACAGCTGTGGCAGGAGAAAATGTTACTTTCAACTCCACGGCCGATACCCAGTGGTCGTGGAGTGGCTCAG
GTAGCTACTTAACTATCTGCAATAGCTCCACTTCCCCAGCATATCCCCAACCAAGTACCAATGCAATGCCAGCCTGT
TCACCCTCATCAACGCTTCCACCCTGGACAATGGACTCTATGTAGGCTATGTACCCTTTGGTGGGCAAGGAAAGACCC
ACGCTTACAACCTGGAAGTTCGCCAGCCCAGAACCACTACCCAAGCTTCTCCCACCACCACCACCACCACCACCACCA
CCATCACCAGCAGCAGCAGCAGCCACAGCAGCAGCAGCAGATTATTGACTTTGGTTTTGGCCAGCTCATCTGCCGCTA
CCCAGGCCATCTACAGCTCTGTGCCCGAAACCACTCAGATCCACCGCCCAGAAACGACCACCGCCACCACCCTACACA
CCTCCAGCGATCAGATGCCGACCAACATCACCCCCTTGGCTCTTCAAATGGGACTTACAAGCCCCACTCCAAAACCAG
TGGATGCGGCCGAGGTCTCCGCCCTCGTCAATGACTGGGCGGGGCTGGGAATGTGGTGGTTCGCATAGGCATGATGG
CGCTCTGCCTGCTTCTGCTCTGGCTCATCTGCTGCCTCCACCGCAGGCGAGCCAGACCCCCATCTATAGACCCATCA
TTGTCCTGAACCCCGATAATGATGGGATCCATAGATTGGATGGCCTGAAAAACCTACTTTTTTCTTTTACAGTATGAT
AAATTGAGACATGCCTCGCATTTTCTTGTACATGTTCCTTCTCCCACCTTTTCTGGGGTGTTCTACGCTGGCCGCTGT
GTCTCACCTGGAGGTAGACTGCCTCTCACCCTTCACTGTCTACCTGCTTTACGGATTGGTCACCCTCACTCTCATCTG
CAGCCTAATCACAGTAATCATCGCCTTCATCCAGTGCATTGATTACATCTGTGTGCGCCTCGCATACTTCAGACACCA
CCCGCAGTACCGAGACAGGAACATTGCCCAACTTCTAAGACTGCTCTAATCATGCATAAGACTGTGATCTGCCTTCTG
ATCCTCTGCATCCTGCCCACCCTCACCTCCTGCCAGTACACCACAAAATCTCCGCGCAAAAGACATGCCTCCTGCCGC
TTCACCCAACTGTGGAATATACCCAAATGCTACAACGAAAAGAGCGAGCTCTCCGAAGCTTGGCTGTATGGGGTCATC
TGTGTCTTAGTTTTCTGCAGCACTGTCTTTGCCCTCATGATCTACCCCTACTTTGATTTGGGATGGAACGCGATCGAT
GCCATGAATTACCCCACCTTTCCCGCACCCGAGATAATTCCACTGCGACAAGTTGTACCCGTTGTCGTTAATCAACGC
CCCCCATCCCCTACGCCCACTGAAATCAGCTACTTTAACCTAACAGGCGGAGATGACTGACGCCCTAGATCTAGAAAT
GGACGGCATCAGTACCGAGCAGCGTCTCCTAGAGAGGCGCAGGCAGGCGGCTGAGCAAGAGCGCCTCAATCAGGAGCT
CCGAGATCTCGTTAACCTGCACCAGTGCAAAAGAGGCATCTTTTGTCTGGTAAAGCAGGCCAAAGTCACCTACGAGAA
GACCGGCAACAGCCACCGCCTCAGTTACAAATTGCCCACCCAGCGCCAGAAGCTGGTGCTCATGGTGGGTGAGAATCC
CATCACCGTCACCCAGCACTCGGTAGAGACCGAGGGGTGTCTGCACTCTCCCTGTCGGGGTCCAGAAGACCTCTGCAC
CCTGGTAAAGACCCTGTGCGGTCTCAGAGATTTAGTCCCCTTTAACTAATCAAACACTGGAATCAATAAAAAGAATCA
CTTACTTAAAATCAGACAGCAGGTCTCTGTCCAGTTTATTCAGCAGCACCTCCTTCCCCTCCTCCCAACTCTGGTACT
CCAAACGCCTTCTGGCGGCAAACTTCCTCCACACCCTGAAGGGAATGTCAGATTCTTGCTCCTGTCCCTCCGCACCCA
CTATCTTCATGTTGTTGCAGATGAAGCGCACCAAAACGTCTGACGAGAGCTTCAACCCCGTGTACCCCTATGACACGG
AAAGCGGCCCTCCCTCCGTCCCTTTCCTCACCCCTCCCTTCGTGTCTCCCGATGGATTCAAGAAAGCCCCCCGGGG
TCCTGTCTCTGAACCTGGCCGAGCCCCTGGTCACTTCCCACGGCATGCTCGCCCTGAAAATGGGAAGTGGCCTCTCCC
TGGACGACGCTGGCAACCTCACCTCTCAAGATATCACCACCGCTAGCCCTCCCCTCAAAAAAACCAAGACCAACCTCA
```

Fig. 6G

```
GCCTAGAAACCTCATCCCCCCTAACTGTAAGCACCTCAGGCGCCCTCACCGTAGCAGCCGCCGCTCCCCTGGCAGTGG
CCGGCACCTCCCTCACCATGCAATCAGAGGCCCCCCTGACAGTACAGGATGCAAAACTCACCCTGGCCACCAAAGGCC
CCCTGACCGTGTCTGAAGGCAAACTGGCCTTGCAAACATCGGCCCCGCTGACGGCCGCTGACAGCAGCACCCTCACCG
TTAGCGCCACACCACCAATTAATGTAAGCAGTGGAAGTTTAGGCTTAGACATGGAAGACCCTATGTATACTCACGATG
GAAAACTGGGAATAAGAATTGGGGGTCCACTAAGAGTAGTAGACAGCTTGCACACACTCACTGTAGTTACCGGAAATG
GACTAACTGTAGATAACAATGCCCTCCAAACTAGAGTTACGGGCGCCCTAGGTTATGACACATCAGGAAATCTACAAT
TGAGAGCTGCAGGAGGTATGCGAATTGATGCAAATGGCCAACTTATCCTTAATGTGGCATACCCATTTGATGCTCAGA
ACAATCTCAGCCTTAGACTTGGTCAGGGACCCCTGTATATAAACACAGACCACAACCTGGATTTGAATTGCAACAGAG
GTCTAACCACAACTACCACCAACAACACAAAAAAACTTGAGACTAAAATTAGCTCAGGCTTAGACTATGACACCAATG
GTGCTGTCATTATTAAACTTGGCACTGGTCTAAGCTTCGACAACACAGGCGCCCTAACTGTGGGAAACACTGGTGATG
ATAAACTGACTCTGTGGACGACCCCAGACCCATCTCCAAATTGCAGAATTCACTCAGACAAAGACTGCAAGTTTACTC
TAGTCCTAACTAAGTGTGGAAGCCAAATCCTGGCCTCTGTCGCCGCCCTAGCGGTATCAGGAAATCTGGCTTCGATAA
CAGGCACCGTTGCCAGCGTTACCATCTTTCTCAGATTTGATCAGAATGGAGTGCTTATGGAAAACTCCTCGCTAGACA
GGCAGTACTGGAACTTCAGAAATGGCAACTCAACTAACGCTGCCCCCTACACCAATGCAGTTGGGTTCATGCCAAACC
TCGCAGCATACCCCAAAACGCAAAGCCAGACTGCTAAAAACAACATTGTAAGTCAGGTTTACTTGAATGGAGACAAAT
CCAAACCCATGACCCTTACCATCACCCTCAATGGAACTAATGAATCCAGTGAAACTAGCCAGGTGAGTCACTACTCCA
TGTCATTTACATGGGCTTGGGAAAGTGGGCAATATGCCACTGAAACCTTTGCCACCAACTCCTTCACCTTTTCTTACA
TTGCTGAACAATAAAAAGCATGACACTGATGTTCATTTCTGATTCTTATTTTATTATTTTCAAACACAACAAAATCAT
TCAAGTCATTCTTCCATCTTAGCTTAATAGACACAGTAGCTTAATAGACCCAGTAGTGCAAAGCCCCATTCTAGCTTA
TAGATCAGACAGTGATAATTAACCACCACCACCACCTTTTGATTCAGGAAATCATGATCATCACAGGATCCTA
GTCTTCAGGCCGCCCCCTCCCTCCCAAGACACAGAATACACAGTCCTCTCCCCCGACTGGCTTTAAATAACACCATC
TGGTTGGTCACAGACATGTTCTTAGGGGTTATATTCCACACGGTCTCCTGCCGCGCCAGGCGCTCGTCGGTGATGTTG
ATAAACTCTCCCGGCAGCTCGCTCAAGTTCACGTCGCTGTCCAGCGGCTGAACCTCCGGCTGACGCGATAACTGTGCG
ACCGGCTGCTGGCACAAACGGAGGCCGCGCCTACAAGGGGGTAGAGTCATAATCCTCGGTCAGGATAGGGCGGTGATGC
AGCAGCAGCGAGCGAAACATCTGCTGCCGCCGCCGCTCCGTCCGGCAGGAAAACAACAAGCCGGTGGTCTCCTCCGCG
ATAATCCGCACCGCCCGCAGCATCAGCTTCCTCGTTCTCCGCGCGCAGCACCTCACCCTGATCTCGCTCAAGTCGGCG
CAGTAGGTACAGCACGACCACGATGTTATTCATGATCCACAGTGCAGGGCGCTGTATCCAAAGCTCATGCCGGGA
ACCACCGCCCCCACGTGGCCATCGTACCACAAGCGCACGTAAATTAAGTGTCGACCCCTCATGAACGTGCTGGACACA
AACATTACTTCCTTGGGCATGTTGTAATTCACCACCTCCCGGTACCAGATAAACCTCTGGTTAAACAGGGCACCTTCC
ACCACCATCCTGAACCAAGAGGCCAGAACCTGCCCACCGGCTATGCACTGCAGGGAACCCGGGTTGGAACAATGACAA
TGCAGACTCCAAGGCTCGTAACCGTGGATCATCCGGCTGCTGAAGGCATCGATGTTGGCACAACACAGACACACGTGC
ATGCACTTTCTCATGATTAGCAGCTCTTCCCTCGTCAGGATCATATCCCAAGGAATAACCCATTCTTGAATCAACGTA
AAACCCACACAGCAGGGAAGGCCTCGCACATAACTCACGTTGTGCATGGTCAGCGTGTTGCATTCTGGAAACAGCGGA
TGATCCTCCAGTATCGAGGCGCGGGTCTCCTTCTCACAGGGAGGTAAAGGGTCCCTGCTGTACGGACTGCGCCGGGAC
GACCGAGATCGTGTTGAGCGTAGTGTCATGGAAAAGGGAACGCCGGACGTGGTCATACTTCTTGAAGCAGAACCAGGT
TCGCGCGTGGCAGGCCTCCTTGCCGTCTGCCGGTCTCGCCGTCTAGCTCGCTCCGTGTGATAGTTGTAGTACAGCCACTC
CCGCAGAGCGTCGAGGCGCACCCTGGCTTCCGGATCTATGTAGACTCCGTCTTGCACCGCGGCCCTGATAATATCCAC
CACCGTAGAATAAGCAACACCCAGCCAAGCAATACACTCGCTCTGCGAGCGGCAGACAGGAGGAGCGGGCAGAGATGG
GAGAACCATGATAAAAACTTTTTTTAAAGAATATTTTCCAATTCTTCGAAAGTAAGATCTATCAAGTGGCAGCGCTC
CCCTCCACTGGCGCGGTCAAACTCTACGGCAAAGCACAGACAACGGCATTTCTAAGATGTTCCTTAATGGCGTCCAA
AAGACACACCGCTCTCAAGTTGCAGTAAACTATGAATGAAAACCCATCCGGCTGATTTTCCAATATAGACGCGCCGGC
GGCGTCCACCAAACCCAGATAATTTTCTTCTCTCCAGCGGTTTAGAATCTGTCTAAGCAAATCCCTTATATCAAGTCC
GGCCATGCCAAAAATCTGCTCAAGAGCGCCCTCCACCTTCATGACCAAGCAGCGCATCATGATTGCAAAAATTCAGGT
TCTTCAGAGACCTGTATAAGATTCAAATGGGAACATTAACAAAAATTCCTCTGTCGCGCAGATCCCTTCGCAGGGCA
AGCTGAACATAATCAGACAGGTCTGAACGGACCAGTGAGGCCAAATCCCCACCAGGAACCAGATCCAGAGACCCTATA
CTGATTATGACGCGATACTCGGGGCTATGCTGACCAGCGCCGATGTAGGCGCCGTGCTGCATGGGCGGCGAGATA
AAATGCAAAGTGCTGGTTAAAAAATCAGGCAAAGCCTCGCGCAAAAAAGCTAACACATCATAATCATGCTCATGCAGG
TAGTTGCAGGTAAGCTCAGGAACCAAAACGGAATAACACACGATTTTCCTCTCAAACATGACTTCGCGGATACTGCGT
AAAACAAAAATTATAAATAAAAAATTAATTAACTTAAACATTGGAAGCCTGTCTCACAACAGGAAAAACCACTTTAAT
CAACATAAGACGGGCCACGGGCATGCCGGCATAGCCGTAAAAAAATTGGTCCCCGTGATTAACAAGTACCACAGACAG
CTCCCCGGTCATGTCGGGGGTCATCATGTGAGACTCTGTATACACGTCTGGATTGTGAACATCAGACAAACAAAGAAA
TCGAGCCACGTAGCCCGGAGGTATAATCACCCGCAGGCGGAGGTACAGCAAAACGACCCCCATAGGAGGAATCACAAA
ATTAGTAGGAGAAAAAAATACATAAACACCAGAAAACCCTGTTGCTGAGGCAAAATAGCGCCCTCCCGATCCAAAAC
AACATAAAGCGCTTCCACAGGAGCAGCCATAACAAAGACCCGAGTCTTACCAGTAAAAGAAAAAAGATCTCTCAACGC
AGCACCAGCACCAACACTTCGCAGTGTAAAAGGCCAAGTGCCGAGAGAGTATATATAGGAATAAAAAGTGACGTAAAC
GGGCAAAGTCCAAAAAACGCCCAGAAAAACCGCACGCGAACCTACGCCCCGAAACGAAAGCCAAAAAACACTAGACAC
TCCCTTCCGGCGTCAACTTCCGCTTTCCCACGCTACGTCACTTGCCCCAGTCAAACAAACTACATATCCCGAACTTCC
AAGTCGCCACGCCCAAAACACCGCCTACACCTCCCCGCCCGCCGGCCCGCCCCAAACCCGCCTCCCGCCCCGCGCCC
CGCCTCGCGCCGCCCATCTCATTATCATATTGGCTTCAATCCAAAATAAGGTATATTATTGATGATG
```

Fig. 6H

```
CATCATCAATAATATACCTCAAACTTTTGGTGCGCGTTAATATGCAAATGAGGTGTTTGAATTTGGGGATGCGGGGCG
CTGATTGCTGAGAGACGGGCGACCGTTAGGGGCGGGGCGGGTGACGTTTTGATGACGTGGCCGTGAGGCGGAGCCGG
TTTGCAAGTTCTCGTGGGAAAAGTGACGTCAAACGAGGTGTGGTTTGAACACGGAAATACTCAATTTTCCCGCGCTCT
CTGACAGGAAATGAGGTGTTTCTGGGCGGATGCAAGTGAAAACGGGCCATTTTCGCGCGAAAACTGAATGAGGAAGTG
AAAATCTGAGTAATTCCGCGTTTATGGCAGGGAGGAGTATTTGCCGAGGGCCGAGTAGACTTTGACCGATTACGTGGG
GGTTTCGATTACCGTATTTTTCACCTAAATTTCCGCGTACGGTGTCAAAGTCCGGTGTTTTTACGTAGGCGTCAGCTG
ATCGCCAGGGTATTTAAACCTGCGCTCTCTAGTCAAGAGGCCACTCTTGAGTGCCAGCGAGTAGAGTTTTCTCCTCCG
CGCCGCGAGTCAGATCTACACTTTGAAAGATGAGGCACCTGAGAGACCTGCCCGGTAATGTTTTCCTGGCTACTGGGA
ACGAGATTCTGGAACTGGTGGTGGACGCCATGATGGGTGACGACCCTCCCGAGCCCCCTACCCCATTTGAGGCGCCTT
CGCTGTACGATTTGTATGATCTGGAGGTGGATGTGCCCGAGAACGACCCCAACGAGGAGGCGGTGAATGATTTGTTTA
GCGATGCCGCGCTGCTGGCTGCCGAGCAGGCTAATACGGACTCTGGCTCAGACAGCGATTCCTCTCTTCATACCCCGA
GACCCGGCAGAGGTGAGAAAAAGATCCCCGAGCTTAAAGGGGAAGAGCTCGACCTGCGCTGCTATGAGGAATGCTTGC
CTCCGAGCGATGATGAGGAGGACGAGGAGGCGATTCGAGCTGCAGCGAGCGAGGGAGTGAAAGTTGCGGGCGAGAGCT
TTAGCCTGGACTGTCCTACTCTGCCCGGACACGGCTGTAAGTCTTGTGAATTTCATCGCATGAATACTGGAGATAAGA
ATGTGATGTGTGCCCTGTGCTATATGAGAGCTTACAACCATTGTGTTTACAGTAAGTGTGATTAACTTTAGTTGGGAA
GGCAGAGGGTGACTGGGTGCTGACTGGTTTATTTATGTATATGTTTTTTTATGTGTAGGTCCCGTCTCTGACGTAGAT
GAGACCCCCACTTCAGAGTGCATTTCATCACCCCCAGAAATTGGCGAGGAACCGCCCGAAGATATTATTCATAGACCA
GTTGCAGTGAGAGTCACCGGGCGGAGAGCAGCTGTGGAGAGTTTGGATGACTTGCTACAGGGTGGGGATGAACCTTTG
GACTTGTGTACCCGGAAACGCCCCAGGCACTAAGTGCCACACATGTGTGTTTACTTAAGGTGATGTCAGTATTTATAG
GGTGTGGAGTGCAATAAAAATATGTGTTGACTTTAAGTGCGTGGTTTATGACTCAGGGGTGGGGACTGTGGGTATATA
AGCAGGTGCAGACCTGTGTGGTCAGTTCAGAGCAGGACTCATGGAGATCTGGACGGTCTTGGAAGACTTTCACCAGAC
TAGACAGCTGCTAGAGAACTCATCGGCGGAAGTCTCTTACCTGTGGAGATTCTGCTTCGGTGGGCCTCTAGCTAAGCT
AGTCTATAGGGCCAAGCAGGATTATAAGGATCAATTTGAGGATATTTTGAGAGAGTGTCCTGGTATTTTTGACTCTCT
CAACTTGGGCCATCAGTCTCACTTTAACCAGAGTATTCTGAGAGCCCTTGACTTTTCCACTCCTGGCAGAACTACCGC
CGCGGTAGCCTTTTTTGCCTTTATCCTTGACAAATGGAGTCAAGAAACCCATTTCAGCAGGGATTACCGTCTGGACTG
CTTAGCAGTAGCTTTGTGGAGAACATGGAGGTGCCAGCGCCTGAATGCAATCTCCGGCTACTTGCCAGTACAGCCGGT
AGACACGCTGAGGATCCTGAGTCTCCAGTCACCCCAGGAACACCAACGCCGCCAGCAGCCGCAGCAGGAGCAGCAGCA
AGAGGAGGAGGAGGACCGAGAAGAGAACCTGAGAGCCGGTCTGGACCCTCCGGTGGCGGAGGAGGAGGAGTAGCTGAC
TTGTTTCCCGAGCTGCGCCGGGTGCTGACTAGGTCTTCCAGTGGACGGGAGAGGGGGATTAAGCGGGAGAGGCATGAG
GAGACTAGCCACAGAACTGAACTGACTGTCAGTCTGATGAGCCGCAGGCGCCCAGAATCGGTGTGGTGGCATGAGGTG
CAGTCGCAGGGGATAGATGAGGTCTCAGTGATGCATGAGAAATATTCCCTAGAACAAGTCAAGACTTGTTGGTTGGAG
CCTGAGGATGATTGGGAGGTAGCCATCAGGAATTATGCCAAGCTGGCTCTGAAGCCAGACAAGAAGTACAAGATTACC
AAAACTGATTAATATCAGAAATTCCTGCTACATTTCAGGGAATGGGGCCGAGGTGGAGATCAGTACCCAGGAGAGGGCG
GCCTTCAGATGTTGTATGATGAATATGTACCCGGGGGTGGTGGGCATGGAGGGAGTCACCTTTATGAACACGAGGTTC
AGGGGTGATGGGTATAATGGGGTGGTCTTTATGGCCAACACCAAGTTGACAGTGCACGGATGCTCCTTCTTTGGCTTC
AATAACATGTGCATCGAGGCCTGGGGCAGTGTTTCAGTGAGGGGATGCAGCTTTTCAGCCAACTGGATGGGGGTCGTG
GGCAGAACCAAGAGCGTGGTTTCAGTGAAGAAATGCCTGTTTGAGAGGTGCCACCTGGGGGTGATGAGCGAGGCGAA
GCCAAAGTCAAACACTGCGCCTCTACCGAGACGGGCTGCTTTGTGCTGATCAAGGGCAATGCCAAAGTCAAGCATAAC
ATGATCTGTGGGGCCTCGGATGAGCGCGGCTACCAGATGCTGACCTGCGCCGGTGGGAACAGCCATATGCTGGCCACC
GTGCATGTGGCCTCGCACCCCCGCAAGACATGGCCCGAGTTCGAGCACAACGTCATGACCCGCTGCAATGTGCACCTG
GGGTCCCGCCGAGGCATGTTCATGCCCTACCAGTGCAACATGCAATTTGTGAAGGTGCTGCTGGAGCCCGATGCCATG
TCCAGAGTGAGCCTGACGGGGGTGTTTGACATGAATGTGGAGCTGTGGAAAATTCTGAGATATGATGAATCCAAGACC
AGGTGCCGGGCCTGCGAATGCGGAGGCAAGCACGCCAGGCTTCAGCCCGTGTGTGTGGAGGTGACGGAGGACCTGCGA
CCCGATCATTTGGTGTTGTCCTGCAACGGGACGGAGTTCGGCTCCAGCGGGGAAGAATCTGACTAGAGTGAGTAGTGT
TTGGGGGTGGGTGGGAGCCTGCATGATGGGCAGAATGACTAAAATCTGTGTTTTTCTGTGTGTTGCAGCAGCATGAGC
GGAAGCGCCTCCTTTGAGGGAGGGGTATTCAGCCCTTATCTGACGGGGCGTCTCCCCTCCTGGGCGGGAGTGCGTCAG
AATGTGATGGGATCCACGGTGGACGGCCGGCCCGTGCAGCCGCGAACTCTTCAACCCTGACCTACGCGACCCTGAGC
TCCTCGTCCGTGGACGCAGCTGCCGCCGCAGCTGCTGCTTCCGCCGCCAGCGCCGTGCGCGGAATGGCCCTGGGCGCC
GGCTACTACAGCTCTCTGGTGGCCAACTCGAGTTCCACCAATAATCCCGCCAGCCTGAACGAGGAGAAGCTGTTGCTG
CTGATGCCCAGCTCGAGGCCCTCGACCCAGCGCCTCGGGCGAGCTGACCCAGCAGGTGGCTCAGCTGCAGGCGGAGACG
CGGGCCGCGGTTGCCACGGTGAAAACCAAATAAAAAATGAATCAATAAATAAACGGAGACGGTTGTTGATTTTAACAC
AGAGTCTTGAATCTTTATTTGATTTTTCGCGCGCGGTAGGCCCTGGACCACCGGTCTCGATCATTGAGCACCCGGTGG
ATCTTTTCCAGGACCCGGTAGAGGTGGGCTTGGATGTTGAGGTACATGGGCATGAGCCCGTCCCGGGGGTGGAGGTAG
CTCCATTGCAGGGCCTCGTGCTCGGGGGTGGTGTTGTAAATCACCCAGTCATAGCAGGGGCGCAGGGCGTGGTGCTGC
ACGATGTCTTTGAGGAGGAGACTGATGGCCACGGGCAGCCCCTTGGTGTAGGTGTTGACGAACCTATTGAGCTGGGAG
GGATGCATGCGGGGGGAGATGAGATGCATCTTGGCCTGGATCTTGAGATTGGCGATGTTCCCGCCCAGATCCCGCCGG
GGGTTCATGTTGTGCAGGACCACCAGCACGGTGTATCCGGTGCACTTGGGGAATTTGTCATGCAACTTGGAAGGGAAG
GCGTGAAAGAATTTGGAGACGCCCTTGTGACCGCCCAGGTTTTCCATGCACTCATCCATGATGGCGATGGCCCCGTG
TGGGCGGCGGCCTGGGCAAAGACGTTTCGGGGGTCGGACACATCGTAGTTGTTGGTCCTGGGTGAGCTCGTCATAGGCC
ATTTTAATGAATTTGGGGCGGAGGGTACCCGACTGGGGGACAAAGGTGCCCTCGATCCCGGGGCGTAGTTCCCCTCG
```

Fig. 7A

```
CAGATCTGCATCTCCCAGGCCTTGAGCTCGGAGGGGGGGATCATGTCCACCTGCGGGGCGATGAAAAAAACGGTTTCC
GGGGCGGGGGAGATGAGCTGCGCCGAAAGCAGGTTCCGGAGCAGCTGGGACTTGCCGCAGCCGGTGGGGCCGTAGATG
ACCCCGATGACCGGCTGCAGGTGGTAGTTGAGGGAGAGACAGCTGCCGTCCTCGCGGAGGAGGGGGGCCACCTCGTTC
ATCATCTCGCGCACATGCATGTTCTCGCGCACGAGTTCCGCCAGGAGGCGCTCGCCCCCCAGCGAGAGGAGCTCTTGC
AGCGAGGCGAAGTTTTTCAGCGGCTTGAGCCCGTCGGCCATGGGCATTTTGGAGAGGGTCTGTTGCAAGAGTTCCAGA
CGGTCCCAGAGCTCGGTGATGTGCTCTAGGGCATCTCGATCCAGCAGACCTCCTCGTTTCGCGGGTTGGGGCGACTGC
GGGAGTAGGGCACCAGGCGATGGGCGTCCAGCGAGGCCAGGGTCCGGTCCTTCCAGGGTCGCAGGGTCCGCGTCAGCG
TGGTCTCCGTCACGGTGAAGGGGTGCGCGCCGGGCTGGGCGCTTGCGAGGGTGCGCTTCAGGCTCATCCGGCTGGTCG
AGAACCGCTCCCGGTCGGCGCCCTGCGCGTCGGCCAGGTAGCAATTGAGCATGAGTTCGTAGTTGAGCGCCTCGGCCG
CGTGGCCCTTGGCGCGGAGCTTACCTTTGGAAGTGTGTCCGCAGACGGGACAGAGGAGGGACTTGAGGGCGTAGAGCT
TGGGGGCGAGGAAGACGGACTCGGGGGCGTAGGCGTCCGCGCCAGCTGGCGCAGACGGTCTCGCACTCCACGAGCC
AGGTGAGGTCGGGGCGGTCGGGGTCAAAAACGAGGTTTCCTCCGTGCTTTTTGATGCGTTTCTTACCTCTGGTCTCCA
TGAGCTCGTGTCCCCGCTGGGTGACAAAGAGGCTGTCCGTGTCCCCGTAGACCGACTTTATGGGCCGGTCCTCGAGCG
GGGTGCCGCGGTCCTCGTCGTAGAGGAACCCCGCCCACTCCGAGACGAAGGCCCGGGTCCAGGCCAGCACGAAGGAGG
CCACGTGGGAGGGGTAGCGGTCGTTGTCCACCAGCGGGTCCACCTTCTCCAGGGTATGCAAGCACATGTCCCCCTCGT
CCACATCCAGGAAGGTGATTGGCTTGTAAGTGTAGGCCACGTGACCGGGGGTCCCGGCCGGGGGGGTATAAAAGGGGG
CGGGCCCCTGCTCGTCCTCACTGTCTTCCGGATCGCTGTCCAGGAGCGCCAGCTGTTGGGGTAGGTATTCCCTCTCGA
AGGCGGGCATGACCTCGGCACTCAGGTTGTCAGTTTCTAGAAACGAGGAGGATTTGATATTGACGGTGCCGTTGGAGA
CGCCTTTCATGAGCCCCTCGTCCATCTGGTCAGAAAAGACGATCTTTTTGTTGTCGAGCTTGGTGGCGAAGGAGCCGT
AGAGGGCGTTGGAGAGCAGCTTGGCGATGGAGCGCATGGTCTGGTTCTTTTCCTTGTCGGCGCGCTCCTTGGCGGCGA
TGTTGAGCTGCACGTACTCGCGCGCCACGCACTTCCATTCGGGGAAGACGGTGGTGAGCTCGTCGGGCACGATTCTGA
CCCGCCAGCCGCGGTTGTGCAGGGTGATGAGGTCCACGCTGGTGGCCACCTCGCCGCGCAGGGGCTCGTTGGTCCAGC
AGAGGCGCCCGCCCTTGCGCGAGCAGAAGGGGGGCAGCGGGTCCAGCATGAGCTCGTCGGGGGGGTCGGCGTCCACGG
TGAAGATGCCGGGCAGGAGCTCGGGGTCGAAGTAGCTGATGCAGGTGCCCAGATCGTCCAGACTTGCTTGCCAGTCGC
GCACGGCCAGCGCGCGCTCGTAGGGGCTGAGGGGCGTGCCCCAGGGCATGGGGTGCGTGAGCGCGGAGGCGTACATGC
CGCAGATGTCGTAGACGTAGAGGGGCTCCTGGAGGACGCGATGTAGGTGGGGTAGCAGCGCCCCCCGCGGATGCTGG
CGCGCACGTAGTCGTACAGCTCGTGCGAGGGCGCGAGGAGCCCCGTGCCGAGATTGGAGCGCTGCGGCTTTTCGGCGC
GGTAGACGATCTGGCGGAAGATGGCGTGGGAGTTGGAGGAGATGGTGGGCCTCTGGAAGATGTTGAAGTGGGCATGGG
GCAGTCCGACCGAGTCCCTGATGAAGTGGGCGTAGGAGTCCTGCAGCTTGGCGACGAGCTCGGCGGTGACGAGGACGT
CCAGGGCGCAGTAGTCGAGGGTCTCTTGGATGATGTCGTACTTGAGCTGGCCCTTCTGCTTCCACAGCTCGCGGTTGA
GAAGGAACTCTTCGCGGTCCTTCCAGTACTCTTCGAGGGGGAACCCGTCCTGATCGGCACGGTAAGAGCCCACCATGT
AGAACTGGTTGACGGCCTTGTAGGCGCAGCAGCCCTTCTCCACGGGGAGGGCGTAAGCTTGCGCGGCCTTGCGCAGGG
AGGTGTGGGTGAGGGCGAAGGTGTCGCGCACCATGACTTTGAGGAACTGGTGCTTGAAGTCGAGGTCGTCGCAGCCGC
CCTGCTCCCAGAGCTGGAAGTCCGTGCGCTTCTTGTAGGCGGGGTTGGGCAAAGCGAAAGTAACATCGTTGAAGAGGA
TCTTGCCCGCGCGGGGCATGAAGTTGCGAGTGATGCGGAAAGGCTGGGGCACCTCGGCCGGTTGTTGATGACCTGGG
CGGCGAGGACGATCTCGTCGAAGCCGTTGATGTTGTGCCCGACGATGTAGAGTTCCACGAATCGCGGGCGGCCCTTGA
CGTGGGGCAGCTTCTTGAGCTCGTCGTAGGTGAGCTCGGCGGGGTCGCTGAGCCCGTGCTGCTCGAGGGCCCAGTCGG
CGACGTGGGGGTTGGCGCTGAGGAAGGAAGTCCAGAGATCCACGGCCAGGGCGGTCTGCAAGCGGTCCCGGTACTGAC
GGAACTGCTGGCCCACGGCCATTTTTTCGGGGGTGACGCAGTAGAAGGTGCGGGGGTCGCCGTGCCAGCGGTCCCACT
TGAGCTGGAGGGCGAGGTCGTGGGCGAGCTCGACGAGCGGCGGGTCCCCGGAGAGTTTCATGACCAGCATGAAGGGGA
CGAGCTGCTTGCCGAAGGACCCCATCCAGGTGTAGGTTTCCACATCGTAGGTGAGGAAGAGCCTTTCGGTGCGAGGAT
GCGAGCCGATGGGGAAGAACTGGATCTCCTGCCACCAGTTGGAGGAATGGCTGTTGATGTGATGGAAGTAGAAATGCC
GACGGCGCGCCGAGCACTCGTGCTTGTGTTTATACAAGCGTCCGCAGTGCTCGCAACGCTGCACGGGATGCACGTGCT
GCACGAGCTGTACCTGGGTTCCTTTGACGAGGAATTTCAGTGGGCAGTGGAGCGCTGGCGGCTGCATCTGGTGCTGTA
CTACGTCCTGGCCATCGGCGTGGCCATCGTCTGCCTCGATGGTGGTCATGCTGACGAGCCCGCGCGGGAGGCAGGTCC
AGACCTCGGCTCGGACGGGTCGGAGAGCGAGGACGAGGGCGCGCAGGCCGGAGCTGTCCAGGGTCCTGAGACGCTGCG
GAGTCAGGTCAGTGGGCAGCGGCGCGCGCGGTTGACTTGCAGGAGCTTTTCCAGGGCGCGCGGGAGGTCAGATGGT
ACTTGATCTCCACGGCGCCGTTGGTGGCGACGTCCACGGCTTGCAGGGTCCCGTGCCCCTGGGGCGCCACCACCGTGC
CCCGTTTCTTCTTGGGCGGCGGCGGCTCCATGCTTAGAAGCGGCGGCGAGGACGCGCGCCCGGGCGGCAGGGCGGCTC
GGGGCCCGGAGGCAGGGCGGCAGGGGCACGTCGGCGCCGCGCGCGGGCAGGTTCTGGTACTGCGCCCGGAGAAGACT
GGCGTGAGCGACGACGCGACGGTTGACGTCCTGGATCTGACGCCTCTGGGTGAAGGCCACGGGACCCGTGAGTTTGAA
CCTGAAAGAGAGTTCGACAGAATCAATCTCGGTATCGTTGACGGCGGCCTGCCGCAGGATCTCTTGCACGTCGCCCGA
GTTGTCCTGGTAGGCGATCTCGGTCATGAACTGCTCGATCTCCTCCTCCTGAAGGTCTCCGGCCGGCGCGCTCGAC
GGTGGCCGCGAGGTCGTTGGAGATGCGGCCCATGAGCTGCGAGAAGGCGTTCATGCCGGCCTCGTTCCAGACGCGGCT
GTAGACCACGGCTCCGTCGGGGTCGCGCGCGCGCATGACCACCTGGGCGAGGTTGAGCTCGACGTGGCGCGTGAAGAC
CGCGTAGTTGCAGAGGCGCTGGTAGAGGTAGTTGAGCGTGGTGGCGATGTGCTCGGTGACGAAGAAGTACATGATCCA
GCGGCGGAGCGGCATCTCGCTGACGTCGCCCAGGGCTTCCAAGCGCTCCATGGCCTCGTAGAAGTCCACGGCGAAGTT
GAAAAACTGGGAGTTGCGCGCCGAGACGGTCAACTCCTCCTCCAGAAGACGGATGAGCTCGGCGATGGTGGCGCGCAC
CTCGCGCTCGAAGGCCCCGGGGGGCTCCTCTTCCATTTCCTCCTCTTCCTCCTCCACTAACATCTCTTCTACTTCCTC
CTCAGGAGGCGGCGGCGGGGAGGGGCCCTGCGTCGCCGGCGGCGCACGGGCAGACGGTCGATGAAGCGCTCGATGGT
```

Fig. 7B

```
CTCCCCGCGCCGGCGACGCATGGTCTCGGTGACGGCGCGCCCGTCCTCGCGGGGCCGCAGCGTGAAGACGCCGCCGCG
CATCTCCAGGTGGCCGCCGGGGGGGTCTCCGTTGGGCAGGGAGAGGGCGCTGACGATGCATCTTATCAATTGACCCGT
AGGGACTCCGCGCAAGGACCTGAGCGTCTCGAGATCCACGGGATCCGAAAACCGCTGAACGAAGGCTTCGAGCCAGTC
GCAGTCGCAAGGTAGGCTGAGCCCGGTTTCTTGTTCTTCGGGTATTTGGTCGGGAGGCGGGCGGGCGATGCTGCTGGT
GATGAAGTTGAAGTAGGCGGTCCTGAGACGGCGGATGGTGGCGAGGAGCACCAGGTCCTTGGGCCCGGCTTGCTGGAT
GCGCAGACGGTCGGCCATGCCCCAGGCGTGGTCCTGACACCTGGCGAGGTCCTTGTAGTAGTCCTGCATGAGCCGCTC
CACGGGCACCTCCTCCTCGCCCGCCGCGCCGTGCATGCGCGTGAGCCCGAACCCGCGCTGCGGCTGGACGAGCGCCAG
GTCGGCGACGACGCGCTCGGCGAGGATGGCCTGCTGGATCTGGGTGAGGGTGGTCTGGAAGTCGTCGAAGTCGACGAA
GCGGTGGTAGGCTCCGGTGTTGATGGTGTAGGAGCAGTTGGCCATGACGGACCAGTTGACGGTCTGGTGGCCGGGGCG
CACGAGCTCGTGGTACTTGAGGCGCGAGTAGGCGCGCGTGTCGAAGATGTAGTCGTTGCAGGTGCGCACGAGGTACTG
GTATCCGACGAGGAAGTGCGGCGGCGGCTGGCGGTAGAGCGGCCATCGCTCGGTGGCGGGGGCGCCGGGCGCGAGGTC
CTCGAGCATGAGGCGGTGGTAGCCGTAGATGTACCTGGACATCCAGGTGATGCCGGCGGCGGTGGTGGAGGCGCGCGG
GAACTCGCGGACGCGGTTCCAGATGTTGCGCAGCGGCAGGAAGTAGTTCATGGTGGCCGCGGTCTGGCCCGTGAGGCG
CGCGCAGTCGTGGATGCTCTAGACATACGGGCAAAAACGAAAGCGGTCAGCGGCTCGACTCCGTGGCCTGGAGGCTAA
GCGAACGGGTTGGGCTGCGCGTGTACCCCGGTTCGAATCTCGAATCAGGCTGGAGCCGCAGCTAACGTGGTACTGGCA
CTCCCGTCTCGACCCAAGCCTGCTAACGAAACCTCCAGGATACGGAGGCGGGTCGTTTTTTGGCCTTGGTCGCTGGTC
ATGAAAAACTAGTAAGCGCGGAAAGCGGCCGCCCGCGATGGCTCGCTGCCGTAGTCTGGAGAAAGAATCGCCAGGGTT
GCGTTGCGGTGTGCCCCGGTTCGAGCCTCAGCGCTCGGCGCCGGCCGGATTCCGCGGCTAACGTGGGCGTGGCTGCCC
CGTCGTTTCCAAGACCCCTTAGCCAGCCGACTTCTCCAGTTACGGAGCGAGCCCCTCTTTTTTTCTTGTGTTTTTGCC
AGATGCATCCCGTACTGCGGCAGATGCGCCCCCACCCTCCACCACAACCGCCCCTACCGCAGCAGCAGCAACAGCCGG
CGCTTCTGCCCCCGCCCCAGCAGCAGCAGCCAGCCACTACCGCGGCGGCCGCCGTGAGCGGAGCCGGCGTTCAGTATG
ACCTGGCCTTGGAAGAGGGCGAGGGGCTGGCGCGGCTGGGGGCGTCGTCGCCGGAGCGGCCACCCGCGCGTGCAGATGA
AAAGGGACGCTCGCGAGGCCTACGTGCCCAAGCAGAACCTGTTCAGAGACAGGAGCGGCGAGGAGCCCGAGGAGATGC
GCGCCTCCCGCTTCCACGCGGGGCGGGAGCTGCGGCGCGGCCTGGACCGAAAGCGGGTGCTGAGGGACGAGGATTTCG
AGGCGGACGAGCTGACGGGGATCAGCCCCGCGCGCGCACGTGGCCGCGGCCAACCTGGTCACGGCGTACGAGCAGA
CCGTGAAGGAGGAGGACAACTTCCAAAAATCCTTCAACAACCACGTGCCGCAGCGTGATCGCGCGCGAGGAGGTGACCC
TGGGCCTGATGCACCTGTGGGACCTGCTGGAGGCCATCGTGCAGAACCCCACGAGCAAGCCGCTGACGGCGCAGCTGT
TTCTGGTGGTGCAGCACAGTCGGGACAACGAGACGTTCAGGGAGGCGCTGCTGAATATCACCGAGCCCGAGGGCCGCT
GGCTCCTGGACCTGGTGAACATTCTGCAGAGCATCGTGGTGCAGGAGCGCGGGCTGCCGCTGTCCGAGAAGCTGGCGG
CCATCAACTTCTCGGTGCTGAGCCTGGGCAAGTACTACGCTAGGAAGATCTACAAGACCCCGTACGTGCCCATAGACA
AGGAGGTGAAGATCGATGGGTTTTACATGCCATGACCCTGAAAGTGCTGACCCTGAGCGACGATCTGGGGGTGTACC
GCAACGACAGGATGCACCGCGCGGTGAGCGCCAGCCGCCGGCGCGAGCTGAGCGACCAGGAGCTGATGCACAGCCTGC
AGCGGGCCCTGACCGGGGCCGGGACCGAGGGGGAGAGCTACTTTGACATGGGCGCGGACCTGCGCTGGCAGCCCAGCC
GCCGGGCCTTGGAAGCTGCCGGCGGCGTGCCCTACGTGGAGGAGGTGGACGATGAGGAGGAGGAGGAGCCGAGTACCTGG
AAGACTGATGGCGCGACCGTATTTTTGCTAGATGCAGCAACAGCCACCGCCGCCGCCTCCTGATCCCGCGATGCGGGC
GGCGCTGCAGAGCCAGCCGTCCGGCATTAACTCCTCGGACGATTGGACCCAGGCCATGCAACGCATCATGGCGCTGAC
GACCCGCAATCCCGAAGCCTTTAGACAGCAGCCTCAGGCCAACCGGCTCTCGGCCATCCTGGAGGCCGTGGTGCCCTC
GCGCTCGAACCCCACGCACGAGAAGGTGCTGGCCATCGTGAACGCGCTGGTGGAGAACAAGGCCATCCGCGGCGACGA
GGCCGGGCTGGTGTACAACGCGCTGCTGGAGCGCGTGGCCCGCTACAACAGCACCAACGTGCAGACGAACCTGGACCG
CATGGTGACCGACGTGCGCGAGGCGGTGTCGCAGCGCGAGCGGTTCCACCGCGAGTCGAACCTGGGCTCCATGGTGGC
GCTGAACGCCTTCCTGAGCACGCAGCCCGCCAACGTGCCCCGGGGCCAGGAGGACTACACCAACTTCATCAGCGCGCT
GCGGCTGATGGTGGCCGAGGTGCCCCAGAGCGAGGTGTACCAGTCGGGGCCGGACTACTTCTTCCAGACCAGTCGCCA
GGGCTTGCAGACCGTGAACCTGAGCCAGGCTTTCAAGAACTTGCAGGGACTGTGGGGCGTGCAGGCCCCGGTCGGGGA
CCGCGCGACGGTGTCGAGCCTGCTGACGCCGAACTCGCGCCTGCTGCTGCTGCTGGTGGCGCCCTTCACGGACAGCGG
CAGCGTGAGCCGCGACTCGTACCTGGGCTACCTGCTTAACCTGTACCGCGAGCATCGGGCAGGCGCACGTGGACGA
GCAGACCTACCAGGAGATCACCCACGTGAGCCGCGCGCTGGGCCAGGAGGACCCGGGCAACCTGGAGGCCACCCTGAA
CTTCCTGCTGACCAACCGGTCGCAGAAGATCCCGCCCCAGTACGCGCTGAGCACCGAGGAGGAGCGCATCCTGCGCTA
CGTGCAGCAGAGCGTGGGGCTGTTCTTGATGCAGGAGGGGGCCACGCCCAGCGCCGCGCTCGACATGACCGCGCGCAA
CATGGAGCCCAGCATGTACGCCCGCAACCGCCGTTCATCAATAAGCTGATGGACTACTTGCATCGGGCGGCCGCCAT
GAACTCGGACTACTTTACCAACGCCATCTTGAACCCGCACTGGCTCCCGCCGCCCGGGTTCTACACGGGCGAGTACGA
CATGCCCGACCCCAACGACGGGTTCCTGTGGGACGACGTGGACAGCAGCGTGTTCTCGCCGCGGCCCACCACCACCAC
CGTGTGGAAGAAAGAGGGCGGGGACCGGCGGCCGTCCTCGGCGCTGTCCGGTCGCGCGGGTGCTGCCGGCGGTGCC
CGAGGCTGCCAGCCCCTTCCCGAGCCTGCCCTTTTCGCTGAACAGCGTGCGCAGCAGCGAGCTGGGTCGGCTGACGCG
GCCGCGCCTGCTGGGCGAGGAGGAGTACCTGAACGACTCCTTGTTGAAGCCCGAGCGCGAGAAGAACTTCCCCAATAA
CGGGATAGAGAGCCTGGTGGACAAGATGAGCCGCTGGAAGACGTACGCGCACGAGCACAGGGACGAGCCCCGAGCTAG
CAGCGCAGGCACCCGTAGACGCCAGCGGCACGACAGGCAGCGGGGACTGGTGTGGGACGATGAGGATTCCGCCGACGA
CAGCAGCGTGTTGGACTTGGGTGGGAGTGGTGGTGGTAACCCGTTCGCTCACCTGCGCCCCCGTATCGGGCGCCTGAT
GTAAGAATCTGAAAAAATAAAAGACGGTACTCACCAAGGCCATGGCGACCAGCGTGCGTTCTTCTCTGTTGTTTGTAG
TAGTATGATGAGGCGCGTGTACCCGGAGGGTCCTCCTCCCTCGTACGAGAGCGTGATGCAGCAGGCGGTGGCGGCGGC
GATGCAGCCCCCGCTGGAGGCGCCTTACGTGCCCCCGCGGTACCTGGCGCCTACGAGGGGCGGAACAGCATTCGTTA
CTCGGAGCTGGCACCCTTGTACGATACCACCCGGTTGTACCTGGTGGACAACAAGTCGGCGGACATCGCCTCGCTGAA
```

Fig. 7C

```
CTACCAGAACGACCACAGCAACTTCCTGACCACCGTGGTGCAGAACAACGATTTCACCCCCACGGAGGCCAGCACCCA
GACCATCAACTTTGACGAGCGCTCGCGGTGGGGCGGCCAGCTGAAAACCATCATGCACACCAACATGCCCAACGTGAA
CGAGTTCATGTACAGCAACAAGTTCAAGGCGCGGGTGATGGTCTCGCGCAAGACCCCCAACGGGGTCACGGTAGGGGA
TGATTATGATGGTAGTCAGGACGAGCTGACCTACGAGTGGGTGGAGTTTGAGCTGCCCGAGGGCAACTTCTCGGTGAC
CATGACCATCGATCTGATGAACAACGCCATCATCGACAACTACTTGGCGGTGGGGCGGCAGAACGGGGTGCTGGAGAG
CGACATCGGCGTGAAGTTCGACACGCGCAACTTCCGGCTGGGCTGGGACCCCGTGACCGAGCTGGTGATGCCGGGCGT
GTACACCAACGAGGCCTTCCACCCCGACATCGTCCTGCTGCCCGGCTGCGGCGTGGACTTCACCGAGAGCCGCCTCAG
CAACCTGCTGGGCATCCGCAAGCGGCAGCCCTTCCAGGAGGGCTTCCAGATCCTGTACGAGGACCTGGAGGGGGGCAA
CATCCCCGCGCTCTTGGATGTCGAAGCCTATGAAGAAAGTAAGGAAAAAGCAGAGGCTGAGGCAACTACAGCCGTGGC
TACCGCCGCGACTGTGGCAGATGCCACTGTCACCAGGGGCGATACATTCGCCACCCAGGCGGAGGAAGCAGCCGCCCT
AGCGGCGACCGATGATAGTGAAAGTAAGATAGTCATCAAGCCGGTGGAGAAGGACAGCAAGAACAGGAGCTACAACGT
TCTACCGGATGGAAAGAACACCGCCTACCGCAGCTGGTACCTGGCCTACAACTACGGCGACCCCGAGAAGGGCGTGCG
CTCCTGGACGCTGCTCACCACCTCGGACGTCACCTGCGGCGTGGAGCAAGTCTACTGGTCGCTGCCCGACATGATGCA
AGACCCGGTCACCTTCCGCTCCACGCGACAAGTTAGCAACTACCCGGTGGTGGGCGCCGAGCTCCTGCCCGTCTACTC
CAAGAGCTTCTTCAACGAGCAGGCCGTCTACTCGCAGCAGCTGCGTGCCTTCACCTCGCTCACGCACGTCTTCAACCG
CTTCCCCGAGAACCAGATCCTCGTCCGCCCGCCCGCGCCCACCATTACCACCGTCAGTGAAAACGTTCCTGCTCTCAC
AGATCACGGGACCCTGCCGCTGCGCAGCAGTATCCGGGGAGTCCAGCGCGTGACCGTCACTGACGCCAGACGCCGCAC
CTGCCCCTACGTCTACAAGGCCCTGGGCGTAGTCGCGCCGCGCGTCCTCTCGAGCCGCACCTTCTAAAAAAATGTCCAT
TCTCATCTCGCCCAGTAATAACACCGGTTGGGGCCTGCGCGCGCCCAGCAAGATGTACGGAGGCGCTCGCCAACGCTC
CACGCAACACCCCGTGCGCGTGCGCGGGCACTTCCGCGCTCCCTGGGGCGCCCTCAAGGGCCGCGTGCGCTCGCGCAC
CACCGTCGACGACGTGATCGACCAGGTGGTGGCCGACGCGCGCAACTACACGCCCGCCGCCGCGCCCGCCTCCACCGT
GGACGCCGTCATCGACAGCGTGGTGGCCGACGCGCGCCGGTACGCCCGCGCCAAGAGCCGGCGGCGGCGCATCGCCCG
GCGGCACCGGAGCACCCCCGCCATGCGCGCGGCGCGAGCCTTGCTGCGCAGGGCCAGGCGCACGGGACGCAGGGCCAT
GCTCAGGGCGGCCAGACGCGCGGCCTCCGGCAGCAGCAGCGCCGGCAGGACCCGCAGACGCCGCAGGTGCTGCGCTGG
GGCGGCCATCGCCAGCATGTCCCGCCCGCGGCGCGGCAACGTGTACTGGGTGCGCGACGCCGCCACCGGTGTGCGCGT
GCCCGTGCGCACCCGCCCCCCTCGCACTTGAAGATGCTGACTTCGCGATGTTGATGTGTCCCAGCGGCGAGGAGGATG
TCCAAGCGCAAATACAAGGAAGAGATGCTCCAGGTCATCGCGCCTGAGATCTACGGCCCCGCGGCGGCGGTGAAGGAG
GAAAGAAAGCCCCGCAAACTGAAGCGGGTCAAAAAGGACAAAAAGGAGGAGGAAGATGACGGACTGGTGGAGTTTGTG
CGCGAGTTCGCCCCCCGGCGGCGCGTGCAGTGGCGCGGGCGGAAAGTGAAACCGGTGCTGCGGCCCGGCACCACGGTG
GTCTTCACGCCCGGCGAGCGTTCCGGCTCCGCCTCCAAGCGCTCCTACGACGAGGTGTACGGGGACGAGGACATCCTC
GAGCAGGCGGTCGAGCGTCTGGGCGAGTTTGCTTACGGCAAGCGCAGCCGCCCCGCGCCCTTGAAAGAGGAGGCGGTG
TCCATCCCGCTGGACCACGGCAACCCCACGCCGAGCCTGAAGCCGGTGACCCTGCAGCAGGTGCTGCCGAGCGCGCAG
CCGCGCCGGGGCTTCAAGCGCGAGGGCGGCGAGGATCTGTACCCGACCATGCAGCTGATGGTGCCCAAGCGCCAGAAG
CTGGAGGACGTGCTGGAGCACATGAAGGTGGACCCCGAGGTGCAGCCCGAGGTCAAGGTGCGGCCCATCAAGCAGGTG
GCCCCCGGGCCTGGGCGTGCAGACCCGTGGACATCAAGATCCCCACGGAGCCCATGGAAACGCAGACCGAGCCCGTGAAG
CCCAGCACCAGCACCATGGAGGTGCAGACGGATCCCTGACTGCCAGCGGCTTCCACCACCACCACTCGCCGAAGACGC
AAGTACGGCGCGGCCAGCCTGCTGATGCCCAACTACGCGCTGCATCCTTCCATCATCCCCACGCCGGGCTACCGCGGC
ACGCGCTTCTACCGCGGCTACACCAGCAGCCGCCGCCGCAAGACCACCACCCGCCGCCGTCGTCGCAGCCGCCGCAGC
AGCACCGCGACTTCCGCCTTGGTGCGGAGAGTGTATCGCAGCGGGCGCGGCGCGCGAGCCTCTGACCCTGCCGCGCGCGCTAC
CACCCGAGCATCGCCATTTAACTACCGCCTCTACTTGCAGATATGGCCCTCACATGCCGCCTCCGCGTCCCCATTAC
GGGCTACCGAGGAAGAAAGCCGCGCCGTAGAAGGCTGACGGGGAACGGGCTGCGTCGCCATCACCACCGGCGGCGGCG
CGCCATCAGCAAGCGGTTGGGGGGAGGCTTCCTGCCCGCGCTGATCCCCATCATCGCCGCGGCGATCGGGCGATCCC
CGGCATAGCTTCCGTGGCGGTGCAGGCCTCTCAGCGCCACTGAGACACAAAAAAGCATGGATTTGTAATAAAAAAATG
GACTGACGCTCCTGGTCCTGTGATGTGTGTTTTAGATGGAAGACATCAATTTTTCGTCCCTGGCCACCGCGACACGGC
ACGCGGCCGTTTATGGGCACCTGGAGCGACATCGGCAACAGCCAACTGAACGGGGGCGCCTTCAATTGGAGCAGTCTC
TGGAGCGGGCTTAAGAATTTCGGGTCCACGCTCAAAACCTATGGCAACAAGGCGTGGAACAGCAGCACAGGGCAGGCG
CTGAGGGAAAAGCTGAAAGAGCAGAACTTCCAGCAGAAGGTGGTCGATGGCCTGGCCTCGGGCATCAACGGGGTGGTG
GACCTGGCCAACCAGGCCGTGCAGAAACAGATCAACAGCCGCCTGGACGCGGTCCCGCCGGCGGGGTCCGTGGAGATG
CCCCAGGTGGAGGAGGAGCTGCCTCCCCTGGACAAGCGCGGCGACAAGCGACCGCGTCCCGACGCGGAGGAGACGCTG
CTGACGCACACGGACGAGCCGCCCCCGTACGAGGAGGCGGTGAAACTGGGTCTGCCCACCACGCGGCCCGTGGCGCCT
CTGGCCACCGGGGTGCTGAAACCCAGCAGCAGCAGCCAGCCCGCGACCCTGGACTTGCCTCCGCCTGCTTCCCGCCCC
TCCACAGTGGCTAAGCCCCTGCCGCCGGTGGCCGTCGCGCGCGCGCCCCCGAGGCCGCCCCCAGGCGAACTGGCAG
AGCACTCTGAACAGCATCGTGGGTCTGGGAGTGCAGAGTGTGAAGCGCCGCCGCTGCTATTAAAAGACACTGTAGCGC
TTAACTTGCTTGTCTGTGTGTGTATATGTATGTCCGCCGACCAGAAGGAGGAAGAGGCGCGTCGCCGAGTTGCAAGAT
GGCCACCCCATCGATGCTGCCCCAGTGGGCGTACATGCACATCGCCGGACAGGACGCTTCGGAGTACCTGAGTCCGGG
TCTGGTGCAGTTCGCCCGCGCCACAGACAACCTACTTCAGTCTGGGGAACAAGTTTAGGAACCCCACGGTGGCGCCCAC
GCACGATGTGACCACCGACCGCAGCCAGCGGCTGACGCTGCGCTTCGTGCCCGTGGACCGCGAGGACAACACCTACTC
GTACAAAGTGCGCTACACGCTGGCCGTGGGCGACAACCGCGTGCTGGACATGGCCAGCACCTACTTTGACATCCGCGG
CGTGCTGGATCGGGGCCCCAGCTTCAAACCCTACTCCGGCACCGCCTACAACAGCCTAGCTCCCAAGGGAGCGCCCAA
CACCTCACAGTGGAAGGATTCCGACAGCAAAATGCATACTTTTGGAGTTGCTGCCATGCCCGGTGTTGTTGGTAAAAA
```

Fig. 7D

```
AATAGAAGCCGATGGTCTGCCTATTGGAATAGATTCATCCTCTGGAACTGACACCATAATTTATGCTGATAAAACTTT
CCAACCAGAGCCACAGGTTGGAAGTGACAGTTGGGTCGACACCAATGGTGCAGAGGAAAAATATGGAGGTAGAGCTCT
TAAGGACACTACAAACATGAAGCCCTGCTACGGTTCTTTTGCCAGGCCTACCAACAAAGAAGGTGGACAGGCTAACAT
AAAAGATTCTGAAACTGCCAGCACTACTCCTAACTATGATATAGATTTGGCATTCTTTGACAGCAAAAATATTGCAGC
TAACTACGATCCAGATATTGTAATGTACACAGAAAATGTTGAGTTGCAAACTCCAGATACTCATATTGTGTTTAAGCC
AGGAACTTCAGATGAAAGTTCAGAAGCCAATTTGGGCCAGCAGGCCATGCCCAACAGACCCAACTACATCGGGTTCAG
AGACAACTTTATCGGGCTCATGTACTACAACAGCACTGGCAATATGGGTGTACTGGCTGGTCAGGCCTCCCAGCTAAA
TGCTGTGGTGGACTTGCAGGACAGAAACACCGAACTGTCCTACCAGCTCTTGCTTGACTCTCTGGGTGACAGAACCAG
GTATTTCAGTATGTGGAATCAGGCGGTGGACAGCTATGACCCCGATGTGCGCATTATTGAAAATCACGGTGTGGAGGA
TGAACTCCCCAATTATTGCTTCCCTTTGAATGGTGTAGGCTTTACAGATACTTACCAGGGTGTTAAAGTTAAGACAGA
TACAGCCGCTACTGGTACCAATGGAACGCAGTGGGACAAAGATGATACCACAGTCAGCACTGCCAATGAGATCCACTC
AGGCAATCCTTTCGCCATGGAGATCAACATCCAGGCCAACCTGTGGCGGAACTTCCTCTACGCGAACGTGGCGCTGTA
CCTGCCCGACTCCTACAAGTACACGCCGGCCAACATCACGCTGCCGACCAACACCAACACCTACGATTACATGAACGG
CCGCGTGGTGGCGCCCTCGCTGGTGGACGCCTACATCAACATCGGGGCGCGCTGGTCGCTGGACCCCATGGACAACGT
CAACCCCTTCAACCACCACCGCAACGCGGGCCTGCGCTACCGCTCCATGCTCCTGGGCAACGGGCGCTACGTGCCCTT
CCACATCCAGGTGCCCCAAAAGTTTTTCGCCATCAAGAGCCTCCTGCTCCTGCCCGGGTCCTACACCTACGAGTGGAA
CTTCCGCAAGGACGTCAACATGATCCTGCAGAGCTCCCTCGGCAACGACCTGCGCACGGACGGGGCCTCCATCGCCTT
CACCAGCATCAACCTCTACGCCACCTTCTTCCCCATGGCGCACAACACCGCCTCCACGCTCGAGGCCATGCTGCGCAA
CGACACCAACGACCAGTCCTTCAACGACTACCTCTCGGCGGCCAACATGCTCTACCCCATCCCGGCCAACGCCACCAA
CGTGCCCATCTCCATCCCCTCGCGCAACTGGGCCGCCTTCCGCGGATGGTCCTTCACGCGCCTCAAGACCCGCGAGAC
GCCCTCGCTCGGCTCCGGGTTCGACCCCTACTTCGTCTACTCGGGCTCCATCCCCTACCTCGACGGCACCTTCTACCT
CAACCACACCTTCAAGAAGGTCTCCATCACCTTCGACTCCTCCGTCAGCTGGCCCGGCAACGACCGCCTCCTGACGCC
CAACGAGTTCGAAATCAAGCGCACCGTCGACGGAGAGGGATACAACGTGGCCCAGTGCAACATGACCAAGGACTGGTT
CCTGGTCCAGATGCTGGCCCACTACAACATCGGCTACCAGGGCTTCTACGTGCCCGAGGGCTACAAGGACCGCATGTA
CTCCTTCTTCCGCAACTTCCAGCCCATGAGCCGCCAGGTCGTGGACGAGGTCAACTACAAGGACTACCAGGCCGTCAC
CCTGGCCTACCAGCACAACAACTCGGGCTTCGTCGGCTACCTCGCGCCCACCATGCGCCAGGGCCAGCCCTACCCCGC
CAACTACCCCTACCCGCTCATCGGCAAGAGCGCCGTCGCCAGCGTCACCCAGAAAAAGTTCCTCTGCGACCGGGTCAT
GTGGCGCATCCCCTTCTCCAGCAACTTCATGTCCATGGGCGCGCTCACCGACCTCGGCCAGAACATGCTCTACGCCAA
CTCCGCCCACGCGCTAGACATGAATTTCGAAGTCGACCCCATGGATGAGTCCACCCTTCTCTATGTTGTCTTCGAAGT
CTTCGACGTCGTCCGAGTGCACCAGCCCCACCGCGGCGTCATCGAGGCCGTCTACCTGCGCACGCCCTTCTCGGCCGG
CAACGCCACCACCTAAAGCCCCGCTCTTGCTTCTTGCAAGATGACGGCCTGTGGCTCCGGCGAGCAGGAGCTCAGGGC
CATCCTCCGCGACCTGGGCTGCGGGCCCTGCTTCCTGGGCACCTTCGACAAGCGCTTCCCGGGATTCATGGCCCCGCA
CAAGCTGGCCTGCGCCATCGTCAACACGGCCGGCCGCGAGACCGGGGGCGAGCACTGGCTGGCCTTCGCCTGGAACCC
GCGCTCCCACACCTGCTACCTCTTCGACCCCTTCGGGTTCTCGGACGAGCGCCTCAAGCAGATCTACCAGTTCGAGTA
CGAGGGCCTGCTGCGCCGCAGCGCCCTGGCCACCGAGGACCGCTGCATCACCCTGGAAAAGTCCACCCAGACCGTGCA
GGGTCCGCGCTCGGCCGCTGCGGGCTCTTCTGCTGCATGTTCCTGCACGCCTTCGTGCACTGGCCCGACCGCCCCAT
GGACAAGAACCCCACCATGAACTTGCTGACGGGGGTGCCCAACGGCATGCTCCAGTCGCCCCAGGTGGAACCCACCCT
GCGCCGCAACCAGGAGGCGCTCTACCGCTTCCTCAACGCCCACTCCGCCTACTTTCGCTCCCACCGCGCGCGCATCGA
GAAGGCCACCGCCTTCGACCGCATGAATCAAGACATGTAAACTGTGTGTATGTGAATGCTTTATTCATCATAATAAAC
AGCACATGTTTATGCCACCTTCTCTGAGGCTCTGACTTTATTTAGAAATCGAAGGGGTTCTGCCGGCTCTCGGCGTGC
CCCGCGGGCAGGGATACGTTGCGGAACTGGTACTTGGGCAGCCACTTGAACTCGGGGATCAGCAGCTTCGGCACGGGG
AGGTCGGGGAACGAGTCGCTCCACAGCTTGCGCGTGAGTTGCAGGGCGCCCAGCAGGTCGGGCGCGGAGATCTTGAAA
TCGCAGTTGGACCCGCGTTCTGCGCGCGAGAGTTGCAGCGGGGTTGCAGCACTGGAACACCATCAGGGCCGGG
TGCTTCACGCTCGCCAGCACCGTCGCGTCGGTGATGCCCTCCACGTCCAGATCCTCGGCGTTGGCCATCCCGAAGGGG
GTCATCTTGCAGGTCTGCCGCCCCATGCTGGGCACGCAGCCGGGCTTGTGGTTGCAATCGCAGTGCAGGGGGATCAGC
ATCATCTGAGCCTGCTCGGAGCTCATGCCCGGGTACATGGCCTTCATGAAAGCCTCCAGCTGGCGGAAGGCCTGCTGC
GCCTTGCCGCCCTCGGTGAAGAAGACCCCACAGGACTTGCTAGAGAACTGGTTGGTGGCGCAGCCCGCGTCGTGCACG
CAGCAGCGCGCGTCGTTGTTGGCCAGCTGCACCACGCTGCGCCCCCAGCGGTTCTGGGTGATCTTGGCCCGGTCGGGG
TTCTCCTTCAGCGCGCGCTGCCCGTTCTCGCTCGCCACATCCATCTCGATCGTGTGCTCCTTCTGGATCATCACGGTC
CCGTGCAGGCACCGCAGCTTGCCCTCGGCCTCGGTGCACCCGTGCAGCCACAGCGCGCAGCCGGTGCACTCCCAGTTC
TTGTGGGCGATCTGGGAGTGCGAGTGCACGAAGCCCTGCAGGAAGCGGCCCATCATCGTGGTCAGGGTCTTGTTGCTG
GTGAAGGTCAGCGGGATGCCGCGGTGCTCCTCGTTCACATACAGGTGGCAGATCGGCGGTACACCTCGCCCTGCTCG
GGCATCAGCTGGAAGGCGGACTTCAGGTCGCTCTCCACGCGGTACCGCTCCATCAGCAGCGTCATCACTTCCATGCCC
TTCTCCCAGGCCGAAACGATCGGCAGGCTCAGGGGGTTCTTCACCGTCATCTTAGTCGCCGCCGCCGAAGTCAGGGGG
TCGTTCTCGTCCAGGGTCTCAAACACTCGCTTGCCGTCCTTCTCGGTGATGCGCACGGGGGGAAAGCTGAAGCCCACG
GCCGCCAGCTCCTCCTCGGCCTGCCTTTCGTCCTCGCTGTCCTGGCTGATGTCTTGCAAAGGCACATGCTTGGTCTTG
CGGGGTTTCTTTTTGGGCGGCAGAGGCGGCGGCGGAGACGTGCTGGGCGAGCGCGAGTTCTCGCTCACCACGACTATT
TCTTCTTCTTGGCCGTCGTCCGAGACCACGCGGCGGTAGGCATGCCTCTTCTGGGGCAGAGGCGGAGGCGACGGGCTC
TCGCGGTTCGGCGGGCGGCTGGCAGAGCCCCTTCCGCGTTCGGGGGTGCGCTCCTGGCGGCGCTGCTCTGACTGACTT
```

Fig. 7E

```
CCTCCGCGGCCGGCCATTGTGTTCTCCTAGGGAGCAACAAGCATGGAGACTCAGCCATCGTCGCCAACATCGCCATCT
GCCCCCGCCGCCGACGAGAACCAGCAGCAGCAGAATGAAAGCTTAACCGCCCCGCCGCCCAGCCCCACCTCCGACGCC
GCCGCGGCCCCAGACATGCAAGAGATGGAGGAATCCATCGAGATTGACCTGGGCTACGTGACGCCCGCGGAGCACGAG
GAGGAGCTGGCAGCGCGCTTTTCAGCCCCGGAAGAGAACCACCAAGAGCAGCCAGAGCAGGAAGCAGAGAGCGAGCAG
CAGCAGGCTGGGCTCGAGCATGGCGACTACCTGAGCGGGGCAGAGGACGTGCTCATCAAGCATCTGGCCCGCAAAGC
ATCATCGTCAAGGACGCGCTGCTCGACCGCGCCGAGGTGCCCCTCAGCGTGGCGGAGCTCAGCCGCGCCTACGAGCGC
AACCTCTTCTCGCCGCCGCGTGCCCCCCAAGCGCCAACGGCACCTGCGAGCCCAACCCGCGCCTCAACTTCTAC
CCGGTCTTCGCGGTGCCCGAGGCCCTGGCCACCTACCACCTCTTTTTCAAGAACCAAAGGATCCCCGTCTCCTGCCGC
GCCAACCGCACCCGCGCCGACGCCCTGCTCAACCTGGGTCCCGGCGCCCGCCTACCTGATATCACCTCCTTGGAAGAG
GTTCCCAAGATCTTCGAGGGTCTGGGCAGCGACGAGACTCGGGCCGCGAACGCTCTGCAAGGAAGCGGAGAGGAGCAT
GAGCACCACAGCGCCCTGGTGGAGTTGGAAGGCGACAACGCGCCCTGGCGGTGCTCAAGCGCACGGTCGAGCTGACC
CACTTCGCCTACCCGGCGCTCAACCTGCCCCCCAAGGTCATGAGCGCCGTCATGGACCAGGTGCTCATCAAGCGCGCC
TCGCCCCTCTCAGAGGAGGAGATGCAGGACCCCGAGAGCTCGGACGAGGGCAAGCCCGTGGTCAGCGACGAGCAGCTG
GCGCGCTGGCTGGGAGCGAGCAGCACCCCCAGAGCCTGGAAGAGCGGCGCAAGCTCATGATGGCCGTGGTCCTGGTG
ACCGTGGAGCTGGAGTGTCTGCGCCGCTTCTTCGCCGACGCGGACCCTGCGCAAGGTCGAGGAGAACCTGCACTAC
CTCTTCAGGCACGGGTTCGTGCGCCAGGCCTGCAAGATCTCCAACGTGGAGCTGACCAACCTGGTCTCCTACATGGGC
ATCCTGCACGAGAACCGCCTGGGGCAGAACGTGCTGCACACCACCCTGCGCGGGGAGGCCCGCCGCGACTACATCCGC
GACTGCGCTACCTGTACCTCTGCCACACCTGGCAGACGGGCATGGGCGTGTGGCAGCAGTGCCTGGAGGAGCAGAAC
CTGAAAGAGCTCTGCAAGCTCCTGCAGAAGAACCTCAAGGCCCTGTGGACCGGGTTCGACGAGCGCACCACCGCCTCG
GACCTGGCCGACCTCATCTTCCCCGAGCGCCTGCGGCTGACGCTGCGCAACGGGCTGCCCGACTTATGAGCCAAAGC
ATGTTGCAAAACTTTCGCTCTTTCATCCTCGAACGCTCCGGGATCCTGCCCGCCACCTGCTCCGCACTGCCCTCGGAC
TTCGTGCCGCTGACCTTCCGCGAGTGCCCCCCGCCGCTCTGGAGCCACTGCTACTTGCTGCGCCTGGCCAACTACCTG
GCCTACCACTCGGACGTGATCGAGGACGTCAGCAGCGAGGGTCTGCTCGAGTGCCACTGCCGCTGCAACCTCTGCACG
CCGCACCGCTCCTTGGCCTGCAACCCCCAGCTGCTGAGCGAGACCCAGATCATCGGCACCTTCGAGTTGCAAGGCCCC
GGCGAGGGCAAGGGGGGTCTCAAACTCACCCCGGGGCTGTGGACCTCGGCCTACTTGCGCAAGTTCGTGCCCGAGGAC
TACCATCCCTTCGAGATCAGGTTCTACGAGGACCAATCCCAGCCGCCCAAGGCCGAGCTGTCGGCCTGCGTCATCACC
CAGGGGGCCATCCTGGCCCAATTGCAAGCCATCCAGAAATCCCGCCAAGAATTTCTGCTGAAAAAGGGCCACGGGGTC
TACTTGGACCCCCAGACCGGAGAGGAGCTCAACCCCAGCTTCCCCCAGGATGCCCCGAGGAAGCAGCAAGAAGCTGAA
AGTGGAGCTGCCGCTGCCGCCGGAGGATTTGGAGGAAGACTGGGAGAGCAGTCAGGCAGAGGAGATGGAAGACTGGGA
CAGCACTCAGGCAGAGGAGGACAGCCTGCAAGACAGTCTGGAGGAGGAAGACGAGGTGGAGGAGGAGGCAGAGGAAGA
AGCAGCCGCCGCCAGACCGTCGTCCTCGGCGGAGGAGAAAGCAAGCAGCACGGATACCATCTCCGCTCCGGGTCGGGG
TCGCGGCGGCCGGGCCCACAGTAGATGGACGAGACCGGGCGCTTCCCGAACCCCACCACCCAGACCGGTAAGAAGGA
GCGGCAGGGATACAAGTCCTGGCGGGGGCACAAAAACGCCATCGTCTCCTGCTTGCAAGCCTGCGGGGGCAACATCTC
CTTCACCCGGCCGTACCTGCTCTTCCACCGCGGGGTGAACTTCCCCGCAACATCTTGCATTACTACCGTCACCTCCA
CAGCCCCTACTACTGTTTCCAAGAAGAGGCAGAAACCCAGCAGCAGCAGCAGAAAACCAGCGGCAGCAGCAGCAGCTA
GAAAATCCACAGCGGCGGCAGGTGGACTGAGGATCGCGGCGAACGAGCCGGCGCAGACCCGGGAGCTGAGGAACCGGA
TCTTTCCCACCCTCTATGCCATCTTCCAGCAGAGTCGGGGGCAGGAGCAGGAACTGAAAGTCAAGAACCGTTCTCTGC
GCTCGCTCACCCGCCAGTTGTCTGTATCACAAGAGCGAAGACCAACTTCAGCGCACTCTCGAGGACGCCGAGGCTCTCT
TCAACAAGTACTGCGCGCTCACTCTTAAAGAGTAGCCCGCGCCCGCCCACACACGGAAAAAGGCGGGAATTACGTCAC
CACCTGCGCCCTTCGCCCGACCATCATCATGAGCAAAGAGATTCCCACGCCTTACATGTGGAGCTACCAGCCCCAGAT
GGGCCTGGCCGCCGGCGCCTGGCCGCTGGACTACTCCACCCGCCATGAACTGGCTCAGTGCCCGGGCCCGCGATGATCTCACG
GGTGAATGACATCCGCGCCCACCGAAACCAGATACTCCTAGAACAGTCAGCGATCACCGCCACGCCCCGCCATCACCT
TAATCCGCGTAATTGGCCCGCCGCCCTGGTGTACCAGGAAATTCCCCAGCCCACGACCGTACTACTTCCGCGAGACGC
CCAGGCCGAAGTCCAGCTGACTAACTCAGGTGTCCAGCTGGCCGGCGGCGCCGCCCGTGTCGTCACCGCCCCGCTCA
GGGTATAAAGCGGCTGGTGATCCGAGGCAGAGGCACACAGCTCAACGACGAGGTGGTGAGCTCTTCGCTGGGTCTGCG
ACCTGACGGAGTCTTCCAACTCGCCGGATCGGGGAGATCTTCCTTCACGCCTCGTCAGGCCGTCCTGACTTTGGAGAG
TTCGTCCTCGCAGCCCCGCTCGGGCGGCATCGGCACTCTCCAGTTCGTGGAGGAGTTCACTCCCTCGGTCTACTTCAA
CCCCCTTCTCCGGCTCCCCCGGCCACTACCCGGACGAGTTCATCCCGAACTTCGACGCCATCAGCGAGTCGGTGGACGG
CTACGATTGAATGTCCCATGGTGGCGCGGCTGACCTAGCTCGGCTTCGACACCTGGACCACTGCCGCCGCCTTCGCTG
CTTCGCTCGGGATCTCGCCGAGTTTGCCTACTTTGAGCTGCCCGAGGAGCACCCTCAGGGCCCGGCCCACGGAGTGCG
GATCGTCGTCGAAGGGGGCCTCGACTCCCACCTGCTTCGGATTTTCAGCCAGCGTCCGATCCTGGTCGAGCGCGAGCA
AGGACAGACCCTTCTGACCCTGTACTGCATCTGCAACCACCCCGGCCTGCATGAAAGTCTTTGTTGTCTGCTGTGTAC
TGAGTATAATAAAAGCTGAGATCAGCGACTACTCCGGACTCGATTGTGGTGTTCCTGCTATCAACCGGTCCCTGTTCT
TCACCGGGAACGAGACCGAGCTCCAGCTCCAGTGTAAGCCCCACAAGAAGTATCTCACCTGGCTGTTCCAGGGCTCTC
CGATCGCCGTTGTCAACCACTGCGACAACGACGGAGTCCTGCTGAGCGGCCCTGCCAACCTTACTTTTCCACCCGCA
GAAGCAAGCTCCAGCTCTTCCAACCCTTCCTCCCCGGGACCTATCAGTGCGTCTCGGGACCCTGCCATCACACCTTCC
ACCTGATCCCGAATACCACAGCGCCGCTCCCCGCTACTAACAACCAAACTACCCACCAACGCCACCGTCGCGACCTTT
CTGAATCTAATACTACCACCCACACCGGAGGTGAGCTCCGAGGTCGACCAACCTCTGGGATTTACTACGGCCCCTGGG
AGGTGGTAGGGTTAATAGCGCTAGGCCTAGTTGCGGGTGGCTTTTGGCTCTCTGCTACCTATACCTCCCTTGCTGTT
CGTACTTAGTGGTGCTGTGTTGCTGGTTTAAGAAATGGGGAAGATCACCCTAGTGAGCTGCGGTGTGCTGGTGGCGGT
```

Fig. 7F

```
GGTGCTTTCGATTGTGGGACTGGGCGGCGCGGCTGTAGTGAAGGAGGAGAAGGCCGATCCCTGCTTGCATTTCAATCC
CGACAAATGCCAGCTGAGTTTTCAGCCCGATGGCAATCGGTGCACGGTGCTGATCAAGTGCGGATGGGAATGCGAGAA
CGTGAGAATCGAGTACAATAACAAGACTCGGAACAATACTCTCGCGTCCGTGTGGCAGCCCGGGGACCCCGAGTGGTA
CACCGTCTCTGTCCCCGGTGCTGACGGCTCCCCGCGCACCGTGAACAATACTTTCATTTTTGCGCACATGTGCGACAC
GGTCATGTGGATGAGCAAGCAGTACGATATGTGGCCCCCCACGAAGGAGAACATCGTGGTCTTCTCCATCGCTTACAG
CCTGTGCACGGCGCTAATCACCGCTATCGTGTGCCTGAGCATTCACATGCTCATCGCTATTCGCCCCAGAAATAATGC
CGAAAAAGAGAAACAGCCATAACACGTTTTTTCACACACCTTTTTCAGACCATGGCCTCTGTTACTGCCCTAACTATT
TTTTTGGGCCTTGTGGGTACTAGCAGCACTTTTCAGCATATAAACAAAACTGTTTATGCTGGTTCTAATTCTGTATTA
CCTGGGCATCAATCACACCAGAAAGTTTCATGGTACTGGTATGATAAAAGTAACACGCCAGTCACACTCTGCAAGGGT
CATCAAACACCCATAAACCGTAGTGGAATTTTTTTTAAATGTAATCATAATAATATTACACTACTTTCAATTACAAAG
CACTATTCTGGTACTTACTATGGAACCAATTTTAACATAAAACAGGACACTTACTATAGTGTCACAGTATTGGATCCA
ACTACTCCTAGAACAACTACAAAACCCACAACTACTAAGAGGCACACTAAACCTAAAACTACCAAGAAAACCACTGTC
AAAACTACAACAACTAGGACCACCACAACTACAGAGGCTACCACCAGCACAACACTTGCTGCCACTACACACACACAC
ACTGAGCTAACCTTACAGACCACTAATGATTTGATCGCCCTGTTGCAAAAGGGGGATAACAGCACCACTTCCAATGAG
GAGATACCCAGATCCATGATTGGCATTATTGTTGCTGTAGTGGTGTGCATGTTGATCATCGCCTTGTGCATGGTGTAC
TATGCCTTCTGCTACAGAAAGCACAGACTGAACGACAAGCTGGAACACTTACTAAGTGTTGAATTTTAATTTTTTAGA
ACCATGAAGATCCTAGGCCTTTTTAGTTTTTCTATCATTACCTCTACTCTTTGTGAATCAGTGGATAAAGATGTTACT
ATTACCACTGGTTCTAATTATACACTGAAAGGGCCACCCTCAGGTATGCTTTCGTGGTATTGCTATTTTGGAACTGAC
ACTGATCAAACTGAATTATGCAATTTTCAAAAAGGCAAAACCTCAAACTCTAAAATCTCTAATTATCAATGCAATGGC
ACTGATCTGATACTACTCAATGTCACGAAAGCATATGGTGGCAGTTATTCTTGCCCTGGACAAAACACTGAGGATATG
ATTTTTTACAAAGTGGAAGTGGTTGATCCCACTACTCCACCGCCCACCACCACAACTACTCACACCACACACACAGAA
CAAACACCAGAGGCAGCAGAAGCAGAGTTGGCCTTCCAGGTTCACGGAGATTCCTTTGCTGTCAATACCCCTACACCC
GATCAGCGGTGTCCGGGGCTGCTCGTCAGCGGCATTGTCGGTGTGCTTTCGGGATTAGCAGTCATAATCATCTGCATG
TTCATTTTTGCTTGCTGCTATAGAAGGCTTTACCGACAAAAATCAGACCCACTGCTGAACCTCTATGTTTAATTTTTT
CCAGAGCCATGAAGGCAGTTAGCGCTCTAGTTTTTGTTCTTTGATTGGCATTGTTTTTAGTGCTGGGTTTTTGAAAA
ATCTTACCATTTATGAAGGTGAGAATGCCACTCTAGTGGGCATCAGTGGTCAAAATGTCAGCTGGCTAAAATACCATC
TAGATGGTGGAAAGACATTTGCGATTGGAATGTCACTGTGTATACATGTAATGGAGTTAACCTCACCATTACTAATG
CCACCCAAGATCAGAATGGTAGGTTTAAGGGCCAGAGTTTCACTAGAAATAATGGGTATGAATCCCATAACATGTTTA
TCTATGACGTCACTGTCATCAGAAATGAGACTGCCACCACCACACAGATGCCCACTACACACAGTTCTACCACTACTA
CCATGCAAACCACACAGACAACCACTTTTTATACATCAACTCAGCATATGACCACCACTACAGCAGCAAAGCCAAGTA
GTGCAGCGCCTCAGCCCCAGGCTTTGGCTTTGATAGCTGCACAACCTAGTACAACTACTAGGACCAATGAGCAGACTA
CTGATTTTTTGTCCACTGTCGAGAGCCACACCACAGCTACCTCCAGTGCCTTCTCTAGCACCGCCAATCTCTCCTCGC
TTTCCTCTACACCAATCAGTCCCGCTACTACTACTCCTAGCCCCGCTCCTCTTCCCACTCCCCTGAAGCAAACTGAGG
ACAGCGGCATGCAATGGCAGATCACCCTGCTCATTGTGATCGGGTTGGTCATTCTGGCCGTGTTGCTCTACTACATCT
TCTGCCGCCGCATTCCCAACGCGCACCGCAAGCCGGTCTACAAGCCCATCGTTGACGGGCAACCGGAGCCGCTTCAGG
TGGAAGGGGGTCTAAGGAATCTTCTCTTCTCTTTTACAGTATGGTGATTGAACTATGATTCCTAGACAATTCTTGATC
ACTATTCTTATCTGCCTCCTCCAAGTCTGTGCCACCCTCGCTCTGGTGGCCAACGCCAGTCCAGACTGTATTGGGCCC
TTCGCCTCCTACGTGCTCTTTGCCTTCGTCACCTGCATCTGCTGCTGTAGCATAGTCTGCCTGCTTATCACCTTCTTC
CAGTTCATTGACTGGATCTTTGTGCGCATCGCCTACCTGCGCCACCACCCCCAGTACCGCGACCAGCAGTGGCGCGG
CTGCTCAGGCTCCTCTGATAAGCATGCGGGCTCTGCTACTTCTCGCGCTTCTGCTGTTAGTGCTCCCCCGTCCCGTCA
ACCCCCGGTCCCCCACTCAGTCCCCCGAGGAGGTCCGCAAATGCAAATTCCAAGAACCCTGGAAATTCCTCAAATGCT
ACCGCCAAAAATCAGACATGCATCCCAGCTGGATCATGATCATTGGGATCGTGAACATTCTGGCCTGCACCCTCATCT
CCTTTGTGATTTACCCCTGCTTTGACTTTGGTTGGAACTCGCCAGAGGCGCTCTATCTCCCGCCTGAACCTGACACAC
CACCACAGCAACCTCAGGCACACGCACTACCACCACCACAGCCTAGGCCACAATACATGCCCATATTAGACTATGAGG
CCGAGCCACAGCGACCCATGCTCCCCGCTATTAGTTACTTCAATCTAACCGGCGGAGATGACTGACCCACTGGCCAAC
AACAACGTCAACGACCTTCTCCTGGACATGGACGGCCGCGCCTCGGAGCAGCCGACTCGCCCAACTTCGCATTCGCCAG
CAGCAGGAGAGAGCCGTCAAGGAGCTGCAGGACGGCATAGCCATCCACCAGTGCAAGAAAGGCATCTTCTGCCTGGTG
AAACAGGCCAAGATCTCCTACGAGGTCACCCAGACCGACCATCGCCTCTCCTACGAGCTCCTGCAGCAGCGCCAGAAG
TTCACCTGCCTGGTCGGAGTCAACCCCATCGTCATCACCCAGCAGTCGGGCGATACCAAGGGGTGCATCCACTGCTCC
TGCGACTCCCCCGACTGCGTCCACACTCTGATCAAGACCCTCTGCGGCCTCCGCGACCTCCTCCCCATGAACTAATCA
CCCCCTTATCCAGTGAAATAAAGATCATATTGATGATGATTTTACAGAAATAAAGATACAATCATATTGATGATTTGA
GTTTAATAAAAAATAAAGAATCACTTACTTGAAATCTGATACCAGGTCTCTGTCCATGTTTTCTGCCAACACCACTTC
ACTCCCCTCTTCCCAGCTCTGGTACTGCAGGCCCCGGCGGGCTGCAAACTTCCTCCACACGCTGAAGGGGATGTCAAA
TTCCTCCTGTCCTCAATCTTCATTTTATCTTCTATCAGATGTCCAAAAAGCGCGTCCGGGTGGATGATGACTTCGAC
CCCGTCTACCCCTACGATGCAGACAACGCACCGACCGTGCCCTTCATCAACCCCCCCTTCGTCTCTTCAGATGGATTC
CAAGAGAAGCCCCTGGGGGTGCTGTCCCTGCGACTGGCCGACCCCGTCACCACCAAGAACGGGGAAATCACCCTCAAG
CTGGGAGAGGGGTGGACCTCGACTCCTCGGGAAAACTCATCTCCAACACGGCCACCAAGGCCGCCGCCCCTCTCAGT
TTTTCCAACAACACCATTTCCCTTAACATGGATCACCCCTTTTACACTAAAGATGAAAATTATCCTTACAAGTTTCT
CCACCATTAAATATACTGAGAACAAGCATTCTAAACACACTAGCTTTAGGTTTTGGATCAGGTTTAGGACTCCGTGGC
```

Fig. 7G

```
TCTGCCTTGGCAGTACAGTTAGTCTCTCCACTTACATTTGATACTGATGGAAACATAAAGCTTACCTTAGACAGAGGT
TTGCATGTTACAACAGGAGATGCAATTGAAAGCAACATAAGCTGGGCTAAAGGTTTAAAATTTGAAGATGGAGCCATA
GCAACCAACATTGGAAATGGGTTAGAGTTTGGAAGCAGTAGTACAGAAACAGGTGTTGATGATGCTTACCCAATCCAA
GTTAAACTTGGATCTGGCCTTAGCTTTGACAGTACAGGAGCCATAATGGCTGGTAACAAAGAAGACGATAAACTCACT
TTGTGGACAACACCTGATCCATCGCCAAACTGTCAAATACTCGCAGAAAATGATGCAAAACTAACACTTTGCTTGACT
AAATGTGGTAGTCAAATACTGGCCACTGTGTCAGTCTTAGTTGTAGGAAGTGGAAACCTAAACCCCATTACTGGCACC
GTAAGCAGTGCTCAGGTGTTTCTACGTTTTGATGCAAACGGTGTTCTTTTAACAGAACATTCTACACTAAAAAAATAC
TGGGGGTATAGGCAGGGAGATAGCATAGATGGCACTCCATATACCAATGCTGTAGGATTCATGCCCAATTTAAAAGCT
TATCCAAAGTCACAAAGTTCTACTACTAAAAATAATATAGTAGGGCAAGTATACATGAATGGAGATGTTTCAAAACCT
ATGCTTCTCACTATAACCCTCAATGGTACTGATGACAGCAACAGTACATATTCAATGTCATTTTCATACACCTGGACT
AATGGAAGCTATGTTGGAGCAACATTTGGGGCTAACTCTTATACCTTCTCATACATCGCCCAAGAATGAACACTGTAT
CCCACCCTGCATGCCAACCCTTCCCACCCCACTCTGTGGAAAAAACTCTGAAACACAAAATAAAATAAAGTTCAAGTG
TTTTATTGATTCAACAGTTTTACAGGATTCGAGCAGTTATTTTTCCTCCACCCTCCCAGGACATGGAATACACCACCC
TCTCCCCCCGCACAGCCTTGAACATCTGAACGCCATTGGTGATGGACATGCTTTTGGTCTCCACGTTCCACACAGTTT
CAGAGCGAGCCAGTCTCGGGTCGGTCAGGGAGATGAAACCCTCCGGGCACTCCCGCATCTGCACCTCACAGCTCAACA
GCTGAGGATTGTCCTCGGTGGTCGGGATCACGGTTATCTGGAAGAAGCAGAAGAGCGGCGGTGGGAATCATAGTCCGC
GAACGGGATCGGCCGGTGGTGTCGCATCAGGCCCCGCAGCAGTCGCTGTCGCCGCCGCTCCGTCAAGCTGCTGCTCAG
GGGGTCCGGGTCCAGGGACTCCCTCAGCATGATGCCCACGGCCCTCAGCATCAGTCGTCTGGTGCGGCGGGCGCAGCA
GCGCATGCGGATCTCGCTCAGGTCGCTGCAGTACGTGCAACACAGGACCACCAGGTTGTTCAACAGTCCATAGTTCAA
CACGCTCCAGCCGAAACTCATCGCGGGAAGGATGCTACCCACGTGGCCGTCGTACCAGATCCTCAGGTAAATCAAGTG
GCGCCCCTCCAGAACACGCTGCCCATGTACATGATCTCCTTGGGCATGTGGCGGTTCACCACCTCCCGGTACCACAT
CACCCTCTGGTTGAACATGCAGCCCCGGATGATCCTGCGGAACCACAGGGCCAGCACCGCCCCGCCCGCCATGCAGCG
AAGAGACCCCGGGTCCCGGCAATGGCAATGGAGGACCCACCGCTCGTACCCGTGGATCATCTGGGAGCTGAACAAGTC
TATGTTGGCACAGCACAGGCACACGCTCATGCATCTCTTCAGCACTCTCAGCTCCTCGGGGGTCAAAACCATATCCCA
GGGCACGGGGAACTCTTGCAGGACAGCGAACCCCGCAGAACAGGGCAATCCTCGCACAGAACTTACATTGTGCATGGA
CAGGGTATCGCAATCAGGCAGCACCGGGTGATCCTCCACCAGGGAAGCGCGGGTCTCGGTCTCCTCACAGCGTGGTAA
GGGGGCCGGCCGATACGGGTGATGGCGGGACGCGGCTGATCGTGCTCGCGACCGTGTCATGATGCAGTTGCTTTCGGA
CATTTTCGTACTTGCTGTAGCAGAACCTGGTCCGGGCGCTGCACACCGATCGCCGGCGGCGGTCCCGGCGCTTGGAAC
GCTCGGTGTTGAAGTTGTAAAACAGCCACTCTCTCAGACCGTGCAGCAGATCTAGGGCCTCAGGAGTGATGAAAATCC
CATCATGCCTGATAGCTCTGATCACATCGACCACCGTGGAATGGGCCAGACCCAGCCAGATGATGCAATTTTGTTGGG
TTTCGGTAACGGCGGGGGAGGGAAGAACAGGAAGAACCATGATTAACTTTTAATCCAAACGGTCTCGGAGCACTTCAA
AATGAAGATCGCGGAGATGGCACCTCTCGCCCCCGCTGTGTTGGTGGAAAATAACAGCCAGGTCAAAGGTGATACGGT
TCTCGAGATGTTCCACGGTGGCTTCCAGCAAAGCCTCCACGCGCACATCCAGAAACAAGACAATAGCGAAAGCGGGAG
GGTTCTCTAATTCCTCAATCATCATGTTACACTCCTGCACCATCCCCAGATAATTTTCATTTTTCCAGCCTTGAATGA
TTCGAACTAGTTCCTGAGGTAAATCCAAGCCAGCCATGATAAAGAGCTCGCGCAGAGCGCCCTCCACCGGCATTCTTA
AGCACACCCTCATAATTCCAAGATATTCTGCTCCTGGTTCACCTGCAGCAGATTGACAAGCGGAATATCAAACTCTCT
GCCGCGATCCCTAAGCTCCTCCCTCAGCAATAACTGTAAGTACTCTTTCATATCCTCTCCGAAATTTTAGCCATAGG
ACCGCCAGGAATAAGATTAGGGCAAGCCACAGTACAGATAAACCGAAGTCCTCCCCAGTGAGCATTGCCAAATGCAAG
ACTGCTATAAGCATGCTGGCTAGACCCGGTGATATCTTCCAGATAACTGGACAGAAAATCGCCCAGGCAATTTTTAAG
AAAATCAACAAAAGAAAAATCCTCCAGGTGCACGTTTAGAGCCTCGGGAACAACGATGGAGTAAATGCAAGCGGTGCG
TTCCAGCATGGTTAGTTAGCTGATCTGTAGAAAAAACAAAAATGAACATTAAACCATGCTAGCCTGGCGAACAGGTGG
GTAAATCGTTCTTTCCAGCACCAGGCAGGCCACGGGGTCTCCGGCACGACCCTCGTAAAAATTGTCGCTATGATTGAA
AACCATCACAGAGAGACGTTCCCGGTGGCCGGCGTGAATGATTCGACAAGATGAATACACCCCCGGAACATTGGCGTC
CGCGAGTGAAAAAAAGCGCCCGAGGAAGCAATAAGGCACTACAATGCTCAGTCTCAAGTCCAGCAAAGCGATGCCATG
CGGATGAAGCACAAAATTCTCAGGTGCGTACAAAATGTAATTACTCCCCTCCTGCACAGGCAGCAAAGCCCCCGATCC
CTCCAGGTACACATACAAAGCCTCAGCGTCCATAGCTTACCGAGCAGCAGCAGCAGCACACAACAGGCGCAAGAGTCA
GAGAAAGGCTGAGCTCTAACCTGTCCACCCGCTCTCTGCTCAATATATAGCCCAGATCTACACTGACGTAAAGGCCAA
AGTCTAAAAATACCCGCCAAATAGTCACACACGCCCAGCACACGCCCAGAAACCGGTGACACACTCAAAAAAATACGC
GCACTTCCTCAAACGCCCAAACTGCCGTCATTTCCGGGTTCCCACGCTACGTCATCAAAACACGACTTTCAAATTCCG
TCGACCGTTAAAAACGTCACCCGCCCCGCCCCTAACGGTCGCCCGTCTCTCAGCCAATCAGCGCCCCGCATCCCCAAA
TTCAAACACCTCATTTGCATATTAACGCGCACCAAAAGTTTGAGGTATATTATTGATGATG
```

Fig. 7H

```
CATCATCAATAATATACCTCAAACTTTTGGTGCGCGTTAATATGCAAATGAGGTGTTTGAATTTGGGGATGCGGGGCG
CTGATTGGCTGAGAGACGGGCGACCGTTAGGGGCGGGGCGGGTGACGTTTTGATGACGTGGCCGTGAGGCGGAGCCGG
TTTGCAAGTTCTCGTGGGAAAAGTGACGTCAAACGAGGTGTGGTTTGAACACGGAAATACTCAATTTTCCCGCGCTCT
CTGACAGGAAATGAGGTGTTTCTGGGCGGATGCAAGTGAAAACGGGCCATTTTCGCGCGAAAACTGAATGAGGAAGTG
AAAATCTGAGTAATTCCGCGTTTATGGCAGGGAGGAGTATTTGCCGAGGGCCGAGTAGACTTTGACCGATTACGTGGG
GGTTTCGATTACCGTATTTTTCACCTAAATTTCCGCGTACGGTGTCAAAGTCCGGTGTTTTTACGATCCCATTGCATA
CGTTGTATCCATATCATAATATGTACATTTATATTGGCTCATGTCCAACATTACCGCCATGTTGACATTGATTATTGA
CTAGTTATTAATAGTAATCAATTACGGGGTCATTAGTTCATAGCCCATATATGGAGTTCCGCGTTACATAACTTACGG
TAAATGGCCCGCCTGGCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGACGTCAATGGGAGTTTGTTTTGGC
ACCAAAATCAACGGGACTTTCCAAAATGTCGTAACAACTCCGCCCCATTGACGCAAATGGGCGGTAGGCGTGTACGGT
GGGAGGTCTATATAAGCAGAGCTCGTTTAGTGAACCGTCAGATCGCCTGGAGACGCCATCCACGCTGTTTTGACCTCC
ATAGAAGACACCGGGACCGATCCAGCCTCCGCGGCCGGGAACGGTGCATTGGAACGCGGATTCCCCGTGCCAAGAGTG
AGATCTGCCACCATGGCGCCCATCACGGCCTACTCCCAACAGACGCGGGGCCTACTTGGTTGCATCATCACTAGCCTT
ACAGGCCGGGACAAGAACCAGGTCGAGGGAGAGGTTCAGGTGGTTTCCACCGCAACACAATCCTTCCTGGCGACCTGC
GTCAACGGCGTGTGTTGGACCGTTTACCATGGTGCTGGCTCAAAGACCTTAGCCGGCCCAAAGGGGCCAATCACCCAG
ATGTACACTAATGTGGACCAGGACCTCGTCGGCTGGCAGGCGCCCCCCGGGGCGCGTTCCTTGACACCATGCACCTGT
GGCAGCTCAGACCTTTACTTGGTCACGAGACATGCTGACGTCATTCCGGTGCGCCGGCGGGGCGACAGTAGGGGGAGC
CTGCTCTCCCCCAGGCCTGTCTCCTACTTGAAGGGCTCTTCGGGTGGTCCACTGCTCTGCCCTTCGGGGCACGCTGTG
GGCATCTTCCGGGCTGCCGTATGCACCCGGGGGTTGCGAAGGCGGTGGACTTTGTGCCCGTAGAGTCCATGGAAACT
ACTATGCGGTCTCCGGTCTTCACGGACAACTCATCCCCCCGGCCGTACCGCAGTCATTTCAAGTGGCCCACCTACAC
GCTCCCACTGGCAGCGGCAAGAGTACTAAAGTGCCGGCTGCATATGCAGCCCAAGGGTACAAGGTGCTCGTCCTCAAT
CCGTCCGTTGCCGCTACCTTAGGGTTTGGGGCGTATATGTCTAAGGCACACGGTATTGACCCCAACATCAGAACTGGG
GTAAGGACCATTACCACAGGCGCCCCCGTCACATACTCTACCTATGGCAAGTTTCTTGCCGATGGTGGTTGCTCTGGG
GGCGCTTATGACATCATAATATGTGATGAGTGCCATTCGACTCGACTACAATCTTGGGCATCGGCACAGTCCTG
GACCAAGCGGAGACGGCTGGAGCGCGGCTTGTCGTGCTCGCCACCGCTACGCCTCCGGGATCGGTCACCGTGCCACAC
CCAAACATCGAGGAGGTGGCCTTGTCTAATACTGGAGAGATCCCCTTCTATGGCAAAGCCATCCCCATTGAAGCCATC
AGGGGGGGAAGGCATCTCATTTTCTGTCATTCAAGAAGAAGAAGTGCGAGCTCGCCGCAAAGCTGTCAGGCCTCGGA
ATCAACGCTGTGGCGTATTACCGGGGGCTCGATGTGTCCGTCATACCAACTATCGGAGACGTCGTTGTCGTGGCAACA
GACGCTCTGATGACGGGCTATACGGGCGACTTTGACTCAGTGATCGACTGTAACACATGTGTCACCCAGACAGTCGAC
TTCAGCTTGGATCCCACCTTCACCATTGAGACGACGACCGTGCCTCAAGACGCAGTGTCGCGCTCGCAGCGGCGGGGT
AGGACTGGCAGGGGTAGGAGAGGCATCTACAGGTTTGTGACTCCGGGAGAACGGCCCTCGGGCATGTTCGAAACCTACGCTGCAC
GTCCTGTGTGAGTGCTATGACGCGGGCTGTGCTTGGTACGAGCTCACCCCCGCCGAGACCTCGGTTAGGTTGCGGGCC
TACCTGAACACACCAGGGTTGCCCGTTTGCCAGGACCACCTGGAGTTCTGGGAGAGTGTCTTCACAGGCCTCACCCAC
ATAGATGCACACTTCTTGTCCCAGACCAAGCAGGCAGGAGACAACTTCCCCTACCTGGTAGCATACCAAGCCACGGTG
TGCGCCAGGGCTCAGGCCCCACCTCCATCATGGGATCAAATGTGGAAGTGTCTCATACGGCTGAAACCTACGCTGCAC
GGGCCAACACCCTTGCTGTACAGGCTGGGAGCCGTCCAAAATGAGGTCACCCTCACCCACCCCATAACCAAATACATC
ATGGCATGCATGTCGGCTGACCTGGAGGTCGTCACTAGCACCTGGGTGCTGGTGGGCGGAGTCCTTGCAGCTCTGGCC
GCGTATTGCCTGACAACAGGCAGTGTGGTCATTGTGGGTAGGATTATCTTGTCCGGGAGGCCGGCTATTGTTCCCGAC
AGGGAGTTTCTACCAGGAGTTCGATGAAATGGAAGAGTGCCGCTCGCACCTCCCTTACATCGAGCAGGGAATGCAG
CTCGCCGAGCAATTCAAGCAGAAAGCGCTCGGGTTACTGCAAACAGCCACCAAACAAGCGGAGGCTGCTGCTCCCGTG
GTGGAGTCCAAGTGGCGAGCCCTTGAGACATTCTGGGCGAAGCACATGTGGAATTTCATCAGCGGGATACAGTACTTA
GCAGGCTTATCCACTCTGCCTGGGAACCCCGCAATAGCATCATTGATGGCATTCACAGCCTCTATCACCAGCCCGCTC
ACCACCCAAAGTACCCTCCTGTTTAACATCTTGGGGGGGTGGGTGGCTGCCCAACTCGCCCCCCCAGCGCCGCTTCG
GCTTTCGTGGGCGCCGGCATCGCCGGTGCGGCTGTTGGCAGCATAGGCCTTGGGAAGGTGCTTGTGGACATTCTGGCG
GGTTATGGAGCAGGAGTGGCCGGCGCGCTCGTGGCCTTCAAGGTCATGAGCGGCGAGATGCCCTCCACCGAGGACCTG
GTCAATCTACTTCCTGCCATCCTCTCTCCTGGCGCCCTGGTCGTCGGGGTCGTGTGTGCAGCAATACTGCGTCGACAC
GTGGGTCCGGGAGAGGGGCTGTGCAGTGGATGAACCGGCTGATAGCGTTCGCCTCGCGGGTAATCATGTTTCCCCC
ACGCACTATGTGCCTGAGAGCGACGCCGCAGCGCGTGTTACTCAGATCCTCTCCAGCCTTACCATCACTCAGCTGCTG
AAAAGGCTCCACCAGTGGATTAATGAAGACTGCTCCACACCGTGTTCCGGCTCGTGGCTAAGGGATGTTTGGGACTGG
ATATGCACGGTGTTGACTTCAAGACCTGCTCCAGTCCAAGCTCCTGCCGCAGCTACCGGGAGTCCCTTTTTTC
TCGTGCCAACGCGGGTACAAGGGAGTCTGGCGGGGAGACGGCATCATGCAAACCACCTGCCCATGTGGAGCACAGATC
ACCGGACATGTCAAAAACGGTTCCATGAGGATCGTCGGGCCTAAGACCTGCAGCAACACGTGGCATGAACATTCCCC
ATCAACGCATACACCACGGGCCCCTGCACACCCTCTCCAGCGCCAAACTATTCTAGGGCGCTGTGGCGGGTGGCCGCT
GAGGAGTACGTGGAGGTCACGCGGGTGGGGATTTCCACTACGTGACGGGCATGACCACTGACAACGTAAAGTGCCCA
TGCCAGGTTCCGGCTCCTGAATTCTTCACGGAGGTGGACGGAGTGCGGTTGCACAGGTACGCTCCGGCGTGCAGGCCT
```

Fig. 10A

```
CTCCTACGGGAGGAGGTTACATTCCAGGTCGGGCTCAACCAATACCTGGTTGGGTCACAGCTACCATGCGAGCCCGAA
CCGGATGTAGCAGTGCTCACTTCCATGCTCACCGACCCCTCCCACATCACAGCAGAAACGGCTAAGCGTAGGTTGGCC
AGGGGGTCTCCCCCCTCCTTGGCCAGCTCTTCAGCTAGCCAGTTGTCTGCGCCTTCCTTGAAGGCGACATGCACTACC
CACCATGTCTCTCCGGACGCTGACCTCATCGAGGCCAACCTCCTGTGGCGGCAGGAGATGGGCGGGAACATCACCCGC
GTGGAGTCGGAGAACAAGGTGGTAGTCCTGGACTCTTTCGACCCGCTTCGAGCGGAGGAGGATGAGAGGGAAGTATCC
GTTCCGGCGGAGATCCTGCGGAAATCCAAGAAGTTCCCCGCAGCGATGCCCATCTGGGCGCGCCCGGATTACAACCCT
CCACTGTTAGAGTCCTGGAAGGACCCGGACTACGTCCCTCCGGTGGTGCACGGGTGCCCGTTGCCACCTATCAAGGCC
CCTCCAATACCACCTCCACGGAGAAAGAGGACGGTTGTCCTAACAGAGTCCTCCGTGTCTTCTGCCTTAGCGGAGCTC
GCTACTAAGACCTTCGGCAGCTCCGAATCATCGGCCGTCGACAGCGGCACGGCGACCGCCCTTCCTGACCAGGCCTCC
GACGACGGTGACAAAGGATCCGACGTTGAGTCGTACTCCTCCATGCCCCCCCTTGAGGGGGAACCGGGGGACCCCGAT
CTCAGTGACGGGTCTTGGTCTACCGTGAGCGAGGAAGCTAGTGAGGATGTCGTCTGCTGCTCAATGTCCTACACATGG
ACAGGCGCCTTGATCACGCCATGCGCTGCGGAGGAAAGCAAGCTGCCCATCAACGCGTTGAGCAACTCTTTGCTGCGC
CACCATAACATGGTTTATGCCACAACATCTCGCAGCGCAGGCCTGCGGCAGAAGAAGGTCACCTTTGACAGACTGCAA
GTCCTGGACGACCACTACCGGGACGTGCTCAAGGAGATGAAGGCGAAGGCGTCCACAGTTAAGGCTAAACTCCTATCC
GTAGAGGAAGCCTGCAAGCTGACGCCCCCACATTCGGCCAAATCCAAGTTTGGCTATGGGGCAAAGGACGTCCGGAAC
CTATCCAGCAAGGCCGTTAACCACATCCACTCCGTGTGGAAGGACTTGCTGGAAGACACTGTGACACCAATTGACACC
ACCATCATGGCAAAAAATGAGGTTTTCTGTGTCCAACCAGAGAAAGGAGGCCGTAAGCCAGCCCGCCTTATCGTATTC
CCAGATCTGGGAGTCCGTGTATGCGAGAAGATGGCCCTCTATGATGTGGTCTCCACCCTTCCTCAGGTCGTGATGGGC
TCCTCATACGGATTCCAGTACTCTCCTGGGCAGCGAGTCGAGTTCCTGGTGAATACCTGGAAATCAAAGAAAAACCCC
ATGGGCTTTTCATATGACACTCGCTGTTTCGACTCAACGGTCACCGAGAACGACATCCGTGTTGAGGAGTCAATTTAC
CAATGTTGTGACTTGGCCCCCGAAGCCAGACAGGCCATAAAATCGCTCACAGAGCGGCTTTATATCGGGGGTCCTCTG
ACTAATTCAAAAGGGCAGAACTGCGCGGTTATCGCCGGTGCCGCGCGAGCGGCGTGCTGACGACTAGCTGCGGTAACACC
CTCACATGTTACTTGAAGGCCTCTGCAGCCTGTCGAGCTGCGAAGCTCCAGGACTGCACGATGCTCGTGAACGCCGCC
GGCCTTGTCGTTATCTGTGAAAGCGCGGGAACCCAAGAGGACGCGGCGAGCCTACGAGTCTTCACGGAGGCTATGACT
AGGTACTCTGCCCCCCCCGGGGACCCGCCCCAACCAGAATACGACTTGGAGCTGATAACATCATGTTCCTCCAATGTG
TCGGTCGCCCACGATGCATCAGGCAAAAGGGTGTACTACCTCACCCGTGATCCCACCACCCCCCTCGCACGGGCTGCG
TGGGAAACAGCTAGACACACTCCAGTTAACTCCTGGCTAGGCAACATTATCATGTATGCGCCCACTTTGTGGGCAAGG
ATGATTCTGATGACTCACTTCTTCTCCATCCTTCTAGCACAGGAGCAACTTGAAAAAGCCCTGGACTGCCAGATCTAC
GGGGCCTGTTACTCCATTGAGCCACTTGACCTACCTCAGATCATTGAACGACTCCATGGCCTTAGCGCATTTTCACTC
CATAGTTACTCTCCAGGTGAGATCAATAGGGTGGCTTCATGCCTCAGGAAACTTGGGGTACCACCCTTGCGAGTCTGG
AGACATCGGGCCAGGAGCGTCCGCGCTAGGCTACTGTCCCAGGGGGGGAGGGCCGCCACTTGTGCAAGTACCTCTTC
AACTGGGCAGTGAAGACCAAACTCAAACTCACTCCAATCCCGGCTGCGTCCCAGCTGGACTTGTCCGGCTGGTTCGTT
GCTGGTTACAGCGGGGGAGACATATATCACAGCCTGTCTCGTGCCCGACCCCGCTGGTTCATGCTGTGCCTACTCCTA
CTTTCTGTAGGGGTAGGCATCTACCTGCTCCCCAACCGATAAATCTAGAGCTGTGCCTTCTAGTTGCCAGCCATCTGT
TGTTTGCCCCTCCCCCGTGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGTGGGGCAGCACAGCAAGGGGGAGGATTGGGA
AGACAATAGCAGGCATGCTGGGGATGCCGGTGGGCTCTAGATGTAGCGATCGCGTGAGTAGTGTTTGGGGGTGGGTGGG
AGCCTGCATGATGGGCAGAATGACTAAAATCTGTGTTTTTCTGTGTGTTGCAGCAGCATGAGCGGAAGCGCCTCCTTT
GAGGGAGGGGTATTCAGCCCTTATCTGACGGGGCGTCTCCCCTCCTGGGCGGGAGTGCGTCAGAATGTGATGGGATCC
ACGGTGGACGGCCGGCCCGTGCAGCCCGCGAACTCTTCAACCCTGACCTACGCGACCCTGAGCTCCTCGTCCGTGGAC
GCAGCTGCCGCCGCAGCTGCTGCTTCCGCCGCCAGCGCCGTGCGCGGAATGGCCCTGGGCGCCGGCTACTACAGCTCT
CTGGTGGCCAACTCGAGTTCCACCAATAATCCCGCTGACCTGAACGAGGAGAAGCTGTTGCTGCTGATGGCCCAGCTC
GAGGCCCTGACCCAGCGCCTGGGCGAGCTGACCCAGCAGGTGGCTCAGCTGCAGGCGGAGACGCGGGCCGCGGTTGCC
ACGGTGAAAACCAAATAAAAAATGAATCAATAAATAAACGGAGACGGTTGTTGATTTTAACACAGAGTCTTGAATCTT
TATTTGATTTTTCGCGCGCGGTAGGCCCTGGACCACCGGTCTCGATCATTGAGCACCCGGTGGATCTTTTCCAGGACC
CGGTAGAGGTGGGCTTGGATGTTGAGGTACATGGGCATGAGCCCGTCCCGGGGGTGGAGGTAGCTCCATTGCAGGGCC
TCGTGCTCGGGGGTGGTGTTGTAAATCACCCAGTCATAGCAGGGGCGCAGGGCGTGGTGCTGCACGATGTCTTTGAGG
AGGAGACTGATGGCCACGGGCAGCCCCTTGGTGTAGGTGTTGACGAACCTATTGAGCTGGGAGGGATGCATGCGGGGG
GAGATGAGATGCATCTTGCCTGGATCTTGAGATTGGCGATGTTCCCGCCCAGATCCGCCAGGGGTTCATGTTGTGC
AGGACCACCAGCACGGTGTATCCGGTGCACTTGGGGAATTTGTCATGCAACTTGGAAGGGAAGGCGTGAAAGAATTTG
GAGACGCCCTTGTGACCGCCCAGGTTTTCCATGCACTCATCCATGATGATGGCGATGGGCCCGTGGGCGGCGGCCTGG
GCAAAGACGTTTCGGGGGTCGGACACATCGTAGTTGTGGTCCTGGGTGAGCTCGTCATAGGCCATTTTAATGAATTTG
GGGCGAGGGTACCCGACTGGGGGACAAAGGTGCCCTCGATCCCGGGGGCGTAGTTCCCCTCGCAGATCTGCATCTCC
CAGGCCTTGAGCTCGGAGGGGGGGGATCATGTCCACCTGCGGGGCGATGAAAAAAACGGTTTCCGGGGCGGGGGAGATG
AGCTGCGCCGAAAGCAGGTTCCGGAGCAGCTGGGACTTGCCGCAGCCGGTGGGGCCGTAGATGACCCCGATGACCGGC
TGCAGGTGGTAGTTGAGGGAGAGACAGCTGCCGTCCTCGCGGAGGAGGGGGCCACCTCGTTCATCATCTCGCGCACA
```

Fig. 10B

```
TGCATGTTCTCGCGCACGAGTTCCGCCAGGAGGCGCTCGCCCCCAGCGAGAGGAGCTCTTGCAGCGAGGCGAAGTTT
TTCAGCGGCTTGAGCCCGTCGGCCATGGGCATTTTGGAGAGGGTCTGTTGCAAGAGTTCCAGACGGTCCCAGAGCTCG
GTGATGTGCTCTAGGGCATCTCGATCCAGCAGACCTCCTCGTTTCGCGGGTTGGGGCGACTGCGGGAGTAGGGCACCA
GGCGATGGGCGTCCAGCGAGGCCAGGGTCCGGTCCTTCCAGGGTCGCAGGGTCCGCGTCAGCGTGGTCTCCGTCACGG
TGAAGGGGTGCGCGCCGGGCTGGGCGCTTGCGAGGGTGCGCTTCAGGCTCATCCGGCTGGTCGAGAACCGCTCCCGGT
CGGCGCCCTGCGCGTCGGCCAGGTAGCAATTGAGCATGAGTTCGTAGTTGAGCGCCTCGGCCGCGTGGCCCTTGGCGC
GGAGCTTACCTTTGGAAGTGTGTCCGCAGACGGGACAGAGGAGGGACTTGAGGGCGTAGAGCTTGGGGGCGAGGAAGA
CGGACTCGGGGGCGTAGGCGTCCGCGCCGCAGCTGGCGCAGACGGTCTCGCACTCCACGAGCCAGGTGAGGTCGGGGC
GGTCGGGGTCAAAAACGAGGTTTCCTCCGTGCTTTTTGATGCGTTTCTTACCTCTGGTCTCCATGAGCTCGTGTCCCC
GCTGGGTGACAAAGAGGCTGTCCGTGTCCCCGTAGACCGACTTTATGGCCGGTCCTCGAGCGGGGTGCCGCGGTCCT
CGTCGTAGAGGAACCCCGCCCACTCCGAGACGAAGGCCCGGGTCCAGGCCAGCACGAAGGAGGCCACGTGGGAGGGGT
AGCGGTCGTTGTCCACCAGCGGGTCCACCTTCTCCAGGGTATGCAAGCACATGTCCCCCTCGTCCACATCCAGGAAGG
TGATTGGCTTGTAAGTGTAGGCCACGTGACCGGGGGTCCCGGCCGGGGGGGTATAAAAGGGGGCGGGCCCCTGCTCGT
CCTCACTGTCTTCCGGATCGCTGTCCAGGAGCGCCAGCTGTTGGGGTAGGTATTCCCTCTCGAAGGCGGGCATGACCT
CGGCACTCAGGTTGTCAGTTTCTAGAAACGAGGAGGATTTGATATTGACGGTGCCGTTGGAGACGCCTTTCATGAGCC
CCTCGTCCATCTGGTCAGAAAAGACGATCTTTTTGTTGTCGAGCTTGGTGGCGAAGGAGCCGTAGAGGGCGTTGGAGA
GCAGCTTGGCGATGGAGCGCATGGTCTGGTTCTTTTCCTTGTCGGCGCGCTCCTTGGCGGCGATGTTGAGCTGCACGT
ACTCGCGCGCCACGCACTTCCATTCGGGGAAGACGGTGGTGAGCTCGTCGGGCACGATTCTGACCCGCCAGCCGCGGT
TGTGCAGGGTGATGAGGTCCACGCTGGTGGCCACCTCGCCGCGCAGGGGCTCGTTGGTCCAGCAGAGGCGCCCGCCCT
TGCGCGAGCAGAAGGGGGGCAGCGGGTCCAGCATGAGCTCGTCGGGGGGTCGGCGTCCACGGTGAAGATGCCGGGCA
GGAGCTCGGGGTCGAAGTAGCTGATGCAGGTGCCCAGATCGTCCAGACTTGCTTGCCAGTCGCGCACGGCCAGCGCGC
GCTCGTAGGGGCTGAGGGGCGTGCCCCAGGGCATGGGGTGCGTGAGCGCGGAGGCGTACATGCCGCAGATGTCGTAGA
CGTAGAGGGGCTCCTGGAGGACGCCGATGTAGGTGGGGTAGCAGCGCCCCCGCGGATGCTGGCGCGCACGTAGTCGT
ACAGCTCGTGCGAGGGCGCGAGGAGCCCCGTGCCGAGATTGGAGCGCTGCGGCTTTTCGGCGCGGTAGACGATCTGGC
GGAAGATGCGTGGGAGTTGGAGGAGATGGTGGGCCTCTGGAAGATGTTGAAGTGGGCATGGGGCAGTCCGACCGAGT
CCCTGATGAAGTGGGCGTAGGAGTCCTGCAGCTTGGCGACGAGCTCGGCGGTGACGAGGACGTCCAGGGCGCAGTAGT
CGAGGGTCTCTTGGATGATGTCGTACTTGAGCTGGCCCTTCTGCTTCCACAGCTCGCGGTTGAGAAGGAACTCTTCGC
GGTCCTTCCAGTACTCTTCGAGGGGGAACCCGTCCTGATCGGCACGGTAAGAGCCCACCATGTAGAACTGGTTGACGG
CCTTGTAGGCGCAGCAGCCCTTCTCCACGGGGAGGGCGTAAGCTTGCGCGGCCTTGCGCAGGGAGGTGTGGGTGAGGG
CGAAGGTGTCGCGCACCATGACTTTGAGGAACTGGTGCTTGAAGTCGAGGTCGTCGCAGCCGCCCTGCTCCCAGAGCT
GGAAGTCCGTGCGCTTCTTGTAGGCGGGGTTGGGCAAAGCGAAAGTAACATCGTTGAAGAGGATCTTGCCCGCGCGGG
GCATGAAGTTGCGAGTGATGCGGAAAGGCTGGGGCACCTCGGCCCGGTTGTTGATGACCTGGGCGGCGAGGACGATCT
CGTCGAAGCCGTTGATGTTGTGCCCGACGATGTAGAGTTCCACGAATCGCGGGCGGCCCTTGACGTGGGGCAGCTTCT
TGAGCTCGTCGTAGGTGAGCTCGGCGGGGTCGCTGAGCCCGTGCTGCTCGAGGGCCCAGTCGGCGACGTGGGGGTTGG
CGCTGAGGAAGGAAGTCCAGAGATCCACGGCCAGGGCGGTCTGCAAGCGGTCCCGGTACTGACGGAACTGCTGGCCCA
CGGCCATTTTTTCGGGGGTGACGCAGTAGAAGGTGCGGGGGTCGCCGTGCCAGCGGTCCCACTTGAGCTGGAGGGCGA
GGTCGTGGGCGAGCTCGACGAGCGGCGGGTCCCCGGAGAGTTTCATGACCAGCATGAAGGGGACGAGCTGCTTGCCGA
AGGACCCCATCCAGGTGTAGGTTTCCACATCGTAGGTGAGGAAGAGCCTTTCGGTGCGAGGATGCGAGCCGATGGGGA
AGAACTGGATCTCCTGCCACCAGTTGGAGGAATGGCTGTTGATGTGATGGAAGTAGAAATGCCGACGGCGCGCCGAGC
ACTCGTGCTTGTGTTTATACAAGCGTCCGCAGTGCTCGCAACGCTGCACGGGATGCACGTGCTGCACGAGCTGTACCT
GGGTTCCTTTGACGAGGAATTTCAGTGGGCAGTGGAGCGCTGGCGGCTGCATCTGGTGCTGTACTACGTCCTGGCCAT
CGGCGTGGCCATCGTCTGCCTCGATGGTGGTCATGCTGACGAGCCCGCGCGGGAGGCAGGTCCAGACCTCGGCTCGGA
CGGGTCGAGAGCGAGGACGAGGGCGCGCAGGCCGGAGCTGTCCAGGGTCCTGAGACGCTGCGGAGTCAGGTCAGTGG
GCAGCGGCGGCGCGCGGTTGACTTGCAGGAGCTTTTCCAGGGCGCGCGGGAGGTCCAGATGGTACTTGATCTCCACGG
CGCCGTTGGTGGCGACGTCCACGGCTTGCAGGGTCCCGTGCCCCTGGGGCGCCACCACCGTGCCCCGTTTCTTCTTGG
GCGGCGGCGGCTCCATGCTTAGAAGCGGCGGCGAGGACGCGCGCCGGGCGGCAGGGGCGGCTCGGGGCCCGGAGGCAG
GGGCGGCAGGGGCACGTCGGCGCCGCGCGGGCAGGTTCTGGTACTGCGCCCGGAGAAGACTGGCGTGAGCGACGAC
GCGACGGTTGACGTCCTGGATCTGACGCCTCTGGGTGAAGGCCACGGGACCCGTGAGTTTGAACCTGAAAGAGAGTTC
GACAGAATCAATCTCGGTATCGTTGACGGCGGCCTGCCGCAGGATCTCTTGCACGTCGCCCGAGTTGTCCTGGTAGGC
GATCTCGGTCATGAACTGCTCGATCTCCTCCTCCTGAAGGTCTCCGCGGCCGGCGCTCGACGGTGGCCGCGAGGTC
GTTGGAGATGCGGCCCATGAGCTGCGAGAAGGCGTTCATGCCGGCCTCGTTCCAGACGCGGCTGTAGACCACGGCTCC
GTCGGGGTCGCGCGCGCGCATGACCACCTGGGCGAGGTTGAGCTCGACGTGGCGCGTGAAGACCGCGTAGTTGCAGAG
GCGCTGGTAGAGGTAGTTGAGCGTGGTGGCGATGTGCTCGGTGACGAAGAAGTACATGATCCAGCGGCGGAGCGGCAT
CTCGCTGACGTCGCCCAGGGCTTCCAAGCGCTCCATGGCCTCGTAGAAGTCCACGGCGAAGTTGAAAAACTGGGAGTT
GCGCGCCGAGACGGTCAACTCCTCCTCAGAAGACGGATGAGCTCGGCGATGGTGGCGCGCACCTCGCGCTCGAAGGC
CCCGGGGGCTCCTCTTCCATTTCCTCCTCTTCCTCCTCCACTAACATCTCTTCTACTTCCTCCTCAGGAGGCGGCGG
```

Fig. 10C

```
CGGGGGAGGGGCCCTGCGTCGCCGGCGGCGCACGGGCAGACGGTCGATGAAGCGCTCGATGGTCTCCCCGCGCCGGCG
ACGCATGGTCTCGGTGACGGCGCGCCCGTCCTCGCGGGGCCGCAGCGTGAAGACGCCGCCGCGCATCTCCAGGTGGCC
GCCGGGGGGGTCTCCGTTGGGCAGGGAGAGGGCGCTGACGATGCATCTTATCAATTGACCCGTAGGGACTCCGCGCAA
GGACCTGAGCGTCTCGAGATCCACGGGATCCGAAAACCGCTGAACGAAGGCTTCGAGCCAGTCGCAGTCGCAAGGTAG
GCTGAGCCCGGTTTCTTGTTCTTCGGGTATTTGGTCGGGAGGCGGGCGGGCGATGCTGCTGGTGATGAAGTTGAAGTA
GGCGGTCCTGAGACGGCGGATGGTGGCGAGGAGCACCAGGTCCTTGGGCCCGGCTTGCTGGATGCGCAGACGGTCGGC
CATGCCCCAGGCGTGGTCCTGACACCTGGCGAGGTCCTTGTAGTAGTCCTGCATGAGCCGCTCCACGGGCACCTCCTC
CTCGCCCGCGCGGCCGTGCATGCGCGTGAGCCCGAACCCGCGCTGCGGCTGGACGAGCGCCAGGTCGGCGACGACGCG
CTCGGCGAGGATGGCCTGCTGGATCTGGGTGAGGGTGGTCTGGAAGTCGTCGAAGTCGACGAAGCGGTGGTAGGCTCC
GGTGTTGATGGTGTAGGAGCAGTTGGCCATGACGGACCAGTTGACGGTCTGGTGGCCGGGGCGCACGAGCTCGTGGTA
CTTGAGGCGCGAGTAGGCGCGCGTGTCGAAGATGTAGTCGTTGCAGGTGCGCACGAGGTACTGGTATCCGACGAGGAA
GTGCGGCGGCGGCTGGCGGTAGAGCGGCCATCGCTCGGTGGCGGGGCGCCGGGCGCGAGGTCCTCGAGCATGAGGCG
GTGGTAGCCGTAGATGTACCTGGACATCCAGGTGATGCCGGCGGCGGTGGTGGAGGCGCGCGGGAACTCGCGGACGCG
GTTCCAGATGTTGCGCAGCGGCAGGAAGTAGTTCATGGTGGCCGCGGTCTGGCCCGTGAGGCGCGCGCAGTCGTGGAT
GCTCTAGACATACGGGCAAAAACGAAAGCGGTCAGCGGCTCGACTCCGTGGCCTGGAGGCTAAGCGAACGGGTTGGGC
TGCGCGTGTACCCCGGTTCGAATCTCGAATCAGGCTGGAGCCGCAGCTAACGTGGTACTGGCACTCCCGTCTCGACCC
AAGCCTGCTAACGAAACCTCCAGGATACGGAGGCGGGTCGTTTTTTGGCCTTGGTCGCTGGTCATGAAAAACTAGTAA
GCGCGGAAAGCGGCCGCCCGCGATGGCTCGCTGCCGTAGTCTGGAGAAAGAATCGCCAGGGTTGCGTTGCGGTGTGCC
CCGGTTCGAGCCTCAGCGCTCGGCGCCGGCCGGATTCCGCGGCTAACGTGGGCGTGGCTGCCCCGTCGTTTCCAAGAC
CCCTTAGCCAGCCGACTTCTCCAGTTACGGAGCGAGCCCCTCTTTTTTTCTTGTGTTTTTGCCAGATGCATCCCGTAC
TGCGGCAGATGCGCCCCACCCTCCACCACAACCGCCCCTACCGCAGCAGCAGCAACAGCCGGCGCTTCTGCCCCCGC
CCCAGCAGCAGCAGCCAGCCACTACCGCGGCGGCCGCCGTGAGCGGAGCCGGCGTTCAGTATGACCTGGCCTTGAAG
AGGGCGAGGGGCTGGCGCGGCTGGGGGCGTCGTCGCCGGAGCGGCACCCGCGCGTGCAGATGAAAAGGGACGCTCGCG
AGGCCTACGTGCCCAAGCAGAACCTGTTCAGAGACAGGAGCGGCGAGGAGCCCGAGGAGATGCGCGCCTCCCGCTTCC
ACGCGGGGCGGGAGCTGCGGCGCGGCCTGGACCGAAAGCGGGTGCTGAGGGACGAGGATTTCGAGGCGGACGAGCTGA
CGGGGATCAGCCCCGCGCGCGCGCACGTGGCCGCGGCCAACCTGGTCACGGCGTACGAGCAGACCGTGAAGGAGGAGA
GCAACTTCCAAAAATCCTTCAACAACCACGTGCGCACGCTGATCGCGCGCGAGGAGGTGACCCTGGGCCTGATGCACC
TGTGGGACCTGCTGGAGGCCATCGTGCAGAACCCCACGAGCAAGCCGCTGACGGCGCAGCTGTTTCTGGTGGTGCAGC
ACAGTCGGGACAACGAGACGTTCAGGGAGGCGCTGCTGAATATCACCGAGCCCGAGGGCCGCTGGCTCCTGGACCTGG
TGAACATTCTGCAGAGCATCGTGGTGCAGGAGCGCGGGCTGCCGCTGTCCGAGAAGCTGGCGGCCATCAACTTCTCGG
TGCTGAGCCTGGGCAAGTACTACGCTAGGAAGATCTACAAGACCCCGTACGTGCCCATAGACAAGGAGGTGAAGATCG
ATGGGTTTTACATGCGCATGACCCTGAAAGTGCTGACCCTGAGCGACGATCTGGGGGTGTACCGCAACGACAGGATGC
ACCGCGCGGTGAGCGCCAGCCGCCGGCGCGAGCTGAGCGACCAGGAGCTGATGCACAGCCTGCAGCGGGCCCTGACCG
GGGCCGGGACCGAGGGGGAGAGCTACTTTGACATGGGCGCGGACCTGCGCTGGCAGCCCAGCCGCCGGGCCTTGGAAG
CTGCCGGCGGCGTGCCCTACGTGGAGGAGGTGGACGATGAGGAGGAGGAGGGCGAGTACCTGGAAGACTGATGGCGCG
ACCGTATTTTTGCTAGATGCAGCAACAGCCACCGCCGCCGCCTCCTGATCCCGCGATCGGGCGGCGCTGCAGAGCCA
GCCGTCCGGCATTAACTCCTCGGACGATTGGACCCAGGCCATGCAACGCATCATGGCGCTGACGACCCGCAATCCCGA
AGCCTTTAGACAGCAGCCTCAGGCCAACCGGCTCTCGGCCATCCTGGAGGCCGTGGTGCCCTCGCGCTCGAACCCCAC
GCACGAGAAGGTGCTGGCCATCGTGAACGCGCTGGTGGAGAACAAGCGCCATCCGCGGCGACGAGGCCGGGCTGGTGTA
CAACGCGCTGCTGGAGCGCGTGGCCCCGCTACAACAGCACCAACGTGCAGACGAACCTGGACCGCATGGTGACCGACGT
GCGCGAGGCGGTGTCGCAGCGCGAGCGGTTCCACCGCGAGTCGAACCTGGGCTCCATGGTGGCGCTGAACGCCTTCCT
GAGCACGCAGCCCGCCAACGTGCCCCGGGGCCAGGAGGACTACACCAACTTCATCAGCGCGCTGCAGGGCTTGCAGACCGT
CGAGGTGCCCCAGAGCGAGGTGTACCAGTCGGGGCCGGACTACTTCTTCCAGACCAGTCGCCAGGGCTTGCAGACCGT
GAACCTGAGCCAGGCTTTCAAGAACTTGCAGGGACTGTGGGGCGTGCAGGCCCCGGTCGGGGACCGCGCGACGGTGTC
GAGCCTGCTGACGCCGAACTCGCGCCTGCTGCTGCTGCTGGTGGCGCCCTTCACGGACAGCGGCAGCGTGAGCCGCGA
CTCGTACCTGGGCTACCTGCTTAACCTGTACCGCGAGGCCATCGGGCAGGCGCACGTGGACGAGCAGACCTACCAGGA
GATCACCCACGTGAGCCGCGCGCTGGGCCAGGAGGACCCGGGCAACCTGGAGGCCACCCTGAACTTCCTGCTGACCAA
CCGGTCGCAGAAGATCCCGCCCCAGTACGCGCTGAGCACCGAGGAGGAGCGCATCCTGCGCTACGTGCAGCAGAGCGT
GGGGCTGTTCTTGATGCAGGAGGGGGCCACGCCCAGCGCCGCGCTCGACATGACCGCGCGCAACATGGAGCCCAGCAT
GTACGCCCGCAACCGCCCGTTCATCAATAAGCTGATGACTACTTGCATCGGGCGGCCGCCATGAACTCGGACTACTT
TACCAACGCCATCTTGAACCCGCACTGGCTCCCGCCGCCCGGGTTCTACACGGGCGAGTACGACATGCCCGACCCCAA
CGACGGGTTCCTGTGGGACGACGTGGACAGCAGCGTGTTCTCGCCGCGGCCCACCACCACCACCGTGTGGAAGAAAGA
GGGCGGGGACCGGCGGCCGTCCTCGGCGCTGTCCGGTCGCGCGGGTGCTGCCGCGGCGGTGCCCGAGGCTGCCAGCCC
CTTCCCGAGCCTGCCCTTTTCGCTGAACAGCGTGCGCAGCAGCGAGCTGGGTCGGCTGACGCGGCCGCGCCTGCTGGG
CGAGGAGGAGTACCTGAACGACTCCTTGTTGAAGCCCGAGCGCGAGAAGAACTTCCCCAATAACGGGATAGAGAGCCT
GGTGGACAAGATGAGCCGCTGGAAGACGTACGCGCACGAGCACAGGGACGAGCCCCGAGCTAGCAGCGCAGGCACCCG
TAGACGCCAGCGGCACGACAGGCAGCGGGGACTGGTGTGGGACGATGAGGATTCCGCCGACGACAGCAGCGTGTTGGA
```

Fig. 10D

```
CTTGGGTGGGAGTGGTGGTGGTAACCCGTTCGCTCACCTGCGCCCCCGTATCGGGCGCCTGATGTAAGAATCTGAAAA
AATAAAAGACGGTACTCACCAAGGCCATGGCGACCAGCGTGCGTTCTTCTCTGTTGTTTGTAGTAGTATGATGAGGCG
CGTGTACCCGGAGGGTCCTCCTCCCTCGTACGAGAGCGTGATGCAGCAGGCGGTGGCGGCGGCGATGCAGCCCCCGCT
GGAGGCGCCTTACGTGCCCCCGCGGTACCTGGCGCCTACGGAGGGGCGGAACAGCATTCGTTACTCGGAGCTGGCACC
CTTGTACGATACCACCCGGTTGTACCTGGTGGACAACAAGTCGGCGGACATCGCCTCGCTGAACTACCAGAACGACCA
CAGCAACTTCCTGACCACCGTGGTGCAGAACAACGATTTCACCCCCACGGAGGCCAGCACCCAGACCATCAACTTTGA
CGAGCGCTCGCGGTGGGGCGGCCAGCTGAAAACCATCATGCACACCAACATGCCCAACGTGAACGAGTTCATGTACAG
CAACAAGTTCAAGGCGCGGGTGATGGTCTCGCGCAAGACCCCCAACGGGGTCACGGTAGGGGATGATTATGATGGTAG
TCAGGACGAGCTGACCTACGAGTGGGTGGAGTTTGAGCTGCCCGAGGGCAACTTCTCGGTGACCATGACCATCGATCT
GATGAACAACGCCATCATCGACAACTACTTGGCGGTGGGGCGGCAGAACGGGGTGCTGGAGAGCGACATCGGCGTGAA
GTTCGACACGCGCAACTTCCGGCTGGGCTGGGACCCCGTGACCGAGCTGGTGATGCCGGGCGTGTACACCAACGAGGC
CTTCCACCCCGACATCGTCCTGCTGCCCGGCTGCGGCGTGGACTTCACCGAGAGCCGCCTCAGCAACCTGCTGGGCAT
CCGCAAGCGGCAGCCCTTCCAGGAGGGCTTCCAGATCCTGTACGAGGACCTGGAGGGGGGCAACATCCCCGCGCTCTT
GGATGTCGAAGCCTATGAAGAAAGTAAGGAAAAAGCAGAGGCTGAGGCAACTACAGCCGTGGCTACCGCCGCGACTGT
GGCAGATGCCACTGTCACCAGGGGCGATACATTCGCCACCCAGGCGGAGGAAGCAGCCGCCCTAGCGGCGACCGATGA
TAGTGAAAGTAAGATAGTCATCAAGCCGGTGGAGAAGGACAGCAAGAACAGGAGCTACAACGTTCTACCGGATGGAAA
GAACACCGCCTACCGCAGCTGGTACCTGGCCTACAACTACGGCGACCCCGAGAAGGGCGTGCGCTCCTGGACGCTGCT
CACCACCTCGGACGTCACCTGCGGCGTGGAGCAAGTCTACTGGTCGCTGCCCGACATGATGCAAGACCCGGTCACCTT
CCGCTCCACGCGACAAGTTAGCAACTACCCGGTGGTGGGCGCCGAGCTCCTGCCCGTCTACTCCAAGAGCTTCTTCAA
CGAGCAGGCCGTCTACTCGCAGCAGCTGCGTGCCTTCACCTCGCTCACGCACGTCTTCAACCGCTTCCCCGAGAACCA
GATCCTCGTCCGCCCGCCCGCGCCCACCATTACCACCGTCAGTGAAAACGTTCCTGCTCTCACAGATCACGGGACCCT
GCCGCTGCGCAGCAGTATCCGGGGAGTCCAGCGCGTGACCGTCACTGACGCCAGACGCCGCACCTGCCCCTACGTCTA
CAAGGCCCTGGGCGTAGTCGCGCCGCGGTCCTCTCGAGCCGCACCTTCTAAAAAATGTCCATTCTCATCTCGCCCAG
TAATAACACCGGTTGGGGCCTGCGCGCGCCCAGCAAGATGTACGGAGGCGCTCGCCAACGCTCCACGCAACACCCCGT
GCGCGTGCGCGGGCACTTCCGCGCTCCCTGGGGCGCCCTCAAGGGCCGCGTGCGCTCGCGCACCACCGTCGACGACGT
GATCGACCAGGTGGTGGCCGACGCGCGCAACTACACGCCCGCCGCCGCGCCCGCCTCCACCGTGGACGCCGTCATCGA
CAGCGTGGTGGCCGACGCGCGCCGGTACGCCCGCCCAAGAGCCGGCGGCGGCGCATCGCCCGGCGGCACCGGAGCAC
CCCCGCCATGCGCGCGGCGCGAGCCTTGCTGCGCAGGGCCAGGCGCACGGGACGCAGGGCCATGCTCAGGGCGGCCAG
ACGCGCGGCCTCCGGCAGCAGCAGCGCCGGCAGGACCCGCAGACGCGCGGCCACGGCGGCGGCGGCGGCCATCGCCAG
CATGTCCCGCCCGCGGCGCGGCAACGTGTACTGGGTGCGCGACGCCGCCACCGGTGTGCGCGTGCCCGTGCGCACCCG
CCCCCCTCGCACTTGAAGATGCTGACTTCGCGATGTTGATGTGTCCCAGCGGCGAGGAGGATGTCCAAGCGCAAATAC
AAGGAAGAGATGCTCCAGGTCATCGCGCCTGAGATCTACGGCCCCGCGGCGGCGGTGAAGGAGGAAAGAAAGCCCCGC
AAACTGAAGCGGGTCAAAAAGGACAAAAAGGAGGAGGAAGATGACGGACTGGTGGAGTTTGTGCGCGAGTTCGCCCCC
CGGCGGCGCGTGCAGTGGCGCGGGCGGAAAGTGAAACCGGTGCTGCGGCCCGGCACCACGGTGGTCTTCACGCCCGGC
GAGCGTTCCGGCTCCGCCTCCAAGCGCTCCTACGACGAGGTGTACGGGGACGAGGACATCCTCGAGCAGGCGGTCGAG
CGTCTGGGCGAGTTTGCTTACGGCAAGCGCAGCCGCCCCGCGCCCTTGAAAGAGGAGGCGGTGTCCATCCCGCTGGAC
CACGGCAACCCCACGCCGAGCCTGAAGCCGGTGACCCTGCAGCAGGTGCTGCCGAGCGCGGCGCCGCGCCGGGGCTTC
AAGCGCGAGGGCGGCGAGGATCTGTACCCGACCATGCAGCTGATGGTGCCCAAGCGCCAGAAGCTGGAGGACGTGCTG
GAGCACATGAAGGTGGACCCCGAGGTGCAGCCCGAGGTCAAGGTGCGGCCCATCAAGCAGGTGGCCCCGGGCCTGGGC
GTGCAGACCGTGGACATCAAGATCCCCACGGAGCCCATGGAAACGCAGACCGAGCCCGTGAAGCCCAGCACCAGCACC
ATGGAGGTGCAGACGGATCCCTGGATGCCAGCGGCTTCCACCACCACCACTCGCCGAAGACGCAAGTACGGCGCGGCC
AGCCTGCTGATGCCCAACTACGCGCTGCATCCTTCCATCATCCCCACGCCGGCGTACCGCGGCGCACGCGCTTCTACCGC
GGCTACCAGCAGCCGCCGCCGCCCAAGACCACCACCCCGCCGCGTCGTCGCAGCCGCCGCAGCAGCACCGCGACTTCC
GCCTTGGTGCGGAGAGTGTATCGCAGCGGGCGCGAGCCTCTGACCCTGCCGCGCGCGCGCTACCACCCGAGCATCGCC
ATTTAACTACCGCCTCCTACTTGCAGATATGGCCCTCACATGCCGCCTCCGCGTCCCCATTACGGGCTACCGAGGAAG
AAAGCCGCCGCCGTAGAAGGCTGACGGGAACGGGCTGCGTCGCCATCACCACCGGCGGCGGCGCCATCAGCAAGCG
GTTGGGGGGAGGCTTCCTGCCCGCGCTGATCCCCATCATCGCCGCGGCGATCGGGGCGATCCCCGGCATAGCTTCCGT
GGCGGTGCAGGCCTCTCAGCGCCACTGAGACACAAAAAAGCATGGATTTGTAATAAAAAAATGGACTGACGCTCCTGG
TCCTGTGATGTGTGTTTTTAGATGGAAGACATCAATTTTTCGTCCCTGGCACCGCGACACGGCACGCGGCCGTTTATG
GGCACCTGGAGCGACATCGGCAACAGCCAACTGAACGGGGGCGCCTTCAATTGGAGCAGTCTCTGGAGCGGGCTTAAG
AATTTCGGGTCCACGCTCAAAACCTATGGCAACAAGGCGTGGAACAGCAGCACAGGGCAGGCGCTGAGGGAAAAGCTG
AAAGAGCAGAACTTCCAGCAGAAGGTGGTCGATGCCCTGGCCTCGGGCATCAACGGGGTGGTGGACCTGGCCAACCAG
GCCGTGCAGAAACAGATCAACAGCCGCCTGGACGCGGTCCCGCCCGCGGGGTCCGTGGAGATGCCCCAGGTGGAGGAG
GAGCTGCCTCCCCTGGACAAGCGCGGCGACAAGCGACCGCGTCCCGACGCGGAGGAGACGCTGCTGACGCACACGGAC
GAGCCGCCCCCGTACGAGGAGGCGGTGAAACTGGGTCTGCCCACCACGCGGCCCGTGGCGCCTCTGGCCACCGGGGTG
CTGAAACCCAGCAGCAGCAGCCAGCCCGCGACCCTGGACTTGCCTCCGCCTGCTTCCCGCCCCTCCACAGTGGCTAAG
CCCCTGCCGCCGGTGGCCGTCGCGTCGCGCGCCCCCCGAGGCCGCCCCCAGGCGAACTGGCAGAGCACTCTGAACAGC
```

Fig. 10E

```
ATCGTGGGTCTGGGAGTGCAGAGTGTGAAGCGCCGCCGCTGCTATTAAAAGACACTGTAGCGCTTAACTTGCTTGTCT
GTGTGTGTATATGTATGTCCGCCGACCAGAAGGAGGAAGAGGCGCGTCGCCGAGTTGCAAGATGGCCACCCCATCGAT
GCTGCCCCAGTGGGCGTACATGCACATCGCCGGACAGGACGCTTCGGAGTACCTGAGTCCGGGTCTGGTGCAGTTCGC
CCGCGCCACAGACACCTACTTCAGTCTGGGGAACAAGTTTAGGAACCCCACGGTGGCGCCCACGCACGATGTGACCAC
CGACCGCAGCCAGCGGCTGACGCTGCGCTTCGTGCCCGTGGACCGCGAGGACAACACCTACTCGTACAAAGTGCGCTA
CACGCTGGCCGTGGGCGACAACCGCGTGCTGGACATGGCCAGCACCTACTTTGACATCCGCGGCGTGCTGGATCGGGG
CCCCAGCTTCAAACCCTACTCCGGCACCGCCTACAACAGCCTAGCTCCCAAGGGAGCGCCCAACACCTCACAGTGGAA
GGATTCCGACAGCAAAATGCATACTTTTGGAGTTGCTGCCATGCCCGGTGTTGTTGGTAAAAAAATAGAAGCCGATGG
TCTGCCTATTGAATAGATTCATCCTCTGGAACTGACACCATAATTTATGCTGATAAAACTTTCCAACCAGAGCCACA
GGTTGGAAGTGACAGTTGGGTCGACACCAATGGTGCAGAGGAAAAATATGGAGGTAGAGCTCTTAAGGACACTACAAA
CATGAAGCCCTGCTACGGTTCTTTTGCCAGGCCTACCAACAAAGAAGGTGGACAGGCTAACATAAAAGATTCTGAAAC
TGCCAGCACTACTCCTAACTATGATATAGATTTGGCATTCTTTGACAGCAAAAATATTGCAGCTAACTACGATCCAGA
TATTGTAATGTACACAGAAATGTTGAGTTGCAAACTCCAGATACTCATATTGTGTTTAAGCCAGGAACTTCAGATGA
AAGTTCAGAAGCCAATTTGGGCCAGCAGGCCATGCCCAACAGACCCAACTACATCGGGTTCAGAGACAACTTTATCGG
GCTCATGTACTACAACAGCACTGGCAATATGGGTGTACTGGCTGGTCAGGCCTCCCAGCTAAATGCTGTGGTGGACTT
GCAGGACAGAAACACCGAACTGTCCTACCAGCTCTTGCTTGACTCTCTGGGTGACAGAACCAGGTATTTCAGTATGTG
GAATCAGGCGGTGGACAGCTATGACCCCGATGCGCATTATTGAAAATCACGGTGTGGAGGATGAACTCCCCAATTA
TTGCTTCCCTTTGAATGGTGTAGGCTTTACAGATACTTACCAGGGTGTTAAAGTTAAGACAGATACAGCCGCTACTGG
TACCAATGGAACGCAGTGGGACAAAGATGATACCACAGTCAGCACTGCCAATGAGATCCACTCAGGCAATCCTTTCGC
CATGGAGATCAACATCCAGGCCAACCTGTGGCGGAACTTCCTCTACGCGAACGTGGCGCTGTACCTGCCCGACTCCTA
CAAGTACACGCCGGCCAACATCACGCTGCCGACCAACACCAACACCTACGATTACATGAACGGCCGCGTGGTGGCGCC
CTCGCTGGTGGACGCCTACATCAACATCGGGGCGCTGTCTCGCTGGCCGCCCCATGGACAACGTCAACCCCTTCAACCA
CCACCGCAACGCGGGCCTGCGCTACCGCTCCATGCTCCTGGGCAACGGGCGCTACGTGCCCTTCCACATCCAGGTGCC
CCAAAAGTTTTTCGCCATCAAGAGCCTCCTGCTCCTGCCCGGGTCCTACACCTACGAGTGGAACTTCCGCAAGGACGT
CAACATGATCCTGCAGAGCTCCCTCGGCAACGACCTGCGCACGGACGGGGCCTCCATCGCCTTCACCAGCATCAACCT
CTACGCCACCTTCTTCCCCATGGCGCACAACACCGCCTCCACGCTCGAGGCCATGCTGCGCAACGACACCAACGACCA
GTCCTTCAACGACTACCTCTCGGCGGCCAACATGCTCTACCCCATCCCGGCCAACGCCACCAACGTGCCCATCTCCAT
CCCCTCGCGCAACTGGGCCGCCTTCCGCGGATGTGCCTTCACGCGCCTCAAGACCCGCGAGACGCCCTCGCTCGGCTC
CGGGTTCGACCCCTACTTCGTCTACTCGGGCTCCATCCCCTACCTCGACGGCACCTTCTACCTCAACCACACCTTCAA
GAAGGTCTCCATCACCTTCGACTCCTCCGTCAGCTGGCCCGGCAACGACCGCCTCCTGACGCCCAACTACCCCTACCC
CAAGCGCACCGTCGACGGAGAGGGGATCAACGTGGCCCAGTGCAACATGACCAAGGACTGGTTCCTGGTCCAGATGCT
GGCCCACTACAACATCGGCTACCAGGGCTTCTACGTGCCCGAGGGCTACAAGGACCGCATGTACTCCTTCTTCCGCAA
CTTCCAGCCCATGAGCCGCCAGGTCGTGGACGAGGTCAACTACAAGGACTACCAGGCCGTCACCCTGGCCTACCAGCA
CAACAACTCGGGCTTCGTCGGCTACCTCGCGCCCACCATGCGCCAGGGCCAGCCCTACCCGCCAACTACCCCTACCC
GCTCATCGGCAAGAGCGCCGTCGCCAGCGTCACCCAGAAAAAGTTCCTCTGCGACCGGGTCATGTGGCGCATCCCCTT
CTCCAGCAACTTCATGTCCATGGGCGCGCTCACCGACCTCGGCCAGAACATGCTCTACGCCAACTCCGCCCACGCGCT
AGACATGAATTTCGAAGTCGACCCCATGGATGAGTCCACCCTTCTCTATGTTGTCTTCGAAGTCTTCGACGTCGTCCG
AGTGCACCAGCCCCACCGCGGCGTCATCGAGGCCGTCTACCTGCCGCACGCCCTTCTCGGCCGGCAACGCCACCACCTA
AAGCCCCGCTCTTGCTTCTTGCAAGATGACGGCCTGTGGCTCCGGCGAGCAGGAGTCAGGGCCATCCTCCGCGACCT
GGGCTGCGGGCCCTGCTTCCTGGGCACCTTCGACAAGCGCTTCCCGGGATTCATGGCCCCGCACAAGCTGGCCTGCGC
CATCGTCAACACGGCCGGCCGCGAGACCGGGGGCGAGCACCTGGCTGGCCTTCGCCTGGAACCCGCGCTCCCACACCTG
CTACCTCTTCGACCCCTTCGGGTTCTCGGACGAGCGCCTCAAGCAGATCTACCAGTTCGAGTACGAGGGCCTGCTGCG
CCGCAGCGCCCTGGCCACCGAGGACCGCTGCATCACCCTGGAAAAGTCCACCCAGACCGTGCAGGGTCCGCGCTCGGC
CGCCTGCGGGCTCTTCTGCTGCATGTTCCTGCACGCCTTCGTGCACTGGCCCGACCGCCCCATGGACAAGAACCCCAC
CATGAACTTGCTGACGGGGTGCCCAACGGCATGCTCCAGTCGCCCCAGGTGGAACCCACCCTGCGCCGCAACCAGGA
GGCGCTCTACCGCTTCCTCAACGCCCACTCCGCCTACTTTCGCTCCCACCGCGCGCGCATCGAGAAGGCCACCGCCTT
CGACCGCATGAATCAAGACATGTAAACTGTGTGTATGTGAATGCTTTATTCATCATAATAAACAGCACATGTTTATGC
CACCTTCTCTGAGGCTCTGACTTTATTTAGAAATCGAAGGGGTTCTGCCGGCTCTCGGCGTGCCCCGCGGGCAGGGAT
ACGTTGCGGAACTGGTACTTGGGCAGCCACTTGAACTCGGGGATCAGCAGCTTCGGCACGGGGAGGTCGGGGAACGAG
TCGCTCCACAGCTTGCGCGTGAGTTGCAGGGCGCCCAGCAGGTCGGGCGCGGAGATCTTGAAATCGCAGTTGGGACCC
GCGTTCTGCGCGCGAGAGTTGCGGTACACGGGGTTGCAGCACTGGAACACCATCAGGGCCGGGTGCTTCACGCTCGCC
AGCACCGTCGCGTCGGTGATGCCCTCCACGTCCAGATCCTCGGCGTTGGCCATCCCGAAGGGGGTCATCTTGCAGGTC
TGCCGCCCCATGCTGGGCACGCAGCCGGGCTTGTGGTTGCAATCGCAGTGCAGGGGGATCAGCATCATCTGAGCCTGC
TCGGAGCTCATGCCCGGGTACATGGCCTTCATGAAAGCCTCCAGCTGGCGGAAGGCCTGCTGCGCCTTGCCGCCCTCG
GTGAAGAAGACCCCACAGGACTTGCTAGAGAACTGGTTGGTGGCGCAGCCCGCGTCGTGCACGCAGCAGCGCGCGTCG
TTGTTGGCCAGCTGCACCACGCTGCGCCCCAGCGGTTCTGGGTGATCTTGGCCCGGTCGGGGTTCTCCTTCAGCGCG
CGCTGCCCGTTCTCGCTCGCCACATCCATCTCGATCGTGTGCTCCTTCTGGATCATCACGGTCCCGTGCAGGCACCGC
```

Fig. 10F

```
AGCTTGCCCTCGGCCTCGGTGCACCCGTGCAGCCACAGCGCGCAGCCGGTGCACTCCCAGTTCTTGTGGGCGATCTGG
GAGTGCGAGTGCACGAAGCCCTGCAGGAAGCGGCCCATCATCGTGGTCAGGGTCTTGTTGCTGGTGAAGGTCAGCGGG
ATGCCGCGGTGCTCCTCGTTCACATACAGGTGGCAGATGCGGCGGTACACCTCGCCCTGCTCGGGCATCAGCTGGAAG
GCGGACTTCAGGTCGCTCTCCACGCGGTACCGCTCCATCAGCAGCGTCATCACTTCCATGCCCTTCTCCCAGGCCGAA
ACGATCGGCAGGCTCAGGGGGTTCTTCACCGTCATCTTAGTCGCCGCCGCCGAAGTCAGGGGGTCGTTCTCGTCCAGG
GTCTCAAACACTCGCTTGCCGTCCTTCTCGGTGATGCGCACGGGGGGAAAGCTGAAGCCCACGGCCGCCAGCTCCTCC
TCGGCCTGCCTTTCGTCCTCGCTGTCCTGGCTGATGTCTTGCAAAGGCACATGCTTGGTCTTGCGGGGTTTCTTTTTG
GGCGGCAGAGGCGGCGGCGGAGACGTGCTGGGCGAGCGCGAGTTCTCGCTCACCACGACTATTTCTTCTTCTTGGCCG
TCGTCCGAGACCACGCGGCGGTAGGCATGCCTCTTCTGGGGCAGAGGCGGAGGCGACGGGCTCTCGCGGTTCGGCGGG
CGGCTGGCAGAGCCCCTTCCGCGTTCGGGGTGCGCTCCTGGCGGCGCTGCTCTGACTGACTTCCTCCGCGGCCGGCC
ATTGTGTTCTCCTAGGGAGCAACAAGCATGGAGACTCAGCCATCGTCGCCAACATCGCCATCTGCCCCCGCCGCCGAC
GAGAACCAGCAGCAGCAGAATGAAAGCTTAACCGCCCCGCCGCCCAGCCCCACCTCCGACGCCGCCGCGCCCCAGAC
ATGCAAGAGATGGAGGAATCCATCGAGATTGACCTGGGCTACGTGACGCCCGCGGAGCACGAGGAGGAGCTGGCAGCG
CGCTTTTCAGCCCCGGAAGAGAACCACCAAGAGCAGCCAGAGCAGGAAGCAGAGAGCGAGCAGCAGCAGGCTGGGCTC
GAGCATGGCGACTACCTGAGCGGGGCAGAGGACGTGCTCATCAAGCATCTGGCCCGCCAAAGCATCATCGTCAAGGAC
GCGCTGCTCGACCGCGCCGAGGTGCCCCTCAGCGTGGCGGAGCTCAGCCGCGCCTACGAGCGCAACCTCTTCTCGCCG
CGCGTGCCCCCCAAGCGCCAGCCCAACGGCACCTGCGAGCCCAACCCGCGCCTCAACTTCTACCCGGTCTTCGCGGTG
CCCGAGGCCCTGGCCACCTACCACCTCTTTTTTCAAGAACCAAAGGATCCCCGTCTCCTGCCGCGCCAACCGCACCCGC
GCCGACGCCCTGCTCAACCTGGGTCCCGGCGCCCGCCTACCTGATATCACCTCCTTGGAAGAGGTTCCCAAGATCTTC
GAGGGTCTGGGCAGCGACGAGACTCGGGCCGCGAACGCTCTGCAAGGAAGCGGAGAGGAGCATGAGCACCACAGCGCC
CTGGTGGAGTTGGAAGGCGACAACGCGCGCCTGGCGGTGCTCAAGCGCACGGTCGAGCTGACCCACTTCGCCTACCCG
GCGCTCAACCTGCCCCCCAAGGTCATGAGCGCCGTCATGGACCAGGTGCTCATCAAGCGCGCCTCGCCCCTCTCAGAG
GAGGAGATGCAGGACCCCGAGAGCTCGGACGAGGGCAAGCCCGTGGTCAGCGACGAGCAGCAGCAGCAGCAGCAGCAGCGGCGCGGTGGCTGGGA
GCGAGCAGCACCCCCCAGAGCCTGGAAGAGCGGCGCAAGCTCATGATGGCCGTGGTCCTGGTGACCGTGGAGCTGGAG
TGTCTGCGCCGCTTCTTCGCCGACGCGGAGACCCTGCGCAAGGTCGAGGAGAACCTGCACTACCTCTTCAGGCACGGG
TTCGTGCGCCAGGCCTGCAAGATCTCCAACGTGGAGCTGACCAACCTGGTCTCCTACATGGGCATCCTGCACGAGAAC
CGCCTGGGGCAGAACGTGCTGCACACACCCCTGCGCGGGGAGGCCCGCCGCGACTACATCCGCGACTGCGTCTACCTG
TACCTCTGCCACACCTGGCAGACGGGCATGGGCGTGTGGCAGCAGTGCCTGGAGGAGCAGAACCTGAAAGAGCTCTGC
AAGCTCCTGCAGAAGAACCTCAAGGCCCTGTGGACCGGGTTCGACGAGCGCACCACCGCCTCGGACCTGGCCGACCTC
ATCTTCCCCGAGCGCCTGCGGCTGACGCTGCGCAACGGGCTGCCCGACTTTATGAGCCAAAGCATGTTGCAAAACTTT
CGCTCTTTCATCCTCGAACGCTCCGGGATCCTGCCCGCCACCTGCTCCGCACTGCCCTCGGACTTCGTGCGCGTCGACC
TTCCGCGAGTGCCCCCCGCCGCTCTGGAGCCACTGCTACTTGCTGCGCCTGGCCAACTACCTGGCCTACCACTCGGAC
GTGATCGAGGACGTCAGCAGCGAGGGTCTGCTCGAGTGCCACTGCCGCTGCAACCTCTGCACGCCGCACCGCTCCTTG
GCCTGCAACCCCCAGCTGCTGAGCGAGACCCAGATCATCGGCACCTTCGAGTTGCAAGGCCCCGGCGAGGGCAAGGGG
GGTCTCAAACTCACCCCGGGCGTGTGGACCTCGGCCTACTTGCGCAAGTTCGTGCCCGAGGACTACCATCCCTTCGAG
ATCAGGTTCTACGAGGACCAATCCCAGCCGCCCAAGGCCGAGCTGTCGGCCTGCGTCATCACCCAGGGGGCCATCCTG
GCCCAATTGCAAGCCATCCAGAAATCCCGCCAAGAATTTCTGCTGAAAAAGGGCCACGGGGTCTACTTGGACCCCCAG
ACCGGAGAGGAGCTCAACCCCAGCTTCCCCCAGGATGCCCCGAGGAAGCAGCAAGAAGCTGAAAGTGGAGCTGCCGCT
GCCGCCGGAGGATTTGGAGGAAGACTGGGAGAGCAGTCCAGGCAGAGGAGATGGAAGACTGGGACAGCACTCAGGCAGA
GGAGGACAGCCTGCAAGACAGTCTGGAGGAGGAAGACGAGGTGGAGGAGGAGGCAGAGGAAGAAGCAGCCGCCGCCAG
ACCGTCGTCCTCGGCGGAGGAGAAAGCAAGCAGCACGGATACCATCTCCGCTCCGGGTCGGGGTCGCGGCGGCCGGGC
CCACAGTAGATGGGACGAGACCGGGCGCTTCCCGAAGCCCACCACCCAGACCGGTAAGAAGGAGCGGCAGGGATACAA
GTCCTGGCGGGGGCACAAAAACGCCATCGTCTCCTGCTTGCAAGCCTGCGGGGGCAACATCTCCTTCACCCGGCGCTA
CCTGCTCTTCCACCGCGGGGTGAACTTCCCCCGCAACATCTTGCATTACTACCGTCACCTCCACAGCCCCTACTACTG
TTTCCAAGAAGAGGCAGAAACCCAGCAGCAGCAGCAGAAAACCAGCGGCAGCAGCAGCAGTAGAAAATCCACAGCGG
CGGCAGGTGGACTGAGGATCGCGGCGAACGAGCCGGCGCAGACCCGGGAGCTGAGGAACCGGATCTTTCCCACCCTCT
ATGCCATCTTCCAGCAGAGTCGGGGGCAGGAGCAGGAACTGAAAGTCAAGAACCGTTCTCTGCGCTCGCTCACCCGCA
GTTGTCTGTATCACAAGAGCGAAGACCAACTTCAGCGCACTCTCGAGGACGCCGAGGCTCTCTTCAACAAGTACTGCG
CGCTCACTCTTAAAGAGTAGCCCGCGCCCGCCCACACACGGAAAAAGGCGGGAATTACGTCACCACCTGCGCCCTTCG
CCCGACCATCATCATGAGCAAAGAGATTCCCACGCCTTACATGTGGAGCTACCAGCCCCAGATGGGCCTGGCCGCCGG
CGCCGCCCAGGACTACTCCACCCGCATGAACTGGCTCAGTGCCGGGCCCGCGATGATCTCACGGGTGAATGACATCCG
CGCCCACCGAAACCAGATACTCCTAGAACAGTCAGCGATCACCGCCACGCCCCGCCATCACCTTAATCCGCGTAATTG
GCCCGCCGCCCTGGTGTACCAGGAAATTCCCCAGCCCACGACCGTACTACTTCCGCGAGACGCCCAGGCCGAAGTCCA
GCTGACTAACTCAGGTGTCCAGCTGGCCGGCGGCGCCGCCGCCGTCTGTGTCGTCACCGCCCGCGCTCAGGGTATAAAGCGGCT
GGTGATCCGAGGCAGAGGCACACAGCTCAACGACGAGGTGGTGAGCTCTTCGCTGGGTCTGCGACCTGACGGAGTCTT
CCAACTCGCCGGATCGGGGAGATCTTCCTTCACGCCTCGTCAGGCCGTCCTGACTTTGGAGAGTTCGTCCTCGCAGCC
CCGCTCGGGCGGCATCGGCACTCTCCAGTTCGTGGAGGAGTTCACTCCCTCGGTCTACTTCAACCCCTTCTCCGGCTC
CCCCGGCCACTACCCGGACGAGTTCATCCCGAACTTCGACGCCATCAGCGAGTCGGTGGACGGCTACGATTGAATGTC
```

Fig. 10G

```
CCATGGTGGCGCGGCTGACCTAGCTCGGCTTCGACACCTGGACCACTGTTAATTAATCGCCTCTCCTACGAGCTCCTG
CAGCAGCGCCAGAAGTTCACCTGCCTGGTCGGAGTCAACCCCATCGTCATCACCCAGCAGTCGGGCGATACCAAGGGG
TGCATCCACTGCTCCTGCGACTCCCCCGACTGCGTCCACACTCTGATCAAGACCCTCTGCGGCCTCCGCGACCTCCTC
CCCATGAACTAATCACCCCCTTATCCAGTGAAATAAAGATCATATTGATGATGATTTTACAGAAATAAAGATACAATC
ATATTGATGATTTGAGTTTAATAAAAAATAAAGAATCACTTACTTGAAATCTGATACCAGGTCTCTGTCCATGTTTTC
TGCCAACACCACTTCACTCCCCTCTTCCCAGCTCTGGTACTGCAGGCCCCGGCGGGCTGCAAACTTCCTCCACACGCT
GAAGGGGATGTCAAATTCCTCCTGTCCCTCAATCTTCATTTTATCTTCTATCAGATGTCCAAAAAGCGCGTCCGGGTG
GATGATGACTTCGACCCCGTCTACCCCTACGATGCAGACAACGCACCGACCGTGCCCTTCATCAACCCCCCCTTCGTC
TCTTCAGATGGATTCCAAGAGAAGCCCCTGGGGGTGCTGTCCCTGCGACTGGCCGACCCCGTCACCACCAAGAACGGG
GAAATCACCCTCAAGCTGGGAGAGGGGGTGGACCTCGACTCCTCGGGAAAACTCATCTCCAACACGGCCACCAAGGCC
GCCGCCCCTCTCAGTTTTTCCAACAACACCATTTCCCTTAACATGGATCACCCCTTTTACACTAAAGATGGAAAATTA
TCCTTACAAGTTTCTCCACCATTAAATATACTGAGAACAAGCATTCTAAACACACTAGCTTTAGGTTTTGGATCAGGT
TTAGGACTCCGTGGCTCTGCCTTGGCAGTACAGTTAGTCTCTCCACTTACATTTGATACTGATGGAAACATAAAGCTT
ACCTTAGACAGAGGTTTGCATGTTACAACAGGAGATGCAATTGAAAGCAACATAAGCTGGGCTAAAGGTTTAAAATTT
GAAGATGGAGCCATAGCAACCAACATTGGAAATGGGTTAGAGTTTGGAAGCAGTAGTACAGAAACAGGTGTTGATGAT
GCTTACCCAATCCAAGTTAAACTTGGATCTGGCCTTAGCTTTGACAGTACAGGAGCCATAATGGCTGGTAACAAAGAA
GACGATAAACTCACTTTGTGGACAACACCTGATCCATCGCCAAACTGTCAAATACTCGCAGAAAATGATGCAAAACTA
ACACTTTGCTTGACTAAATGTGGTAGTCAAATACTGGCCACTGTGTCAGTCTTAGTTGTAGGAAGTGGAAACCTAAAC
CCCATTACTGGCACCGTAAGCAGTGCTCAGGTGTTTCTACGTTTTGATGCAAACGGTGTTCTTTTAACAGAACATTCT
ACACTAAAAAAATACTGGGGGTATAGGCAGGGAGATAGCATAGATGGCACTCCATATACCAATGCTGTAGGATTCATG
CCCAATTTAAAAGCTTATCCAAAGTCACAAAGTTCTACTACTAAAAATAATATAGTAGGGCAAGTATACATGAATGGA
GATGTTTCAAAACCTATGCTTCTCACTATAACCCTCAATGGTACTGATGACAGCAACAGTACATATTCAATGTCATTT
TCATACACCTGGACTAATGGAAGCTATGTTGGAGCAACATTTGGGGCTAACTCTTATACCTTCTCATACATCGCCCAA
GAATGAACACTGTATCCCACCCTGCATGCCAACCCTTCCCACCCCACTCTGTGGAAAAAACTCTGAAACACAAAATAA
AATAAAGTTCAAGTGTTTTATTGATTCAACAGTTTTACAGGATTCGAGCAGTTATTTTTCCTCCACCCTCCCAGGACA
TGGAATACACCACCCTCTCCCCCCGCACAGCCTTGAACATCTGAACGCCATTGGTGATGGACATGCTTTTGGTCTCCA
CGTTCCACACAGTTTCAGAGCGAGCCAGTCTCGGGTCGGTCAGGGAGATGAAACCCTCCGGGCACAATTGGGAGAAGT
ACTCGCCTACATGGGGGTAGAGTCATAATCGTGCATCAGGATAGGGCGGTGGTGCTGCAGCAGCGCGCGAATAAACTG
CTGCCGCCGCCGCTCCGTCCTGCAGGAATACAACATGGCAGTGGTCTCCTCAGCGATGATTCGCACCGCCCGCAGCAT
AAGGCGCCTTGTCCTCCGGGCACAGCAGCGCACCCTGATCTCACTTAAATCAGCACAGTAACTGCAGCACAGCACCAC
AATATTGTTCAAAATCCCACAGTGCAAGGCGCTGTATCCAAAGCTCATGGCGGGGACCACAGAACCCACGTGGCCATC
ATACCACAAGCGCAGGTAGATTAAGTGGCGACCCCTCATAAACACGCTGGACATAAACATTACCTCTTTTGGCATGTT
GTAATTCACCACCTCCCGGTACCATATAAACCTCTGATTAAACATGGCGCCATCCACCACCATCCTAAACCAGCTGGC
CAAAACCTGCCCGCCGGCTATACACTGCAGGGAACCGGGACTGGAACAATGACAGTGGAGAGCCCAGGACTCGTAACC
ATGGATCATCATGCTCGTCATGATATCAATGTTGGCACAACACAGGCACACGTGCATACACTTCCTCAGGATTACAAG
CTCCTCCCGCGTTAGAACCATATCCCAGGGAACAACCCATTCCTGAATCAGCGTAAATCCCACACTGCAGGGAAGACC
TCGCACGTAACTCACGTTGTGCATTGTCAAAGTGTTACATTCGGGCAGCAGCGGATGATCCTCCAGTATGGTAGCGCG
GGTTTCTGTCTCAAAAGGAGGTAGACGATCCCTACTGTACGGAGTGCGCCGAGACAACCGAGATCGTGTTGGTCGTAG
TGTCATGCCAAATGGAACGCCGGACGTAGTCATATTTCCTGAAGTCTTGGCGCGCCAAAGTCTAGACAGCGTCCATAG
CTTACCGAGCAGCAGCAGCAGCACACAACAGGCGCAAGAGTCAGAGAAAGGCTGAGCTCTAACCTGTCCACCCGCTCT
CTGCTCAATATATAGCCCAGATCTACACTGACGTAAAGGCCAAAGTCTAAAAATACCCGCCAAATAGTCACACACGCC
CAGCACACGCCCAGAAACCGGTGACACACTCAAAAAAATACGCGCACTTCCTCAAACGCCCAAACTGCCGTCATTTCC
GGGTTCCCACGCTACGTCATCAAAACGACTTTCAAATTCCGTCGACCGTTAAAAACGTCACCCGCCCCGCCCCTAA
CGGTCGCCCGTCTCTCAGCCAATCAGCGCCCCGCATCCCCAAATTCAAACACCTCATTTGCATATTAACGCGCACCAA
AAGTTTGAGGTATATTATTGATGATG
```

Fig. 10H

SEQUENCE LISTING

<160> NUMBER OF SEQ ID NOS: 33

<210> SEQ ID NO 1
<211> LENGTH: 2675
<212> TYPE: PRT
<213> ORGANISM: Artificial Sequence
<220> FEATURE:
<223> OTHER INFORMATION: Chimeric HCV polypeptide

<400> SEQUENCE: 1

-continued

```
Met Ala Pro Ile Thr Ala Tyr Ala Gln Gln Thr Arg Gly Leu Leu Gly
 1               5                  10                  15

Thr Ile Val Thr Ser Leu Thr Gly Arg Asp Lys Asn Val Val Ala Gly
                20                  25                  30

Glu Val Gln Val Leu Ser Thr Ala Thr Gln Thr Phe Leu Gly Thr Thr
             35                  40                  45

Val Gly Gly Val Met Trp Thr Val Tyr His Gly Ala Gly Ser Arg Thr
 50                  55                  60

Leu Ala Gly Val Lys His Pro Ala Leu Gln Met Tyr Thr Asn Val Asp
 65                  70                  75                  80

Gln Asp Leu Val Gly Trp Pro Ala Pro Gly Ala Lys Ser Leu Glu
                 85                  90                  95

Pro Cys Thr Cys Gly Ser Ala Asp Leu Tyr Leu Val Thr Arg Asp Ala
                100                 105                 110

Asp Val Ile Pro Ala Arg Arg Gly Asp Ser Thr Ala Ser Leu Leu
             115                 120                 125

Ser Pro Arg Pro Leu Ala Arg Leu Lys Gly Ser Ser Gly Gly Pro Val
            130                 135                 140

Met Cys Pro Ser Gly His Val Ala Gly Ile Phe Arg Ala Ala Val Cys
145                 150                 155                 160

Thr Arg Gly Val Ala Lys Ala Leu Gln Phe Ile Pro Val Glu Thr Leu
                165                 170                 175

Ser Thr Gln Ala Arg Ser Pro Ser Phe Ser Asp Asn Ser Thr Pro Pro
                180                 185                 190

Ala Val Pro Gln Ser Tyr Gln Val Gly Tyr Leu His Ala Pro Thr Gly
            195                 200                 205

Ser Gly Lys Ser Thr Lys Val Pro Ala Ala Tyr Val Ala Gln Gly Tyr
        210                 215                 220

Asn Val Leu Val Leu Asn Pro Ser Val Ala Ala Thr Leu Gly Phe Gly
225                 230                 235                 240

Ser Phe Met Ser Arg Ala Tyr Gly Ile Asp Pro Asn Ile Arg Thr Gly
                245                 250                 255

Asn Arg Thr Val Thr Thr Gly Ala Lys Leu Thr Tyr Ser Thr Tyr Gly
                260                 265                 270

Lys Phe Leu Ala Gly Gly Gly Cys Ser Gly Gly Ala Tyr Asp Val Ile
            275                 280                 285

Ile Cys Asp Asp Cys His Ala Gln Asp Ala Thr Ser Ile Leu Gly Ile
        290                 295                 300

Gly Thr Val Leu Asp Gln Ala Glu Thr Ala Gly Val Arg Leu Thr Val
305                 310                 315                 320

Leu Ala Thr Ala Thr Pro Pro Gly Ser Ile Thr Val Pro His Ser Asn
                325                 330                 335

Ile Glu Glu Val Ala Leu Gly Ser Glu Gly Glu Ile Pro Phe Tyr Gly
            340                 345                 350

Lys Ala Ile Pro Ile Ala Cys Ile Lys Gly Gly Arg His Leu Ile Phe
            355                 360                 365

Cys His Ser Lys Lys Lys Cys Asp Lys Met Ala Ser Lys Leu Arg Gly
            370                 375                 380

Met Gly Leu Asn Ala Val Ala Tyr Tyr Arg Gly Leu Asp Val Ser Val
385                 390                 395                 400

Ile Pro Thr Thr Gly Asp Val Val Val Cys Ala Thr Asp Ala Leu Met
                405                 410                 415
```

```
Thr Gly Phe Thr Gly Asp Phe Asp Ser Val Ile Asp Cys Asn Val Ala
            420                 425                 430

Val Glu Gln Tyr Val Asp Phe Ser Leu Asp Pro Thr Phe Ser Ile Glu
        435                 440                 445

Thr Cys Thr Ala Pro Gln Asp Ala Val Ser Arg Ser Gln Arg Arg Gly
    450                 455                 460

Arg Thr Gly Arg Gly Arg Leu Gly Thr Tyr Arg Tyr Val Thr Pro Gly
465                 470                 475                 480

Glu Arg Pro Ser Gly Met Phe Asp Ser Val Val Leu Cys Glu Cys Tyr
                485                 490                 495

Asp Ala Gly Cys Ser Trp Tyr Asp Leu Gln Pro Ala Glu Thr Thr Val
            500                 505                 510

Arg Leu Arg Ala Tyr Leu Ser Thr Pro Gly Leu Pro Val Cys Gln Asp
        515                 520                 525

His Leu Asp Leu Trp Glu Ser Val Phe Thr Gly Leu Thr His Ile Asp
    530                 535                 540

Ala His Phe Leu Ser Gln Thr Lys Gln Ala Gly Leu Asn Phe Ser Tyr
545                 550                 555                 560

Leu Thr Ala Tyr Gln Ala Thr Val Cys Ala Arg Ala Gln Ala Pro Pro
                565                 570                 575

Pro Ser Trp Asp Glu Thr Trp Lys Cys Leu Val Arg Leu Lys Pro Thr
            580                 585                 590

Leu His Gly Pro Thr Pro Leu Leu Tyr Arg Leu Gly Pro Val Gln Asn
        595                 600                 605

Glu Ile Cys Leu Thr His Pro Ile Thr Lys Tyr Val Met Ala Cys Met
    610                 615                 620

Ser Ala Asp Leu Glu Val Thr Thr Ser Thr Trp Val Leu Leu Gly Gly
625                 630                 635                 640

Val Leu Ala Ala Val Ala Ala Tyr Cys Leu Ser Val Gly Cys Val Val
                645                 650                 655

Ile Val Gly His Ile Glu Leu Gly Gly Lys Pro Ala Leu Val Pro Asp
            660                 665                 670

Lys Glu Val Leu Tyr Gln Gln Tyr Asp Glu Met Glu Glu Cys Ser Gln
        675                 680                 685

Ala Arg Met Ala Pro Ile Thr Ala Tyr Ser Gln Gln Thr Arg Gly Leu
    690                 695                 700

Leu Gly Cys Ile Ile Thr Ser Leu Thr Gly Arg Asp Lys Asn Gln Val
705                 710                 715                 720

Glu Gly Glu Val Gln Val Val Ser Thr Ala Thr Gln Ser Phe Leu Ala
                725                 730                 735

Thr Cys Val Asn Gly Val Cys Trp Thr Val Tyr His Gly Ala Gly Ser
            740                 745                 750

Lys Thr Leu Ala Gly Pro Lys Gly Pro Ile Thr Gln Met Tyr Thr Asn
        755                 760                 765

Val Asp Gln Asp Leu Val Gly Trp Gln Ala Pro Gly Ala Arg Ser
    770                 775                 780

Leu Thr Pro Cys Thr Cys Gly Ser Ser Asp Leu Tyr Leu Val Thr Arg
785                 790                 795                 800

His Ala Asp Val Ile Pro Val Arg Arg Gly Asp Ser Arg Gly Ser
                805                 810                 815

Leu Leu Ser Pro Arg Pro Val Ser Tyr Leu Lys Gly Ser Ser Gly Gly
            820                 825                 830

Pro Leu Leu Cys Pro Ser Gly His Ala Val Gly Ile Phe Arg Ala Ala
```

```
            835                 840                 845
Val Cys Thr Arg Gly Val Ala Lys Ala Val Asp Phe Val Pro Val Glu
850                 855                 860

Ser Met Glu Thr Thr Met Arg Ser Pro Val Phe Thr Asp Asn Ser Ser
865                 870                 875                 880

Pro Pro Ala Val Pro Gln Ser Phe Gln Val Ala His Leu His Ala Pro
                885                 890                 895

Thr Gly Ser Gly Lys Ser Thr Lys Val Pro Ala Ala Tyr Ala Ala Gln
                900                 905                 910

Gly Tyr Lys Val Leu Val Leu Asn Pro Ser Val Ala Ala Thr Leu Gly
                915                 920                 925

Phe Gly Ala Tyr Met Ser Lys Ala His Gly Ile Asp Pro Asn Ile Arg
                930                 935                 940

Thr Gly Val Arg Thr Ile Thr Thr Gly Ala Pro Val Thr Tyr Ser Thr
945                 950                 955                 960

Tyr Gly Lys Phe Leu Ala Asp Gly Gly Cys Ser Gly Gly Ala Tyr Asp
                965                 970                 975

Ile Ile Ile Cys Asp Glu Cys His Ser Thr Asp Ser Thr Thr Ile Leu
                980                 985                 990

Gly Ile Gly Thr Val Leu Asp Gln Ala Glu Thr Ala Gly Ala Arg Leu
                995                 1000                1005

Val Val Leu Ala Thr Ala Thr Pro Pro Gly Ser Val Thr Val Pro His
                1010                1015                1020

Pro Asn Ile Glu Glu Val Ala Leu Ser Asn Thr Gly Glu Ile Pro Phe
1025                1030                1035                1040

Tyr Gly Lys Ala Ile Pro Ile Glu Ala Ile Arg Gly Gly Arg His Leu
                1045                1050                1055

Ile Phe Cys His Ser Lys Lys Lys Cys Asp Glu Leu Ala Ala Lys Leu
                1060                1065                1070

Ser Gly Leu Gly Ile Asn Ala Val Ala Tyr Tyr Arg Gly Leu Asp Val
                1075                1080                1085

Ser Val Ile Pro Thr Ile Gly Asp Val Val Val Val Ala Thr Asp Ala
                1090                1095                1100

Leu Met Thr Gly Tyr Thr Gly Asp Phe Asp Ser Val Ile Asp Cys Asn
1105                1110                1115                1120

Thr Cys Val Thr Gln Thr Val Asp Phe Ser Leu Asp Pro Thr Phe Thr
                1125                1130                1135

Ile Glu Thr Thr Thr Val Pro Gln Asp Ala Val Ser Arg Ser Gln Arg
                1140                1145                1150

Arg Gly Arg Thr Gly Arg Gly Arg Gly Ile Tyr Arg Phe Val Thr
                1155                1160                1165

Pro Gly Glu Arg Pro Ser Gly Met Phe Asp Ser Ser Val Leu Cys Glu
                1170                1175                1180

Cys Tyr Asp Ala Gly Cys Ala Trp Tyr Glu Leu Thr Pro Ala Glu Thr
                1185                1190                1195                1200

Ser Val Arg Leu Arg Ala Tyr Leu Asn Thr Pro Gly Leu Pro Val Cys
                1205                1210                1215

Gln Asp His Leu Glu Phe Trp Glu Ser Val Phe Thr Gly Leu Thr His
                1220                1225                1230

Ile Asp Ala His Phe Leu Ser Gln Thr Lys Gln Ala Gly Asp Asn Phe
                1235                1240                1245

Pro Tyr Leu Val Ala Tyr Gln Ala Thr Val Cys Ala Arg Ala Gln Ala
                1250                1255                1260
```

-continued

```
Pro Pro Pro Ser Trp Asp Gln Met Trp Lys Cys Leu Ile Arg Leu Lys
1265                1270                1275                1280

Pro Thr Leu His Gly Pro Thr Pro Leu Leu Tyr Arg Leu Gly Ala Val
            1285                1290                1295

Gln Asn Glu Val Thr Leu Thr His Pro Ile Thr Lys Tyr Ile Met Ala
        1300                1305                1310

Cys Met Ser Ala Asp Leu Glu Val Val Thr Ser Thr Trp Val Leu Val
    1315                1320                1325

Gly Gly Val Leu Ala Ala Leu Ala Ala Tyr Cys Leu Thr Thr Gly Ser
1330                1335                1340

Val Val Ile Val Gly Arg Ile Ile Leu Ser Gly Arg Pro Ala Ile Val
1345                1350                1355                1360

Pro Asp Arg Glu Phe Leu Tyr Gln Glu Phe Asp Glu Met Glu Glu Cys
            1365                1370                1375

Ala Ser His Leu Pro Tyr Ile Glu Gln Gly Met Gln Leu Ala Glu Gln
        1380                1385                1390

Phe Lys Gln Lys Ala Leu Gly Leu Leu Gln Thr Ala Thr Lys Gln Ala
    1395                1400                1405

Glu Ala Ala Pro Val Val Glu Ser Lys Trp Arg Ala Leu Glu Thr
    1410                1415                1420

Phe Trp Ala Lys His Met Trp Asn Phe Ile Ser Gly Ile Gln Tyr Leu
1425                1430                1435                1440

Ala Gly Leu Ser Thr Leu Pro Gly Asn Pro Ala Ile Ala Ser Leu Met
            1445                1450                1455

Ala Phe Thr Ala Ser Ile Thr Ser Pro Leu Thr Thr Gln Ser Thr Leu
        1460                1465                1470

Leu Phe Asn Ile Leu Gly Gly Trp Val Ala Ala Gln Leu Ala Pro Pro
    1475                1480                1485

Ser Ala Ala Ser Ala Phe Val Gly Ala Gly Ile Ala Gly Ala Ala Val
    1490                1495                1500

Gly Ser Ile Gly Leu Gly Lys Val Leu Val Asp Ile Leu Ala Gly Tyr
1505                1510                1515                1520

Gly Ala Gly Val Ala Gly Ala Leu Val Ala Phe Lys Val Met Ser Gly
            1525                1530                1535

Glu Met Pro Ser Thr Glu Asp Leu Val Asn Leu Leu Pro Ala Ile Leu
        1540                1545                1550

Ser Pro Gly Ala Leu Val Val Gly Val Val Cys Ala Ala Ile Leu Arg
    1555                1560                1565

Arg His Val Gly Pro Gly Glu Gly Ala Val Gln Trp Met Asn Arg Leu
    1570                1575                1580

Ile Ala Phe Ala Ser Arg Gly Asn His Val Ser Pro Thr His Tyr Val
1585                1590                1595                1600

Pro Glu Ser Asp Ala Ala Ala Arg Val Thr Gln Ile Leu Ser Ser Leu
            1605                1610                1615

Thr Ile Thr Gln Leu Leu Lys Arg Leu His Gln Trp Ile Asn Glu Asp
        1620                1625                1630

Cys Ser Thr Pro Cys Ser Gly Ser Trp Leu Arg Asp Val Trp Asp Trp
    1635                1640                1645

Ile Cys Thr Val Leu Thr Asp Phe Lys Thr Trp Leu Gln Ser Lys Leu
    1650                1655                1660

Leu Pro Gln Leu Pro Gly Val Pro Phe Phe Ser Cys Gln Arg Gly Tyr
1665                1670                1675                1680
```

```
Lys Gly Val Trp Arg Gly Asp Gly Ile Met Gln Thr Thr Cys Pro Cys
            1685                1690                1695

Gly Ala Gln Ile Thr Gly His Val Lys Asn Gly Ser Met Arg Ile Val
        1700                1705                1710

Gly Pro Lys Thr Cys Ser Asn Thr Trp His Gly Thr Phe Pro Ile Asn
    1715                1720                1725

Ala Tyr Thr Thr Gly Pro Cys Thr Pro Ser Pro Ala Pro Asn Tyr Ser
1730                1735                1740

Arg Ala Leu Trp Arg Val Ala Ala Glu Glu Tyr Val Glu Val Thr Arg
1745                1750                1755                1760

Val Gly Asp Phe His Tyr Val Thr Gly Met Thr Thr Asp Asn Val Lys
            1765                1770                1775

Cys Pro Cys Gln Val Pro Ala Pro Glu Phe Phe Thr Glu Val Asp Gly
        1780                1785                1790

Val Arg Leu His Arg Tyr Ala Pro Ala Cys Arg Pro Leu Leu Arg Glu
    1795                1800                1805

Glu Val Thr Phe Gln Val Gly Leu Asn Gln Tyr Leu Val Gly Ser Gln
1810                1815                1820

Leu Pro Cys Glu Pro Glu Pro Asp Val Ala Val Leu Thr Ser Met Leu
1825                1830                1835                1840

Thr Asp Pro Ser His Ile Thr Ala Glu Thr Ala Lys Arg Arg Leu Ala
            1845                1850                1855

Arg Gly Ser Pro Pro Ser Leu Ala Ser Ser Ala Ser Gln Leu Ser
        1860                1865                1870

Ala Pro Ser Leu Lys Ala Thr Cys Thr Thr His His Val Ser Pro Asp
    1875                1880                1885

Ala Asp Leu Ile Glu Ala Asn Leu Leu Trp Arg Gln Glu Met Gly Gly
1890                1895                1900

Asn Ile Thr Arg Val Glu Ser Glu Asn Lys Val Val Val Leu Asp Ser
1905                1910                1915                1920

Phe Asp Pro Leu Arg Ala Glu Glu Asp Glu Arg Glu Val Ser Val Pro
            1925                1930                1935

Ala Glu Ile Leu Arg Lys Ser Lys Lys Phe Pro Ala Ala Met Pro Ile
        1940                1945                1950

Trp Ala Arg Pro Asp Tyr Asn Pro Pro Leu Leu Glu Ser Trp Lys Asp
    1955                1960                1965

Pro Asp Tyr Val Pro Pro Val Val His Gly Cys Pro Leu Pro Pro Ile
1970                1975                1980

Lys Ala Pro Pro Ile Pro Pro Pro Arg Arg Lys Arg Thr Val Val Leu
1985                1990                1995                2000

Thr Glu Ser Ser Val Ser Ser Ala Leu Ala Glu Leu Ala Thr Lys Thr
            2005                2010                2015

Phe Gly Ser Ser Glu Ser Ser Ala Val Asp Ser Gly Thr Ala Thr Ala
        2020                2025                2030

Leu Pro Asp Gln Ala Ser Asp Asp Gly Asp Lys Gly Ser Asp Val Glu
    2035                2040                2045

Ser Tyr Ser Ser Met Pro Pro Leu Glu Gly Glu Pro Gly Asp Pro Asp
2050                2055                2060

Leu Ser Asp Gly Ser Trp Ser Thr Val Ser Glu Glu Ala Ser Glu Asp
2065                2070                2075                2080

Val Val Cys Cys Ser Met Ser Tyr Thr Trp Thr Gly Ala Leu Ile Thr
            2085                2090                2095

Pro Cys Ala Ala Glu Glu Ser Lys Leu Pro Ile Asn Ala Leu Ser Asn
```

```
                   2100                2105                 2110
        Ser Leu Leu Arg His His Asn Met Val Tyr Ala Thr Thr Ser Arg Ser
                2115                2120                2125

Ala Gly Leu Arg Gln Lys Lys Val Thr Phe Asp Arg Leu Gln Val Leu
                2130                2135                2140

Asp Asp His Tyr Arg Asp Val Leu Lys Glu Met Lys Ala Lys Ala Ser
        2145                2150                2155                2160

Thr Val Lys Ala Lys Leu Leu Ser Val Glu Glu Ala Cys Lys Leu Thr
                            2165                2170                2175

Pro Pro His Ser Ala Lys Ser Lys Phe Gly Tyr Gly Ala Lys Asp Val
                        2180                2185                2190

Arg Asn Leu Ser Ser Lys Ala Val Asn His Ile His Ser Val Trp Lys
                    2195                2200                2205

Asp Leu Leu Glu Asp Thr Val Thr Pro Ile Asp Thr Thr Ile Met Ala
                2210                2215                2220

Lys Asn Glu Val Phe Cys Val Gln Pro Glu Lys Gly Gly Arg Lys Pro
        2225                2230                2235                2240

Ala Arg Leu Ile Val Phe Pro Asp Leu Gly Val Arg Val Cys Glu Lys
                            2245                2250                2255

Met Ala Leu Tyr Asp Val Val Ser Thr Leu Pro Gln Val Val Met Gly
                        2260                2265                2270

Ser Ser Tyr Gly Phe Gln Tyr Ser Pro Gly Gln Arg Val Glu Phe Leu
                    2275                2280                2285

Val Asn Thr Trp Lys Ser Lys Lys Asn Pro Met Gly Phe Ser Tyr Asp
                2290                2295                2300

Thr Arg Cys Phe Asp Ser Thr Val Thr Glu Asn Asp Ile Arg Val Glu
        2305                2310                2315                2320

Glu Ser Ile Tyr Gln Cys Cys Asp Leu Ala Pro Glu Ala Arg Gln Ala
                            2325                2330                2335

Ile Lys Ser Leu Thr Glu Arg Leu Tyr Ile Gly Gly Pro Leu Thr Asn
                        2340                2345                2350

Ser Lys Gly Gln Asn Cys Gly Tyr Arg Arg Cys Arg Ala Ser Gly Val
                    2355                2360                2365

Leu Thr Thr Ser Cys Gly Asn Thr Leu Thr Cys Tyr Leu Lys Ala Ser
                2370                2375                2380

Ala Ala Cys Arg Ala Ala Lys Leu Gln Asp Cys Thr Met Leu Val Asn
        2385                2390                2395                2400

Ala Ala Gly Leu Val Val Ile Cys Glu Ser Ala Gly Thr Gln Glu Asp
                            2405                2410                2415

Ala Ala Ser Leu Arg Val Phe Thr Glu Ala Met Thr Arg Tyr Ser Ala
                        2420                2425                2430

Pro Pro Gly Asp Pro Pro Gln Pro Glu Tyr Asp Leu Glu Leu Ile Thr
                    2435                2440                2445

Ser Cys Ser Ser Asn Val Ser Val Ala His Asp Ala Ser Gly Lys Arg
                2450                2455                2460

Val Tyr Tyr Leu Thr Arg Asp Pro Thr Thr Pro Leu Ala Arg Ala Ala
        2465                2470                2475                2480

Trp Glu Thr Ala Arg His Thr Pro Val Asn Ser Trp Leu Gly Asn Ile
                            2485                2490                2495

Ile Met Tyr Ala Pro Thr Leu Trp Ala Arg Met Ile Leu Met Thr His
                        2500                2505                2510

Phe Phe Ser Ile Leu Leu Ala Gln Glu Gln Leu Glu Lys Ala Leu Asp
                    2515                2520                2525
```

-continued

```
Cys Gln Ile Tyr Gly Ala Cys Tyr Ser Ile Glu Pro Leu Asp Leu Pro
        2530                2535                2540

Gln Ile Ile Glu Arg Leu His Gly Leu Ser Ala Phe Ser Leu His Ser
2545                2550                2555                2560

Tyr Ser Pro Gly Glu Ile Asn Arg Val Ala Ser Cys Leu Arg Lys Leu
                2565                2570                2575

Gly Val Pro Pro Leu Arg Val Trp His Arg Ala Arg Ser Val Arg
                2580                2585                2590

Ala Arg Leu Leu Ser Gln Gly Gly Arg Ala Ala Thr Cys Gly Lys Tyr
            2595                2600                2605

Leu Phe Asn Trp Ala Val Lys Thr Lys Leu Lys Leu Thr Pro Ile Pro
    2610                2615                2620

Ala Ala Ser Gln Leu Asp Leu Ser Gly Trp Phe Val Ala Gly Tyr Ser
2625                2630                2635                2640

Gly Gly Asp Ile Tyr His Ser Leu Ser Arg Ala Arg Pro Arg Trp Phe
                2645                2650                2655

Met Leu Cys Leu Leu Leu Ser Val Gly Val Gly Ile Tyr Leu Leu
            2660                2665                2670

Pro Asn Arg
        2675

<210> SEQ ID NO 2
<211> LENGTH: 12939
<212> TYPE: DNA
<213> ORGANISM: Artificial Sequence
<220> FEATURE:
<223> OTHER INFORMATION: Plasmid containing an expression cassette
      encoding a chimeric HCV polypeptide

<400> SEQUENCE: 2
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tggaggtct atataagcag     900 agctcgttta gtgaaccgtc agatcgcctg gagacgccat ccacgctgtt tgacctcca     960 tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgctt ccttatgcta    1140
```

```
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtccttagaa ttccgccacc atggccccta tcaccgccta tgcccagcag    1920
acaagaggcc tgctgggcac catcgtgaca agcctgaccg gcagagacaa gaatgtggtg    1980
gccggcgaag tgcaggtgct gagcaccgcc acccagacat ttctgggcac cacagtgggc    2040
ggcgtgatgt ggacagtgta ccacggagcc ggctctagaa cactggccgg cgtgaagcac    2100
cctgccctgc agatgtatac caacgtggat caggatcttg tggggtggcc tgcccctcct    2160
ggcgccaagt ctctggagcc ttgtacctgc ggcagcgccg atctgtacct ggtgaccagg    2220
gacgccgatg tgatccccgc cagaagaaga ggcgatagca ccgccagcct gctgtctccg    2280
cggccgctgg ccagactgaa gggaagcagc ggcggacctg tgatgtgtcc tagcggccac    2340
gtggccggca tctttagagc cgccgtgtgt acaagaggcg tggccaaggc cctgcagttt    2400
atccctgtgg agaccctgag cacccaggcc agaagcccta gcttcagcga caacagcacc    2460
cctcctgccg tgcctcagag ctaccaagtg ggctacctgc acgcccctac aggctctggc    2520
aagtccacca agtgcctgcc cgcctatgtg gcccagggct acaatgtgct ggtgctgaac    2580
ccttctgtgg ccgccacact gggctttggc agcttcatga gcagggccta cggcatcgac    2640
cccaatatcc ggaccggcaa cagaaccgtg acaaccggcg ccaagctgac ctacagcacc    2700
tacggcaagt tcctggccgg aggaggatgt agcggcggag cctacgacgt gatcatctgc    2760
gacgattgcc acgcccagga tgccacaagc atcctgggca tcgggaccgt gctggatcag    2820
gccgaaacag ccggagtgag actgacagtg ctggccacag ccacacctcc tggcagcatc    2880
acagtgcccc acagcaatat cgaagaagtg gccctgggca gcgagggcga tatccctttt    2940
tacgggaagg ccatccctat cgcctgtatc aagggcggca ggcacctgat cttctgccac    3000
agcaagaaaa agtgtgacaa gatggccagc aagctgagag catgggcct gaatgccgtg    3060 gcctactaca gaggcctgga cgtgtctgtg atccctacca ccggcgatgt ggtggtgtgt    3120
gccaccgatg ccctgatgac cggcttcacc ggcgatttcg acagcgtgat cgattgcaac    3180
gtggccgtgg agcagtacgt ggacttcagc ctggacccta cattcagcat cgagacctgc    3240
acagctcctc aggatgccgt gtcccggtct cagagaagag gcagaaccgg cagaggcaga    3300
ctgggcacct acagatacgt gaccccctgg cgagagaccta gcggcatgtt tgacagcgtg    3360
gtgctgtgcg agtgttacga tgccggctgc tcctggtacg atctgcagcc tgccgagacc    3420
actgtgaggc tgagagccta cctgtctacc cctggcctgc ctgtgtgtca ggatcacctg    3480
```

```
gacctgtggg agagcgtgtt taccggcctg acacacatcg acgcccactt tctgagccag   3540
acaaaacagg ccggcctgaa cttcagctac ctgaccgcct accaggccac agtgtgtgct   3600
agagcccagg cccctcctcc tagctgggat gagacctgga agtgccttgt gagactgaag   3660
ccaaccctgc acggacctac cccactgctg tatagactgg gccccgtgca gaacgagatc   3720
tgcctgaccc accctatcac caagtacgtg atggcctgca tgagcgctga tctggaagtg   3780
accacctcca cttgggtgct gctgggggc gtgctagccg ccgtggccgc ctattgtctg   3840
tctgtgggct gcgtggtgat tgtgggccac atcgagctgg aggaaagcc tgccctggtg   3900 cccgataagg aagtgctcta ccagcagtac gacgagatgg aggagtgtag ccaggctaga   3960
atggccccca tcaccgccta cagccagcag acccgcggcc tgctgggctg catcatcacc   4020
agcctgaccg gccgcgacaa gaaccaggtg gagggcgagg tgcaggtggt gagcaccgcc   4080
acccagagct tcctggccac ctgcgtgaac ggcgtgtgct ggaccgtgta ccacggcgcc   4140
ggcagcaaga ccctggccgg ccccaagggc cccatcaccc agatgtacac caacgtggac   4200
caggacctgg tgggctggca ggcccccccc ggcgcccgca gctgaccccc ctgcacctgc   4260
ggcagcagcg acctgtacct ggtgacccgc cacgccgacg tgatcccgt gcgccgccgc   4320 ggcgacagcg gcggcagcct gctgagcccc cgccccgtga gctacctgaa gggcagcagc   4380
ggcggccccc tgctgtgccc cagcggccac gccgtgggca tcttccgcgc cgccgtgtgc   4440
acccgcggcg tggccaaggc cgtggacttc gtgcccgtgg agagcatgga gaccaccatg   4500
cgcagccccg tgttcaccga caacagcagc ccccccgccg tgccccagag cttccaggtg   4560
gcccacctgc acgcccccac cggcagcggc aagagcacca aggtgcccgc cgcctacgcc   4620
gcccagggct acaaggtgct ggtgctgaac cccagcgtgg ccgccaccct gggcttcggc   4680
gcctacatga gcaaggccca cggcatcgac cccaacatcc gcaccggcgt gcgcaccatc   4740
accaccggcg cccccgtgac ctacagcacc tacggcaagt tcctggccga cggcggctgc   4800
agcggcggcg cctacgacat catcatctgc gacgagtgcc acagcaccga cagcaccacc   4860
atcctgggca tcggcaccgt gctggaccag gccgagaccg ccggcgcccg cctggtggtg   4920
ctggccaccg ccaccccccc cggcagcgtg accgtgcccc accccaacat cgaggaggtg   4980
gccctgagca cacccggcga tccccttc tacggcaagg ccatccccat cgaggccatc   5040
cgcggcggcc gccaccctgat cttctgccac agcaagaaga agtgcgacga gctgccgcc   5100 aagctgagcg gcctgggcat caacgccgtg gcctactacc gcggcctgga cgtgagcgtg   5160
atccccacca tcggcgacgt ggtggtggtg gccaccgacg ccctgatgac cggctacacc   5220
ggcgacttcg acagcgtgat cgactgcaac acctgcgtga cccagaccgt ggacttcagc   5280
ctggacccca ccttcaccat cgagaccacc accgtgcccc aggacgccgt gagccgcagc   5340
cagcgccgcg gccgcaccgg ccgcggccgc cgcggcatct accgcttcgt gaccccggc   5400 gagcgcccca cgcggcatgtt cgacagcagc gtgctgtgcg agtgctacga cgccggctgc   5460
gcctggtacg agctgacccc cgccgagacc agcgtgcgcg tgcgcgccta cctgaacacc   5520
cccggcctgc ccgtgtgcca ggaccacctg gagttctggg agagcgtgtt caccggcctg   5580
acccacatcg acgcccactt cctgagccag accaagcagg ccggcgacaa cttccctac   5640 ctggtggcct accaggccac cgtgtgcgcc cgcgccagg cccccccccc cagctgggac   5700
cagatgtgga agtgcctgat ccgcctgaag cccaccctgc acggcccac cccctgctg   5760 taccgcctgg gcgccgtgca gaacgaggtg accctgaccc accccatcac caagtacatc   5820
atggcctgca tgagcgccga cctggaggtg gtgaccagca cctgggtgct ggtgggcggc   5880
```

```
gtgctggccg ccctggccgc ctactgcctg accaccggca gcgtggtgat cgtgggccgc    5940
atcatcctga gcggccgccc cgccatcgtg cccgaccgca gttcctgta ccaggagttc     6000 gacgagatgg aggagtgcgc cagccacctg ccctacatcg agcagggcat gcagctggcc    6060
gagcagttca gcagaaggcc cctgggcctg ctgcagaccg ccaccaagca ggccgaggcc    6120 gccgccccg tggtggagag caagtggcgc gccctggaga ccttctgggc caagcacatg    6180
tggaacttca tcagcggcat ccagtacctg gcggcctga gcaccctgcc cggcaacccc    6240
gccatcgcca gcctgatggc cttcaccgcc agcatcacca ccccctgac acccagagc     6300 accctgctgt tcaacatcct gggcggctgg gtggccgccc agctggcccc cccagcgcc    6360 gccagcgcct tcgtgggcgc cggcatcgcc ggcgccgccg tgggcagcat cggcctgggc    6420
aaggtgctgg tggacatcct ggccggctac ggcgccggcg tggccggcgc cctggtggcc    6480
ttcaaggtga tgagcggcga gatgcccagc accgaggacc tggtgaacct gctgcccgcc    6540
atcctgagcc ccgcgccct ggtggtgggc gtggtgtgcg ccgccatcct cgccgccac    6600 gtgggccccg gcgagggcgc cgtgcagtgg atgaaccgcc tgatcgcctt cgccagccgc    6660
ggcaaccacg tgagccccac ccactacgtg cccgagagcg acgccgccgc ccgcgtgacc    6720
cagatcctga gcagcctgac catcacccag ctgctgaagc gcctgcacca gtggatcaac    6780
gaggactgca gcaccccctg cagcggcagc tggctgcgcg acgtgtggga ctggatctgc    6840
accgtgctga ccgacttcaa gacctggctg cagagcaagc tgctgcccca gctgcccggc    6900
gtgcccttct tcagctgcca gcgcggctac aagggcgtgt ggcgcggcga cggcatcatg    6960
cagaccacct gccctgcgg cgcccagatc accggccacg tgaagaacgg cagcatgcgc    7020
atcgtgggcc ccaagacctg cagcaacacc tggcacggca ccttccccat caacgcctac    7080
accaccggcc cctgcacccc cagccccgcc cccaactaca gccgcgccct gtggcgcgtg    7140
gccgccgagg agtacgtgga ggtgaccccg gtgggcgact ccactacgt gaccggcatg    7200 accaccgaca acgtgaagtg cccctgccag gtgcccgccc ccgagttctt caccgaggtg    7260
gacggcgtgc gcctgcaccg ctacgccccc gcctgccgcc cctgctgcg cgaggaggtg    7320 accttccagg tgggcctgaa ccagtacctg gtgggcagcc agctgccctg cgagcccgag    7380
cccgacgtgg ccgtgctgac cagcatgctg accgacccca gccacatcac cgccgagacc    7440 gccagcgcc gcctggcccg cggcagcccc cccagcctgg ccagcagcag cgccagccag    7500
ctgagcgccc ccagcctgaa ggccacctgc accacccacc acgtgagccc cgacgccgac    7560
ctgatcgagg ccaacctgct gtggcgccag gagatgggcg caacatcac ccgcgtggag    7620 agcgagaaca aggtggtggt gctggacagc ttcgaccccc tgcgcgccga ggaggacgag    7680
cgcgaggtga gcgtgcccgc cgagatcctg cgcaagagca gaagttccc cgccgccatg    7740 cccatctggg cccgccccga ctacaacccc cccctgctgg agagctggaa ggaccccgac    7800
tacgtgcccc ccgtggtgca cggctgcccc ctgcccccca tcaaggcccc cccatcccc    7860 cccccccgcc gcaagcgcac cgtggtgctg accgagagca gcgtgagcag cgccctggcc    7920
gagctggcca ccaagacctt cggcagcagc gagagcagcg ccgtggacag cggcaccgcc    7980
accgccctgc ccgaccaggc cagcgacgac ggcgacaagg cagcgacgt ggagagctac    8040 agcagcatgc ccccctgga gggcgagccc ggcgaccccg acctgagcga cggcagctgg    8100
agcaccgtga gcgaggaggc cagcgaggac gtggtgtgct gcagcatgag ctacacctgg    8160
accggcgccc tgatcacccc ctgcgccgcc gaggagagca agctgcccat caacgccctg    8220
```

```
agcaacagcc tgctgcgcca ccacaacatg gtgtacgcca ccaccagccg cagcgccggc    8280
ctgcgccaga agaaggtgac cttcgaccgc ctgcaggtgc tggacgacca ctaccgcgac    8340
gtgctgaagg agatgaaggc caaggccagc accgtgaagg ccaagctgct gagcgtggag    8400
gaggcctgca agctgacccc cccccacagc gccaagagca agttcggcta cggcgccaag    8460
gacgtgcgca acctgagcag caaggccgtg aaccacatcc acagcgtgtg gaaggacctg    8520
ctggaggaca ccgtgacccc catcgacacc accatcatgg ccaagaacga ggtgttctgc    8580
gtgcagcccg agaagggcgg ccgcaagccc gcccgcctga tcgtgttccc cgacctgggc    8640
gtgcgcgtgt gcgagaagat ggccctgtac gacgtggtga gcaccctgcc ccaggtggtg    8700
atgggcagca gctacggctt ccagtacagc cccggccagc gcgtggagtt cctggtgaac    8760
acctggaaga gcaagaagaa ccccatgggc ttcagctacg acacccgctg cttcgacagc    8820
accgtgaccg agaacgacat ccgcgtggag gagagcatct accagtgctg cgacctggcc    8880
cccgaggccc gccaggccat caagagcctg accgagcgcc tgtacatcgg cggccccctg    8940
accaacagca agggccagaa ctgcggctac cgccgctgcc gcgccagcgg cgtgctgacc    9000
accagctgcg gcaacaccct gacctgctac ctgaaggcca cgccgcctg ccgcgccgcc    9060 aagctgcagg actgcaccat gctggtgaac gccgccggcc tggtggtgat ctgcgagagc    9120
gccggcaccc aggaggacgc cgccagcctg cgcgtgttca ccgaggccat gacccgctac    9180 agcgccccc ccggcgaccc ccccagcccc gagtacgacc tggagctgat caccagctgc    9240
agcagcaacg tgagcgtggc ccacgacgcc agcggcaagc gcgtgtacta cctgacccgc    9300 gacccccacca cccccctggc ccgcgccgcc tgggagaccg cccgcacac ccccgtgaac    9360 agctggctgg gcaacatcat catgtacgcc cccaccctgt gggcccgcat gatcctgatg    9420
acccacttct tcagcatcct gctggcccag gagcagctgg agaaggccct ggactgccag    9480
atctacggcg cctgctacag catcgagccc ctggacctgc cccagatcat cgagcgcctg    9540
cacgccctga gcgccttcag cctgcacagc tacagccccg cgagatcaa ccgcgtggcc    9600 agctgcctgc gcaagctggg cgtgccccc ctgcgcgtgt ggcgccaccg cgcccgcagc    9660
gtgcgcgccc gcctgctgag ccagggcggc gcgccgcca cctgcggcaa gtacctgttc    9720
aactgggccg tgaagaccaa gctgaagctg accccatcc ccgccgccag ccagctggac    9780
ctgagcggct ggttcgtggc cggctacagc ggcggcgaca tctaccacag cctgagccgc    9840 gcccgcccc gctggttcat gctgtgcctg ctgctgctga gcgtgggcgt gggcatctac    9900
ctgctgccca accgctaaat ttaaatgttt aaacgtcgac agcggccgcg atctgctgtg    9960
ccttctagtt gccagccatc tgttgtttgc ccctcccccg tgccttcctt gaccctggaa   10020
ggtgccactc ccactgtcct ttcctaataa aatgaggaaa ttgcatcgca ttgtctgagt   10080
aggtgtcatt ctattctggg gggtggggtg ggcaggaca gcaaggggga ggattgggaa   10140
gacaatagca ggcatgctgg ggatgcggtg ggctctatgg ccgcagcggc caggtgctga   10200
agaattgacc cggttcctcc tgggccagaa agaagcaggc acatcccctt ctctgtgaca   10260 cacccctgtcc acgcccctgg ttcttagttc cagccccact cataggacac tcatagctca   10320
ggagggctcc gccttcaatc ccacccgcta agtacttgg agcggtctct ccctccctca   10380
tcagcccacc aaaccaaacc tagcctccaa gagtgggaag aaattaaagc aagataggct   10440
attaagtgca gagggagaga aaatgcctcc aacatgtgag gaagtaatga gagaaatcat   10500
agaatttctt ccgcttcctc gctcactgac tcgctgcgct cggtcgttcg gctgcggcga   10560
gcggtatcag ctcactcaaa ggcggtaata cggttatcca cagaatcagg ggataacgca   10620
```

-continued

```
ggaaagaaca tgtgagcaaa aggccagcaa aaggccagga accgtaaaaa ggccgcgttg    10680
ctggcgtttt tccataggct ccgcccccct gacgagcatc acaaaaatcg acgctcaagt    10740
cagaggtggc gaaacccgac aggactataa agataccagg cgtttccccc tggaagctcc    10800
ctcgtgcgct ctcctgttcc gaccctgccg cttaccggat acctgtccgc ctttctccct    10860
tcgggaagcg tggcgctttc tcatagctca cgctgtaggt atctcagttc ggtgtaggtc    10920
gttcgctcca agctgggctg tgtgcacgaa ccccccgttc agcccgaccg ctgcgcctta    10980
tccggtaact atcgtcttga gtccaacccg gtaagacacg acttatcgcc actggcagca    11040
gccactggta acaggattag cagagcgagg tatgtaggcg gtgctacaga gttcttgaag    11100
tggtggccta actacggcta cactagaaga acagtatttg gtatctgcgc tctgctgaag    11160
ccagttacct tcggaaaaag agttggtagc tcttgatccg gcaaacaaac caccgctggt    11220
agcggtggtt ttttttgttg caagcagcag attacgcgca gaaaaaaagg atctcaagaa    11280
gatcctttga tcttttctac ggggtctgac gctcagtgga acgaaaactc acgttaaggg    11340
attttggtca tgagattatc aaaaaggatc ttcacctaga tccttttaaa ttaaaaatga    11400
agttttaaat caatctaaag tatatatgag taaacttggt ctgacagtta ccaatgctta    11460
atcagtgagg cacctatctc agcgatctgt ctatttcgtt catccatagt tgcctgactc    11520
gggggggggg ggcgctgagg tctgcctcgt gaagaaggtg ttgctgactc ataccaggcc    11580
tgaatcgccc catcatccag ccagaaagtg agggagccac ggttgatgag agctttgttg    11640
taggtggacc agttggtgat tttgaacttt gctttgcca cggaacggtc tgcgttgtcg    11700
ggaagatgcg tgatctgatc cttcaactca gcaaaagttc gatttattca acaaagccgc    11760
cgtcccgtca gtcagcgta atgctctgcc agtgttacaa ccaattaacc aattctgatt    11820
agaaaaactc atcgagcatc aaatgaaact gcaatttatt catatcagga ttatcaatac    11880 catattttg aaaagccgt ttctgtaatg aaggagaaaa ctcaccgagg cagttccata    11940
ggatggcaag atcctggtat cggtctgcga ttccgactcg tccaacatca atacaaccta    12000
ttaatttccc ctcgtcaaaa ataaggttat caagtgagaa atcaccatga gtgacgactg    12060
aatccggtga gaatggcaaa agcttatgca tttctttcca gacttgttca acaggccagc    12120
cattacgctc gtcatcaaaa tcactcgcat caaccaaacc gttattcatt cgtgattgcg    12180
cctgagcgag acgaaatacg cgatcgctgt taaaaggaca attacaaaca ggaatcgaat    12240
gcaaccggcg caggaacact gccagcgcat caacaatatt ttcacctgaa tcaggatatt    12300
cttctaatac ctggaatgct gttttcccgg ggatcgcagt ggtgagtaac catgcatcat    12360
caggagtacg gataaaatgc ttgatggtcg gaagaggcat aaattccgtc agccagttta    12420
gtctgaccat ctcatctgta acatcattgg caacgctacc tttgccatgt ttcagaaaca    12480
actctggcgc atcgggcttc ccatacaatc gatagattgt cgcacctgat tgcccgacat    12540
tatcgcgagc ccatttatac ccatataaat cagcatccat gttggaattt aatcgcggcc    12600
tcgagcaaga cgtttcccgt tgaatatggc tcataacacc ccttgtatta ctgtttatgt    12660
aagcagacag ttttattgtt catgatgata tatttttatc ttgtgcaatg taacatcaga    12720
gattttgaga cacaacgtgg ctttcccccc ccccccatta ttgaagcatt tatcagggtt    12780
attgtctcat gagcggatac atatttgaat gtatttagaa aaataaacaa ataggggttc    12840
cgcgcacatt tccccgaaaa gtgccacctg acgtctaaga aaccattatt atcatgacat    12900
taacctataa aaataggcgt atcacgaggc cctttcgtc                          12939
```

<210> SEQ ID NO 3
<211> LENGTH: 543
<212> TYPE: PRT
<213> ORGANISM: ChAd3

<400> SEQUENCE: 3

```
Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Asn Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
    210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
        275                 280                 285

Gly Pro Leu Tyr Ile Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380
```

```
Val Leu Thr Lys Cys Gly Ser Gln Ile Leu Ala Ser Val Ala Leu
385                 390                 395                 400

Ala Val Ser Gly Asn Leu Ala Ser Ile Thr Gly Val Ala Ser Val
            405                 410                 415

Thr Ile Phe Leu Arg Phe Asp Gln Asn Gly Val Leu Met Glu Asn Ser
        420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 4
<211> LENGTH: 1683
<212> TYPE: DNA
<213> ORGANISM: ChAd3

<400> SEQUENCE: 4
atgtcagatt cttgctcctg tccctccgca cccactatct tcatgttgtt gcagatgaag      60
cgcaccaaaa cgtctgacga gagcttcaac cccgtgtacc cctatgacac ggaaagcggc     120
cctccctccg tccctttcct caccctctcc ttcgtgtctc ccgatggatt ccaagaaagc     180
ccccccgggg tcctgtctct gaacctggcc gagcccctgg tcacttccca cggcatgctc     240
gccctgaaaa tgggaagtgg cctctccctg acgacgctg gcaacctcac ctctcaagat      300
atcaccaccg ctagccctcc cctcaaaaaa accaagacca acctcagcct agaaacctca     360
tcccccctaa ctgtaagcac ctcaggcgcc ctcaccgtag cagccgccgc tcccctggca     420
gtggccggca cctccctcac catgcaatca gaggcccccc tgacagtaca ggatgcaaaa     480
ctcaccctgg ccaccaaagg cccccctgacc gtgtctgaag caaactggc cttgcaaaca      540
tcggccccgc tgacggccgc tgacagcagc accctcaccg ttagcgccac accaccaatt     600
aatgtaagca gtggaagttt aggcttagac atggaagacc ctatgtatac tcacgatgga     660
aaactgggaa taagaattgg gggtccacta agagtagtag acagcttgca cacactcact     720
gtagttaccg gaaatggact aactgtagat aacaatgccc tccaaactag agttacgggc     780
gccctaggtt atgacacatc aggaaatcta caattgagag ctgcaggagg tatgcgaatt     840
gatgcaaatg ccaacttat ccttaatgtg gcataccat ttgatgctca gaacaatctc      900
agccttagac ttggtcaggg accctgtat ataaacacag accacaacct ggatttgaat      960
tgcaacagag gtctaaccac aactaccacc aacaacacaa aaaaacttga gactaaaatt     1020
agctcaggct agactatga caccaatggt gctgtcatta ttaaacttgg cactggtcta     1080
agcttcgaca acacaggcgc cctaactgtg gaaacactg gtgatgataa actgactctg     1140
tggacgaccc cagacccatc tccaaattgc agaattcact cagacaaaga ctgcaagttt     1200
```

```
actctagtcc taactaagtg tggaagccaa atcctggcct ctgtcgccgc cctagcggta   1260
tcaggaaatc tggcttcgat aacaggcacc gttgccagcg ttaccatctt tctcagattt   1320
gatcagaatg gagtgcttat ggaaaactcc tcgctagaca ggcagtactg gaacttcaga   1380
aatggcaact caactaacgc tgcccccatc accaatgcag ttgggttcat gccaaacctc   1440
gcagcatacc ccaaaacgca aagccagact gctaaaaaca acattgtaag tcaggtttac   1500
ttgaatggag acaaatccaa acccatgacc cttaccatca ccctcaatgg aactaatgaa   1560
tccagtgaaa ctagccaggt gagtcactac tccatgtcat ttacatgggc ttgggaaagt   1620
gggcaatatg ccactgaaac ctttgccacc aactccttca cctttctta cattgctgaa   1680 caa                                                                 1683
```

<210> SEQ ID NO 5
<211> LENGTH: 960
<212> TYPE: PRT
<213> ORGANISM: ChAd3

<400> SEQUENCE: 5

```
Met Ala Thr Pro Ser Met Met Pro Gln Trp Ser Tyr Met His Ile Ser
  1               5                  10                  15

Gly Gln Asp Ala Ser Glu Tyr Leu Ser Pro Gly Leu Val Gln Phe Ala
             20                  25                  30

Arg Ala Thr Glu Ser Tyr Phe Ser Leu Ser Asn Lys Phe Arg Asn Pro
         35                  40                  45

Thr Val Ala Pro Thr His Asp Val Thr Thr Asp Arg Ser Gln Arg Leu
     50                  55                  60

Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Glu Thr Gln Ala Val Glu
    130                 135                 140

Glu Ala Ala Glu Glu Glu Glu Asp Ala Asp Gly Gln Ala Glu Glu
145                 150                 155                 160

Glu Gln Ala Ala Thr Lys Lys Thr His Val Tyr Ala Gln Ala Pro Leu
                165                 170                 175

Ser Gly Glu Lys Ile Ser Lys Asp Gly Leu Gln Ile Gly Thr Asp Ala
            180                 185                 190

Thr Ala Thr Glu Gln Lys Pro Ile Tyr Ala Asp Pro Thr Phe Gln Pro
        195                 200                 205

Glu Pro Gln Ile Gly Glu Ser Gln Trp Asn Glu Ala Asp Ala Thr Val
    210                 215                 220

Ala Gly Gly Arg Val Leu Lys Lys Ser Thr Pro Met Lys Pro Cys Tyr
225                 230                 235                 240

Gly Ser Tyr Ala Arg Pro Thr Asn Ala Asn Gly Gly Gln Gly Val Leu
                245                 250                 255

Thr Ala Asn Ala Gln Gly Gln Leu Glu Ser Gln Val Glu Met Gln Phe
            260                 265                 270

Phe Ser Thr Ser Glu Asn Ala Arg Asn Glu Ala Asn Asn Ile Gln Pro
        275                 280                 285
```

```
Lys Leu Val Leu Tyr Ser Glu Asp Val His Met Glu Thr Pro Asp Thr
    290                 295                 300

His Leu Ser Tyr Lys Pro Ala Lys Ser Asp Asp Asn Ser Lys Ile Met
305                 310                 315                 320

Leu Gly Gln Gln Ser Met Pro Asn Arg Pro Asn Tyr Ile Gly Phe Arg
                325                 330                 335

Asp Asn Phe Ile Gly Leu Met Tyr Tyr Asn Ser Thr Gly Asn Met Gly
            340                 345                 350

Val Leu Ala Gly Gln Ala Ser Gln Leu Asn Ala Val Val Asp Leu Gln
        355                 360                 365

Asp Arg Asn Thr Glu Leu Ser Tyr Gln Leu Leu Leu Asp Ser Met Gly
    370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
            420                 425                 430

Gln Ala Val Lys Thr Asn Asn Gly Asn Asn Gly Gln Val Thr Trp
        435                 440                 445

Thr Lys Asp Glu Thr Phe Ala Asp Arg Asn Glu Ile Gly Val Gly Asn
    450                 455                 460

Asn Phe Ala Met Glu Ile Asn Leu Ser Ala Asn Leu Trp Arg Asn Phe
465                 470                 475                 480

Leu Tyr Ser Asn Val Ala Leu Tyr Leu Pro Asp Lys Leu Lys Tyr Asn
                485                 490                 495

Pro Ser Asn Val Asp Ile Ser Asp Asn Pro Asn Thr Tyr Asp Tyr Met
            500                 505                 510

Asn Lys Arg Val Val Ala Pro Gly Leu Val Asp Cys Tyr Ile Asn Leu
        515                 520                 525

Gly Ala Arg Trp Ser Leu Asp Tyr Met Asp Asn Val Asn Pro Phe Asn
    530                 535                 540

His His Arg Asn Ala Gly Leu Arg Tyr Arg Ser Met Leu Leu Gly Asn
545                 550                 555                 560

Gly Arg Tyr Val Pro Phe His Ile Gln Val Pro Gln Lys Phe Phe Ala
                565                 570                 575

Ile Lys Asn Leu Leu Leu Leu Pro Gly Ser Tyr Thr Tyr Glu Trp Asn
            580                 585                 590

Phe Arg Lys Asp Val Asn Met Val Leu Gln Ser Ser Leu Gly Asn Asp
        595                 600                 605

Leu Arg Val Asp Gly Ala Ser Ile Lys Phe Glu Ser Ile Cys Leu Tyr
    610                 615                 620

Ala Thr Phe Phe Pro Met Ala His Asn Thr Ala Ser Thr Leu Glu Ala
625                 630                 635                 640

Met Leu Arg Asn Asp Thr Asn Asp Gln Ser Phe Asn Asp Tyr Leu Ser
                645                 650                 655

Ala Ala Asn Met Leu Tyr Pro Ile Pro Ala Asn Ala Thr Asn Val Pro
            660                 665                 670

Ile Ser Ile Pro Ser Arg Asn Trp Ala Ala Phe Arg Gly Trp Ala Phe
        675                 680                 685

Thr Arg Leu Lys Thr Lys Glu Thr Pro Ser Leu Gly Ser Gly Phe Asp
    690                 695                 700
```

```
Pro Tyr Tyr Thr Tyr Ser Gly Ser Ile Pro Tyr Leu Asp Gly Thr Phe
705                 710                 715                 720

Tyr Leu Asn His Thr Phe Lys Lys Val Ser Val Thr Phe Asp Ser Ser
            725                 730                 735

Val Ser Trp Pro Gly Asn Asp Arg Leu Leu Thr Pro Asn Glu Phe Glu
        740                 745                 750

Ile Lys Arg Ser Val Asp Gly Glu Gly Tyr Asn Val Ala Gln Cys Asn
    755                 760                 765

Met Thr Lys Asp Trp Phe Leu Val Gln Met Leu Ala Asn Tyr Asn Ile
770                 775                 780

Gly Tyr Gln Gly Phe Tyr Ile Pro Glu Ser Tyr Lys Asp Arg Met Tyr
785                 790                 795                 800

Ser Phe Phe Arg Asn Phe Gln Pro Met Ser Arg Gln Val Val Asp Gln
                805                 810                 815

Thr Lys Tyr Lys Asp Tyr Gln Glu Val Gly Ile Ile His Gln His Asn
            820                 825                 830

Asn Ser Gly Phe Val Gly Tyr Leu Ala Pro Thr Met Arg Glu Gly Gln
        835                 840                 845

Ala Tyr Pro Ala Asn Phe Pro Tyr Pro Leu Ile Gly Lys Thr Ala Val
850                 855                 860

Asp Ser Ile Thr Gln Lys Lys Phe Leu Cys Asp Arg Thr Leu Trp Arg
865                 870                 875                 880

Ile Pro Phe Ser Ser Asn Phe Met Ser Met Gly Ala Leu Ser Asp Leu
                885                 890                 895

Gly Gln Asn Leu Leu Tyr Ala Asn Ser Ala His Ala Leu Asp Met Thr
            900                 905                 910

Phe Glu Val Asp Pro Met Asp Glu Pro Thr Leu Leu Tyr Val Leu Phe
        915                 920                 925

Glu Val Phe Asp Val Val Arg Val His Gln Pro His Arg Gly Val Ile
930                 935                 940

Glu Thr Val Tyr Leu Arg Thr Pro Phe Ser Ala Gly Asn Ala Thr Thr
945                 950                 955                 960

<210> SEQ ID NO 6
<211> LENGTH: 2880
<212> TYPE: DNA
<213> ORGANISM: ChAd3

<400> SEQUENCE: 6
atggcgaccc catcgatgat gccgcagtgg tcgtacatgc acatctcggg ccaggacgcc    60
tcggagtacc tgagccccgg gctggtgcag ttcgcccgcg ccaccgagag ctacttcagc   120
ctgagtaaca gtttaggaa ccccacggtg gcgcccacgc acgatgtgac caccgaccgg   180
tctcagcgcc tgacgctgcg gttcattccc gtggaccgcg aggacaccgc gtactcgtac   240
aaggcgcggt tcaccctggc cgtgggcgac aaccgcgtgc tggacatggc ctccacctac   300
tttgacatcc gcggggtgct ggaccggggt cccactttca gccctactc tggcaccgcc   360 tacaactccc tggcccccaa gggcgctccc aactcctgcg agtgggagca agaggaaact   420
caggcagttg aagaagcagc agaagaggaa gaagaagatg ctgacggtca agctgaggaa   480
gagcaagcag ctaccaaaaa gactcatgta tatgctcagg ctccccttc tggcgaaaaa   540 attagtaaag atggtctgca aataggaacg gacgctacag ctacagaaca aaaacctatt   600
tatgcagacc tacattcca gcccgaaccc caaatcgggg agtcccagtg gaatgaggca   660
gatgctacag tcgccggcgg tagagtgcta agaaatcta ctcccatgaa accatgctat   720
```

```
ggttcctatg caagacccac aaatgctaat ggaggtcagg gtgtactaac ggcaaatgcc      780
cagggacagc tagaatctca ggttgaaatg caattctttt caacttctga aaacgcccgt      840
aacgaggcta acaacattca gcccaaattg gtgctgtata gtgaggatgt gcacatggag      900
accccggata cgcacctttc ttacaagccc gcaaaaagcg atgacaattc aaaaatcatg      960
ctgggtcagc agtccatgcc aacagacct aattacatcg gcttcagaga caactttatc     1020
ggcctcatgt attacaatag cactggcaac atgggagtgc ttgcaggtca ggcctctcag     1080
ttgaatgcag tggtggactt gcaagacaga acacagaac tgtcctacca gctcttgctt     1140
gattccatgg gtgacagaac cagatacttt tccatgtgga atcaggcagt ggacagttat     1200
gacccagatg ttagaattat tgaaaatcat ggaactgaag acgagctccc caactattgt     1260
ttccctctgg gtggcatagg ggtaactgac acttaccagg ctgttaaaac caacaatggc     1320
aataacgggg gccaggtgac ttggacaaaa gatgaaactt ttgcagatcg caatgaaata     1380
ggggtgggaa acaatttcgc tatggagatc aacctcagtg ccaacctgtg gagaaacttc     1440
ctgtactcca acgtggcgct gtacctacca gacaagctta agtacaaccc ctccaatgtg     1500
gacatctctg acaaccccaa cacctacgat tacatgaaca agcgagtggt ggccccgggg     1560
ctggtggact gctacatcaa cctgggcgcg cgctggtcgc tggactacat ggacaacgtc     1620
aaccccttca ccaccaccg caatgcgggc ctgcgctacc gctccatgct cctgggcaac     1680
gggcgctacg tgcccttcca catccaggtg ccccagaagt tctttgccat caagaacctc     1740
ctcctcctgc cgggctccta cacctacgag tggaacttca ggaaggatgt caacatggtc     1800
ctccagagct ctctgggtaa cgatctcagg gtggacgggg ccagcatcaa gttcgagagc     1860
atctgcctct acgccacctt cttccccatg gcccacaaca cggcctccac gctcgaggcc     1920
atgctcagga acgacaccaa cgaccagtcc ttcaatgact acctttccgc cgccaacatg     1980
ctctacccca tacccgccaa cgccaccaac gtccccatct ccatcccctc gcgcaactgg     2040
gcggccttcc gcggctgggc cttcacccgc tcaagacca aggagacccc ctccctgggc     2100
tcgggattcg accctactac cacctactcg ggctctattc cctacctgga cggcaccttc     2160
tacctcaacc acactttcaa gaaggtctcg gtcaccttcg actcctcggt cagctggccg     2220
ggcaacgacc gtctgctcac ccccaacgag ttcgagatca gcgctcggt cgacggggaa     2280 ggctacaacg tggcccagtg caacatgacc aaggactggt tcctggtcca gatgctggcc     2340
aactacaaca tcggctacca gggcttctac atcccagaga gctacaagga caggatgtac     2400
tccttcttca ggaacttcca gcccatgagc cggcaggtgg tggaccagac caagtacaag     2460
gactaccagg aggtgggcat catccaccag cacaacaact cgggcttcgt gggctacctc     2520
gcccccacca tgcgcgaggg acaggcctac cccgccaact cccctaccc gctcataggc     2580 aagaccgcgg tcgacagcat caccagaaa agttcctct gcgaccgcac cctctggcgc     2640 atcccctct ccagcaactt catgtccatg gtgcgctct cggacctggg ccagaacttg     2700
ctctacgcca actccgccca cgccctcgac atgaccttcg aggtcgaccc catggacgag     2760 cccaccttc tctatgttct gttcgaagtc tttgacgtgg tccgggtcca ccagccgcac     2820
cgcggcgtca tcgagaccgt gtacctgcgt acgcccttct cggccggcaa cgccaccacc     2880
```

<210> SEQ ID NO 7
<211> LENGTH: 593
<212> TYPE: PRT
<213> ORGANISM: ChAd3

<400> SEQUENCE: 7

```
Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
        35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
290                 295                 300

Thr Thr Pro Ala Ala Ser Ala Ala Glu Gln Gly Glu Asp Ala Ala
305                 310                 315                 320

Asp Thr Ala Ala Asp Gly Ala Glu Ala Asp Pro Ala Met Val Val
                325                 330                 335

Glu Ala Pro Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
        355                 360                 365

Ala Ala Glu Glu Lys Gln Leu Ala Ala Ala Ala Ala Ala Ala Leu
370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
                405                 410                 415
```

Leu Lys Asp Ser Thr Asn Thr Ala Tyr Arg Ser Trp Tyr Leu Ala Tyr
            420                 425                 430

Asn Tyr Gly Asp Pro Ser Thr Gly Val Arg Ser Trp Thr Leu Leu Cys
            435                 440                 445

Thr Pro Asp Val Thr Cys Gly Ser Glu Gln Val Tyr Trp Ser Leu Pro
450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
            485                 490                 495

Phe Tyr Asn Asp Gln Ala Val Tyr Ser Gln Leu Ile Arg Gln Phe Thr
            500                 505                 510

Ser Leu Thr His Val Phe Asn Arg Phe Pro Glu Asn Gln Ile Leu Ala
            515                 520                 525

Arg Pro Pro Ala Pro Thr Ile Thr Thr Val Ser Glu Asn Val Pro Ala
            530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Thr Cys Pro Tyr Val
            565                 570                 575

Tyr Lys Ala Leu Gly Ile Val Ser Pro Arg Val Leu Ser Ser Arg Thr
            580                 585                 590

Phe

<210> SEQ ID NO 8
<211> LENGTH: 1779
<212> TYPE: DNA
<213> ORGANISM: ChAd3

<400> SEQUENCE: 8

```
atgcgccgcg cggcgatgta ccaggaggga cctcctccct cttacgagag cgtggtgggc      60
gcggcggcgg cggcgccctc ttctcccttt gcgtcgcagc tgctggagcc gccgtacgtg     120
cctccgcgct acctgcggcc tacggggggg agaaacagca tccgttactc ggagctggcg     180
ccctgttcg  acaccacccg ggtgtacctg gtggacaaca agtcggcgga cgtggcctcc     240
ctgaactacc agaacgacca cagcaatttt ttgaccacgg tcatccagaa caatgactac     300
agcccgagcg aggccagcac ccagaccatc aatctggatg accggtcgca ctggggcggc     360
gacctgaaaa ccatcctgca caccaacatg cccaacgtga cgagttcat  gttcaccaat     420
aagttcaagg cgcgggtgat ggtgtcgcgc tcgcaccaca aggaagaccg ggtggagctg     480
aagtacgagt gggtggagtt cgagctgcca gagggcaact actccgagac catgaccatt     540
gacctgatga caacgcgat  cgtggagcac tatctgaaag tgggcaggca aaacggggtc     600
ctggagagcg acatcgggt  caagttcgac accaggaact tccgcctggg gctgaccccc     660
gtgaccgggc tggttatgcc cggggtgtac accaacgagg ccttccatcc cgacatcatc     720
ctgctgcccg gctgcgggt  ggacttcact tacagccgcc tgagcaacct cctgggcatc     780
cgcaagcggc agcccttcca ggagggcttc aggatcacct acgaggacct ggaggggggc     840
aacatccccg cgctcctcga tgtggaggcc taccaggata gcttgaagga aaatgaggcg     900
ggacaggagg ataccacccc cgccgcctcg gccgccgccg agcagggcga ggatgctgct     960
gacaccgcgc cgcgcgacgg ggcagaggcc gaccccgcta tggtggtgga ggctcccgag    1020
caggaggagg atatgaatga cagtgcggtg cgcggagaca ccttcgtcac ccggggggag    1080
```

-continued

```
gaaaagcaag cggaggccga ggccgcggcc gaggaaaagc aactggcggc agcagcggcg    1140
gcggcggcgt tggccgcggc ggaggctgag tctgagggga ccaagcccgc caaggagccc    1200
gtgattaagc ccctgaccga agatagcaag aagcgcagtt acaacctgct caaggacagc    1260
accaacaccg cgtaccgcag ctggtacctg gcctacaact acggcgaccc gtcgacgggg    1320
gtgcgctcct ggaccctgct gtgcacgccg gacgtgacct cggctcgga gcaggtgtac    1380 tggtcgctgc ccgacatgat gcaagacccc gtgaccttcc gctccacgcg gcaggtcagc    1440
aacttcccgg tggtgggcgc cgagctgctg cccgtgcact ccaagagctt ctacaacgac    1500
caggccgtct actcccagct catccgccag ttcacctctc tgacccacgt gttcaatcgc    1560
tttcctgaga accagattct ggcgcgcccg ccgcccca ccatcaccac cgtcagtgaa    1620
aacgttcctg ctctcacaga tcacgggacg ctaccgctgc gcaacagcat cggaggagtc    1680
cagcgagtga ccgttactga cgccagacgc cgcacctgcc cctacgttta caaggccttg    1740
ggcatagtct cgccgcgcgt cctttccagc cgcactttt                           1779
```

<210> SEQ ID NO 9
<211> LENGTH: 425
<212> TYPE: PRT
<213> ORGANISM: ChAd63

<400> SEQUENCE: 9

```
Met Ser Lys Lys Arg Val Arg Val Asp Asp Asp Phe Asp Pro Val Tyr
  1               5                  10                  15

Pro Tyr Asp Ala Asp Asn Ala Pro Thr Val Pro Phe Ile Asn Pro Pro
             20                  25                  30

Phe Val Ser Ser Asp Gly Phe Gln Glu Lys Pro Leu Gly Val Leu Ser
         35                  40                  45

Leu Arg Leu Ala Asp Pro Val Thr Thr Lys Asn Gly Glu Ile Thr Leu
     50                  55                  60

Lys Leu Gly Glu Gly Val Asp Leu Asp Ser Ser Gly Lys Leu Ile Ser
 65                  70                  75                  80

Asn Thr Ala Thr Lys Ala Ala Pro Leu Ser Phe Ser Asn Asn Thr
                 85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
    130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
```

```
                    245                 250                 255
Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
            275                 280                 285

Gly Ser Gly Asn Leu Asn Pro Ile Thr Gly Thr Val Ser Ser Ala Gln
            290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
            355                 360                 365

Tyr Met Asn Gly Asp Val Ser Lys Pro Met Leu Leu Thr Ile Thr Leu
            370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
            420                 425

<210> SEQ ID NO 10
<211> LENGTH: 1278
<212> TYPE: DNA
<213> ORGANISM: ChAd63

<400> SEQUENCE: 10
atgtccaaaa agcgcgtccg ggtggatgat gacttcgacc ccgtctaccc ctacgatgca      60
gacaacgcac cgaccgtgcc cttcatcaac ccccccttcg tctcttcaga tggattccaa     120
gagaagcccc tggggggtgct gtccctgcga ctggccgacc ccgtcaccac caagaacggg     180
gaaatcaccc tcaagctggg agaggggggtg gacctcgact cctcgggaaa actcatcctcc    240
aacacggcca ccaaggccgc cgcccctctc agttttttcca acaacaccat ttcccttaac     300
atggatcacc ccttttacac taagatgga aaattatcct acaagtttc tccaccatta      360
aatatactga aacaagcat tctaaacaca ctagctttag gttttggatc aggtttagga      420
ctccgtggct ctgccttggc agtacagtta gtctctccac ttacatttga tactgatgga     480
aacataaagc ttaccttaga cagaggtttg catgttacaa caggagatgc aattgaaagc     540
aacataagct gggctaaagg tttaaaattt gaagatggag ccatagcaac caacattgga     600
aatgggttag agtttggaag cagtagtaca gaaacaggtg ttgatgatgc ttacccaatc     660
caagttaaac ttggatctgg ccttagcttt gacagtacag agccataat ggctggtaac     720
aaagaagacg ataaactcac tttgtggaca cacctgatc catcgccaaa ctgtcaaata     780
ctcgcagaaa atgatgcaaa actaacactt tgcttgacta atgtggtag tcaaatactg     840
gccactgtgt cagtcttagt tgtaggaagt ggaaacctaa accccattac tggcaccgta     900
agcagtgctc aggtgtttct acgttttgat gcaaacggtg ttcttttaac agaacattct     960
acactaaaaa aatactgggg gtataggcag ggagatagca tagatggcac tccatatacc    1020
aatgctgtag gattcatgcc caatttaaaa gcttatccaa agtcacaaag ttctactact    1080
```

-continued

```
aaaaataata tagtagggca agtatacatg aatggagatg tttcaaaacc tatgcttctc    1140
actataaccc tcaatggtac tgatgacagc aacagtacat attcaatgtc attttcatac    1200
acctggacta atggaagcta tgttggagca acatttgggg ctaactctta taccttctca    1260
tacatcgccc aagaatga                                                  1278
```

<210> SEQ ID NO 11
<211> LENGTH: 941
<212> TYPE: PRT
<213> ORGANISM: ChAd63

<400> SEQUENCE: 11

```
Met Ala Thr Pro Ser Met Leu Pro Gln Trp Ala Tyr Met His Ile Ala
  1               5                  10                  15

Gly Gln Asp Ala Ser Glu Tyr Leu Ser Pro Gly Leu Val Gln Phe Ala
             20                  25                  30

Arg Ala Thr Asp Thr Tyr Phe Ser Leu Gly Asn Lys Phe Arg Asn Pro
         35                  40                  45

Thr Val Ala Pro Thr His Asp Val Thr Thr Asp Arg Ser Gln Arg Leu
     50                  55                  60

Thr Leu Arg Phe Val Pro Val Asp Arg Glu Asp Asn Thr Tyr Ser Tyr
 65                  70                  75                  80

Lys Val Arg Tyr Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Lys Asp Ser Asp Ser Lys Met His Thr
    130                 135                 140

Phe Gly Val Ala Ala Met Pro Gly Val Val Gly Lys Lys Ile Glu Ala
145                 150                 155                 160

Asp Gly Leu Pro Ile Gly Ile Asp Ser Ser Ser Gly Thr Asp Thr Ile
                165                 170                 175

Ile Tyr Ala Asp Lys Thr Phe Gln Pro Glu Pro Gln Val Gly Ser Asp
            180                 185                 190

Ser Trp Val Asp Thr Asn Gly Ala Glu Glu Lys Tyr Gly Gly Arg Ala
        195                 200                 205

Leu Lys Asp Thr Thr Asn Met Lys Pro Cys Tyr Gly Ser Phe Ala Arg
    210                 215                 220

Pro Thr Asn Lys Glu Gly Gly Gln Ala Asn Ile Lys Asp Ser Glu Thr
225                 230                 235                 240

Ala Ser Thr Thr Pro Asn Tyr Asp Ile Asp Leu Ala Phe Phe Asp Ser
                245                 250                 255

Lys Asn Ile Ala Ala Asn Tyr Asp Pro Asp Ile Val Met Tyr Thr Glu
            260                 265                 270

Asn Val Glu Leu Gln Thr Pro Asp Thr His Ile Val Phe Lys Pro Gly
        275                 280                 285

Thr Ser Asp Glu Ser Ser Glu Ala Asn Leu Gly Gln Gln Ala Met Pro
    290                 295                 300

Asn Arg Pro Asn Tyr Ile Gly Phe Arg Asp Asn Phe Ile Gly Leu Met
305                 310                 315                 320

Tyr Tyr Asn Ser Thr Gly Asn Met Gly Val Leu Ala Gly Gln Ala Ser
                325                 330                 335
```

```
Gln Leu Asn Ala Val Val Asp Leu Gln Asp Arg Asn Thr Glu Leu Ser
            340                 345                 350
Tyr Gln Leu Leu Leu Asp Ser Leu Gly Asp Arg Thr Arg Tyr Phe Ser
        355                 360                 365
Met Trp Asn Gln Ala Val Asp Ser Tyr Asp Pro Asp Val Arg Ile Ile
    370                 375                 380
Glu Asn His Gly Val Glu Asp Glu Leu Pro Asn Tyr Cys Phe Pro Leu
385                 390                 395                 400
Asn Gly Val Gly Phe Thr Asp Thr Tyr Gln Gly Val Lys Val Lys Thr
                405                 410                 415
Asp Thr Ala Ala Thr Gly Thr Asn Gly Thr Gln Trp Asp Lys Asp Asp
            420                 425                 430
Thr Thr Val Ser Thr Ala Asn Glu Ile His Ser Gly Asn Pro Phe Ala
        435                 440                 445
Met Glu Ile Asn Ile Gln Ala Asn Leu Trp Arg Asn Phe Leu Tyr Ala
    450                 455                 460
Asn Val Ala Leu Tyr Leu Pro Asp Ser Tyr Lys Tyr Thr Pro Ala Asn
465                 470                 475                 480
Ile Thr Leu Pro Thr Asn Thr Asn Thr Tyr Asp Tyr Met Asn Gly Arg
                485                 490                 495
Val Val Ala Pro Ser Leu Val Asp Ala Tyr Ile Asn Ile Gly Ala Arg
            500                 505                 510
Trp Ser Leu Asp Pro Met Asp Asn Val Asn Pro Phe Asn His His Arg
        515                 520                 525
Asn Ala Gly Leu Arg Tyr Arg Ser Met Leu Leu Gly Asn Gly Arg Tyr
    530                 535                 540
Val Pro Phe His Ile Gln Val Pro Gln Lys Phe Phe Ala Ile Lys Ser
545                 550                 555                 560
Leu Leu Leu Leu Pro Gly Ser Tyr Thr Tyr Glu Trp Asn Phe Arg Lys
                565                 570                 575
Asp Val Asn Met Ile Leu Gln Ser Ser Leu Gly Asn Asp Leu Arg Thr
            580                 585                 590
Asp Gly Ala Ser Ile Ala Phe Thr Ser Ile Asn Leu Tyr Ala Thr Phe
        595                 600                 605
Phe Pro Met Ala His Asn Thr Ala Ser Thr Leu Glu Ala Met Leu Arg
    610                 615                 620
Asn Asp Thr Asn Asp Gln Ser Phe Asn Asp Tyr Leu Ser Ala Ala Asn
625                 630                 635                 640
Met Leu Tyr Pro Ile Pro Ala Asn Ala Thr Asn Val Pro Ile Ser Ile
                645                 650                 655
Pro Ser Arg Asn Trp Ala Ala Phe Arg Gly Trp Ser Phe Thr Arg Leu
            660                 665                 670
Lys Thr Arg Glu Thr Pro Ser Leu Gly Ser Gly Phe Asp Pro Tyr Phe
        675                 680                 685
Val Tyr Ser Gly Ser Ile Pro Tyr Leu Asp Gly Thr Phe Tyr Leu Asn
    690                 695                 700
His Thr Phe Lys Lys Val Ser Ile Thr Phe Asp Ser Ser Val Ser Trp
705                 710                 715                 720
Pro Gly Asn Asp Arg Leu Leu Thr Pro Asn Glu Phe Glu Ile Lys Arg
                725                 730                 735
Thr Val Asp Gly Glu Gly Tyr Asn Val Ala Gln Cys Asn Met Thr Lys
            740                 745                 750
Asp Trp Phe Leu Val Gln Met Leu Ala His Tyr Asn Ile Gly Tyr Gln
```

```
                755                 760                 765
Gly Phe Tyr Val Pro Glu Gly Tyr Lys Asp Arg Met Tyr Ser Phe Phe
    770                 775                 780

Arg Asn Phe Gln Pro Met Ser Arg Gln Val Val Asp Glu Val Asn Tyr
785                 790                 795                 800

Lys Asp Tyr Gln Ala Val Thr Leu Ala Tyr Gln His Asn Asn Ser Gly
                805                 810                 815

Phe Val Gly Tyr Leu Ala Pro Thr Met Arg Gln Gly Gln Pro Tyr Pro
            820                 825                 830

Ala Asn Tyr Pro Tyr Pro Leu Ile Gly Lys Ser Ala Val Ala Ser Val
        835                 840                 845

Thr Gln Lys Lys Phe Leu Cys Asp Arg Val Met Trp Arg Ile Pro Phe
    850                 855                 860

Ser Ser Asn Phe Met Ser Met Gly Ala Leu Thr Asp Leu Gly Gln Asn
865                 870                 875                 880

Met Leu Tyr Ala Asn Ser Ala His Ala Leu Asp Met Asn Phe Glu Val
                885                 890                 895

Asp Pro Met Asp Glu Ser Thr Leu Leu Tyr Val Val Phe Glu Val Phe
            900                 905                 910

Asp Val Val Arg Val His Gln Pro His Arg Gly Val Ile Glu Ala Val
        915                 920                 925

Tyr Leu Arg Thr Pro Phe Ser Ala Gly Asn Ala Thr Thr
    930                 935                 940

<210> SEQ ID NO 12
<211> LENGTH: 2877
<212> TYPE: DNA
<213> ORGANISM: ChAd63

<400> SEQUENCE: 12
atgtatgtcc gccgaccaga aggaggaaga ggcgcgtcgc cgagttgcaa gatggccacc      60
ccatcgatgc tgccccagtg gcgtacatg cacatcgccg acaggacgc ttcggagtac      120 ctgagtccgg gtctggtgca gttcgcccgc gccacagaca cctacttcag tctggggaac      180
aagtttagga accccacggt ggcgcccacg cacgatgtga ccaccgaccg cagccagcgg      240
ctgacgctgc gcttcgtgcc cgtggaccgc gaggacaaca cctactcgta caaagtgcgc      300
tacacgctgg ccgtgggcga caaccgcgtg ctggacatgg ccagcaccta ctttgacatc      360
cgcggcgtgc tggatcgggg cccccagctc aaacccctact ccggcaccgc ctacaacagc      420
ctagctccca agggagcgcc caacacctca cagtggaagg attccgacag caaaatgcat      480 actttggag ttgctgccat gcccggtgtt gttggtaaaa aaatagaagc cgatggtctg      540
cctattggaa tagattcatc ctctggaact gacaccataa tttatgctga taaactttc      600 caaccagagc cacaggttgg aagtgacagt tgggtcgaca ccaatggtgc agaggaaaaa      660
tatggaggta gagctcttaa ggacactaca aacatgaagc cctgctacgg ttctttttgcc      720 aggcctacca caaagaagg tggacaggct aacataaaag attctgaaac tgccagcact      780
actcctaact atgatataga tttggcattc tttgacagca aaatattgc agctaactac      840 gatccagata ttgtaatgta cacagaaaat gttgagttgc aaactccaga tactcatatt      900
gtgtttaagc aggaacttc agatgaaagt tcagaagcca atttgggcca gcaggccatg      960
cccaacagac ccaactacat cgggttcaga gacaacttta tcgggctcat gtactacaac      1020
agcactggca atatgggtgt actggctggt caggcctccc agctaaatgc tgtggtggac      1080
```

```
ttgcaggaca gaaacaccga actgtcctac cagctcttgc ttgactctct gggtgacaga      1140
accaggtatt tcagtatgtg gaatcaggcg gtggacagct atgacccga tgtgcgcatt       1200
attgaaaatc acggtgtgga ggatgaactc cccaattatt gcttcccttt gaatggtgta      1260
ggctttacag atacttacca gggtgttaaa gttaagacag atacagccgc tactggtacc      1320
aatggaacgc agtgggacaa agatgatacc acagtcagca ctgccaatga gatccactca      1380
ggcaatcctt cgccatgga gatcaacatc caggccaacc tgtggcggaa cttcctctac       1440
gcgaacgtgg cgctgtacct gcccgactcc tacaagtaca cgccggccaa catcacgctg      1500
ccgaccaaca ccaacaccta cgattacatg aacggccgcg tggtggcgcc ctcgctggtg      1560
gacgcctaca tcaacatcgg ggcgcgctgg tcgctggacc ccatggacaa cgtcaacccc      1620
ttcaaccacc accgcaacgc gggcctgcgc taccgctcca tgctcctggg caacgggcgc      1680
tacgtgccct tccacatcca ggtgccccaa aagttttcg ccatcaagag cctcctgctc       1740
ctgcccggt cctacaccta cgagtggaac ttccgcaagg acgtcaacat gatcctgcag       1800
agctccctcg gcaacgacct cgcacggacc ggggcctcca tcgccttcac cagcatcaac      1860
ctctacgcca ccttcttccc catggcgcac aacaccgcct ccacgctcga ggccatgctg      1920
cgcaacgaca ccaacgacca gtccttcaac gactacctct cggcggccaa catgctctac      1980
cccatcccgg ccaacgccac caacgtgccc atctccatcc cctcgcgcaa ctgggccgcc      2040
ttccgcggat ggtccttcac gcgcctcaag acccgcgaga cgccctcgct cggctccggg      2100
ttcgacccct acttcgtcta ctcgggctcc atcccctacc tcgacggcac cttctacctc      2160
aaccacacct tcaagaaggt ctccatcacc ttcgactcct ccgtcagctg gcccggcaac      2220
gaccgcctcc tgacgcccaa cgagttcgaa atcaagcgca ccgtcgacgg agagggatac      2280
aacgtggccc agtgcaacat gaccaaggac tggttcctgg tccagatgct ggcccactac      2340
aacatcggct accagggctt ctacgtgccc gagggctaca aggaccgcat gtactccttc      2400
ttccgcaact tccagcccat gagccgcag gtcgtggacg aggtcaacta caaggactac      2460
caggccgtca ccctggccta ccagcacaac aactcgggct tcgtcggcta cctcgcgccc      2520
accatgcgcc agggccagcc ctaccccgcc aactacccct accgctcat cggcaagagc      2580
gccgtcgcca gcgtcaccca gaaaaagttc ctctgcgacc gggtcatgtg cgcatccccc      2640
ttctccagca acttcatgtc catgggcgcg ctcaccgacc tcggccagaa catgctctac      2700
gccaactccg cccacgcgct agacatgaat ttcgaagtcg accccatgga tgagtccacc      2760
cttctctatg ttgtcttcga agtcttcgac gtcgtccgag tgcaccagcc ccaccgcggc      2820
gtcatcgagg ccgtctacct gcgcacgccc ttctcggccg gcaacgccac cacctaa         2877
```

<210> SEQ ID NO 13
<211> LENGTH: 35890
<212> TYPE: DNA
<213> ORGANISM: Artificial Sequence
<220> FEATURE:
<223> OTHER INFORMATION: ChAd3 delta E1,3,4, Ad5 E4orf6, NSmut

<400> SEQUENCE: 13

```
catcatcaat aatatacctt attttggatt gaagccaata tgataatgag atgggcggcg       60
cgaggcgggg cgcggggcgg gaggcgggtt tggggggcggg ccggcggggcg gggcggtgtg    120
gcggaagtgg actttgtaag tgtggcggat gtgacttgct agtgccgggc gcggtaaaag     180
tgacgttttc cgtgcgcgac aacgccccg ggaagtgaca tttttcccgc ggttttacc      240
ggatgttgta gtgaatttgg gcgtaaccaa gtaagatttg gccattttcg cgggaaaact     300
```

```
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctccgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctcgtttag tgaaccgtca   1140
gatcgcctgg agacgccatc cacgctgttt tgacctccat agaagacacc gggaccgatc   1200
cagcctccgc ggccgggaac ggtgcattgg aacgcggatt ccccgtgcca agagtgagat   1260
ctgccaccat ggcgcccatc acggcctact cccaacagac gcgggccta cttggttgca    1320 tcatcactag ccttacaggc cgggacaaga accaggtcga gggagaggtt caggtggttt   1380
ccaccgcaac acaatccttc ctggcgacct gcgtcaacgg cgtgtgttgg accgtttacc   1440
atggtgctgg ctcaaagacc ttagccggcc caaaggggcc aatcacccag atgtacacta   1500
atgtggacca ggacctcgtc ggctggcagg cgcccccgg ggcgcgttcc ttgacaccat    1560
gcacctgtgg cagctcagac ctttacttgg tcacgagaca tgctgacgtc attccggtgc   1620
gccggcgggg cgacagtagg gggagcctgc tctcccccag gcctgtctcc tacttgaagg   1680
gctcttcggg tggtccactg ctctgcccctt cggggcacgc tgtgggcatc ttccgggctg   1740
ccgtatgcac ccgggggggtt gcgaaggcgg tggactttgt gcccgtagag tccatggaaa   1800
ctactatgcg gtctccggtc ttcacggaca actcatcccc cccggccgta ccgcagtcat   1860
ttcaagtggc ccacctacac gctcccactg gcagcggcaa gagtactaaa gtgccggctg   1920
catatgcagc ccaagggtac aaggtgctcg tcctcaatcc gtccgttgcc gctaccttag   1980
ggtttggggc gtatatgtct aaggcacacg gtattgaccc caacatcaga actggggtaa   2040
ggaccattac cacaggcgcc cccgtcacat actctaccta tggcaagttt cttgccgatg   2100
gtggttgctc tggggggcgct tatgacatca taatatgtga tgagtgccat tcaactgact   2160
cgactacaat cttgggcatc ggcacagtcc tggaccaagc ggagacggct ggagcgcggc   2220
ttgtcgtgct cgccaccgct acgcctccgg gatcggtcac cgtgccacac ccaaacatcg   2280
aggaggtggc cttgtctaat actggagaga tccccttcta tggcaaagcc atccccattg   2340
aagccatcag ggggggaagg catctcattt tctgtcattc caagaagaag tgcgacgagc   2400
tcgccgcaaa gctgtcaggc ctcggaatca acgctgtggc gtattaccgg gggctcgatg   2460
tgtccgtcat accaactatc ggagacgtcg ttgtcgtggc aacagacgct ctgatgacgg   2520
gctatacggg cgactttgac tcagtgatcg actgtaacac atgtgtcacc cagacagtcg   2580
acttcagctt ggatcccacc ttcaccattg agacgacgac cgtgcctcaa gacgcagtgt   2640
```

```
cgcgctcgca gcggcggggt aggactggca ggggtaggag aggcatctac aggtttgtga    2700
ctccgggaga acggccctcg ggcatgttcg attcctcggt cctgtgtgag tgctatgacg    2760
cgggctgtgc ttggtacgag ctcaccccg ccgagacctc ggttaggttg cgggcctacc     2820
tgaacacacc agggttgccc gtttgccagg accacctgga gttctgggag agtgtcttca    2880
caggcctcac ccacatagat gcacacttct tgtcccagac caagcaggca ggagacaact    2940 tccctacct ggtagcatac caagccacgg tgtgcgccag ggctcaggcc ccacctccat     3000
catgggatca aatgtggaag tgtctcatac ggctgaaacc tacgctgcac gggccaacac    3060
ccttgctgta caggctggga gccgtccaaa atgaggtcac cctcacccac cccataacca    3120
aatacatcat ggcatgcatg tcggctgacc tggaggtcgt cactagcacc tgggtgctgg    3180
tgggcggagt ccttgcagct ctggccgcgt attgcctgac aacaggcagt gtggtcattg    3240
tgggtaggat tatcttgtcc gggaggccgg ctattgttcc cgacagggag tttctctacc    3300
aggagttcga tgaaatggaa gagtgcgcct cgcacctccc ttacatcgag cagggaatgc    3360
agctcgccga gcaattcaag cagaaagcgc tcgggttact gcaaacagcc accaaacaag    3420
cggaggctgc tgctcccgtg gtggagtcca agtggcgagc ccttgagaca ttctgggcga    3480
agcacatgtg gaatttcatc agcgggatac agtacttagc aggcttatcc actctgcctg    3540
ggaaccccgc aatagcatca ttgatggcat tcacagcctc tatcaccagc ccgctcacca    3600
cccaaagtac cctcctgttt aacatcttgg ggggtgggt ggctgcccaa ctcgcccccc     3660
ccagcgccgc ttcggctttc gtgggcgccg gcatcgccgg tgcggctgtt ggcagcatag    3720
gccttgggaa ggtgcttgtg gacattctgg cgggttatgg agcaggagtg gccggcgcgc    3780
tcgtggcctt caaggtcatg agcggcgaga tgccctccac cgaggacctg gtcaatctac    3840
ttcctgccat cctctctcct ggcgcctgg tcgtcggggt cgtgtgtgca gcaatactgc     3900
gtcgacacgt gggtccggga gaggggctg tgcagtggat gaaccggctg atagcgttcg     3960
cctcgcgggg taatcatgtt tccccccacgc actatgtgcc tgagagcgac gccgcagcgc    4020
gtgttactca gatcctctcc agccttacca tcactcagct gctgaaaagg ctccaccagt    4080
ggattaatga agactgctcc acaccgtgtt ccggctcgtg gctaagggat gtttgggact    4140
ggatatgcac ggtgttgact gacttcaaga cctggctcca gtccaagctc ctgccgcagc    4200
taccgggagt cccttttttc tcgtgccaac gcggtacaa gggagtctgg cggggagacg     4260
gcatcatgca aaccacctgc ccatgtggag cacagatcac cggacatgtc aaaaacggtt    4320
ccatgaggat cgtcgggcct aagacctgca gcaacgtg gcatggaaca ttccccatca      4380
acgcatacac cacgggcccc tgcacaccct ctccagcgcc aaactattct agggcgctgt    4440
ggcgggtggc cgctgaggag tacgtggagg tcacgcgggt gggggatttc cactacgtga    4500
cgggcatgac cactgacaac gtaaagtgcc catgccaggt tccggctcct gaattcttca    4560
cggaggtgga cggagtgcgg ttgcacaggt acgctccggc gtgcaggcct ctcctacggg    4620
aggaggttac attccaggtc gggctcaacc aatacctggt tgggtcacag ctaccatgcg    4680
agcccgaacc ggatgtagca gtgctcactt ccatgctcac cgaccctcc cacatcacag     4740 cagaaacggc taagcgtagg ttggccaggg ggtctccccc ctccttggcc agctcttcag    4800
ctagccagtt gtctgcgcct tccttgaagg cgacatgcac tacccaccat gtctctccgg    4860
acgctgacct catcgaggcc aacctcctgt ggcggcagga gatgggcggg aacatcaccc    4920
gcgtggagtc ggagaacaag gtggtagtcc tggactcttt cgacccgctt cgagcggagg    4980
aggatgagag ggaagtatcc gttccggcgg agatcctgcg gaaatccaag aagttccccg    5040
```

```
cagcgatgcc catctgggcg cgcccggatt acaaccctcc actgttagag tcctggaagg    5100
acccggacta cgtccctccg gtggtgcacg ggtgcccgtt gccacctatc aaggcccctc    5160
caataccacc tccacggaga aagaggacgg ttgtcctaac agagtcctcc gtgtcttctg    5220
ccttagcgga gctcgctact aagaccttcg gcagctccga atcatcggcc gtcgacagcg    5280
gcacggcgac cgcccttcct gaccaggcct ccgacgacgg tgacaaagga tccgacgttg    5340
agtcgtactc ctccatgccc ccccttgagg gggaaccggg ggaccccgat ctcagtgacg    5400
ggtcttggtc taccgtgagc gaggaagcta gtgaggatgt cgtctgctgc tcaatgtcct    5460
acacatggac aggcgccttg atcacgccat gcgctgcgga ggaaagcaag ctgcccatca    5520
acgcgttgag caactctttg ctgcgccacc ataacatggt ttatgccaca acatctcgca    5580
gcgcaggcct gcggcagaag aaggtcacct ttgacagact gcaagtcctg gacgaccact    5640
accgggacgt gctcaaggag atgaaggcga aggcgtccac agttaaggct aaactcctat    5700
ccgtagagga agcctgcaag ctgacgcccc cacattcggc caaatccaag tttggctatg    5760
gggcaaagga cgtccggaac ctatccagca aggccgttaa ccacatccac tccgtgtgga    5820
aggacttgct ggaagacact gtgacaccaa ttgacaccac catcatggca aaaaatgagg    5880
ttttctgtgt ccaaccagag aaaggaggcc gtaagccagc ccgccttatc gtattcccag    5940
atctgggagt ccgtgtatgc gagaagatgg ccctctatga tgtggtctcc acccttcctc    6000
aggtcgtgat gggctcctca tacggattcc agtactctcc tgggcagcga gtcgagttcc    6060
tggtgaatac ctggaaatca agaaaaaacc ccatgggctt ttcatatgac actcgctgtt    6120
tcgactcaac ggtcaccgag aacgacatcc gtgttgagga gtcaatttac caatgttgtg    6180
acttggcccc cgaagccaga caggccataa aatcgctcac agagcggctt tatatcgggg    6240
gtcctctgac taattcaaaa gggcagaact gcggttatcg ccggtgccgc gcgagcggcg    6300
tgctgacgac tagctgcggt aacaccctca catgttactt gaaggcctct gcagcctgtc    6360
gagctgcgaa gctccaggac tgcacgatgc tcgtgaacgc cgccggcctt gtcgttatct    6420
gtgaaagcgc gggaacccaa gaggacgcgg cgagcctacg agtcttcacg gaggctatga    6480
ctaggtactc tgccccccccc ggggaccccgc cccaaccaga atacgacttg gagctgataa    6540
catcatgttc ctccaatgtg tcggtcgccc acgatgcatc aggcaaaagg gtgtactacc    6600
tcacccgtga tcccaccacc cccctcgcac gggctgcgtg ggaaacagct agacacactc    6660
cagttaactc ctggctaggc aacattatca tgtatgcgcc cactttgtgg gcaaggatga    6720
ttctgatgac tcacttcttc tccatccttc tagcacagga gcaacttgaa aaagccctgg    6780
actgccagat ctacggggcc tgttactcca ttgagccact tgacctacct cagatcattg    6840
aacgactcca tggccttagc gcattttcac tccatagtta ctctccaggt gagatcaata    6900
gggtggcttc atgcctcagg aaacttgggg taccacccct tgcgagtctgg agacatcggg    6960 ccaggagcgt ccgcgctagg ctactgtccc agggggggag ggccgccact tgtggcaagt    7020
acctcttcaa ctgggcagtg aagaccaaac tcaaactcac tccaatcccg gctgcgtccc    7080
agctggactt gtccggctgg ttcgttgctg gttacagcgg gggagacata tatcacagcc    7140
tgtctcgtgc ccgaccccgc tggttcatgc tgtgcctact cctactttct gtaggggtag    7200
gcatctacct gctccccaac cgataaatct agagctgtgc cttctagttg ccagccatct    7260
gttgtttgcc cctcccccgt gccttccttg acctggaag gtgccactcc cactgtcctt    7320
tcctaataaa atgaggaaat tgcatcgcat tgtctgagta ggtgtcattc tattctgggg    7380
```

```
ggtggggtgg ggcagcacag caaggggag gattgggaag acaatagcag gcatgctggg      7440
gatgcggtgg gcgatatcag cgatcgctga ggtgggtgag tgggcgtggc ctggggtggt      7500
catgaaaata tataagttgg gggtcttagg gtctctttat ttgtgttgca gagaccgccg      7560
gagccatgag cgggagcagc agcagcagca gtagcagcag cgccttggat ggcagcatcg      7620 tgagcccta tttgacgacg cggatgcccc actgggccgg ggtgcgtcag aatgtgatgg      7680
gctccagcat cgacgccga cccgtcctgc ccgcaaattc cgccacgctg acctatgcga      7740
ccgtcgcggg gacgccgttg gacgccaccg ccgccgccgc cgccaccgca gccgcctcgg      7800
ccgtgcgcag cctggccacg gactttgcat tcctgggacc actggcgaca ggggctactt      7860
ctcgggccgc tgctgccgcc gttcgcgatg acaagctgac cgccctgctg gcgcagttgg      7920
atgcgcttac tcgggaactg ggtgacctt ctcagcaggt catggccctg cgccagcagg      7980
tctcctccct gcaagctggc gggaatgctt ctcccacaaa tgccgtttaa gataaataaa      8040
accagactct gtttggatta aagaaaagta gcaagtgcat tgctctcttt atttcataat      8100
tttccgcgcg cgataggccc tagaccagcg ttctcggtcg ttgagggtgc ggtgtatctt      8160
ctccaggacg tggtagaggt ggctctggac gttgagatac atgggcatga gcccgtcccg      8220
ggggtggagg tagcaccact gcagagcttc atgctccggg gtggtgttgt agatgatcca      8280
gtcgtagcag gagcgctggg catggtgcct aaaaatgtcc ttcagcagca ggccgatggc      8340 caggggagg cccttggtgt aagtgtttac aaaacggtta agttgggaag ggtgcattcg      8400
gggagagatg atgtgcatct tggactgtat ttttagattg gcgatgtttc cgcccagatc      8460
ccttctggga ttcatgttgt gcaggaccac cagtacagtg tatccggtgc acttgggaa      8520 tttgtcatgc agcttagagg gaaaagcgtg gaagaacttg gagacgccct tgtggcctcc      8580 cagatttcc atgcattcgt ccatgatgat ggcaatgggc ccgcgggagg cagcttgggc      8640
aaagatattt ctggggtcgc tgacgtcgta gttgtgttcc agggtgaggt cgtcataggc      8700 cattttaca aagcgcgggc ggagggtgcc cgactggggg atgatggtcc cctctggccc      8760
tggggcgtag ttgccctcgc agatctgcat ttcccaggcc ttaatctcgg agggggggaat      8820 catatccacc tgcggggcga tgaagaaaac ggtttccgga gccggggaga ttaactggga      8880
tgagagcagg tttctaagca gctgtgattt tccacaaccg gtgggcccat aaataacacc      8940
tataaccggg tgcagctggt agtttagaga gctgcagctg ccgtcgtccc ggaggagggg      9000
ggccacctcg ttgagcatgt ccctgacgcg catgttctcc ccgaccagat ccgccagaag      9060
gcgctcgccg cccagggaca gcagctcttg caaggaagca agttttttca gcggcttgag      9120
gccgtccgcc gtgggcatgt ttttcagggt ctggctcagc agctccaggc ggtcccagag      9180
ctcggtgacg tgctctacgg catctctatc cagcatatct cctcgtttcg cgggttgggg      9240
cgactttcgc tgtagggcac caagcggtgg tcgtccagcg gggccaaagt catgtccttc      9300
catgggcgca gggtcctcgt cagggtggtc tgggtcacgg tgaagggtg cgctccgggc      9360 tgagcgcttg ccaaggtgcg cttgaggctg gttctgctgg tgctgaagcg ctgccggtct      9420
tcgccctgcg cgtcggccag gtagcatttg accatggtgt catagtccag cccctccgcg      9480
gcgtgtccct ggcgcgcag cttgcccttg gaggtggcgc cgcacgaggg gcagagcagg      9540
ctcttgagcg cgtagagctt gggggcgagg aagaccgatt cggggagta ggcgtccgcg      9600 ccgcagaccc cgcacacggt ctcgcactcc accagccagg tgagctcggg gcgcgccggg      9660
tcaaaaacca ggtttccccc atgctttttg atgcgtttct tacctcgggt ctccatgagg      9720
tggtgtcccc gctcggtgac gaagaggctg tccgtgtctc cgtagaccga cttgagggt      9780
```

```
cttttctcca gggggtccc tcggtcttcc tcgtagagga actcggacca ctctgagacg    9840
aaggcccgcg tccaggccag gacgaaggag gctatgtggg aggggtagcg gtcgttgtcc    9900 actaggggt ccaccttctc caaggtgtga agacacatgt cgccttcctc ggcgtccagg     9960
aaggtgattg gcttgtaggt gtaggccacg tgaccggggg ttcctgacgg ggggtataa    10020 aaggggtgg gggcgcgctc gtcgtcactc tcttccgcat cgctgtctgc gagggccagc   10080
tgctggggtg agtattccct ctcgaaggcg ggcatgacct ccgcgctgag gttgtcagtt   10140
tccaaaaacg aggaggattt gatgttcacc tgtcccgagg tgatacccttt gagggtaccc  10200 gcgtccatct ggtcagaaaa cacgatcttt ttattgtcca gcttggtggc gaacgacccg   10260
tagagggcgt tggagagcag cttggcgatg gagcgcaggg tctggttctt gtccctgtcg   10320
gcgcgctcct tggccgcgat gttgagctgc acgtactcgc gcgcgacgca gcgccactcg   10380
gggaagacgg tggtgcgctc gtcgggcacc aggcgcacgc gccagccgcg gttgtgcagg   10440
gtgaccaggt ccacgctggt ggcgacctcg ccgcgcaggc gctcgttggt ccagcagaga   10500
cggccgccct tgcgcgagca aaggggggc aggggtcga gctgggtctc gtccgggggg    10560
tccgcgtcca cggtgaaaac cccggggcgc aggcgcgcgt cgaagtagtc tatcttgcaa   10620
ccttgcatgt ccagcgcctg ctgccagtcg cgggcggcga gcgcgcgctc gtaggggttg   10680
agcggcgggc cccagggcat ggggtgggtg agtgcggagg cgtacatgcc gcagatgtca   10740
tagacgtaga ggggctcccg caggaccccg atgtaggtgg ggtagcagcg ccgccgcgg   10800 atgctggcgc gcacgtagtc atacagctcg tgcgaggggg cgaggaggtc ggggcccagg   10860
ttggtgcggg cggggcgctc cgcgcggaag acgatctgcc tgaagatggc atgcgagttg   10920
gaagagatgg tggggcgctg gaagacgttg aagctggcgt cctgcaggcc gacgcgtcg    10980 cgcacgaagg aggcgtagga gtcgcgcagc ttgtgtacca gctcggcggt gacctgcacg   11040
tcgagcgcgc agtagtcgag ggtctcgcgg atgatgtcat atttagcctg ccccttcttt   11100
ttccacagct cgcggttgag gacaaactct tcgcggtctt tccagtactc ttggatcggg   11160
aaaccgtccg gttccgaacg gtaagagcct agcatgtaga actggttgac ggcctggtag   11220
gcgcagcagc ccttctccac ggggagggcg taggcctgcg cggccttgcg gagcgaggtg   11280
tgggtcaggg cgaaggtgtc cctgaccatg actttgaggt actggtgctt gaagtcggag   11340
tcgtcgcagc cgccccgctc ccagagcgag aagtcggtgc gcttcttgga gcgggggttg   11400
ggcagagcga aggtgacatc gttgaagagg attttgcccg cgcggggcat gaagttgcgg   11460
gtgatgcgga agggccccgg cacttcagag cggttgttga tgacctgggc ggcgagcacg   11520
atctcgtcga agccgttgat gttgtggccc acgatgtaga gttccaggaa gcggggccgg   11580 cccttacgg tgggcagctt ctttagctct tcgtaggtga gctcctcggg cgaggcgagg   11640
ccgtgctcgg ccagggccca gtccgcgagg tgcgggttgt ctctgaggaa ggactcccag   11700
aggtcgcggg ccaggagggt ctgcaggcgg tccctgaagg tcctgaactg gcggcccacg   11760 gccattttt cggggtgat gcagtagaag gtgagggggt cttgctgcca gcggtcccag    11820
tcgagctgca gggcgaggtc gcgcgcggcg gtgaccaggc gctcgtcgcc cccgaatttc   11880
atgaccagca tgaagggcac gagctgcttt ccgaaggccc ccatccaagt gtaggtctct   11940
acatcgtagg tgacaaagag gcgctccgtg cgaggatgcg agccgatcgg gaagaactgg   12000
atctcccgcc accagttgga gggagtggctg ttgatgtggt ggaagtagaa gtcccgtcgc   12060
cgggccgaac actcgtgctg gcttttgtaa aagcgagcgc agtactggca gcgctgcacg   12120
```

```
ggctgtacct cctgcacgag atgcaccttt cgcccgcgca cgaggaagcc gaggggaaat   12180
ctgagccccc cgcctggctc gcggcatggc tggtgctctt ctactttgga tgcgtgtccg   12240
tctccgtctg gctcctcgag gggtgttacg gtggagcgga ccaccacgcc gcgcgagccg   12300
caggtccaga tatcgcgcg cggcggtcgg agtttgatga cgacatcgcg cagctgggag   12360
ctgtccatgg tctggagctc ccgcggcggc ggcaggtcag ccgggagttc ttgcaggttc   12420
acctcgcaga gtcgggccag ggcgcggggc aggtctaggt ggtacctgat ctctaggggc   12480
gtgttggtgg cggcgtcgat ggcttgcagg agcccgcatc cccgggggc gacgacggtg    12540 ccccgcgggg tggtggtggt ggtggtggtg gtggtggtgg cggtgcagct cagaagcggt   12600
gccgcgggcg ggcccccgga ggtagggggg gctccggtcc cgccggcagg ggcggcagcg   12660
gcacgtcggc gtggagcgcg ggcaggagtt ggtgctgtgc ccggaggttg ctggcgaagg   12720
cgacgacgcg gcggttgatc tcctggatct ggcgcctctg cgtgaagacg acgggcccgg   12780
tgagcttgaa cctgaaagag agttcgacag aatcaatctc ggtgtcattg accgcggcct   12840
ggcgcaggat ctcctgcacg tctcccgagt tgtcttggta ggcgatctcg gccatgaact   12900
gctcgatctc ttcctcctgg aggtctccgc gtccggcgcg ttccacggtg gccgccaggt   12960
cgttggagat gcgccccatg agctgcgaga aggcgttgag tccgccctcg ttccagactc   13020
ggctgtagac cacgcccccc tggtcatcgc gggcgcgcat gaccacctgc gcgaggttga   13080
gctccacgtg ccgcgcgaag acggcgtagt tgcgcagacg ctggaagagg tagttgaggg   13140
tggtggcggt gtgctcggcc acgaagaagt tcatgaccca gcggcgcaac gtggattcgt   13200
tgatgtcccc caaggcctcc agccgttcca tggcctcgta gaagtccacg cgaagttga   13260 aaaactggga gttgcgcgcc gacacggtca actcctcctc cagaagacgg atgagctcgg   13320
cgacggtgtc gcgcacctcg cgctcgaagg ctatggggat ctcttcctcc gctagcatca   13380
ccacctcctc ctcttcctcc tcttctggca cttccatgat ggcttcctcc tcttcggggg   13440
gcggcggcgg cggcggtggg ggagggggcg ctctgcgccg gcggcggcgc accgggaggc   13500
ggtccacgaa gcgcgcgatc atctccccgc ggcggcggcg catggtctcg gtgacggcgc   13560
ggccgttctc ccggggcgc agttggaaga cgccgccgga catctggtgc tgggcgggt    13620 ggccgtgagg cagcgaaacg gcgctgacga tgcatctcaa caattgctgc gtaggtacgc   13680
cgccgaggga cctgagggag tccatatcca ccggatccga aaccttttcg aggaaggcgt   13740
ctaaccagtc gcagtcgcaa ggtaggctga gcaccgtggc gggcggcggg gggtgggggg   13800
agtgtctggc ggaggtgctg ctgatgatgt aattgaagta ggcggacttg acacggcgga   13860
tggtcgacag gagcaccatg tccttgggtc cggcctgctg gatgcggagg cggtcggcta   13920
tgccccaggc ttcgttctgg catcggcgca ggtccttgta gtagtcttgc atgagccttt   13980
ccaccggcac ctcttctcct tcctcttctg cttcttccat gtctgcttcg gccctggggc   14040
ggcgccgcgc cccctgccc ccatgcgcg tgacccccgaa ccccctgagc ggttggagca    14100
gggccaggtc ggcgacgacg cgctcggcca ggatggcctg ctgcacctgc gtgagggtgg   14160
tttggaagtc atccaagtcc acgaagcggt ggtaggcgcc cgtgttgatg gtgtaggtgc   14220
agttggccat gacggaccag ttgacggtct ggtggcccgg ttgcgacatc tcggtgtacc   14280
tgagtcgcga gtaggcgcgg gagtcgaaga cgtagtcgtt gcaagtccgc accaggtact   14340
ggtagcccac caggaagtgc ggcgcggct ggcggtagag gggccagcgc agggtggcgg    14400
gggctccggg ggccaggtct tccagcatga ggcggtggta ggcgtagatg tacctggaca   14460
tccaggtgat acccgcggcg gtggtggagg cgcgcgggaa gtcgcgcacc cggttccaga   14520
```

```
tgttgcgcag gggcagaaag tgctccatgg taggcgtgct ctgtccagtc agacgcgcgc   14580
agtcgttgat actctagacc agggaaaacg aaagccggtc agcgggcact cttccgtggt   14640
ctggtgaata gatcgcaagg gtatcatggc ggagggcctc ggttcgagcc ccgggtccgg   14700 gccgacggt ccgccatgat ccacgcggtt accgcccgcg tgtcgaaccc aggtgtgcga   14760
cgtcagacaa cggtggagtg ttccttttgg cgttttctg gccgggcgcc ggcgtcgcgt   14820
aagagactaa gccgcgaaag cgaaagcagt aagtggctcg ctccccgtag ccggagggat   14880
ccttgctaag ggttgcgttg cggcgaaccc cggttcgaat cccgtactcg ggccggccgg   14940
acccgcggct aaggtgttgg attggcctcc ccctcgtata aagacccgc ttgcggattg   15000 actccggaca cggggacgag ccccttttat ttttgcttc cccagatgca tccggtgctg   15060
cggcagatgc gccccccgcc ccagcagcag caacaacacc agcaagagcg gcagcaacag   15120
cagcgggagt catgcagggc cccctcaccc accctcggcg ggccggccac ctcggcgtcc   15180
gcggccgtgt ctggcgcctg cggcggcgg ggggggccgg ctgacgaccc cgaggagccc   15240
ccgcggcgca gggccagaca ctacctggac ctggaggagg gcgagggcct ggcgcggctg   15300
ggggcgccgt ctcccgagcg ccaccccgcgg gtgcagctga agcgcgactc gcgcgaggcg   15360
tacgtgcctc ggcagaacct gttcagggac cgcgcgggcg aggagcccga ggagatgcgg   15420
gacaggaggt tcagcgcagg gcgggagctg cggcagggc tgaaccgcga gcggctgctg   15480
cgcgaggagg actttgagcc cgacgcgcgg acggggatca gccccgcgcg cgcgcacgtg   15540
gcggccgccg acctggtgac ggcgtacgag cagacggtga accaggagat caacttccaa   15600
aagagtttca acaaccacgt gcgcacgctg gtggcgcgcg aggaggtgac catcgggctg   15660
atgcacctgt gggactttgt aagcgcgctg gtgcagaacc ccaacagcaa gcctctgacg   15720
gcgcagctgt tcctgatagt gcagcacagc agggacaacg aggcgtttag ggacgcgctg   15780
ctgaacatca ccgagcccga gggtcggtgg ctgctggacc tgattaacat cctgcagagc   15840
atagtggtgc aggagcgcag cctgagcctg gccgacaagg tggcggccat caactactcg   15900
atgctgagcc tggcaagtt ttacgcgcgc aagatctacc agacgccgta cgtgcccata   15960
gacaaggagg tgaagatcga cggttttac atgcgcatgg cgctgaaggt gctcaccctg   16020
agcgacgacc tgggcgtgta ccgcaacgag cgcatccaca aggccgtgag cgtgagccgg   16080 cggcgcagc tgagcgaccg cgagctgatg cacagcctgc agcgggcgct ggcgggcgcc   16140
ggcagcggcg acaggaggc ggagtcctac ttcgatgcgg gggcggacct cgctgggcg   16200 cccagccggc gggccctgga ggccgcgggg gtccgcgagg actatgacga ggacggcgag   16260
gaggatgagg agtacgagct agaggagggc gagtacctgg actaaaccgc gggtggtgtt   16320
tccggtagat gcaagacccg aacgtggtgg accggcgct gcgggcggct ctgcagagcc   16380
agccgtccgg ccttaactcc tcagacgact ggcgacaggt catgaccgc atcatgtcgc   16440 tgacggcgcg taacccggac gcgttccggc agcagccgca ggcaacagg ctctccgcca   16500 tcctggaggc ggtggtgcct gcgcgctcga accccacgca cgagaaggtg ctggccatag   16560
tgaacgcgct ggccgagaac agggccatcc gcccggacga ggccgggctg gtgtacgacg   16620
cgctgctgca gcgcgtggcc cgctacaaca gcggcaacgt gcagaccaac ctggaccggc   16680
tggtggggga cgtgcgcgag gcggtggcgc agcgcgagcg cgcggatcgg cagggcaacc   16740
tgggctccat ggtggcgctg aatgccttcc tgagcacgca gccggccaac gtgccgcggg   16800
ggcaggaaga ctacaccaac tttgtgagcg cgctgcggct gatggtgacc gagacccccc   16860
```

```
agagcgaggt gtaccagtcg ggcccggact acttcttcca gaccagcaga cagggcctgc    16920
agacggtgaa cctgagccag gctttcaaga acctgcgggg gctgtgggc gtgaaggcgc     16980 ccaccggcga ccgggcgacg gtgtccagcc tgctgacgcc caactcgcgc ctgctgctgc    17040
tgctgatcgc gccgttcacg gacagcggca gcgtgtcccg ggacacctac ctggggcacc    17100
tgctgaccct gtaccgcgag gccatcgggc aggcgcaggt ggacgagcac accttccagg    17160
agatcaccag cgtgagccgc gcgctggggc aggaggacac gagcagcctg gaggcgactc    17220
tgaactacct gctgaccaac cggcggcaga agattccctc gctgcacagc ctgacctccg    17280
aggaggagcg catcttgcgc tacgtgcagc agagcgtgag cctgaacctg atgcgcgacg    17340
gggtgacgcc cagcgtggcg ctggacatga ccgcgcgcaa catggaaccg ggcatgtacg    17400
ccgcgcaccg gccttacatc aaccgcctga tggactacct gcatcgcgcg gcggccgtga    17460
accccgagta ctttaccaac gccatcctga acccgcactg gctcccgccg cccgggttct    17520
acagcggggg cttcgaggtc ccggaggcca acgatggctt cctgtgggac gacatggacg    17580
acagcgtgtt ctccccgcgg ccgcaggcgc tggcggaagc gtccctgctg cgtcccaaga    17640
aggaggagga ggaggcgagt cgccgccgcg gcagcagcgg cgtggcttct ctgtccgagc    17700 tggggcggc agccgccgcg cgccccgggt ccctgggcgg cagcccctt ccgagcctgg     17760 tggggtctct gcacagcgag cgcaccaccc gccctcggct gctgggcgag gacgagtacc    17820
tgaataactc cctgctgcag ccggtgcggg agaaaaacct gccccccgcc ttccccaaca    17880
acgggataga gagcctggtg gacaagatga gcagatggaa gacctatgcg caggagcaca    17940
gggacgcgcc cgcgctccgg ccgcccacgc ggcgccagcg ccacgaccgg cagcggggcc    18000
tggtgtggga tgacgaggac tccgcggacg atagcagcgt gctggacctg ggagggagcg    18060
gcaacccgtt cgcgcacctg cgccccccgcc tggggaggat gttttaaaaa aaaaaaagc    18120 aagaagcatg atgcaaaatt aaataaaact caccaaggcc atggcgaccg agcgttggtt    18180
tcttgtgttc ccttcagtat gcggcgcgcg gcgatgtacc aggagggacc tcctccctct    18240
tacgagagcg tggtgggcgc ggcggcggcg gcgccctctt ctcccttgc gtcgcagctg     18300 ctggagccgc cgtacgtgcc tccgcgctac ctgcggccta cggggggag aaacagcatc     18360 cgttactcgg agctggcgcc cctgttcgac accacccggg tgtacctggt ggacaacaag    18420
tcggcggacg tggcctccct gaactaccag aacgaccaca gcaattttt gaccacggtc     18480 atccagaaca atgactacag cccgagcgag gccagcaccc agaccatcaa tctggatgac    18540
cggtcgcact ggggcggcga cctgaaaacc atcctgcaca ccaacatgcc caacgtgaac    18600
gagttcatgt tcaccaataa gttcaaggcg cgggtgatgg tgtcgcgctc gcacaccaag    18660
gaagaccggg tggagctgaa gtacgagtgg gtggagttcg agctgccaga gggcaactac    18720
tccgagacca tgaccattga cctgatgaac aacgcgatcg tggagcacta tctgaaagtg    18780
ggcaggcaaa acgggggtcct ggagagcgac atcggggtca agttcgacac caggaacttc    18840
cgcctggggc tggaccccgt gaccgggctg gttatgcccg gggtgtacac caacgaggcc    18900
ttccatcccg acatcatcct gctgcccggc tgcggggtgg acttcactta cagccgcctg    18960
agcaacctcc tggcatccg caagcggcag ccccttccagg agggcttcag gatcacctac     19020
gaggacctgg agggggcaa catccccgcg ctcctcgatg tggaggccta ccaggatagc    19080
ttgaaggaaa atgaggcggg acaggaggat accacccccg ccgcctccgc cgccgccgag    19140
cagggcgagg atgctgctga caccgcgcc gcggacgggg cagaggccga ccccgctatg     19200
gtggtggagg ctcccgagca ggaggaggat atgaatgaca gtgcggtgcg cggagacacc    19260
```

```
ttcgtcaccc gggggggagga aaagcaagcg gaggccgagg ccgcggccga ggaaaagcaa   19320
ctggcggcag cagcggcggc ggcggcgttg gccgcgcgcg gaggctgagtc tgaggggacc   19380 aagcccgcca aggagcccgt gattaagccc ctgaccgaag atagcaagaa gcgcagttac   19440
aacctgctca aggacagcac caacaccgcg taccgcagct ggtacctggc ctacaactac   19500
ggcgacccgt cgacgggggt gcgctcctgg accctgctgt gcacgccgga cgtgacctgc   19560
ggctcggagc aggtgtactg gtcgctgccc gacatgatgc aagacccgt gaccttccgc   19620 tccacgcggc aggtcagcaa cttcccggtg gtgggcgccg agctgctgcc cgtgcactcc   19680
aagagcttct acaacgacca ggccgtctac tcccagctca tccgccagtt cacctctctg   19740
acccacgtgt tcaatcgctt tcctgagaac cagattctgg cgcgcccgcc cgccccacc   19800 atcaccaccg tcagtgaaaa cgttcctgct ctcacagatc acgggacgct accgctgcgc   19860
aacagcatcg gaggagtcca gcgagtgacc gttactgacg ccagacgccg cacctgcccc   19920
tacgtttaca aggccttggg catagtctcg ccgcgcgtcc tttccagccg cacttttga   19980 gcaacaccac catcatgtcc atcctgatct cacccagcaa taactccggc tggggactgc   20040
tgcgcgcgcc cagcaagatg ttcggagggg cgaggaagcg ttccgagcag caccccgtgc   20100
gcgtgcgcgg gcacttccgc gcccctggg gagcgcacaa acgcggccgc gcggggcgca   20160
ccaccgtgga cgacgccatc gactcggtgg tggagcaggc gcgcaactac aggcccgcgg   20220
tctctaccgt ggacgcggcc atccagaccg tggtgcgggg cgcgcggcgg tacgccaagc   20280
tgaagagccg ccggaagcgc gtgggcccgcc gccaccgccg ccgacccggg gccgccgcca   20340
aacgcgccgc cgcggccctg cttcgccggg ccaagcgcac gggccgccgc gccgccatga   20400
gggccgcgcg ccgcttggcc gccggcatca ccgccgccac catggccccc cgtacccgaa   20460
gacgcgcggc cgccgccgcc gccgccgcca tcagtgacat ggccagcagg cgccggggca   20520
acgtgtactg ggtgcgcgac tcggtgaccg gcacgcgcgt gcccgtgcgc ttccgccccc   20580
cgcggacttg agatgatgtg aaaaaacaac actgagtctc ctgctgttgt gtgtatccca   20640
gcggcggcgg cgcgcgcagc gtcatgtcca agcgcaaaat caaagaagag atgctccagg   20700
tcgtcgcgcc ggagatctat gggcccccga agaaggaaga gcaggattcg aagccccgca   20760
agataaagcg ggtcaaaaag aaaaagaaag atgatgacga tgccgatggg gaggtggagt   20820
tcctgcgcgc cacggcgccc aggcgcccgg tgcagtggaa gggccggcgc gtaaagcgcg   20880
tcctgcgccc cggcaccgcg gtggtcttca cgcccggcga gcgctccacc cggactttca   20940
agcgcgtcta tgacgaggtg tacgcgacg aagacctgct ggagcaggcc aacgagcgct   21000
tcggagagtt tgcttacggg aagcgtcagc gggcgctggg gaaggaggac ctgctggcgc   21060
tgccgctgga ccaggcaac cccacccca gtctgaagcc cgtgaccctg cagcaggtgc   21120
tgccgagcag cgcaccctcc gaggcgaagc ggggtctgaa gcgcgagggc ggcgacctgg   21180
cgcccaccgt gcagctcatg gtgcccaagc ggcagaggct ggaggatgtg ctggagaaaa   21240
tgaaagtaga ccccggtctg cagccggaca tcagggtccg tcccatcaag caggtggcgc   21300
cgggcctcgg cgtgcagacc gtggacgtgg tcatccccac cggcaactcc ccgccgccaa   21360
ccaccactac cgctgcctcc acggacatgg agacacagac cgatcccgcc gcagccgcag   21420
ccgccgccgc agccgcgacc tcctcggcgg aggtgcagac ggaccctggg ctgccgccgg   21480
cgatgtcagc tccccgcgcg cgccgcggac gcagaaagta cggcgccgcc aacgcgctcc   21540
tgcccgagta cgccttgcat ccttccatcg cgcccacccc cggctaccga ggctataccr   21600
```

```
accgcccgcg aagagccaag ggttccaccc gccgtccccg ccgacgcgcc gccgccacca    21660
cccgccgccg ccgccgcaga cgccagcccg cactggctcc agtctccgtg aggagagtgg    21720
cgcgcgacgg acacaccctg gtgctgccca gggcgcgcta ccaccccagc atcgtttaaa    21780
agcctgttgt ggttcttgca gatatggccc tcacttgccg cctccgtttc ccggtgccgg    21840
gataccgagg aggaagatcg cgccgcagga ggggtctggc cggccgcggc ctgagcggag    21900
gcagccgccg cgcgcaccgg cggcgacgcg ccaccagccg acgcatgcgc ggcggggtgc    21960
tgcccctgtt aatcccctg atcgccgcgg cgatcggcgc cgtgcccggg atcgcctccg    22020
tggccttgca agcgtcccag aggcattgac agacttgcaa acttgcaaat atggaaaaaa    22080
aaaaaaaacc ccaataaaaa gtctagactc tcacgctcgc ttggtcctgt gactattttg    22140
tagaatggaa gacatcaact ttgcgtcgct ggccccgcgt cacggctcgc gcccgttcct    22200
gggacactgg aacgatatcg gcaccagcaa catgagcggg ggcgccttca gttgggggctc    22260 tctgtggagc ggcattaaaa gtatcgggtc tgccgttaaa aattacggct cccgggcctg    22320
gaacagcagc acgggccaga tgttgagaga caagttgaaa gagcagaact tccagcagaa    22380
ggtggtggag ggcctggcct ccggcatcaa cggggtggtg gacctggcca accaggccgt    22440
gcagaataaa atcaacagca gactggaccc ccggccgccg gtggaggagg tgccgccggc    22500
gctggagacg gtgtccccg atgggcgtgg cgagaagcgc ccgcggcccg ataggaaga    22560 gaccactctg gtcacgcaga ccgatgagcc gccccgtat gaggaggccc taaagcaagg    22620
tctgcccacc acgcggccca tcgcgcccat ggccaccggg gtggtgggcc gccacacccc    22680
cgccacgctg gacttgcctc cgcccgccga tgtgccgcag cagcagaagg cggcacagcc    22740
gggcccgccc gcgaccgcct cccgttcctc cgccggtcct ctgcgccgcg cggccagcgg    22800 ccccccgcggg ggggtcgcga ggcacggcaa ctggcagagc acgctgaaca gcatcgtggg    22860
tctgggggtg cggtccgtga agcgccgccg atgctactga atagcttagc taacgtgttg    22920
tatgtgtgta tgcgcccat gtcgccgcca gaggagctgc tgagtcgccg ccgttcgcgc    22980
gcccaccacc accgccactc cgcccctcaa gatggcgacc ccatcgatga tgccgcagtg    23040
gtcgtacatg cacatctcgg gccaggacgc ctcggagtac ctgagccccg ggctggtgca    23100
gttcgcccgc gccaccgaga gctacttcag cctgagtaac aagtttagga accccacggt    23160
ggcgcccacg cacgatgtga ccaccgaccg gtctcagcgc ctgacgctgc ggttcattcc    23220
cgtggaccgc gaggacaccg cgtactcgta caaggcgcgg ttcaccctgg ccgtgggcga    23280
caaccgcgtg ctggacatgg cctccaccta ctttgacatc cgcggggtgc tggaccgggg    23340
tcccactttc aagccctact ctggcaccgc ctacaactcc ctggccccca agggcgctcc    23400
caactcctgc gagtgggagc aagaggaaac tcaggcagtt gaagaagcag cagaaggagga    23460 agaagaagat gctgacggtc aagctgagga agagcaagca gctaccaaaa agactcatgt    23520
atatgctcag gctcccctt ctggcgaaaa aattagtaaa gatggtctgc aaataggaac    23580
ggacgctaca gctacagaac aaaaacctat ttatgcagac cctacattcc agcccgaacc    23640
ccaaatcggg gagtcccagt ggaatgaggc agatgctaca gtcgccggcg gtagagtgct    23700
aaagaaatct actcccatga aaccatgcta tggttcctat gcaagaccca caaatgctaa    23760
tggaggtcag ggtgtactaa cggcaaatgc ccagggacag ctagaatctc aggttgaaat    23820
gcaattcttt tcaacttctg aaaacgcccg taacgaggct aacaacattc agcccaaatt    23880
ggtgctgtat agtgaggatg tgcacatgga gaccccggat acgcaccttt cttacaagcc    23940
cgcaaaaagc gatgacaatt caaaaatcat gctgggtcag cagtccatgc ccaacagacc    24000
```

```
taattacatc ggcttcagag acaactttat cggcctcatg tattacaata gcactggcaa    24060
catgggagtg cttgcaggtc aggcctctca gttgaatgca gtggtggact tgcaagacag    24120
aaacacagaa ctgtcctacc agctcttgct tgattccatg ggtgacagaa ccagatactt    24180
ttccatgtgg aatcaggcag tggacagtta tgacccagat gttagaatta ttgaaaatca    24240
tggaactgaa gacgagctcc ccaactattg ttttccctctg gtggcatag gggtaactga    24300
cacttaccag gctgttaaaa ccaacaatgg caataacggg ggccaggtga cttgacaaa    24360
agatgaaact tttgcagatc gcaatgaaat aggggtggga acaatttcg ctatggagat    24420
caacctcagt gccaacctgt ggagaaactt cctgtactcc aacgtggcgc tgtacctacc    24480
agacaagctt aagtacaacc cctccaatgt ggacatctct gacaaccca acacctacga    24540
ttacatgaac aagcgagtgg tggccccggg gctggtggac tgctacatca acctgggcgc    24600
gcgctggtcg ctggactaca tggacaacgt caaccccttc aaccaccacc gcaatgcggg    24660
cctgcgctac cgctccatgc tcctgggcaa cgggcgctac gtgcccttcc acatccaggt    24720
gccccagaag ttctttgcca tcaagaacct cctcctcctg ccgggctcct cacctacga    24780
gtggaacttc aggaaggatg tcaacatggt cctccagagc tctctgggta cgatctcag    24840
ggtggacggg gccagcatca agttcgagag catctgcctc tacgccacct tcttccccat    24900
ggcccacaac acgcctcca cgctcgaggc catgctcagg aacgacacca acgaccagtc    24960
cttcaatgac tacctttccg ccgccaacat gctctacccc atacccgcca acgccaccaa    25020
cgtccccatc tccatcccct cgcgcaactg ggcggccttc cgcggctggg ccttcacccg    25080
cctcaagacc aaggagaccc cctccctggg ctcgggattc gaccctact acacctactc    25140
gggctctatt ccctacctgg acggcacctt ctacctcaac cacactttca gaaaggtctc    25200
ggtcaccttc gactcctcgg tcagctggcc gggcaacgac cgtctgctca cccccaacga    25260
gttcgagatc aagcgctcgg tcgacgggga aggctacaac gtggcccagt gcaacatgac    25320
caaggactgg ttcctggtcc agatgctggc caactacaac atcggctacc agggcttcta    25380
catcccagag agctacaagg acaggatgta ctccttcttc aggaacttcc agcccatgag    25440
ccggcaggtg gtgaccagac ccaagtacaa ggactaccag gaggtgggca tcatccacca    25500
gcacaacaac tcgggcttcg tgggctacct cgcccccacc atgcgcgagg acaggccta    25560
ccccgccaac ttcccctacc cgctcatagg caagaccgcg gtcgacagca tcacccgaa    25620
aaagttcctc tgcgaccgca ccctctggcg catccccttc tccagcaact tcatgtccat    25680
gggtgcgctc tcggacctgg ccagaacttg gctctacgcc aactccgccc acgccctcga    25740
catgaccttc gaggtcgacc ccatggacga gcccacccctt ctctatgttc tgttcgaagt    25800
cttcgacgtg gtccgggtcc accagccgca ccgcggcgtc atcgagaccg tgtacctgcg    25860
tacgcccttc tcggccggca acgccaccac ctaaagaagc aagccgcagt catcgccgcc    25920
tgcatgccgt cgggttccac cgagcaagag ctcagggcca tcgtcagaga cctgggatgc    25980
gggccctatt ttttgggcac cttcgacaag cgcttccctg gctttgtctc cccacacaag    26040
ctggcctgcg ccatcgtcaa cacggccggc cgcgagaccg ggggcgtgca ctggctggcc    26100
tttgcctgga cccgcgctc caaaacatgc ttcctcttg accccttcgg cttttcggac    26160
cagcggctca agcaaatcta cgagttcgag tacgagggct gctgcgtcg cagcgccatc    26220
gcctcctcgc ccgaccgctg cgtcaccctc gaaaagtcca cccagaccgt gcaggggccc    26280
gactcggccg cctgcggtct cttctgctgc atgtttctgc acgcctttgt gcactggcct    26340
```

```
cagagtccca tggaccgcaa ccccaccatg aacttgctga cgggggtgcc caactccatg   26400
ctccaaagcc cccaggtcga gcccaccctg cgccgcaacc aggagcagct ctacagcttc   26460
ctggagcgcc actcgcccta cttccgccgc acagcgcac agatcaggag ggccacctcc    26520
ttctgccact tgcaagagat gcaagaaggg taataacgat gtacacactt ttttctcaat   26580
aaatggcatt ttttttttat ttatacaagc tctctggggt attcatttcc caccaccacc   26640
acccgccgtt gtcgccatct ggctctattt agaaatcgaa agggtctgc cgggagtcgc    26700 cgtgcgccac gggcagggac acgttgcgat actggtagcg ggtgccccac ttgaactcgg   26760
gcaccaccag gcgaggcagc tcggggaagt tttcgctcca caggctgcgg gtcagcacca   26820
gcgcgttcat caggtcgggc gccgagatct tgaagtcgca gttggggccg ccgccctgcg   26880
cgcgcgagtt gcggtacacc gggttgcagc actggaacac caacagcgcc gggtgcttca   26940
cgctggccag cacgctgcgg tcggagatca gctcggcgtc caggtcctcc gcgttgctca   27000
gcgcgaacgg ggtcatcttg ggcacttgcc gccccaggaa gggcgcgtgc cccggttttcg   27060 agttgcagtc gcagcgcagc gggatcagca ggtgcccgtg cccggactcg gcgttggggt    27120
acagcgcgcg catgaaggcc tgcatctggc ggaaggccat ctgggccttg gcgccctccg   27180
agaagaacat gccgcaggac ttgcccgaga actggtttgc ggggcagctg gcgtcgtgca   27240
ggcagcagcg cgcgtcggtg ttggcgatct gcaccacgtt gcgccccac cggttcttca    27300 cgatcttggc cttggacgat tgctccttca gcgcgcgctg cccgttctcg ctggtcacat   27360
ccatctcgat cacatgttcc ttgttcacca tgctgctgcc gtgcagacac ttcagctcgc   27420
cctccgtctc ggtgcagcgg tgctgccaca gcgcgcagcc cgtgggctcg aaagacttgt   27480
aggtcacctc cgcgaaggac tgcaggtacc cctgcaaaaa gcggcccatc atggtcacga   27540
aggtcttgtt gctgctgaag gtcagctgca gcccgcggtg ctcctcgttc agccaggtct   27600
tgcacacggc cgccagcgcc tccacctggt cgggcagcat cttgaagttc accttcagct   27660
cattctccac gtggtacttg tccatcgcg tgcgcgccgc ctccatgccc ttctcccagg    27720
ccgacaccag cggcaggctc acggggttct tcaccatcac cgtggccgcc gcctccgccg   27780
cgctttcgct ttccgccccg ctgttctctt cctcttcctc ctcttcctcg ccgccgccca   27840
ctcgcagccc ccgcaccacg gggtcgtctt cctgcaggcg ctgcaccttg cgcttgccgt   27900 tgcgccctg cttgatgcgc acgggcgggt tgctgaagcc caccatcacc agcgcggcct     27960
cttcttgctc gtcctcgctg tccagaatga cctccgggga gggggggttg gtcatcctca   28020
gtaccgagcc acgcttcttt ttcttcctgg gggcgttcgc cagctccgcg gctgcggccg   28080
ctgccgaggt cgaaggccga gggctgggcg tgcgcggcac cagcgcgtct tgcgagccgt   28140
cctcgtcctc ctcggactcg agacggaggc gggcccgctt cttcgggggc gcgcggggcg   28200
gcggaggcgg cggcggcgac ggagacgggg acgagacatc gtccagggtg ggtggacggc   28260
gggccgcgcc gcgtccgcgc tcggggtgg tttcgcgctg gtcctcttcc cgactggcca    28320
tctcccactg ctccttctcc tataggcaga aagagatcat ggagtctctc atgcgagtcg   28380
agaaggagga ggacagccta accgccccct ctgagccctc caccaccgcc gccaccaccg   28440
ccaatgccgc cgcggacgac gcgcccaccg agaccaccgc cagtaccacc ctccccagcc   28500 acgcacccc gctcgagaat gaagtgctga tcgagcagga cccgggtttt gtgagcggag   28560
aggaggatga ggtggatgag aaggagaagg aggaggtcgc cgcctcagtg ccaaaagagg   28620
ataaaaagca agaccaggac gacgcagata aggatgagac agcagtcggg cggggaacg    28680 gaagccatga tgctgatgac ggctacctag acgtgggaga cgacgtgctg cttaagcacc   28740
```

```
tgcaccgcca gtgcgtcatc gtctgcgacg cgctgcagga gcgctgcgaa gtgcccctgg   28800
acgtggcgga ggtcagccgc gcctacgagc ggcacctctt cgcgccgcac gtgcccccca   28860
agcgccggga gaacggcacc tgcgagccca acccgcgtct caacttctac ccggtcttcg   28920
cggtacccga ggtgctggcc acctaccaca tcttcttcca aaactgcaag atcccctct   28980 cctgccgcgc taaccgcacc cgcgccgaca aaaccctgac cctgcggcag ggcgcccaca   29040
tacctgatat tgcctctctg gaggaagtgc ccaagatctt cgagggtctc ggtcgcgacg   29100
agaaacgggc ggcgaacgct ctgcacggag acagcgaaaa cgagagtcac tcgggggtgc   29160
tggtggagct cgagggcgac aacgcgcgcc tggccgtact caagcgcagc atagaggtca   29220
cccactttgc ctaccggcg ctcaacctgc cccccaaggt catgagtgtg gtcatgggcg   29280
agctcatcat gcgccgcgct cagccctgg ccgcggatgc aaacttgcaa gagtcctccg   29340
aggaaggcct gcccgcggtc agcgacgagc agctagcgcg ctggctggag acccgcgacc   29400
ccgcgcagct ggaggagcgg cgcaagctca tgatggccgc ggtgctggtc accgtggagc   29460
tcgagtgtct gcagcgcttc ttcgcggacc ccagagatgca gcgcaagctc gaggagaccc   29520
tgcactacac cttccgccag ggctacgtgc gccaggcctg caagatctcc aacgtggagc   29580
tctgcaacct ggtctcctac ctgggcatcc tgcacgagaa ccgcctcggg cagaacgtcc   29640
tgcactccac cctcaaaggg gaggcgcgcc gcgactacat ccgcgactgc gcctacctct   29700
tcctctgcta cacctggcag acggccatgg gggtctggca gcagtgcctg gaggagcgca   29760
acctcaagga gctggaaaag ctactcaagc gcaccctcag ggacctctgg acgggcttca   29820
acgagcgctc ggtggccgcc gcgctggcgg acatcatctt ccccgagcgc ctgctcaaga   29880
ccctgcagca gggcctgccc gacttcacca gccagagcat gctgcagaac tttaggactt   29940
tcatcctgga gcgctcgggc atcctgcctg ccacttgctg cgcgctgccc agcgacttcg   30000
tgcccatcaa gtacagggag tgcccgccgc cgctctgggg ccactgctac ctcttccagc   30060
tggccaacta cctcgcctac cactcggacc tcatggaaga cgtgagcggc gagggcctgc   30120
tcgagtgcca ctgccgctgc aacctctgca cgccccaccg ctctctagtc tgcaacccgc   30180
agctgctcag cgagagtcag attatcggta ccttcgagct gcagggtccc tcgcctgacg   30240
agaagtccgc ggctccgggg ctgaaactca ctccggggct gtggacttcc gcctacctac   30300
gcaaatttgt acctgaggac taccacgccc acgagatcag gttctacgaa gaccaatccc   30360
gcccgcccaa ggcggagctc accgcctgcg tcatcaccca ggggcacatc ctgggccaat   30420
tgcaagccat caacaaagcc cgccgagagt tcttgctgaa aaagggtcgg ggggtgtacc   30480
tggaccccca gtccggcgag gagctaaacc cgctacccccc gccgccgccc cagcagcggg   30540
accttgcttc ccaggatggc acccagaaag aagcagcagc cgccgccgcc gcagccatac   30600
atgcttctgg aggaagagga ggaggactgg gacagtcagg cagaggaggt ttcggacgag   30660
gagcaggagg agatgatgga agactggag gaggacagca gcctagacga ggaagcttca   30720
gaggccgaag aggtggcaga cgcaacacca tcaccctcgg tcgcagcccc ctcgccgggg   30780 ccctgaaat cctccgaacc cagcaccagc gctataacct ccgctcctcc ggcgccggcg   30840
ccaccccgcc gcagacccaa ccgtagatgg gacaccacag gaaccggggt cggtaagtcc   30900
aagtgcccgc cgccgccacc gcagcagcag cagcagcgcc agggctaccg ctcgtggcgc   30960
gggcacaaga acgccatagt cgcctgcttg caagactgcg ggggcaacat ctctttcgcc   31020
cggcgcttcc tgctattcca ccacgggtc gcctttcccc gcaatgtcct gcattactac   31080
```

```
cgtcatctct acagccccta ctgcagcggc gacccagagg cggcagcggc agccacagcg    31140
gcgaccacca cctaggaaga tatcctccgc gggcaagaca gcggcagcag cggccaggag    31200
acccgcggca gcagcggcgg gagcggtggg cgcactgcgc ctctcgccca acgaacccct    31260
ctcgacccgg gagctcagac acaggatctt ccccactttg tatgccatct tccaacagag    31320
cagaggccag gagcaggagc tgaaaataaa aaacagatct ctgcgctccc tcacccgcag    31380
ctgtctgtat cacaaaagcg aagatcagct tcggcgcacg ctggaggacg cggaggcact    31440
cttcagcaaa tactgcgcgc tcactcttaa agactagctc cgcgcccttc tcgaatttag    31500
gcgggagaaa actacgtcat cgccggccgc cgcccagccc gcccagccga gatgagcaaa    31560
gagattccca cgccatacat gtggagctac cagccgcaga tgggactcgc ggcgggagcg    31620
gcccaggact actccacccg catgaactac atgagcgcgg gacccacat gatctcacag    31680
gtcaacggga tccgcgccca cgaaaccaa atactgctgg aacaggcggc catcaccgcc    31740
acgccccgcc ataatctcaa ccccgaaat tggcccgccg ccctcgtgta ccaggaaacc    31800
ccctccgcca ccaccgtact acttccgcgt gacgcccagg ccgaagtcca gatgactaac    31860
tcaggggcgc agctcgcggg cggctttcgt cacggggcgc ggccgctccg accaggtata    31920
agacacctga tgatcagagg ccgaggtatc cagctcaacg acgagtcggt gagctcttcg    31980
ctcggtctcc gtccggacgg aactttccag ctcgccggat ccggccgctc ttcgttcacg    32040
ccccgccagg cgtacctgac tctgcagacc tcgtcctcgg agccccgctc cggaggcatc    32100
ggaaccctcc agttcgtgga ggagttcgtg ccctcggtct acttcaaccc cttctcggga    32160
cctcccggac gctaccccga ccagttcatt ccgaactttg acgcggtgaa ggactcggcg    32220
gacggctacg actgaatgtc aggtgccgag gcagagcagc ttcgcctgag acacctcgag    32280
cactgccgcc gccacaagtg cttcgcccgc ggttccggtg agttctgcta ctttcagcta    32340
cccgaggagc ataccgaggg gccggcgcac ggcgtccgcc tgaccaccca gggcgaggtt    32400
acctgttccc tcatccggga gttcaccctc cgtcccctgc tagtggagcg ggagcggggt    32460
ccctgtgtcc taactatcgc ctgcaactgc cctaaccctg gattacatca agatctttgc    32520
tgtcatctct gtgctgagtt taataaacgc tgagatcaga atctactggg aattcgattt    32580
agtccccttt aactaatcaa acactggaat caataaaaag aatcacttac ttaaaatcag    32640
acagcaggtc tctgtccagt ttattcagca gcacctcctt cccctcctcc caactctggt    32700
actccaaacg ccttctggcg gcaaacttcc tccacaccct gaagggaatg tcagattctt    32760
gctcctgtcc ctccgcaccc actatcttca tgttgttgca gatgaagcgc accaaaacgt    32820
ctgacgagag cttcaacccc gtgtacccct atgacacgga aagcggccct ccctccgtcc    32880
ctttcctcac ccctccctc gtgtctcccg atggattcca agaaagcccc ccgggtcc    32940
tgtctctgaa cctggccgag ccctggtca cttcccacgg catgctcgcc ctgaaaatgg    33000
gaagtggcct ctccctggac gacgctggca acctcacctc tcaagatatc accaccgcta    33060
gccctcccct caaaaaaacc aagaccaacc tcagcctaga aacctcatcc cccctaactg    33120
taagcacctc aggcgccctc accgtagcag ccgccgctcc cctggcagtg gccggcacct    33180
ccctcaccat gcaatcagag gcccccctga cagtacagga tgcaaaactc accctggcca    33240
ccaaaggccc cctgaccgtg tctgaaggca aactggcctt gcaaacatcg gccccgctga    33300
cggccgctga cagcagcacc ctcaccgtta gcgccacacc accaattaat gtaagcagtg    33360
gaagtttagg cttagacatg gaagacccta tgtatactca cgatggaaaa ctgggaataa    33420
gaattggggg tccactaaga gtagtagaca gcttgcacac actcactgta gttaccggaa    33480
```

```
atggactaac tgtagataac aatgccctcc aaactagagt tacgggcgcc ctaggttatg    33540
acacatcagg aaatctacaa ttgagagctg caggaggtat gcgaattgat gcaaatggcc    33600
aacttatcct taatgtggca tacccatttg atgctcagaa caatctcagc cttagacttg    33660
gtcagggacc cctgtatata aacacagacc acaacctgga tttgaattgc aacagaggtc    33720
taaccacaac taccaccaac aacacaaaaa aacttgagac taaaattagc tcaggcttag    33780
actatgacac caatggtgct gtcattatta aacttggcac tggtctaagc ttcgacaaca    33840
caggcgccct aactgtggga aacactggtg atgataaact gactctgtgg acgaccccag    33900
acccatctcc aaattgcaga attcactcag acaaagactg caagtttact ctagtcctaa    33960
ctaagtgtgg aagccaaatc ctggcctctg tcgccgccct agcggtatca ggaaatctgg    34020
cttcgataac aggcaccgtt gccagcgtta ccatctttct cagatttgat cagaatggag    34080
tgcttatgga aaactcctcg ctagacaggc agtactggaa cttcagaaat ggcaactcaa    34140
ctaacgctgc cccctacacc aatgcagttg ggttcatgcc aaacctcgca gcatacccca    34200
aaacgcaaag ccagactgct aaaaacaaca ttgtaagtca ggtttacttg aatggagaca    34260
aatccaaacc catgacccct accatcaccc tcaatggaac taatgaatcc agtgaaacta    34320
gccaggtgag tcactactcc atgtcatttta catgggcttg ggaaagtggg caatatgcca    34380
ctgaaacctt tgccaccaac tccttcacct tttcttacat tgctgaacaa taaaaagcat    34440
gacactgatg ttcatttctg attcttattt tattattttc aaacacaaca aaatcattca    34500
agtcattctt ccatcttagc ttaatagaca cagtagctta atagacccag tagtgcaaag    34560
ccccattcta gcttataact agtggagaag tactcgccta catgggggta gagtcataat    34620
cgtgcatcag gatagggcgg tggtgctgca gcagcgcgcg aataaactgc tgccgccgcc    34680
gctccgtcct gcaggaatac aacatggcag tggtctcctc agcgatgatt cgcaccgccc    34740
gcagcataag gcgccttgtc ctccgggcac agcagcgcac cctgatctca cttaaatcag    34800
cacagtaact gcagcacagc accacaatat tgttcaaaat cccacagtgc aaggcgctgt    34860
atccaaagct catggcgggg accacagaac ccacgtggcc atcataccac aagcgcaggt    34920
agattaagtg gcgaccccctc ataaacacgc tggacataaa cattacctct tttggcatgt    34980
tgtaattcac cacctcccgg taccatataa acctctgatt aaacatggcg ccatccacca    35040
ccatcctaaa ccagctggcc aaaacctgcc cgccggctat acactgcagg gaaccggac    35100 tggaacaatg acagtggaga gcccaggact cgtaaccatg gatcatcatg ctcgtcatga    35160
tatcaatgtt ggcacaacac aggcacacgt gcatacactt cctcaggatt acaagctcct    35220
cccgcgttag aaccatatcc cagggaacaa cccattcctg aatcagcgta aatcccacac    35280
tgcagggaag acctcgcacg taactcacgt tgtgcattgt caaagtgtta cattcgggca    35340
gcagcggatg atcctccagt atggtagcgc gggtttctgt ctcaaaagga ggtagacgat    35400
ccctactgta cggagtgcgc cgagacaacc gagatcgtgt tggtcgtagt gtcatgccaa    35460
atggaacgcc ggacgtagtc atatttcctg aagtcttaga tctctcaacg cagcaccagc    35520
accaacactt cgcagtgtaa aaggccaagt gccgagagag tatatatagg aataaaaagt    35580
gacgtaaacg ggcaaagtcc aaaaaacgcc cagaaaaacc gcacgcgaac ctacgccccg    35640
aaacgaaagc caaaaaacac tagacactcc cttccggcgt caacttccgc tttcccacgc    35700
tacgtcactt gccccagtca aacaaactac atatcccgaa cttccaagtc gccacgccca    35760
aaacaccgcc tacacctccc cgcccgccgg cccgccccca aacccgcctc ccgcccgcg    35820
``` cccgccccg cgccgcccat ctcattatca tattggcttc aatccaaaat aaggtatatt    35880
attgatgatg                                                          35890

<210> SEQ ID NO 14
<211> LENGTH: 37741
<212> TYPE: DNA
<213> ORGANISM: ChAd3

<400> SEQUENCE: 14
catcatcaat aatataccct attttggatt gaagccaata tgataatgag atgggcggcg      60
cgaggcgggg cgcggggcgg gaggcgggtt tggggggcggg ccggcgggcg gggcggtgtg    120
gcggaagtgg actttgtaag tgtggcggat gtgacttgct agtgccgggc gcggtaaaag    180
tgacgttttc cgtgcgcgac aacgcccccg ggaagtgaca ttttttcccgc ggttttttacc  240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctccgtttt attattatag tcagctgacg cggagtgtat    480 ttatacccctc tgatctcgtc aagaggccac tcttgagtgc cagcgagtag agttttctcc    540
tctgccgctc tccgctccgc tccgctcggc tctgacaccg gggaaaaaat gagacatttc    600
acctacgatg cggtgtgct caccggccag ctggctgctg aggtcctgga cccctgatc     660 gaggaggtat tggccgataa ttatcctccc tcgactcctt ttgagccacc tacacttcac    720
gaactatacg atctggatgt ggtgggggccc agcgatccga acgagcaggc ggtttccagt    780
ttttttccag agtccatgtt gttggccagc caggaggggg tcgaacttga gacccctcct    840
ccgatcgtgg attccccccga tccgccgcag ctgactaggc agcccgagcg ctgtgcggga    900
cctgagacta tgccccagct gctacctgag gtgatcgatc tcacctgtaa tgagtctggt    960
tttccaccca gcgaggatga ggacgaagag ggtgagcagt tgtgttaga ttctgtggaa    1020 caacccgggc gaggatgcag gtcttgtcaa tatcaccgga aaaacacagg agactcccag   1080
attatgtgtt ctctgtgtta tatgaagatg acctgtatgt ttatttacag taagtttatc   1140
atcggtgggc aggtgggcta tagtgtgggt ggtggtcttt gggggttttt ttaatatatg   1200 tcagggggtta tgctgaagac ttttttattg tgatttttaa aggtccagtg tctgagcccg   1260
agcaagaacc tgaaccggag cctgagcctt ctcgccccag gagaaagcct gtaatcttaa   1320
ctagacccag cgcaccggta gcgagaggcc tcagcagcgc ggagaccacc gactccggtg   1380
cttcctcatc accccccggag attcaccccc tggtgcccct atgtcccgtt aagcccgttg   1440
ccgtgagagt cagtgggcgg cggtctgctg tggagtgcat tgaggacttg cttttttgatt   1500 cacaggaacc tttggacttg agcttgaaac gccccaggca ttaaacctgg tcacctggac   1560
tgaatgagtt gacgcctatg tttgcttttg aatgacttaa tgtgtataga taataaagag   1620
tgagataatg ttttaattgc atggtgtgtt taacttgggc ggagtctgct gggtatataa   1680
gcttccctgg gctaaacttg gttacacttg acctcatgga ggcctgggag tgtttggaga   1740
actttgccgg agttcgtgcc ttgctggacg agagctctaa caataccctct tggtggtgga   1800 ggtatttgtg gggctctccc cagggcaagt tagtttgtag aatcaaggag gattacaagt   1860
gggaatttga agagcttttg aaatcctgtg gtgagctatt ggattctttg aatctaggcc   1920
accaggctct cttccaggag aaggtcatca ggactttgga ttttttccaca ccggggcgca   1980 ttgcagccgc ggttgctttt ctagcttttt tgaaggatag atggagcgaa gagacccact   2040

```
tgagttcggg ctacgtcctg gattttctgg ccatgcaact gtggagagca tggatcagac    2100
acaagaacag gctgcaactg ttgtcttccg tccgcccgtt gctgattccg gcggaggagc    2160
aacaggccgg gtcagaggac cgggcccgtc gggatccgga ggagagggca ccgaggccgg    2220
gcgagaggag cgcgctgaac ctgggaaccg ggctgagcgg ccatccacat cgggagtgaa    2280
tgtcgggcag gtggtggatc ttttccaga actgcggcgg attttgacta ttagggagga    2340
tgggcaattt gttaagggtc ttaagaggga agggggggct tctgagcata acgaggaggc    2400
cagtaattta gcttttagct tgatgaccag acaccgtcca gagtgcatca cttttcagca    2460
gattaaggac aattgtgcca atgagttgga tctgttgggt cagaagtata gcatagagca    2520
gctgaccact tactggctgc agccgggtga tgatctggag gaagctatta gggtgtatgc    2580
taaggtggcc ctgcggcccg attgcaagta caagctcaag gggctggtga atatcaggaa    2640
ttgttgctac atttctggca acggggcgga ggtggagata gagaccgaag acagggtggc    2700
tttcagatgc agcatgatga atatgtggcc ggggtgctg gcatggacg gggtggtgat     2760 tatgaatgtg aggttcacgg ggcccaactt taacggcacg gtgttttggg ggaacaccaa    2820
cctggtcctg cacggggtga gcttctatgg gtttaacaac acctgtgtgg aggcctggac    2880
cgatgtgaag gtccgcggtt gcgccttttta tggatgttgg aaggccatag tgagccgccc    2940
taagagcagg agttccatta agaaatgctt gtttgagagg tgcaccttgg ggatcctggc    3000
cgagggcaac tgcagggtgc gccacaatgt ggcctccgag tgcggttgct tcatgctagt    3060
caagagcgtg gcggtaatca agcataatat ggtgtgcggc aacagcgagg acaaggcctc    3120
acagatgctg acctgcacgg atggcaactg ccacttgctg aagaccatcc atgtaaccag    3180
ccacagccgg aaggcctggc ccgtgttcga gcacaacttg ctgacccgct gctccttgca    3240
tctgggcaac aggcggggg tgttcctgcc ctatcaatgc aactttagtc acaccaagat     3300
cttgctagag cccgagagca tgtccaaggt gaacttgaac ggggtgtttg acatgaccat    3360
gaagatctgg aaggtgctga ggtacgacga gaccaggtcc cggtgcagac cctgcgagtg    3420 cggggggcaag catatgagga accagcccgt gatgctggat gtgaccgagg agctgaggac    3480
agaccacttg gttctggcct gcaccagggc cgagtttggt tctagcgatg aagacacaga    3540
ttgaggtggg tgagtgggcg tggcctgggg tggtcatgaa aatatataag ttggggggtct    3600 tagggtctct ttatttgtgt tgcagagacc gccggagcca tgagcgggag cagcagcagc    3660
agcagtagca gcagcgcctt ggatggcagc atcgtgagcc cttatttgac gacgcggatg    3720
ccccactggg ccggggtgcg tcagaatgtg atgggctcca gcatcgacgg ccgacccgtc    3780
ctgcccgcaa attccgccac gctgacctat gcgaccgtcg cggggacgcc gttggacgcc    3840
accgccgccg ccgccgccac cgcagccgcc tcggccgtgc gcagcctggc cacggacttt    3900
gcattcctgg gaccactggc gacaggggct acttctcggg ccgctgctgc cgccgttcgc    3960
gatgacaagc tgaccgccct gctggcgcag ttggatgcgc ttactcggga actgggtgac    4020
ctttctcagc aggtcatggc cctgcgccag caggtctcct ccctgcaagc tggcgggaat    4080
gcttctccca caaatgccgt ttaagataaa taaaaccaga ctctgtttgg attaaagaaa    4140
agtagcaagt gcattgctct ctttatttca aattttccg cgcgcgatag gccctagacc     4200
agcgttctcg gtcgttgagg gtgcggtgta tcttctccag gacgtggtag aggtggctct    4260
ggacgttgag atacatgggc atgagcccgt cccgggggtg gaggtagcac cactgcagag    4320
cttcatgctc cggggtggtg ttgtagatga tccagtcgta gcaggagcgc tgggcatggt    4380
```

```
gcctaaaaat gtccttcagc agcaggccga tggccagggg gaggcccttg gtgtaagtgt    4440
ttacaaaacg gttaagttgg gaagggtgca ttcggggaga gatgatgtgc atcttggact    4500
gtatttttag attggcgatg tttccgccca gatcccttct gggattcatg ttgtgcagga    4560
ccaccagtac agtgtatccg gtgcacttgg ggaatttgtc atgcagctta gagggaaaag    4620
cgtggaagaa cttggagacg cccttgtggc ctcccagatt ttccatgcat tcgtccatga    4680
tgatggcaat gggcccgcgg gaggcagctt gggcaaagat atttctgggg tcgctgacgt    4740
cgtagttgtg ttccagggtg aggtcgtcat aggccatttt tacaaagcgc gggcggaggg    4800
tgcccgactg ggggatgatg gtcccctctg gccctgggc gtagttgccc tcgcagatct    4860
gcatttccca ggccttaatc tcggaggggg gaatcatatc cacctgcggg gcgatgaaga    4920
aaacggtttc cggagccggg gagattaact gggatgagag caggtttcta agcagctgtg    4980
attttccaca accggtgggc ccataaataa cacctataac cggttgcagc tggtagttta    5040
gagagctgca gctgccgtcg tcccggagga gggggccac ctcgttgagc atgtccctga    5100
cgcgcatgtt ctccccgacc agatccgcca gaaggcgctc gccgcccagg acagcagct    5160
cttgcaagga agcaaagttt ttcagcggct tgaggccgtc cgccgtgggc atgttttca    5220
gggtctggct cagcagctcc aggcggtccc agagctcggt gacgtgctct acggcatctc    5280
tatccagcat atctcctcgt ttcgcgggtt ggggcgactt tcgctgtagg gcaccaagcg    5340
gtggtcgtcc agcggggcca aagtcatgtc cttccatggg cgcagggtcc tcgtcagggt    5400
ggtctgggtc acggtgaagg ggtgcgctcc gggctgagcg cttgccaagg tgcgcttgag    5460
gctggttctg ctggtgctga agcgctgccg gtcttcgccc tgcgcgtcgg ccaggtagca    5520
tttgaccatg gtgtcatagt ccagcccctc cgcggcgtgt cccttggcgc gcagcttgcc    5580
cttgaggtg gcgccgcacg aggggcagag caggctcttg agcgcgtaga gcttggggggc    5640
gaggaagacc gattcggggg agtaggcgtc cgcgccgcag accccgcaca cggtctcgca    5700
ctccaccagc caggtgagct cggggcgcgc cgggtcaaaa accaggtttc ccccatgctt    5760
tttgatgcgt ttcttacctc gggtctccat gaggtggtgt cccgctcgg tgacgaagag    5820
gctgtccgtg tctccgtaga ccgacttgag gggtcttttc tccaggggg tccctcggtc    5880
ttcctcgtag aggaactcgg accactctga gacgaaggcc cgcgtccagg ccaggacgaa    5940
ggaggctatg tgggaggggt agcggtcgtt gtccactagg gggtccacct tctccaaggt    6000
gtgaagacac atgtcgcctt cctcggcgtc caggaaggtg attggcttgt aggtgtaggc    6060
cacgtgaccg ggggttcctg acggggggt ataaaagggg gtggggcgc gctcgtcgtc    6120
actctcttcc gcatcgctgt ctgcgagggc cagctgctgg ggtgagtatt ccctctcgaa    6180
ggcgggcatg acctccgcgc tgaggttgtc agtttccaaa aacgaggagg atttgatgtt    6240
cacctgtccc gaggtgatac ctttgagggt acccgcgtcc atctggtcag aaaacacgat    6300
cttttattg tccagcttgg tggcgaacga cccgtagagg gcgttggaga gcagcttggc    6360
gatggagcgc agggtctggt tcttgtccct gtcggcgcgc tccttggccg cgatgttgag    6420
ctgcacgtac tcgcgcgcga cgcagcgcca ctcggggaag acggtggtgc gctcgtcggg    6480
caccaggcgc acgcgccagc gcggttgtg caggtgacc aggtccacgc tggtggcgac    6540
ctcgccgcgc aggcgctcgt tggtccagca gagacggccg cccttgcgcg agcagaaggg    6600
gggcaggggg tcgagctggg tctcgtccgg ggggtccgcg tccacggtga aaacccggg    6660
gcgcaggcgc gcgtcgaagt agtctatctt gcaaccttgc atgtccagcg cctgctgcca    6720
gtcgcgggcg gcgagcgcgc gctcgtaggg gttgagcggc gggccccagg gcatggggtg    6780
```

```
ggtgagtgcg gaggcgtaca tgccgcagat gtcatagacg tagaggggct cccgcaggac    6840
cccgatgtag gtgggtagc agcggccgcc gcggatgctg gcgcgcacgt agtcatacag     6900
ctcgtgcgag ggggcgagga ggtcgggcc caggttggtg cgggcggggc gctccgcgcg     6960
gaagacgatc tgcctgaaga tggcatgcga gttggaagag atggtggggc gctggaagac    7020
gttgaagctg gcgtcctgca ggccgacggc gtcgcgcacg aaggaggcgt aggagtcgcg    7080
cagcttgtgt accagctcgg cggtgacctg cacgtcgagc gcgcagtagt cgagggtctc    7140
gcggatgatg tcatatttag cctgccccctt cttttccac agctcgcggt tgaggacaaa    7200
ctcttcgcgg tctttccagt actcttggat cgggaaaccg tccggttccg aacggtaaga    7260
gcctagcatg tagaactggt tgacggcctg gtaggcgcag cagcccttct ccacggggag    7320
ggcgtaggcc tgcgcggcct tgcggagcga ggtgtgggtc agggcgaagg tgtccctgac    7380
catgactttg aggtactggt gcttgaagtc ggagtcgtcg cagccgcccc gctcccagag    7440
cgagaagtcg gtgcgcttct tggagcgggg gttgggcaga gcgaaggtga catcgttgaa    7500
gaggattttg cccgcgcggg gcatgaagtt gcgggtgatg cggaagggcc ccggcacttc    7560
agagcggttg ttgatgacct gggcggcgag cacgatctcg tcgaagccgt tgatgttgtg    7620
gcccacgatg tagagttcca ggaagcgggg ccggcccttt acggtgggca gcttctttag    7680
ctcttcgtag gtgagctcct cgggcgaggc gaggccgtgc tcggccaggg cccagtccgc    7740
gaggtgcggg ttgtctctga ggaaggactc ccagaggtcg cgggccagga gggtctgcag    7800
gcggtccctg aaggtcctga actgcgggcc cacggccatt ttttcggggg tgatgcagta    7860
gaaggtgagg gggtcttgct gccagcggtc ccagtcgagc tgcagggcga ggtcgcgcgc    7920
ggcggtgacc aggcgctcgt cgcccccgaa tttcatgacc agcatgaagg gcacgagctg    7980 cttttccgaag gccccccatcc aagtgtaggt ctctacatcg taggtgacaa agaggcgctc    8040
cgtgcgagga tgcgagccga tcgggaagaa ctggatctcc cgccaccagt tggaggagtg    8100
gctgttgatg tggtggaagt agaagtcccg tcgccgggcc gaacactcgt gctggctttt    8160
gtaaaagcga gcgcagtact ggcagcgctg cacgggctgt acctcctgca cgagatgcac    8220 cttttcgcccg cgcacgagga agccgagggg aaatctgagc ccccccgcctg gctcgcggca    8280 tggctggtgc tcttctactt tggatgcgtg tccgtctccg tctggctcct cgaggggtgt    8340
tacggtggag cggaccacca cgccgcgcga ccgcaggtc cagatatcgg cgcgcggcgg     8400
tcggagtttg atgacgacat cgcgcagctg ggagctgtcc atggtctgga gctcccgcgg    8460
cggcggcagg tcagccggga gttcttgcag gttcacctcg cagagtcggg ccagggcgcg    8520
gggcaggtct aggtggtacc tgatctctag gggcgtgttg gtggcggcgt cgatggcttg    8580
caggagcccg catccccggg gggcgacgac ggtgccccgc ggggtggtgg tggtggtggt    8640
ggtggtggtg gtggcggtgc agctcagaag cggtgccgcg ggcgggcccc cggaggtagg    8700
gggggctccg gtcccgccgg cagggcggc agcggcacgt cggcgtggag cgcgggcagg    8760
agttggtgct gtgcccggag gttgctggcg aaggcgacga cgcggcggtt gatctcctgg    8820
atctggcgcc tctgcgtgaa gacgacgggc ccggtgagct tgaacctgaa agagagttcg    8880
acagaatcaa tctcggtgtc attgaccgcg gcctggcgca ggatctcctg cacgtctccc    8940
gagttgtctt ggtaggcgat ctcggccatg aactgctcga tctcttcctc ctggaggtct    9000
ccgcgtccgg cgcgttccac ggtggccgcc aggtcgttgg agatgcgccc catgagctgc    9060
gagaaggcgt tgagtccgcc ctcgttccag actcggctgt agaccacgcc cccctggtca    9120
```

```
tcgcgggcgc gcatgaccac ctgcgcgagg ttgagctcca cgtgccgcgc gaagacggcg    9180
tagttgcgca gacgctggaa gaggtagttg agggtggtgg cggtgtgctc ggccacgaag    9240
aagttcatga cccagcggcg caacgtggat tcgttgatgt cccccaaggc ctccagccgt    9300
tccatggcct cgtagaagtc cacggcgaag ttgaaaaact gggagttgcg cgccgacacg    9360
gtcaactcct cctccagaag acggatgagc tcggcgacgg tgtcgcgcac ctcgcgctcg    9420
aaggctatgg ggatctcttc ctccgctagc atcaccacct cctcctcttc ctcctcttct    9480
ggcacttcca tgatggcttc ctcctcttcg gggggcggcg gcggcggcgg tggggagggg    9540
ggcgctctgc gccggcggcg gcgcaccggg aggcggtcca cgaagcgcgc gatcatctcc    9600
ccgcggcggc ggcgcatggt ctcggtgacg gcgcggccgt tctcccgggg gcgcagttgg    9660
aagacgccgc cggacatctg gtgctggggc gggtggccgt gaggcagcga acgcgcgctg    9720
acgatgcatc tcaacaattg ctgcgtaggt acgccgccga gggacctgag ggagtccata    9780
tccaccggat ccgaaaacct ttcgaggaag gcgtctaacc agtcgcagtc gcaaggtagg    9840
ctgagcaccg tggcgggcgg cggggggtgg ggggagtgtc tggcggaggt gctgctgatg    9900
atgtaattga agtaggcgga cttgacacgg cggatggtcg acaggagcac catgtccttg    9960
ggtccggcct gctggatgcg gaggcggtcg gctatgcccc aggcttcgtt ctggcatcgg   10020
cgcaggtcct tgtagtagtc ttgcatgagc cttccaccg gcacctcttc tccttcctct   10080
tctgcttctt ccatgtctgc ttcggccctg ggcggcgcc gcgcccccct gccccccatg   10140
cgcgtgaccc cgaaccccct gagcggttgg agcagggcca ggtcggcgac gacgcgctcg   10200
gccaggatgg cctgctgcac ctgcgtgagg gtggtttgga agtcatccaa gtccacgaag   10260
cggtggtagg cgcccgtgtt gatggtgtag gtgcagttgg ccatgacgga ccagttgacg   10320
gtctggtggc ccgttgcga catctcggtg tacctgagtc gcgagtaggc gcgggagtcg   10380
aagacgtagt cgttgcaagt ccgcaccagg tactggtagc ccaccaggaa gtgcggcggc   10440
ggctggcggt agaggggcca gcgcaggtg cggggctc cggggccag gtcttccagc   10500
atgaggcggt ggtaggcgta gatgtacctg gacatccagg tgataccgc ggcggtggtg   10560
gaggcgcgcg ggaagtcgcg cacccggttc cagatgttgc gcaggggcag aaagtgctcc   10620
atggtaggcg tgctctgtcc agtcagacgc gcgcagtcgt tgatactcta gaccagggaa   10680
aacgaaagcc ggtcagcggg cactcttccg tggtctggtg aatagatcgc aagggtatca   10740
tggcggaggg cctcggttcg agccccgggt ccggccgga cggtccgcca tgatccacgc   10800
ggttaccgcc cgcgtgtcga acccaggtgt gcgacgtcag acaacggtgg agtgttcctt   10860
ttggcgtttt tctggccggg cgccggcgtc gcgtaagaga ctaagccgcg aaagcgaaag   10920
cagtaagtgg ctcgctcccc gtagccgag ggatccttgc taagggttgc gttgcggcga   10980
accccggttc gaatcccgta ctcgggccgg ccggaccgc ggctaaggtg ttggattggc   11040
ctccccctcg tataaagacc ccgcttgcgg attgactccg gacacgggga cgagcccctt   11100
ttatttttgc ttccccaga tgcatccggt gctgcgcag atgcgccccc cgccccagca   11160
gcagcaacaa caccagcaag agcggcagca acagcagcgg gagtcatgca gggcccctc   11220
acccacccctc ggcgggccgg ccacctcgg gtccgcggcc gtgtctggcg cctgcggcgg   11280
cggcgggggg ccggctgacg accccgagga gccccgcgg cgcagggcca gacactacct   11340
ggacctggag gagggcgagg gcctggcgcg gctgggggcg ccgtctcccg agcgccaccc   11400
gcgggtgcag ctgaagcgcg actcgcgcga ggcgtacgtg cctcggcaga acctgttcag   11460
ggaccgcgcg ggcgaggagc ccgaggagat gcgggacagg aggttcagcg cagggcggga   11520
```

```
gctgcggcag gggctgaacc gcgagcggct gctgcgcgag gaggactttg agcccgacgc   11580
gcggacgggg atcagccccg cgcgcgcgca cgtggcggcc gccgacctgg tgacggcgta   11640
cgagcagacg gtgaaccagg agatcaactt ccaaaagagt ttcaacaacc acgtgcgcac   11700
gctggtggcg cgcgaggagg tgaccatcgg gctgatgcac ctgtgggact tgtaagcgc    11760 gctggtgcag aaccccaaca gcaagcctct gacggcgcag ctgttcctga tagtgcagca   11820
cagcagggac aacgaggcgt ttagggacgc gctgctgaac atcaccgagc ccagggtcg    11880 gtggctgctg gacctgatta acatcctgca gagcatagtg gtgcaggagc gcagcctgag   11940
cctggccgac aaggtggcgg ccatcaacta ctcgatgctg agcctgggca gttttacgc    12000 gcgcaagatc taccagacgc cgtacgtgcc catagacaag gaggtgaaga tcgacggttt   12060
ttacatgcgc atggcgctga aggtgctcac cctgagcgac gacctgggcg tgtaccgcaa   12120
cgagcgcatc cacaaggccg tgagcgtgag ccggcggcgc gagctgagcg accgcgagct   12180
gatgcacagc ctgcagcggg cgctggcggg cgccggcagc ggcgacaggg aggcggagtc   12240
ctacttcgat gcggggcgg acctgcgctg ggcgcccagc cggcgggccc tggaggccgc    12300
gggggtccgc gaggactatg acgaggacgg cgaggaggat gaggagtacg agctagagga   12360
gggcgagtac ctggactaaa ccgcgggtgg tgtttccggt agatgcaaga cccgaacgtg   12420
gtggacccgg cgctgcgggc ggctctgcag agccagccgt ccggccttaa ctcctcagac   12480
gactggcgac aggtcatgga ccgcatcatg tcgctgacgg cgcgtaaccc ggacgcgttc   12540
cggcagcagc cgcaggccaa caggctctcc gccatcctgg aggcggtggt gcctgcgcgc   12600
tcgaacccca cgcacgagaa ggtgctggcc atagtgaacg cgctggccga gaacagggcc   12660
atccgcccgg acgaggccgg gctggtgtac gacgcgctgc tgcagcgcgt ggcccgctac   12720
aacagcggca acgtgcagac caacctggac cggctggtgg gggacgtgcg cgaggcggtg   12780
gcgcagcgcg agcgcgcgga tcggcagggc aacctgggct ccatggtggc gctgaatgcc   12840
ttcctgagca cgcagccggc caacgtgccg cgggggcagg aagactacac caactttgtg   12900
agcgcgctgc ggctgatggt gaccgagacc ccccagagcg aggtgtacca gtcgggcccg   12960
gactacttct tccagaccag cagacagggc ctgcagacgt tgaacctgag ccaggctttc   13020
aagaacctgc gggggctgtg gggcgtgaag gcgcccaccg cgaccgggc gacggtgtcc    13080 agcctgctga cgcccaactc gcgcctgctg ctgctgctga tcgcgccgtt cacggacagc   13140
ggcagcgtgt cccgggacac ctacctgggg cacctgctga ccctgtaccg cgaggccatc   13200
gggcaggcgc aggtggacga gcacaccttc caggagatca ccagcgtgag ccgcgcgctg   13260
gggcaggagg acacgagcag cctggaggcg actctgaact acctgctgac caaccggcgg   13320
cagaagattc cctcgctgca cagcctgacc tccgaggagg agcgcatctt cgctacgtg    13380 cagcagagcg tgagcctgaa cctgatgcgc gacggggtga cgcccagcgt ggcgctggac   13440
atgaccgcgc gcaacatgga accgggcatg tacgccgcgc accggcctta catcaaccgc   13500
ctgatggact acctgcatcg cgcggcggcc gtgaaccccg agtactttac caacgccatc   13560
ctgaacccgc actggctccc gccgcccggg ttctacagcg ggggcttcga ggtcccggag   13620
gccaacgatg gcttcctgtg ggacgacatg gacgacagcg tgttctcccc gcggccgcag   13680
gcgctggcgg aagcgtccct gctgcgtccc aagaaggagg aggaggaggc gagtcgccgc   13740
cgcggcagca gcgcgcgtgg cttctctgtc gagctggggg cggcagccgc cgcgcgcccc   13800
gggtccctgg gcggcagccc ctttccgagc ctggtggggt ctctgcacag cgagcgcacc   13860
```

-continued

```
acccgccctc ggctgctggg cgaggacgag tacctgaata actccctgct gcagccggtg    13920
cgggagaaaa acctgccccc cgccttcccc aacaacggga tagagagcct ggtggacaag    13980
atgagcagat ggaagaccta tgcgcaggag cacagggacg cgcccgcgct ccggccgccc    14040
acgcggcgcc agcgccacga ccggcagcgg gggctggtgt gggatgacga ggactccgcg    14100
gacgatagca gcgtgctgga cctgggaggg agcggcaacc cgttcgcgca cctgcgcccc    14160
cgcctgggga ggatgtttta aaaaaaaaaa aagcaagaag catgatgcaa aattaaataa    14220
aactcaccaa ggccatggcg accgagcgtt ggtttcttgt gttcccttca gtatgcggcg    14280
cgcggcgatg taccaggagg gacctcctcc ctcttacgag agcgtggtgg gcgcggcggc    14340
ggcggcgccc tcttctccct ttgcgtcgca gctgctggag ccgccgtacg tgcctccgcg    14400
ctacctgcgg cctacggggg ggagaaacag catccgttac tcggagctgg cgcccctgtt    14460
cgacaccacc cgggtgtacc tggtggacaa caagtcggcg gacgtggcct ccctgaacta    14520
ccagaacgac cacagcaatt ttttgaccac ggtcatccag aacaatgact acagcccgag    14580
cgaggccagc acccagacca tcaatctgga tgaccggtcg cactggggcg gcgacctgaa    14640
aaccatcctg cacaccaaca tgcccaacgt gaacgagttc atgttcacca ataagttcaa    14700
ggcgcgggtg atggtgtcgc gctcgcacac caaggaagac cgggtggagc tgaagtacga    14760
gtgggtggag ttcgagctgc cagagggcaa ctactccgag accatgacca ttgacctgat    14820
gaacaacgcg atcgtggagc actatctgaa agtgggcagg caaaacgggg tcctggagag    14880
cgacatcggg gtcaagttcg acaccaggaa cttccgcctg gggctggacc ccgtgaccgg    14940
gctggttatg cccggggtgt acaccaacga ggccttccat cccgacatca tcctgctgcc    15000
cggctgcggg gtggacttca cttacagccg cctgagcaac ctcctgggca tccgcaagcg    15060
gcagcccttc caggagggct tcaggatcac ctacgaggac ctggaggggg gcaacatccc    15120
cgcgctcctc gatgtggagg cctaccagga tagcttgaag gaaaatgagg cgggacagga    15180
ggataccacc cccgccgcct ccgccgccgc cgagcagggc gaggatgctg ctgacaccgc    15240
ggccgcggac ggggcagagg ccgaccccgc tatggtggtg gaggctcccg agcaggagga    15300
ggatatgaat gacagtgcgg tgcgcggaga caccttcgtc acccgggggg aggaaaagca    15360
agcggaggcc gaggccgcgg ccgaggaaaa gcaactggcg gcagcagcgg cggcggcggc    15420
gttggccgcg gcggaggctg agtctgaggg gaccaagccc gccaaggagc ccgtgattaa    15480
gcccctgacc gaagatagca agaagcgcag ttacaacctg ctcaaggaca gcaccaacac    15540
cgcgtaccgc agctggtacc tggcctacaa ctacggcgac ccgtcgacgg gggtgcgctc    15600
ctggaccctg ctgtgcacgc cggacgtgac ctgcggctcg gagcaggtgt actggtcgct    15660
gcccgacatg atgcaagacc ccgtgacctt ccgctccacg cggcaggtca gcaacttccc    15720
ggtggtgggc gccgagctgc tgcccgtgca ctccaagagc ttctacaacg accaggccgt    15780
ctactcccag ctcatccgcc agttcacctc tctgacccac gtgttcaatc gctttcctga    15840
gaaccagatt ctggcgcgcc cgcccgcccc caccatcacc accgtcagtg aaaacgttcc    15900
tgctctcaca gatcacggga cgctaccgct gcgcaacagc atcggaggag tccagcgagt    15960
gaccgttact gacgccagac gccgcacctg ccctacgtt tacaaggcct tgggcatagt    16020
ctcgccgcgc gtcctttcca gccgcacttt ttgagcaaca ccaccatcat gtccatcctg    16080
atctcaccca gcaataactc cggctgggga ctgctgcgcg cgcccagcaa gatgttcgga    16140
ggggcgagga agcgttccga gcagcacccc gtgcgcgtgc gcgggcactt ccgcgccccc    16200
tggggagcgc acaaacgcgg ccgcgcgggg cgcaccaccg tggacgacgc catcgactcg    16260
```

```
gtggtggagc aggcgcgcaa ctacaggccc gcggtctcta ccgtggacgc ggccatccag    16320
accgtggtgc ggggcgcgcg gcggtacgcc aagctgaaga gccgccggaa gcgcgtggcc    16380
cgccgccacc gccgccgacc cggggccgcc gccaaacgcg ccgccgcggc cctgcttcgc    16440
cgggccaagc gcacgggccg ccgcgccgcc atgagggccg cgcgccgctt ggccgccggc    16500
atcaccgccg ccaccatggc cccccgtacc cgaagacgcg cggccgccgc cgccgccgcc    16560
gccatcagtg acatggccag caggcgccgg ggcaacgtgt actgggtgcg cgactcggtg    16620
accggcacgc gcgtgcccgt gcgcttccgc cccccgcgga cttgagatga tgtgaaaaaa    16680
caacactgag tctcctgctg ttgtgtgtat cccagcggcg gcggcgcgcg cagcgtcatg    16740
tccaagcgca aaatcaaaga agagatgctc caggtcgtcg cgccggagat ctatgggccc    16800
ccgaagaagg aagagcagga ttcgaagccc cgcaagataa agcgggtcaa aaagaaaaag    16860
aaagatgatg acgatgccga tggggaggtg gagttcctgc gcgccacggc gcccaggcgc    16920
ccggtgcagt ggaagggccg gcgcgtaaag cgcgtcctgc gccccggcac cgcggtggtc    16980
ttcacgcccg gcgagcgctc caccccggact ttcaagcgcg tctatgacga ggtgtacggc    17040
```
(partial — note: verify line 17040 shows cccggact with extra c? original: cacccggact)

```
gtggcgagaa gcgcccgcgg cccgataggg aagagaccac tctggtcacg cagaccgatg    18660
agccgccccc gtatgaggag gccctaaagc aaggtctgcc caccacgcgg cccatcgcgc    18720
ccatggccac cggggtggtg ggccgccaca cccccgccac gctggacttg cctccgcccg    18780
ccgatgtgcc gcagcagcag aaggcggcac agccgggccc gcccgcgacc gcctcccgtt    18840
cctccgccgg tcctctgcgc cgcgcggcca gcggcccccg cggggggtc gcgaggcacg     18900 gcaactggca gagcacgctg aacagcatcg tgggtctggg ggtgcggtcc gtgaagcgcc    18960
gccgatgcta ctgaatagct tagctaacgt gttgtatgtg tgtatgcgcc ctatgtcgcc    19020
gccagaggag ctgctgagtc gccgccgttc gcgcgcccac caccaccgcc actccgcccc    19080
tcaagatggc gaccccatcg atgatgccgc agtggtcgta catgcacatc tcgggccagg    19140
acgcctcgga gtacctgagc cccgggctgg tgcagttcgc ccgcgccacc gagagctact    19200
tcagcctgag taacaagttt aggaaccccca cggtggcgcc cacgcacgat gtgaccaccg    19260
accggtctca gcgcctgacg ctgcggttca ttcccgtgga ccgcgaggac accgcgtact    19320
cgtacaaggc gcggttcacc ctggccgtgg gcgacaaccg cgtgctggac atggcctcca    19380
cctactttga catccgcggg gtgctggacc ggggtcccac tttcaagccc tactctggca    19440
ccgcctacaa ctccctggcc cccaagggcg ctcccaactc ctgcgagtgg gagcaagagg    19500
aaactcaggc agttgaagaa gcagcagaag aggaagaaga agatgctgac ggtcaagctg    19560
aggaagagca agcagctacc aaaaagactc atgtatatgc tcaggctccc ctttctggcg    19620
aaaaaattag taaagatggt ctgcaaatag gaacggacgc tacagctaca gaacaaaaac    19680
ctatttatgc agaccctaca ttccagcccg aaccccaaat cggggagtcc cagtggaatg    19740
aggcagatgc tacagtcgcc ggcggtagag tgctaaagaa atctactccc atgaaaccat    19800
gctatggttc ctatgcaaga cccacaaatg ctaatgagg tcagggtgta ctaacggcaa     19860
atgcccaggg acagctagaa tctcaggttg aaatgcaatt cttttcaact tctgaaaacg    19920
cccgtaacga ggctaacaac attcagccca aattggtgct gtatagtgag gatgtgcaca    19980
tggagacccc ggatacgcac cttctcttaca agcccgcaaa aagcgatgac aattcaaaaa    20040
tcatgctggg tcagcagtcc atgcccaaca gacctaatta catcggcttc agagacaact    20100
ttatcggcct catgtattac aatagcactg gcaacatggg agtgcttgca ggtcaggcct    20160
ctcagttgaa tgcagtggtg gacttgcaag acagaaacac agaactgtcc taccagctct    20220
tgcttgattc catgggtgac agaaccagat acttttccat gtggaatcag gcagtggaca    20280
gttatgaccc agatgttaga attattgaaa atcatggaac tgaagacgag ctccccaact    20340
attgtttccc tctgggtggc atagggtaa ctgacactta ccaggctgtt aaaaccaaca     20400
atggcaataa cggggccag gtgacttgga caaaagatga aacttttgca gatcgcaatg     20460 aaatagggt gggaaacaat ttcgctatgg agatcaacct cagtgccaac ctgtggagaa     20520
acttcctgta ctccaacgtg gcgctgtacc taccagacaa gcttaagtac aaccccctcca   20580 atgtggacat ctctgacaac cccaacacct acgattacat gaacaagcga gtggtggccc    20640
cggggctggt ggactgctac atcaacctgg gcgcgcgctg gtcgctggac tacatggaca    20700
acgtcaaccc cttcaaccac caccgcaatg cgggcctgcg ctaccgctcc atgctcctgg    20760
gcaacgggcg ctacgtgccc ttccacatcc aggtgcccca gaagttcttt gccatcaaga    20820
acctcctcct cctgccgggc tcctacacct acgagtggaa cttcaggaag gatgtcaaca    20880
tggtcctcca gagctctctg ggtaacgatc tcagggtgga cggggccagc atcaagttcg    20940
agagcatctg cctctacgcc accttcttcc ccatggccca caacacggcc tccacgctcg    21000
```

```
aggccatgct caggaacgac accaacgacc agtccttcaa tgactacctt tccgccgcca   21060
acatgctcta ccccataccc gccaacgcca ccaacgtccc catctccatc ccctcgcgca   21120
actgggcggc cttccgcggc tgggccttca cccgcctcaa gaccaaggag accccctccc   21180
tgggctcggg attcgacccc tactacacct actcgggctc tattccctac ctggacggca   21240
ccttctacct caaccacact ttcaagaagg tctcggtcac cttcgactcc tcggtcagct   21300
ggccgggcaa cgaccgtctg ctcacccccca acgagttcga gatcaagcgc tcggtcgacg   21360
gggaaggcta caacgtggcc cagtgcaaca tgaccaagga ctggttcctg gtccagatgc   21420
tggccaacta caacatcggc taccagggct tctacatccc agagagctac aaggacagga   21480
tgtactcctt cttcaggaac ttccagccca tgagccggca ggtggtggac cagaccaagt   21540
acaaggacta ccaggaggtg ggcatcatcc accagcacaa caactcgggc ttcgtgggct   21600
acctcgcccc caccatgcgc gagggacagg cctaccccgc caacttcccc tacccgctca   21660
taggcaagac cgcggtcgac agcatcaccc agaaaaagtt cctctgcgac cgcaccctct   21720
ggcgcatccc cttctccagc aacttcatgt ccatgggtgc gctctcggac ctgggccaga   21780
acttgctcta cgccaactcc gcccacgccc tcgacatgac cttcgaggtc gaccccatgg   21840
acgagcccac ccttctctat gttctgttcg aagtctttga cgtggtccgg gtccaccagc   21900
cgcaccgcgg cgtcatcgag accgtgtacc tgcgtacgcc cttctcggcc ggcaacgcca   21960
ccacctaaag aagcaagccg cagtcatcgc cgcctgcatg ccgtcgggtt ccaccgagca   22020
agagctcagg gccatcgtca gagacctggg atgcgggccc tattttttgg gcaccttcga   22080
caagcgcttc cctggctttg tctccccaca caagctggcc tgcgccatcg tcaacacggc   22140
cggccgcgag accgggggcg tgcactggct ggcctttgcc tggaacccgc gctccaaaac   22200
atgcttcctc tttgaccccct tcggcttttc ggaccagcgg ctcaagcaaa tctacgagtt   22260
cgagtacgag ggcttgctgc gtcgcagcgc catcgcctcc tcgcccgacc gctgcgtcac   22320
cctcgaaaag tccacccaga ccgtgcaggg gcccgactcg gccgcctgcg gtctcttctg   22380
ctgcatgttt ctgcacgcct ttgtgcactg gcctcagagt cccatggacc gcaaccccac   22440
catgaacttg ctgacggggg tgcccaactc catgctccaa gcccccagg tcgagcccac   22500
cctgcgccgc aaccaggagc agctctacag cttcctggag cgccactcgc cctacttccg   22560
ccgccacagc gcacagatca ggagggccac ctccttctgc cacttgcaag agatgcaaga   22620
agggtaataa cgatgtacac actttttttct caataaatgg cattttttt ttatttatac   22680
aagctctctg gggtattcat ttcccaccac caccacccgc cgttgtcgcc atctggctct   22740
atttagaaat cgaagggtt ctgccgggag tcgccgtgcg ccacgggcag ggacacgttg   22800
cgatactggt agcgggtgcc ccacttgaac tcgggcacca ccaggcgagg cagctcgggg   22860
aagttttcgc tccacaggct gcgggtcagc accagcgcgt tcatcaggtc gggcgccgag   22920
atcttgaagt cgcagttggg gccgccgccc tgcgcgcgcg agttgcggta caccgggttg   22980
cagcactgga acaccaacag cgccgggtgc ttcacgctgg ccagcacgct gcggtcgag   23040
atcagctcgg cgtccaggtc ctccgcgttg ctcagcgcga acgggtcat cttgggcact   23100
tgccgcccca ggaagggcgc gtgccccggt ttcgagttgc agtcgcagcg cagcgggatc   23160
agcaggtgcc cgtgcccgga ctcggcgttg gggtacagcg cgcgcatgaa ggcctgcatc   23220
tggcggaagg ccatctgggc cttggcgccc tccgagaaga acatgccgca ggacttgccc   23280
gagaactggt ttgcggggca gctggcgtcg tgcaggcagc agcgcgcgtc ggtgttggcg   23340
```

```
atctgcacca cgttgcgccc ccaccggttc ttcacgatct tggccttgga cgattgctcc   23400
ttcagcgcgc gctgcccgtt ctcgctggtc acatccatct cgatcacatg ttccttgttc   23460
accatgctgc tgccgtgcag acacttcagc tcgccctccg tctcggtgca gcggtgctgc   23520
cacagcgcgc agcccgtggg ctcgaaagac ttgtaggtca cctccgcgaa ggactgcagg   23580
taccctgca  aaaagcggcc catcatggtc acgaaggtct tgttgctgct gaaggtcagc   23640
tgcagcccgc ggtgctcctc gttcagccag gtcttgcaca cggccgccag cgcctccacc   23700
tggtcgggca gcatcttgaa gttcaccttc agctcattct ccacgtggta cttgtccatc   23760
agcgtgcgcg ccgcctccat gcccttctcc caggccgaca ccagcggcag gctcacgggg   23820
ttcttcacca tcaccgtggc cgccgcctcc gccgcgcttt cgctttccgc cccgctgttc   23880
tcttcctctt cctcctcttc ctcgccgccg cccactcgca gccccgcac  acgggtcg    23940
tcttcctgca ggcgctgcac cttgcgcttg ccgttgcgcc cctgcttgat gcgcacgggc   24000
gggttgctga agcccaccat caccagcgcg gcctcttctt gctcgtcctc gctgtccaga   24060
atgacctccg gggaggggg  gttggtcatc ctcagtaccg aggcacgctt ctttttcttc   24120
ctggggggcgt tcgccagctc cgcggctgcg gccgctgccg aggtcgaagg ccgagggctg   24180
ggcgtgcgcg gcaccagcgc gtcttgcgag ccgtcctcgt cctcctcgga ctcgagacgg   24240
aggcgggccc gcttcttcgg gggcgcgcgg ggcggcggag gcggcggcgg cgacggagac   24300
ggggacgaga catcgtccag ggtggtggga cggcgggccg cgccgcgtcc gcgctcgggg   24360
gtggtttcgc gctggtcctc ttcccgactg gccatctccc actgctcctt ctcctatagg   24420
cagaaagaga tcatggagtc tctcatgcga gtcgagaagg aggaggacag cctaaccgcc   24480
ccctctgagc cctccaccac cgccgccacc accgccaatg ccgccgcgga cgacgcgccc   24540
accgagacca ccgccagtac caccctcccc agcgacgcac ccccgctcga gaatgaagtg   24600
ctgatcgagc aggacccggg ttttgtgagc ggagaggagg atgaggtgga tgagaaggag   24660
aaggaggagg tcgccgcctc agtgccaaaa gaggataaaa agcaagacca ggacgacgca   24720
gataaggatg agacagcagt cgggcggggg aacggaagcc atgatgctga tgacggctac   24780
ctagacgtgg gagacgacgt gctgcttaag cacctgcacc gccagtgcgt catcgtctgc   24840
gacgcgctgc aggagcgctg cgaagtgccc ctggacgtgg cggaggtcag ccgcgcctac   24900
gagcggcacc tcttcgcgcc gcacgtgccc ccaagcgcc  gggagaacgg cacctgcgag   24960
cccaacccgc gtctcaactt ctacccggtc ttcgcggtac ccgaggtgct ggccacctac   25020
cacatcttct tccaaaactg caagatcccc ctctcctgcc gcgctaaccg cacccgcgcc   25080
gacaaaaccc tgaccctgcg gcagggcgcc cacatacctg atattgcctc tctggaggaa   25140
gtgcccaaga tcttcgaggg tctcggtcgc gacgagaaac gggcggcgaa cgctctgcac   25200
ggagacagcg aaaacgagag tcactcgggg gtgctggtgg agctcgaggg cgacaacgcg   25260
cgcctggccg tactcaagcg cagcatagag gtcaccccact ttgcctaccc ggcgctcaac   25320
ctgcccccca aggtcatgag tgtggtcatg ggcgagctca tcatgcgccg cgctcagccc   25380
ctggccgcgg atgcaaactt gcaagagtcc tccgaggaag gcctgcccgc ggtcagcgac   25440
gagcagctag cgcgctggct ggagacccgc gaccccgcgc agctggagga gcggcgcaag   25500
ctcatgatgg ccgcggtgct ggtcaccgtg gagctcgagt gtctgcagcg cttcttcgcg   25560
gaccccgaga tgcagcgcaa gctcgaggag accctgcact acaccttccg ccagggctac   25620
gtgcgccagg cctgcaagat ctccaacgtg gagctctgca acctggtctc ctacctgggc   25680
atcctgcacg agaaccgcct cgggcagaac gtcctgcact ccaccctcaa agggggaggcg   25740
```

```
cgccgcgact acatccgcga ctgcgcctac ctcttcctct gctacacctg gcagacggcc   25800 atggggtct ggcagcagtg cctggaggag cgcaacctca aggagctgga aaagctactc    25860
aagcgcaccc tcagggacct ctggacgggc ttcaacgagc gctcggtggc cgccgcgctg   25920
gcggacatca tcttccccga cgcctgctc aagaccctgc agcagggcct gcccgacttc    25980
accagccaga gcatgctgca gaactttagg actttcatcc tggagcgctc gggcatcctg   26040
cctgccactt gctgcgcgct gcccagcgac ttcgtgccca tcaagtacag ggagtgcccg   26100
ccgccgctct ggggccactg ctacctcttc cagctggcca actacctcgc ctaccactcg   26160
gacctcatgg aagacgtgag cggcgagggc ctgctcgagt gccactgccg ctgcaacctc   26220
tgcacgcccc accgctctct agtctgcaac ccgcagctgc tcagcgagag tcagattatc   26280
ggtaccttcg agctgcaggg tccctcgcct gacgagaagt ccgcggctcc ggggctgaaa   26340
ctcactccgg ggctgtggac ttccgcctac ctacgcaaat ttgtacctga ggactaccac   26400
gcccacgaga tcaggttcta cgaagaccaa tcccgcccgc caaggcgga gctcaccgcc    26460 tgcgtcatca cccaggggca catcctgggc caattgcaag ccatcaacaa agcccgccga   26520
gagttcttgc tgaaaaaggg tcgggggtg tacctggacc cccagtccgg cgaggagcta    26580
aacccgctac ccccgccgcc gccccagcag cgggaccttg cttcccagga tggcacccag   26640
aaagaagcag cagccgccgc cgccgcagcc atacatgctt ctggaggaag aggaggagga   26700
ctgggacagt caggcagagg aggtttcgga cgaggagcag gaggagatga tggaagactg   26760
ggaggaggac agcagcctag acgaggaagc ttcagaggcc gaagaggtgg cagacgcaac   26820
accatcaccc tcggtcgcag cccctcgcc ggggcccctg aaatcctccg aacccagcac    26880
cagcgctata acctccgctc ctccggcgcc ggcgccaccc gcccgcagac caaccgtag    26940 atgggacacc acaggaaccg gggtcggtaa gtccaagtgc ccgccgccgc caccgcagca   27000
gcagcagcag cgccagggct accgctcgtg gcgcgggcac aagaacgcca tagtcgcctg   27060
cttgcaagac tgcgggggca acatctcttt cgcccggcgc ttcctgctat tccaccacgg   27120
ggtcgccttt ccccgcaatg tcctgcatta ctaccgtcat ctctacagcc cctactgcag   27180
cggcgaccca gaggcggcag cggcagccac agcggcgacc accacctagg aagatatcct   27240
ccgcgggcaa gacagcggca gcagcggcca ggagacccgc ggcagcagcg gcgggagcgg   27300
tgggcgcact gcgcctctcg cccaacgaac ccctctcgac ccgggagctc agacacagga   27360
tcttccccac tttgtatgcc atcttccaac agagcagagg ccaggagcag gagctgaaaa   27420
taaaaaacag atctctgcgc tccctcaccc gcagctgtct gtatcacaaa agcgaagatc   27480
agcttcggcg cacgctggag gacgcggagg cactcttcag caaatactgc gcgctcactc   27540
ttaaagacta gctccgcgcc cttctcgaat ttaggcggga gaaaactacg tcatcgccgg   27600
ccgccgccca gcccgcccag ccgagatgag caaagagatt cccacgccat acatgtggag   27660
ctaccagccg cagatgggac tcgcggcggg agcggcccag gactactcca cccgcatgaa   27720
ctacatgagc gcgggacccc acatgatctc acaggtcaac gggatccgcg cccagcgaaa   27780
ccaaatactg ctggaacagg cggccatcac cgccacgccc cgccataatc tcaaccccg    27840 aaattggccc gccgccctcg tgtaccagga accccctcc gccaccaccg tactacttcc    27900
gcgtgacgcc caggccgaag tccagatgac taactcaggg gcgcagctcg cgggcggctt   27960
tcgtcacggg gcgcggccgc tccgaccagg tataagacac ctgatgatca gaggccgagg   28020
tatccagctc aacgacgagt cggtgagctc ttcgctcggt ctccgtccgg acggaacttt   28080
```

```
ccagctcgcc ggatccggcc gctcttcgtt cacgccccgc caggcgtacc tgactctgca    28140
gacctcgtcc tcggagcccc gctccggagg catcggaacc ctccagttcg tggaggagtt    28200
cgtgccctcg gtctacttca acccCttctc gggacctccc ggacgctacc ccgaccagtt    28260
cattccgaac tttgacgcgg tgaaggactc ggcggacggc tacgactgaa tgtcaggtgc    28320
cgaggcagag cagcttcgcc tgagacacct cgagcactgc cgccgccaca agtgcttcgc    28380
ccgcggttcc ggtgagttct gctactttca gctacccgag gagcataccg aggggccggc    28440
gcacggcgtc cgcctgacca cccagggcga ggttacctgt tccctcatcc gggagttcac    28500
cctccgtccc ctgctagtgg agcgggagcg gggtccctgt gtcctaacta tcgcctgcaa    28560
ctgccctaac cctggattac atcaagatct ttgctgtcat ctctgtgctg agtttaataa    28620
acgctgagat cagaatctac tggggctcct gtcgccatcc tgtgaacgcc accgtcttca    28680
cccaccccga ccaggcccag gcgaacctca cctgcggtct gcatcggagg gccaagaagt    28740
acctcacctg gtacttcaac ggcacccct tgtggtttta caacagcttc gacggggacg    28800
gagtctccct gaaagaccag ctctccggtc tcagctactc catccacaag aacaccaccc    28860
tccaactctt ccctccctac ctgccgggaa cctacgagtg cgtcaccggc cgctgcaccc    28920
acctcacccg cctgatcgta aaccagagct ttccgggaac agataactcc ctcttcccca    28980
gaacaggagg tgagctcagg aaactccccg gggaccaggg cggagacgta ccttcgaccc    29040
ttgtggggtt aggatttttt attaccgggt tgctggctct tttaatcaaa gcttccttga    29100
gatttgttct ttccttctac gtgtatgaac acctcagcct ccaataactc tacccttttct    29160
tcggaatcag gtgacttctc tgaaatcggg cttggtgtgc tgcttactct gttgattttt    29220
ttccttatca tactcagcct tctgtgcctc aggctcgccg cctgctgcgc acacatctat    29280
atctactgct ggttgctcaa gtgcaggggt cgccacccaa gatgaacagg tacatggtcc    29340
tatcgatcct aggcctgctg gccctggcgg cctgcagcgc cgccaaaaaa gagattacct    29400
ttgaggagcc cgcttgcaat gtaactttca gcccgaggg tgaccaatgc caccctcg    29460
tcaaatgcgt taccaatcat gagaggctgc gcatcgacta caaaaacaaa actggccagt    29520
ttgcggtcta tagtgtgttt acgcccggag acccctctaa ctactctgtc accgtcttcc    29580
agggcggaca gtctaagata ttcaattaca ctttccctttttat gagtta tgcgatgcgg    29640
tcatgtacat gtcaaaacag tacaacctgt ggcctccctc tccccaggcg tgtgtggaaa    29700
atactgggtc ttactgctgt atggctttgg caatcactac gctcgctcta atctgcacgg    29760
tgctatacat aaaattcagg cagaggcgaa tctttatcga tgaaaagaaa atgccttgat    29820
cgctaacacc ggcttttctat ctgcagaatg aatgcaatca cctccctact aatcaccacc    29880
accctccttg cgattgccca tgggttgaca cgaatcgaag tgccagtggg gtccaatgtc    29940
accatggtgg gccccgccgg caattccacc ctcatgtggg aaaaatttgt ccgcaatcaa    30000
tgggttcatt tctgctctaa ccgaatcagt atcaagccca gagccatctg cgatgggcaa    30060
aatctaactc tgatcaatgt gcaaatgatg gatgctgggt actattacgg gcagcgggga    30120
gaaatcatta attactggcg accccacaag gactacatgc tgcatgtagt cgaggcactt    30180
cccactacca cccccactac cacctctccc accaccacta ccaccactac tactactact    30240
actaccacta ccgctgcccg ccatacccgc aaaagcacca tgattagcac aaagcccct    30300
cgtgctcact cccacgccgg cgggcccatc ggtgcgacct cagaaaccac cgagctttgc    30360
ttctgccaat gcactaacgc cagcgctcat gaactgttcg acctggagaa tgaggatgcc    30420
cagcagagct ccgcttgcct gacccaggag gctgtggagc ccgttgccct gaagcagatc    30480
```

```
ggtgattcaa taattgactc ttcttctttt gccactcccg aatacccctcc cgattctact   30540
ttccacatca cgggtaccaa agaccctaac ctctctttct acctgatgct gctgctctgt   30600
atctctgtgg tctcttccgc gctgatgtta ctggggatgt tctgctgcct gatctgccgc   30660
agaaagagaa aagctcgctc tcagggccaa ccactgatgc ccttcccta ccccccggat    30720
tttgcagata caagatatg agctcgctgc tgacactaac cgctttacta gcctgcgctc    30780
taaccccttgt cgcttgcgac tcgagattcc acaatgtcac agctgtggca ggagaaaatg  30840
ttactttcaa ctccacggcc gatacccagt ggtcgtggag tggctcaggt agctacttaa  30900
ctatctgcaa tagctccact tcccccagca tatccccaac caagtaccaa tgcaatgcca  30960
gcctgttcac cctcatcaac gcttccaccc tggacaatgg actctatgta ggctatgtac  31020
cctttggtgg gcaaggaaag acccacgctt acaacctgga agttcgccag cccagaacca  31080
ctacccaagc ttctcccacc accaccacca ccaccaccac caccatcacc agcagcagca  31140
gcagccacag cagcagcagc agattattga ctttggtttt ggccagctca tctgccgcta  31200
cccaggccat ctacagctct gtgcccgaaa ccactcagat ccaccgccca gaaacgacca  31260
ccgccaccac cctacacacc tccagcgatc agatgccgac caacatcacc cccttggctc  31320
ttcaaatggg acttacaagc cccactccaa aaccagtgga tgcggccgag gtctccgccc  31380
tcgtcaatga ctgggcgggg ctgggaatgt ggtggttcgc cataggcatg atggcgctct  31440
gcctgcttct gctctggctc atctgctgcc tccaccgcag gcgagccaga cccccccatct 31500
atagacccat cattgtcctg aaccccgata atgatgggat ccatagattg gatggcctga  31560
aaaacctact ttttctttt acagtatgat aaattgagac atgcctcgca ttttcttgta   31620
catgttcctt ctcccacctt ttctggggtg ttctacgctg gccgctgtgt ctcacctgga  31680
ggtagactgc ctctcacccct tcactgtcta cctgctttac ggattggtca ccctcactct  31740
catctgcagc ctaatcacag taatcatcgc cttcatccag tgcattgatt acatctgtgt  31800
gcgcctcgca tacttcagac accacccgca gtaccgagac aggaacattg cccaacttct  31860
aagactgctc taatcatgca taagactgtg atctgccttc tgatcctctg catcctgccc  31920
accctcacct cctgccagta caccacaaaa tctccgcgca aaagacatgc ctcctgccgc  31980
ttcacccaac tgtggaatat acccaaatgc tacaacgaaa agagcgagct ctccgaagct  32040
tggctgtatg gggtcatctg tgtcttagtt ttctgcagca ctgtctttgc cctcatgatc  32100
taccccctact ttgatttggg atggaacgcg atcgatgcca tgaattaccc caccttccc   32160
gcacccgaga taattccact gcgacaagtt gtacccgttg tcgttaatca acgccccca   32220
tccccctacgc ccactgaaat cagctacttt aacctaacag gcggagatga ctgacgccct  32280
agatctagaa atggacggca tcagtaccga gcagcgtctc ctagagaggc gcaggcaggc  32340
ggctgagcaa gagcgcctca atcaggagct ccgagatctc gttaacctgc accagtgcaa  32400
aagaggcatc ttttgtctgg taaagcaggc caaagtcacc tacgagaaga ccggcaacag  32460
ccaccgcctc agttacaaat tgcccaccca gcgccagaag ctggtgctca tggtgggtga  32520
gaatcccatc accgtcaccc agcactcggt agagaccgag gggtgtctgc actctccctg  32580
tcggggtcca gaagacctct gcaccctggt aaagaccctg tgcggtctca gagatttagt  32640
cccctttaac taatcaaaca ctggaatcaa taaaaagaat cacttactta aaatcagaca  32700
gcaggtctct gtccagttta ttcagcagca cctccttccc ctcctcccaa ctctggtact  32760
ccaaacgcct tctggcggca aacttcctcc acaccctgaa gggaatgtca gattcttgct  32820
```

```
cctgtccctc cgcacccact atcttcatgt tgttgcagat gaagcgcacc aaaacgtctg   32880
acgagagctt caaccccgtg taccoctatg acacggaaag cggccctccc tccgtccctt   32940
tcctcacccc tcccttcgtg tctcccgatg gattccaaga aagccccccc ggggtcctgt   33000
ctctgaacct ggccgagccc ctggtcactt cccacggcat gctcgccctg aaaatgggaa   33060
gtggcctctc cctggacgac gctggcaacc tcacctctca agatatcacc accgctagcc   33120
ctccoctcaa aaaaccaag accaacctca gcctagaaac ctcatccccc ctaactgtaa    33180
gcacctcagg cgccctcacc gtagcagccg ccgctcccct ggcagtggcc ggcacctccc   33240
tcaccatgca atcagaggcc ccctgacag tacaggatgc aaaactcacc ctggccacca    33300
aaggccccct gaccgtgtct gaaggcaaac tggccttgca acatcggcc ccgctgacgg     33360
ccgctgacag cagcaccctc accgttagcg ccacaccacc aattaatgta agcagtggaa   33420
gtttaggctt agacatggaa gaccctatgt atactcacga tggaaaactg ggaataagaa   33480
ttggggggtcc actaagagta gtagacagct tgcacacact cactgtagtt accggaaatg  33540
gactaactgt agataacaat gccctccaaa ctagagttac gggcgcccta ggttatgaca   33600
catcaggaaa tctacaattg agagctgcag gaggtatgcg aattgatgca aatggccaac   33660
ttatccttaa tgtggcatac ccatttgatg ctcagaacaa tctcagcctt agacttggtc   33720
agggacccct gtatataaac acagaccaca acctggattt gaattgcaac agaggtctaa   33780
ccacaactac caccaacaac acaaaaaaac ttgagactaa aattagctca ggcttagact   33840
atgacaccaa tggtgctgtc attattaaac ttggcactgg tctaagcttc gacaacacag   33900
gcgccctaac tgtgggaaac actggtgatg ataaactgac tctgtggacg accccagacc   33960
catctccaaa ttgcagaatt cactcagaca aagactgcaa gtttactcta gtcctaacta   34020
agtgtggaag ccaaatcctg gcctctgtcg ccgccctagc ggtatcagga atctggctt    34080
cgataacagg caccgttgcc agcgttacca tctttctcag atttgatcag aatggagtgc   34140
ttatggaaaa ctcctcgcta gacaggcagt actggaactt cagaaatggc aactcaacta   34200
acgctgcccc ctacaccaat gcagttgggt tcatgccaaa cctcgcagca taccccaaaa   34260
cgcaaagcca gactgctaaa aacaacattg taagtcaggt ttacttgaat ggagacaaat   34320
ccaaacccat gacccttacc atcaccctca atggaactaa tgaatccagt gaaactagcc   34380
aggtgagtca ctactccatg tcatttacat gggcttggga aagtgggcaa tatgccactg   34440
aaaccttttgc caccaactcc ttcaccttttt cttacattgc tgaacaataa aaagcatgac  34500
actgatgttc atttctgatt cttattttat tattttcaaa cacaacaaaa tcattcaagt   34560
cattcttcca tcttagctta atagacacag tagcttaata gacccagtag tgcaaagccc   34620
cattctagct tatagatcag acagtgataa ttaaccacca ccaccaccat acctttttgat  34680
tcaggaaatc atgatcatca caggatccta gtcttcaggc cgcccctcc ctcccaagac    34740
acagaataca cagtcctctc cccccgactg gctttaaata acaccatctg ttggtcaca    34800
gacatgttct taggggttat attccacacg gtctcctgcc gcgccaggcg ctcgtcggtg   34860
atgttgataa actctcccgg cagctcgctc aagttcacgt cgctgtccag cggctgaacc   34920
tccggctgac gcgataactg tgcgaccggc tgctggacaa acgaggccg cgcctacaag    34980
ggggtagagt cataatcctc ggtcaggata gggcggtgat gcagcagcag cgagcgaaac   35040
atctgctgcc gccgccgctc cgtccggcag gaaaacaaca agccggtggt ctcctccgcg   35100
ataatccgca ccgcccgcag catcagcttc ctcgttctcc gcgcgcagca cctcaccctg   35160
atctcgctca agtcggcgca gtaggtacag cacagcacca cgatgttatt catgatccca   35220
```

```
cagtgcaggg cgctgtatcc aaagctcatg ccgggaacca ccgcccccac gtggccatcg    35280
taccacaagc gcacgtaaat taagtgtcga cccctcatga acgtgctgga cacaaacatt    35340
acttccttgg gcatgttgta attcaccacc tcccggtacc agataaacct ctggttaaac    35400
agggcacctt ccaccaccat cctgaaccaa gaggccagaa cctgcccacc ggctatgcac    35460
tgcagggaac ccgggttgga acaatgacaa tgcagactcc aaggctcgta accgtggatc    35520
atccggctgc tgaaggcatc gatgttggca caacacagac acgtgcat gcactttctc     35580 atgattagca gctcttccct cgtcaggatc atatcccaag gaataaccca ttcttgaatc    35640
aacgtaaaac ccacacagca gggaaggcct cgcacataac tcacgttgtg catggtcagc    35700
gtgttgcatt ctggaaacag cggatgatcc tccagtatcg aggcgcgggt ctccttctca    35760
cagggaggta aagggtccct gctgtacgga ctgcgccggg acgaccgaga tcgtgttgag    35820
cgtagtgtca tggaaaaggg aacgccggac gtggtcatac ttcttgaagc agaaccaggt    35880
tcgcgcgtgg caggcctcct tgcgtctgcg gtctcgccgt ctagctcgct ccgtgtgata    35940
gttgtagtac agccactccc gcagagcgtc gaggcgcacc ctggcttccg gatctatgta    36000
gactccgtct tgcaccgcgg ccctgataat atccaccacc gtagaataag caacacccag    36060
ccaagcaata cactcgctct gcgagcggca gacaggagga gcgggcagag atgggagaac    36120
catgataaaa aacttttttt aaagaatatt ttccaattct tcgaaagtaa gatctatcaa    36180
gtggcagcgc tcccctccac tggcgcggtc aaactctacg gccaaagcac agacaacggc    36240
atttctaaga tgttccttaa tggcgtccaa aagacacacc gctctcaagt tgcagtaaac    36300
tatgaatgaa aacccatccg gctgattttc caatatagac gcgccggcgg cgtccaccaa    36360
acccagataa ttttcttctc tccagcggtt tagaatctgt ctaagcaaat cccttatatc    36420
aagtccggcc atgccaaaaa tctgctcaag agcgccctcc accttcatga ccaagcagcg    36480
catcatgatt gcaaaaattc aggttcttca gagacctgta taagattcaa aatgggaaca    36540
ttaacaaaaa ttcctctgtc gcgcagatcc cttcgcaggg caagctgaac ataatcagac    36600
aggtctgaac ggaccagtga ggccaaatcc ccaccaggaa ccagatccag agaccctata    36660
ctgattatga cgcgcatact cggggctatg ctgaccagcg tagcgccgat gtaggcgtgc    36720
tgcatgggcg gcgagataaa atgcaaagtg ctggttaaaa aatcaggcaa agcctcgcgc    36780
aaaaaagcta acacatcata atcatgctca tgcaggtagt tgcaggtaag ctcaggaacc    36840
aaaacggaat aacacacgat tttcctctca aacatgactt cgcggatact gcgtaaaaca    36900
aaaattataa ataaaaaatt aattaactta aacattggaa gcctgtctca caacaggaaa    36960
aaccacttta atcaacataa gacgggccac gggcatgccg gcatagccgt aaaaaaattg    37020
gtccccgtga ttaacaagta ccacagacag ctccccggtc atgtcggggg tcatcatgtg    37080
agactctgta tacacgtctg gattgtgaac atcagacaaa caagaaatc gagccacgta     37140 gcccggaggt ataatcaccc gcaggcgag gtacagcaaa acgaccccca taggaggaat      37200
cacaaaatta gtaggagaaa aaatacata aacaccagaa aaaccctgtt gctgaggcaa     37260
aatagcgccc tcccgatcca aaacaacata aagcgcttcc acaggagcag ccataacaaa    37320
gacccgagtc ttaccagtaa aagaaaaaag atctctcaac gcagcaccag caccaacact    37380
tcgcagtgta aaaggccaag tgccgagaga gtatatatag gaataaaaag tgacgtaaac    37440
gggcaaagtc caaaaaacgc ccagaaaaac cgcacgcgaa cctacgcccc gaaacgaaag    37500
ccaaaaaaca ctagacactc ccttccggcg tcaacttccg ctttcccacg ctacgtcact    37560
```

-continued

| | |
|---|---|
| tgccccagtc aaacaaacta catatcccga acttccaagt cgccacgccc aaaacaccgc | 37620 |
| ctacacctcc ccgcccgccg gcccgccccc aaacccgcct cccgcccgc gccccgcctc | 37680 |
| gcgccgccca tctcattatc atattggctt caatccaaaa taaggtatat tattgatgat | 37740 |
| g | 37741 |

<210> SEQ ID NO 15
<211> LENGTH: 36643
<212> TYPE: DNA
<213> ORGANISM: ChAd63

<400> SEQUENCE: 15

| | |
|---|---|
| catcatcaat aatatacctc aaacttttgg tgcgcgttaa tatgcaaatg aggtgtttga | 60 |
| atttggggat gcgggcgct gattggctga gagacgggcg accgttaggg gcggggcggg | 120 |
| tgacgttttg atgacgtggc cgtgaggcgg agccggtttg caagttctcg tgggaaaagt | 180 |
| gacgtcaaac gaggtgtggt ttgaacacgg aaatactcaa ttttcccgcg ctctctgaca | 240 |
| ggaaatgagg tgtttctggg cggatgcaag tgaaaacggg ccattttcgc gcgaaaactg | 300 |
| aatgaggaag tgaaaatctg agtaattccg cgtttatggc agggaggagt atttgccgag | 360 |
| ggccgagtag acttttgaccg attacgtggg ggtttcgatt accgtatttt tcacctaaat | 420 |
| ttccgcgtac ggtgtcaaag tccggtgttt ttacgtaggc gtcagctgat cgccagggta | 480 |
| tttaaacctg cgctctctag tcaagaggcc actcttgagt gccagcgagt agagttttct | 540 |
| cctccgcgcc gcgagtcaga tctacacttt gaaagatgag gcacctgaga gacctgcccg | 600 |
| gtaatgtttt cctggctact gggaacgaga ttctggaact ggtggtggac gccatgatgg | 660 |
| gtgacgaccc tcccgagccc cctaccccat tgaggcgcc ttcgctgtac gatttgtatg | 720 |
| atctggaggt ggatgtgccc gagaacgacc ccaacgagga ggcggtgaat gatttgttta | 780 |
| gcgatgccgc gctgctggct gccgagcagg ctaatacgga ctctggctca gacagcgatt | 840 |
| cctctcttca taccccgaga cccggcagag gtgagaaaaa gatccccgag cttaaagggg | 900 |
| aagagctcga cctgcgctgc tatgaggaat gcttgcctcc gagcgatgat gaggaggacg | 960 |
| aggaggcgat tcgagctgca gcgagcgagg gagtgaaagt tgcgggcgag agctttagcc | 1020 |
| tggactgtcc tactctgccc ggacacggct gtaagtcttg tgaatttcat cgcatgaata | 1080 |
| ctggagataa gaatgtgatg tgtgccctgt gctatatgag agcttacaac cattgtgttt | 1140 |
| acagtaagtg tgattaactt tagttgggaa ggcagagggt gactgggtgc tgactggttt | 1200 |
| atttatgtat atgttttttt atgtgtaggt cccgtctctg acgtagatga acccccact | 1260 |
| tcagagtgca tttcatcacc cccagaaatt ggcgaggaac cgcccgaaga tattattcat | 1320 |
| agaccagttg cagtgagagt caccgggcgg agagcagctg tggagagttt ggatgacttg | 1380 |
| ctacagggtg gggatgaacc tttggacttg tgtacccgga acgccccag gcactaagtg | 1440 |
| ccacacatgt gtgtttactt aaggtgatgt cagtatttat agggtgtgga gtgcaataaa | 1500 |
| aatatgtgtt gactttaagt gcgtggttta tgactcaggg gtggggactg tgggtatata | 1560 |
| agcaggtgca gacctgtgtg gtcagttcag agcaggactc atggagatct ggacggtctt | 1620 |
| ggaagacttt caccagacta gacagctgct agagaactca tcggcggaag tctcttacct | 1680 |
| gtggagattc tgcttcggtg ggcctctagc taagctagtc tatagggcca agcaggatta | 1740 |
| taaggatcaa tttgaggata ttttgagaga gtgtcctggt attttgact ctctcaactt | 1800 |
| gggccatcag tctcacttta accagagtat tctgagagcc cttgactttt ccactcctgg | 1860 |
| cagaactacc gccgcggtag cctttttttgc ctttatcctt gacaaatgga gtcaagaaac | 1920 |

```
ccatttcagc agggattacc gtctggactg cttagcagta gctttgtgga gaacatggag    1980
gtgccagcgc ctgaatgcaa tctccggcta cttgccagta cagccggtag acacgctgag    2040
gatcctgagt ctccagtcac cccaggaaca ccaacgccgc cagcagccgc agcaggagca    2100
gcagcaagag gaggaggagg accgagaaga gaacctgaga gccggtctgg accctccggt    2160
ggcggaggag gaggagtagc tgacttgttt cccgagctgc gccgggtgct gactaggtct    2220
tccagtggac gggagagggg gattaagcgg gagaggcatg aggagactag ccacagaact    2280
gaactgactg tcagtctgat gagccgcagg cgcccagaat cggtgtggtg gcatgaggtg    2340
cagtcgcagg ggatagatga ggtctcagtg atgcatgaga aatattccct agaacaagtc    2400
aagacttgtt ggttggagcc tgaggatgat tgggaggtag ccatcaggaa ttatgccaag    2460
ctggctctga agccagacaa gaagtacaag attaccaaac tgattaatat cagaaattcc    2520
tgctacattt cagggaatgg ggccgaggtg gagatcagta cccaggagag ggcggccttc    2580
agatgttgta tgatgaatat gtacccgggg gtggtgggca tggagggagt caccttatg     2640 aacacgaggt tcaggggtga tgggtataat ggggtggtct ttatggccaa caccaagttg    2700
acagtgcacg gatgctcctt ctttggcttc aataacatgt gcatcgaggc ctggggcagt    2760
gtttcagtga ggggatgcag cttttcagcc aactggatgg gggtcgtggg cagaaccaag    2820
agcgtggttt cagtgaagaa atgcctgttt gagaggtgcc acctgggggt gatgagcgag    2880
ggcgaagcca aagtcaaaca ctgcgcctct accgagacgg gctgctttgt gctgatcaag    2940
ggcaatgcca aagtcaagca taacatgatc tgtgggcct cggatgagcg cggctaccag     3000
atgctgacct gcgccggtgg gaacagccat atgctggcca ccgtgcatgt ggcctcgcac    3060
ccccgcaaga catggcccga gttcgagcac aacgtcatga cccgctgcaa tgtgcacctg    3120
gggtcccgcc gaggcatgtt catgccctac cagtgcaaca tgcaatttgt gaaggtgctg    3180
ctggagcccg atgccatgtc cagagtgagc ctgacggggg tgtttgacat gaatgtggag    3240
ctgtggaaaa ttctgagata tgatgaatcc aagaccaggt gccgggcctg cgaatgcgga    3300
ggcaagcacg ccaggcttca gcccgtgtgt gtggaggtga cggaggacct gcgacccgat    3360
catttggtgt tgtcctgcaa cgggacggag ttcggctcca gcggggaaga atctgactag    3420
agtgagtagt gtttggggt gggtgggagc ctgcatgatg ggcagaatga ctaaaatctg     3480
tgtttttctg tgtgttgcag cagcatgagc ggaagcgcct cctttgaggg agggg tattc   3540 agcccttatc tgacggggcg tctcccctcc tgggcgggag tgcgtcagaa tgtgatggga    3600
tccacggtgg acgccggcc cgtgcagccc gcgaactctt caaccctgac ctacgcgacc     3660
ctgagctcct cgtccgtgga cgcagctgcc gccgcagctg ctgcttccgc cgccagcgcc    3720
gtgcgcggaa tggccctggg cgccggctac tacagctctc tggtggccaa ctcgagttcc    3780
accaataatc ccgccagcct gaacgaggag aagctgttgc tgctgatggc ccagctcgag    3840
gccctgaccc agcgcctggg cgagctgacc agcaggtgg ctcagctgca ggcggagacg     3900
cgggccgcgg ttgccacggt gaaaaccaaa taaaaaatga atcaataaat aaacggagac    3960
ggttgttgat tttaacacag agtcttgaat ctttatttga ttttcgcgc gcggtaggcc     4020 ctggaccacc ggtctcgatc attgagcacc cggtggatct tttccaggac ccggtagagg    4080
tgggcttgga tgttgaggta catgggcatg agcccgtccc gggggtggag gtagctccat    4140
tgcagggcct cgtgctcggg ggtggtgttg taaatcaccc agtcatagca ggggcgcagg    4200
gcgtggtgct gcacgatgtc tttgaggagg agactgatgg ccacgggcag ccccttggtg    4260
```

```
taggtgttga cgaacctatt gagctgggag ggatgcatgc ggggggagat gagatgcatc    4320
ttggcctgga tcttgagatt ggcgatgttc ccgcccagat cccgccgggg gttcatgttg    4380
tgcaggacca ccagcacggt gtatccggtg cacttgggga atttgtcatg caacttggaa    4440
gggaaggcgt gaaagaattt ggagacgccc ttgtgaccgc ccaggttttc catgcactca    4500
tccatgatga tggcgatggg cccgtgggcg gcggcctggg caaagacgtt tcggggtcg     4560
gacacatcgt agttgtggtc ctgggtgagc tcgtcatagg ccattttaat gaatttgggg    4620
cggagggtac ccgactgggg gacaaaggtg ccctcgatcc cggggcgta gttcccctcg     4680
cagatctgca tctcccaggc cttgagctcg gagggggga tcatgtccac ctgcggggcg     4740
atgaaaaaaa cggtttccgg ggcggggag atgagctgcg ccgaaagcag gttccggagc     4800
agctgggact gccgcagcc ggtgggccg tagatgaccc cgatgaccgg ctgcaggtgg      4860
tagttgaggg agagacagct gccgtcctcg cggaggaggg gggccacctc gttcatcatc    4920
tcgcgcacat gcatgttctc gcgcacgagt tccgccagga ggcgctcgcc ccccagcgag    4980
aggagctctt gcagcgaggc gaagtttttc agcggcttga cccgtcggc catgggcatt     5040
ttggagaggg tctgttgcaa gagttccaga cggtcccaga gctcggtgat gtgctctagg    5100
gcatctcgat ccagcagacc tcctcgtttc gcggttggg gcgactgcgg gagtagggca     5160
ccaggcgatg ggcgtccagc gaggccaggg tccggtcctt ccagggtcgc agggtccgcg    5220
tcagcgtggt ctccgtcacg gtgaagggg gcgcgccggg ctgggcgctt gcgagggtgc    5280
gcttcaggct catccggctg gtcgagaacc gctcccggtc ggcgccctgc gcgtcggcca    5340
ggtagcaatt gagcatgagt tcgtagttga gcgcctcggc cgcgtggccc ttggcgcgga    5400
gcttaccttt ggaagtgtgt ccgcagacgg gacagaggag ggacttgagg gcgtagagct    5460
tgggggcgag gaagacggac tcgggggcgt aggcgtccgc gccgcagctg gcgcagacgg    5520
tctcgcactc cacgagccag gtgaggtcgg ggcggtcggg gtcaaaaacg aggtttcctc    5580
cgtgcttttt gatgcgtttc ttacctctgg tctccatgag ctcgtgtccc cgctgggtga    5640
caaagaggct gtccgtgtcc ccgtagaccg actttatggg ccggtcctcg agcggggtgc    5700
cgcggtcctc gtcgtagagg aaccccgccc actccgagac gaaggccggg tccaggcca    5760
gcacgaagga ggccacgtgg gagggtagc ggtcgttgtc caccagcggg tccaccttct    5820
ccagggtatg caagcacatg tccccctcgt ccacatccag gaaggtgatt ggcttgtaag    5880
tgtaggccac gtgaccgggg gtcccggccg ggggggtata aaaggggggcg ggcccctgct   5940
cgtcctcact gtcttccgga tcgctgtcca ggagcgccag ctgttggggt aggtattccc    6000
tctcgaaggc gggcatgacc tcggcactca ggttgtcagt ttctagaaac gaggaggatt    6060
tgatattgac ggtgccgttg gagacgcctt tcatgagccc ctcgtccatc tggtcagaaa    6120
agacgatctt tttgttgtcg agcttggtgg cgaaggagcc gtagagggcg ttggagagca    6180
gcttggcgat ggagcgcatg gtctggttct tttccttgtc ggcgcgctcc ttggcggcga    6240
tgttgagctg cacgtactcg cgcgccacgc acttccattc ggggaagacg gtggtgagct    6300
cgtcgggcac gattctgacc cgccagccgc ggttgtgcag ggtgatgagg tccacgctgg    6360
tggccacctc gccgcgcagg ggctcgttgg tccagcagag gcgcccgccc ttgcgcgagc    6420
agaaggggg cagcgggtcc agcatgagct cgtcgggggg gtcggcgtcc acggtgaaga    6480
tgccgggcag gagctcgggg tcgaagtagc tgatgcaggt gcccagatcg tccagacttg    6540
cttgccagtc gcgcacggcc agcgcgcgct cgtaggggct gaggggcgtg ccccagggca    6600
tggggtgcgt gagcgcggag gcgtacatgc cgcagatgtc gtagacgtag aggggctcct    6660
```

```
ggaggacgcc gatgtaggtg gggtagcagc gccccccgcg gatgctggcg cgcacgtagt   6720
cgtacagctc gtgcgagggc gcgaggagcc ccgtgccgag attggagcgc tgcggctttt   6780
cggcgcggta gacgatctgg cggaagatgg cgtgggagtt ggaggagatg gtgggcctct   6840
ggaagatgtt gaagtgggca tggggcagtc cgaccgagtc cctgatgaag tgggcgtagg   6900
agtcctgcag cttggcgacg agctcggcgg tgacgaggac gtccagggcg cagtagtcga   6960
gggtctcttg gatgatgtcg tacttgagct ggcccttctg cttccacagc tcgcggttga   7020
gaaggaactc ttcgcggtcc ttccagtact cttcgagggg gaacccgtcc tgatcggcac   7080
ggtaagagcc caccatgtag aactggttga cggccttgta ggcgcagcag cccttctcca   7140
cggggagggc gtaagcttgc gcggccttgc gcagggaggt gtgggtgagg gcgaaggtgt   7200
cgcgcaccat gactttgagg aactggtgct tgaagtcgag gtcgtcgcag ccgccctgct   7260
cccagagctg gaagtccgtg cgcttcttgt aggcggggtt gggcaaagcg aaagtaacat   7320
cgttgaagag gatcttgccc gcgcggggca tgaagttgcg agtgatgcgg aaaggctggg   7380
gcacctcggc ccggttgttg atgacctggg cggcgaggac gatctcgtcg aagccgttga   7440
tgttgtgccc gacgatgtag agttccacga atcgcgggcg gcccttgacg tggggcagct   7500
tcttgagctc gtcgtaggtg agctcggcgg ggtcgctgag cccgtgctgc tcgagggccc   7560
agtcggcgac gtggggttg gcgctgagga aggaagtcca gagatccacg ccagggcgg    7620 tctgcaagcg gtcccggtac tgacggaact gctggcccac ggccattttt cgggggtga    7680 cgcagtagaa ggtgcggggg tcgccgtgcc agcggtccca cttgagctgg agggcgaggt   7740
cgtgggcgag ctcgacgagc ggcgggtccc cggagagttt catgaccagc atgaagggga   7800
cgagctgctt gccgaaggac cccatccagg tgtaggtttc cacatcgtag gtgaggaaga   7860
gcctttcggt gcgaggatgc gagccgatgg ggaagaactg gatctcctgc caccagttgg   7920
aggaatggct gttgatgtga tggaagtaga aatgccgacg gcgcgccgag cactcgtgct   7980
tgtgtttata caagcgtccg cagtgctcgc aacgctgcac gggatgcacg tgctgcacga   8040
gctgtacctg ggttcctttg acgaggaatt tcagtgggca gtggagcgct ggcggctgca   8100
tctggtgctg tactacgtcc tggccatcgg cgtggccatc gtctgcctcg atggtggtca   8160
tgctgacgag cccgcgcggg aggcaggtcc agacctcggc tcggacgggt cggagagcga   8220
ggacgagggc gcgcaggccg gagctgtcca gggtcctgag acgctgcgga gtcaggtcag   8280
tgggcagcgg cggcgcgcgg ttgacttgca ggagcttttc cagggcgcgc gggaggtcca   8340
gatggtactt gatctccacg gcgccgttgg tggcgacgtc cacggcttgc agggtcccgt   8400
gcccctgggg cgccaccacc gtgccccgtt tcttcttggg cggcggcggc tccatgctta   8460
gaagcggcgc gaggacgcg cgccgggcgg caggggcggc tcgggcccg gaggcagggg   8520 cggcaggggc acgtcggcgc cgcgcgcggg caggttctgg tactgcgccc ggagaagact   8580 ggcgtgagc acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcctgaag gtctccgcgg ccggcgcgct cgacggtggc   8820
cgcgaggtcg ttggagatgc ggcccatgag ctgcgagaag gcgttcatgc cggcctcgtt   8880
ccagacgcgc ctgtagacca cggctccgtc ggggtcgcgc gcgcgcatga ccacctgggc   8940
gaggttgagc tcgacgtggc gcgtgaagac cgcgtagttg cagaggcgct ggtagaggta   9000
```

-continued

```
gttgagcgtg gtggcgatgt gctcggtgac gaagaagtac atgatccagc ggcggagcgg    9060
catctcgctg acgtcgccca gggcttccaa gcgctccatg cctcgtaga agtccacggc    9120
gaagttgaaa actgggagt tgcgcgccga cacggtcaac tcctcctcca gaagacggat    9180
gagctcggcg atggtggcgc gcacctcgcg ctcgaaggcc ccggggggct cctcttccat    9240
ttcctcctct tcctcctcca ctaacatctc ttctacttcc tcctcaggag gcggcggcgg    9300
gggaggggcc ctgcgtcgcc ggcggcgcac gggcagacgg tcgatgaagc gctcgatggt    9360
ctccccgcgc cggcgacgca tggtctcggt gacggcgcgc ccgtcctcgc ggggccgcag    9420
cgtgaagacg ccgccgcgca tctccaggtg gccgccgggg gggtctccgt tgggcaggga    9480
gagggcgctg acgatgcatc ttatcaattg acccgtaggg actccgcgca aggacctgag    9540
cgtctcgaga tccacgggat ccgaaaaccg ctgaacgaag gcttcgagcc agtcgcagtc    9600
gcaaggtagg ctgagcccgg tttcttgttc ttcgggtatt tggtcgggag gcgggcggc    9660
gatgctgctg gtgatgaagt tgaagtaggc ggtcctgaga cggcggatgg tggcgaggag    9720
caccaggtcc ttgggcccgg cttgctggat gcgcagacgg tcggccatgc cccaggcgtg    9780
gtcctgacac ctggcgaggt ccttgtagta gtcctgcatg agccgctcca cgggcacctc    9840
ctcctcgccc gcgcggccgt gcatgcgcgt gagcccgaac ccgcgctgcg gctggacgag    9900
cgccaggtcg cgacgacgc gctcggcgag gatggcctgc tggatctggg tgagggtggt    9960
ctggaagtcg tcgaagtcga cgaagcgtg gtaggctccg tgttgatgg tgtaggagca   10020
gttggccatg acggaccagt tgacggtctg gtggccgggg cgcacgagct cgtggtactt   10080
gaggcgcgag taggcgcgcg tgtcgaagat gtagtcgttg caggtgcgca cgaggtactg   10140
gtatccgacg aggaagtgcg gcggcggctg gcggtagagc ggccatcgct cggtggcggg   10200
ggcgccgggc gcgaggtcct cgagcatgag gcggtggtag ccgtagatgt acctggacat   10260
ccaggtgatg ccggcggcgg tggtggaggc gcgcgggaac tcgcggacgc ggttccagat   10320
gttgcgcagc ggcaggaagt agttcatggt ggccgcggtc tggcccgtga ggcgcgcgca   10380
gtcgtggatg ctctagacat acgggcaaaa acgaaagcgg tcagcggctc gactccgtgg   10440
cctgggaggct aagcgaacgg gttgggctgc gcgtgtaccc cggttcgaat ctcgaatcag   10500
gctggagccg cagctaacgt ggtactggca ctcccgtctc gacccaagcc tgctaacgaa   10560
acctccagga tacggaggcg ggtcgttttt tggccttggt cgctggtcat gaaaaactag   10620
taagcgcgga aagcggccgc ccgcgatggc tcgctgccgt agtctggaga aagaatcgcc   10680
agggttgcgt tgcggtgtgc cccggttcga gcctcagcgc tcggcgccgg ccggattccg   10740
cggctaacgt gggcgtggct gccccgtcgt ttccaagacc ccttagccag ccgacttctc   10800
cagttacgga gcgagcccct ctttttttct tgtgttttg ccagatgcat cccgtactgc   10860
ggcagatgcg cccccaccct ccaccacaac cgcccctacc gcagcagcag caacagccgg   10920
cgcttctgcc cccgccccag cagcagcagc cagccactac cgcggcggcc gccgtgagcg   10980
gagccggcgt tcagtatgac ctggccttgg aagagggcga ggggctggcg cggctggggg   11040
cgtcgtcgcc ggagcggcac ccgcgcgtgc agatgaaaag ggacgctcgc gaggcctacg   11100
tgcccaagca gaacctgttc agagacagga gcggcgagga gcccgaggag atgcgcgcct   11160
cccgcttcca cgcggggcgg gagctgcggc gcggcctgga ccgaaagcgg gtgctgaggg   11220
acgaggattt cgaggcggac gagctgacgg ggatcagccc cgcgcgcgcg cacgtggccg   11280
cggccaacct ggtcacggcg tacgagcaga ccgtgaagga ggagagcaac ttccaaaaat   11340
ccttcaacaa ccacgtgcgc acgctgatcg cgcgcgagga ggtgaccctg ggcctgatgc   11400
```

```
acctgtggga cctgctggag gccatcgtgc agaaccccac gagcaagccg ctgacggcgc   11460
agctgtttct ggtggtgcag cacagtcggg acaacgagac gttcagggag gcgctgctga   11520
atatcaccga gcccgagggc cgctggctcc tggacctggt gaacattctg cagagcatcg   11580
tggtgcagga gcgcgggctg ccgctgtccg agaagctggc ggccatcaac ttctcggtgc   11640
tgagcctggg caagtactac gctaggaaga tctacaagac cccgtacgtg cccatagaca   11700
aggaggtgaa gatcgatggg ttttacatgc gcatgaccct gaaagtgctg accctgagcg   11760
acgatctggg ggtgtaccgc aacgacagga tgcaccgcgc ggtgagcgcc agccgccggc   11820
gcgagctgag cgaccaggag ctgatgcaca gcctgcagcg ggccctgacc ggggccggga   11880
ccgaggggga gagctacttt gacatgggcg cggacctgcg ctggcagccc agccgccggg   11940
ccttggaagc tgccgcggc gtgccctacg tggaggaggt ggacgatgag gaggaggagg   12000
gcgagtacct ggaagactga tggcgcgacc gtattttttgc tagatgcagc aacagccacc   12060
gccgccgcct cctgatcccg cgatgcgggc ggcgctgcag agccagccgt ccggcattaa   12120
ctcctcggac gattggaccc aggccatgca acgcatcatg gcgctgacga cccgcaatcc   12180
cgaagccttt agacagcagc ctcaggccaa ccggctctcg gccatcctgg aggccgtggt   12240
gccctcgcgc tcgaacccca cgcacgagaa ggtgctggcc atcgtgaacg cgctggtgga   12300
gaacaaggcc atccgcggcg acgaggccgg gctggtgtac aacgcgctgc tggagcgcgt   12360
ggcccgctac aacagcacca acgtgcagac gaacctggac cgcatggtga ccgacgtgcg   12420
cgaggcggtg tcgcagcgcg agcggttcca ccgcgagtcg aacctgggct ccatggtggc   12480
gctgaacgcc ttcctgagca cgcagcccgc caacgtgccc cggggccagg aggactacac   12540
caacttcatc agcgcgctgc ggctgatggt ggccgaggtg ccccagagcg aggtgtacca   12600
gtcggggccg gactacttct ccagaccag tcgccagggc ttgcagaccg tgaacctgag   12660
ccaggctttc aagaacttgc agggactgtg gggcgtgcag gccccggtcg gggaccgcgc   12720
gacggtgtcg agcctgctga cgccgaactc gcgcctgctg ctgctgctgg tggcgccctt   12780
cacggacagc ggcagcgtga ccgcgactc gtacctgggc tacctgctta acctgtaccg   12840
cgaggccatc gggcaggcgc acgtggacga gcagacctac caggagatca cccacgtgag   12900
ccgcgcgctg ggccaggagg acccgggcaa cctggaggcc accctgaact tcctgctgac   12960
caaccggtcg cagaagatcc cgccccagta cgcgctgagc accgaggagg agcgcatcct   13020
gcgctacgtg cagcagagcg tggggctgtt cttgatgcag gaggggggcca cgcccagcgc   13080 cgcgctcgac atgaccgcgc gcaacatgga gcccagcatg tacgcccgca accgccgtt   13140 catcaataag ctgatggact acttgcatcg ggcggccgcc atgaactcgg actactttac   13200
caacgccatc ttgaacccgc actggctccc gccgccggg ttctacacgg gcgagtacga   13260
catgcccgac cccaacgacg ggttcctgtg ggacgacgtg gacagcagcg tgttctcgcc   13320
gcggcccacc accaccaccg tgtggaagaa agagggcggg gaccggcggc cgtcctcggc   13380
gctgtccggt cgcgcgggtg ctgccgcggc ggtgcccgag gctgccagcc ccttccccgag   13440 cctgcccttt tcgctgaaca gcgtgcgcag cagcgagctg ggtcggctga cgcggccgcg   13500
cctgctgggc gaggaggagt acctgaacga ctccttgttg aagcccgagc gcgagaagaa   13560
cttccccaat aacgggatag agagcctggt ggacaagatg agccgctgga agacgtacgc   13620
gcacgagcac agggacagagc cccgagctag cagcgcaggc acccgtagac gccagcggca   13680
cgacaggcag cggggactgg tgtgggacga tgaggattcc gccgacgaca gcagcgtgtt   13740
```

```
ggacttgggt gggagtggtg gtggtaaccc gttcgctcac ctgcgccccc gtatcgggcg   13800
cctgatgtaa gaatctgaaa aaataaaaga cggtactcac caaggccatg gcgaccagcg   13860
tgcgttcttc tctgttgttt gtagtagtat gatgaggcgc gtgtacccgg agggtcctcc   13920
tccctcgtac gagagcgtga tgcagcaggc ggtggcggcg gcgatgcagc cccgctgga    13980 ggcgccttac gtgcccccgc ggtacctggc gcctacggag gggcggaaca gcattcgtta   14040
ctcggagctg gcaccttgt  acgataccac ccggttgtac ctggtggaca acaagtcggc   14100
ggacatcgcc tcgctgaact accagaacga ccacagcaac ttcctgacca ccgtggtgca   14160
gaacaacgat ttcacccca  cggaggccag cacccagacc atcaactttg acgagcgctc   14220
gcggtggggc ggccagctga aaaccatcat gcacaccaac atgcccaacg tgaacgagtt   14280
catgtacagc aacaagttca aggcgcgggt gatggtctcg cgcaagaccc ccaacggggt   14340
cacggtaggg gatgattatg atggtagtca ggacgagctg acctacgagt gggtggagtt   14400
tgagctgccc gagggcaact tctcggtgac catgaccatc gatctgatga acaacgccat   14460
catcgacaac tacttggcgg tggggcggca gaacgggtg  ctggagagcg acatcggcgt   14520
gaagttcgac acgcgcaact tccggctggg ctgggacccc gtgaccgagc tggtgatgcc   14580
gggcgtgtac accaacgagg ccttccaccc cgacatcgtc ctgctgcccg gctgcggcgt   14640
ggacttcacc gagagccgcc tcagcaacct gctgggcatc gcaagcggc  agcccttcca   14700 ggagggcttc cagatcctgt acgaggacct ggaggggggc aacatccccg cgctcttgga   14760
tgtcgaagcc tatgaagaaa gtaaggaaaa agcagaggct gaggcaacta cagccgtggc   14820
taccgccgcg actgtggcag atgccactgt caccaggggc gatacattcg ccacccagcc   14880
ggaggaagca gccgccctag cggcgaccga tgatagtgaa agtaagatag tcatcaagcc   14940
ggtggagaag gacagcaaga acaggagcta caacgttcta ccggatggaa agaacaccgc   15000
ctaccgcagc tggtacctgg cctacaacta cggcgacccc gagaagggcg tgcgctcctg   15060
gacgctgctc accacctcgg acgtcacctg cggcgtggag caagtctact ggtcgctgcc   15120
cgacatgatg caagacccgg tcaccttccg ctccacgcga caagttagca actacccggt   15180
ggtgggcgcc gagctcctgc ccgtctactc caagagcttc ttcaacgagc aggccgtcta   15240
ctcgcagcag ctgcgtgcct tcacctcgct cacgcacgtc ttcaaccgct tccccgagaa   15300
ccagatcctc gtccgcccgc ccgcgcccac cattaccacc gtcagtgaaa acgttcctgc   15360
tctcacagat cacgggaccc tgccgctgcg cagcagtatc cggggagtcc agcgcgtgac   15420
cgtcactgac gccagacgcc gcacctgccc ctacgtctac aaggccctgg gcgtagtcgc   15480
gccgcgcgtc ctctcgagcc gcaccttcta aaaaatgtcc attctcatct cgcccagtaa   15540
taacaccggt tgggggcctgc gcgcgcccag caagatgtac ggaggcgctc gccaacgctc   15600
cacgcaacac cccgtgcgcg tgcgcgggca cttccgcgct ccctggggcg ccctcaaggg   15660
ccgcgtgcgc tcgcgcacca ccgtcgacga cgtgatcgac caggtggtgg ccgacgcgcg   15720
caactacacg cccgccgccg cgcccgcctc caccgtggac gccgtcatcg acagcgtggt   15780
ggccgacgcg cgccggtacg ccgcgccaa  gagccggcgg cggcgcatcg cccggcggca   15840
ccggagcacc cccgccatgc gcgcggcgcg agccttgctg cgcagggcca ggcgcacggg   15900
acgcagggcc atgctcaggg cggccagacg cgcggcctcc ggcagcagca gcgccggcag   15960
gacccgcaga cgcgcggcca cggcggcggc ggcggccatc gccagcatgt cccgcccgcg   16020
gcgcggcaac gtgtactggg tgcgcgacgc cgccaccggt gtgcgcgtgc ccgtgcgcac   16080
ccgcccccct cgcacttgaa gatgctgact tcgcgatgtt gatgtgtccc agcggcgagg   16140
```

```
aggatgtcca agcgcaaata caaggaagag atgctccagg tcatcgcgcc tgagatctac   16200
ggccccgcgg cggcggtgaa ggaggaaaga aagccccgca aactgaagcg ggtcaaaaag   16260
gacaaaaagg aggaggaaga tgacggactg gtggagtttg tgcgcgagtt cgccccccgg   16320
cggcgcgtgc agtggcgcgg gcggaaagtg aaaccggtgc tgcggcccgg caccacggtg   16380
gtcttcacgc ccggcgagcg ttccggctcc gcctccaagc gctcctacga cgaggtgtac   16440
ggggacgagg acatcctcga gcaggcggtc gagcgtctgg gcgagtttgc ttacggcaag   16500
cgcagccgcc ccgcgccctt gaaagaggag gcggtgtcca tcccgctgga ccacggcaac   16560
cccacgccga gcctgaagcc ggtgaccctg cagcaggtgc tgccgagcgc ggcgccgcgc   16620
cggggcttca agcgcgaggg cggcgaggat ctgtacccga ccatgcagct gatggtgccc   16680
aagcgccaga gctggagga cgtgctggag cacatgaagg tggaccccga ggtgcagccc   16740
gaggtcaagg tgcggcccat caagcaggtg gccccgggcc tgggcgtgca gaccgtggac   16800
atcaagatcc ccacggagcc catggaaacg cagaccgagc ccgtgaagcc cagcaccagc   16860
accatggagg tgcagacgga tccctggatg ccagcggctt ccaccaccac cactcgccga   16920
agacgcaagt acgcgcgggc cagcctgctg atgcccaact acgcgctgca tccttccatc   16980
atccccacgc cgggctaccg cggcacgcgc ttctaccgcg gctacaccag cagccgccgc   17040
cgcaagacca ccacccgccg ccgtcgtcgc agccgccgca gcagcaccgc gacttccgcc   17100
ttggtgcgga gagtgtatcg cagcgggcgc gagcctctga ccctgccgcg cgcgcgctac   17160
cacccgagca tcgccattta actaccgcct cctacttgca gatatggccc tcacatgccg   17220
cctccgcgtc cccattacgg gctaccgagg aagaaagccg cgccgtagaa ggctgacggg   17280
gaacgggctg cgtcgccatc accaccgcg gcggcgcgcc atcagcaagc ggttgggggg   17340
aggcttcctg cccgcgctga tccccatcat cgccgcggcg atcggggcga tccccggcat   17400
agcttccgtg gcggtgcagg cctctcagcg ccactgagac acaaaaaagc atggatttgt   17460
aataaaaaaa tggactgacg ctcctggtcc tgtgatgtgt gttttttagat ggaagacatc   17520 aattttttcgt ccctggcacc gcgacacggc acgcggccgt ttatgggcac ctggagcgac   17580
atcggcaaca gccaactgaa cggggggcgcc ttcaattgga gcagtctctg gagcgggctt   17640
aagaatttcg ggtccacgct caaaacctat ggcaacaagg cgtggaacag cagcacaggg   17700
caggcgctga gggaaaagct gaaagagcag aacttccagc agaaggtggt cgatggcctg   17760
gcctcgggca tcaacggggt ggtggacctg gccaaccagg ccgtgcagaa acagatcaac   17820
agccgcctga cgcggtccc gcccgcgggg tccgtggaga tgcccaggt ggaggaggag   17880 ctgcctcccc tggacaagcg cggcgacaag cgaccgcgtc ccgacgcgga ggagacgctg   17940
ctgacgcaca cggacgagcc gccccgtac gaggaggcg tgaaactggg tctgcccacc   18000
acgcggcccg tggcgcctct ggccaccggg gtgctgaaac ccagcagcag cagccagccc   18060
gcgaccctgg acttgcctcc gcctgcttcc cgccccctcca cagtggctaa gcccctgccg   18120
ccggtggccg tcgcgtcgcg cgccccccga ggccgccccc aggcgaactg gcagagcact   18180
ctgaacagca tcgtgggtct gggagtgcag agtgtgaagc gccgccgctg ctattaaaag   18240
acactgtagc gcttaacttg cttgtctgtg tgtgtatatg tatgtccgcc gaccagaagg   18300
aggaagaggc gcgtcgccga gttgcaagat ggccaccca tcgatgctgc cccagtgggc   18360
gtacatgcac atcgccggac aggacgcttc ggagtacctg agtccgggtc tggtgcagtt   18420 cgccccgcgcc acagacacct acttcagtct ggggaacaag tttaggaacc ccacggtggc   18480
```

| | |
|---|---|
| gcccacgcac gatgtgacca ccgaccgcag ccagcggctg acgctgcgct tcgtgcccgt | 18540 |
| ggaccgcgag gacaacacct actcgtacaa agtgcgctac acgctggccg tgggcgacaa | 18600 |
| ccgcgtgctg gacatggcca gcacctactt tgacatccgc ggcgtgctgg atcggggccc | 18660 |
| cagcttcaaa ccctactccg gcaccgccta acacagccta gctcccaagg gagcgcccaa | 18720 |
| cacctcacag tggaaggatt ccgacagcaa aatgcatact tttggagttg ctgccatgcc | 18780 |
| cggtgttgtt ggtaaaaaaa tagaagccga tggtctgcct attggaatag attcatcctc | 18840 |
| tggaactgac accataattt atgctgataa aactttccaa ccagagccac aggttggaag | 18900 |
| tgacagttgg gtcgacacca atggtgcaga ggaaaaatat ggaggtagag ctcttaagga | 18960 |
| cactacaaac atgaagccct gctacggttc ttttgccagg cctaccaaca agaaggtgg | 19020 |
| acaggctaac ataaaagatt ctgaaactgc cagcactact cctaactatg atatagattt | 19080 |
| ggcattcttt gacagcaaaa atattgcagc taactacgat ccagatattg taatgtacac | 19140 |
| agaaaatgtt gagttgcaaa ctccagatac tcatattgtg tttaagccag gaacttcaga | 19200 |
| tgaaagttca gaagccaatt tgggccagca ggccatgccc aacagaccca actacatcgg | 19260 |
| gttcagagac aactttatcg ggctcatgta ctacaacagc actggcaata tgggtgtact | 19320 |
| ggctggtcag gcctcccagc taaatgctgt ggtggacttg caggacagaa acaccgaact | 19380 |
| gtcctaccag ctcttgcttg actctctggg tgacagaacc aggtatttca gtatgtggaa | 19440 |
| tcaggcggtg gacagctatg accccgatgt gcgcattatt gaaaatcacg gtgtggagga | 19500 |
| tgaactcccc aattattgct tccctttgaa tggtgtaggc tttacagata cttaccaggg | 19560 |
| tgttaaagtt aagacagata cagccgctac tggtaccaat ggaacgcagt gggacaaaga | 19620 |
| tgataccaca gtcagcactg ccaatgagat ccactcaggc aatcctttcg ccatggagat | 19680 |
| caacatccag gccaacctgt ggcggaactt cctctacgcg aacgtggcgc tgtacctgcc | 19740 |
| cgactcctac aagtacacgc cggccaacat cacgctgccg accaacacca cacctacga | 19800 |
| ttacatgaac ggccgcgtgg tggcgccctc gctggtggac gcctcatca acatcggggc | 19860 |
| gcgctggtcg ctggacccca tggacaacgt caaccccttc aaccaccacc gcaacgcggg | 19920 |
| cctgcgctac cgctccatgc tcctgggcaa cgggcgctac gtgcccttcc acatccaggt | 19980 |
| gccccaaaag ttttttcgcca tcaagagcct cctgctcctg cccgggtcct acacctacga | 20040 |
| gtggaacttc cgcaaggacg tcaacatgat cctgcagagc tccctcggca acgacctgcg | 20100 |
| cacggacggg gcctccatcg ccttcaccag catcaacctc tacgccacct tcttccccat | 20160 |
| ggcgcacaac accgcctcca cgctcgaggc catgctgcgc aacgacacca acgaccagtc | 20220 |
| cttcaacgac tacctctcgg cggccaacat gctctacccc atcccggcca acgccaccaa | 20280 |
| cgtgcccatc tccatccct cgcgcaactg ggccgcttc cgcggatggt ccttcacgcg | 20340 |
| cctcaagacc cgcgagacgc cctcgctcgg ctccgggttc gacccctact tcgtctactc | 20400 |
| gggctccatc ccctacctcg acggcacctt ctacctcaac cacaccttca gaaggtctc | 20460 |
| catcaccttc gactcctccg tcagctggcc cggcaacgac cgcctcctga cgcccaacga | 20520 |
| gttcgaaatc aagcgcaccg tcgacggaga gggatacaac gtggcccagt gcaacatgac | 20580 |
| caaggactgg ttcctggtcc agatgctggc ccactacaac atcggctacc agggcttcta | 20640 |
| cgtgcccgag ggctacaagg accgcatgta ctccttcttc cgcaacttcc agcccatgag | 20700 |
| ccgccaggtc gtggacgagg tcaactacaa ggactaccag gccgtcaccc tggcctacca | 20760 |
| gcacaacaac tcgggcttcg tcggctacct cgcgcccacc atgcgccagg ccagcccta | 20820 |
| ccccgccaac taccccctacc cgctcatcgg caagagcgcc gtcgccagcg tcacccagaa | 20880 |

```
aaagttcctc tgcgaccggg tcatgtggcg catcccttc tccagcaact tcatgtccat    20940
gggcgcgctc accgacctcg gccagaacat gctctacgcc aactccgccc acgcgctaga    21000
catgaatttc gaagtcgacc ccatggatga gtccaccctt ctctatgttg tcttcgaagt    21060
cttcgacgtc gtccgagtgc accagcccca ccgcggcgtc atcgaggccg tctacctgcg    21120
cacgcccttc tcggccggca acgccaccac ctaaagcccc gctcttgctt cttgcaagat    21180
gacggcctgt ggctccggcg agcaggagct cagggccatc ctccgcgacc tgggctgcgg    21240
gccctgcttc ctgggcacct tcgacaagcg cttcccggga ttcatggccc cgcacaagct    21300
ggcctgcgcc atcgtcaaca cggccggccg cgagaccggg ggcgagcact ggctggcctt    21360
cgcctggaac ccgcgctccc acacctgcta cctcttcgac cccttcgggt tctcggacga    21420
gcgcctcaag cagatctacc agttcgagta cgagggcctg ctgcgccgca gcgccctggc    21480
caccgaggac cgctgcatca ccctggaaaa gtccacccag accgtgcagg gtccgcgctc    21540
ggccgcctgc gggctcttct gctgcatgtt cctgcacgcc ttcgtgcact ggcccgaccg    21600
ccccatggac aagaacccca ccatgaactt gctgacgggg gtgcccaacg gcatgctcca    21660
gtcgccccag gtggaaccca ccctgcgccg caaccaggag gcgctctacc gcttcctcaa    21720
cgcccactcc gcctactttc gctcccaccg cgcgcgcatc gagaaggcca ccgccttcga    21780
ccgcatgaat caagacatgt aaactgtgtg tatgtaatg ctttattcat cataataaac    21840
agcacatgtt tatgccacct tctctgaggc tctgacttta tttagaaatc gaaggggttc    21900
tgccggctct cggcgtgccc cgcgggcagg gatacgttgc ggaactggta cttgggcagc    21960
cacttgaact cggggatcag cagcttcggc acggggaggt cggggaacga gtcgctccac    22020
agcttgcgcg tgagttgcag ggcgcccagc aggtcgggcg cggagatctt gaaatcgcag    22080
ttgggacccg cgttctgcgc gcgagagttg cggtacacgg ggttgcagca ctggaacacc    22140
atcagggccg ggtgcttcac gctcgccagc accgtcgcgt cggtgatgcc ctccacgtcc    22200
agatcctcgg cgttggccat cccgaagggg gtcatcttgc aggtctgccg ccccatgctg    22260
ggcacgcagc cgggcttgtg gttgcaatcg cagtgcaggg ggatcagcat catctgagcc    22320
tgctcggagc tcatgcccgg gtacatggcc ttcatgaaag cctccagctg gcggaaggcc    22380
tgctgcgcct tgccgccctc ggtgaagaag accccacagg acttgctaga gaactggttg    22440
gtggcgcagc ccgcgtcgtg cacgcagcag cgcgcgtcgt tgttggccag ctgcaccacg    22500
ctgcgccccc agcggttctg ggtgatcttg gcccggtcgg ggttctcctt cagcgcgcgc    22560
tgcccgttct cgctcgccac atccatctcg atcgtgtgct ccttctggat catcacggtc    22620
ccgtgcaggc accgcagctt gccctcggcc tcggtgcacc cgtgcagcca cagcgcgcag    22680
ccggtgcact cccagttctt gtgggcgatc tgggagtgcg agtgcacgaa gccctgcagg    22740
aagcggccca tcatcgtggt cagggtcttg ttgctggtga aggtcagcgg gatgccgcgg    22800
tgctcctcgt tcacatacag gtggcagatg cggcggtaca cctcgccctg ctcgggcatc    22860
agctggaagg cggacttcag gtcgctctcc acgcggtacc gctccatcag cagcgtcatc    22920
acttccatgc ccttctccca ggccgaaacg atcggcaggc tcaggggtt cttcaccgtc    22980 atcttagtcg ccgccgccga agtcagggg tcgttctcgt ccagggtctc aaacactcgc    23040
ttgccgtcct tctcggtgat gcgcacgggg ggaaagctga agcccacggc cgccagctcc    23100
tcctcggcct gcctttcgtc ctcgctgtcc tggctgatgt cttgcaaagg cacatgcttg    23160
gtcttgcggg gtttcttttt gggcggcaga ggcggcggcg gagacgtgct gggcgagcgc    23220
```

```
gagttctcgc tcaccacgac tatttcttct tcttggccgt cgtccgagac cacgcggcgg   23280
taggcatgcc tcttctgggg cagaggcgga ggcgacgggc tctcgcggtt cggcgggcgg   23340
ctggcagagc cccttccgcg ttcggggttg cgctcctggc ggcgctgctc tgactgactt   23400
cctccgcggc cggccattgt gttctcctag ggagcaacaa gcatggagac tcagccatcg   23460
tcgccaacat cgccatctgc ccccgccgcc gacgagaacc agcagcagca gaatgaaagc   23520
ttaaccgccc cgccgcccag ccccacctcc gacgccgccg cggccccaga catgcaagag   23580
atggaggaat ccatcgagat tgacctgggc tacgtgacgc ccgcggagca cgaggaggag   23640
ctggcagcgc gcttttcagc cccggaagag aaccaccaag agcagccaga gcaggaagca   23700
gagagcgagc agcagcaggc tgggctcgag catggcgact acctgagcgg ggcagaggac   23760
gtgctcatca agcatctggc ccgccaaagc atcatcgtca aggacgcgct gctcgaccgc   23820
gccgaggtgc ccctcagcgt ggcggagctc agccgcgcct acgagcgcaa cctcttctcg   23880
ccgcgcgtgc cccccaagcg ccagcccaac ggcacctgcg agcccaaccc cgcgcctcaac   23940 ttctacccgg tcttcgcggt gcccgaggcc ctggccacct accacctctt tttcaagaac   24000
caaaggatcc ccgtctcctg ccgcgccaac cgcacccgcg ccgacgccct gctcaacctg   24060
ggtcccggcg cccgcctacc tgatatcacc tccttggaag aggttcccaa gatcttcgag   24120
ggtctgggca gcgacgagac tcgggccgcg aacgctctgc aaggaagcgg agaggagcat   24180
gagcaccaca gcgccctggt ggagttggaa ggcgacaacg cgcgcctggc ggtgctcaag   24240
cgcacggtcg agctgaccca cttcgcctac ccggcgctca acctgccccc caaggtcatg   24300
agcgccgtca tggaccaggt gctcatcaag cgcgcctcgc ccctctcaga ggaggagatg   24360
caggaccccg agagctcgga cgagggcaag cccgtggtca gcgacgagca gctggcgcgc   24420
tggctgggag cgagcagcac cccccagagc ctggaagagc ggcgcaagct catgatggcc   24480
gtggtcctgg tgaccgtgga gctggagtgt ctgcgccgct tcttcgccga cgcggagacc   24540
ctgcgcaagg tcgaggagaa cctgcactac ctcttcaggc acgggttcgt gcgccaggcc   24600
tgcaagatct ccaacgtgga gctgaccaac ctggtctcct acatgggcat cctgcacgag   24660
aaccgcctgg ggcagaacgt gctgcacacc accctgcgcg gggaggcccg ccgcgactac   24720
atccgcgact gcgtctacct gtacctctgc cacacctggc agacgggcat gggcgtgtgg   24780
cagcagtgcc tggaggagca gaacctgaaa gagctctgca agctcctgca gaagaacctc   24840
aaggccctgt ggaccgggtt cgacgagcgc accaccgcct cggacctggc cgacctcatc   24900
ttccccgagc gcctgcggct gacgctgcgc aacgggctgc ccgactttat gagccaaagc   24960
atgttgcaaa actttcgctc tttcatcctc gaacgctccg ggatcctgcc cgccacctgc   25020
tccgcactgc cctcggactt cgtgccgctg accttccgcg agtgccccccc gccgctctgg   25080 agccactgct acttgctgcg cctggccaac tacctggcct accactcgga cgtgatcgag   25140
gacgtcagca gcgagggtct gctcgagtgc cactgccgct gcaacctctg cacgccgcac   25200
cgctccttgg cctgcaaccc ccagctgctg agcgagaccc agatcatcgg caccttcgag   25260
ttgcaaggcc ccggcgaggg caagggggt ctcaaactca ccccggggct gtggaccctcg   25320 gcctacttgc gcaagttcgt gcccgaggac taccatccct tcgagatcag gttctacgag   25380
gaccaatccc agccgcccaa ggccgagctg tcggcctgcg tcatcaccca ggggggccatc   25440 ctggcccaat tgcaagccat ccagaaatcc cgccaagaat ttctgctgaa aaagggccac   25500
ggggtctact tggaccccca gaccggagag gagctcaacc ccagcttccc ccaggatgcc   25560
ccgaggaagc agcaagaagc tgaaagtgga gctgccgctg ccgccggagg atttggagga   25620
```

```
agactgggag agcagtcagg cagaggagat ggaagactgg gacagcactc aggcagagga    25680
ggacagcctg caagacagtc tggaggagga agacgaggtg gaggaggagg cagaggaaga    25740
agcagccgcc gccagaccgt cgtcctcggc ggaggagaaa gcaagcagca cggataccat    25800
ctccgctccg ggtcggggtc gcggcggccg ggcccacagt agatgggacg agaccgggcg    25860
cttcccgaac cccaccaccc agaccggtaa gaaggagcgg cagggataca agtcctggcg    25920
ggggcacaaa aacgccatcg tctcctgctt gcaagcctgc ggggggcaaca tctccttcac    25980 ccggcgctac ctgctcttcc accgcggggt gaacttcccc cgcaacatct tgcattacta    26040
ccgtcacctc cacagcccct actactgttt ccaagaagag gcagaaaccc agcagcagca    26100
gcagaaaacc agcggcagca gcagcagcta gaaaatccac agcggcggca ggtggactga    26160
ggatcgcggc gaacgagccg gcgcagaccc gggagctgag gaaccggatc tttcccaccc    26220
tctatgccat cttccagcag agtcgggggc aggagcagga actgaaagtc aagaaccgtt    26280
ctctgcgctc gctcacccgc agttgtctgt atcacaagag cgaagaccaa cttcagcgca    26340
ctctcgagga cgccgaggct ctcttcaaca agtactgcgc gctcactctt aaagagtagc    26400
ccgcgcccgc ccacacacgg aaaaaggcgg gaattacgtc accacctgcg cccttcgccc    26460
gaccatcatc atgagcaaag agattcccac gccttacatg tggagctacc agccccagat    26520
gggcctggcc gccggcgccg cccaggacta ctccacccgc atgaactggc tcagtgccgg    26580
gcccgcgatg atctcacggg tgaatgacat ccgcgcccac cgaaaccaga tactcctaga    26640
acagtcagcg atcaccgcca cgccccgcca tcaccttaat ccgcgtaatt ggcccgccgc    26700
cctggtgtac caggaaattc cccagcccac gaccgtacta cttccgcgag acgcccaggc    26760
cgaagtccag ctgactaact caggtgtcca gctggccggc ggcgccgccc tgtgtcgtca    26820 ccgcccccgct cagggtataa agcggctggt gatccgaggc agaggcacac agctcaacga    26880
cgaggtggtg agctcttcgc tgggtctgcg acctgacgga gtcttccaac tcgccggatc    26940
ggggagatct tccttcacgc ctcgtcaggc cgtcctgact ttggagagtt cgtcctcgca    27000
gccccgctcg ggcggcatcg gcactctcca gttcgtggag gagttcactc cctcggtcta    27060
cttcaacccc ttctccggct cccccggcca ctacccggac gagttcatcc cgaacttcga    27120
cgccatcagc gagtcggtgg acggctacga ttgaatgtcc catggtggcg cggctgacct    27180
agctcggctt cgacacctgg accactgccg ccgcttccgc tgcttcgctc gggatctcgc    27240
cgagtttgcc tactttgagc tgcccgagga gcaccctcag ggcccggccc acggagtgcg    27300
gatcgtcgtc gaaggggggcc tcgactccca cctgcttcgg attttcagcc agcgtccgat    27360
cctggtcgag cgcgagcaag gacagaccct tctgaccctg tactgcatct gcaaccaccc    27420
cggcctgcat gaaagtcttt gttgtctgct gtgtactgag tataataaaa gctgagatca    27480
gcgactactc cggactcgat tgtggtgttc ctgctatcaa ccggtccctg ttcttcaccg    27540
ggaacgagac cgagctccag ctccagtgta agccccacaa gaagtatctc acctggctgt    27600
tccagggctc tccgatcgcc gttgtcaacc actgcgacaa cgacggagtc ctgctgagcg    27660
gccctgccaa ccttactttt tccacccgca gaagcaagct ccagctcttc caacccttcc    27720
tccccgggac ctatcagtgc gtctcgggac cctgccatca caccttccac ctgatcccga    27780
ataccacagc gccgctcccc gctactaaca accaaactac ccaccaacgc caccgtcgcg    27840
acctttctga atctaatact accacccaca ccggaggtga gctccgaggt cgaccaacct    27900
ctgggattta ctacggcccc tgggaggtgg tagggttaat agcgctaggc ctagttgcgg    27960
```

```
gtgggctttt ggctctctgc tacctatacc tcccttgctg ttcgtactta gtggtgctgt    28020
gttgctggtt taagaaatgg ggaagatcac cctagtgagc tgcggtgtgc tggtggcggt    28080
ggtgctttcg attgtgggac tgggcggcgc ggctgtagtg aaggaggaga aggccgatcc    28140
ctgcttgcat ttcaatcccg acaaatgcca gctgagtttt cagcccgatg caatcggtg    28200 cacggtgctg atcaagtgcg gatgggaatg cgagaacgtg agaatcgagt acaataacaa    28260
gactcggaac aatactctcg cgtccgtgtg gcagcccggg gaccccgagt ggtacaccgt    28320
ctctgtcccc ggtgctgacg gctccccgcg caccgtgaac aatactttca tttttgcgca    28380
catgtgcgac acggtcatgt ggatgagcaa gcagtacgat atgtggcccc ccacgaagga    28440
gaacatcgtg gtcttctcca tcgcttacag cctgtgcacg gcgctaatca ccgctatcgt    28500
gtgcctgagc attcacatgc tcatcgctat tcgccccaga aataatgccg aaaaagagaa    28560
acagccataa cacgtttttt cacacacctt tttcagacca tggcctctgt tactgcccta    28620
actatttttt tgggccttgt gggtactagc agcacttttc agcatataaa caaaactgtt    28680
tatgctggtt ctaattctgt attacctggg catcaatcac accagaaagt ttcatggtac    28740
tggtatgata aaagtaacac gccagtcaca ctctgcaagg gtcatcaaac acccataaac    28800
cgtagtggaa tttttttaa atgtaatcat aataatatta cactactttc aattacaaag    28860
cactattctg gtacttacta tggaaccaat tttaacataa aacaggacac ttactatagt    28920
gtcacagtat tggatccaac tactcctaga acaactacaa aacccacaac tactaagagg    28980
cacactaaac ctaaaactac caagaaaacc actgtcaaaa ctacaacaac taggaccacc    29040
acaactacag aggctaccac cagcacaaca cttgctgcca ctacacacac acacactgag    29100
ctaaccttac agaccactaa tgatttgatc gccctgttgc aaaaggggga taacagcacc    29160
acttccaatg aggagatacc cagatccatg attggcatta ttgttgctgt agtggtgtgc    29220
atgttgatca tcgccttgtg catggtgtac tatgccttct gctacagaaa gcacagactg    29280
aacgacaagc tggaacactt actaagtgtt gaatttttaat ttttagaac catgaagatc    29340 ctaggccttt ttagtttttc tatcattacc tctactcttt gtgaatcagt ggataaagat    29400
gttactatta ccactggttc taattataca ctgaaagggc caccctcagg tatgctttcg    29460
tggtattgct attttggaac tgacactgat caaactgaat tatgcaattt tcaaaaaggc    29520
aaaacctcaa actctaaaat ctctaattat caatgcaatg gcactgatct gatactactc    29580
aatgtcacga aagcatatgg tggcagttat tcttgccctg acaaaacac tgaggatatg    29640 attttttaca aagtggaagt ggttgatccc actactccac cgcccaccac cacaactact    29700
cacaccacac acacagaaca aacaccagag gcagcagaag cagagttggc cttccaggtt    29760
cacggagatt cctttgctgt caatacccct acacccgatc agcggtgtcc ggggctgctc    29820
gtcagcggca ttgtcggtgt gctttcggga ttagcagtca taatcatctg catgttcatt    29880
tttgcttgct gctatagaag gctttaccga caaaaatcag acccactgct gaacctctat    29940
gtttaatttt ttccagagcc atgaaggcag ttagcgctct agttttttgt tctttgattg    30000
gcattgtttt tagtgctggg ttttttgaaaa atcttaccat ttatgaaggt gagaatgcca    30060
ctctagtggg catcagtggt caaaatgtca gctggctaaa ataccatcta gatgggtgga    30120
aagacatttg cgattggaat gtcactgtgt atacatgtaa tggagttaac ctcaccatta    30180
ctaatgccac ccaagatcag aatggtaggt ttaagggcca gagtttcact agaaataatg    30240
ggtatgaatc ccataacatg tttatctatg acgtcactgt catcagaaat gagactgcca    30300
ccaccacaca gatgcccact acacacagtt ctaccactac taccatgcaa accacacaga    30360
```

```
caaccacttt ttatacatca actcagcata tgaccaccac tacagcagca aagccaagta   30420
gtgcagcgcc tcagcccag gctttggctt tgatagctgc acaacctagt acaactacta    30480
ggaccaatga gcagactact gattttttgt ccactgtcga gagccacacc acagctacct   30540
ccagtgcctt ctctagcacc gccaatctct cctcgctttc ctctacacca atcagtcccg   30600
ctactactac tcctagcccc gctcctcttc ccactcccct gaagcaaact gaggacagcg   30660
gcatgcaatg gcagatcacc ctgctcattg tgatcgggtt ggtcattctg gccgtgttgc   30720
tctactacat cttctgccgc cgcattccca acgcgcaccg caagccggtc tacaagccca   30780
tcgttgacgg gcaaccggag ccgcttcagg tggaagggg tctaaggaat cttctcttct    30840
cttttacagt atggtgattg aactatgatt cctagacaat tcttgatcac tattcttatc   30900
tgcctcctcc aagtctgtgc caccctcgct ctggtggcca acgccagtcc agactgtatt   30960
gggcccttcg cctcctacgt gctctttgcc ttcgtcacct gcatctgctg ctgtagcata   31020
gtctgcctgc ttatcacctt cttccagttc attgactgga tctttgtgcg catcgcctac   31080
ctgcgccacc accccagta ccgcgaccag cgagtggcgc ggctgctcag gctcctctga    31140
taagcatgcg ggctctgcta cttctcgcgc ttctgctgtt agtgctcccc cgtcccgtca   31200
acccccggtc ccccactcag tccccgagg aggtccgcaa atgcaaattc caagaaccct    31260
ggaaattcct caaatgctac cgccaaaaat cagacatgca tcccagctgg atcatgatca   31320
ttgggatcgt gaacattctg gcctgcaccc tcatctcctt tgtgatttac ccctgctttg   31380
actttggttg gaactcgcca gaggcgctct atctcccgcc tgaacctgac acaccaccac   31440
agcaacctca ggcacacgca ctaccaccac cacagcctag gccacaatac atgcccatat   31500
tagactatga ggccgagcca cagcgaccca tgctccccgc tattagttac ttcaatctaa   31560
ccggcggaga tgactgaccc actggccaac aacaacgtca acgaccttct cctggacatg   31620
gacggccgcg cctcggagca gcgactcgcc caacttcgca ttcgccagca gcaggagaga   31680
gccgtcaagg agctgcagga cggcatagcc atccaccagt gcaagaaagg catcttctgc   31740
ctggtgaaac aggccaagat ctcctacgag gtcacccaga ccgaccatcg cctctcctac   31800
gagctcctgc agcagcgcca gaagttcacc tgcctggtcg gagtcaaccc catcgtcatc   31860
acccagcagt cgggcgatac caaggggtgc atccactgct cctgcgactc ccccgactgc   31920
gtccacactc tgatcaagac cctctgcggc ctccgcgacc tcctcccat gaactaatca    31980 ccccttatc cagtgaaata aagatcatat tgatgatgat tttacagaaa taaagataca    32040
atcatattga tgatttgagt ttaataaaaa ataaagaatc acttacttga aatctgatac   32100
caggtctctg tccatgtttt ctgccaacac cacttcactc ccctcttccc agctctggta   32160
ctgcaggccc cggcgggctg caaacttcct ccacacgctg aagggggatgt caaattcctc   32220 ctgtccctca atcttcattt tatcttctat cagatgtcca aaaagcgcgt ccgggtggat   32280
gatgacttcg accccgtcta ccctacgat gcagacaacg caccgaccgt gcccttcatc    32340 aacccccct tcgtctcttc agatggattc caagagaagc cctgggggt gctgtccctg     32400 cgactggccg accccgtcac caccaagaac ggggaaatca ccctcaagct gggagagggg   32460
gtggacctcg actcctcggg aaaactcatc tccaacacgg ccaccaaggc cgccgcccct   32520
ctcagttttt ccaacaacac catttccctt aacatggatc accccttta cactaaagat    32580 ggaaaattat ccttacaagt ttctccacca ttaaatatac tgagaacaag cattctaaac   32640
acactagctt taggtttgg atcaggttta ggactccgtg gctctgcctt ggcagtacag    32700
```

| | |
|---|---|
| ttagtctctc cacttacatt tgatactgat ggaaacataa agcttacctt agacagaggt | 32760 |
| ttgcatgtta caacaggaga tgcaattgaa agcaacataa gctgggctaa aggtttaaaa | 32820 |
| tttgaagatg gagccatagc aaccaacatt ggaaatgggt tagagtttgg aagcagtagt | 32880 |
| acagaaacag gtgttgatga tgcttaccca atccaagtta aacttggatc tggccttagc | 32940 |
| tttgacagta caggagccat aatggctggt aacaaagaag acgataaact cactttgtgg | 33000 |
| acaacacctg atccatcgcc aaactgtcaa atactcgcag aaaatgatgc aaaactaaca | 33060 |
| cttTgcttga ctaaatgtgg tagtcaaata ctggccactg tgtcagtctt agttgtagga | 33120 |
| agtggaaacc taaaccccat tactggcacc gtaagcagtg ctcaggtgtt tctacgtttt | 33180 |
| gatgcaaacg gtgttctttt aacagaacat tctacactaa aaaatactg ggggtatagg | 33240 |
| cagggagata gcatagatgg cactccatat accaatgctg taggattcat gcccaattta | 33300 |
| aaagcttatc caaagtcaca aagttctact actaaaaata atatagtagg gcaagtatac | 33360 |
| atgaatggag atgttTcaaa acctatgctt ctcactataa ccctcaatgg tactgatgac | 33420 |
| agcaacagta catattcaat gtcattttca tacacctgga ctaatggaag ctatgttgga | 33480 |
| gcaacatttg gggctaactc ttatacctTc tcatacatcg cccaagaatg aacactgtat | 33540 |
| cccacccTgc atgccaaccc ttcccacccc actctgtgga aaaaactctg aaacacaaaa | 33600 |
| taaaataaag ttcaagtgtt ttattgattc aacagtttta caggattcga gcagttattt | 33660 |
| ttcctccacc ctcccaggac atggaataca ccacccTctc cccccgcaca gccttgaaca | 33720 |
| tctgaacgcc attggtgatg acatgctttt ggtctccac gttccacaca gtttcagagc | 33780 |
| gagccagtct cgggtcggtc agggagatga aaccctccgg gcactcccgc atctgcacct | 33840 |
| cacagctcaa cagctgagga ttgtcctcgg tggtcgggat cacggttatc tggaagaagc | 33900 |
| agaagagcgg cggtgggaat catagtccgc gaacgggatc ggccggtggt gtcgcatcag | 33960 |
| gccccgcagc agtcgctgtc gccgccgctc cgtcaagctg ctgctcaggg ggtccgggtc | 34020 |
| cagggactcc ctcagcatga tgcccacggc cctcagcatc agtcgtctgg tgcggcgggc | 34080 |
| gcagcagcgc atgcggatct cgctcaggtc gctgcagtac gtgcaacaca ggaccaccag | 34140 |
| gttgttcaac agtccatagt tcaacacgct ccagccgaaa ctcatcgcgg gaaggatgct | 34200 |
| acccacgtgg ccgtcgtacc agatcctcag gtaaatcaag tggcgccccc tccagaacac | 34260 |
| gctgccatg tacatgatct ccttgggcat gtggcggttc accacctccc ggtaccacat | 34320 |
| caccctctgg ttgaacatgc agccccggat gatcctgcgg aaccacaggg ccagcaccgc | 34380 |
| cccgcccgcc atgcagcgaa gagacccggg gtcccggcaa tggcaatgga ggacccaccg | 34440 |
| ctcgtacccg tggatcatct gggagctgaa caagtctatg ttggcacagc acaggcacac | 34500 |
| gctcatgcat ctcttcagca ctctcagctc ctcgggggtc aaaaccatat cccagggcac | 34560 |
| ggggaactct tgcaggacag cgaaccccgc agaacagggc aatcctcgca cagaacttac | 34620 |
| attgtgcatg gacagggtat cgcaatcagg cagcaccggg tgatcctcca ccagggaagc | 34680 |
| gcgggtctcg gtctcctcac agcgtggtaa gggggccggc cgatacgggt gatggcggga | 34740 |
| cgcggctgat cgtgctcgcg accgtgtcat gatgcagttg ctttcggaca ttttcgtact | 34800 |
| tgctgtagca gaacctggtc cgggcgctgc acaccgatcg ccggcggcgg tcccggcgct | 34860 |
| tggaacgctc ggtgttgaag ttgtaaaaca gccactctct cagaccgtgc agcagatcta | 34920 |
| gggcctcagg agtgatgaaa atcccatcat gcctgatagc tctgatcaca tcgaccaccg | 34980 |
| tggaatgggc cagacccagc cagatgatgc aattttgttg ggtttcggta acggcggggg | 35040 |
| agggaagaac aggaagaacc atgattaact tttaatccaa acggtctcgg agcacttcaa | 35100 |

```
aatgaagatc gcggagatgg cacctctcgc ccccgctgtg ttggtggaaa ataacagcca    35160
ggtcaaaggt gatacggttc tcgagatgtt ccacggtggc ttccagcaaa gcctccacgc    35220
gcacatccag aaacaagaca atagcgaaag cgggagggtt ctctaattcc tcaatcatca    35280
tgttacactc ctgcaccatc cccagataat tttcattttt ccagccttga atgattcgaa    35340
ctagttcctg aggtaaatcc aagccagcca tgataaagag ctcgcgcaga gcgccctcca    35400
ccggcattct taagcacacc ctcataattc aagatattc tgctcctggt tcacctgcag     35460
cagattgaca agcggaatat caaactctct gccgcgatcc ctaagctcct ccctcagcaa    35520
taactgtaag tactctttca tcctctcc gaaattttta gccataggac cgccaggaat     35580
aagattaggg caagccacag tacagataaa ccgaagtcct ccccagtgag cattgccaaa    35640
tgcaagactg ctataagcat gctggctaga cccggtgata tcttccagat aactggacag    35700
aaaatcgccc aggcaatttt taagaaaatc aacaaagaa aaatcctcca ggtgcacgtt     35760
tagagcctcg ggacaacga tggagtaaat gcaagcggtg cgttccagca tggttagtta    35820
gctgatctgt agaaaaaaca aaaatgaaca ttaaaccatg ctagcctggc gaacaggtgg    35880
gtaaatcgtt ctttccagca ccaggcaggc cacggggtct ccggcacgac cctcgtaaaa    35940
attgtcgcta tgattgaaaa ccatcacaga gagacgttcc cggtggccgg cgtgaatgat    36000
tcgacaagat gaatacaccc ccggaacatt ggcgtccgcg agtgaaaaaa agcgcccgag    36060
gaagcaataa ggcactacaa tgctcagtct caagtccagc aaagcgatgc catgcggatg    36120
aagcacaaaa ttctcaggtg cgtacaaaat gtaattactc ccctcctgca caggcagcaa    36180
agcccccgat ccctccaggt acacatacaa agcctcagcg tccatagctt accgagcagc    36240
agcagcagca cacaacaggc gcaagagtca gagaaaggct gagctctaac ctgtccaccc    36300
gctctctgct caatatatag cccagatcta cactgacgta aaggccaaag tctaaaaata    36360
cccgccaaat agtcacacac gcccagcaca cgcccagaaa ccggtgacac actcaaaaaa    36420
atacgcgcac ttcctcaaac gcccaaactg ccgtcatttc cgggttccca cgctacgtca    36480
tcaaaacacg actttcaaat tccgtcgacc gttaaaaacg tcacccgccc cgcccctaac    36540
ggtcgcccgt ctctcagcca atcagcgccc cgcatcccca aattcaaaca cctcatttgc    36600
atattaacgc gcaccaaaag tttgaggtat attattgatg atg                      36643
```

<210> SEQ ID NO 16
<211> LENGTH: 1985
<212> TYPE: PRT
<213> ORGANISM: Artificial Sequence
<220> FEATURE:
<223> OTHER INFORMATION: met-NS3-NS5B

<400> SEQUENCE: 16

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Lys Asn Gln Val Glu Gly
                20                  25                  30

Glu Val Gln Val Val Ser Thr Ala Thr Gln Ser Phe Leu Ala Thr Cys
            35                  40                  45

Val Asn Gly Val Cys Trp Thr Val Tyr His Gly Ala Gly Ser Lys Thr
        50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr

-continued

```
                85                  90                  95
Pro Cys Thr Cys Gly Ser Ser Asp Leu Tyr Leu Val Thr Arg His Ala
            100                 105                 110
Asp Val Ile Pro Val Arg Arg Gly Asp Ser Arg Gly Ser Leu Leu
            115                 120                 125
Ser Pro Arg Pro Val Ser Tyr Leu Lys Gly Ser Gly Gly Pro Leu
            130                 135                 140
Leu Cys Pro Ser Gly His Ala Val Gly Ile Phe Arg Ala Ala Val Cys
145                 150                 155                 160
Thr Arg Gly Val Ala Lys Ala Val Asp Phe Val Pro Val Glu Ser Met
                165                 170                 175
Glu Thr Thr Met Arg Ser Pro Val Phe Thr Asp Asn Ser Ser Pro Pro
                180                 185                 190
Ala Val Pro Gln Ser Phe Gln Val Ala His Leu His Ala Pro Thr Gly
                195                 200                 205
Ser Gly Lys Ser Thr Lys Val Pro Ala Ala Tyr Ala Ala Gln Gly Tyr
                210                 215                 220
Lys Val Leu Val Leu Asn Pro Ser Val Ala Ala Thr Leu Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ala Pro Val Thr Tyr Ser Thr Tyr Gly
                260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ser Thr Thr Ile Leu Gly Ile
                290                 295                 300
Gly Thr Val Leu Asp Gln Ala Glu Thr Ala Gly Ala Arg Leu Val Val
305                 310                 315                 320
Leu Ala Thr Ala Thr Pro Pro Gly Ser Val Thr Val Pro His Pro Asn
                325                 330                 335
Ile Glu Glu Val Ala Leu Ser Asn Thr Gly Glu Ile Pro Phe Tyr Gly
                340                 345                 350
Lys Ala Ile Pro Ile Glu Ala Ile Arg Gly Gly Arg His Leu Ile Phe
                355                 360                 365
Cys His Ser Lys Lys Lys Cys Asp Glu Leu Ala Ala Lys Leu Ser Gly
                370                 375                 380
Leu Gly Ile Asn Ala Val Ala Tyr Tyr Arg Gly Leu Asp Val Ser Val
385                 390                 395                 400
Ile Pro Thr Ile Gly Asp Val Val Val Ala Thr Asp Ala Leu Met
                405                 410                 415
Thr Gly Tyr Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
                435                 440                 445
Thr Thr Thr Val Pro Gln Asp Ala Val Ser Arg Ser Gln Arg Arg Gly
                450                 455                 460
Arg Thr Gly Arg Gly Arg Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Ser Val
                500                 505                 510
```

Arg Leu Arg Ala Tyr Leu Asn Thr Pro Gly Leu Pro Val Cys Gln Asp
            515                 520                 525

His Leu Glu Phe Trp Glu Ser Val Phe Thr Gly Leu Thr His Ile Asp
            530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Ile Thr Lys Tyr Ile Met Ala Cys Met
            610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Arg Pro Ala Ile Val Pro Asp
            660                 665                 670

Arg Glu Phe Leu Tyr Gln Glu Phe Asp Glu Met Glu Glu Cys Ala Ser
            675                 680                 685

His Leu Pro Tyr Ile Glu Gln Gly Met Gln Leu Ala Glu Gln Phe Lys
            690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
            755                 760                 765

Thr Ala Ser Ile Thr Ser Pro Leu Thr Thr Gln Ser Thr Leu Leu Phe
            770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
            835                 840                 845

Pro Ser Thr Glu Asp Leu Val Asn Leu Leu Pro Ala Ile Leu Ser Pro
850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Ser Leu Thr Ile
            915                 920                 925

```
Thr Gln Leu Leu Lys Arg Leu His Gln Trp Ile Asn Glu Asp Cys Ser
        930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
                965                 970                 975

Gln Leu Pro Gly Val Pro Phe Phe Ser Cys Gln Arg Gly Tyr Lys Gly
            980                 985                 990

Val Trp Arg Gly Asp Gly Ile Met Gln Thr Thr Cys Pro Cys Gly Ala
        995                 1000                1005

Gln Ile Thr Gly His Val Lys Asn Gly Ser Met Arg Ile Val Gly Pro
1010                1015                1020

Lys Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
                1045                1050                1055

Leu Trp Arg Val Ala Ala Glu Glu Tyr Val Glu Val Thr Arg Val Gly
            1060                1065                1070

Asp Phe His Tyr Val Thr Gly Met Thr Thr Asp Asn Val Lys Cys Pro
        1075                1080                1085

Cys Gln Val Pro Ala Pro Glu Phe Phe Thr Glu Val Asp Gly Val Arg
    1090                1095                1100

Leu His Arg Tyr Ala Pro Ala Cys Arg Pro Leu Leu Arg Glu Glu Val
1105                1110                1115                1120

Thr Phe Gln Val Gly Leu Asn Gln Tyr Leu Val Gly Ser Gln Leu Pro
                1125                1130                1135

Cys Glu Pro Glu Pro Asp Val Ala Val Leu Thr Ser Met Leu Thr Asp
            1140                1145                1150

Pro Ser His Ile Thr Ala Glu Thr Ala Lys Arg Arg Leu Ala Arg Gly
        1155                1160                1165

Ser Pro Pro Ser Leu Ala Ser Ser Ser Ala Ser Gln Leu Ser Ala Pro
    1170                1175                1180

Ser Leu Lys Ala Thr Cys Thr Thr His His Val Ser Pro Asp Ala Asp
1185                1190                1195                1200

Leu Ile Glu Ala Asn Leu Leu Trp Arg Gln Glu Met Gly Gly Asn Ile
                1205                1210                1215

Thr Arg Val Glu Ser Glu Asn Lys Val Val Leu Asp Ser Phe Asp
            1220                1225                1230

Pro Leu Arg Ala Glu Glu Asp Glu Arg Glu Val Ser Val Pro Ala Glu
        1235                1240                1245

Ile Leu Arg Lys Ser Lys Lys Phe Pro Ala Ala Met Pro Ile Trp Ala
    1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ile Lys Ala
                1285                1290                1295

Pro Pro Ile Pro Pro Pro Arg Arg Lys Arg Thr Val Val Leu Thr Glu
            1300                1305                1310

Ser Ser Val Ser Ser Ala Leu Ala Glu Leu Ala Thr Lys Thr Phe Gly
        1315                1320                1325

Ser Ser Glu Ser Ser Ala Val Asp Ser Gly Thr Ala Thr Ala Leu Pro
    1330                1335                1340

Asp Gln Ala Ser Asp Asp Gly Asp Lys Gly Ser Asp Val Glu Ser Tyr
```

```
                1345                1350                1355                1360
Ser Ser Met Pro Pro Leu Glu Gly Glu Pro Gly Asp Pro Asp Leu Ser
                1365                1370                1375

Asp Gly Ser Trp Ser Thr Val Ser Glu Glu Ala Ser Glu Asp Val Val
                1380                1385                1390

Cys Cys Ser Met Ser Tyr Thr Trp Thr Gly Ala Leu Ile Thr Pro Cys
                1395                1400                1405

Ala Ala Glu Glu Ser Lys Leu Pro Ile Asn Ala Leu Ser Asn Ser Leu
                1410                1415                1420

Leu Arg His His Asn Met Val Tyr Ala Thr Thr Ser Arg Ser Ala Gly
1425                1430                1435                1440

Leu Arg Gln Lys Lys Val Thr Phe Asp Arg Leu Gln Val Leu Asp Asp
                1445                1450                1455

His Tyr Arg Asp Val Leu Lys Glu Met Lys Ala Lys Ala Ser Thr Val
                1460                1465                1470

Lys Ala Lys Leu Leu Ser Val Glu Glu Ala Cys Lys Leu Thr Pro Pro
                1475                1480                1485

His Ser Ala Lys Ser Lys Phe Gly Tyr Gly Ala Lys Asp Val Arg Asn
                1490                1495                1500

Leu Ser Ser Lys Ala Val Asn His Ile His Ser Val Trp Lys Asp Leu
1505                1510                1515                1520

Leu Glu Asp Thr Val Thr Pro Ile Asp Thr Thr Ile Met Ala Lys Asn
                1525                1530                1535

Glu Val Phe Cys Val Gln Pro Glu Lys Gly Gly Arg Lys Pro Ala Arg
                1540                1545                1550

Leu Ile Val Phe Pro Asp Leu Gly Val Arg Val Cys Glu Lys Met Ala
                1555                1560                1565

Leu Tyr Asp Val Val Ser Thr Leu Pro Gln Val Val Met Gly Ser Ser
                1570                1575                1580

Tyr Gly Phe Gln Tyr Ser Pro Gly Gln Arg Val Glu Phe Leu Val Asn
1585                1590                1595                1600

Thr Trp Lys Ser Lys Lys Asn Pro Met Gly Phe Ser Tyr Asp Thr Arg
                1605                1610                1615

Cys Phe Asp Ser Thr Val Thr Glu Asn Asp Ile Arg Val Glu Glu Ser
                1620                1625                1630

Ile Tyr Gln Cys Cys Asp Leu Ala Pro Glu Ala Arg Gln Ala Ile Lys
                1635                1640                1645

Ser Leu Thr Glu Arg Leu Tyr Ile Gly Gly Pro Leu Thr Asn Ser Lys
                1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ser Ala Ala
                1685                1690                1695

Cys Arg Ala Ala Lys Leu Gln Asp Cys Thr Met Leu Val Asn Ala Ala
                1700                1705                1710

Gly Leu Val Val Ile Cys Glu Ser Ala Gly Thr Gln Glu Asp Ala Ala
                1715                1720                1725

Ser Leu Arg Val Phe Thr Glu Ala Met Thr Arg Tyr Ser Ala Pro Pro
                1730                1735                1740

Gly Asp Pro Pro Gln Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
                1765                1770                1775
```

Tyr Leu Thr Arg Asp Pro Thr Thr Pro Leu Ala Arg Ala Ala Trp Glu
                1780                1785                1790

Thr Ala Arg His Thr Pro Val Asn Ser Trp Leu Gly Asn Ile Ile Met
        1795                1800                1805

Tyr Ala Pro Thr Leu Trp Ala Arg Met Ile Leu Met Thr His Phe Phe
    1810                1815                1820

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
            1845                1850                1855

Ile Glu Arg Leu His Gly Leu Ser Ala Phe Ser Leu His Ser Tyr Ser
            1860                1865                1870

Pro Gly Glu Ile Asn Arg Val Ala Ser Cys Leu Arg Lys Leu Gly Val
            1875                1880                1885

Pro Pro Leu Arg Val Trp Arg His Arg Ala Arg Ser Val Arg Ala Arg
        1890                1895                1900

Leu Leu Ser Gln Gly Gly Arg Ala Ala Thr Cys Gly Lys Tyr Leu Phe
1905                1910                1915                1920

Asn Trp Ala Val Lys Thr Lys Leu Lys Leu Thr Pro Ile Pro Ala Ala
            1925                1930                1935

Ser Gln Leu Asp Leu Ser Gly Trp Phe Val Ala Gly Tyr Ser Gly Gly
            1940                1945                1950

Asp Ile Tyr His Ser Leu Ser Arg Ala Arg Pro Arg Trp Phe Met Leu
            1955                1960                1965

Cys Leu Leu Leu Ser Val Gly Val Gly Ile Tyr Leu Leu Pro Asn
            1970                1975                1980

Arg
1985

<210> SEQ ID NO 17
<211> LENGTH: 34658
<212> TYPE: DNA
<213> ORGANISM: Artificial Sequence
<220> FEATURE:
<223> OTHER INFORMATION: ChAd63 delta E1,3,4, Ad5 E4orf6, NSmut

<400> SEQUENCE: 17
catcatcaat aatatacctc aaacttttgg tgcgcgttaa tatgcaaatg aggtgtttga      60
atttggggat gcgggcgct gattggctga gagacgggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaattccg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgatccc attgcatacg ttgtatccat     480
atcataatat gtacatttat attggctcat gtccaacatt accgccatgt tgacattgat     540
tattgactag ttattaatag taatcaatta cggggtcatt agttcatagc ccatatatgg     600
agttccgcgt tacataactt acggtaaatg gcccgcctgg ctgaccgccc aacgacccc      660 gcccattgac gtcaataatg acgtatgttc ccatagtaac gccaataggg actttccatt     720
gacgtcaatg ggtggagtat ttacggtaaa ctgcccactt ggcagtacat caagtgtatc     780

```
atatgccaag tacgcccct attgacgtca atgacggtaa atggcccgcc tggcattatg     840
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt tccaagtctc cacccattg acgtcaatgg gagtttgttt tggcaccaaa    1020
atcaacggga ctttccaaaa tgtcgtaaca actccgcccc attgacgcaa atgggcggta   1080
ggcgtgtacg gtgggaggtc tatataagca gagctcgttt agtgaaccgt cagatcgcct   1140
ggagacgcca tccacgctgt tttgacctcc atagaagaca ccgggaccga tccagcctcc   1200
gcggccggga acggtgcatt ggaacgcgga ttccccgtgc caagagtgag atctgccacc   1260
atggcgccca tcacggccta ctcccaacag acgcggggcc tacttggttg catcatcact   1320
agccttacag gccgggacaa gaaccaggtc gagggagagg ttcaggtggt tccaccgca    1380
acacaatcct tcctggcgac ctgcgtcaac ggcgtgtgtt ggaccgttta ccatggtgct   1440
ggctcaaaga ccttagccgg cccaaagggg ccaatcaccc agatgtacac taatgtggac   1500
caggacctcg tcggctggca ggcgcccccc ggggcgcgtt ccttgacacc atgcacctgt   1560
ggcagctcag acctttactt ggtcacgaga catgctgacg tcattccggt gcgccggcgg   1620
ggcgacagta gggggagcct gctctccccc aggcctgtct cctacttgaa gggctcttcg   1680
ggtggtccac tgctctgccc ttcggggcac gctgtgggca tcttccgggc tgccgtatgc   1740
acccgggggg ttgcgaaggc ggtggacttt gtgcccgtag agtccatgga aactactatg   1800
cggtctccgg tcttcacgga caactcatcc ccccggccg taccgcagtc atttcaagtg    1860
gcccacctac acgctcccac tggcagcggc aagagtacta aagtgccggc tgcatatgca   1920
gcccaagggt acaaggtgct cgtcctcaat ccgtccgttg ccgctacctt agggtttggg   1980
gcgtatatgt ctaaggcaca cggtattgac cccaacatca gaactggggt aaggaccatt   2040
accacaggcg cccccgtcac atactctacc tatggcaagt tccttgccga tggtggttgc   2100
tctggggcg cttatgacat cataatatgt gatgagtgcc attcaactga ctcgactaca   2160
atcttgggca tcggcacagt cctggaccaa gcggagacgg ctggagcgcg cttgtcgtg   2220
ctcgccaccg ctacgcctcc gggatcggtc accgtgccac acccaaacat cgaggaggtg   2280
gccttgtcta atactggaga gatccccttc tatggcaaag ccatccccat tgaagccatc   2340
agggggggaa ggcatctcat tttctgtcat tccaagaaga gtgcgacga gctcgccgca   2400
aagctgtcag gcctcggaat caacgctgtg gcgtattacc gggggctcga tgtgtccgtc   2460
ataccaacta tcggagacgt cgttgtcgtg gcaacagacg ctctgatgac gggctatacg   2520
ggcgactttg actcagtgat cgactgtaac acatgtgtca cccagacagt cgacttcagc   2580
ttggatccca ccttcaccat tgagacgacg accgtgcctc aagacgcagt gtcgcgctcg   2640
cagcggcggg gtaggactgg caggggtagg agaggcatct acaggtttgt gactccggga   2700
gaacggccct cggcatgtt cgattcctcg gtcctgtgtg agtgctatga cgcgggctgt   2760
gcttggtacg agctcacccc cgccgagacc tcggttaggt tgcgggccta cctgaacaca   2820
ccagggttgc ccgtttgcca ggaccacctg gagttctggg agagtgtctt cacaggcctc   2880
acccacatag atgcacactt cttgtcccag accaagcagg caggagacaa cttcccctac   2940
ctggtagcat accaagccac ggtgtgcgcc agggctcagg ccccacctcc atcatgggat   3000
caaatgtgga agtgtctcat acggctgaaa cctacgctgc acgggccaac acccttgctg   3060
tacaggctgg gagccgtcca aaatgaggtc accctcaccc accccataac caaatacatc   3120
atggcatgca tgtcggctga cctggaggtc gtcactagca cctgggtgct ggtgggcgga   3180
```

```
gtccttgcag ctctggccgc gtattgcctg acaacaggca gtgtggtcat tgtgggtagg    3240
attatcttgt ccgggaggcc ggctattgtt cccgacaggg agtttctcta ccaggagttc    3300
gatgaaatgg aagagtgcgc ctcgcacctc ccttacatcg agcagggaat gcagctcgcc    3360
gagcaattca agcagaaagc gctcgggtta ctgcaaacag ccaccaaaca gcggaggct     3420 gctgctcccg tggtggagtc caagtggcga gcccttgaga cattctgggc gaagcacatg    3480
tggaatttca tcagcgggat acagtactta gcaggcttat ccactctgcc tgggaacccc    3540
gcaatagcat cattgatggc attcacagcc tctatcacca gcccgctcac cacccaaagt    3600
accctcctgt ttaacatctt gggggggtgg gtggctgccc aactcgcccc cccagcgcc    3660 gcttcggctt tcgtgggcgc cggcatcgcc ggtgcggctg ttggcagcat aggccttggg    3720
aaggtgcttg tggacattct ggcgggttat ggagcaggag tggccggcgc gctcgtggcc    3780
ttcaaggtca tgagcggcga gatgccctcc accgaggacc tggtcaatct acttcctgcc    3840
atcctctctc ctggcgccct ggtcgtcggg gtcgtgtgtg cagcaatact gcgtcgacac    3900
gtgggtccgg gagaggggc tgtgcagtgg atgaaccggc tgatagcgtt cgcctcgcgg    3960
ggtaatcatg tttcccccac gcactatgtg cctgagagcg acgccgcagc gcgtgttact    4020
cagatcctct ccagccttac catcactcag ctgctgaaaa ggctccacca gtggattaat    4080
gaagactgct ccacaccgtg ttccggctcg tggctaaggg atgtttggga ctggatatgc    4140
acggtgttga ctgacttcaa gacctggctc cagtccaagc tcctgccgca gctaccggga    4200 gtccctttt tctcgtgcca acgcgggtac aaggagtct ggcggggaga cggcatcatg    4260
caaaccacct gcccatgtgg agcacagatc accggacatg tcaaaaacgg ttccatgagg    4320
atcgtcgggc ctaagacctg cagcaacacg tggcatggaa cattccccat caacgcatac    4380
accacgggcc cctgcacacc ctctccagcg ccaaactatt ctagggcgct gtggcgggtg    4440
gccgctgagg agtacgtgga ggtcacgcgg gtgggggatt tccactacgt gacgggcatg    4500
accactgaca acgtaaagtg cccatgccag gttccggctc ctgaattctt cacggaggtg    4560
gacggagtgc ggttgcacag gtacgctccg gcgtgcaggc ctctcctacg ggaggaggtt    4620
acattccagg tcgggctcaa ccaataccctg gttgggtcac agctaccatg cgagcccgaa    4680
ccggatgtag cagtgctcac ttccatgctc accgacccct cccacatcac agcagaaacg    4740
gctaagcgta ggttggccag ggggtctccc ccctccttgg ccagctcttc agctagccag    4800
ttgtctgcgc cttccttgaa ggcgacatgc actacccacc atgtctctcc ggacgctgac    4860
ctcatcgagg ccaacctcct gtggcggcag gagatgggcg gaacatcac ccgcgtggag    4920 tcggagaaca aggtggtagt cctggactct ttcgacccgc ttcgagcgga ggaggatgag    4980
agggaagtat ccgttccggc ggagatcctg cggaaatcca agaagttccc cgcagcgatg    5040
cccatctggg cgcgcccgga ttacaaccct ccactgttag agtcctggaa ggacccggac    5100
tacgtccctc cggtggtgca cgggtgcccg ttgccaccta tcaaggcccc tccaatacca    5160
cctccacgga gaaagaggac ggttgtccta acagagtcct ccgtgtcttc tgccttagcg    5220
gagctcgcta ctaagacctt cggcagctcc gaatcatcgg ccgtcgacag cggcacggcg    5280
accgcccttc ctgaccaggc ctccgacgac ggtgacaaag gatccgacgt tgagtcgtac    5340
tcctccatgc cccccttga ggggaaccg ggggacccg atctcagtga cgggtcttgg    5400
tctaccgtga gcgaggaagc tagtgaggat gtcgtctgct gctcaatgtc ctacacatgg    5460
acaggcgcct tgatcacgcc atgcgctgcg gaggaaagca agctgcccat caacgcgttg    5520
```

```
agcaactctt tgctgcgcca ccataacatg gtttatgcca caacatctcg cagcgcaggc    5580
ctgcggcaga agaaggtcac ctttgacaga ctgcaagtcc tggacgacca ctaccgggac    5640
gtgctcaagg agatgaaggc gaaggcgtcc acagttaagg ctaaactcct atccgtagag    5700
gaagcctgca agctgacgcc cccacattcg gccaaatcca agtttggcta tggggcaaag    5760
gacgtccgga acctatccag caaggccgtt aaccacatcc actccgtgtg gaaggacttg    5820
ctggaagaca ctgtgacacc aattgacacc accatcatgg caaaaaatga ggttttctgt    5880
gtccaaccag agaaggagg ccgtaagcca gcccgcctta tcgtattccc agatctggga    5940
gtccgtgtat gcgagaagat ggccctctat gatgtggtct ccaccccttcc tcaggtcgtg    6000 atgggctcct catacggatt ccagtactct cctgggcagc gagtcgagtt cctggtgaat    6060
acctggaaat caagaaaaa ccccatgggc ttttcatatg acactcgctg tttcgactca    6120
acggtcaccg agaacgacat ccgtgttgag gagtcaattt accaatgttg tgacttggcc    6180
cccgaagcca gacaggccat aaaatcgctc acagagcggc tttatatcgg gggtcctctg    6240
actaattcaa aagggcagaa ctgcggttat cgccggtgcc gcgcgagcgg cgtgctgacg    6300
actagctgcg gtaacaccct cacatgttac ttgaaggcct ctgcagcctg tcgagctgcg    6360
aagctccagg actgcacgat gctcgtgaac gccgccggcc ttgtcgttat ctgtgaaagc    6420
gcgggaaccc aagaggacgc ggcgagccta cgagtcttca cggaggctat gactaggtac    6480 tctgccccc ccggggaccc gcccaacca gaatacgact tggagctgat aacatcatgt     6540
tcctccaatg tgtcggtcgc ccacgatgca tcaggcaaaa gggtgtacta cctcacccgt    6600
gatcccacca cccccctcgc acgggctgcg tgggaaacag ctagacacac tccagttaac    6660
tcctggctag gcaacattat catgtatgcg cccactttgt gggcaaggat gattctgatg    6720
actcacttct tctccatcct tctagcacag gagcaacttg aaaaagccct ggactgccag    6780
atctacgggg cctgttactc cattgagcca cttgacctac ctcagatcat tgaacgactc    6840
catgccctta gcgcattttc actccatagt tactctccag gtgagatcaa tagggtggct    6900
tcatgcctca ggaaacttgg ggtaccaccc ttgcgagtct ggagacatcg ggccaggagc    6960
gtccgcgcta ggctactgtc ccagggggg agggccgcca cttgtggcaa gtacctcttc    7020
aactgggcag tgaagaccaa actcaaactc actccaatcc cggctgcgtc ccagctggac    7080
ttgtccggct ggttcgttgc tggttacagc ggggagaca tatatcacag cctgtctcgt    7140
gcccgacccc gctggttcat gctgtgccta ctcctacttt ctgtaggggt aggcatctac    7200
ctgctcccca accgataaat ctagagctgt gccttctagt tgccagccat ctgttgtttg    7260 cccctcccc gtgccttcct tgaccctgga aggtgccact cccactgtcc tttcctaata    7320
aaatgaggaa attgcatcgc attgtctgag taggtgtcat tctattctgg ggggtggggt    7380
ggggcagcac agcaaggggg aggattggga agacaatagc aggcatgctg gggatgcggt    7440
gggctctaga tgtagcgatc gcgtgagtag tgtttggggg tgggtgggag cctgcatgat    7500
gggcagaatg actaaaatct gtgttttct gtgtgttgca gcagcatgag cggaagcgcc    7560
tcctttgagg gaggggtatt cagcccttat ctgacggggc gtctcccctc tgggcgggga    7620
gtgcgtcaga atgtgatggg atccacggtg gacggccggc ccgtgcagcc cgcgaactct    7680
tcaaccctga cctacgcgac cctgagctcc tcgtccgtgg acgcagctgc cgccgcagct    7740
gctgcttccg ccgccagcgc cgtgcgcgga atggccctgg cgccggcta ctacagctct    7800 ctggtggcca actcgagttc caccaataat cccgccagcc tgaacgagga gaagctgttg    7860
ctgctgatgg cccagctcga ggccctgacc cagcgcctgg gcgagctgac ccagcaggtg    7920
```

```
gctcagctgc aggcggagac gcgggccgcg gttgccacgg tgaaaaccaa ataaaaaatg    7980
aatcaataaa taaacggaga cggttgttga ttttaacaca gagtcttgaa tctttatttg    8040
atttttcgcg cgcggtaggc cctggaccac cggtctcgat cattgagcac ccggtggatc    8100
ttttccagga cccggtagag gtgggcttgg atgttgaggt acatgggcat gagcccgtcc    8160 cggggtgga ggtagctcca ttgcagggcc tcgtgctcgg gggtggtgtt gtaaatcacc     8220
cagtcatagc aggggcgcag ggcgtggtgc tgcacgatgt cttttgaggag gagactgatg    8280 gccacgggca gccccttggt gtaggtgttg acgaacctat tgagctggga gggatgcatg    8340
cggggggaga tgagatgcat cttggcctgg atcttgagat tggcgatgtt cccgcccaga    8400
tcccgccggg ggttcatgtt gtgcaggacc accagcacgg tgtatccggt gcacttgggg    8460
aatttgtcat gcaacttgga agggaaggcg tgaaagaatt tggagacgcc cttgtgaccg    8520
cccaggtttt ccatgcactc atccatgatg atggcgatgg gcccgtgggc ggcggcctgg    8580
gcaaagacgt ttcgggggtc ggacacatcg tagttgtggt cctgggtgag ctcgtcatag    8640 gccatttta tgaatttggg gcggagggta cccgactggg ggacaaaggt gccctcgatc     8700
ccgggggcgt agttccccctc gcagatctgc atctcccagg ccttgagctc ggagggggg    8760 atcatgtcca cctgcggggc gatgaaaaaa acggtttccg gggcggggga gatgagctgc    8820
gccgaaagca ggttccggag cagctgggac ttgccgcagc cggtgggggcc gtagatgacc    8880 ccgatgaccg gctgcaggtg gtagttgagg gagagacagc tgccgtcctc gcggaggagg    8940
ggggccacct cgttcatcat ctcgcgcaca tgcatgttct cgcgcacgag ttccgccagg    9000
aggcgctcgc cccccagcga gaggagctct tgcagcgagg cgaagttttt cagcggcttg    9060
agcccgtcgg ccatgggcat tttggagagg gtctgttgca agagttccag acggtcccag    9120
agctcggtga tgtgctctag ggcatctcga tccagcagac ctcctcgttt cgcgggttgg    9180
ggcgactgcg ggagtagggc accaggcgat gggcgtccag cgaggccagg gtccggtcct    9240
tccagggtcg cagggtccgc gtcagcgtgg tctccgtcac ggtgaagggg tgcgcgccgg    9300
gctgggcgct tgcgagggtg cgcttcaggc tcatccggct ggtcgagaac cgctcccggt    9360
cggcgccctg cgcgtcggcc aggtagcaat tgagcatgag ttcgtagttg agcgcctcgg    9420
ccgcgtggcc cttggcgcgg agcttacctt tggaagtgtg tccgcagacg gacagagga    9480 gggacttgag ggcgtagagc ttgggggcga ggaagacgga ctcgggggcg taggcgtccg    9540
cgccgcagct ggcgcagacg gtctcgcact ccacgagcca ggtgaggtcg ggcggtcgg    9600 ggtcaaaaac gaggtttcct ccgtgctttt tgatgcgttt cttacctctg gtctccatga    9660
gctcgtgtcc ccgctgggtg acaaagaggc tgtccgtgtc cccgtagacc gactttatgg    9720
gccggtcctc gagcggggtg ccgcggtcct cgtcgtagag gaaccccgcc cactccgaga    9780
cgaaggcccg ggtccaggcc agcacgaagg aggccacgtg ggagggggtag cggtcgttgt    9840 ccaccagcgg gtccaccttc tccagggtat gcaagcacat gtcccctcg tccacatcca     9900 ggaaggtgat tggcttgtaa gtgtaggcca cgtgaccggg ggtcccggcc ggggggtat     9960 aaaagggggc gggcccctgc tcgtcctcac tgtcttccgg atcgctgtcc aggagcgcca   10020
gctgttgggg taggtattcc ctctcgaagg cgggcatgac ctcggcactc aggttgtcag   10080
tttctagaaa cgaggaggat ttgatattga cggtgccgtt ggagacgcct ttcatgagcc   10140
cctcgtccat ctggtcagaa aagacgatct ttttgttgtc gagcttggtg gcgaaggagc   10200
cgtagagggc gttggagagc agcttggcga tggagcgcat ggtctggttc ttttccttgt   10260
```

```
cggcgcgctc cttggcggcg atgttgagct gcacgtactc gcgcgccacg cacttccatt   10320
cggggaagac ggtggtgagc tcgtcgggca cgattctgac ccgccagccg cggttgtgca   10380
gggtgatgag gtccacgctg gtggccacct cgccgcgcag gggctcgttg gtccagcaga   10440
ggcgcccgcc cttgcgcgag cagaaggggg gcagcgggtc cagcatgagc tcgtcggggg   10500
ggtcggcgtc cacggtgaag atgccgggca ggagctcggg gtcgaagtag ctgatgcagg   10560
tgcccagatc gtccagactt gcttgccagt cgcgcacggc cagcgcgcgc tcgtaggggc   10620
tgaggggcgt gccccagggc atgggtgcg tgagcgcgga ggcgtacatg ccgcagatgt    10680
cgtagacgta gaggggctcc tggaggacgc cgatgtaggt ggggtagcag cgccccccgc   10740
ggatgctggc gcgcacgtag tcgtacagct cgtgcgaggg gcgaggagc cccgtgccga    10800
gattggagcg ctgcggcttt tcggcgcggt agacgatctg gcggaagatg gcgtgggagt   10860
tggaggagat ggtgggcctc tggaagatgt tgaagtgggc atggggcagt ccgaccgagt   10920
ccctgatgaa gtgggcgtag gagtcctgca gcttggcgac gagctcggcg gtgacgagga   10980
cgtccagggc gcagtagtcg agggtctctt ggatgatgtc gtacttgagc tggcccttct   11040
gcttccacag ctcgcggttg agaaggaact cttcgcggtc cttccagtac tcttcgaggg   11100
ggaacccgtc ctgatcggca cggtaagagc ccaccatgta gaactggttg acggccttgt   11160
aggcgcagca gcccttctcc acggggaggg cgtaagcttg cgcggccttg cgcagggagg   11220
tgtgggtgag ggcgaaggtg tcgcgcacca tgactttgag gaactggtgc ttgaagtcga   11280
ggtcgtcgca gccgccctgc tcccagagct ggaagtccgt gcgcttcttg taggcggggt   11340
tgggcaaagc gaaagtaaca tcgttgaaga ggatcttgcc cgcgcggggc atgaagttgc   11400
gagtgatgcg gaaaggctgg ggcacctcgg cccggttgtt gatgacctgg gcggcgagga   11460
cgatctcgtc gaagccgttg atgttgtgcc cgacgatgta gagttccacg aatcgcgggc   11520
ggcccttgac gtggggcagc ttcttgagct cgtcgtaggt gagctcggcg gggtcgctga   11580
gcccgtgctg ctcgagggcc cagtcggcga cgtgggggtt ggcgctgagg aaggaagtcc   11640
agagatccac ggccagggcg gtctgcaagc ggtcccggta ctgacggaac tgctggccca   11700
cggccatttt tcggggggtg acgcagtaga aggtgcgggg gtcgccgtgc cagcggtccc   11760
acttgagctg gagggcgagg tcgtgggcga gctcgacgag cggcgggtcc ccggagagtt   11820
tcatgaccag catgaagggg acgagctgct tgccgaagga ccccatccag gtgtaggttt   11880
ccacatcgta ggtgaggaag agcctttcgg tgcgaggatg cgagccgatg gggaagaact   11940
ggatctcctg ccaccagttg gaggaatggc tgttgatgtg atggaagtag aaatgccgac   12000
ggcgcgccga gcactcgtgc ttgtgtttat acaagcgtcc gcagtgctcg caacgctgca   12060
cgggatgcac gtgctgcacg agctgtacct gggttccttt gacgaggaat ttcagtgggc   12120
agtggagcgc tggcggctgc atctggtgct gtactacgtc ctggccatcg gcgtggccat   12180
cgtctgcctc gatggtggtc atgctgacga gcccgcgcgg gaggcaggtc cagacctcgg   12240
ctcggacggg tcgagagcg aggacgaggg cgcgcaggcc ggagctgtcc agggtcctga    12300
gacgctgcgg agtcaggtca gtgggcagcg gcggcgcgcg gttgacttgc aggagctttt   12360
ccagggcgcg cggggaggtcc agatggtact tgatctccac ggcgccgttg gtggcgacgt   12420
ccacggcttg cagggtcccg tgccctgggg gcgccaccac cgtgccccgt ttcttcttgg   12480
gcggcggcgc ctccatgctt agaagcggcg gcgaggacgc gcgccgggcg caggggcgg    12540
ctcgggccc ggaggcaggg gcggcagggg cacgtcggcg ccgcgcgcgg gcaggttctg    12600
gtactgcgcc cggagaagac tggcgtgagc gacgacgcga cggttgacgt cctggatctg   12660
```

```
acgcctctgg gtgaaggcca cgggacccgt gagtttgaac ctgaaagaga gttcgacaga    12720
atcaatctcg gtatcgttga cggcggcctg ccgcaggatc tcttgcacgt cgcccgagtt    12780
gtcctggtag gcgatctcgg tcatgaactg ctcgatctcc tcctcctgaa ggtctccgcg    12840
gccggcgcgc tcgacggtgg ccgcgaggtc gttggagatg cggcccatga gctgcgagaa    12900
ggcgttcatg ccggcctcgt tccagacgcg gctgtagacc acggctccgt cggggtcgcg    12960
cgcgcgcatg accacctggg cgaggttgag ctcgacgtgg cgcgtgaaga ccgcgtagtt    13020
gcagaggcgc tggtagaggt agttgagcgt ggtggcgatg tgctcggtga cgaagaagta    13080
catgatccag cggcggagcg gcatctcgct gacgtcgccc agggcttcca agcgctccat    13140
ggcctcgtag aagtccacgg cgaagttgaa aaactgggag ttgcgcgccg agacggtcaa    13200
ctcctcctcc agaagacgga tgagctcggc gatggtggcg cgcacctcgc gctcgaaggc    13260 cccgggggc tcctcttcca tttcctcctc ttcctcctcc actaacatct cttctacttc    13320
ctcctcagga ggcggcggcg ggggaggggc cctgcgtcgc cggcggcgca cgggcagacg    13380
gtcgatgaag cgctcgatgg tctccccgcg ccggcgacgc atggtctcgg tgacggcgcg    13440
cccgtcctcg cggggccgca gcgtgaagac gccgccgcgc atctccaggt ggccgccggg    13500
ggggtctccg ttgggcaggg agagggcgct gacgatgcat cttatcaatt gacccgtagg    13560
gactccgcgc aaggacctga gcgtctcgag atccacggga tccgaaaacc gctgaacgaa    13620
ggcttcgagc cagtcgcagt cgcaaggtag gctgagcccg gtttcttgtt cttcgggtat    13680
ttggtcggga ggcgggcggg cgatgctgct ggtgatgaag ttgaagtagg cggtcctgag    13740
acggcggatg gtggcgagga gcaccaggtc cttgggcccg gcttgctgga tgcgcagacg    13800
gtcggccatg ccccaggcgt ggtcctgaca cctggcgagg tccttgtagt agtcctgcat    13860
gagccgctcc acgggcacct cctcctcgcc cgcgcggccg tgcatgcgcg tgagcccgaa    13920
cccgcgctgc ggctggacga gcgccaggtc ggcgacgacg cgctcggcga ggatggcctg    13980
ctggatctgg gtgagggtgg tctggaagtc gtcgaagtcg acgaagcggt ggtaggctcc    14040
ggtgttgatg gtgtaggagc agttggccat gacggaccag ttgacggtct ggtggccggg    14100
gcgcacgagc tcgtggtact tgaggcgcga gtaggcgcgc gtgtcgaaga tgtagtcgtt    14160
gcaggtgcgc acgaggtact ggtatccgac gaggaagtgc ggcggcggct ggcggtagag    14220
cggccatcgc tcgtggcgg gggcgccggg cgcgaggtcc tcgagcatga ggcggtggta    14280
gccgtagatg tacctggaca tccaggtgat gccggcggcg gtggtggagg cgcgcgggaa    14340
ctcgcggacg cggttccaga tgttgcgcag cggcaggaag tagttcatgg tggccgcggt    14400
ctggcccgtg aggcgcgcgc agtcgtggat gctctagaca tacgggcaaa aacgaaagcg    14460
gtcagcggct cgactccgtg gcctggaggc taagcgaacg ggttgggctg cgcgtgtacc    14520
ccggttcgaa tctcgaatca ggctggagcc gcagctaacg tggtactggc actccgtct    14580 cgacccaagc ctgctaacga aacctccagg atacggaggc gggtcgtttt ttggccttgg    14640
tcgctggtca tgaaaaacta gtaagcgcgg aaagcggccg cccgcgatgg ctcgctgccg    14700
tagtctggag aaagaatcgc cagggttgcg ttgcggtgtg cccgggttcg agcctcagcg    14760
ctcggcgccg gccggattcc gcggctaacg tgggcgtggc tgccccgtcg tttccaagac    14820
cccttagcca gccgacttct ccagttacgg agcgagcccc tctttttttc ttgtgttttt    14880
gccagatgca tcccgtactg cggcagatgc gcccccaccc tccaccacaa ccgccctac    14940 cgcagcagca gcaacagccg gcgcttctgc ccccgcccca gcagcagcag ccagccacta    15000
```

```
ccgcggcggc cgccgtgagc ggagccggcg ttcagtatga cctggccttg gaagagggcg    15060
aggggctggc gcggctgggg gcgtcgtcgc cggagcggca cccgcgcgtg cagatgaaaa    15120
gggacgctcg cgaggcctac gtgcccaagc agaacctgtt cagagacagg agcggcgagg    15180
agcccgagga gatgcgcgcc tcccgcttcc acgcggggcg ggagctgcgg cgcggcctgg    15240
accgaaagcg ggtgctgagg gacgaggatt tcgaggcgga cgagctgacg gggatcagcc    15300
ccgcgcgcgc gcacgtggcc gcggccaacc tggtcacggc gtacgagcag accgtgaagg    15360
aggagagcaa cttccaaaaa tccttcaaca accacgtgcg cacgctgatc gcgcgcgagg    15420
aggtgaccct gggcctgatg cacctgtggg acctgctgga ggccatcgtg cagaacccca    15480
cgagcaagcc gctgacggcg cagctgtttc tggtggtgca gcacagtcgg acaacgaga    15540
cgttcaggga ggcgctgctg aatatcaccg agcccgaggg ccgctggctc ctggacctgg    15600
tgaacattct gcagagcatc gtggtgcagg agcgcgggct gccgctgtcc gagaagctgg    15660
cggccatcaa cttctcggtg ctgagcctgg gcaagtacta cgctaggaag atctacaaga    15720
ccccgtacgt gcccatagac aaggaggtga agatcgatgg gttttacatg cgcatgaccc    15780
tgaaagtgct gaccctgagc gacgatctgg gggtgtaccg caacgacagg atgcaccgcg    15840
cggtgagcgc cagccgccgg cgcgagctga gcgaccagga gctgatgcac agcctgcagc    15900
gggccctgac cggggccggg accgaggggg agagctactt tgacatgggc gcggacctgc    15960
gctggcagcc cagccgccgg gccttggaag ctgccggcgg cgtgccctac gtggaggagg    16020
tggacgatga ggaggaggag ggcgagtacc tggaagactg atggcgcgac cgtatttttg    16080
ctagatgcag caacagccac cgccgccgcc tcctgatccc gcgatgcggg cggcgctgca    16140
gagccagccg tccggcatta actcctcgga cgattggacc caggccatgc aacgcatcat    16200
ggcgctgacg acccgcaatc ccgaagcctt tagacagcag cctcaggcca accggctctc    16260
ggccatcctg gaggccgtgg tgccctcgcg ctcgaacccc acgcacgaga aggtgctggc    16320
catcgtgaac gcgctggtgg agaacaaggc catccgcggc gacgaggccg gctggtgta    16380
caacgcgctg ctggagcgcg tggcccgcta caacagcacc aacgtgcaga cgaacctgga    16440
ccgcatggtg accgacgtgc gcgaggcggt gtcgcagcgc gagcggttcc accgcgagtc    16500
gaacctgggc tccatggtgg cgctgaacgc cttcctgagc acgcagcccg ccaacgtgcc    16560
ccggggccag gaggactaca ccaacttcat cagcgcgctg cggctgatgg tggccgaggt    16620
gccccagagc gaggtgtacc agtcggggcc ggactacttc ttccagacca gtcgccaggg    16680
cttgcagacc gtgaacctga gccaggcttt caagaacttg cagggactgt ggggcgtgca    16740
ggccccggtc ggggaccgcg cgacggtgtc gagcctgctg acgccgaact cgcgcctgct    16800
gctgctgctg gtggcgccct tcacggacag cggcagcgtg agccgcgact cgtacctggg    16860
ctacctgctt aacctgtacc gcgaggccat cgggcaggcg cacgtggacg agcagaccta    16920
ccaggagatc acccacgtga gccgcgcgct gggccaggag gacccgggca acctggaggc    16980
caccctgaac ttcctgctga ccaaccggtc gcagaagatc ccgccccagt acgcgctgag    17040
caccgaggag gagcgcatcc tgcgctacgt gcagcagagc gtggggctgt tcttgatgca    17100
ggagggggcc acgcccagcg ccgcgctcga catgaccgcg cgcaacatgg agcccagcat    17160
gtacgcccgc aaccgcccgt tcatcaataa gctgatggac tacttgcatc gggcggccgc    17220
catgaactcg gactacttta ccaacgccat cttgaacccg cactggctcc cgccgccgg    17280
gttctacacg ggcgagtacg acatgcccga ccccaacgac gggttcctgt gggacgcgt    17340
ggacagcagc gtgttctcgc cgcggcccac caccaccacc gtgtggaaga agagggcgg    17400
```

```
ggaccggcgg ccgtcctcgg cgctgtccgg tcgcgcgggt gctgccgcgg cggtgcccga   17460
ggctgccagc cccttcccga gcctgccctt ttcgctgaac agcgtgcgca gcagcgagct   17520
gggtcggctg acgcggccgc gcctgctggg cgaggaggag tacctgaacg actccttgtt   17580
gaagcccgag cgcgagaaga acttcccaa taacggata gagagcctgg tggacaagat    17640
gagccgctgg aagacgtacg cgcacgagca cagggacgag ccccgagcta gcagcgcagg   17700
cacccgtaga cgccagcggc acgacaggca gcggggactg gtgtgggacg atgaggattc   17760
cgccgacgac agcagcgtgt tggacttggg tgggagtggt ggtggtaacc cgttcgctca   17820
cctgcgcccc cgtatcgggc gcctgatgta agaatctgaa aaataaaag acggtactca    17880 ccaaggccat ggcgaccagc gtgcgttctt ctctgttgtt tgtagtagta tgatgaggcg   17940
cgtgtacccg gagggtcctc ctccctcgta cgagagcgtg atgcagcagg cggtggcggc   18000
ggcgatgcag ccccgctgg aggcgcctta cgtgcccccg cggtacctgg cgcctacgga    18060
ggggcggaac agcattcgtt actcggagct ggcaccttg tacgatacca cccggttgta    18120
cctggtggac aacaagtcgg cggacatcgc ctcgctgaac taccagaacg accacagcaa   18180
cttcctgacc accgtggtgc agaacaacga tttcacccc acggaggcca gcacccagac    18240
catcaacttt gacgagcgct cgcggtgggg cggccagctg aaaaccatca tgcacaccaa   18300
catgcccaac gtgaacgagt tcatgtacag caacaagttc aaggcgcggg tgatggtctc   18360
gcgcaagacc cccaacgggg tcacggtagg ggatgattat gatggtagtc aggacgagct   18420
gacctacgag tgggtggagt ttgagctgcc cgagggcaac ttctcggtga ccatgaccat   18480
cgatctgatg aacaacgcca tcatcgacaa ctacttggcg gtggggcggc agaacggggt   18540
gctggagagc gacatcggcg tgaagttcga cacgcgcaac ttccggctgg gctgggaccc   18600
cgtgaccgag ctggtgatgc cgggcgtgta caccaacgag gccttccacc ccgacatcgt   18660
cctgctgccc ggctgcggcg tggacttcac cgagagccgc ctcagcaacc tgctgggcat   18720
ccgcaagcgg cagcccttcc aggagggctt ccagatcctg tacgaggacc tggaggggg    18780 caacatcccc gcgctcttgg atgtcgaagc ctatgaagaa agtaaggaaa agcagaggc    18840 tgaggcaact acagccgtgg ctaccgccgc gactgtggca gatgccactg tcaccagggg   18900
cgatacattc gccacccagg cggaggaagc agccgcccta gcggcgaccg atgatagtga   18960
aagtaagata gtcatcaagc cggtggagaa ggacagcaag aacaggagct acaacgttct   19020
accggatgga aagaacaccg cctaccgcag ctggtacctg gcctacaact acggcgaccc   19080
cgagaagggc gtgcgctcct ggacgctgct caccacctcg gacgtcacct gcggcgtgga   19140
gcaagtctac tggtcgctgc ccgacatgat gcaagacccg gtcaccttcc gctccacgcg   19200
acaagttagc aactacccgg tggtgggcgc cgagctcctg cccgtctact ccaagagctt   19260
cttcaacgag caggccgtct actcgcagca gctgcgtgcc ttcacctcgc tcacgcacgt   19320
cttcaaccgc ttccccgaga accagatcct cgtccgcccg cccgcgccca ccattaccac   19380
cgtcagtgaa aacgttcctg ctctcacaga tcacgggacc ctgccgctgc gcagcagtat   19440
ccggggagtc cagcgcgtga ccgtcactga cgccagacgc cgcacctgcc cctacgtcta   19500
caaggccctg ggcgtagtcg cgccgcgcgt cctctcgagc cgcaccttct aaaaaatgtc   19560
cattctcatc tcgcccagta ataacaccgg ttggggcctg cgcgcgccca gcaagatgta   19620
cggaggcgct cgccaacgct ccacgcaaca cccgtgcgc gtgcgcgggc acttccgcgc    19680
tccctggggc gccctcaagg gccgcgtgcg ctcgcgcacc accgtcgacg acgtgatcga   19740
```

| | |
|---|---|
| ccaggtggtg gccgacgcgc gcaactacac gcccgccgcc gcgcccgcct ccaccgtgga | 19800 |
| cgccgtcatc gacagcgtgg tggccgacgc gcgccggtac gcccgcgcca agagccggcg | 19860 |
| gcggcgcatc gcccggcggc accggagcac ccccgccatg cgcgcggcgc gagccttgct | 19920 |
| gcgcagggcc aggcgcacgg gacgcagggc catgctcagg gcggccagac gcgcggcctc | 19980 |
| cggcagcagc agcgccggca ggacccgcag acgcgcggcc acgcggcgg cggcggccat | 20040 |
| cgccagcatg tcccgcccgc ggcgcggcaa cgtgtactgg gtgcgcgacg ccgccaccgg | 20100 |
| tgtgcgcgtg cccgtgcgca cccgcccccc tcgcacttga agatgctgac ttcgcgatgt | 20160 |
| tgatgtgtcc cagcggcgag gaggatgtcc aagcgcaaat acaaggaaga gatgctccag | 20220 |
| gtcatcgcgc ctgagatcta cggccccgcg gcggcggtga aggaggaaag aaagcccgc | 20280 |
| aaactgaagc gggtcaaaaa ggacaaaaag gaggaggaag atgacggact ggtggagttt | 20340 |
| gtgcgcgagt tcgcccccg gcggcgcgtg cagtggcgcg ggcggaaagt gaaaccggtg | 20400 |
| ctgcggcccg gcaccacggt ggtcttcacg cccggcgagc gttccggctc cgcctccaag | 20460 |
| cgctcctacg acgaggtgta cggggacgag gacatcctcg agcaggcggt cgagcgtctg | 20520 |
| ggcgagtttg cttacggcaa gcgcagccgc cccgcgccct tgaaagagga ggcggtgtcc | 20580 |
| atcccgctgg accacggcaa ccccacgccg agcctgaagc cggtgaccct gcagcaggtg | 20640 |
| ctgccgagcg cggcgccgcg ccggggcttc aagcgcgagg gcggcgagga tctgtacccg | 20700 |
| accatgcagc tgatggtgcc caagcgccag aagctggagg acgtgctgga gcacatgaag | 20760 |
| gtggaccccg aggtgcagcc cgaggtcaag gtgcggccca tcaagcaggt ggcccccggc | 20820 |
| ctgggcgtgc agaccgtgga catcaagatc cccacggagc ccatggaaac gcagaccgag | 20880 |
| cccgtgaagc ccagcaccag caccatggag gtgcagacgg atccctggat gccagcggct | 20940 |
| tccaccacca ccactcgccg aagacgcaag tacggcgcgg ccagcctgct gatgcccaac | 21000 |
| tacgcgctgc atccttccat catccccacg ccgggctacc gcggcacgcg cttctaccgc | 21060 |
| ggctacacca gcagccgccg ccgcaagacc accaccgcc gcgtcgtcg cagccgccgc | 21120 |
| agcagcaccg cgacttccgc cttggtgcgg agagtgtatc gcagcgggcg cgagcctctg | 21180 |
| accctgccgc gcgcgcgcta ccacccgagc atcgccattt aactaccgcc tcctacttgc | 21240 |
| agatatggcc ctcacatgcc gcctccgcgt ccccattacg ggctaccgag aagaaagcc | 21300 |
| gcgccgtaga aggctgacgg ggaacgggct gcgtcgccat caccaccggc ggcggcgcgc | 21360 |
| catcagcaag cggttggggg gaggcttcct gcccgcgctg atccccatca tcgccgcggc | 21420 |
| gatcggggcg atccccggca tagcttccgt ggcggtgcag gcctctcagc gccactgaga | 21480 |
| cacaaaaaag catggatttg taataaaaaa atggactgac gctcctggtc ctgtgatgtg | 21540 |
| tgttttaga tggaagacat caatttttcg tccctggcac cgcgacacgg cacgcggccg | 21600 |
| tttatgggca cctggagcga catcggcaac agccaactga acggggcgc cttcaattgg | 21660 |
| agcagtctct ggagcgggct taagaatttc gggtccacgc tcaaaaccta tggcaacaag | 21720 |
| gcgtggaaca gcagcacagg gcaggcgctg agggaaaagc tgaaagagca gaacttccag | 21780 |
| cagaaggtgg tcgatggcct ggcctcgggc atcaacgggg tggtggacct ggccaaccag | 21840 |
| gccgtgcaga aacagatcaa cagccgcctg acgcgggtcc cgcccgcggg gtccgtggag | 21900 |
| atgcccagg tggaggagga gctgcctccc ctggacaagc gcggcgacaa gcgaccgcgt | 21960 |
| cccgacgcgg aggagacgct gctgacgcac acgacgagc cgccccgta cgaggaggcg | 22020 |
| gtgaaactgg gtctgcccac cacgcggccc gtggcgcctc tggccaccgg ggtgctgaaa | 22080 |
| cccagcagca gcagccagcc cgcgaccctg gacttgcctc cgcctgcttc ccgcccctcc | 22140 |

-continued

```
acagtggcta agcccctgcc gccggtggcc gtcgcgtcgc gcgcccccg aggccgcccc   22200
caggcgaact ggcagagcac tctgaacagc atcgtgggtc tgggagtgca gagtgtgaag   22260
cgccgccgct gctattaaaa gacactgtag cgcttaactt gcttgtctgt gtgtgtatat   22320
gtatgtccgc cgaccagaag gaggaagagg cgcgtcgccg agttgcaaga tggccacccc   22380
atcgatgctg ccccagtggg cgtacatgca catcgccgga caggacgctt cggagtacct   22440
gagtccgggt ctggtgcagt tcgcccgcgc cacagacacc tacttcagtc tggggaacaa   22500
gtttaggaac cccacggtgg cgcccacgca cgatgtgacc accgaccgca gccagcggct   22560
gacgctgcgc ttcgtgcccg tggaccgcga ggacaacacc tactcgtaca aagtgcgcta   22620
cacgctggcc gtgggcgaca accgcgtgct ggacatggcc agcacctact ttgacatccg   22680
cggcgtgctg gatcggggcc ccagcttcaa accctactcc ggcaccgcct acaacagcct   22740
agctcccaag ggagcgccca cacctcaca gtggaaggat tccgacagca aaatgcatac   22800
ttttggagtt gctgccatgc ccggtgttgt tggtaaaaaa atagaagccg atggtctgcc   22860
tattggaata gattcatcct ctggaactga caccataatt tatgctgata aactttcca   22920
accagagcca caggttggaa gtgacagttg ggtcgacacc aatggtgcag aggaaaaata   22980
tggaggtaga gctcttaagg acactacaaa catgaagccc tgctacggtt cttttgccag   23040
gcctaccaac aaagaaggtg gacaggctaa cataaaagat tctgaaactg ccagcactac   23100
tcctaactat gatatagatt tggcattctt tgacagcaaa aatattgcag ctaactacga   23160
tccagatatt gtaatgtaca cagaaaaatgt tgagttgcaa actccagata ctcatattgt   23220
gtttaagcca ggaacttcag atgaaagttc agaagccaat ttgggccagc aggccatgcc   23280
caacagaccc aactcatcg ggttcagaga caactttatc gggctcatgt actcaaacag   23340
cactggcaat atgggtgtac tggctggtca ggcctcccag ctaaatgctg tggtggactt   23400
gcaggacaga aacaccgaac tgtcctacca gctcttgctt gactctctgg gtgacagaac   23460
caggtatttc agtatgtgga atcaggcggt ggacagctat gaccccgatg tgcgcattat   23520
tgaaaatcac ggtgtggagg atgaactccc caattattgc ttccctttga atggtgtagg   23580
ctttacagat acttaccagg gtgttaaagt taagacagat acagccgcta ctggtaccaa   23640
tggaacgcag tgggacaaag atgataccac agtcagcact gccaatgaga tccactcagg   23700
caatcctttc gccatggaga tcaacatcca ggccaacctg tggcggaact tcctctacgc   23760
gaacgtggcg ctgtacctgc ccgactccta caagtacacg ccggccaaca tcacgctgcc   23820
gaccaacacc aacacctacg attacatgaa cggccgcgtg gtggcgccct cgctggtgga   23880
cgcctacatc aacatcgggg cgcgctggtc gctggaccc atggacaacg tcaacccctt   23940
caaccaccac cgcaacgcgg gcctgcgcta ccgctccatg ctcctgggca cgggcgcta   24000
cgtgcccttc cacatccagg tgccccaaaa gttttcgcc atcaagagcc tcctgctcct   24060
gcccgggtcc tacacctacg agtggaactt ccgcaaggac gtcaacatga tcctgcagag   24120
ctccctcggc aacgacctgc gcacggacgg ggcctccatc gccttcacca gcatcaacct   24180
ctacgccacc ttcttcccca tggcgcacaa cacgcctcc acgctcgagg ccatgctgcg   24240
caacgacacc aacgaccagt ccttcaacga ctacctctcg gcggcaaca tgctctaccc   24300
catcccggcc aacgccacca acgtgcccat ctccatcccc tcgcgcaact gggccgcctt   24360
ccgcggatgg tccttcacgc gcctcaagac ccgcagacg ccctcgctcg gctccggtt   24420
cgaccctac ttcgtctact cgggctccat cccctacctc gacggcacct tctacctcaa   24480
```

-continued

```
ccacaccttc aagaaggtct ccatcacctt cgactcctcc gtcagctggc ccggcaacga   24540
ccgcctcctg acgcccaacg agttcgaaat caagcgcacc gtcgacggag agggatacaa   24600
cgtggcccag tgcaacatga ccaaggactg gttcctggtc cagatgctgg cccactacaa   24660
catcggctac cagggcttct acgtgcccga gggctacaag gaccgcatgt actccttctt   24720
ccgcaacttc cagcccatga gccgccaggt cgtggacgag gtcaactaca aggactacca   24780
ggccgtcacc ctggcctacc agcacaacaa ctcgggcttc gtcggctacc tcgcgcccac   24840
catgcgccag ggccagccct accccgccaa ctaccccctac ccgctcatcg gcaagagcgc   24900
cgtcgccagc gtcacccaga aaagttcct ctgcgaccgg tcatgtggc gcatcccctt   24960 ctccagcaac ttcatgtcca tgggcgcgct caccgacctc ggccagaaca tgctctacgc   25020
caactccgcc cacgcgctag acatgaattt cgaagtcgac cccatggatg agtccaccct   25080
tctctatgtt gtcttcgaag tcttcgacgt cgtccgagtg caccagcccc accgcggcgt   25140
catcgaggcc gtctacctgc gcacgcccctt ctcggccggc aacgccacca cctaaagccc   25200
cgctcttgct tcttgcaaga tgacggcctg tggctccggc gagcaggagc tcagggccat   25260
cctccgcgac ctgggctgcg ggccctgctt cctgggcacc ttcgacaagc gcttcccggg   25320
attcatggcc ccgcacaagc tggcctgcgc catcgtcaac acggccggcc gcgagaccgg   25380
gggcgagcac tggctggcct tcgcctggaa cccgcgctcc cacacctgct acctcttcga   25440 cccccttcggg ttctcggacg agcgcctcaa gcagatctac cagttcgagt acgagggcct   25500
gctgcgccgc agcgccctgg ccaccgagga ccgctgcatc accctggaaa agtccaccca   25560
gaccgtgcag ggtccgcgct cggccgcctg cgggctcttc tgctgcatgt tcctgcacgc   25620
cttcgtgcac tggcccgacc gccccatgga caagaacccc accatgaact gctgacgggg   25680
ggtgcccaac ggcatgctcc agtcgcccca ggtggaaccc accctgcgcc gcaaccagga   25740
ggcgctctac cgcttcctca acgcccactc cgcctactttt cgctcccacc gcgcgcgcat   25800
cgagaaggcc accgccttcg accgcatgaa tcaagacatg taaactgtgt gtatgtgaat   25860
gctttattca tcataataaa cagcacatgt ttatgccacc ttctctgagg ctctgacttt   25920
atttagaaat cgaaggggtt ctgccggctc tcggcgtgcc ccgcgggcag ggatacgttg   25980
cggaactggt acttgggcag ccacttgaac tcggggatca gcagcttcgg cacggggagg   26040
tcggggaacg agtcgctcca cagcttgcgc gtgagttgca gggcgcccag caggtcgggc   26100
gcggagatct tgaaatcgca gttgggaccc gcgttctgcg cgcgagagtt gcggtacacg   26160
gggttgcagc actggaacac catcagggcc gggtgcttca cgctcgccag caccgtcgcg   26220
tcggtgatgc cctccacgtc cagatcctcg gcgttggcca tcccgaaggg ggtcatcttg   26280
caggtctgcc gccccatgct gggcacgcag ccgggcttgt ggttgcaatc gcagtgcagg   26340
gggatcagca tcatctgagc ctgctcggag ctcatgcccg ggtacatggc cttcatgaaa   26400
gcctccagct ggcggaaggc ctgctgcgcc ttgccgccct cggtgaagaa gaccccacag   26460
gacttgctag agaactggtt ggtggcgcag cccgcgtcgt gcacgcagca gcgcgcgtcg   26520
ttgttggcca gctgcaccac gctgcgcccc cagcggttct gggtgatctt ggcccggtcg   26580
gggttctcct tcagcgcgcg ctgccgttc tcgctcgcca catccatctc gatcgtgtgc   26640
tccttctgga tcatcacggt cccgtgcagg caccgcagct tgccctcggc tcggtgcac   26700 ccgtgcagcc acagcgcgca gccggtgcac tcccagttct tgtgggcgat ctgggagtgc   26760
gagtgcacga agccctgcag gaagcggccc atcatcgtgg tcagggtctt gttgctggtg   26820
aaggtcagcg ggatgccgcg gtgctcctcg ttcacataca ggtggcagat gcggcggtac   26880
```

```
acctcgccct gctcgggcat cagctggaag gcggacttca ggtcgctctc cacgcggtac  26940
cgctccatca gcagcgtcat cacttccatg cccttctccc aggccgaaac gatcggcagg  27000
ctcaggggt tcttcaccgt catcttagtc gccgccgccg aagtcagggg gtcgttctcg    27060
tccagggtct caaacactcg cttgccgtcc ttctcggtga tgcgcacggg gggaaagctg   27120
aagcccacgg ccgccagctc ctcctcggcc tgcctttcgt cctcgctgtc ctggctgatg   27180
tcttgcaaag gcacatgctt ggtcttgcgg ggtttctttt tgggcggcag aggcggcggc   27240
ggagacgtgc tgggcgagcg cgagttctcg ctcaccacga ctatttcttc ttcttggccg   27300
tcgtccgaga ccacgcggcg gtaggcatgc ctcttctggg gcagaggcgg aggcgacggg   27360
ctctcgcggt tcggcgggcg gctggcagag ccccttccgc gttcggggt gcgctcctgg    27420
cggcgctgct ctgactgact tcctccgcgg ccggccattg tgttctccta gggagcaaca   27480
agcatggaga ctcagccatc gtcgccaaca tcgccatctg cccccgccgc cgacgagaac   27540
cagcagcagc agaatgaaag cttaaccgcc ccgccgccca gccccacctc cgacgccgcc   27600
gcggccccag acatgcaaga gatggaggaa tccatcgaga ttgacctggg ctacgtgacg   27660
cccgcggagc acgaggagga gctggcagcg cgcttttcag ccccggaaga gaaccaccaa   27720
gagcagccag agcaggaagc agagagcgag cagcagcagg ctgggctcga gcatggcgac   27780
tacctgagcg gggcagagga cgtgctcatc aagcatctgg cccgcaaag catcatcgtc   27840
aaggacgcgc tgctcgaccg cgccgaggtg cccctcagcg tggcggagct cagccgcgcc   27900
tacgagcgca acctcttctc gccgcgcgtg cccccaagc gccagcccaa cggcacctgc    27960
gagcccaacc cgcgcctcaa cttctaccg gtcttcgcgg tgcccgaggc cctggccacc    28020
taccacctct ttttcaagaa ccaaaggatc ccgtctcct gccgcgccaa ccgcacccgc    28080
gccgacgccc tgctcaacct gggtcccggc gccgcctac ctgatatcac ctccttggaa    28140
gaggttccca agatcttcga gggtctgggc agcgacgaga ctcggccgc gaacgctctg    28200
caaggaagcg gagaggagca tgagcaccac agcgccctgg tggagttgga aggcgacaac   28260
gcgcgcctgg cggtgctcaa gcgcacggtc gagctgaccc acttcgccta cccggcgctc   28320
aacctgcccc ccaaggtcat gagcgccgtc atggaccagg tgctcatcaa gcgcgcctcg   28380
cccctctcag aggaggagat gcaggacccc gagagctcgg acgagggcaa gcccgtggtc   28440
agcgacgagc agctggcgcg ctggctggga gcgagcagca ccccccagag cctgaaagag    28500
cggcgcaagc tcatgatggc cgtggtcctg gtgaccgtgg agctggagtg tctgcgccgc   28560
ttcttcgccg acgcggagac cctgcgcaag gtcgaggaga acctgcacta cctcttcagg   28620
cacgggttcg tgcgccaggc ctgcaagatc tccaacgtgg agctgaccaa cctggtctcc   28680
tacatgggca tcctgcacga gaaccgcctg ggcagaacg tgctgcacac caccctgcgc    28740
ggggaggccc gccgcgacta catccgcgac tgcgtctacc tgtacctctg ccacacctgg   28800
cagacgggca tgggcgtgtg gcagcagtgc ctggaggagc agaacctgaa agagctctgc   28860
aagctcctgc agaagaacct caaggccctg tggaccgggt tcgacgagcg caccaccgcc   28920
tcggacctgg ccgacctcat cttccccgag cgcctgcggc tgacgctgcg caacgggctg   28980
cccgactta tgagccaaag catgttgcaa aactttcgct ctttcatcct cgaacgctcc    29040
gggatcctgc ccgccacctg ctccgcactg ccctcggact tcgtgccgct gaccttccgc   29100
gagtgccccc cgccgctctg gagccactgc tacttgctgc gcctggccaa ctacctggcc   29160
taccactcgg acgtgatcga ggacgtcagc agcgagggtc tgctcgagtg ccactgccgc   29220
```

```
tgcaacctct gcacgccgca ccgctccttg gcctgcaacc cccagctgct gagcgagacc   29280
cagatcatcg gcaccttcga gttgcaaggc cccggcgagg gcaagggggg tctcaaactc   29340
accccggggc tgtggacctc ggcctacttg cgcaagttcg tgcccgagga ctaccatccc   29400
ttcgagatca ggttctacga ggaccaatcc cagccgccca aggccgagct gtcggcctgc   29460
gtcatcaccc agggggccat cctggcccaa ttgcaagcca tccagaaatc ccgccaagaa   29520
tttctgctga aaaagggcca cggggtctac ttggaccccc agaccggaga ggagctcaac   29580
cccagcttcc cccaggatgc cccgaggaag cagcaagaag ctgaaagtgg agctgccgct   29640
gccgccggag gatttggagg aagactggga gagcagtcag gcagaggaga tggaagactg   29700
ggacagcact caggcagagg aggacagcct gcaagacagt ctggaggagg aagacgaggt   29760
ggaggaggag gcagaggaag aagcagccgc cgccagaccg tcgtcctcgg cggaggagaa   29820
agcaagcagc acggatacca tctccgctcc gggtcggggt cgcggcggcc gggcccacag   29880
tagatgggac gagaccgggc gcttcccgaa ccccaccacc cagaccggta agaaggagcg   29940
gcagggatac aagtcctggc gggggcacaa aaacgccatc gtctcctgct tgcaagcctg   30000 cggggcaac atctccttca cccggcgcta cctgctcttc caccgcgggg tgaacttccc   30060
ccgcaacatc ttgcattact accgtcacct ccacagcccc tactactgtt tccaagaaga   30120
ggcagaaacc cagcagcagc agcagaaaac cagcggcagc agcagcagct agaaaatcca   30180
cagcggcggc aggtggactg aggatcgcgg cgaacgagcc ggcgcagacc cgggagctga   30240
ggaaccggat ctttcccacc ctctatgcca tcttccagca gagtcggggg caggagcagg   30300
aactgaaagt caagaaccgt tctctgcgct cgctcacccg cagttgtctg tatcacaaga   30360
gcgaagacca acttcagcgc actctcgagg acgccgaggc tctcttcaac aagtactgcg   30420
cgctcactct taaagagtag cccgcgcccg cccacacacg gaaaaaggcg ggaattacgt   30480
caccacctgc gcccttcgcc cgaccatcat catgagcaaa gagattccca cgccttacat   30540
gtggagctac cagccccaga tgggcctggc cgccggcgcc gcccaggact actccacccg   30600
catgaactgg ctcagtgccg ggcccgcgat gatctcacgg gtgaatgaca tccgcgccca   30660
ccgaaaccag atactcctag aacagtcagc gatcaccgcc acgccccgcc atcaccttaa   30720
tccgcgtaat tggcccgccg ccctggtgta ccaggaaatt ccccagccca cgaccgtact   30780
acttccgcga gacgcccagg ccgaagtcca gctgactaac tcaggtgtcc agctggccgg   30840
cggcgccgcc ctgtgtcgtc accgccccgc tcagggtata agcggctgg tgatccgagg   30900 cagaggcaca cagctcaacg acgaggtggt gagctcttcg ctgggtctgc gacctgacgg   30960
agtcttccaa ctcgccggat cggggagatc ttccttcacg cctcgtcagg ccgtcctgac   31020
tttggagagt tcgtcctcgc agcccgctc gggcggcatc ggcactctcc agttcgtgga   31080
ggagttcact ccctcggtct acttcaaccc cttctccggc tcccccggcc actacccgga   31140
cgagttcatc ccgaacttcg acgccatcag cgagtcggtg gacggctacg attgaatgtc   31200
ccatggtggc gcggctgacc tagctcggct tcgacacctg gaccactgtt aattaatcgc   31260
ctctcctacg agctcctgca gcagcgccag aagttcacct gcctggtcgg agtcaacccc   31320
atcgtcatca cccagcagtc gggcgatacc aaggggtgca tccactgctc ctgcgactcc   31380
cccgactgcg tccacactct gatcaagacc ctctgcggcc tccgcgacct cctccccatg   31440
aactaatcac ccccttatcc agtgaaataa agatcatatt gatgatgatt ttacagaaat   31500
aaagatacaa tcatattgat gatttgagtt taataaaaaa taagaatca cttacttgaa   31560 atctgatacc aggtctctgt ccatgttttc tgccaacacc acttcactcc cctcttccca   31620
```

```
gctctggtac tgcaggcccc ggcgggctgc aaacttcctc cacacgctga agggatgtc    31680 aaattcctcc tgtccctcaa tcttcatttt atcttctatc agatgtccaa aaagcgcgtc    31740
cgggtggatg atgacttcga ccccgtctac ccctacgatg cagacaacgc accgaccgtg    31800
cccttcatca accccccctt cgtctcttca gatggattcc aagagaagcc cctgggggtg    31860
ctgtccctgc gactggccga ccccgtcacc accaagaacg gggaaatcac cctcaagctg    31920 ggagagggg tggacctcga ctcctcggga aaactcatct ccaacacggc caccaaggcc    31980
gccgcccctc tcagttttc caacaacacc atttccctta acatggatca ccccttttac    32040
actaaagatg gaaaattatc cttacaagtt tctccaccat aaatatact gagaacaagc    32100 attctaaaca cactagcttt aggttttgga tcaggtttag gactccgtgg ctctgccttg    32160
gcagtacagt tagtctctcc acttacattt gatactgatg aaacataaa gcttaccta    32220 gacagaggtt tgcatgttac aacaggagat gcaattgaaa gcaacataag ctgggctaaa    32280
ggtttaaaat ttgaagatgg agccatagca accaacattg gaaatgggtt agagtttgga    32340
agcagtagta cagaaacagg tgttgatgat gcttacccaa tccaagttaa acttggatct    32400
ggccttagct ttgacagtac aggagccata atggctggta acaaagaaga cgataaactc    32460
actttgtgga caacacctga tccatcgcca aactgtcaaa tactcgcaga aatgatgca    32520 aaactaacac tttgcttgac taaatgtggt agtcaaatac tggccactgt gtcagtctta    32580
gttgtaggaa gtggaaacct aaaccccatt actggcaccg taagcagtgc tcaggtgttt    32640
ctacgttttg atgcaaacgg tgttcttta acagaacatt ctacactaaa aaaatactgg    32700
gggtataggc agggagatag catagatggc actccatata ccaatgctgt aggattcatg    32760
cccaatttaa aagcttatcc aaagtcacaa agttctacta ctaaaaataa tatagtaggg    32820
caagtataca tgaatggaga tgtttcaaaa cctatgcttc tcactataac cctcaatggt    32880
actgatgaca gcaacagtac atattcaatg tcattttcat acacctggac taatggaagc    32940
tatgttggag caacatttgg ggctaactct tataccttct catacatcgc ccaagaatga    33000
acactgtatc ccaccctgca tgccaaccct tcccaccca ctctgtggaa aaaactctga    33060
aacacaaaat aaaataaagt tcaagtgttt tattgattca acagttttac aggattcgag    33120
cagttatttt tcctccaccc tcccaggaca tggaatacac cacctctcc ccccgcacag    33180 ccttgaacat ctgaacgcca ttggtgatgg acatgctttt ggtctccacg ttccacacag    33240
tttcagagcg agccagtctc gggtcggtca gggagatgaa accctccggg cacaattggg    33300
agaagtactc gcctacatgg gggtagagtc ataatcgtgc atcaggatag ggcggtggtg    33360
ctgcagcagc gcgcgaataa actgctgccg ccgccgctcc gtcctgcagg aatacaacat    33420
ggcagtggtc tcctcagcga tgattcgcac cgcccgcagc ataaggcgcc ttgtcctccg    33480
ggcacagcag cgcaccctga tctcacttaa atcagcacag taactgcagc acagcaccac    33540
aatattgttc aaaatcccac agtgcaaggc gctgtatcca aagctcatgg cggggaccac    33600
agaacccacg tggccatcat accacaagcg caggtagatt aagtggcgac ccctcataaa    33660
cacgctggac ataaacatta cctcttttgg catgttgtaa ttcaccacct cccggtacca    33720
tataaacctc tgattaaaca tggcgccatc caccaccatc ctaaaccagc tggccaaaac    33780
ctgcccgccg gctatacact gcagggaacc gggactggaa caatgacagt ggagagccca    33840
ggactcgtaa cctatggatca tcatgctcgt catgatatca atgttggcac aacacaggca    33900
cacgtgcata cacttcctca ggattacaag ctcctcccgc gttagaacca tatcccaggg    33960
```

```
aacaacccat tcctgaatca gcgtaaatcc cacactgcag ggaagacctc gcacgtaact    34020
cacgttgtgc attgtcaaag tgttacattc gggcagcagc ggatgatcct ccagtatggt    34080
agcgcgggtt tctgtctcaa aaggaggtag acgatccctc ctgtacggag tgcgccgaga    34140
caaccgagat cgtgttggtc gtagtgtcat gccaaatgga acgccggacg tagtcatatt    34200
tcctgaagtc ttggcgcgcc aaagtctaga cagcgtccat agcttaccga gcagcagcag    34260
cagcacacaa caggcgcaag agtcagagaa aggctgagct ctaacctgtc cacccgctct    34320
ctgctcaata tatagcccag atctacactg acgtaaaggc caaagtctaa aaatacccgc    34380
caaatagtca cacacgccca gcacacgccc agaaaccggt gacacactca aaaaaatacg    34440
cgcacttcct caaacgccca aactgccgtc atttccgggt tcccacgcta cgtcatcaaa    34500
acacgacttt caaattccgt cgaccgttaa aaacgtcacc cgccccgccc ctaacggtcg    34560
cccgtctctc agccaatcag cgccccgcat ccccaaattc aaacacctca tttgcatatt    34620
aacgcgcacc aaaagtttga ggtatattat tgatgatg                            34658
```

```
<210> SEQ ID NO 18
<211> LENGTH: 10
<212> TYPE: DNA
<213> ORGANISM: Artificial Sequence
<220> FEATURE:
<223> OTHER INFORMATION: Ribosome binding site

<400> SEQUENCE: 18
gccaccaugg                                                          10

<210> SEQ ID NO 19
<211> LENGTH: 49
<212> TYPE: DNA
<213> ORGANISM: Artificial Sequence
<220> FEATURE:
<223> OTHER INFORMATION: Synthetic polyadenylation signal

<400> SEQUENCE: 19
aauaaaagau cuuuauuuuc auuagaucug uguuggguu uuuugugug                 49

<210> SEQ ID NO 20
<211> LENGTH: 33
<212> TYPE: DNA
<213> ORGANISM: Artificial Sequence
<220> FEATURE:
<223> OTHER INFORMATION: PCR Primer

<400> SEQUENCE: 20
tattctgcga tcgctgaggt gggtgagtgg gcg                                 33

<210> SEQ ID NO 21
<211> LENGTH: 31
<212> TYPE: DNA
<213> ORGANISM: Artificial Sequence
<220> FEATURE:
<223> OTHER INFORMATION: PCR Primer

<400> SEQUENCE: 21
taggcgcgcc cttaaacggc atttgtggga g                                   31

<210> SEQ ID NO 22
<211> LENGTH: 27
<212> TYPE: DNA
<213> ORGANISM: Artificial Sequence
<220> FEATURE:
<223> OTHER INFORMATION: PCR Primer
```

<400> SEQUENCE: 22
cgtctagaag acccgagtct taccagt                                27

<210> SEQ ID NO 23
<211> LENGTH: 39
<212> TYPE: DNA
<213> ORGANISM: Artificial Sequence
<220> FEATURE:
<223> OTHER INFORMATION: PCR Primer

<400> SEQUENCE: 23
cgggatccgt ttaaaccatc atcaataata taccttatt                   39

<210> SEQ ID NO 24
<211> LENGTH: 37
<212> TYPE: DNA
<213> ORGANISM: Artificial Sequence
<220> FEATURE:
<223> OTHER INFORMATION: PCR Primer

<400> SEQUENCE: 24
atggaattcg tttaaaccat catcaataat atacctt                     37

<210> SEQ ID NO 25
<211> LENGTH: 45
<212> TYPE: DNA
<213> ORGANISM: Artificial Sequence
<220> FEATURE:
<223> OTHER INFORMATION: PCR Primer

<400> SEQUENCE: 25
atgacgcgat cgctgatatc ctataataat aaaacgcaga ctttg            45

<210> SEQ ID NO 26
<211> LENGTH: 27
<212> TYPE: DNA
<213> ORGANISM: Artificial Sequence
<220> FEATURE:
<223> OTHER INFORMATION: PCR Primer

<400> SEQUENCE: 26
cgtctagaca gcgtccatag cttaccg                                27

<210> SEQ ID NO 27
<211> LENGTH: 40
<212> TYPE: DNA
<213> ORGANISM: Artificial Sequence
<220> FEATURE:
<223> OTHER INFORMATION: PCR Primer

<400> SEQUENCE: 27
cgggatccgt ttaaaccatc atcaataata tacctcaaac                  40

<210> SEQ ID NO 28
<211> LENGTH: 32
<212> TYPE: DNA
<213> ORGANISM: Artificial Sequence
<220> FEATURE:
<223> OTHER INFORMATION: PCR Primer

<400> SEQUENCE: 28
atgcgcgatc gcgtgagtag tgtttggggg tg                          32

<210> SEQ ID NO 29

```
<211> LENGTH: 32
<212> TYPE: DNA
<213> ORGANISM: Artificial Sequence
<220> FEATURE:
<223> OTHER INFORMATION: PCR Primer

<400> SEQUENCE: 29
taggcgcgcc gcttctcctc gttcaggctg gc                                    32

<210> SEQ ID NO 30
<211> LENGTH: 41
<212> TYPE: DNA
<213> ORGANISM: Artificial Sequence
<220> FEATURE:
<223> OTHER INFORMATION: PCR Primer

<400> SEQUENCE: 30
atggaattcg tttaaaccat catcaataat atacctcaaa c                          41

<210> SEQ ID NO 31
<211> LENGTH: 32
<212> TYPE: DNA
<213> ORGANISM: Artificial Sequence
<220> FEATURE:
<223> OTHER INFORMATION: PCR Primer

<400> SEQUENCE: 31
tcaagatatc cgtaaaaaca ccggactttg ac                                    32

<210> SEQ ID NO 32
<211> LENGTH: 32
<212> TYPE: DNA
<213> ORGANISM: Artificial Sequence
<220> FEATURE:
<223> OTHER INFORMATION: PCR Primer

<400> SEQUENCE: 32
tgatatccca ttgcatacgt tgtatccata tc                                    32

<210> SEQ ID NO 33
<211> LENGTH: 25
<212> TYPE: DNA
<213> ORGANISM: Artificial Sequence
<220> FEATURE:
<223> OTHER INFORMATION: PCR Primer

<400> SEQUENCE: 33
tgatatctag agcccaccgc atccc                                            25
```

HEPATITIS C VIRUS NUCLEIC ACID VACCINE

RELATED APPLICATIONS

The present application claims priority to U.S. Provisional Application No. 60/691,523, filed Jun. 17, 2005, and U.S. Provisional Application No. 60/699,514, filed Jul. 15, 2005, each of which are hereby incorporated by reference herein.

SEQUENCE LISTING

The present application is being filed along with duplicate copies of a CD-ROM marked "Copy 1" and "Copy 2" containing a Sequence Listing in electronic format. The duplicate copies of the CD-ROM each contain a file entitled "Case ITR0103Y PCT Sequence Listing Filed 6-13-2006.txt" created on Dec. 12, 2007, which is 268,000 Bytes in size. The information on these duplicate CD-ROMs is incorporated herein by reference in its entirety.

BACKGROUND OF THE INVENTION

The references cited in the present application are not admitted to be prior art to the claimed invention.

About 3% of the world's population is infected with the Hepatitis C virus (HCV). (Wasley et al., *Semin. Liver Dis.* 20, 1-16, 2000.) Exposure to HCV results in an overt acute disease in a small percentage of cases, while in most instances the virus establishes a chronic infection causing liver inflammation and slowly progresses into liver failure and cirrhosis. (Iwarson, *FEMS Microbiol. Rev.* 14, 201-204, 1994.) In addition, epidemiological surveys indicate HCV plays an important role in the pathogenesis of hepatocellular carcinoma. (Kew, *FEMS Microbiol. Rev.* 14, 211-220, 1994, Alter, *Blood* 85, 1681-1695, 1995.)

Prior to the implementation of routine blood screening for HCV in 1992, most infections were contracted by inadvertent exposure to contaminated blood, blood products or transplanted organs. In those areas where blood screening of HCV is carried out, HCV is primarily contracted through intravenous drug use. Less frequent methods of transmission include perinatal exposure, hemodialysis, and sexual contact with an HCV infected person. (Alter et al., *N. Engl. J. Med.* 341(8), 556-562, 1999, Alter, *J. Hepatol.* 31 Suppl. 88-91, 1999, Wasley et al., *Semin. Liver. Dis.* 201, 1-16, 2000.)

The HCV genome consists of a single strand RNA about 9.5 kb encoding a precursor polyprotein of about 3000 amino acids. (Choo et al., *Science* 244, 362-364, 1989, Choo et al., *Science* 244, 359-362, 1989, Takamizawa et al., *J. Virol.* 65, 1105-1113, 1991.) The HCV polyprotein contains the viral proteins in the order: C-E1-E2-p7-NS2-NS3-NS4A-NS4B-NS5A-NS5B.

The use of a HCV nucleic acid sequence providing one or more HCV non-structural antigens to generate a CMI response is mentioned, for example, by Cho et al., *Vaccine* 17:1136-1144, 1999; Paliard et al., International Publication Number WO 01/30812; Coit et al., International Publication Number WO 01/38360; and Emini et al., International Publication Number WO 03/031588.

SUMMARY OF THE INVENTION

The present invention features nucleic acid constructs that can be used as a HCV nucleic acid vaccine, vaccine component, or in the production of a HCV vaccine. Described constructs include those: (1) encoding for a chimeric HCV polypeptide containing a NS3-4A region based on a first HCV strain and an NS3-NS4A-NS4B-NS5A or an NS3-NS4A-NS4B-NS5A-NS5B region based on a second strain; and (2) a chimpanzee based adenovector encoding an HCV polypeptide.

Thus, a first aspect of the present invention describes a nucleic acid comprising a nucleotide sequence encoding a HCV chimeric polypeptide. The polypeptide comprises a HCV NS3-4a region comprising an amino acid sequence substantially similar to a HCV NS3-4-a from a first HCV strain and a HCV NS3-NS4A-NS4B-NS5A region comprising an amino acid sequence substantially similar to HCV NS3-NS4A-NS4B-NS5A from a second HCV strain, where the NS3-4A sequences present in the two regions have different sequences. The first region is located at either the amino or carboxyl side of the second region.

Reference to a "substantially similar sequence" with respect to an amino acid sequence indicates an identity of at least about 70% to a reference sequence. Percent identity (also referred to as percent identical) to a reference sequence is determined by aligning the polypeptide region with the corresponding reference region to obtain the maximal number of identical amino acids and determining the number of identical amino acids in the corresponding regions. This number is divided by the total number of amino acids in the reference region and then multiplied by 100 and rounded to the nearest whole number. For example, regions for HCV NS3-4A, NS3-NS4A-NS4B-NS5A, and NS3-NS4A-NS4B-NS5A-NS5B, can be the corresponding HCV region present in different HCV strains.

A different NS3-4A sequence present in the first and second regions is reflected by one or more amino acid differences. Each amino acid difference is independently an addition, substitution, or deletion.

In a preferred embodiment, the nucleic acid is an expression vector capable of expressing the encoded HCV polypeptide in a human cell. Expression inside a human cell has therapeutic applications for actively treating an HCV infection and for prophylactically treating against an HCV infection.

An expression vector contains a nucleotide sequence encoding a polypeptide along with regulatory elements for proper transcription and processing. The regulatory elements that may be present include those naturally associated with the nucleotide sequence encoding the polypeptide and exogenous regulatory elements not naturally associated with the nucleotide sequence. Exogenous regulatory elements such as an exogenous promoter can be useful for expression in a particular host, such as in a human cell.

A preferred expression vector is a recombinant adenovirus genome having one or more deleted regions. The recombinant adenovirus genome may contain different regions substantially similar to one or more adenovirus serotypes. Reference to a deleted region indicates a deletion of all or part of the indicated region.

Another aspect of the present invention describes a recombinant adenovector comprising:

a) an expression cassette encoding an HCV polypeptide, wherein the HCV polypeptide comprises HCV NS3-NS4A-NS4B-NS5A; and b) a recombinant adenovirus genome containing an E1 deletion, an E3 deletion, and optionally containing an E4 deletion; provided that the adenovirus genome encodes at least one of: (i) a fiber region with an amino acid sequence substantially similar to SEQ ID NO: 3 or 9; (ii) a hexon region with an amino acid sequence substantially similar to either SEQ ID NO: 5 or 11; and (iii) a penton region with an amino acid sequence substantially similar to SEQ ID NO: 7.

The expression cassette is located at either the E1 or E3 deletion. An expression cassette is considered to be located at either the E1 or E3 deletion if all or part of the expression cassette is in a position corresponding to the deleted region.

Reference to HCV polypeptide or amino acid sequence includes naturally occurring HCV sequences, derivatives of naturally occurring sequences that are substantially similar to a naturally occurring sequence or an indicated sequence, and chimeric HCV polypeptides. Chimeric HCV polypeptides include those described in the first aspect of the invention supra.

Another aspect of the present invention describes a recombinant adenovirus particle. The particle is encoded by a recombinant adenovirus genome described herein and packages a copy of the genome.

Another aspect of the present invention describes a method of making a recombinant adenovirus particle comprising the steps of: (a) producing the particle using an E1 complementing cell to express the recombinant adenovirus genome; and (b) substantially purifying the particle. Reference to substantially purifying the particle indicates removing all or most of the cell and cell debris from which the particle was generated.

Another aspect of the present invention describes a pharmaceutical composition comprising a therapeutically effective amount of nucleic acid encoding a HCV polypeptide and a pharmaceutically acceptable carrier.

Another aspect of the present invention describes a method of treating a patient comprising the step of administering to the patient a therapeutically effective amount of a nucleic acid encoding an HCV polypeptide.

Reference to "treating" includes treating a patient infected with HCV or treating a patient to prophylactically to reduce the likelihood or severity of an active HCV infection. A "patient" refers to a mammal capable of being infected with HCV. A patient may or may not be infected with HCV. Examples of patients are humans and chimpanzees.

For a patient infected with HCV, an effective amount is sufficient to achieve one or more of the following effects: reduce the ability of HCV to replicate, reduce HCV load, increase viral clearance, and increase one or more HCV specific CMI responses.

For a patient not infected with HCV, an effective amount is sufficient to achieve one or more of the following: an increased ability to produce one or more components of a HCV specific CMI response to a HCV infection, a reduced susceptibility to HCV infection, and a reduced ability of the infecting virus to establish persistent infection for chronic disease.

Reference to open-ended terms such as "comprises" allows for additional elements or steps. Occasionally phrases such as "one or more" are used with or without open-ended terms to highlight the possibility of additional elements or steps.

Unless explicitly stated, reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 provides the amino acid sequence of SEQ ID NO: 1. Amino acids 1-686 provide a NS3-NS4A region, which is based on HCV 3a. Amino acids 687-690 provide the first 4 amino acids of the HCV 3a NS4B region and provide a cleavage junction for HCV 3a NS3-NS4A region. Amino acids 691-2675 provide a NS3-NS4A-NS4B-NS5A-NS5B region based on HCV 1b. The NS3-NS4A region and the NS3-NS4A-NS4B-NS5A-NS5B region also contain an addition of an initial methionine.

FIGS. 2A-2C provide the nucleic acid sequence of SEQ ID NO: 2.

Nucleotides 318-10182 provide an expression cassette containing:
HCMV promoter: nt 318-905
Int A: nt 1040-1865
Kozaq sequence: nt 1885-1890
HCV Met-NS3-NS4A (based on 3a, optimized): nt 1891-3948
HCV first 4 amino acids of NS4B (based on 3a): nt 3949-3960
HCV Met-NS3-5B (based on 1b, Bk strain, optimized): nt 3961-9915
TAAA terminator: nt 9916-9919
BGH: nt 9956-10179.

FIG. 3 provides a met-NS3-5B sequence (SEQ ID NO: 16).

FIGS. 4A-4J provides the amino acid sequence for ChAd3 fiber (FIG. 4A, SEQ ID NO: 3), ChAd3 hexon (FIG. 4B, SEQ ID NO: 5), ChAd3 penton (FIG. 4C, SEQ ID NO: 7), ChAd63 fiber (FIG. 4D, SEQ ID NO: 9), ChAd63 hexon (FIG. 4E, SEQ ID NO: 11); and encoding nucleic acid for ChAd3 fiber (FIG. 4F, SEQ ID NO: 4), ChAd3 hexon (FIG. 4G, SEQ ID NO: 6), ChAd3 penton (FIG. 4H, SEQ ID NO: 8), ChAd63 fiber (FIG. 4I, SEQ ID NO: 10), and ChAd63 hexon (FIG. 4J, SEQ ID NO: 12).

FIGS. 5A-5H provide the nucleic acid sequence of ChAd3ΔE1,3,4, Ad5 E4orf6, NSmut −35,890 bp (ChAd3NSmut, SEQ ID NO: 13). Deletion coordinates of the wild type genome are: E1 deletion from nt 461 to nt 3541 (3080 bp), E3 deletion from nt 28644 to nt 32633 (3989 bp), E4 deletion from nt 34634 to nt 37349 (2715 bp). The different regions are as follows:
ChAd3 left ITR+packaging signal: nt 1-460
HCMV promoter: nt 467-1257
Kozak consensus sequence: nt 1263-1268
HCV NS3-5B (BK strain): nt 1269-7223
TAA terminator: nt 7224-7226
BGH polyA: nt 7234-7452
ChAd3 backbone: nt 7468-35890
Ad5 E4orf6: nt 34601-35482.

FIGS. 6A-6H provides the nucleic acid sequence for the wild-type ChAd3 (SEQ ID NO: 14).

FIGS. 7A-7H provide the nucleic acid sequence for the wild-type ChAd63 (SEQ ID NO: 15).

Figure 8:
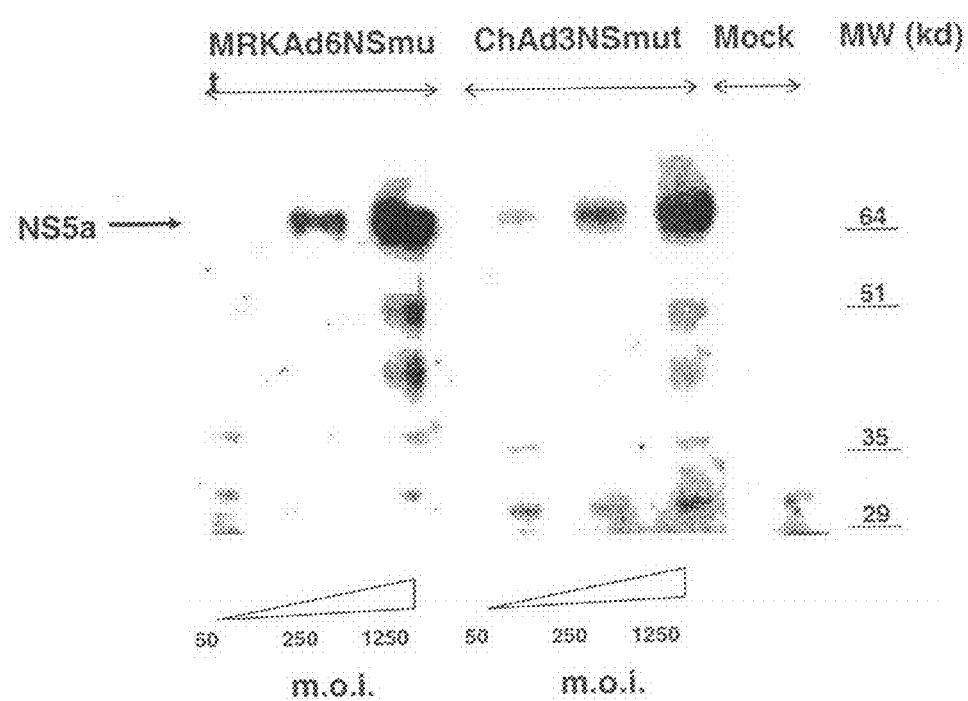

FIG. 8 provides a comparison of expression of HCV NS protein in HeLa cells infected with ChAd3NSmut (SEQ ID NO: 13) and MRKAd6NSmut.

Figure 9:
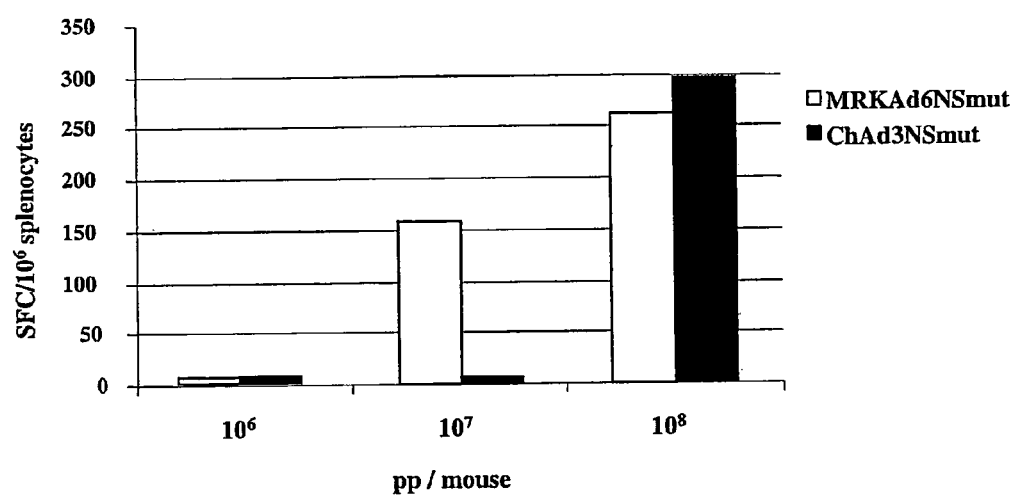

FIG. 9 provides a comparison of the ability of ChAd3NSmut (SEQ ID NO: 13) and MRKAd6NSmut to induce cell mediated immunity in C57/B6 mice.

FIGS. 10A-10H provide the nucleic acid sequence of ChAd63ΔE1,3,4, Ad5 E4orf6, NSmut (SEQ ID NO: 17). Deletions coordinates of the wild type genome are: E1 deletion from nt 455 to nt 3421 (2967 bp), E3 deletion from nt 27207 to nt 31778 (4582 bp), E4 deletion from nt 33825 to nt 36215 (2390 bp). The different regions are as follows:

ChAd63 left ITR+packaging signal: nt 1-454
HCMV promoter: nt 458-1248
Kozak consensus sequence: nt 1254-1259
HCV NS3-5B (BK strain): nt 1260-7214
TAA terminator: nt 7215-7217
BGH polyA: nt 7227-7447
ChAd63 backbone: nt 7458-34658
Ad5 E4orf6: nt 33316-34197.

Figure 11:
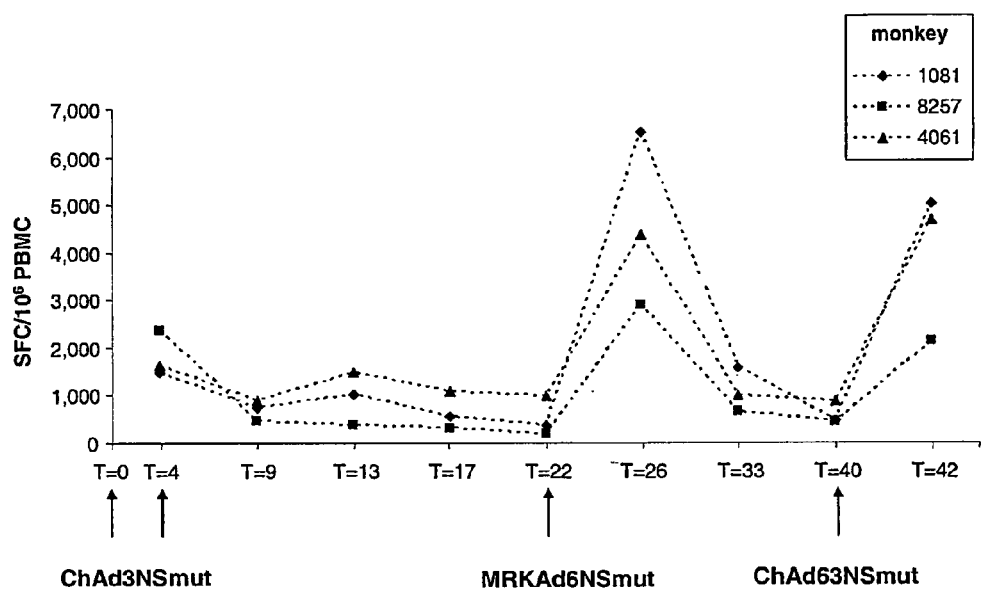

FIG. 11 illustrates the time course of the immune response measured by IFN-γ ELISPOT expressed as the sum of the responses observed on the different HCV NS peptide pools at any given time point.

Figure 12:
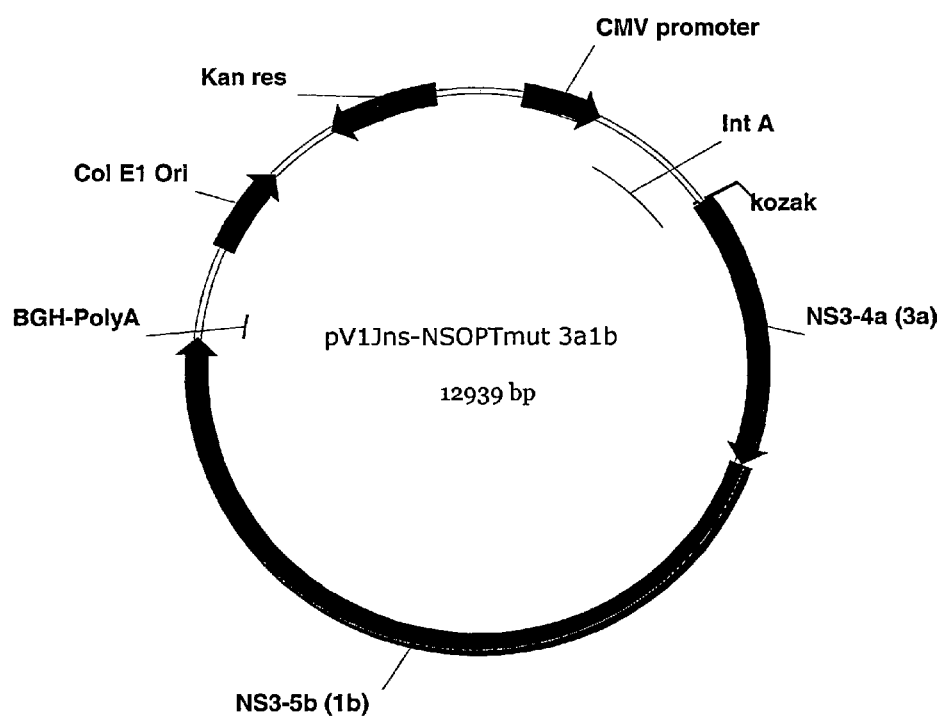

FIG. 12 illustrates different components of pV1JnsNSOPTmut 3a-1b.

Figure 13:
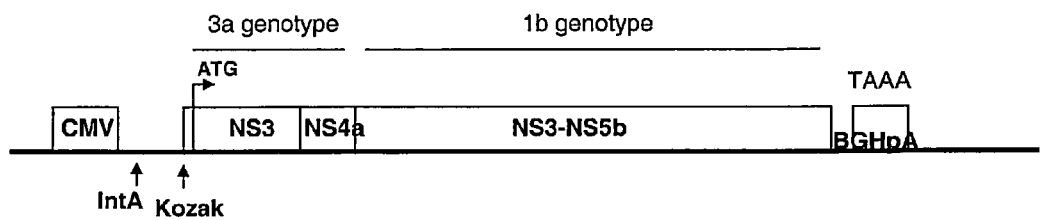

FIG. 13 illustrates the genetic structure of the pV1JnsNSOPTmut 3a-1b expression cassette coding for a chimeric HCV polypeptide. The different nucleotide regions are:

human CMV promoter: 318-905;
Intron A: 1040-1865;
Kozaq sequence: 1885-1894;
HCV MetNS3-NS4A (genotype 3a): 1891-3960;
HCV MetNS3-NS5BOPTmut (genotype 1b): 3961-9915;
TAAA terminator: 9916-9919; and
BGH polyA: 9965-10182.

Figure 14:
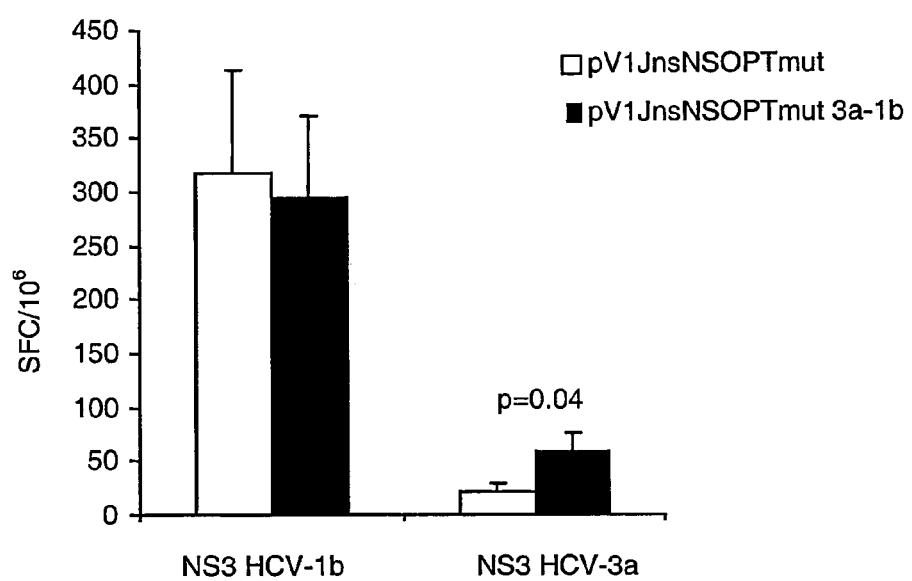

FIG. 14 shows the number of T cells secreting IFN-gamma (expressed as spot forming cells per million splenocytes) in response to NS3 protein from HCV 1b and 3a in animals (CD1 mice) immunized with the chimeric plasmid (pV1Jns-NSOPTmut 3a-1b) or with pV1Jns-NSOPTmut.

DETAILED DESCRIPTION OF THE INVENTION

The present invention includes nucleic acid encoding a HCV chimeric polypeptide providing for HCV non-structural proteins based on different HCV strains and the use of a chimpanzee adenovector for expressing HCV polypeptides. Uses of the described nucleic acid include use as a vaccine component to introduce into a cell an HCV polypeptide that provides a broad range of antigens for generating a CMI response against HCV, and as an intermediate for producing such a vaccine component.

The adaptive cellular immune response can function to recognize viral antigens in HCV infected cells throughout the body due to the ubiquitous distribution of major histocompatibility complex (MHC) class I and II expression, to induce immunological memory, and to maintain immunological memory. These functions are attributed to antigen-specific CD4+ T helper (Th) and CD8+ cytotoxic T cells (CTL).

Upon activation via their specific T cell receptors, HCV specific Th cells fulfill a variety of immunoregulatory functions, most of them mediated by Th1 and Th2 cytokines. HCV specific Th cells assist in the activation and differentiation of B cells and induction and stimulation of virus-specific cytotoxic T cells. Together with CTL, Th cells may also secrete IFN-γ and TNF-α that inhibit replication and gene expression of several viruses. Additionally, Th cells and CTL, the main effector cells, can induce apoptosis and lysis of virus infected cells.

HCV specific CTL are generated in response to antigens processed by professional antigen presenting cells (pAPCs). Antigens can be either synthesized within or introduced into pAPCs. Antigen synthesis in a pAPC can be brought about by introducing into the cell an expression cassette encoding the antigen.

A preferred route of nucleic acid vaccine administration is an intramuscular route. Intramuscular administration appears to result in the introduction and expression of nucleic acid into somatic cells and pAPCs. HCV antigens produced in the somatic cells can be transferred to pAPCs for presentation in the context of MHC class I molecules. (Donnelly et al., *Annu. Rev. Immunol.* 15:617-648, 1997.)

pAPCs process longer length antigens into smaller peptide antigens in the proteasome complex. The antigen is translocated into the endoplasmic reticulum/Golgi complex secretory pathway for association with MHC class I proteins. CD8+ T lymphocytes recognize antigen associated with class I MHC via the T cell receptor (TCR) and the CD8 cell surface protein.

The use of a chimpanzee adenovirus based vector as a vehicle for introducing HCV antigens provides an alternative to a human adenovector. The chimpanzee adenovirus based vector is particularly useful when used in conjunction with a multiple immunization strategy, where the patient being treated has developed an immune response to an initially employed adenovector. Repeated exposure to the same type of adenovirus based vector may result in decreased effectiveness due to an immune response against adenovirus proteins. Some initial exposure may be the result of adenovirus infection, possibly supplemented with the use of an adenovector to treat a disease other than HCV.

Based on the guidance provided herein a sufficiently strong immune response can be generated to achieve a beneficial effect in a patient. The provided guidance includes information concerning HCV sequence selection, vector selection, vector production, combination treatment, and administration.

I. Chimeric Sequences

A HCV chimeric polypeptide providing regions with different NS3-4A sequences can be used as a vaccine component to provide antigens targeting different HCV strains. A major feature of HCV is the heterogeneity of its genome. (Pawlotsky, *Clin. Liver Dis*, 7:45-66, 2003, Simmonds, *J. General. Virol*, 85:3173-3188, 2004.) In addition, mutations resulting from the typical error-prone RNA-dependent RNA polymerase and lacking proofreading activity common to RNA viruses as well as from the host, are responsible for HCV circulating in the host as a complex viral population referred to as quasispecies. (Blight et al., Science 290:1972-1974, 2000.)

A different NS3-4A sequence present in different regions of a chimeric construct is reflected by one or more amino acid differences. Each amino acid difference is independently an addition, substitution, or deletion. In different embodiments, the NS3-4A sequences of the first and second regions differ by at least about 5%, at least 10%, at least 15%; or there are at least 1, 5, 10, 15, 20 or 25 amino acid alterations. In addition to the NS3-4A sequence, a NS3-4A region may contain additional amino acids such as an amino terminus methionine and/or an introduced cleavage site.

The percent difference can be determined by subtracting the sequence identity from 100. For example, an 85% sequence identity provides a difference of 15%.

The first region and second polypeptide regions present in a chimeric polypeptide can be readily produced based on numerous examples of naturally occurring HCV isolates. HCV isolates can be classified into the following six major genotypes comprising one or more subtypes: HCV-1/(1a, 1b, 1c), HCV-2/(2a, 2b, 2c), HCV-3/(3a, 3b, 10a), HCV-4/(4a), HCV-5/(5a) and HCV-6/(6a, 6b, 7b, 8b, 9a, 11a). (Simmonds,

*J. Gen. Virol.*, 693-712, 2001.) Particular HCV sequences such as HCV-BK, HCV-J, HCV-N, and HCV-H, have been deposited in GenBank and described in various publications. (E.g., Chamberlain et al., *J. Gen. Virol.*, 1341-1347, 1997.)

Preferably, both the first region and the second region are processed in vivo by HCV protease to provide individual proteins corresponding to the individual protein present in the HCV chimeric polypeptide. The individual HCV proteins can be further processed by the cell.

In different embodiments concerning the first region, the region is or contains an amino acid sequence substantially similar to the NS3-NS4A region present in: amino acids 1-686 of SEQ ID NO: 1; HCV 1a (Acc. No. M62321); HCV 2a (Acc. No. D00944; HCV 3a (Acc. No: D28917); HCV 4a (Acc. No: Y11604); HCV 5a (Acc. No: Y13184) or HCV 6a (Acc. No: D84264).

In different embodiments concerning the second region, the region is or contains a NS3-NS4A-NS4B-NS5A or NS3-NS4A-NS4B-NS5A-NS5B* sequence substantially similar to the corresponding region present in: amino acids 686-2675, amino acids 691-2675, or amino acids 692-2675, of SEQ ID NO: 1; HCV 1a (Acc. No. M62321); HCV 2a (Acc. No. D00944; HCV 3a (Acc. No: D28917); HCV 4a (Acc. No: Y11604); HCV 5a (Acc. No: Y13184) or HCV 6a (Acc. No: D84264). Reference to a "NS5B*", indicates an inactive NS5B.

Preferably, the second region contains an amino acid cleavage site compatible with the protease activity from the first region. A cleavage site can be added based on know cleavages sequences.

Reference to a "substantially similar sequence" with respect to amino acid sequences indicates an identity of at least about 70% to a reference sequence. Percent identity (also referred to as percent identical) to a reference sequence is determined by aligning the polypeptide region with the corresponding reference region to obtain the maximal number of identical amino acids and determining the number of identical amino acids in the corresponding regions. This number is divided by the total number of amino acids in the reference region and then multiplied by 100 and rounded to the nearest whole number.

In different embodiments, substantially similar sequences have an identity of at least 75%, at least 80%, at least 85%, at least 90%, at least 95%; or differ by 0, 1, 2, 3, 4, 5, 6, 7, 8, 9, 10, 11, 12, 13, 14, 15, 16, 17, 18, 19, or 20 amino acid alterations. Each alteration is independently an insertion, substitution, or addition.

Modifications to a naturally occurring HCV sequences can be produced to obtain different substantially similar sequences. Differences in naturally occurring amino acids are due to different amino acid side chains (R groups). An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids to maintain activity, it is preferable to exchange amino acids having similar properties. Substituting different amino acids within a particular group, such as substituting valine for leucine, arginine for lysine, and asparagine for glutamine are good candidates for not causing a change in polypeptide tertiary structure.

Amino acid modifications preferably maintain or add T-cell antigen regions. Different modifications can be made to naturally occurring HCV polypeptide sequences to produce polypeptides able to elicit a broad range of T cell responses. Factors influencing the ability of a polypeptide to elicit a broad T cell response include the preservation or introduction of HCV specific T cell antigen regions and prevalence of different T cell antigen regions in different HCV isolates.

HCV T cell antigens can be identified by, for example, empirical experimentation. One way of identifying T cell antigens involves generating a series of overlapping short peptides from a longer length polypeptide and then screening the T-cell populations from infected patients for positive clones. Positive clones are activated/primed by a particular peptide. Techniques such as IFNγ-ELISPOT, IFNγ-Intracellular staining and bulk CTL assays can be used to measure peptide activity. Peptides thus identified can be considered to represent T-cell epitopes of the respective pathogen.

The ability of a HCV polypeptide to process itself and produce a CMI response can be determined using techniques described herein or well known in the art. (See for example, Emini et al., International Publication Number WO 03/031588.) Such techniques include the use of IFNγ-ELISPOT, IFNγ-Intracellular staining and bulk CTL assays to measure a HCV specific CMI response.

Small modifications can be made in NS5B to produce an inactive polymerase by targeting motifs essentially for replication. Examples of motifs critical for NS5B activity and modifications that can be made to produce an inactive NS5B are described by Lohmann et al., *Journal of Virology* 71:8416-8426, 1997, Kolykhalov et al., *Journal of Virology* 74:2046-2051, 2000, and Emini et al., International Publication Number WO 03/031588.

Additional factors to take into account when producing modifications to a chimeric HCV polypeptide include maintaining the ability to self-process and maintaining T cell antigens. The ability of the polypeptide to process itself is determined to a large extent by functional protease activity. Modifications that maintain protease activity can be obtained by taking into account NS3 protease, NS4A which serves as a cofactor for NS3, and protease recognition sites present within the HCV polypeptide.

II. Chimeric $NS3_1$-$NS4A_1$-$NS3_2$-$NS4A_2$-$NS4B_2$-$NS5A_2$-$NS5B^*_2$

A preferred chimeric HCV polypeptide is $NS3_1$-$NS4A_1$-$NS3_2$-$NS4A_2$-$NS4B_2$-$NS5A_2$-$NS5B^*_2$, where subscripts 1 and 2 denotes regions sequence substantially similar to the corresponding region in different HCV strains and "NS5B*" denotes enzymatically inactive NS5B. $NS3_1$-$NS4A_1$ and $NS3_2$-$NS4A_2$ differ by at least one amino acid. In different embodiments, $NS3_1$-$NS4A_1$ and $NS3_2$-$NS4A_2$ differ by at least about 5%, at least about 10%, at least about 15%; or there are at least 1, 5, 10, 15, 20 or 25 amino acid alterations.

Preferably, the $NS3_1$-$NS4A_1$-$NS3_2$-$NS4A_2$-$NS4B_2$-$NS5A_2$-$NS5B_2^*$ polypeptide provides sufficient protease activity in vivo for the first and second regions to each produce one or more individual HCV peptides. In a preferred embodiment, the polypeptide can produce as individual peptides $NS3_1$, $NS4A_1$, $NS3_2$, $NS4A_2$, $NS4B_2$, $NS5A_2$, and $NS5B_2^*$.

Different $NS3_1$-$NS4A_1$ and $NS3_2$-$NS4A_2$-$NS4B_2$-$NS5A_2$-$NS5B_2^*$ regions can be provided as described in Section I supra. In different embodiments, the $NS3_1$-$NS4A_1$ region is or contains a sequence substantially similar to amino acids 1-686, or amino acids 2-686, of SEQ ID NO: 1; the $NS3_2$-

NS4A$_2$-NS4B$_2$-NS5A$_2$-NS5B$_2$* region is or contains a sequence substantially similar to amino acids 687-2675, 691-2675, or 692-2675, of SEQ ID NO:1; or NS3$_1$-NS4A$_1$-NS3$_2$-NS4A$_2$-NS4B$_2$-NS5A$_2$-NS5B$_2$* as a whole is substantially similar to SEQ ID NO 1. In different embodiments each region is substantially similar to the corresponding region in SEQ ID NO: 1 by at least 75%, at least 80%, at least 85%, at least 90%, at least 95%; or differ by 0, 1, 2, 3, 4, 5, 6, 7, 8, 9, 10, 11, 12, 13, 14, 15, 16, 17, 18, 19, or 20 amino acid alterations.

III. Gene Expression Cassettes

A gene expression cassette encoding a polypeptide contains elements needed for polypeptide expression. Reference to "polypeptide" can be a chimeric polypeptide.

III.A. Encoded Polypeptide Sequence

HCV polypeptide encoded sequences described herein can be used in different vectors. Specific examples include chimeric polypeptide sequences such as described in Sections I and II supra, and HCV polypeptide sequences Met-NS3-NS4A-NS4B-NS5A-NS5B* such as sequences substantially similar to SEQ ID NO: 16 (See, Emini et al., International Publication Number WO 03/031588). A sequence substantially similar to SEQ ID NO: 16 can be used, for example, in conjunction with a Chimpanzee vector described in Section V infra.

In different embodiments, the SEQ ID NO: 16 substantially similar sequence has a sequence identify to SEQ ID NO: 16 of at 75%, at least 80%, at least 85%, at least 90%, at least 95%; or differs by 0, 1, 2, 3, 4, 5, 6, 7, 8, 9, 10, 11, 12, 13, 14, 15, 16, 17, 18, 19, or 20 amino acid alterations.

III.B. Encoded Polypeptide Sequence

Regulatory elements present in a gene expression cassette generally include: (a) a promoter transcriptionally coupled to a nucleotide sequence encoding the polypeptide, (b) a 5' ribosome binding site functionally coupled to the nucleotide sequence, (c) a terminator joined to the 3' end of the nucleotide sequence, and (d) a 3' polyadenylation signal functionally coupled to the nucleotide sequence. Additional regulatory elements useful for enhancing or regulating gene expression or polypeptide processing may also be present.

Promoters are genetic elements that are recognized by an RNA polymerase and mediate transcription of downstream regions. Preferred promoters are strong promoters that provide for increased levels of transcription. Examples of strong promoters are the immediate early human cytomegalovirus promoter (CMV), and CMV with intron A. (Chapman et al, *Nucl. Acids Res.* 19:3979-3986, 1991.) Additional examples of promoters include naturally occurring promoters such as the EF1 alpha promoter, the murine CMV promoter, Rous sarcoma virus promoter, and SV40 early/late promoters and the β-actin promoter; and artificial promoters such as a synthetic muscle specific promoter and a chimeric muscle-specific/CMV promoter (Li et al., *Nat. Biotechnol.* 17:241-245, 1999, Hagstrom et al., *Blood* 95:2536-2542, 2000).

The ribosome binding site is located at or near the initiation codon. Examples of ribosome binding sites include CCACCAUGG, CCGCCAUGG, and ACCAUGG, where AUG is the initiation codon. (Kozak, *Cell* 44:283-292, 1986.) Another example of a ribosome binding site is provided by SEQ ID NO: 18.

The polyadenylation signal is responsible for cleaving the transcribed RNA and the addition of a poly (A) tail to the RNA. The polyadenylation signal in higher eukaryotes contains an AAUAAA sequence about 11-30 nucleotides from the polyadenylation addition site. The AAUAAA sequence is involved in signaling RNA cleavage. (Lewin, Genes IV, Oxford University Press, NY, 1990.) The poly (A) tail is important for the mRNA processing.

Polyadenylation signals that can be used as part of a gene expression cassette include the minimal rabbit β-globin polyadenylation signal and the bovine growth hormone polyadenylation (BGH) signal. (Xu et al., *Gene* 272:149-156, 2001, Post et al., U.S. Pat. No. 5,122,458.) Additional examples include the Synthetic Polyadenylation Signal (SPA) and SV40 polyadenylation signal. The SPA sequence is provided by SEQ ID NO: 19.

Reference to "transcriptionally coupled" indicates that the promoter is positioned such that transcription of the nucleotide sequence can be brought about by RNA polymerase binding at the promoter. Transcriptionally coupled does not require that the sequence being transcribed is adjacent to the promoter.

Reference to "functionally coupled" indicates the ability to mediate an effect on the nucleotide sequence. Functionally coupled does not require that the coupled sequences be adjacent to each other. A 3' polyadenylation signal functionally coupled to the nucleotide sequence facilitates cleavage and polyadenylation of the transcribed RNA. A 5' ribosome binding site functionally coupled to the nucleotide sequence facilitates ribosome binding.

Examples of additional regulatory elements useful for enhancing or regulating gene expression or polypeptide processing that may be present include an enhancer, a leader sequence and an operator. An enhancer region increases transcription. Examples of enhancer regions include the CMV enhancer and the SV40 enhancer. (Hitt et al., *Methods in Molecular Genetics* 7:13-30, 1995, Xu, et al., *Gene* 272:149-156, 2001.) An enhancer region can be associated with a promoter.

A leader sequence is an amino acid region on a polypeptide that directs the polypeptide into the proteasome. Nucleic acid encoding the leader sequence is 5' of a structural gene and is transcribed along the structural gene. An example of a leader sequences is tPA.

An operator sequence can be used to regulate gene expression. For example, the Tet operator sequence can be used to repress gene expression.

IV. Encoding Nucleic Acid Sequence

An encoding nucleic acid sequence provide codons coding for a particular amino acid sequence. Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons".

The translation of a particular codon into a particular amino acid is well known in the art (see, e.g., Lewin *GENES IV*, p. 119, Oxford University Press, 1990). Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU Q=Gln=Glutamine: codons CAA, CAG R=Arg=Arginine: codons AGA, AGG, CGA, CGC, CGG, CGU S=Ser=Serine: codons AGC, AGU, UCA, UCC, UCG, UCU T=Thr=Threonine: codons ACA, ACC, ACG, ACU V=Val=Valine: codons GUA, GUC, GUG, GUU W=Trp=Tryptophan: codon UGG Y=Tyr=Tyrosine: codons UAC, UAU.

Nucleotides 1269-7223 of SEQ ID NO: 13 provides an example of a NS3-NS4A-NS4B-NS5A-NS5B* sequence. Sequences substantially similar to nucleotides 1269-7223 of SEQ ID NO: 13 can be used as part of an vaccine component. (Emini et al., International Publication Number WO 03/031588.) For example, such substantially similar sequences can be used as part of a ChA3 or ChA63 based adenovector.

Reference to a "substantially similar sequence" with respect to nucleotide sequences indicates an identity of at least about 70% to a reference sequence. Percent identity (also referred to as percent identical) to a reference sequence is determined by aligning a nucleotides region with the corresponding reference region to obtain maximal identity and determining the number of identical nucleotides in the corresponding regions. This number is divided by the total number of nucleotides in the reference region and then multiplied by 100 and rounded to the nearest whole number.

Nucleic acid sequences can be optimized in an effort to enhance expression in a host. Factors to be considered include C:G content, preferred codons, and the avoidance of inhibitory secondary structure. These factors can be combined in different ways in an attempt to obtain nucleic acid sequences having enhanced expression in a particular host. (See, for example, Donnelly et al., International Publication Number WO 97/47358.)

Optimization of HCV encoding nucleic acid is also described in Emini et al., International Publication Number WO 03/031588. WO 03/031588 provides examples of different optimized sequences encoding NS3-NS4A-NS4B-NS5A-NS5B*.

An example of a codon optimized sequence for $NS3_1$-$NS4A_1$-$NS3_2$-$NS4A_2$-$NS4B_2$-$NS5A_2$-$NS5B_2$* is provided by nucleotides 1891-9915 of SEQ ID NO: 2. Nucleotides 1891-1893 provide a methionine codon for the $NS3_1$-$NS4A_1$ region. Nucleotides 3949-3960 provide the $NS3_2$-$NS4A_2$ region with the first four amino acids based on HCV 3a, followed by a methionine.

In different embodiments of the present invention, the $NS3_1$-$NS4A_1$-$NS3_2$-$NS4A_2$-$NS4B_2$-$NS5A_2$-$NS5B_2$* encoding region is substantially similar to nucleotides 1891-9915 or 1894-9915 of SEQ ID NO: 2. In different embodiments, the nucleotide sequence has an identity to nucleotides 1891-9915 or 1894-9915 of SEQ ID NO: 2 of at least 80%, at least 85%, at least 90%, or at least 95%; or differs by 0, 1, 2, 3, 4, 5, 6, 7, 8, 9, 10, 11, 12, 13, 14, 15, 16, 17, 18, 19, 20, or 1-50 nucleotides.

V. Nucleic Acid Vectors

Nucleic acid encoding a HCV polypeptide can be used as therapeutic vectors or in the production of therapeutic vectors. Vectors used in the production of therapeutic vectors include shuttle vectors and adenovirus genome plasmids.

Therapeutic vectors are used to introduce and express a HCV polypeptide in a cell. Suitable vectors can deliver nucleic acid into a target cell without causing an unacceptable side effect. Cellular expression is achieved using a gene expression cassette encoding the HCV polypeptide.

Examples of vectors that can be used for therapeutic applications include first and second generation adenovectors, helper dependent adenovectors, adeno-associated viral vectors, retroviral vectors, alpha virus vectors, Venezuelan Equine Encephalitis virus vector, and plasmid vectors. (Hitt, et al., *Advances in Pharmacology* 40:137-206, 1997, Johnston et al., U.S. Pat. No. 6,156,588, Johnston et al., International Publication Number WO 95/32733, Emini et al., International Publication Number WO 03/031588.)

V.A. Adenovectors

Adenovectors employ a recombinant adenovirus genome for expression of a desired protein or polypeptide in a target cell. A wild-type adenovirus has a double-stranded linear genome with inverted terminal repeats at both ends. During viral replication, the genome is packaged inside a viral capsid to form a virion. The virus enters its target cell through viral attachment followed by internalization. (Hitt et al., *Advances in Pharmacology* 40:137-206, 1997.)

The adenovirus genome provide different elements needed for adenovirus replication and processing. Each extremity of the adenoviral genome contains inverted terminal repeat (ITRs), which are necessary for viral replication. The virus also encodes protease activity necessary for processing some of the structural proteins required to produce infectious virions.

The structure of the adenoviral genome can be described based on the expression order of viral genes following host cell transduction. Viral genes are referred to as early (E) or late (L) genes according to whether transcription occurs prior to or after onset of DNA replication. In the early phase of transduction, the E1, E2, E3 and E4 genes are expressed to prepare the host cell for viral replication. The virus can be rendered replication defective by deletion of the essential early-region 1 (E1) of the viral genome. (Brody et al, *Ann. N.Y. Acad. Sci.,* 716:90-101, 1994.)

During the late phase, expression of the late genes L1-L5, which encode the structural components of the virus particles is switched on. All of the late genes are under the control of a single promoter and encode proteins including the penton (L2), the hexon (L3), the 100 kDa scaffolding protein (L4), and the fiber protein (L5), which form the new virus particle into which the adenoviral DNA becomes encapsidated. Ultimately, the wild-type adenoviral replication process causes cells lysis.

Adenovectors can be based on different adenovirus serotypes such as those found in humans or animals. Examples of animal adenoviruses include bovine, porcine, chimpanzee, murine, canine, and avian (CELO). Human adenovirus include Group B, C, D, or E serotypes such as type 2 ("Ad2"), 4 ("Ad4"), 5 ("Ad5"), 6 ("Ad6"), 24 ("Ad24"), 26 ("Ad26"), 34 ("Ad34") and 35 ("Ad35"). Adenovectors can contain regions from a single adenovirus or from two or more different adenoviruses.

In different embodiments, adenovectors are based on Ad5, Ad6, ChAd3, ChAd63, or a combination thereof. Ad5 is described by Chroboczek, et al., *J. Virology* 186:280-285, 1992. Ad5 and Ad6 based vectors are described in Emini et al., International Publication Number WO 03/031588. The full length nucleic acid sequence for ChAd3 is provided in FIGS. 6A-6H. The full length nucleic acid sequence of ChAd63 is provided in FIGS. 7A-7H.

In an embodiment of the present invention, the adenovector contains one or more surface exposed chimpanzee ChAd3 or ChAd63 structural proteins. Surface exposed proteins include fiber, hexon, and penton. An adenovector including such proteins, as opposed to human adenovirus proteins, is less likely to be affected by the immune response when the patient was previously exposed to a human adenovirus.

In different embodiments the recombinant adenovector genome encodes at least one of:

a) a fiber region with an amino acid sequence substantially similar to SEQ ID NO: 3 or 9;

b) a hexon region with an amino acid sequence substantially similar to either SEQ ID NO: 5 or 11; and c) a penton region with an amino acid sequence substantially similar to SEQ ID NO: 7.

In additional different embodiments, sequence similarity is at least 80%, at least 85%, at least 90%, at least 95%; or the sequences differ by 0, 1, 2, 3, 4, 5, 6, 7, 8, 9, 10, 11, 12, 13, 14, 15, 16, 17, 18, 19, or 20 amino acid alterations.

V.A.1 First Generation Adenovectors

First generation adenovectors contain a recombinant adenovirus genome having an E1 deletion, an optional E3 deletion, an optional E4 deletion, and an expression cassette. The extent and combination of deletions are sufficiently large to render the virus replication incompetent and to accommodate a gene expression cassette encoding a desired product. The virus can be made replication incompetent by the E1 deletion.

E1 deletions can be obtained starting at about base pair 342 going up to about base pair 3523 of Ad5, or a corresponding region from other adenoviruses. Preferably, the deleted region involves removing a region from about base pair 450 to about base pair 3511 of Ad5, or a corresponding region from other adenoviruses. Larger E1 region deletions starting at about base pair 341 removes elements that facilitate virus packaging.

E3 deletions can be obtained starting at about base pair 27865 to about base pair 30995 of Ad5, or the corresponding region of other adenovectors. Preferably, the deletion region involves removing a region from about base pair 28134 up to about base pair 30817 of Ad5, or the corresponding region of other adenovectors.

E4 deletions can be obtained starting at about base pair 34634 of ChAd3 to about base pair 37349 or a corresponding region from other adenoviruses. An E4 deletion should either retain native E4orf6, or an E4orf6 from a different adenovirus can be inserted. Bett et al., International Publication Number WO2004/018627 illustrates that use of heterologous E4 orf6.

The combination of deletions to E1, E3 and E4 should be sufficiently large so that the overall size of the recombinant genome containing the gene expression cassette does not exceed about 105% of the wild type adenovirus genome. For example, as a recombinant adenovirus Ad5 genome increases in size above about 105% the genome becomes unstable. (Bett et al., *Journal of Virology* 67:5911-5921, 1993.)

Preferably, the size of the recombinant adenovirus genome containing the gene expression cassette is about 85% to about 105% the size of the wild type adenovirus genome. In different embodiments, the size of the recombinant adenovirus genome containing the expression cassette is about 100% to about 105.2%, or about 100%, the size of the wild type genome.

Approximately 7,500 kb can be inserted into an Ad5 or Ad6 genome with an E1 and E3 deletion. Without any deletion, the Ad5 genome is 35,935 base pairs and the Ad6 genome is 35,759 base pairs.

ChAd3 and ChAd63 vectors have an increased capacity of insertion of nucleic acid compared to Ad5, due to the larger genomic size bigger and the presence of a larger E3 region that can be deleted. The ChAd3 genome is 37,741 base pairs, and the ChAd63 genome is 36,643 base pairs.

Approximately up to 10,800 bp can be inserted into a ChAd3 and ChAd63 adenovector carrying the deletion of E1, E3, and the substitution of E4 with Ad5 E4 orf6. The substitution of the E4 with Ad5 E4 orf6 is both a deletion and a substitution, in that the substituted Ad5 E4orf6 is less than what was deleted. An insert of 10,800 bp for these vectors reaches the limit of 105% of the size of the wild type genome.

Replication of first generation adenovectors can be performed by supplying the E1 gene product in trans. The E1 gene product can be supplied in trans, for example, by using cell lines transformed with the adenovirus E1 region. Examples of cells and cell lines transformed with the adenovirus E1 region are HEK 293 cells, 911 cells, PERC.6™ cells, and transfected primary human aminocytes cells. (Graham et al., *Journal of Virology* 36:59-72, 1977, Schiedner et al., *Human Gene Therapy* 11:2105-2116, 2000, Fallaux et al., *Human Gene Therapy* 9:1909-1917, 1998, Bout et al., U.S. Pat. No. 6,033,908.)

Substitution in cis of the chimp adenovirus native E4 region with Ad5 E4 orf6 should facilitate growth and/or increase the yield of chimp adenoviral vectors of varying serotypes propagated in Ad5 complementing cell line. The Ad5 E1 sequences in 293 and PER.C6 cells do not fully complement the replication of serotypes outside of human adenovirus belonging to group C like chimp adenoviruses.

An expression cassette should be inserted into a recombinant adenovirus genome in the region corresponding to the deleted E1 region or the deleted E3 region. The expression cassette can have a parallel or anti-parallel orientation. In a parallel orientation the transcription direction of the inserted gene is the same direction as the deleted E1 or E3 gene. In an anti-parallel orientation transcription the opposite strand serves as a template and the transcription direction is in the opposite direction.

In an embodiment of the present invention the adenovector contains an E4 deletion and an insertion of a sequence substantially similar to the Ad5 E4orf6 sequence provided by nucleotides 34601-35482 of SEQ ID NO: 13. In different embodiments, the sequence identity is at least 75%, at least 80%, at least 85%, at least 90%, at least 95%; or differs from nucleotides 34601-35482 of SEQ ID NO: 13 by 0, 1, 2, 3, 4, 5, 6, 7, 8, 9, 10, 11, 12, 13, 14, 15, 16, 17, 18, 19, 20, or 1-50 nucleotides.

In an embodiment of the present invention the adenovector backbone has a nucleotide sequence identity to nucleotides 1460 and 7468-35890 of SEQ ID NO: 13, or to nucleotides 1-454 and 7458-34658 of SEQ ID NO: 17, of at least 70%, at least 75%, at least 80%, at least 85%, at least 90%, at least 95%; or differs from nucleotides 1460 and 7468-35890 of SEQ ID NO: 13, or to nucleotides 1454 and 7458-34658 of SEQ ID NO: 17, by 0, 1, 2, 3, 4, 5, 6, 7, 8, 9, 10, 11, 12, 13, 14, 15, 16, 17, 18, 19, 20, or 1-50 nucleotides.

In another embodiment of the adenovector containing an expression cassette has a nucleotide sequence identity to SEQ ID NO: 13 or 17 of at least 70%, at least 75%, at least 80%, at least 85%, at least 90%, at least 95%; or differs from SEQ ID NO: 13 or 17 by 0, 1, 2, 3, 4, 5, 6, 7, 8, 9, 10, 11, 12, 13, 14, 15, 16, 17, 18, 19, 20, or 1-50 nucleotides.

V.A.2 Second Generation Adenovectors

Second generation adenovectors contain less adenoviral genome than first generation vectors and can be used in conjugation with complementing cell lines and/or helper vectors supplying adenoviral proteins. Second generation adenovectors in general are described in different references such as Russell, *Journal of General Virology* 81:2573-2604, 2000; Hitt et al., 1997, Human Ad vectors for Gene Transfer, Advances in Pharmacology, Vol. 40 Academic Press, Catalucci et al. *Journal of Virology* 79: 6400-6409, 2005. Second generation adenovectors can be based on different types of adenovirus, including human and chimpanzee adenovirus.

V.B. DNA Plasmid Vectors

DNA vaccine plasmid vectors contain a gene expression cassette along with elements facilitating replication and preferably vector selection. Preferred elements provide for replication in non-mammalian cells and a selectable marker. Therapeutic vectors should not contain elements providing for replication in human cells or for integration into human nucleic acid.

The selectable marker facilitates selection of nucleic acids containing the marker. Preferred selectable markers are those conferring antibiotic resistance. Examples of antibiotic selection genes include nucleic acid encoding resistance to ampicillin, neomycin, and kanamycin.

Suitable DNA vaccine vectors can be produced starting with a plasmid containing a bacterial origin of replication and a selectable marker. Examples of bacterial origins of replication providing for higher yields include the ColE1 plasmid-derived bacterial origin of replication. (Donnelly et al., *Annu. Rev. Immunol.* 15:617-648, 1997.)

The presence of the bacterial origin of replication and selectable marker allows for the production of the DNA vector in a bacterial strain such as *E. coli*. The selectable marker is used to eliminate bacteria not containing the DNA vector.

SEQ ID NO: 2 provides an example of a plasmid vector containing an expression cassette coding for an HCV polypeptide. In an embodiment of the present invention the plasmid vector has a nucleotide similarity sequence to SEQ ID NO: 2 of at least 70%, at least 75%, at least 80%, at least 85%, at least 90%, at least 95% or differs from SEQ ID NO: 2 by 0, 1, 2, 3, 4, 5, 6, 7, 8, 9, 10, 11, 12, 13, 14, 15, 16, 17, 18, 19, 20, or 1-50 nucleotides.

VI. Vector Production

Vectors can be produced using recombinant nucleic acid techniques such as those involving the use of restriction enzymes, nucleic acid ligation, and homologous recombination. Recombinant nucleic acid techniques are well known in the art. (Ausubel, *Current Protocols in Molecular Biology*, John Wiley, 1987-1998, and Sambrook et al., *Molecular Cloning, A Laboratory Manual*, 2$^{nd}$ Edition, Cold Spring Harbor Laboratory Press, 1989.)

Intermediate vectors are used to derive a therapeutic vector or to transfer an expression cassette or portion thereof from one vector to another vector. Examples of intermediate vectors include adenovirus genome plasmids and shuttle vectors.

Useful elements in an intermediate vector include an origin of replication, a selectable marker, homologous recombination regions, and convenient restriction sites. Convenient restriction sites can be used to facilitate cloning or release of a nucleic acid sequence.

Homologous recombination regions provide nucleic acid sequence regions that are homologous to a target region in another nucleic acid molecule. The homologous regions flank the nucleic acid sequence that is inserted into the target region. In different embodiments homologous regions are about 150 to 600 nucleotides in length, or about 100 to 500 nucleotides in length.

An embodiment of the present invention describes a shuttle vector containing an HCV polypeptide expressing expression cassette, a selectable marker, a bacterial origin of replication, a first adenovirus homology region and a second adenovirus homologous region that target the expression cassette to insert in or replace an E1 region. The first and second homology regions flank the expression cassette. The first homology region contains at least about 100 base pairs substantially homologous to at least the right end (3' end) of a wild-type adenovirus region from about base pairs 4450. The second homology contains at least about 100 base pairs substantially homologous to at least the left end (5' end) of Ad5 from about base pairs 3511-5792, or the corresponding region from another adenovirus.

Reference to "substantially homologous" indicates a sufficient degree of homology to specifically recombine with a target region. In different embodiments substantially homologous refers to at least 85%, at least 95%, or 100% sequence identity.

One method of producing adenovectors is through the creation of a pre-adenovirus genome plasmid containing an expression cassette. The pre-adenovirus plasmid contains all the adenovirus sequences needed for replication in the desired complimenting cell line. The pre-adenovirus plasmid is then digested with a restriction enzyme to release the viral ITR's and transfected into the complementing cell line for virus rescue. The ITR's must be released from plasmid sequences to allow replication to occur. Adenovector rescue results in the production of an adenovector containing the expression cassette. (See, for example, Emini et al., International Publication Number WO 03/031588.)

VI.A. Adenovirus Genome Plasmids

Adenovirus genome plasmids contain an adenovector sequence inside a longer-length plasmid (which may be a cosmid). The longer-length plasmid may contain additional elements such as those facilitating growth and selection in eukaryotic or bacterial cells depending upon the procedures employed to produce and maintain the plasmid. Adenovirus genome plasmids preferably have a gene expression cassette inserted into a E1 or E3 deleted region.

Techniques for producing adenovirus genome plasmids include those involving the use of shuttle vectors and homologous recombination, and those involving the insertion of a gene expression cassette into an adenovirus cosmid. (Hitt et al., *Methods in Molecular Genetics* 7:13-30, 1995, Danthinne et al., *Gene Therapy* 7:1707-1714, 2000.)

An embodiment of the present invention describes a method of making an adenovector involving a homologous recombination step to produce an adenovirus genome plasmid and an adenovirus rescue step. The homologous recombination step involves the use of a shuttle vector containing a HCV polypeptide expression cassette flanked by adenovirus homology regions. The adenovirus homology regions target the expression cassette into either the E1 or E3 deleted region.

VI.B. Adenovector Rescue

An adenovector can be rescued from a recombinant adenovirus genome plasmid using techniques well known in the art or described herein. Examples of techniques for adenovirus rescue well known in the art are provided by Hitt et al., *Methods in Molecular Genetics* 7:13-30, 1995, and Danthinne et al., *Gene Therapy* 7:1707-1714, 2000.

A example of a method for rescuing an adenovector involves boosting adenoviral replication. Boosting adenoviral replication can be performed, for example, by supplying adenoviral functions such as E2 proteins (polymerase, pre-terminal protein and DNA binding protein) as well as E4 orf6 on a separate plasmid. (Emini et al., International Publication Number WO 03/031588.)

VII. HCV Combination Treatment

An HCV nucleic acid vaccine can be used by itself to treat a patient, can be used in conjunction with other HCV therapeutics, and can be used with agents targeting other types of diseases. Additional therapeutics include therapeutic agents to treat HCV and diseases having a high prevalence in HCV infected persons. Agents targeting other types of disease include vaccines directed against HIV and HBV.

Additional therapeutics for treating HCV include vaccines and non-vaccine agents. (Zein, *Expert Opin. Investig. Drugs* 10: 1457-1469, 2001.) Examples of additional HCV vaccines include vaccines designed to elicit an immune response against an HCV core, E1, E2 or p7 region. Examples of vaccine components include naturally occurring HCV polypeptides, HCV mimotope polypeptides or nucleic acid encoding such polypeptides.

References describing techniques for producing mimotopes in general and describing different HCV mimotopes are provided in Felici et al. U.S. Pat. No. 5,994,083 and Nicosia et al., International Application Number WO 99/60132. A HCV mimotope can be fused to a naturally occurring HCV antigen.

Currently approved anti-HCV agents are interferon alpha, and interferon alpha in combination with ribavirin. Different forms of interferon alpha, such as recombinant interferon and peglyated interferons, can be used to treat HCV infections. (De Francesco et al., *Antiviral Research* 58:1-16, 2003, Walker et al., *Antiviral Chemistry & Chemotherapy* 14:1-21, 2003.)

A variety of different anti-HCV agents are in different phases of clinical developments. The different anti-HCV agents being developed include agents directed against different HCV targets. Examples of different HCV targets include HCV polymerase and HCV NS3-NS4A protease. (De Francesco et al., *Antiviral Research* 58:1-16, 2003, Walker et al., *Antiviral Chemistry & Chemotherapy* 14:1-21, 2003.)

VIII. Pharmaceutical Administration

HCV vaccines can be formulated and administered to a patient using the guidance provided herein along with techniques well known in the art. Guidelines for pharmaceutical administration in general are provided in, for example, *Modern Vaccinology*, Ed. Kurstak, Plenum Med. Co. 1994; *Remington's Pharmaceutical Sciences* 18$^{th}$ Edition, Ed. Gennaro, Mack Publishing, 1990; and *Modern Pharmaceutics* 2$^{nd}$ Edition, Eds. Banker and Rhodes, Marcel Dekker, Inc., 1990, each of which are hereby incorporated by reference herein.

HCV vaccines can be administered by different routes such intravenous, intraperitoneal, subcutaneous, intramuscular, intradermal, impression through the skin, or nasal. A preferred route is intramuscular.

Intramuscular administration can be preformed using different techniques such as by injection with or without one or more electric pulses. Electric mediated transfer can assist genetic immunization by stimulating both humoral and cellular immune responses.

Vaccine injection can be performed using different techniques, such as by employing a needle or a needless injection system. An example of a needless injection system is a jet injection device. (Donnelly et al., International Publication Number WO 99/52463.)

Electrically mediated transfer or Gene Electro-Transfer (GET) can be performed by delivering suitable electric pulses after nucleic acid injection. (See Mathiesen, International Publication Number WO 98/43702 and Emini et al. International Publication Number WO 03/031588.)

VIII.A. Pharmaceutical Carriers

Pharmaceutically acceptable carriers facilitate storage and administration of a vaccine to a subject. Examples of pharmaceutically acceptable carriers are described herein. Additional pharmaceutical acceptable carriers are well known in the art.

Pharmaceutically acceptable carriers may contain different components such a buffer, normal saline or phosphate buffered saline, sucrose, salts and polysorbate. An example of a pharmaceutically acceptable carrier is: 2.5-10 mM TRIS buffer; 25-100 mM NaCl; 2.5-10% sucrose; 0.01-2 mM $MgCl_2$; and 0.001%-0.01% polysorbate 80 (plant derived). The pH can be about 7.0-9.0. A specific example of a carrier contains 5 mM TRIS, 75 mM NaCl, 5% sucrose, 1 mM $MgCl_2$, 0.005% polysorbate 80 at pH 8.0.

VIII.B. Dosing Regimes

Suitable dosing regimens can be determined taking into account the efficacy of a particular vaccine and factors such as age, weight, sex and medical condition of a patient; the route of administration; the desired effect; and the number of doses. The efficacy of a particular vaccine depends on different factors such as the ability of a particular vaccine to produce polypeptide that is expressed and processed in a cell and presented in the context of MHC class I and II complexes.

HCV polypeptide encoding nucleic acid administered to a patient can be part of different types of vectors including viral vectors such as adenovector, and DNA plasmid vaccines. In different embodiments concerning administration of a DNA plasmid, about 0.1 to 10 mg of plasmid is administered to a patient, and about 1 to 5 mg of plasmid is administered to a patient. In different embodiments concerning administration of a viral vector, preferably an adenoviral vector, about $10^5$ to $10^{11}$ viral particles are administered to a patient, and about $10^7$ to $10^{10}$ viral particles are administered to a patient.

Viral vector vaccines and DNA plasmid vaccines may be administered alone, or may be part of a prime and boost administration regimen. A mixed modality priming and booster inoculation involves either priming with a DNA vaccine and boosting with viral vector vaccine, or priming with a viral vector vaccine and boosting with a DNA vaccine.

Multiple priming, for example, about to 24 times or more may be used. The length of time between priming and boost may typically vary from about four months to a year, but other time frames may be used. The use of a priming regimen with a DNA vaccine may be preferred in situations where a person has a pre-existing anti-adenovirus immune response.

In an embodiment of the present invention, initial vaccination is performed with a DNA vaccine directly into muscle tissue. Following initial vaccination a boost is performed with an adenovector or DNA vaccine.

Agents such as interleukin-12, GM-CSF, B7-1, B7-2, IP10, and Mig-1 can be coadministered to boost the immune response. The agents can be coadministered as proteins or through use of nucleic acid vectors.

VIII.C. Heterologous Prime-Boost

Heterologous prime-boost is a mixed modality involving the use of one type of viral vector for priming and another type of viral vector for boosting. The heterologous prime-boost can involve related vectors such as vectors based on different adenovirus serotypes and more distantly related viruses such adenovirus from a different animal and poxvirus. The use of poxvirus and adenovectors to protect mice against malaria is illustrated by Gilbert et al., *Vaccine* 20:1039-1045, 2002. The chimpanzee adenovectors expressing a HCV polypeptide provide a vector that can be used in a heterologous prime boost.

The length of time between priming and boosting typically varies from about four months to a year, but other time frames may be used. The minimum time frame should be sufficient to allow for an immunological rest. In an embodiment, this rest is for a period of at least 6 months. Priming may involve multiple priming with one type of vector, such as 2-4 primings.

Expression cassettes present in a poxvirus vector should contain a promoter either native to, or derived from, the poxvirus of interest or another poxvirus member. Different strategies for constructing and employing different types of poxvirus based vectors including those based on vaccinia virus, modified vaccinia virus, avipoxvirus, raccoon poxvirus, modified vaccinia virus Ankara, canarypoxviruses (such as ALVAC), fowlpoxviruses, cowpoxviruses, and NYVAC are well known in the art. (Moss, *Current Topics in Microbiology and Immunology* 158:25-38, 1982; Earl et al., In *Current Protocols in Molecular Biology*, Ausubel et al. eds., New York: Greene Publishing Associates & Wiley Interscience; 1991:16.16.1-16.16.7; Child et al., *Virology* 174(2):625-9, 1990; Tartaglia et al., *Virology* 188:217-232, 1992; U.S. Pat. Nos. 4,603,112, 4,722,848, 4,769,330, 5,110,587, 5,174,993, 5,185,146, 5,266,313, 5,505,941, 5,863,542, and 5,942,235.)

VIII.D. Adjuvants

HCV vaccines can be formulated with an adjuvant. Adjuvants are substances that can assist an immunogen in producing an immune response. Adjuvants can function by different mechanisms such as increasing the biologic or immunologic half-life, providing immunomodulatory agents, or inducing production of immunomodulatory cytokines. Different adjuvants can be used in combination.

HCV vaccines can be formulated with an adjuvant. Examples of adjuvants are alum, AlPO$_4$, alhydrogel, Lipid-A and derivatives or variants thereof, Freund's incomplete adjuvant, neutral liposomes, liposomes containing the vaccine and cytokines, non-ionic block copolymers, chemokines, and immunodulatory agents.

Non-ionic block polymers containing polyoxyethylene (POE) and polyxylpropylene (POP), such as POE-POP-POE block copolymers may be used as an adjuvant. (Newman et al., *Critical Reviews in Therapeutic Drug Carrier Systems* 15:89-142, 1998.) The immune response of a nucleic acid can be enhanced using a non-ionic block copolymer combined with an anionic surfactant.

Different types of compounds can be used as immunodulatory agents, such as a cytokine, a hormone, a lipidic derivative and a small molecule. Examples of immunomodulatory agents include anti-CTLA-4, anti-CD137, anti-CD40, anti-CD28, anti-CD4, anti-CD25, antiPD1, anti-PD-L1, anti-PD-L2, FOXP3-blocking agents, Flt-3 ligand, imiquimod, granulocyte-macrophage colony-stimulating factor (GM-CSF), sargramostin, Toll-like receptor (TLR)-7 agonists, and TLR-9 agonist.

A specific example of an adjuvant formulation is one containing CRL-1005 (CytRx Research Laboratories), DNA, and benzylalkonium chloride (BAK). A CRL-1005 formulation can be prepared, for example, as described by Emini et al., International Publication Number WO 03/031588.

VIII.E. Vaccine Storage

Vaccines can be stored using different types of buffers. For example, buffer A 105 described in Emini et al., International Publication Number WO 03/031588 can be employed.

Storage of DNA can be enhanced by removal or chelation of trace metal ions. Reagents such as succinic or malic acid, and chelators can be used to enhance DNA vaccine stability. Examples of chelators include multiple phosphate ligands and EDTA. The inclusion of non-reducing free radical scavengers, such as ethanol or glycerol, can also be useful to prevent damage of DNA plasmid from free radical production. Furthermore, the buffer type, pH, salt concentration, light exposure, as well as the type of sterilization process used to prepare the vials, may be controlled in the formulation to optimize the stability of the DNA vaccine.

IX. EXAMPLES

Examples are provided below to further illustrate different features of the present invention. The examples also illustrate useful methodology for practicing the invention. These examples do not limit the claimed invention.

Example 1

Annotation of ChAd63 and ChAd3 Genome Sequences

ChAd63 and ChAd3 were blasted against a local database built with all the protein sequences of the "Human adenovirus C" group (HAdV-C; Taxonomy ID: 129951). Protein sequences were downloaded from the NCBI server by searching for the specific Taxonomy IDs. The blast search was performed using the blastx program. The number of sequences to show in the alignment was set to 1000 and the Filter switched off. Blast results were then analyzed with MSPcrunch, a BLAST enhancement tool for large-scale sequence similarity analysis.

Every resulting CDS annotation on the two genome sequences was manually confirmed by looking at the position of ATG and STOP codons and when necessary at the position of the splicing sites. All products were searched with blastp into the previously built database of adenoviral proteins to validate the prediction of such products by homology. The plain genome sequences of ChAd63 and ChAd3 were annotated with VNTI in accordance with the MSPcrunch results and the manual revision. ChAd3 and ChAd63 of gene products are provided in Tables 1 and 2.

TABLE 1

ChAd3 Gene Products

| CDS | Products | CDS boundaries (NCBI format) | strand |
|---|---|---|---|
| CDS1 | E1A 25.5K | 589...991, 1243...1544 | direct |
| CDS2 | E1A 30.8K | 589...1129, 1243...1544 | direct |
| CDS3 | E1B 22K | 1716...2279 | direct |
| CDS4 | E1B 57K | 2021...3544 | direct |
| CDS5 | IX | 3640...4104 | direct |
| CDS6 | IVa2 | 4163...5499, 5778...5790 | complement |
| CDS7 | Pol | 5269...8865, 14228...14236 | complement |
| CDS8 | pTP | 8664...10667, 14228...14236 | complement |
| CDS9 | 48K product | 11120...12379 | direct |
| CDS10 | pIIIa | 12403...14181 | direct |
| CDS11 | III | 14273...16054 | direct |
| CDS12 | pVII | 16069...16665 | direct |
| CDS13 | V | 16738...17853 | direct |
| CDS14 | pX | 17878...18123 | direct |
| CDS15 | pVI | 18219...18974 | direct |
| CDS16 | Exon | 19086...21968 | direct |
| CDS17 | Protease | 21998...22627 | direct |
| CDS18 | DBP | 22743...24395 | complement |
| CDS19 | 92K product | 24445...26940 | direct |
| CDS20 | 22K product | 26630...27229 | direct |
| CDS21 | 33K product | 26630...26966, 27169...27551 | direct |
| CDS22 | pVIII | 27626...28309 | direct |
| CDS23 | E3 12K | 28310...28627 | direct |
| CDS24 | E3 CR1-alphap0 | 29125...29325 | direct |

TABLE 1-continued

ChAd3 Gene Products

| CDS | Products | CDS boundaries (NCBI format) | strand |
|---|---|---|---|
| CDS25 | E3 gp18K | 29328 . . . 29819 | direct |
| CDS26 | E3 33K | 29848 . . . 30738 | direct |
| CDS27 | E3A 11K | 31293 . . . 31589 | direct |
| CDS28 | E3 RID alpha | 31601 . . . 31873 | direct |
| CDS29 | E3 RID beta | 31876 . . . 32274 | direct |
| CDS30 | E3 15K | 32267 . . . 32653 | direct |
| CDS31 | U exon | 32684 . . . 32848 | complement |
| CDS32 | Fiber | 32859 . . . 34490 | direct |
| CDS33 | E4 ORF6/7 | 34698 . . . 34973, 35685 . . . 35858 | complement |
| CDS34 | E4 ORF6 | 34974 . . . 35858 | complement |
| CDS35 | E4 ORF4 | 35758 . . . 36123 | complement |
| CDS36 | E4 ORF3 | 36139 . . . 36486 | complement |
| CDS37 | E4 ORF2 | 36483 . . . 36875 | complement |
| CDS38 | E4 ORF1 | 36928 . . . 37314 | complement |

TABLE 2

ChAd63 Gene Products

| CDS | Products | CDS boundaries (GenBank format) | strand |
|---|---|---|---|
| CDS1 | E1A 24.6K | 576 . . . 1050, 1229 . . . 1437 | direct |
| CDS2 | E1A 28.3K | 576 . . . 1143, 1229 . . . 1437 | direct |
| CDS3 | E1B 22.6K | 1601 . . . 2179 | direct |
| CDS4 | E1B 9.9K | 1906 . . . 2186, 3322 . . . 3340 | direct |
| CDS5 | E1B 18.4K | 1906 . . . 2216, 3204 . . . 3420 | direct |
| CDS6 | E1B 55.7K | 1906 . . . 3420 | direct |
| CDS7 | IX | 3505 . . . 3933 | direct |
| CDS8 | IVa2 | 3993 . . . 5326, 5605 . . . 5617 | complement |
| CDS9 | Pol | 5096 . . . 8455 | complement |
| CDS10 | 21.1K product | 7877 . . . 8461 | direct |
| CDS11 | pTP 72.5K | 8458 . . . 10347 | complement |
| CDS12 | 44.3K product | 10845 . . . 12020 | direct |
| CDS13 | 65.5K product | 12044 . . . 13810 | direct |
| CDS14 | pIII | 13889 . . . 15511 | direct |
| CDS15 | pVII | 15515 . . . 16099 | direct |
| CDS16 | pV | 16144 . . . 17181 | direct |
| CDS17 | 8.5K product | 17204 . . . 17437 | direct |
| CDS18 | pVI | 17509 . . . 18237 | direct |
| CDS19 | Exon | 18329 . . . 21154 | direct |
| CDS20 | 23.6K product | 21179 . . . 21802 | direct |
| CDS21 | E2A | 21882 . . . 23417 | complement |
| CDS22 | 88.5K product | 23443 . . . 25842 | direct |
| CDS23 | 24.9K product | 25556 . . . 25886, 26056 . . . 26399 | direct |
| CDS24 | pVIII | 26471 . . . 27154 | direct |
| CDS25 | E3 12.1K | 27155 . . . 27475 | direct |
| CDS26 | E3 23K | 27429 . . . 27503, 27692 . . . 28055 | direct |
| CDS27 | E3 19.6K | 28037 . . . 28570 | direct |
| CDS28 | E3 22.3K | 29332 . . . 29946 | direct |
| CDS29 | E3 32.5K | 29961 . . . 30857 | direct |
| CDS30 | E3 26.7K | 28600 . . . 29319 | direct |
| CDS31 | E3 10.5K | 30865 . . . 31140 | direct |
| CDS32 | E3 16.4K | 31146 . . . 31577 | direct |
| CDS33 | E3 15.2K | 31570 . . . 31977 | direct |
| CDS34 | Fiber | 32254 . . . 33531 | direct |
| CDS35 | E4 15.7K | 33638 . . . 33889, 34621 . . . 34791 | complement |
| CDS36 | E4 34.9K | 33886 . . . 34791 | complement |
| CDS37 | E4 13.9K | 34697 . . . 35062 | complement |
| CDS38 | E4 13.6K | 35072 . . . 35425 | complement |
| CDS39 | E4 14.6K | 35422 . . . 35811 | complement |
| CDS40 | E4 13.8K | 35851 . . . 36225 | complement |

Example 2

ChAd3 Vector Construction

Construction of ChAd3 ΔE1,E3,E4, E4Ad5orf6 vector involved the following steps:

I. Construction of a Subgroup C Shuttle Vector

The ChAd3 viral genome was fully sequenced (SEQ ID NO: 14) and the information used to construct a shuttle vector to facilitate cloning by homologous recombination of entire genome. Briefly, the shuttle vector used to clone subgroup C chimp adenovirus 3, referred to herein as pChAd3EGFP, was constructed as follows: a ChAd3 DNA fragment (nt 3542-4105) containing pix coding region was amplified by PCR with the primers of SEQ ID NOs: 20 and 21, digested with SgfI-AscI then cloned into pARSCV32-3 and digested with SgfI-AscI generating pARS-ChAd3D. ChAd3 right end (nt 37320-37441) was amplified by PCR with primers of SEQ ID NOs: 22 and 23, digested with XbaI and BamHI then ligated to pARS-ChAd3D restricted with XbaI and BamHI, generating pARS-ChAd3RD. ChAd3 viral DNA left end (nt 1-460) was amplified by PCR with primers of SEQ ID NOs: 24 and 25, digested with EcoRI and SgfI then cloned pARS-ChAd3RD digested with EcoRI and SgfI, thus generating pARS-ChAd3RLD. The viral DNA cassette was also designed to contain restriction enzyme sites (PmeI) located at the end of both ITR's so that digestion will release viral DNA from plasmid DNA.

II. Construction of ΔE1 ChAd3 Vector

ChAd3 vector was constructed by homologous recombination in *E. coli* strain BJ5183. BJ5183 cells were co-transformed with ChAd3 purified viral DNA and pChAd3EGFP shuttle vector digested with BstEII and Bst1107I. Homologous recombination between pIX genes, right ITR DNA sequences present at the ends of linearized pChAd3EGFP and viral genomic DNA allowed its insertion in the plasmid vector, deleting at the same time the E1 region that was substituted by EGFP expression cassette. The HCV NS region expression cassette based on human cytomegalovirus (HCMV) promoter and bovine growth hormone polyadenylation signal (Bgh polyA) was constructed as described in Emini et al., International Publication Number WO 03/031588 and inserted into ChAd3ΔE1 EGFP vector by homologous recombination in *E. coli* strain BJ5183 exploiting the homologies between HCMV and Bgh polyA DNA sequences.

III. E3 Region Deletion

To introduce the deletion of the entire E3 region in the ChAd3 vector backbone, the two DNA regions flanking the E3 genes were amplified by PCR obtaining two DNA fragments. A 486 bp fragment spanning from nt 28159 to nt 28644 (3' of pVIII gene, upstream the E3 region) and a 474 bp DNA fragment containing the 3' end of the fiber gene (bp 32633 to bp 33106, downstream the E3 region). EcoRI restriction sites were introduced at the 3' end of the first DNA fragment and at the 5' end of the second fragment. The two PCR fragments were digested with EcoRI and were joined by in vitro ligation. The DNA fragment obtained (988 bp) was then further amplified using the pVIII forward oligo and the Fiber reverse oligo.

The 988 bp DNA fragment containing the 3' and the 5' DNA flanking regions of E3 region joined together was recombined with pChAd3ΔE1/EGFP linearized with HpaI (cutting within the E3 region at 32384 bp in ChAd3 wild-type) by co-transforming BJ5183 cells, thus introducing the E3 deletion. The final recombination product was the pChAd3ΔE1,E3/EGFP preadeno plasmid.

IV. Deletion of E4 Region and Insertion of Ad5 E4 orf6

In order to substitute ChAd3 E4 region with Ad5 E4orf6, Ad5 E4orf6 was introduced into a shuttle plasmid containing the last 393 bp derived from the right end of ChAd3 genome (bp 37349 to bp 37741). Subsequently, a DNA fragment of 144 bp derived from the fiber 3' end and including the E4 polyA (from bp 34491 to bp 34634 of ChAd3 map) was introduced downstream Ad5E4orf6 generating the plasmid pARSChAd3Ad5E4orf6-2.

Finally, a DNA fragment from pARSChAd3Ad5E4orf6-2 containing at the boundaries the fiber 3' end/E4 polyA and the ChAd3 right end was introduced by homologous recombination into pChAd3 ΔE1,E3/EGFP linearized with PacI restriction enzyme (PacI site, nt 36924 of ChAd3 wt) by cotransforming E. coli strain BJ5183, thus generating pChAd3 ΔE1, 3,4 Ad5orf6 EGFP.

Following this strategy, the entire ChAd3 E4 coding region was deleted and substituted with Ad5E4orf6 gene cloned 62 bp downstream the putative E4 TATA signal under the control of the ChAd3 E4 promoter.

Example 3

ChAd63 Vector Construction

A ChAd63 vector analogous to the ChAd3 ΔE1,E3,E4, E4Ad5orf6 vector was constructed as follows
I. Construction of a Subgroup E Shuttle Vector The ChAd63 viral genome was fully sequenced and the information used to construct a shuttle vector to facilitate cloning by homologous recombination of entire genome. Briefly, the shuttle vector used to clone subgroup E chimp adenovirus 63, referred to herein as pARSChAd63_EGFP was constructed as described below.

ChAd63 right end (nt 36216-36643) was amplified by PCR with primers of SEQ ID NOs: 26 and 27, digested with XbaI and BamHI then ligated to pARSChAd3-RLD restricted with XbaI and BamHI, generating pARS-ChAd63R. A ChAd63 DNA fragment (nt 3422-3814) containing pIx coding region was amplified by PCR with the primers of SEQ ID NOs: 28 and 29, digested with SgfI-AscI then cloned into pARS-ChAd63R digested with SgfI-AscI, generating pARS-ChAd63RD. ChAd63 viral DNA left end (nt 1-455) was amplified by PCR with primers of SEQ ID NOs: 30 and 31, digested with EcoRI and EcoRV then cloned pARS-ChAd63RD digested with EcoRI and EcoRV, thus generating pARS-ChAd63RLD. The HCMV-EGFP-bgh polyA cassette was amplified by PCR using the primers of SEQ ID NOs: 32 and 33, digested with EcoRV then cloned into pARS-ChAd63RLD digested with EcoRV, generating pARS-ChAd63RLD-EGFP. The viral DNA cassette was also designed to contain restriction enzyme sites (PmeI) located at the end of both ITR's so that digestion will release viral DNA from plasmid DNA.
II. Construction of ΔE1 ChAd63 Vector ChAd63 vector was constructed by homologous recombination in E. coli strain BJ5183. BJ5183 cells were co-transformed with ChAd63 purified viral DNA and pARS-ChAd63RLD-EGFP digested with AscI. Homologous recombination between pIX genes, right ITR DNA sequences present at the ends of linearized pARS-ChAd63RLD-EGFP and viral genomic DNA allowed its insertion in the plasmid vector, deleting at the same time the E1 region that was substituted by EGFP expression cassette.
III. E3 Region Deletion and ChAd63NSmut Vector Construction To introduce the deletion of the entire E3 region in the ChAd63 vector backbone, the two DNA regions flanking the E3 genes were amplified by PCR obtaining two DNA fragments. A 567 bp fragment spanning from nt 26665 to nt 27207 (3' of pVIII gene, upstream the E3 region) and a 563 bp DNA fragment containing the 3' end of the fiber gene (bp 31788 to bp 32326, downstream the E3 region). PacI restriction sites were introduced at the 3' end of the first DNA fragment and at the 5' end of the second fragment. The two PCR fragments were digested with PacI and were joined by in vitro ligation. The DNA fragment obtained (1112 bp) was then further amplified using the pVIII forward and the Fiber reverse oligonucleotides.

The 1112 bp DNA fragment containing the 3' and the 5' DNA flanking regions of E3 region joined together was recombined with pChAd63ΔE1/EGFP linearized with HpaI (cutting within the E3 region at 30168 bp in ChAd63 wildtype) by co-transforming BJ5183 cells, thus introducing the E3 deletion. The final recombination product was the pChAd63ΔE1, E3/EGFP preadeno plasmid.

The HCV NS region expression cassette based on human cytomegalovirus (HCMV) promoter and bovine growth hormone polyadenylation signal (Bgh polyA) was constructed as described in Emini et al., International Publication Number WO 03/031588 and inserted into pChAd63ΔE1,E3/EGFP vector by homologous recombination in E. coli strain BJ5183 exploiting the homologies between HCMV and Bgh polyA DNA sequences thus generating ChAd63NSmut.
IV. Deletion of E4 Region and Insertion of Ad5 E4 orf6

In order to substitute ChAd63 E4 region with Ad5 E4orf6, Ad5 E4orf6 was introduced into pARS-ChAd63RLD-EGFP downstream the 428 bp derived from the right end of ChAd63 genome (bp 36216 to bp 36643). Subsequently, a DNA fragment of 200 bp derived from the fiber 3' end and including the E4 polyA (from bp 33624 to bp 33823 of ChAd63 map) was introduced downstream Ad5E4orf6 generating the plasmid pARSChAd63Ad5E4orf6-2. Finally, a DNA fragment from pARSChAd63Ad5E4orf6-2 containing at the boundaries the fiber 3' end/E4 polyA and the ChAd63 left end was introduced by homologous recombination into pChAd63 ΔE1,E3/EGFP digested with PmeI restriction enzyme (releasing viral DNA from plasmid DNA) by cotransforming E. coli strain BJ5183, thus generating pChAd63 ΔE1,3,4 Ad5orf6 EGFP.

Following this strategy, the entire ChAd63 E4 coding region was deleted and substituted with AdSE4orf6 gene cloned 131 bp downstream the putative E4 TATA signal under the control of the ChAd63 E4 promoter.

Example 4

ChAd3NSmut (SEQ ID NO: 13) Expression

ChAd3NSmut was tested for expression of HCV proteins using techniques along the lines described in Catalucci et al., Journal of Virology 79: 6400-6409, 2005. HeLa cells were infected with ChAd3NSmut and MRKAd6NSmut. MRKAd6NSmut is described by Emini et al., International Publication Number WO 03/031588. Cell extracts were analyzed by an Immuno-blot with an anti-NS5A monoclonal antibody. As shown in FIG. 8, HCV proteins are expressed by ChAd3 NSmut similarly to the human Ad6 based vector (MRKAd6NSmut).

Example 5

ChAd3NSmut (SEQ ID NO: 13) Stability

ChAd3NSmut was checked for genetic stability using techniques along the lines described in Catalucci et al., Journal of Virology 79:6400-6409, 2000. Restriction analysis was performed on the viral DNA extracted from 5 independent clones (at passage 10). Pre ChAd3 NSmut plasmid was

Example 6

ChAd3NSmut (SEQ ID NO: 13) and ChAd63NSmut (SEQ ID NO: 17) Induced CMI in Mice The ability of ChAd3NSmut and ChAd63NSmut to induce cell mediated immunity was tested in C57/B6 mice using techniques along the lines described in Emini et al., International Publication Number WO 03/031588. FIG. 9 provides a comparison of the ability of ChAd3NSmut (SEQ ID NO: 13), ChAd63NSmut (SEQ ID NO: 17) and MRKAd6NSmut to induce cell mediated immunity in C57/B6 mice. FIG. 9 shows a IFN-γ ELIspot experiment (with a H2Kb restricted peptide, mapping in NS3 protease), done 3 weeks post injection (data shown as average; N=5). The CMI is elicited in mice at $10^8$ and $10^9$ doses by ChAd3NSmut and ChAd63NSmut is comparable to MRKAd6NSmut.

Example 7

ChAd3NSmut and ChAd63NSmut Induced CMI in Rhesus

The ability of ChAd3NSmut (SEQ ID NO: 13) and ChAd63NSmut (SEQ ID NO: 17) to induce CMI was confirmed in non human primates by immunizing rhesus macaques using techniques along the lines described in Emini et al., International Publication Number WO 03/031588 and Cirillo et al. International Publication Number WO 2005/071093. The vectors were evaluated in a group of three monkeys immunized with a heterologous prime/boost regimen based on the serial injection of three different non cross-reactive vectors. The three animals were primed with two injections of ChAd3NSmut at the dose of $10^{10}$ vp/monkey at week 0 and 4 followed by the injections of MRKAd6NSmut at week 22 and ChAd63NSmut at week 42. The time course of the immune response measured by IFN-γ ELISPOT is reported in FIG. 11 expressed as the sum of the responses observed on the different HCV NS peptide pools at any given time point. The results showed that efficient priming was obtained in all animals by ChAd3NS injection and that the CMI can be strongly boosted by both MRKAd6NSmut and ChAd63NSmut administration.

Example 8

Construction of Plasmid DNA Encoding a Chimeric HCV Polypeptide (SEQ ID NO: 1)

The plasmid encoding for a chimeric HCV polypeptide containing a NS3-4A region which is based on HCV 3a and an NS3-NS4A-NS4B-NS5A-NS5B region based on HCV 1b referred to herein as pV1JnsNSOPTmut 3a-1b (FIGS. 12 and 13) was obtained via homologous recombination in BJ5183 E. coli strain.

A plasmid encoding for a fully codon-optimized NS3-4a from HCV 3a with an optimal translation initiation (Kozak) sequence and a methionine start codon fused to the first amino acid of the mature NS3 sequence was synthetically generated. The NS3-4a coding sequence is flanked by two recombination regions for the insertion in the pV1JnsNSOPTmut acceptor plasmid (Emini et al., International Publication Number WO 03/031588) homologous to the IntronA sequence and to the beginning of NS3 (HCV 1b) coding sequence. HindIII restriction sites were introduced at both ends of the new NS3-4-a sequence for insert excision from the parental plasmid.

The pV1JnsOPTmut plasmid was linearized by HpaI unique site digestion. The linearized pV1JnsOPTmut plasmid and the HindIII digested NS3-4a (3a) insert were co-transformed in BJ5183 bacterial strain, to generate pV1JnsNSOPTmut 3a-1b. The genetic structure shown in FIG. 13 of the resulting pV1JnsNSOPTmut 3a-1b was verified by restriction enzyme and DNA sequence analysis.

Example 9

Plasmid DNA Encoding a Chimeric HCV Polypeptide Induced CMI in Mice

The ability of a plasmid DNA encoding for a chimeric HCV polypeptide to induce cell mediated immunity against different HCV genotypes was tested in mice. The chimeric polypeptide (SEQ ID NO: 1) contained a NS3-4A region which is based on HCV 3a and an NS3-NS4A-NS4B-NS5A-NS5B region based on HCV 1b (pV1Jns-NSOPTmut 3a-1b).

Three different strains of mice (two inbred: Balb/c, C57B1/6 and one outbred: CD1) were injected intramuscularly with 50 µg of DNA followed by electrical pluses. Each animal received two doses of either the chimeric plasmid (pV1Jns-NSOPTmut 3a-1b) or the pV1Jns-NSOPTmut plasmid (Emini et al., International Publication Number WO 03/031588) that encodes an NS3-NS4A-NS4B-NS5A-NS5B region based on HCV 1b. CMI specific for viral proteins from HCV 1b and 3a was measured using techniques described in Emini et al., International Publication Number WO 03/031588. FIG. 14 shows the number of T cells secreting IFN-γ (expressed as spot forming cells per million splenocytes) in response to NS3 protein from HCV 1b and 3a in CD1 mice (outbred strain). The specific T cell response against the 1b NS3 protein is similar with both plasmids while the chimeric construct induces a higher response against the 3a NS3 protein (p=0.04 by Student T test). The CMI induced in the two inbred strains of mice (Balb/c and C57B1/6) in response to NS3 protein from HCV 1b and 3a was similar with both constructs.

Other embodiments are within the following claims. While several embodiments have been shown and described, various modifications may be made without departing from the spirit and scope of the present invention.

What is claimed is:

1. A recombinant adenovector comprising:
   a) an expression cassette encoding an HCV polypeptide, wherein said HCV polypeptide comprises HCV NS3-NS4A-NS4B-NS5A; and
   b) an adenovirus genome containing an E1 deletion, an E3 deletion, and an optional E4 deletion; provided that said genome encodes:

i) a fiber region with an amino acid sequence having an identity of at least 70% to SEQ ID NO: 3 or of at least 80% to SEQ ID NO: 9;

ii) a hexon region with an amino acid sequence having an identity of at least 95% to either SEQ ID NO: 5 or 11; and iii) a penton region with an amino acid sequence having an identity of at least 85% to SEQ ID NO: 7, wherein said expression cassette is located at either the E1 or E3 deletion.

2. A pharmaceutical formulation comprising a therapeutically effective amount of the recombinant adenovector of claim 1.

3. A method of treatment or prophylaxis of hepatitis C in a patient comprising the step of administering to said patient a therapeutically effective amount of the recombinant adenovector of claim 1.

4. The recombinant adenovector of claim 1, wherein said HCV polypeptide comprises HCV NS3-NS4A-NS4B-NS5A-NS5B and produces sufficient activity in vivo to process itself to produce an NS5B protein and said NS5B protein is enzymatically inactive; and said adenovirus genome contains an E4 deletion and insertion of an Ad5 E4orf6 sequence substantially similar to nucleotides 34601-35482 of SEQ ID NO:13.

5. The recombinant adenovector of claim 1, wherein said vector is substantially similar to SEQ ID NO:13 or SEQ ID NO:17.

6. The recombinant adenovector of claim 5, wherein said vector consists of the nucleic acid sequence of SEQ ID NO:13 or SEQ ID NO:17.

7. A recombinant adenovirus particle comprising the recombinant adenovirus genome of claim 1, wherein said particle is encoded by said recombinant adenovirus genome.

8. A recombinant adenovirus particle comprising the recombinant adenovirus genome of claim 4, wherein said particle is encoded by said recombinant adenovirus genome.

9. A recombinant adenovirus particle comprising the recombinant adenovirus genome of claim 5, wherein said particle is encoded by said recombinant adenovirus genome.

10. A recombinant adenovirus particle comprising the recombinant adenovirus genome of claim 6, wherein said particle is encoded by said recombinant adenovirus genome.

11. A pharmaceutical formulation comprising a therapeutically effective amount of the recombinant adenovector of claim 4 and a pharmaceutically acceptable carrier.

12. A pharmaceutical formulation comprising a therapeutically effective amount of the recombinant adenovector of claim 5 and a pharmaceutically acceptable carrier.

13. A pharmaceutical formulation comprising a therapeutically effective amount of the recombinant adenovector of claim 6 and a pharmaceutically acceptable carrier.

14. A method of treatment or prophylaxis of hepatitis C in a patient comprising the step of administering to said patient a therapeutically active amount of the recombinant adenovector of claim 4.

15. A method of treatment or prophylaxis of hepatitis C in a patient comprising the step of administering to said patient a therapeutically active amount of the recombinant adenovector of claim 5.

16. A method of treatment or prophylaxis of hepatitis C in a patient comprising the step of administering to said patient a therapeutically active amount of the recombinant adenovector of claim 6.

17. The recombinant adenovector of claim 1, wherein the adenovirus genome encodes:
   i) a fiber region with an amino acid sequence having an identity of at least 80% to SEQ ID NO: 3 or of at least 85% to SEQ ID NO: 9;
   ii) a hexon region with an amino acid sequence having an identity of at least 95% to either SEQ ID NO: 5 or 11; and
   iii) a penton region with an amino acid sequence having an identity of at least 90% to SEQ ID NO: 7.

18. The recombinant adenovector of claim 17, wherein the adenovirus genome encodes:
   i) a fiber region with an amino acid sequence having an identity of at least 95% to SEQ ID NO: 3 or of at least 95% to SEQ ID NO: 9;
   ii) a hexon region with an amino acid sequence having an identity of at least 95% to either SEQ ID NO: 5 or 11; and
   iii) a penton region with an amino acid sequence having an identity of at least 95% to SEQ ID NO: 7.

* * * * *